(12) United States Patent
Neumann et al.

(10) Patent No.: US 11,931,414 B2
(45) Date of Patent: Mar. 19, 2024

(54) QUATERNIZED NICOTINAMIDE ADENINE DINUCLEOTIDE SALVAGE PATHWAY INHIBITOR CONJUGATES

(71) Applicant: Seagen Inc., Bothell, WA (US)

(72) Inventors: Christopher Scott Neumann, Seattle, WA (US); Kathleen Olivas, Tacoma, WA (US); Robert Lyon, Sammamish, WA (US); Kung-Pern Wang, Bothell, WA (US)

(73) Assignee: Seagen Inc., Bothell, WA (US)

( * ) Notice: Subject to any disclaimer, the term of this patent is extended or adjusted under 35 U.S.C. 154(b) by 968 days.

(21) Appl. No.: 16/608,748

(22) PCT Filed: Apr. 27, 2018

(86) PCT No.: PCT/US2018/030018
§ 371 (c)(1),
(2) Date: Oct. 25, 2019

(87) PCT Pub. No.: WO2018/201087
PCT Pub. Date: Nov. 1, 2018

(65) Prior Publication Data
US 2020/0197524 A1 Jun. 25, 2020

Related U.S. Application Data

(60) Provisional application No. 62/573,987, filed on Oct. 18, 2017, provisional application No. 62/490,733, filed on Apr. 27, 2017.

(51) Int. Cl.
| | | |
|---|---|---|
| *C07D 401/12* | (2006.01) | |
| *A61K 31/4545* | (2006.01) | |
| *A61K 47/54* | (2017.01) | |
| *A61K 47/65* | (2017.01) | |
| *A61K 47/68* | (2017.01) | |
| *A61P 35/00* | (2006.01) | |
| *A61P 37/00* | (2006.01) | |
| *C07H 15/26* | (2006.01) | |

(52) U.S. Cl.
CPC .......... *A61K 47/549* (2017.08); *A61K 47/545* (2017.08); *A61K 47/6803* (2017.08); *A61K 47/6851* (2017.08); *A61P 35/00* (2018.01)

(58) Field of Classification Search
CPC .... C07D 401/12; C07H 15/26; A61K 47/549; A61K 47/545; A61K 47/6803; A61K 47/6851; A61K 47/6849; A61K 47/6859; A61K 47/65; A61K 31/4545; A61P 35/00; A61P 37/00
See application file for complete search history.

(56) References Cited

U.S. PATENT DOCUMENTS

| | | |
|---|---|---|
| 4,816,397 A | 3/1989 | Boss |
| 4,816,567 A | 3/1989 | Cabilly |
| 5,225,539 A | 7/1993 | Winter |
| 5,585,089 A | 12/1996 | Queen |
| 6,214,345 B1 | 4/2001 | Firestone |
| 6,451,816 B1 | 9/2002 | Biedermann et al. |
| 7,091,186 B2 | 8/2006 | Senter |
| 7,498,298 B2 | 3/2009 | Doronina |
| 7,553,816 B2 | 6/2009 | Senter |
| 7,754,681 B2 | 7/2010 | Feng |
| 7,968,687 B2 | 6/2011 | Mcdonagh |
| 7,989,434 B2 | 8/2011 | Feng |
| 8,163,888 B2 | 4/2012 | Steeves |
| 8,257,706 B2 | 9/2012 | Mcdonagh |
| 8,324,165 B2 | 12/2012 | Penta et al. |
| 10,272,072 B2 | 4/2019 | Bair et al. |
| 2005/0256030 A1 | 11/2005 | Feng |
| 2006/0014804 A1 | 1/2006 | Binderup |
| 2009/0018086 A1 | 1/2009 | Doronina |
| 2009/0111756 A1 | 4/2009 | Doronina |
| 2009/0274713 A1 | 11/2009 | Chari |
| 2011/0288024 A1 | 11/2011 | Penta et al. |
| 2012/0122842 A1 | 5/2012 | Curtin et al. |
| 2012/0270900 A1 | 10/2012 | Olesen et al. |
| 2013/0259860 A1 | 10/2013 | Smith |
| 2013/0309223 A1 | 11/2013 | Sutherland |
| 2014/0357599 A1 | 12/2014 | Christensen et al. |
| 2017/0247412 A1 | 8/2017 | Burke |

(Continued)

FOREIGN PATENT DOCUMENTS

| | | |
|---|---|---|
| EP | 0012023 A1 | 6/1980 |
| EP | 0171496 A2 | 2/1986 |
| EP | 0173494 A2 | 3/1986 |

(Continued)

OTHER PUBLICATIONS

PCT International Search Report and Written Opinion in International Appln. No. 11201903013S, dated Aug. 27, 2020, 8 pages.
Alouane, A. et al. (Jun. 22, 2015, e-pub. Jun. 5, 2015). "Self-Immolative Spacers: Kinetic Aspects, Structure-Property Relationships, and Applications," Angew. Chem. Int. Ed. 54(26):7492-7509. (Abstract Only).
Beidler, C.B. et al. (Dec. 1, 1988). "Cloning and High Level Expression of a Chimeric Antibody With Specificity for Human Carcinoembryonic Antigen," J. Immunol. 141(11):4053-4060.
Better, M. et al. (May 20, 1988). "*Escherichia coli* Secretion of an Active Chimerica Antibody Fragment," Science 240:1041-1043.

(Continued)

*Primary Examiner* — Brenda L Coleman
(74) *Attorney, Agent, or Firm* — MORRISON & FOERSTER LLP

(57) ABSTRACT

Compounds and compositions are disclosed in which a NAMPT Drug Unit is conjugated to a targeting Ligand Unit through quaternization by a Linker Unit from which a NAMPT inhibitor compound or derivative thereof is released at the targeted site of action. Methods for treating diseases characterized by the targeted abnormal cells, such as those of cancer or an autoimmune disease, using the compounds and compositions of the invention are also disclosed.

21 Claims, 1 Drawing Sheet

(56) References Cited

U.S. PATENT DOCUMENTS

| | | |
|---|---|---|
| 2019/0314519 A1 | 10/2019 | Neumann et al. |
| 2021/0300867 A1 | 9/2021 | Lyon et al. |

FOREIGN PATENT DOCUMENTS

| | | |
|---|---|---|
| EP | 0184187 A2 | 6/1986 |
| JP | 2012529467 A | 11/2012 |
| TW | 201625316 A | 7/2016 |
| WO | 198601533 A1 | 3/1986 |
| WO | 198702671 A1 | 5/1987 |
| WO | 199734631 A1 | 9/1997 |
| WO | 199748397 A1 | 12/1997 |
| WO | 199854144 A1 | 12/1998 |
| WO | 200061559 A1 | 10/2000 |
| WO | 2003097602 A1 | 11/2003 |
| WO | 2004010957 A2 | 2/2004 |
| WO | 2004010957 A3 | 6/2004 |
| WO | 2007038658 A2 | 4/2007 |
| WO | 2007038658 A3 | 10/2007 |
| WO | 2009086835 A1 | 7/2009 |
| WO | 2009099741 A1 | 8/2009 |
| WO | 2009156421 A1 | 12/2009 |
| WO | 2010023307 A1 | 3/2010 |
| WO | 2010142735 A1 | 12/2010 |
| WO | 2011006988 A1 | 1/2011 |
| WO | 2012031196 A1 | 3/2012 |
| WO | 2012031197 A1 | 3/2012 |
| WO | 2012067963 A1 | 5/2012 |
| WO | 2012067965 A1 | 5/2012 |
| WO | 2012150952 A1 | 11/2012 |
| WO | 2012154194 A1 | 11/2012 |
| WO | 2012177782 A1 | 12/2012 |
| WO | 2013067710 A1 | 5/2013 |
| WO | 2013082150 A1 | 6/2013 |
| WO | 2013123152 A2 | 8/2013 |
| WO | 2013127268 A1 | 9/2013 |
| WO | 2013130935 A1 | 9/2013 |
| WO | 2013130943 A1 | 9/2013 |
| WO | 2013170112 A1 | 11/2013 |
| WO | 2013170113 A1 | 11/2013 |
| WO | 2013170115 A1 | 11/2013 |
| WO | 2013170118 A1 | 11/2013 |
| WO | 2013170191 A1 | 11/2013 |
| WO | 2014068443 A1 | 5/2014 |
| WO | 2014074715 A1 | 5/2014 |
| WO | 2014111871 A1 | 7/2014 |
| WO | 2013123152 A3 | 11/2014 |
| WO | 2014178001 A1 | 11/2014 |
| WO | 2015054060 A1 | 4/2015 |
| WO | 2015057699 A2 | 4/2015 |
| WO | 2015095755 A1 | 6/2015 |
| WO | 2015057699 A3 | 9/2015 |
| WO | 2015161142 A1 | 10/2015 |
| WO | 2015179759 A1 | 11/2015 |
| WO | 2016012958 A1 | 1/2016 |
| WO | 2016040684 A1 | 3/2016 |
| WO | 2016095581 A1 | 6/2016 |
| WO | 2016118565 A1 | 7/2016 |
| WO | 2018075600 A1 | 4/2018 |
| WO | WO 2018/201087 | 11/2018 |

OTHER PUBLICATIONS

Blencowe, C.A. et al. (2011). "Self-immolative Linkers in Polymeric Delivery Systems," Polymer Chem 2:773-790.

Burke, P.J. et al. (May 2016). "Development of Novel Quaternary Ammonium linkers for Antibody-Drug Conjugates", Molecular Cancer Therapy, 15(5):938-945.

Chandra, N. et al. (2011). "Virtual Screening, Identification and Experimental Testing of Novel Inhibitors of PBEF1/Visfatin/NMPRTase for Glioma Therapy," Journal of Clinical Bio. 1 5, 12 pages.

Chen, W. et al. (Dec. 14, 2017). "Dual NAMPT/HDAC Inhibitors as a New Strategy for Multitargeting Antitumor Drug Discovery", ASC Medical Chemistry Letters, 9:34-38.

Christensen, M.K. et al. (2013) "Nicotinamide Phosphoribosyltransferase Inhibitors, Design, Preparation, and Structure-Activity Relationships," J. Med. Chem. 56:9071-9088, 57 pages.

Colombano, G. et al. (2009, e-pub. Dec. 4, 2009). "A Novel Potent Nicotinamide Phosphoribosyltransferase Inhibitor Synthesized by Click Chemistry," J. Med. Chem. 53:616-623.

Dragovich, P.S. et al. (Feb. 1, 2014, e-pub. Dec. 21, 2013). "Fragment-Based Design of 3-Aminopyridine-Derived Amides as Potent Inhibitors of Human Nicotinamide Phosphoribosyltransferase (NAMPT)," Bioorg. Med. Chem. Lett. 24:954-962.

EP Patent Application No. 17862746.9, Supplemental European Search Report and Search Opinion, 6 pages, dated May 25, 2020, 6 pages.

Fridkin, M. et al. (1974). "Peptide Synthesis," Ann. Rev. Blochem. 43:419-443.

Gaertner, H.F. et al. (Mar. 11, 1994). "Chemo-Enzymic Backbone Engineering of Proteins," J. Biol. Chem. 269(10):7224-7230.

Galli, U. et al. (2008) "Synthesis and Biological Evaluation of Isosteric Analogues of FK866, an Inhibitor of NAD Salvage," Chem. Med. Chem. 3:771-779.

Galli, U. et al. (2013) "Medicinal Chemistry of Nicotinamide Phosphoribosyltransferase (NAMPT) Inhibitors," J. Med. Chem. 56:6279-6296, 19 pages.

Giannetti, A.M. et al. (Feb. 13, 2014, e-pub. Jan. 22, 2014) "Fragment-Based Identification of Amides Derived From Trans-2-(Pyridin-3-yl)Cyclopropane Carboxylic Acid as Potent Inhibitors of Human Nicotinamide Phosphoribosyltransferase (NAMPT)," J. Med. Chem. 57:770-792.

Greenwald, R.B. et al. (1999, e-pub. Aug. 13, 1999). "Drug Delivery Systems Employing 1,4- or 1,6-Elimination: Poly(Ethylene Glycol) Prodrugs of Amine-Containing Compounds," J. Med. Chem. 42(18):3657-3667.

Gunzner-Toste, J. et al. (Jun. 15, 2013, e-pub. Apr. 25, 2013). "Discovery of Potent and Efficacious Urea-Containing Nicotinamide Phosphoribosyltransferase (NAMPT) Inhibitors With Reduced CYP209 Inhibition Properties," Bioorg. Med. Chem. Lett. 23:3531-3538.

Han, S.-Y. et al. (2004). "Recent Development of Peptide Coupling Agents in Organic Synthesis," Tet. 60:2447-2476.

Hasmann, M. et al. (Nov. 1, 2003). "FK866, A Highly Specific Noncompetitive Inhibitor of Nicotinamide Phosphorisbosyltransferase, Represents a Novel Mechanism for Induction of Tumor Cell Apoptosis," Cancer Research 63:7436-7442.

Hay, M.P. et al. (Aug. 2, 1999). "A 2-nitroimidazole Carbamate Prodrug of 5-amino-1-(chloromethyl)-3-[(5,6,7-trimethoxyindol-2-yl)carbonyl]-1,2-dihydro-3H-benz[e]indole (amino-seco-CBI-TMI) for Use With ADEPT and GDEPT," Bioorganic & Medicinal Chemistry Letters 9(15):2237-2242.

International Preliminary Report on Patentability, dated Apr. 23, 2019, for PCT Application No. PCT/US2017/057116, filed Oct. 18, 2017, 12 pages.

International Preliminary Report on Patentability, dated Oct. 29, 2019, for PCT Application No. PCT/US2017/030018, filed Apr. 27, 2018, 7 pages.

International Search Report and Written Opinion, dated Feb. 12, 2018, for PCT Application No. PCT/US2017/057116, filed Oct. 18, 2017, 12 pages.

International Search Report and Written Opinion, dated Jul. 4, 2018, for PCT Application No. PCT/US2017/030018, filed Apr. 27, 2018, 10 pages.

International Union of Pure and Applied Chemistry (Nov. 5, 1960). "Definitive Rules for Nomenclature of Organic Chemistry," J. Am. Chem. Soc. 82:5545-5473, 30 pages.

Jain, N. et al. (Nov. 2015, e-pub. Mar. 11, 2015). "Current ADC Linker Chemistry," Pharma Res 32 (11):3526-3540.

Jeffrey, S.C. et al. (May-Jun. 2006, e-pub. May 3, 2006). "Development and Properties of β-Glucuronide Linkers for Monoclonal Antibody-Drug Conjugates," American Chemical Society 17(3):831-840.

Jones, P.T. et al. (May 29, 1986). "Replacing the Complementarity-Determining Regions in a Human Antibody With Those From a Mouse," Nature 321:522-525.

(56) References Cited

OTHER PUBLICATIONS

Kabat, E.A. et al. (1991). Sequences of Proteins of Immunological Interest, 5th Ed. Public Health Service, National Institutes of Health, Bethesda MD., Table of Contents, 21 pages.

Kabat, E.A. et al. (Sep. 1980). "Origins of Antibody Complementarity and Specificity-Hypervariable Regions and the Minigene Hypothesis," J Immunology 125(3):961-969.

Karpov, A.S. et al. (2018). "Nicotinaride Phosphoribosyltransferase Inhibitor as a Novel Payload for Antibody-Drug Conjugates," ACS Medicinal Chemistry Letters, pp. A-E, 5 pages.

Kolakowski, R. V. et al. (Jul. 4, 2016, e-pub. May 20, 2016). "The Methylene Alkoxy Carbamate Self-Immolative Unit: Utilization for the Targeted Delivery of Alcohol-Containing Payloads with Antibody-Drug Conjugates," Angewandte Chemie 55(28):7948-7951.

Kolakowski, R.V. et al. (2016). "The Methylene Alkoxy Carbamate Self-Immolative Unit: Utilization for the Targeted Delivery of Alcohol-Containing Payloads with Antibody-Drug Conjugates," Angew. Chem. 128:8080-8083.

Kozbor, D. et al. (1983). "The Production of Monoclonal Antibodies From Human Lymphocytes," Immunology Today 4(3):72-79.

Laguzza, B.C. et al. (Mar. 1989). "New Antitumor Monoclonal Antibody-Vinca Conjugates LY203725 and Related Compounds: Design, Preparation, and Respresentative in Vivo Activity," J. Med. Chem. 32(3):548-555.

Liu, A.Y. et al. (May 1987). "Chimeric Mouse-Human IgG1 Antibody That Can Mediate Lysis of Cancer Cells," Proc. Natl. Acad. Sci. USA 84:3439-3443.

Liu, A.Y. et al. (Nov. 15, 1987). "Production of a Mouse-Human Chimeric Monoclonal Antibody to CD20 With Potent Fc-Dependent Biologic Activity," J. Immunol. 139(10):3521-3526.

Lockman, J.W. et al. (Dec. 23, 2010, e-pub. Nov. 16, 2010). "Analogues of 44(7-bromo-2-methyl-4-oxo-3H-quinazolin-6-yl)methylprop-2-ynylaminol-N-(3-pyridylmethypbenzamide (CB-30865) as Potent Inhibitors of Nicotinamide Phosphoribosyltransferase (NAMPT)," J. Med. Chem. 53:8734-8746.

Lyon, R.P. et al. (Jul. 2015; e-pub. Jun. 15, 2015). "Reducing Hydrophobicity of Homogeneous Antibody-Drug Conjugates Improves Pharmacokinetics and Therapeutic Index," Nat Biotechnol 33(7):733-735.

Lyon, R.P. et al. (Oct. 2014, e-pub. Sep. 7, 2014). "Self-hydrolyzing Maleimides Improve the Stability and Pharmacological Properties of Antibody-Drug Conjugates," Nat Biotechnol 32(10): 1059-1062.

Morrison, S.L. (Sep. 1985). "Transfectomas Provide Novel Chimeric Antibodies," Science 229 (4719):1202-1207.

NCBI Accession No. NP_005737. 1, (Apr. 9, 2017). "Nicotinamide phosphoribosyltransferase Precursor [*Homo sapiens*]," 3 pages.

Nishimura, Y. et al. (Feb. 15, 1987). "Recombinant Human-Mouse Chimeric Monoclonal Antibody Specific for Common Acute Lymphocytic Leukemia Antigen," Cancer. Res. 47(4):999-1005.

Oi, V.T. et al. (1986). "Chimeric Antibodies," Bio Techniques 4(3):214-219.

Olsson, L. et al. (1983), "Human-Human Monoclonal Antibody-Producing Hybridomas: Technical Aspects," Meth Enzymol. 92:3-16.

Rose, K. et al. (May-Jun. 1991). "Preparation of Well-Defined Protein Conjugates Using Enzyme-Assisted Reverse Proteolysis," Bioconjugate Chem. 2(3):154-159.

Roulston, A. et al. (2016, e-pub. Jan. 2016) "New Strategies to Maximize Therapeutic Opportunities for NAMPT Inhibitors in Oncology," Mol. Cell. Oncol. 3(1):e1052180, 13 pages.

Sadrerafi, K. et al. (2018). "Clickable Prodrugs Bearing Potent and Hydrolytically Cleavable Nicotinamide Phosphoribosyltransferase Inhibitors" Drug Design Development and Therapy 12:987-995.

Sampath, D. et al. (Jul. 2015, e-pub. Feb. 21, 2015) "Inhibition of Nicotinamide Phosphoribosyl-20 Transferase (NAMPT) as a Therapeutic Strategy," Pharmacol Ther. 151:16-31, 17 pages.

Schmidt, M.M. et al. (Oct. 2009). "A Modeling Analysis of the Effects of Molecular Size and Binding Affinity on Tumor Targeting," Mol. Cancer Ther. 8(10):2861-2871.

Schwarz, A. et al. (1990). "Enzymatic C-Terminal Biotinylation of Proteins," Methods Enzymol. 184:160-162. (Abstract Only).

SG International Search Report and Written Opinion in International Appln. No. 11201903013S,dated Aug. 27, 2020, 8 pages.

Shaw, D.R. et al. (Dec. 7, 1988). "Mouse/Human Chimeric Antibodies to a Tumor-Associated Antigen: Biologic Activity of the Four Human IgG Subclasses," J. Natl. Cancer Inst. 80(19):1553-1559.

Sun, L.K. et al. (Jan. 1987). "Chimeric Antibody With Human Constant Regions and Mouse Variable Regions Directed Against Carcinoma-Associated Antigen 17-1A," Proc. Natl. Acad. Scl. USA 84(1):214-218.

Teng, N.N.H et al. (Dec. 1983). "Construction and Testing of Mouse-Human Heteromyelomas for Human Monocional Antibody Production," Proc. Natl. Acad. Sci. USA. 80:7308-7312.

Verhoeyan, M. et al. (Mar. 25, 1988). "Reshaping Human Antibodies: Grafting an Antilysozyme Activity," Science 239:1534-1536.

Veronese, F.M. et al. (Nov. 2005). "PEGylation, Successful Approach to Drug Delivery," Drug Discovery Today 10(21): 1451-1458.

Wood. C.R. et al. (Apr. 4, 1985). "The Synthesis and in vivo Assembly of Functional Antibodies in Yeast," Nature 314(6010):446-449.

You, H. et al. (Apr. 2011, e-pub. Jan. 31, 2011) "Design, Synthesis and X-Ray Crystallographic Study of NAmPRTase Inhibitors as Anti-Cancer Agents," Eur. J. Med. Chem. 46:1153-1164.

Zak, M. et al. (Feb. 1, 2015, e-pub. Dec. 17, 2014) "Identification of Nicotinamide Phosphoribosyltransferase (NAMPT) Transferase Inhibitors With No Evidence of CYP3A4 Time-Dependent Inhibition and Improved Aqueous Solubility," Bloorg. Med. Chem. Lett. 25(3):529-541.

Zheng, X. (Aug. 22, 2013, e-pub. Jul. 31, 2013). "Structure-Based Discovery of Novel Amide-Containing Nicotinamide Phosphoribosyltransferase (NAMPT) Inhibitors," J. Med. Chem. 56:6413-6433.

Wei, Y. et al. (Sep. 7, 2022). "Review of Various NAMPT Inhibitors for the Treatment of Cancer," Front. Pharmacol. 13:970553, 23 pages.

Non-Final Office Action, dated Apr. 5, 2023, for U.S. Appl. No. 17/111,982, filed Dec. 4, 2020, 16 pages.

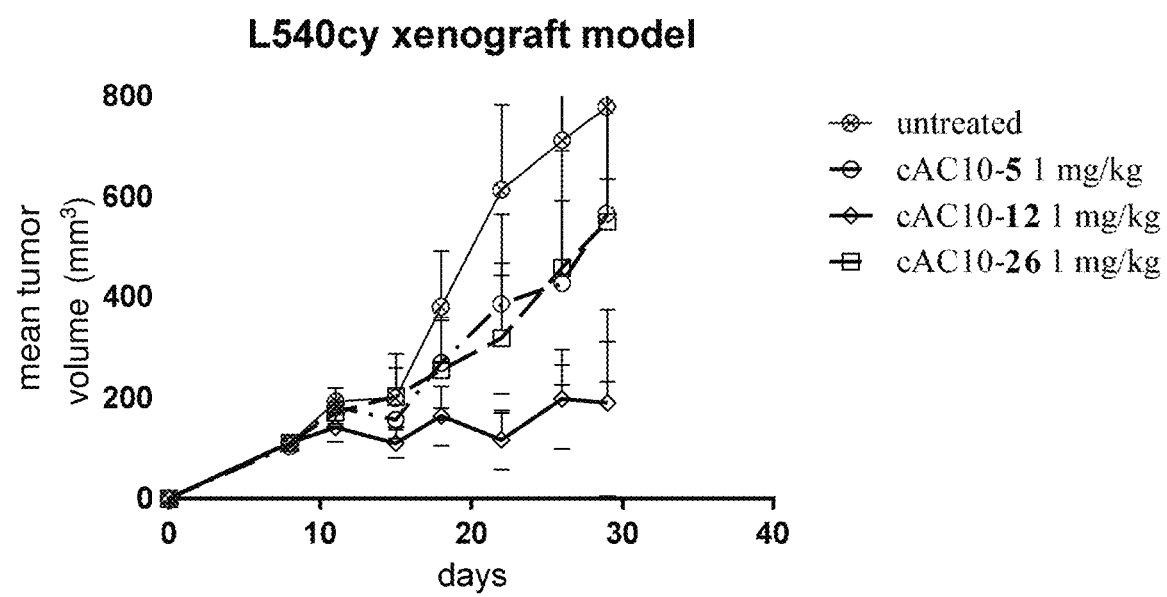

QUATERNIZED NICOTINAMIDE ADENINE DINUCLEOTIDE SALVAGE PATHWAY INHIBITOR CONJUGATES

CROSS REFERENCE TO RELATED APPLICATIONS

This application is a U.S. national stage filing under 35 USC § 371 of International Application No. PCT/US2018/030018, filed Apr. 27, 2018, which claims the benefit of priority to U.S. Application Nos. 62/490,733, filed Apr. 27, 2017 and 62/573,987, filed Oct. 18, 2017, each of which are incorporated by reference in their entireties.

BACKGROUND OF THE INVENTION

The invention relates to Ligand-Drug Conjugates for targeted delivery of compounds that inhibit intracellular production of nicotinamide adenine dinucleotide (NAD) within abnormal cells that are associated with a given disease state. Abnormal cells, which typically are abnormal mammalian cells, have increased energy demands in comparison to normal cells distant from the site of the abnormal cells due to their persistent or heightened metabolic activity. The ATP levels for meeting those demands are reliant on commensurate levels of $NAD^+$ for shuttling electrons in the oxidative phosphorylation and glycolytic pathways, both of which contribute to ATP production in eukaryotic cells. In addition to meeting the increased energy demand, continuous production of $NAD^+$ is required due to turnover of that cofactor by various intracellular enzymes, including poly (ADP ribose) polymerases (PARPs), mono (ADP ribose) transferases (ARTs) and sirturins. Cancer cells, which are one type of abnormal cells, are thought to be particularly sensitive to disruptions in maintaining intracellular concentrations of $NAD^+$ for supporting their energy demands due to significantly increased turnover of that cofactor in comparison to normal cells distant from the site of the cancer cells. That greater sensitivity may also be attributed to greater reliance of those abnormal cells on the glycolytic pathway for producing ATP instead of oxidative phosphorylation, the former of which is less efficient at that task, even when those cancer cells are not under hypoxic conditions.

Intracellular concentrations of $NAD^+$ in eukaryotic cells are produced either by a de novo pathway starting from tryptophan or more efficiently through salvage pathways by uptake of pyridine-containing precursors, such as nicotinic acid, nicotinamide and nicotinamide ribose, from the diet or reuse of these compounds subsequent to the activities of $NAD^+$-consuming enzymes. Nicotinamide is salvaged preferentially over nicotinic acid in mammalian cells for intracellular replenishment of $NAD^+$, the rate limiting enzyme for which is nicotinamide phosphoribosyltransferase (NAMPT). NAMPT synthesizes nicotinamide mononucleotide (NMN) from nicotinamide and 5-phospho-α-D-ribose 1-diphosphate (PRPP), which is followed by conversion of NMN to $NAD^+$ by nicotinamide mononucleotide adenylyl transferase. Inhibition of $NAD^+$ synthesis through the salvage pathway should deplete intracellular $NAD^+$ due to its consumption by the aforementioned enzymes that use it as a substrate. Inhibition of NAMPT in cancer cells to a sufficient extent should then cause a drop in intracellular concentration of ATP to levels that are no longer sufficient for sustaining the continued metabolic activity of these abnormal cells, which should then lead to their death.

Due to its central role in the salvage pathway and the greater sensitivity of cancer cells to disruptions in intracellular concentrations of $NAD^+$, which interferes with maintaining sufficient levels of ATP for supporting their heightened or persistent metabolic activity, targeting of NAMPT by small molecule mimetics of nicotinamide has been explored for the treatment of cancer. As with cancer cells, inflammatory cells, such as polymorphonucleate cells (PMNC) and neutrophils, having persistent activation in inflammatory disease states, such as rheumatoid arthritis, lupus erythematosus and inflammatory bowel diseases, also show elevated NAMPT mRNA and/or protein levels for maintaining sufficient levels of NAD to support the continued metabolic activities of these abnormal cells. Thus, NAMPT inhibitors may also be useful in treating those diseases. However, cytotoxicity towards normal cells, including thrombocytopenia, anemia, hyperglycemia and electrolyte dysfunction, has resulted in repeated failures in developing NAMPT inhibitors as therapeutic agents for treating any disease state when administered as a free drug.

Therefore, there is a long-standing, unmet need in the art for improving the tolerability, which is typically reflected by an increase in therapeutic index, of NAMPT inhibitor (NAMPTi) compounds for treatment of disease states attributable to abnormal cells that have a heightened and/or continual demand for ATP, which needs to be supported by commensurate intracellular concentrations of $NAD^+$. Ligand Drug Conjugates described herein corresponding to or incorporating a NAMPTi compound as a quaternized Drug Unit ($D^+$) and whose Ligand Unit targets those abnormal cells, or the vicinity of such cells, addresses that unmet need.

SUMMARY OF THE INVENTION

Principle embodiments of the invention are Ligand Drug Conjugate compositions represented by Formula 1:

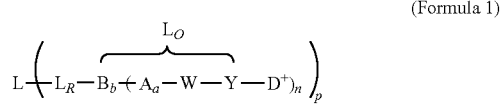

(Formula 1)

or a salt thereof, preferably a pharmaceutically acceptable salt thereof, wherein L is a Ligand Unit; W is a Peptide Cleavable Unit and Y is a self-immolative Spacer Unit comprised of a PAB or PAB-type moiety, or W—Y is replaced by a Glucuronide Unit of formula —Y(W'), wherein W' represents a carbohydrate moiety with glycosidic bonding to Y through an optionally substituted heteroatom, wherein Y is as previously defined; $D^+$ is a quaternized NAMPT Drug Unit covalently attached to the remainder of the Formula 1 composition structure through a quaternized skeletal aromatic nitrogen atom of an optionally substituted $C_5$-$C_{24}$ heteroaryl, or a quaternized skeletal non-aromatic nitrogen atom of a partially unsaturated or partially aromatic optionally substituted $C_9$-$C_{24}$ heterocyclyl, wherein non-enzymatic or enzymatic action on W/W' of a drug linker moiety of a Ligand Drug Conjugate compound of the composition initiates release of the quaternized NAMPT Drug ($D^+$) Unit as a NAMPTi compound comprised of an optionally substituted $C_5$-$C_{24}$ or $C_9$-$C_{24}$ heteroaryl having a skeletal non-quaternized aromatic nitrogen atom corresponding to the previously quaternized skeletal nitrogen atom; and wherein the Ligand Drug Conjugate compound is represented by Formula 1 in which subscript p is replaced by p';

$L_R$ in the Ligand Drug Conjugate is a primary linker that interconnects the Ligand Unit and quaternized Drug Unit through $L_O$, wherein $L_O$ is an optional secondary linker that is present; subscripts a and b independently are 0 or 1, indicating the absence or presence, respectively, of A or B; subscript n is 1, 2, 3 or 4; A is an first optional Stretcher; B is a Branching Unit that is present, when subscript b is 1 and subscript n is 2, 3 or 4, or B is absent so that subscript b is 0, when subscript n is 1, wherein each of A and B is an independently selected single unit or is optionally comprised or consists of two, three or four independently selected subunits; and subscript p is a number ranging from 1 to 24 and subscript p' is an integer ranging from 1 to 24.

In some aspects, the Ligand Unit of a Ligand Drug Conjugate composition or compound thereof is that of an antibody, thereby defining an Antibody Drug Conjugate (ADC) composition or compound, and the targeted moiety recognized by its targeting antibody Ligand Unit is an cell-surface antigen of abnormal cells, wherein the targeted antigen so bound from said recognition is capable of cellular internalization of a Ligand Drug Conjugate compound of the composition, wherein the antigen is typically present on the abnormal cells in greater copy number in comparison to that of normal cells distant from the site of the abnormal cells.

In other aspects, the antibody Ligand Unit of a Ligand Drug Conjugate composition or compound thereof recognizes an antigen present within the vicinity of abnormal cells in which the antigen is typically present in greater copy number in comparison to that of normal cells distant from the site of the abnormal cells, wherein bonding to the targeted antigen culminates in release of the quaternized NAMPT Drug Unit as a NAMPTi compound in proximity to the abnormal cells, which is followed by entry of the NAMPTi compound from that release into the abnormal cells.

In any one of those aspects, a quaternized NAMPT Drug Unit is released from a Ligand Drug Conjugate compound of the composition as a NAMPTi compound within abnormal cells, or is released in the vicinity of the abnormal cells targeted by the Ligand Drug Conjugate, so as to exert a therapeutic effect due intracellular inhibition of NAMPT in the abnormal cells.

In some aspects a quaternized NAMPT Drug Unit (D$^+$) is represented by the general structure of:

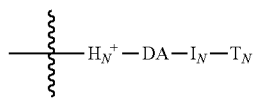

in salt form, preferably in pharmaceutically acceptable salt form, $H_{N^+}$ is a quaternized NAMPT Head Unit as the quaternized component of D$^+$ wherein the optionally substituted $C_5$-$C_{24}$ heteroaryl or partially unsaturated or partially aromatic optionally substituted $C_9$-$C_{24}$ heterocyclyl of that component is comprised of a 5- or 6-membered nitrogen-containing partially unsaturated or heteroaromatic ring system, a skeletal nitrogen atom of which is the site of quaternization to $L_O$, as indicated by the wavy line to $H_{N^+}$;

DA is a Donor-Acceptor Unit wherein the Donor-Acceptor Unit is or is comprised of a hydrogen bond donor or acceptor functional group and is bonded to a carbon skeletal atom at position 2 or 3 of the 5-membered nitrogen-containing partially unsaturated or heteroaromatic ring system or at position 3 or 4 of the 6-membered nitrogen-containing partially unsaturated or heteroaromatic ring system, with optional formal cyclization of DA back to an adjacent skeletal carbon atom of the 6-membered nitrogen-containing ring system through an introduced optionally substituted non-aromatic carbon atom or an optionally substituted nitrogen, oxygen or sulfur atom resulting in a partially unsaturated, partially aromatic or fully aromatic 6,5- or 6,6-fused ring system, wherein said bonding of DA is in relation to a skeletal nitrogen atom of the 5- or 6 membered nitrogen-containing ring system and wherein said formal cyclization to the adjacent carbon atom of the 6-membered nitrogen-containing ring system substantially retains the hydrogen bonding ability of the donor or acceptor functional group of DA in absence of said formal cyclization;

$I_N$ is a NAMPT Interconnecting Unit, wherein the NAMPT Interconnecting Unit is or is comprised of —$X^1$—[C(=O)]$_{0,1}$—, —$X^1$—S(=O)$_{1,2}$—, —$X^2$—$C_6$-$C_{24}$ arylene-[C(=O)]$_{0,1}$—, —$X^2$—$C_6$-$C_{24}$ arylene-[S(=O)$_{1,2}$]$_{0,1}$, —$X^2$—$C_6$-$C_{24}$ arylene-O—, —$X^2$—$C_5$-$C_{24}$ heteroarylene-[C(=O)$_{0,1}$]—, —$X^2$—$C_5$-$C_{24}$ heteroarylene-[S(=O)$_{1,2}$]$_{0,1}$, —$X^2$—$C_5$-$C_{24}$ heteroarylene-O— or —$X^2$—$C_3$-$C_{20}$ heterocyclo-[C(=O)$_{0,1}$]—, wherein the arylene, heteroarylene and heterocyclo are optionally substituted; and wherein $X^1$ is optionally substituted $C_5$-$C_7$ alkylene; and $X^2$ is absent or is an optionally substituted $C_1$-$C_4$ alkylene;

$T_N$ is a NAMPT Tail Unit, wherein the NAMPT Tail Unit is or is comprised of an optionally substituted aminoalcohol residue or a carboxylic acid-alcohol residue, the amino nitrogen or carbonyl carbon of which is bonded to $I_N$, or $T_N$ is or is comprised of an optionally substituted benzamide moiety, the amide nitrogen atom of which is bonded to $I_N$ with optional cyclization of that atom back to $I_N$ or to the remainder of $T_N$, or $T_N$ is or is comprised of an optionally substituted aryl or biaryl moiety, an aromatic skeletal atom of which is bonded to $I_N$, or to the remainder of $T_N$; and wherein $T_N$ or the remainder thereof is bond to $I_N$, wherein said remainder, if present, is an optionally substituted $C_2$-$C_7$ heteroalkylene or an optionally substituted $C_5$-$C_6$ heterocyclo, and wherein enzymatic action on W/W' of a drug linker moiety of a Ligand Drug Conjugate compound of the composition initiates release of the quaternized NAMPT Drug (D$^+$) Unit as a NAMPTi compound of formula $H_N$-DA-$I_N$-$T_N$, wherein $H_N$ is a NAMPT Head Unit that is a fully aromatic optionally substituted $C_5$-$C_{24}$ or $C_9$-$C_{24}$ heteroaryl comprised of a 5- or 6-membered nitrogen-containing heteroaromatic ring system, with optional cyclization of DA to an adjacent skeletal carbon atom of the heteroaryl, and the other variable groups are as previously defined; and wherein $H_N$— or $H_N$-DA- of the NAMPTi compound is capable of interacting with enzymatically competent NAMPT homodimer at its nicotinamide binding site.

Those and other aspects of quaternized NAMPT Drug Units are further described by the embodiments of the invention.

Other principle embodiments of the invention provide for compounds commonly referred to as Drug Linker compounds having the structure of Formula I:

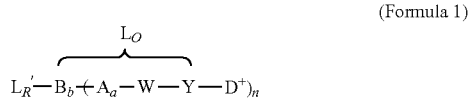

(Formula 1)

or a salt thereof, including pharmaceutically acceptable salts thereof, wherein $L_{R'}$ is a primary linker of the Drug Linker compound having a functional group capable of forming a covalent bond to a targeting moiety that becomes the Ligand Unit of a Ligand Drug Conjugate compound of Formula 1 in which subscript p is replaced by subscript p', wherein the other variable groups are as defined for that formula; and wherein non-enzymatic or enzymatic action on W/W' of the Drug Linker compound or of a drug linker moiety of a Ligand Drug Conjugate compound prepared from the Drug Linker compound initiates release of the quaternized NAMPT Drug ($D^+$) Unit as a NAMPTi compound comprised of an optionally substituted $C_5$-$C_{24}$ or $C_9$-$C_{24}$ heteroaryl having the previously quaternized skeletal nitrogen atom with optional cyclization of DA to an adjacent skeletal carbon atom of the heteroaryl for those instances in which the released NAMPTi compound has the formula of $H_N$-DA-$I_N$-$T_N$ for which the variable groups are as previously defined.

Quaternization of a NAMPTi compound or an intermediate thereof having an optionally substituted $C_5$-$C_{24}$ heteroaryl capable of quaternization for conjugation to a targeting agent to provide a Ligand Drug Conjugate compound of Formula 1 obviates the need for a preexisting handle on the compound or introducing a handle into the compound for that purpose, the latter of which could negatively impact the biological activity of the released parent NAMPT compound so modified.

BRIEF DESCRIPTION OF THE DRAWINGS

The FIGURE shows variation over time (days) in tumor volume (mm3) in a L540cy xenograft model post tumor implant in untreated SCID mice in comparison to those treated with 1 mg/Kg (i.p.) Antibody Drug Conjugates (8 quaternized NAMPT Drug Units/Ab) prepared from chimeric antibody cACIO, which targets Ag2 (CD30) expressed by the implanted tumor cells of the xenograft model, prepared from Drug Linker compounds 5, 12 and 26.

DETAILED DESCRIPTION OF THE INVENTION

Definitions

As used herein and unless otherwise stated or implied by context, terms that are used herein have the meanings defined below. Unless otherwise contraindicated or implied, e.g., by including mutually exclusive elements or options, in those definitions and throughout this specification, the terms "a" and "an" mean one or more and the term "or" means "and/or" where permitted by context. Thus, as used in the specification and the appended claims, the singular forms "a," "an" and "the" include plural referents unless the context clearly dictates otherwise.

At various locations in the present disclosure, e.g., in any disclosed embodiments or in the claims, reference is made to compounds, compositions, or methods that "comprise" one or more specified components, elements or steps. Invention embodiments also specifically include those compounds, compositions, compositions or methods that are, or that consist of, or that consist essentially of those specified components, elements or steps. The term "comprised of" is used interchangeably with the term "comprising" and are to be interpreted as equivalent terms. For example, disclosed compositions, devices, articles of manufacture or methods that "comprise" a component or step are open and they include or read on those compositions or methods plus an additional component(s) or step(s). However, those terms do not encompass unrecited elements that would destroy the functionality of the disclosed compositions, devices, articles of manufacture or methods for its intended purpose. Similarly, disclosed compositions, devices, articles of manufacture or methods that "consist of" a component or step are closed and they would not include or read on those compositions or methods having appreciable amounts of an additional component(s) or an additional step(s). Furthermore, the term "consisting essentially of" admits for the inclusion of unrecited elements that have negligible or no material effect on the functionality of the disclosed compositions, devices, articles of manufacture or methods for its intended purpose as further defined herein. The section headings used herein are for organizational purposes only and are not to be construed as limiting the subject matter described. Unless otherwise indicated, conventional methods of mass spectroscopy, NMR, HPLC, protein chemistry, biochemistry, recombinant DNA techniques and pharmacology are employed.

"About" as used herein when used in connection with a numeric value or range of values, which are provided to describe a particular property of a compound or composition, indicate that the value or range of values may deviate to an extent deemed reasonable to one of ordinary skill in the art while still describing the particular property. Reasonable deviations include those that are within the accuracy or precision of the instrument(s) used in measuring, determining or deriving the particular property. Specifically, the term "about" when used in this context, indicate that the numeric value or range of values can vary by 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1% or 0.01% of the recited value or range of values, typically by 10% to 0.5%, more typically by 5% to 1%, while still describing the particular property.

When used as a modifier to subscript p in formulae of Ligand Drug Conjugates, defined herein as indicating the average number of quaternized Drug Units or quaternized drug linker moieties in a distribution of Ligand Drug Conjugate compounds in a Ligand Drug Conjugate composition, the term "about" represents the variations in drug loading typically expected in the art for the preparation of these compositions. In one example, when conjugation is to cysteine residues from reduced interchain disulfide bonds of an antibody, which provides eight potential sites of conjugation, and a desired drug loading of 4 is desired, compositions will often be obtained having minor amounts of higher loaded and lower loaded Conjugate compound species, with the later sometimes including unconjugated antibody. In that instance compositions may be obtained characterized by subscript p ranging from 3.5 to 4.4, or from 3.6 to 4.3, or from 3.8 to 4.2. In another example when all eight cysteine residues from interchain disulfide bond reduction are to be conjugated by using an excess of Drug Linker compound then Ligand Drug Conjugate compositions are typically obtained that can only have minor amounts of lower loaded Conjugate compound species in which only a negligible amount of unconjugated antibody is present. In that instance Conjugate compositions may be obtained characterized by subscript p ranging from 7.5 to 8, from 7.6 to 8, from 7.7 to 8, from 7.8 to 8 or from 7.9 to 8.

"Essentially retains", "essentially retaining" and like terms as used herein refers to a property, characteristic, function or activity of a compound or composition or moiety thereof that has not detectably changed or is within experimental error of determination of that same activity, characteristic or property of a compound or composition or moiety of related structure.

"Substantially retains", "substantially retaining" and like terms as used herein refers to a measured value of a physical property or characteristic of a compound or composition or moiety thereof that may be statistically different from the determination of that same physical property of another compound or composition or moiety of related structure, but which such difference does not translate to a statistically significant or meaningful difference in biological activity or pharmacological property in a suitable biological test system for evaluating that activity or property (i.e., biological activity or property is essentially retained). Thus the phrase "substantially retains" is made in reference to the effect that a physical property or characteristic of a compound or composition has on a physiochemical or pharmacological property or biological activity that is explicitly associated with that physical property or characteristic.

"Negligibly" or "negligible" as used herein is an amount of an impurity below the level of quantification by HPLC analysis and if present represents from about 0.5% to about 0.1 w/w % or less of the composition that it contaminates. Depending on context those terms may alternatively mean that no statistically significant difference is observed between measured values or outcomes or are within experimental error of the instrumentation used to obtain those values. Negligible differences in values of a parameter determined experimentally do not imply that an impurity characterized by that parameter is present in negligible amount. Likewise, a negligible outcome due to the presence of an impurity does not imply that the impurity is present in negligible amount.

"Predominately containing", "predominately having" and like terms as used herein refers to the major component of a mixture. When the mixture is of two components, then the major component represents more than 50% by weight of the mixture. With a mixture of three or more components the predominant component is the one present in greatest amount in the mixture and may or may not represent a majority of the mass of the mixture.

"Electron-withdrawing group" as the term is used herein refers to a functional group or electronegative atom that draws electron density away from an atom to which it is bonded either inductively and/or through resonance, whichever is more dominant (i.e., a functional group or atom may be electron donating through resonance but may overall be electron withdrawing inductively), and tends to stabilize anions or electron rich moieties. The electron withdrawing effect is typically transmitted inductively, albeit in attenuated form, to other atoms attached to the bonded atom that has been made electron deficient by the electron withdrawing group (EWG) thus increasing the electrophilicity or decreasing the nucleophilicity of a more remote reactive center.

An electron withdrawing group is typically selected from the group consisting of —C(=O)$R^{op}$, —CN, —NO$_2$, —CX$_3$, —X, —C(=O)OR', —C(=O)NH$_2$, —C(=O)N(R')$R^{op}$, —C(=O)R', —C(=O)X, —S(=O)$_2R^{op}$, —S(=O)$_2$OR', —SO$_3$H$_2$, —S(=O)$_2$NH$_2$, —S(=O)$_2$N(R')RP, —PO$_3$H$_2$, —P(=O)(OR')(O$R^{op}$)$_2$, —NO, —NH$_2$, —N(R')($R^{op}$), —N($R^{op}$)$_{3+}$, and salts thereof, wherein X is —F, —Br, —Cl, or —I, and wherein R' is hydrogen or $R^{op}$, wherein $R^{op}$ is selected from a grouping as described elsewhere for optional substituents, and in some aspects are independently selected from the group consisting of C$_1$-C$_{12}$ alkyl, C$_1$-C$_8$ alkyl, C$_1$-C$_6$ alkyl C$_1$-C$_4$ alkyl, C$_5$-C$_{24}$ heteroaryls, C$_5$-C$_{10}$ heteroaryls, C$_5$-C$_6$ heteroaryl, C$_6$-C$_{24}$ aryls and C$_6$-C$_{10}$ aryls and in other aspects are independently selected from the group consisting of C$_1$-C$_6$ alkyl and phenyl. An EWG can also be an aryl (e.g., phenyl) or heteroaryl depending on its substitution and certain electron deficient heteroaryl groups (e.g., pyridine). Thus, in some aspects an "electron withdrawing group" further encompasses electron deficient C$_5$-C$_{24}$ heteroaryls, and C$_6$-C$_{24}$ aryls that are further substituted with electron withdrawing substituents. More typically, an electron withdrawing group is selected from the group consisting of —C(=O)$R^{op}$, —CN, —NO$_2$, —CX$_3$, and —X, wherein X is halogen, independently selected typically from the group consisting of —F and —C$_1$ and $R^{op}$ is C$_1$-C$_6$ alkyl or phenyl. Depending on its substituents, an optionally substituted alkyl moiety may also be an electron withdrawing group and thus in such cases aspects would be encompassed by the term for an electron withdrawing group.

"Electron donating group" as the term is used herein refers to a functional group or electropositive atom that increases electron density of an atom to which it is bonded either inductively and/or through resonance, whichever is more dominant (i.e., a functional group or atom may be electron withdrawing inductively but may overall be electron donating through resonance), and tends to stabilize cations or electron poor systems. The electron donating effect is typically transmitted through resonance to other atoms attached to the bonded atom that has been made electron rich by the electron donating group (EDG) thus increasing the nucleophilicity or decreasing the electrophilicity of a more remote reactive center. Typically, an electron donating group is selected from the group consisting of —OH, —OR', —NH$_2$, —NHR' and N(R')$_2$, wherein each R' is hydrogen or $R^{op}$ wherein $R^{op}$ are independently selected C$_1$-C$_{12}$ alkyl, typically C$_1$-C$_6$ alkyl. Depending on their substituents, a C$_6$-C$_{24}$ aryl, C$_5$-C$_{24}$ heteroaryl or unsaturated C$_3$-C$_{12}$ alkyl moiety may also be an electron donating group, and in some aspects such moieties are encompassed by the term for an electron donating group.

"Moiety" as used herein means a specified segment, fragment or functional group of a molecule or compound. Chemical moieties are sometimes indicated as chemical entities that are embedded in or appended to (i.e., a substituent or variable group of) a molecule, compound or chemical formula.

Unless indicated otherwise, for any substituent group or moiety described herein by a given range of carbon atoms, the designated range means that any individual number of carbon atoms is described. Thus, reference to, e.g., "optionally substituted C$_1$-C$_4$ alkyl" or "optionally substituted C$_2$-C$_6$ alkenyl" specifically means that a 1, 2, 3 or 4 carbon alkyl moiety, optionally substituted, as defined herein, is present, or a 2, 3, 4, 5 or 6 carbon alkenyl moiety, optionally substituted, as defined herein, is present. All such numerical designations are expressly intended to disclose all of the individual carbon atom groups; and thus "optionally substituted $C_1$-$C_4$ alkyl" includes, methyl, ethyl, 3 carbon alkyls, and 4 carbon alkyls, including all of their positional isomers, whether substituted or unsubstituted. Thus, when an alkyl moiety is substituted, the numerical designations refer to an unsubstituted base moiety and are not intended to include alkyl carbon atoms not directly attached to the base moiety that may be present in the substituents of that base moiety. For esters, carbonates, carbamates and ureas as defined herein that are identified by a given range of carbon atoms, the designated range includes the carbonyl carbon of the respective functional group. Thus, a $C_1$ ester refers to a formate ester and a $C_2$ ester refers to an acetate ester.

The organic substituents, moieties and groups described herein, and for other any other moieties described herein, usually will exclude unstable moieties except where such unstable moieties are transient species that one can use to make a compound with sufficient chemical stability for the one or more of the uses described herein. Substituents, moieties or groups by operation of the definitions provided herein that results in those having a pentavalent carbon are specifically excluded.

"Alkyl" as used herein, by itself or as part of another term, unless otherwise stated or implied by context, refers to methyl or a collection of contiguous carbon atoms, one of which is monovalent, wherein one or more of the carbon atoms are saturated (i.e., is comprised of one or more $sp^3$ carbons) and are covalently linked together in normal, secondary, tertiary or cyclic arrangements, i.e., in a linear, branched, cyclic arrangement or some combination thereof. When the contiguous saturated carbon atoms are in a cyclic arrangement such alkyl moieties are, in some aspects, referred to as carbocyclyls as further defined herein.

When referring to an alkyl moiety as a substituent to a Markush structure or another organic moiety, the alkyl is singly bonded to the Markush structure or other organic moiety with which it is associated through a $sp^3$ carbon of the alkyl substituent. An alkyl substituent, as used herein, therefore contains at least one saturated moiety and may also contain one or more unsaturated moieties or groups. Thus, an alkyl substituent may additionally contain one, two, three or more, typically 1, 2 or 3, more typically 1 or 2 independently selected double and/or triple bonds to define an unsaturated alkyl substituent, and may be substituted (i.e., optionally substituted) by other moieties as defined herein for optional substituents excluding alkyl, arylalkyl, heteroarylalkyl, alkenyl and alkynyl. A saturated, unsubstituted alkyl substituent contains saturated carbon atoms (i.e., $sp^3$ carbons) and no $sp^2$ or sp carbon atoms. An unsaturated alkyl substituent contains at least one saturated $sp^3$ carbon atom that is monovalent for its site of attachment to the Markush structure or other organic moiety with which it is associated and at least two $sp^2$ or sp carbon atoms that are in conjugation with each other.

Unless otherwise indicated or implied by context, the term "alkyl" will indicate a saturated, non-cyclic hydrocarbon radical, wherein the hydrocarbon radical is methyl or has the indicated number of covalently linked saturated carbon atoms, e.g., "$C_1$-$C_6$ alkyl" or "C1-C6 alkyl" means a saturated alkyl moiety or group containing 1 saturated carbon atom (i.e., is methyl) or 2, 3, 4, 5 or 6 contiguous, non-cyclic saturated carbon atoms and "$C_1$-$C_8$ alkyl" refers to a saturated alkyl moiety or group having 1 saturated carbon atom or 2, 3, 4, 5, 6, 7 or 8 contiguous saturated, non-cyclic carbon atoms. The number of saturated carbon atoms in an alkyl moiety or group, unless otherwise specified, ranges from 1 to 50, 1 to 30, typically from 1 to 20, or 1 to 12, and more typically from 1 to 8, 1 to 6 or 1 to 4. In some aspects, alkyl refers to a saturated a $C_1$-$C_8$ alkyl, and in other aspects is a saturated $C_1$-$C_6$ or a saturated $C_1$-$C_4$ alkyl moiety, with the latter sometimes referred to as lower alkyl. When the number of carbon atoms is not indicated, a saturated alkyl moiety, group or substituent has from 1 to 8 saturated carbon atoms and an unsaturated alkyl moiety, group or substituent has a total of 1 to 8 saturated and unsaturated non-aromatic carbon atoms in which at least one carbon atom is monovalent $sp^3$ carbon atom and is otherwise fully saturated. In some aspects, an alkyl moiety is unsubstituted and in other aspects it is substituted with 1 to 4, typically 1 to 3, or 1 or 2 independently selected moieties as defined herein, including substituents as defined herein for optional substituents, excluding alkyl, arylalkyl, heteroarylalkyl, alkenyl or alkynyl. When an alkyl moiety is unsaturated such moieties encompass saturated alkyl moieties other than methyl as described herein, but containing within the contiguous carbon chain double and/or triple bond functional group(s), typically one such functional group, and typically are unsaturated $C_3$-$C_{12}$ moieties, and more typically are unsaturated $C_3$-$C_8$ moieties or unsaturated $C_3$-$C_6$ alkyl moieties and may be unsubstituted or similarly substituted (i.e., optionally substituted) at the saturated and/or unsaturated carbon atom(s) of the unsaturated alkyl moeity.

In some aspects when an alkyl substituent, moiety or group is specified, species are those derived from removing a hydrogen atom from a parent alkane (i.e., becomes monovalent) and are exemplified by methyl, ethyl, 1-propyl (n-propyl), 2-propyl (iso-propyl, —CH(CH$_3$)$_2$), 1-butyl (n-butyl), 2-methyl-1-propyl (iso-butyl, —CH$_2$CH(CH$_3$)$_2$), 2-butyl (sec-butyl, —CH(CH$_3$)CH$_2$CH$_3$), 2-methyl-2-propyl (t-butyl, —C(CH$_3$)$_3$), amyl, isoamyl and sec-amyl and in other aspects an alkyl substituent, moiety or group are or are additionally exemplified by other linear and branch chain alkyl moieties.

"Alkylene," as used herein, by itself of as part of another term, unless otherwise stated or implied by context, refers to a saturated, branched or straight chain hydrocarbon diradical, substituted or unsubstituted, wherein one or more of the carbon atoms is saturated (i.e., is comprised of one or more $sp^3$ carbons), of the stated number of carbon atoms ranging from 1 to 50 or 1 to 30, typically 1 to 20 or 1 to 12 carbon atoms, more typically 1 to 8, 1 or 6, or 1 to 4 carbon atoms and having two radical centers (i.e., is divalent) derived by the removal of two hydrogen atoms from the same or two different saturated (i.e., $sp^3$) carbon atoms of a parent alkane. An alkylene moiety in some aspects is an alkyl radical as described herein in which a hydrogen atom has been removed from another of its saturated carbons or from the radical carbon of an alkyl radical to form a diradical. In other aspects, an alkylene moiety is or is further encompassed by a divalent moiety derived from removing a hydrogen atom from a saturated carbon atom of a parent alkyl moiety and are exemplified without limitation by methylene (—CH$_2$—), 1,2-ethylene (—CH$_2$CH$_2$—), 1,3-propylene (—CH$_2$CH$_2$CH$_2$—), 1,4-butylene (—CH$_2$CH$_2$CH$_2$CH$_2$—), and like diradicals. Typically, an alkylene is a branched or straight chain hydrocarbon containing only $sp^3$ carbons (i.e., is fully saturated notwithstanding the radical carbon atoms) and in some aspects is unsubstituted. In other aspects, an alkylene contains an internal site of unsaturation(s) in the form of one or more double and/or triple bond functional groups, typically 1 or 2, more typically 1, such functional groups so that the terminal carbons of the unsaturated alkylene moeity are monovalent $sp^3$ carbon atoms. In still other aspects, the alkylene is substituted with 1 to 4, typically 1 to 3, or 1 or 2 substituents, as defined herein for optional substituents at saturated carbon atom(s) of a saturated alkylene moiety or saturated and/or unsaturated carbon atom(s) of an unsaturated alkylene moiety. Such optional substituent exclude, arylalkyl, heteroarylalkyl, alkenyl, alkynyl and alkyl, unless that alkyl is described as comprising $A_O$, or as acomponent of a Basic Unit.

"Carbocyclyl" as used herein, by itself of as part of another term, unless otherwise stated or implied by context, refers to a radical of a monocyclic, bicyclic or tricyclic ring system, wherein each of the atoms forming the ring system (i.e., skeletal atoms) is a carbon atom and wherein one or more of these carbon atoms in each ring of the cyclic ring system is saturated (i.e., is comprised of one or more $sp^3$ carbons). Thus, a carbocyclyl is a cyclic arrangement of saturated carbons but may also contain unsaturated carbon atom(s) and therefore its carbocyclic ring may be saturated or partially unsaturated or may be fused with an aromatic ring system, wherein the points of fusion to the carbocyclic and aromatic ring systems are to adjacent carbons of each of these ring systems.

When carbocyclyl is used as a Markush group (i.e., a substituent) the carbocyclyl is attached to a Markush formula or another organic moiety with which it is associated through a carbon atom that is involved in the carbocyclic ring system of the carbocyclyl moiety provided the carbon atom is not aromatic. That carbon atom may be from a monovalent $sp^3$ carbon atom of a carbocyclic ring of a saturated or unsaturated carbocyclyl or from a $sp^2$ carbon of an unsaturated ring of an unsaturated carbocyclyl. When an unsaturated carbon of an alkene moiety comprising the carbocyclyl substituent is attached to a Markush formula with which it is associated that carbocyclyl is sometimes referred to as a cycloalkenyl substituent. The number of carbon atoms in a carbocyclyl moiety group or substituent is defined by the total number of skeletal carbon atoms of its carbocyclic ring system. That number, unless specified otherwise, ranges from 3 to 50 or 3 to 30, typically from 3 to 20 or 3 to 12, more typically from 3 to 8 or 3 to 6 skeletal carbon atoms, e.g., $C_3$-$C_8$ carbocyclyl means an carbocyclyl substituent, moiety or group containing 3, 4, 5, 6, 7 or 8 carbocyclic carbon atoms and $C_3$-$C_6$ carbocyclyl means an carbocyclyl substituent, moiety or group containing 3, 4, 5 or 6 carbocyclic carbon atoms. A carbocyclyl in some aspects is unsubstituted and in other aspects is derived by the removal of one hydrogen atom from a skeletal ring atom of a parent cycloalkane or cycloalkene. Representative $C_3$-$C_8$ carbocyclyls are cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, and cyclooctadienyl.

Therefore, carbocyclyl substituents, moieties or groups typically have 3, 4, 5, 6, 7, 8 carbon atoms in its carbocyclic ring system and may contain exo or endo-cyclic double bonds or endo-cyclic triple bonds or a combination of both wherein the endo-cyclic double or triple bonds, or the combination of both, do not form a cyclic conjugated system of 4n+2 electrons. A bicyclic ring system may share two carbon atoms and a tricyclic ring system may share a total of 3 or 4 carbon atoms. In some aspects, a carbocyclyl is a $C_3$-$C_8$ or $C_3$-$C_6$ carbocyclyl that may be substituted (i.e. optionally substituted) with one or more or 1 to 4, typically 1 to 3, or 1 or 2 moieties described herein for alkyl, alkenyl, alkynyl, aryl, arylalkyl, and alkylaryl and/or with other moieties as including substituent(s) as defined herein for optional substituents, and in some aspects is unsubstituted.

In other aspects, a cycloalkyl moiety, group or substituent is a $C_3$-$C_6$ cycloalkyl selected from the group consisting of cyclopropyl, cyclopentyl and cyclohexyl, or is a $C_3$-$C_8$ cycloalkyl that encompasses that group and is further encompasses other cyclic moieties that have no more than 8 carbon atoms in their cyclic ring systems. When the number of carbon atoms is not indicated, a carbocyclyl moiety, group or substituent has from 3 to 8 carbon atoms in its carboxcylic ring system and therefore is a $C_3$-$C_8$ cycloalkyl.

"Carbocyclo," by itself or as part of another term, unless otherwise stated or implied by context, refers to an optionally substituted carbocyclyl as defined above wherein another hydrogen atom of its cycloalkyl ring system has been removed (i.e., it is divalent) and is, unless otherwise specified, a $C_3$-$C_{50}$ or $C_3$-$C_{30}$ carbocyclo, typically a $C_3$-$C_{20}$ or $C_3$-$C_{12}$ carbocyclo, more typically a $C_3$-$C_8$ or $C_3$-$C_6$ carbocyclo and in some aspects is unsubstituted. When the number of carbon atoms is not indicated, a carbocyclo moiety, group or substituent has from 3 to 8 carbon atoms in its carboxcylic ring system and therefore is a $C_3$-$C_8$ carbocyclo. In some aspects that other hydrogen atom is removed from the monovalent carbon atom of the cycloalkyl to form a divalent carbon atom. In those aspects, a carbocyclo moiety, group or substituent is a $C_3$-$C_6$ carbocyclo in the form of a spiro ring system and is selected from the group consisting of cycloprop-1,1-diyl, cyclobutyl-1,1-diyl, cyclopent-1,1-diyl and cyclohex-1,1-diyl, or is a $C_3$-$C_8$ carbocyclo, encompassing that group and is further encompassed by other divalent cyclic moieties that have no more than 8 carbon atoms in their cyclic ring systems. A carbocyclo may be a saturated or an unsaturated carbocyclo, and/or may be unsubstituted or unsubstituted in the same manner as described for a carbocyclyl moeity. If unsaturated, one or both monovalent carbon atoms of the carbocyclo moiety may be $sp^2$ carbon atoms from the same or a different double bond functional group or both monovalent carbon atoms may be $sp^3$ carbon atoms.

"Alkenyl" as the terms are used herein, by itself or as part of another term, unless otherwise stated or implied by context, refers to an organic moiety, substituent or group that comprises one or more double bond functional groups (e.g., a —CH═CH— moiety) or 1, 2, 3, 4, 5 or 6 or more, typically 1, 2 or 3 of such functional groups, more typically one such functional group, and in some aspects may be substituted (i.e., is optionally substituted) with an aryl moiety or group such as phenyl, or may contain non-aromatic linked normal, secondary, tertiary or cyclic carbon atoms, i.e., linear, branched, cyclic or any combination thereof as part of the base moeity unless the alkenyl substituent, moiety or group is a vinyl moiety (e.g., a —CH═CH₂ moiety). An alkenyl moiety, group or substituent having multiple double bonds may have the double bonds arranged contiguously (i.e., a 1,3-butadienyl moiety) or non-contiguously with one or more intervening saturated carbon atoms or a combination thereof, provided that a cyclic, contiguous arrangement of double bonds do not form a cyclic conjugated system of 4n+2 electrons (i.e., is not aromatic).

An alkenyl moiety, group or substituent contains at least one $sp^2$ carbon atom in which that carbon atom is divalent and is doubly bonded to another organic moiety or Markush structure to which it is associated, or contains at least two $sp^2$ carbon atoms in conjugation to each other in which one of the $sp^2$ carbon atoms is monovalent and is singly bonded to another organic moiety or Markush structure to which it is associated. Typically, when alkenyl is used as a Markush group (i.e., is a substituent) the alkenyl is singly bonded to a Markush formula or another organic moiety with which it is associated through a sp² carbon of one of its alkene functional groups. In some aspects when an alkenyl moiety is specified, species encompasses those corresponding to any of the optionally substituted alkyl or carbocyclyl, groups moieties or substituents described herein that has one or more endo double bonds in which a sp² carbon atom thereof is monovalent and monovalent moieties derived from removal of a hydrogen atom from a sp² carbon of a parent alkene compound. Such monovalent moieties are exemplified without limitation by vinyl (—CH=CH$_2$), allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, and cyclohexenyl. In some aspects, the term alkenyl encompasses those and/or other linear, cyclic and branched chained, all carbon-containing moieties containing at least one double bond functional group in which one of the sp² carbon atoms is monovalent.

The number of carbon atoms in an alkenyl moiety is defined by the number of sp² carbon atoms of the alkene functional group that defines it as an alkenyl substituent and the total number of contiguous non-aromatic carbon atoms appended to each of these sp² carbons not including any carbon atom of the other moiety or Markush structure for which the alkenyl moiety is a variable group and from any optional substituent to the alkenyl moiety. That number ranges from 1 to 50 or 1 to 30, typically 1 to 20 or 1 to 12, more typically, 1 to 8, 1 to 6 or 1 to 4 carbon atoms when the double bond functional group is doubly bonded to a Markush structure (e.g. =CH$_2$), or ranges from 2 to 50, typically 2 to 30, 2 to 20 or 2 to 12, more typically 2 to 8, 2 to 6 or 2 to 4 carbon atoms, when the double bond functional group is singly bonded to the Markush structure (e.g., —CH=CH$_2$). For example, C$_2$-C$_8$ alkenyl or C2-C8 alkenyl means an alkenyl moiety containing 2, 3, 4, 5, 6, 7 or 8 carbon atoms in which at least two are sp² carbon atoms in conjugation with each other with one of these carbon atoms being monovalent, and C$_2$-C$_6$ alkenyl or C2-C6 alkenyl means an alkenyl moiety containing 2, 3, 4, 5 or 6 carbon atoms in which at least two are sp² carbons that are in conjugation with each other with one of these carbon atoms being monovalent. In some aspects, an alkenyl substituent or group is a C$_2$-C$_6$ or C$_2$-C$_4$ alkenyl moiety having two sp² carbons that are in conjugation with each other with one of these carbon atoms being monovalent, and in other aspects that alkenyl moiety is unsubstituted or is substituted with 1 to 4 or more, typically 1 to 3, more typically 1 or 2, independently selected substituents as defined herein for optional substituents, excluding alkyl, arylalkyl, heteroarylalkyl, alkenyl and alkynyl. When the number of carbon atoms is not indicated, an alkenyl moiety, group or substituent has from 2 to 8 carbon atoms.

"Alkenylene" as used herein, by itself of as part of another term, unless otherwise stated or implied by context, refers to an organic moiety, substituent or group that comprises one or more double bond moieties, as previously described for alkenyl, of the stated number of carbon atoms and has two radical centers derived by the removal of two hydrogen atoms from the same or two different sp² carbon atoms of an alkene functional group, or from two sp² carbon atoms from two different alkene functional groups, in a parent alkene. In some aspects, an alkenylene moiety is that of an alkenyl radical as described herein in which a hydrogen atom has been removed from the same or different sp² carbon atom of a double bond functional group of the alkenyl radical, or from a sp² carbon from a different double bonded functional group to provide a diradical. Typically, alkenylene moieties encompass diradicals containing the structure of —C=C— or —C=C—X$^1$—C=C— wherein X$^1$ is absent or is an optionally substituted saturated alkylene as defined herein, which is typically a C$_1$-C$_6$ alkylene, which is more typically unsubstituted. The number of carbon atoms in an alkenylene moiety is defined by the number of sp² carbon atoms of its alkene functional group(s) that defines it as an alkenylene moiety and the total number of contiguous non-aromatic carbon atoms appended to each of its sp² carbons not including any carbon atoms of the other moiety or Markush structure in which the alkenyl moiety is a present as a variable group. That number, unless otherwise specified, ranges from 2 to 50 or 2 to 30, typically from 2 to 20 or 2 to 12, more typically from 2 to 8, 2 to 6 or 2 to 4 carbon atoms. For example, C$_2$-C$_8$ alkenylene or C2-C8 alkenylene means an alkenylene moiety containing 2, 3, 4, 5, 6, 7 or 8 carbon atoms, in which at least two are sp² carbons in which one is divalent or both are monovalent, that are in conjugation with each other and C$_2$-C$_6$ alkenylene or C2-C6 alkenylene means an alkenyl moiety containing 2, 3, 4, 5 or 6 carbon atoms in which at least two are sp² carbons, in which at least two are sp² carbons in which one is divalent or both are monovalent, that are in conjugation with each other. In some aspects, an alkenylene moiety is a C$_2$-C$_6$ or C$_2$-C$_4$ alkenylene having two sp² carbons that are in conjugation with each other in which both sp² carbon atoms are monovalent, and in some aspects is unsubstituted. When the number of carbon atoms is not indicated, an alkenylene moiety has from 2 to 8 carbon atoms and is unsubstituted or substituted in the same manner described for an alkenyl moiety.

"Aryl" as the terms are used herein, by itself or as part of another term, unless otherwise stated or implied by context, refers to an organic moiety, substituent or group having an aromatic or fused aromatic ring system with no ring heteroatoms comprising or consisting of 1, 2, 3 or 4 to 6 aromatic rings each of which are independently optionally substituted, typically consisting of 1 to 3 aromatic rings, more typically 1 or 2 aromatic rings each of which are independently optionally substituted, wherein the rings are composed of only carbon atoms that participate in a cyclically conjugated system of 4n+2 electrons (Hückel rule), typically 6, 10 or 14 electrons, some of which may additionally participate in exocyclic conjugation with a heteroatom (cross-conjugated, e.g., quinone). Aryl substituents, moieties or groups are typically formed by six, eight, ten or more contiguous aromatic carbon atoms up to 24 to include C$_6$-C$_{24}$ aryl and in some aspects is a C$_6$-C$_{20}$ or C$_6$-C$_{12}$ aryl. Aryl substituents, moieties or groups are optionally substituted and in some aspects are unsubstituted or are substituted with 1, 2, 3 or more, typically 1 or 2, independently selected substituents as defined herein for alkyl, alkenyl, alkynyl or other moiety described herein, including another aryl or a heteroaryl to form a biaryl and optional substituents as defined herein. In other aspects, aryls are C$_6$-C$_{10}$ aryls such as phenyl and naphthalenyl and phenanthryl. As aromaticity in a neutral aryl moiety requires an even number or electrons, it will be understood that a given range for that moiety will not encompass species with an odd number of aromatic carbons. When aryl is used as a Markush group (i.e., a substituent) the aryl is attached to a Markush formula or another organic moiety with which it is associated through an aromatic carbon of the aryl group.

"Heterocyclyl" as the terms is used herein, by itself or as part of another term, unless otherwise stated or implied by context, refers to a carbocyclyl in which one or more, but not all of the skeletal carbon atoms with their attached hydrogen atoms within the carbocyclic ring system are replaced by independently selected heteroatoms or heteroatom moieties, optionally substituted where permitted, including without limitation N/NH, O, S, Se, B, Si and P, wherein two or more heteroatoms or heteroatom moieties, typically 2, may be adjacent to each other or separated by one or more carbon atoms within the same ring system, typically by 1 to 3 carbon atoms. Those heteroatoms or heteroatom moieties typically are N/NH, O and S. A heterocyclyl typically contains a monovalent skeletal carbon atom or a monovalent heteroatom or heteroatom moeity and has a total of one to ten heteroatoms and/or heteroatom moieties, typically a total of 1 to 5, or more typically a total of 1 to 3, or 1 or 2, provided that not all of the skeletal atoms in any one of the heterocyclic ring(s) in the heterocyclyl are heteroatoms and/or heteroatom moieties (i.e., at least one carbon atom has not been replaced in each cyclic ring and with at least one carbon having been replaced in one of the cyclic rings), wherein each heteroatom or heteroatom moiety in the ring(s), optionally substituted where permitted, is independently selected from the group consisting of N/NH, O and S, with the proviso that any one ring does not contain two adjacent O or S atoms. Exemplary heterocyclyls and heteroaryls are collectively referred to as heterocycles, are provided by Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* 1960, 82:5545-5473 particularly 5566-5573).

When heterocyclyl is used as a Markush group (i.e., as a substituent), a saturated or partially unsaturated heterocyclic ring of the heterocyclyl is attached to a Markush structure or other moiety with which it is associated through a carbon atom or a heteroatom of that heterocyclic ring, where such attachment does not result in an unstable or disallowed formal oxidation state of that carbon or heteroatom. A heterocyclyl in that context is a monovalent moiety in which a heterocyclic ring of the heterocyclic ring system defining it as a heterocyclyl is non-aromatic, but may be fused with a carbocyclic, aryl or heteroaryl ring and includes phenyl- (i.e., benzo) fused heterocyclic moieties.

In some aspects, a heterocyclyl is a $C_3$-$C_{50}$ or $C_3$-$C_{30}$ carbocyclyl, typically a $C_3$-$C_{20}$ or $C_3$-$C_{12}$ carbocyclyl, more typically a $C_3$-$C_8$ or $C_3$-$C_6$ carbocyclyl wherein 1, 2 or 3 or more, but not all of its carbons of its cycloalkyl ring system are replaced along with its attached hydrogens, typically 1, 2, 3 or 4, more typically 1 or 2, are replaced, with a heteroatom or heteroatom moiety independently selected from the group consisting of N/NH, 0 and S, optionally substituted where permitted, and thus is a $C_3$-$C_{50}$ or $C_3$-$C_{30}$ heterocyclyl, typically a $C_3$-$C_{20}$ or $C_3$-$C_{12}$ heterocyclyl, more typically a $C_3$-$C_6$, or $C_5$-$C_6$ heterocyclyl, in which the subscript indicates the total number of skeletal atoms (inclusive of its carbon atoms and heteroatoms) of the heterocyclic ring system(s) of the heterocyclyl with the proviso that any one ring does not contain two adjacent O or S atom. In those aspects, a heterocyclyl typically contains 0 to 2 N, 0 to 2 O or 0 to 1 S skeletal heteroatoms, optionally substituted or some combination thereof provided at least one of said heteroatoms is present in a heterocyclic ring system of the heterocyclyl. A heterocyclyl may be saturated or partially unsaturated and/or unsubstituted or substituted at a skeletal carbon atom with an oxo (=O) moiety, as in pyrrolidin-2-one, and/or at a skeletal heteroatom substituted with one or two oxo moieties so as to contain an oxidized heteroatom as exemplified, but not limited to, —N(=O), —S(=O)— or —S(=O)$_2$—. A saturated or unsaturated heterocyclyl may be substituted or further substituted with an alkyl, (hetero) arylalkyl, alkenyl, alkynyl or other moiety as described herein including optional substituents as defined herein or a combination of 2, 3 or more, typically 1 or 2, such substituents. In certain aspects, heterocyclyl is selected from the group consisting of pyrrolidinyl, piperidinyl, morpholinyl and piperazinyl.

"Heteroaryl" as the term is used herein, by itself or as part of another term, unless otherwise stated or implied by context, refers to an aryl moiety, group or substituent as defined herein in which one or more but not all of the aromatic carbons of an aromatic ring system of an aryl is replaced by a heteroatom. A heteroaryl typically contains a total one to four skeletal heteroatoms in the ring(s) of the heteroaryl ring system, provided that not all of the skeletal atoms of any one ring system in the heteroaryl are heteroatoms, which are optionally substituted where permitted, and have 0 to 3 N, 1 to 3 N or 0 to 3 N skeletal heteroatoms, typically 0 to 1 O and/or 0 to 1 S skeletal heteroatoms, provided that at least one skeletal heteroatom is present. A heteroaryl may be monocyclic, bicyclic or polycyclic. A polycyclic heteroaryl is typically a $C_5$-$C_{50}$ or $C_5$-$C_{30}$ heteroaryl, more typically a $C_5$-$C_{20}$ or $C_5$-$C_{12}$ heteroaryl, a bicyclic heteroaryl is typically a $C_5$-$C_{10}$ heteroaryl, and a monocyclic heteroaryl is a typically is $C_5$-$C_6$ heteroaryl, in which the subscript indicates the total number of skeletal atoms (inclusive of its carbon atoms and heteroatoms) of the aromatic ring system(s) of the heteroaryl. In some aspects, a heteroaryl is a bicyclic aryl moiety wherein one 1, 2, 3, 4 or more, typically 1, 2 or 3, of the carbon atoms of the aromatic ring(s) and their attached hydrogen atoms of a parent bicyclic aryl moiety are replaced by an independently selected heteroatom or heteroatom moiety, or is a monocyclic aryl moiety wherein one 1, 2, 3 or more, typically 1 or 2, of the carbon atoms of the aromatic ring(s) and their attached hydrogen atoms of a parent monocyclic aryl moiety are replaced by an independently selected heteroatom or heteroatom moeity, wherein the heteroatom or heteroatom moiety is optionally substituted where permitted, including N/NH, O and S, provided that not all of the skeletal atoms of any one aromatic ring system in the parent aryl moiety are replaced by heteroatoms and more typically are replaced by oxygen (—O—), sulfur (—S—) nitrogen (=N—) or —NR—, so that the nitrogen heteroatom is optionally substituted, wherein R is —H, a nitrogen protecting group or optionally substituted $C_1$-$C_{20}$ alkyl or is an optionally substituted $C_6$-$C_{24}$ aryl or $C_5$-$C_{24}$ heteroaryl to form a heterobiaryl. In other aspects, 1, 2 or 3 of the carbon atoms of the aromatic ring(s) and their attached hydrogen atoms of a parent aryl moiety are replaced by nitrogen substituted with another organic moiety in a manner which retains the cyclic conjugated system. In still other aspects, the aromatic carbon radical of a parent aryl moeity is replaced with an aromatic nitrogen radical. In either of those aspects, the nitrogen, sulfur or oxygen heteroatom participates in the conjugated system either through pi-bonding with an adjacent atom in the ring system or through a lone pair of electrons on the heteroatom. In still other aspects, a heteroaryl has the structure of a heterocyclyl as defined herein in which a heterocyclic ring system has been aromatized.

Typically, a heteroaryl is monocyclic, which in some aspects is a 5-membered or 6-membered heteroaromatic ring system. A 5-membered heteroaryl is a monocyclic $C_5$-heteroaryl containing 1 to 4 aromatic carbon atoms and the requisite number of aromatic heteroatoms within its heteroaromatic ring system. A 6-membered heteroaryl is a monocyclic C₆ heteroaryl containing 1 to 5 aromatic carbon atoms and the requisite number of aromatic heteroatoms within its heteroaromatic ring system. Heteroaryls that are 5-membered have four, three, two or one aromatic heteroatom(s), and heteroaryls that are 6-membered include heteroaryls having five, four, three, two or one aromatic heteroatom(s). C₅-heteroaryls are monovalent moieties derived from removing a hydrogen atom from a skeletal aromatic carbon or an electron from a skeletal aromatic heteroatom, where permitted, from a parent aromatic heterocycle compound, which is some aspects is selected from the group consisting of pyrrole, furan, thiophene, oxazole, isoxazole, thiazole, isothiazole, imidazole, pyrazole, triazole and tetrazole. C₆ heteroaryls, which are 6-membered, are monovalent moieties derived from removing a hydrogen atom from an aromatic carbon or an electron from an aromatic heteroatom, where permitted, from a parent aromatic heterocycle compound, which is certain aspects is selected from the group consisting of pyridine, pyridazine, pyrimidine, and triazine. A heteroaryl may be substituted or further substituted with an alkyl, (hetero)arylalkyl, alkenyl or alkynyl or aryl or another heteroaryl to form a heterobiaryl or other moiety as described herein including optional substituents as defined herein or a combination of 2, 3 or more, typically 1 or 2, such substituents.

"Heterocyclo", as the term is used herein, by itself or as part of another term, unless otherwise stated or implied by context, refers to a heterocyclyl moiety, group or substituent as defined above wherein a hydrogen atom or an electron, where permitted, from a different carbon atom or an electron from a nitrogen ring atom not already in radical form, if present, is removed to provide a divalent moiety.

"Arylalkyl" or "heteroarylalkyl" as the terms are used herein, by itself or as part of another term, refers to an aryl or heteroaryl moiety bonded to an alkyl moiety, i.e., (aryl)-alkyl-, where alkyl and aryl groups are as described above. Typically, an arylalkyl is a (C₆-C₂₄ aryl)-C₁-C₂₀ alkyl-moiety, group or substituent, and heteroarylalkyl is a (C₅-C₂₄ heteroaryl)-C₁-C₂₀ alkyl-moiety, group or substituent. When (hetero)arylalkyl is used as a Markush group (i.e., a substituent) the alkyl moiety of the (hetero)arylalkyl is attached to a Markush formula with which it is associated through a sp³ carbon of its alkyl moiety. In some aspects, an arylalkyl is a (C₆-C₂₄ aryl)-C₁-C₁₂ alkyl- or a (C₆-C₂₀ aryl)-C₁-C₁₂ alkyl-, typically a (C₆-C₁₂ aryl)-C₁-C₁₂ alkyl- or (C₆-C₁₀ aryl)-C₁-C₁₂ alkyl-, more typically a (C₆-C₁₀ aryl)-C₁-C₆ alkyl-exemplified without limitation, by C₆H₅—CH₂—, C₆H₅—CH(CH₃)CH₂— and C₆H₅—CH₂—CH(CH₂CH₂CH₃)—. An (hetero)arylalkyl may be unsubstituted or substituted in the same manner as described for (hetero)aryl and alkyl moieties.

"Arylene," or "heteroarylene" as used herein, by itself or as part of another term, unless otherwise stated or implied by context, is an aromatic or heteroaromatic diradical moiety that forms two covalent bonds (i.e., it is divalent) within another organic moiety, for which the bonds are in the ortho, meta, or para configuration. Arylene and some heteroarylenes include divalent species by removal of a hydrogen atom from a parent aryl or heteroaryl moiety, group or substituent as defined herein. Other heteroarylenes are divalent species in which hydrogen atoms have been removed from two different aromatic carbon atoms of a parent aromatic heterocycle to form a diradical species, or from removal of a hydrogen atom from an aromatic carbon atom or heteroatom and of another hydrogen atom or electron from different aromatic heteroatom from a parent aromatic heterocycle to form a diradical species in which one aromatic carbon atom and one aromatic heteroatom is monovalent or two different aromatic heteroatoms are each monovalent. Heteroarylene further include those in which heteroatom(s) and/or heteroatom moiety(ies) replace one or more but not all of the aromatic carbon atoms of a parent arylene.

Non-limiting exemplary arylenes, which are optionally substituted at the remaining positions, are phenyl-1,2-ene, phenyl-1,3-ene, and phenyl-1,4-ene, as shown in the following structures:

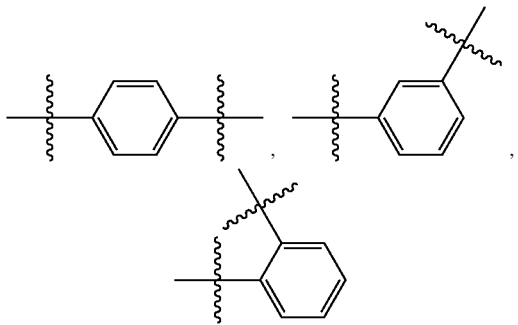

A "5-membered nitrogen-containing heteroarylene" contains at least one aromatic nitrogen atom in its heteroaromatic ring system and is divalent and is similarly related in structure to a 5-membered nitrogen-containing heteroaryl as described above. Likewise, a "6-membered nitrogen-containing heteroarylene is divalent and is similarly related in structure to a 6-membered nitrogen heteroaryl as described above.

"Heteroalkyl," as used herein by itself or in combination with another term, unless otherwise stated or implied by context, refers to an optionally substituted straight or branched chain hydrocarbon, fully saturated or containing from 1 to 3 degrees of unsaturation and having 1 to 12 carbon atom and 1 to 6 heteroatoms, typically 1 to 5 heteroatoms, more typically one or two heteroatoms or heteroatom moieties, selected from the group consisting of O, N/NH, Si and S, optionally substituted where permitted, and includes each nitrogen and sulfur atom independently optionally oxidized to an N-oxide, a sulfoxide or sulfone in which the heteroatom has been substituted with 1 or two oxo (=O) substituents, or having one or more of the nitrogen atoms optionally quaternized. The heteroatom(s) or heteroatom moiety(ies) of O, N/NH, S, and/or Si may be placed at any interior position of the heteroalkyl group or at a terminal position of the optionally substituted alkyl group of the heteroalkyl. In some aspects, the heteroalkyl is fully saturated or contains 1 degree of unsaturation and contain 1 to 6 carbon atoms and 1 to 2 heteroatoms, and in other aspects that heteroalkyl is unsubstituted. Non-limiting examples of heteroalkyls are —CH₂—CH₂—O—CH₃, —CH₂—CH₂—NH—CH₃, —CH₂—CH₂—N(CH₃)—CH₃, —CH₂—S—CH₂—CH₃, —CH₂—CH₂—S(O)—CH₃, —NH—CH₂—CH₂—NH—C(O)—CH₂—CH₃, —CH₂—CH₂—S(O)₂—CH₃, —CH=CH—O—CH₃, —Si(CH₃)₃, —CH₂—CH=N—O—CH₃, and —CH=CH—N(CH₃)—CH₃. Up to two heteroatoms may be consecutive, as exemplified by —CH₂—NH—OCH₃ and —CH₂—O—Si(CH₃)₃.

A heteroalkyl is typically denoted by the number of its contiguous heteroatom(s) and non-aromatic carbon atoms unless indicated otherwise or by context. Thus, —CH₂—CH₂—O—CH₃ and —CH₂—CH₂—S(O)—CH₃ are both $C_4$-heteroalkyls and —$CH_2$—CH=N—O—$CH_3$, and —CH=CH—N($CH_3$)—$CH_3$ are both $C_5$ heteroalkyls. A heteroalkyl may be unsubstituted or substituted (i.e., optionally substituted) at its heteroatom or heteroatom component with any one of the moieties described herein, including an optional substituent as defined herein, and/or at its alkyl component with 1 to 4 or more, typically 1 to 3 or 1 or 2 independently selected moieties as described herein, including optional substituent(s) as defined herein, excluding alkyl, (hetero)arylalkyl, alkenyl and alkynyl.

"Heteroalkylene" as used herein by itself or in combination with another term, unless otherwise stated or implied by context, means a divalent group derived from a heteroalkyl (as discussed above), by removal of a hydrogen atom or a heteroatom electron form a parent heteroalkyl to provide a divalent moeity exemplified by, but not limited to, —$CH_2$—$CH_2$—S—$CH_2$—$CH_2$— and —$CH_2$—S—$CH_2$—$CH_2$—NH—$CH_2$—. For a heteroalkylene, heteroatom(s) thereof may be interior to or may occupy either or both termini of its optionally substituted alkylene chain so that one or both of these heteroatoms are monovalent. When a heteroalkylene is a component of a Linker Unit both orientations of that component within the Linker Unit is permitted unless indicated or implied by context.

"Aminoalkyl" as used herein by itself or in combination with another term, unless otherwise stated or implied by context, refers to a moiety, group or substituent having a basic nitrogen bonded to one radical terminus of an alkylene moiety as defined above to provide a primary amine in which the basic nitrogen is not further substituted, or to provide a secondary or tertiary amine in which the basic amine is further substituted by one or two independent selected optional substituted $C_1$-$C_{12}$ alkyl moieties, respectively, as described above. In some aspects, the optionally substituted alkyl is a $C_1$-$C_8$ alkyl or $C_1$-$C_6$ alkyl and in other aspects that alkyl is unsubstituted. In still other aspects, the basic nitrogen together with its substituents defines an optionally substituted $C_3$-$C_8$ heterocyclyl containing the basic nitrogen as a skeletal atom, typically in the form of a nitrogen-containing $C_3$-$C_6$ or $C_5$-$C_6$ heterocyclyl, optionally substituted.

When aminoalkyl is used as a variable group to a Markush structure, the alkylene moiety of the aminoalkyl is attached to a Markush formula with which it is associated through a monovalent $sp^3$ carbon of that moiety, which is the other radical terminus of the aforementioned alkylene. An aminoalkyl when part of a self-stabilizing Linker Unit ($L_{SS}$) or self-stabilized Linker Unit ($L_S$) as described herein is an exemplary acyclic Basic Unit. An aminoalkyl is typically denoted by the number of contiguous carbon atoms of its alkylene moiety. Thus, a $C_1$ aminoalkyl is exemplified without limitation by —$CH_2NH_2$, —$CH_2NHCH_3$ and —$CH_2N(CH_3)_2$ and a $C_2$ amino alkyl is exemplified without limitation by —$CH_2CH_2NH_2$, —$CH_2CH_2NHCH_3$ and —$CH_2CH_2N(CH_3)_2$. In those instances in which an aminoalkyl is a substituent to alkylene moiety the carbons atoms of that alkylene moiety and the alkylene moiety of the aminoalkyl are treated separately with respect to the carbon count of each of these alkylene moieties.

"Optionally substituted alkyl", "optionally substituted alkenyl", "optionally substituted alkynyl", "optionally substituted arylalkyl", "optionally substituted heterocycle", "optionally substituted aryl", "optionally substituted heteroaryl", "optionally substituted heteroarylalkyl" and like terms refer to an alkyl, alkenyl, alkynyl, arylalkyl heterocycle, aryl, heteroaryl, heteroarylalkyl, or other substituent, moiety or group as defined or disclosed herein wherein hydrogen atom(s) or heteroatom electron(s) of that substituent, moiety or group has been optionally replaced with different moiety(ies) or group(s), or wherein an alicyclic carbon chain that comprise one of those substituents, moiety or group is interrupted by replacing carbon atom(s) of that chain with different moiety(ies) or group(s). In some aspects, an alkene functional group replaces two contiguous $sp^3$ carbon atoms of an alkyl substituent, provided that the radical carbon of the alkyl moiety is not replaced, such that the optionally substituted alkyl becomes an unsaturated alkyl substituent.

Optional substituents replacing hydrogen(s) or heteroatom electron(s) in any one of the foregoing substituents, moieties or groups is independently selected from the group consisting of $C_6$-$C_{24}$ aryl, $C_5$-$C_{24}$ heteroaryl, hydroxyl, $C_1$-$C_{20}$ alkoxy, $C_6$-$C_{24}$ aryloxy, cyano, halogen, nitro, $C_1$-$C_{20}$ fluoroalkoxy, and amino, which encompasses —$NH_2$ and mono-, di- and tri-substituted amino groups, and the protected derivatives thereof, or is selected from the group consisting of —X, —OR', —SR', —$NH_2$, —N(R')($R^{op}$), —N($R^{op}$)$_3$, =NR', —$CX_3$, —CN, —$NO_2$, —NR'C(=O)H, —NR'C(=O)$R^{op}$, —NR'C(=O)$R^{op}$, —C(=O)R', —C(=O)$NH_2$, —C(=O)N(R')$R^{op}$, —S(=O)$_2R^{op}$, —S(=O)$_2NH_2$, —S(=O)$_2$N(R')$R^{op}$, —S(=O)$_2NH_2$, —S(=O)$_2$N(R')$R^{op}$, —S(=O)$_2$OR', —S(=O)$R^{op}$, —OP(=O)(OR')(OR$^{op}$), —OP(OH)$_3$, —P(=O)(OR')(OR$^{op}$), —PO$_3H_2$, —C(=O)R', —C(=S)$R^{op}$, —CO$_2$R', —C(=S)OR$^{op}$, —C(=O)SR', —C(=S)SR', —C(=S)$NH_2$, —C(=S)N(R')($R^{op}$)$_2$, —C(=NR')$NH_2$, —C(=NR')N(R')$R^{op}$, and salts thereof, wherein each X is independently selected from the group consisting of halogens: —F, —Cl, —Br, and —I; and wherein each $R^{op}$ is independently selected from the group consisting of $C_1$-$C_{20}$ alkyl, $C_2$-$C_{20}$ alkenyl, $C_2$-$C_{20}$ alkynyl, $C_6$-$C_{24}$ aryl, $C_3$-$C_{24}$ heterocyclyl, $C_5$-$C_{24}$ heteroaryl, a protecting group, and a prodrug moiety or two of $R^{op}$ together with the heteroatom to which they are attached defines a $C_3$-$C_{24}$ heterocyclyl; and R' is hydrogen or $R^{op}$, wherein $R^{op}$ in some aspects is selected from the group consisting of $C_1$-$C_{20}$ alkyl, $C_6$-$C_{24}$ aryl, $C_3$-$C_{24}$ heterocyclyl, $C_5$-$C_{24}$ heteroaryl, and a protecting group.

In some aspects, optional substituents that are present are selected from the group consisting of —X, —OH, —O$R^{op}$, —SH, —S$R^{op}$, —$NH_2$, —NH($R^{op}$), —NR'($R^{op}$)$_2$, —N($R^{op}$)$_3$, —$NH$, =N$R^{op}$, —$CX_3$, —CN, —$NO_2$, —NR'C(=O)H, NR'C(=O)$R^{op}$, —CO$_2$H, —C(=O)H, —C(=O)$R^{op}$, —C(=O)$NH_2$, —C(=O)NR' $R^{op}$, —S(=O)$_2R^{op}$, —S(=O)$_2NH_2$, —S(=O)$_2$N(R')$R^{op}$, —S(=O)$_2NH_2$, —S(=O)$_2$N(R')($R^{op}$), —S(=O)$_2$OR', —S(=O)$R^{op}$, —C(=S)$R^{op}$, —C(=S)$NH_2$, —C(=S)N(R')$R^{op}$, —C(=NR')N($R^{op}$)$_2$, and salts thereof, wherein each X is independently selected from the group consisting of —F and —Cl, $R^{op}$ is typically selected from the group consisting of $C_1$-$C_6$ alkyl, $C_6$-$C_{10}$ aryl, $C_3$-$C_{10}$ heterocyclyl, $C_5$-$C_{10}$ heteroaryl, and a protecting group; and R' is independently selected from the group typically consisting of hydrogen, $C_1$-$C_6$ alkyl, $C_6$-$C_{10}$ aryl, $C_3$-$C_{10}$ heterocyclyl, $C_5$-$C_{10}$ heteroaryl, and a protecting group, independently selected from $R^{op}$.

In other aspects, optional substituents that are present are selected from the group consisting of —X, —$R^{op}$, —OH, —O$R^{op}$, —$NH_2$, —NH($R^{op}$), —N($R^{op}$)$_2$, —N($R^{op}$)$_3$, —$CX_3$, —$NO_2$, —NHC(=O)H, —NHC(=O)$R^{op}$, —C(=O)$NH_2$, —C(=O)NH$R^{op}$, —C(=O)N($R^{op}$)$_2$, —CO$_2$H, —CO$_2R^{op}$, —C(=O)H, —C(=O)$R^{op}$, —C(=O)$NH_2$, —C(=O)NH($R^{op}$), —C(=O)N($R^{op}$)$_2$, —C(=NR')$NH_2$, —C(=NR')NH($R^{op}$), —C(=NR')N($R^{op}$)$_2$, a protecting group and salts thereof, wherein each X is —F; $R^{op}$ is independently selected from the group consisting of $C_1$-$C_6$ alkyl, $C_6$-$C_{10}$ aryl, $C_5$-$C_{10}$ heteroaryl and a protecting group; and R' is selected from the group consisting of hydrogen, $C_1$-$C_6$ alkyl and a protecting group, independently selected from $R^{op}$.

In some of those aspects, an optional alkyl substituent that is present is selected from the group consisting —$NH_2$, —NH($R^{op}$), —N($R^{op}$)$_2$, —N($R^{op}$)$_3$, —C(=NR')$NH_2$, —C(=NR')NH(RP), and —C(=NR')N($R^{op}$)$_2$, wherein R' and $R^{op}$ is as defined for any one of the R' or $R^{op}$ groups above. In other of those aspects, the R' and/or $R^{op}$ substituents together with the nitrogen atom to which they are attached provide for the basic functional group of a Basic Unit (BU), as when $R^{op}$ is independently selected from the group consisting of hydrogen and $C_1$-$C_6$ alkyl. Alkylene, carbocyclyl, carbocyclo, aryl, arylene, heteroalkyl, heteroalkylene, heterocyclyl, heterocyclo, heteroaryl, and heteroarylene groups as described above are similarly substituted or are unsubstituted.

"Optionally substituted heteroatom" as used herein, unless otherwise stated or implied by context, refers to a heteroatom within a functional group or other organic moiety in which the heteroatom is not further substituted or is substituted by any one of the aforementioned moieties having a monovalent carbon atom including, but not limited to alkyl, cycloalkyl, alkenyl, aryl, heterocyclyl, heteroaryl, heteroalkyl and (hetero)arylalkyl- or is oxidized by substitution with one or two oxo (=O) substituents. In some aspects "optionally substituted heteroatom" refers an aromatic or non-aromatic —NH— moiety that is unsubstituted or in which the hydrogen atom is replaced by any one of the aforementioned substituents. In other aspects, "optionally substituted heteroatom" refers to an aromatic skeletal nitrogen atom of a heteroaryl in which an electron of that heteroatom is replaced by any one of the aforementioned substituents. For encompassing both of those aspects, the nitrogen heteroatom is sometime referred to as an optionally substituted N/NH.

Therefore, for any one of those aspects, an optional substituent of a nitrogen atom that is present is selected from the group consisting of optionally substituted $C_1$-$C_{20}$ alkyl, $C_2$-$C_{20}$ alkenyl, $C_2$-$C_{20}$ alkynyl, $C_6$-$C_{24}$ aryl, $C_5$-$C_{24}$ heteroaryl, ($C_6$-$C_{24}$ aryl)-$C_1$-$C_{20}$ alkyl-, and ($C_5$-$C_{24}$ heteroaryl)-$C_1$-$C_{20}$ alkyl-, as those terms are defined herein. In other aspects, optional substituents of a nitrogen atom that are present are independently selected from the group consisting of optionally substituted $C_1$-$C_{12}$ alkyl, $C_2$-$C_{12}$ alkenyl, $C_2$-$C_{12}$ alkynyl, $C_6$-$C_{24}$ aryl, $C_5$-$C_{24}$ heteroaryl, ($C_6$-$C_{24}$ aryl)-$C_1$-$C_{12}$ alkyl-, and ($C_5$-$C_{24}$ heteroaryl)-$C_1$-$C_{12}$ alkyl-, from the group consisting of $C_1$-$C_8$ alkyl, $C_2$-$C_8$ alkenyl, $C_2$-$C_8$ alkynyl, $C_6$-$C_{10}$ aryl, $C_5$-$C_{10}$ heteroaryl, ($C_6$-$C_{10}$ aryl)-$C_1$-$C_8$ alkyl-, and ($C_5$-$C_{10}$ heteroaryl)-$C_1$-$C_8$ alkyl-, or from the group consisting of $C_1$-$C_6$ alkyl, $C_2$-$C_6$ alkenyl, $C_2$-$C_6$ alkynyl, $C_6$-$C_{10}$ aryl, $C_5$-$C_{10}$ heteroaryl, ($C_6$-$C_{10}$ aryl)-$C_1$-$C_6$ alkyl-, and ($C_5$-$C_{10}$ heteroaryl)-$C_1$-$C_6$ alkyl-.

In some aspects, an optional substituent that is present replaces a carbon atom and hydrogen atoms attached thereto in the acyclic carbon chain of an alkyl or alkylene moiety, group or substituent to provide for a $C_3$-$C_{12}$ heteroalkyl or $C_3$-$C_{12}$ heteroalkylene and for that purpose is typically selected from the group consisting of —O—, —C(=O)—, —C(=O)O—, —S—, —S(=O)—, —S(=O)$_2$—, —NH—, —NHC(=O)—, —C(=O)NH—, S(=O)$_2$NH—, —NHS(=O)$_2$—, —OC(=O)NH—, and —NHC(=O)O, in which —NH— is an optionally substituted heteroatom moeity by replacement of its hydrogen atom by an independently selected substituent from a group previously described for an —NH— optional substituent.

In other aspects, when variable group J/J' of a PAB or PAB-type self-immolative Spacer Unit within a self-immolative Spacer Unit, as described by the embodiments of the invention, is optionally substituted —NH—, the nitrogen atom is so substituted by replacement of its hydrogen atom with a substituent that suitably retains the localization of its nitrogen lone pair electrons on cleavage of the W-J bond in a Linker Unit to allow for self-immolation of the PAB or PAB-type moiety of the self-immolative Spacer Unit comprised of that optionally substituted nitrogen atom. In other aspects, when variable group E' of a glycosidic bond between W' and Y of a Glucuronide Unit, as described by the embodiments of the invention, is an optionally substituted —NH— moiety, the nitrogen atom when substituted has its attached hydrogen atom replaced by a substituent that suitably retains the localization of its nitrogen lone pair electrons in its participation in the glycosidic bond so as to allow for self-immolation of the PAB or PAB-type moiety of the self-immolative Spacer Unit of that Glucuronide Unit upon cleavage of the glycosidic bond and provides for a recognition site for glycosidase cleavage so that cleavage effectively competes with spontaneous hydrolysis of that bond. In a Glucuronide Unit, J', which is the attachment site to the remainder of the Linker Unit (LU), is —O—, —S— or optionally substituted NH, wherein the bond to the remainder of LU is not subject to enzymatic or non-enzymatic cleavage under normal physiological conditions or within or in the vicinity of the targeted abnormal cells.

"O-linked moiety" as used herein, unless otherwise stated or implied by context, refers to a moeity, group or substituent that is attached to a Markush structure or another organic moiety with which it is associated directly through an oxygen atom of the O-linked moiety. A monovalent O-linked moiety is typically —OH, —OC(=O)$R^b$ (acyloxy), wherein $R^b$ is —H, optionally substituted saturated $C_1$-$C_{20}$ alkyl, optionally substituted unsaturated $C_3$-$C_{20}$ alkyl, optionally substituted $C_3$-$C_{20}$ cycloalkyl, wherein the cycloalkyl moiety is saturated or partially unsaturated, optionally substituted $C_3$-$C_{20}$ alkenyl, optionally substituted $C_2$-$C_{20}$ alkynyl, optionally substituted $C_6$-$C_{24}$ aryl, optionally substituted $C_5$-$C_{24}$ heteroaryl or optionally substituted $C_3$-$C_{24}$ heterocyclyl, or $R^b$ is optionally substituted $C_1$-$C_{12}$ alkyl, optionally substituted $C_3$-$C_{12}$ cycloalkyl, optionally substituted $C_2$-$C_{12}$ alkenyl, optionally substituted $C_2$-$C_{12}$ alkynyl, or optionally substituted phenyl, and wherein a monovalent O-linked moiety further encompasses ether groups, which are $C_1$-$C_{12}$ alkyloxy (i.e., $C_1$-$C_{12}$ aliphatic ether), optionally substituted, wherein its alkyl moeity is saturated, or $C_3$-$C_{12}$ alkyloxy, optionally substituted, wherein its alkyl moeity is unsaturated, or $C_6$-$C_{10}$ aryloxy or $C_5$-$C_{10}$ heteroaryloxy in which its aryl or heteroaryl moeity is optionally substituted.

In other aspects, a monovalent O-linked moeity is a monovalent moeity selected from the group consisting of optionally substituted phenoxy, optionally substituted $C_1$-$C_8$ alkyloxy (i.e., $C_1$-$C_8$ aliphatic ether) and —OC(=O)$R^b$, wherein $R^b$ is optionally substituted $C_1$-$C_8$ alkyl, which is typically saturated, or is an unsaturated $C_3$-$C_8$ alkyl, optionally substituted.

In still other aspects, an O-linked moeity is a monovalent moeity selected from the group consisting of —OH, and saturated $C_1$-$C_6$ alkyl ether, unsaturated $C_3$-$C_6$ alkyl ether, optionally substituted, and —OC(=O)$R^b$, wherein $R^b$ is typically $C_1$-$C_6$ saturated alkyl, $C_3$-$C_6$ unsaturated alkyl, $C_3$-$C_6$ cycloalkyl, $C_2$-$C_6$ alkenyl, or phenyl, optionally substituted, or is selected from that group excluding —OH and/or phenyl, or $R^b$ is a monovalent moiety selected from the group consisting of $C_1$-$C_6$ saturated alkyl, $C_3$-$C_6$ unsaturated alkyl and $C_2$-$C_6$ alkenyl, optionally substituted, or an unsubstituted O-linked substituent selected from the group consisting of saturated $C_1$-$C_6$ alkyl ether, unsaturated $C_3$-$C_6$ alkyl ether, and —OC(=O)$R^b$, wherein $R^b$ is an unsubstituted saturated $C_1$-$C_6$ alkyl or unsaturated $C_3$-$C_6$ alkyl.

Other exemplary O-linked substituents are provided by definitions for carbamate and carbonate as disclosed herein in which the monovalent, singly bonded oxygen atom of the carbamate or carbonate functional group of the substituent is bonded to the Markush structure or other organic moiety with which it is associated.

In other aspects, an O-linked moeity to carbon is divalent and encompasses =O and —X—(CH$_2$)$_{n'}$—Y—, wherein X and Y independently are S and O and subscript n' is 2 or 3, to form a spiro ring system with the carbon to which X and Y are both attached.

"Halogen" as used herein, unless otherwise stated or implied by context, refers to fluorine, chlorine, bromine or iodine and is typically —F or —Cl.

"Protecting group" as used herein, unless otherwise stated or implied by context, refers to a moiety that prevents or substantially reduces the ability of the atom or functional group to which it is attached from participating in unwanted reactions. Typical protecting groups for atoms or functional groups are given in Greene (1999), "Protective groups in organic synthesis, 3$^{rd}$ ed.", Wiley Interscience. Protecting groups for heteroatoms such as oxygen, sulfur and nitrogen are sometime used to minimize or avoid their unwanted reactions with electrophilic compounds. Other times the protecting group is used to reduce or eliminate the nucleophilicity and/or basicity of the unprotected heteroatom. Non-limiting examples of protected oxygen are given by —OR$^{PR}$, wherein R$^{PR}$ is a protecting group for hydroxyl, wherein hydroxyl is typically protected as an ester (e.g., acetate, propionate or benzoate). Other protecting groups for hydroxyl avoid its interference with the nucleophilicity of organometallic reagents or other highly basic reagents, for which purpose hydroxyl is typically protected as an ether, including without limitation alkyl or heterocyclyl ethers, (e.g., methyl or tetrahydropyranyl ethers), alkoxymethyl ethers (e.g., methoxymethyl or ethoxymethyl ethers), optionally substituted aryl ethers, and silyl ethers (e.g., trimethylsilyl (TMS), triethylsilyl (TES), tert-butyldiphenylsilyl (TBDPS), tert-butyldimethylsilyl (TBS/TBDMS), triisopropylsilyl (TIPS) and [2-(trimethylsilyl)ethoxy]-methylsilyl (SEM)). Nitrogen protecting groups include those for primary or secondary amines as in —NHR$^{PR}$ or —N(R$^{PR}$)$_2$, wherein least one of R$^{PR}$ is a nitrogen atom protecting group or both R$^{PR}$ together define a nitrogen atom protecting group.

A protecting group is suitable for protecting when it is capable of preventing or substantially avoiding unwanted side-reactions and/or premature loss of the protecting group under reaction conditions required to effect desired chemical transformation(s) elsewhere in the molecule and during purification of the newly formed molecule when desired, and can be removed under conditions that do not adversely affect the structure or stereochemical integrity of that newly formed molecule. In some aspects, suitable protecting groups are those previously described for protecting functional groups. In other aspects, a suitable protecting group is a protecting group used in peptide coupling reactions. For example, a suitable protecting group for the basic nitrogen atom of an acyclic or cyclic Basic Unit is an acid-labile carbamate protecting group such as t-butyloxycarbonyl (BOC).

"Ester" as used herein, unless otherwise stated or implied by context, refers to a substituent, moiety or group having the structure of —C(=O)—O— to define an ester functional group in which the carbonyl carbon atom of that structure is not directly connected to another heteroatom but is directly connected to hydrogen or another carbon atom of an organic moiety with which it is associated, and wherein the monovalent oxygen atom is either attached to the same organic moiety at a different carbon atom to provide a lactone or to some other organic moiety. Typically, esters in addition to the ester functional group comprise or consist of an organic moiety attached at either end of the functional group with each independently containing 1 to 50 carbon atoms, typically 1 to 20 carbon atoms or more typically 1 to 8, 1 to 6 or 1 to 4 carbon atoms and 0 to 10 independently selected heteroatoms (e.g., O, S, N, P, Si, but typically O, S and N), typically 0 to 2 such heteroatoms.

When an ester is a substituent or variable group of a Markush structure or other organic moiety with which it is associated, that substituent is bonded to the structure or other organic moiety through the monovalent oxygen atom of the ester functional group as an exemplary monovalent O-linked moeity, which is sometimes referred to as an acyloxy. In such instances, the organic moiety attached to the carbonyl carbon of the ester functional group typically is a $C_1$-$C_{20}$ alkyl, $C_2$-$C_{20}$ alkenyl, $C_2$-$C_{20}$ alkynyl, $C_6$-$C_{24}$ aryl, $C_5$-$C_{24}$ heteroaryl, $C_3$-$C_{24}$ heterocyclyl or is a substituted derivative of any one of these, e.g., having 1, 2, 3 or 4 substituents, more typically is $C_1$-$C_{12}$ alkyl, $C_2$-$C_{12}$ alkenyl, $C_2$-$C_{12}$ alkynyl, $C_6$-$C_{10}$ aryl, $C_5$-$C_{10}$ heteroaryl, $C_3$-$C_{10}$ heterocyclyl or a substituted derivative of one any of these, e.g., having 1, 2, or 3 substituents or is $C_1$-$C_8$ alkyl, $C_2$-$C_8$ alkenyl, $C_2$-$C_8$ alkynyl, or phenyl or a substituted derivative of any one of these, e.g., having 1 or 2 substituents, wherein each independently selected substituent is as defined herein for optional alkyl substituents, or is unsubstituted $C_1$-$C_6$ alkyl or unsubstituted $C_2$-$C_6$ alkenyl.

Exemplary esters by way of example and not limitation, are acetate, propionate, isopropionate, isobutyrate, butyrate, valerate, isovalerate, caproate, isocaproate, hexanoate, heptanoate, octanoate, phenylacetate esters and benzoate esters or have the structure of —OC(=O)$R^b$ in which $R^b$ is as defined for acyloxy O-linked moieties and is typically selected from the group consisting of methyl, ethyl, propyl, iso-propyl, 3-methyl-prop-1-yl, 2,2-dimethyl-prop-1-yl, prop-2-ene-1-yl, and vinyl.

"Ether" as used herein, unless otherwise stated or implied by context, refers to an organic moiety, group or substituent that comprises or contains 1, 2, 3, 4 or more —O— (i.e., oxy) moieties that are not bonded to carbonyl moiety(ies), typically 1 or 2, wherein no two —O— moieties are immediately adjacent (i.e., directly attached) to each other. Typically, an ether contains the formula of —O-organic moiety wherein organic moiety is as described for an organic moiety bonded to an ester functional group or is as described herein for an optionally substituted alkyl or optionally substituted alkenyl group. When ether is recited as a substituent or variable group of a Markush structure or other organic moiety with which it is associated, the oxygen of the ether functional group is attached to the Markush formula or other organic moiety with which it is associated and is sometimes designated as an "alkoxy" group, which is an exemplary O-linked moiety. In some aspects, an alkoxy substituent is a $C_1$-$C_{20}$ alkoxy or a $C_1$-$C_{12}$ alkoxy, optionally substituted with 1, 2, 3 or 4 substituents, typically 1, 2 or 3, and in other aspects is a $C_1$-$C_8$ alkoxy or $C_1$-$C_6$ alkoxy, optionally substituted with 1 or 2 substituents, wherein each independently selected substituent is as defined herein for optional alkyl substituents, and in still other aspects an ether O-linked substituent is an unsubstituted, saturated $C_1$-$C_4$ alkoxy or an unsubstituted, unsaturated $C_3$-$C_4$ alkoxy such as, by way of example and not limitation, methoxy, ethoxy, propoxy, iso-propoxy, butoxy and allyloxy (i.e., —$OCH_2CH$=$CH_2$).

"Amide" as used herein, unless otherwise stated or implied by context, refers to a moiety having an optionally substituted functional group having the structure of R—C(=O)N($R^c$)— or —C(=O)N($R^c$)$_2$ to which no other heteroatom is directly attached to the carbonyl carbon and wherein each $R^c$ is independently hydrogen, a protecting group or an organic moiety and R is hydrogen or an organic moeity, wherein organic moiety, independently selected, is as described herein for an organic moiety bonded to an ester functional group or is as described herein for an optionally substituted alkyl group or an optionally substituted alkenyl group. When an amide is recited as a substituent or variable group of a Markush structure or other organic moiety with which it is associated, the amide nitrogen atom or carbonyl carbon atom of the amide functional group is bonded to that structure or other organic moiety. An amide bonded to a Markush structure or other moiety to which it is associated through its amide nitrogen atom is an exemplary N-linked moiety. Amides are typically prepared by condensing an acid halide, such an acid chloride, with a molecule containing a primary or secondary amine. Alternatively, amide coupling reactions well-known in the art of peptide synthesis, which oftentimes proceed through an activated ester of a carboxylic acid-containing molecule, are used. Exemplary preparations of amide bonds through peptide coupling methods are provided in Benoiton (2006) "Chemistry of peptide synthesis", CRC Press; Bodansky (1988) "Peptide synthesis: A practical textbook" Springer-Verlag; Frinkin, M. et al. "Peptide Synthesis" *Ann. Rev. Biochem.* (1974) 43: 419-443. Reagents used in the preparation of activated carboxylic acids is provided in Han, et al. "Recent development of peptide coupling agents in organic synthesis" *Tet.* (2004) 60: 2447-2476.

"Carbonate" as used here means a substituent, moiety or group that contains a functional group having the structure of —O—C(=O)—O—, which defines a carbonate functional group. Typically, carbonate groups as used herein are comprised of an organic moiety bonded to one end of the —O—C(=O)—O— structure, wherein the organic moiety is as described herein for an organic moiety bonded to an ester functional group, and thus have the formula of organic moiety-O—C(=O)—O— in which the oxygen radical is bonded to another independently selected organic moiety. When carbonate is recited as a substituent or variable group of a Markush structure or other organic moiety with which it is associated, one of the monovalent, singly bonded oxygen atoms of the carbonate functional group is attached to that structure or organic moiety and the other is bonded to a carbon atom of another organic moiety as previously described for an organic moiety bonded to an ester functional group or is as described herein for an optionally substituted alkyl or an optionally substituted alkenyl. In such instances, carbonate is an exemplary O— linked moiety.

"Carbamate" as used here means a substituent, moiety or group that contains a optionally substituted carbamate functional group structure represented by —O—C(=O)N($R^c$)— or —O—C(=O)N($R^c$)$_2$, or —O—C(=O)NH (optionally substituted alkyl) or —O—C(=O)N (optionally substituted alkyl)$_2$ in which the optionally substituted alkyl(s) are exemplary carbamate functional group substituents, wherein each $R^c$ and optionally substituted alkyl are independently selected, wherein independently selected $R^c$ is hydrogen, a protecting group or an organic moiety, wherein the organic moiety is as described herein for an organic moiety bonded to an ester functional group or is as described herein for an optionally substituted alkyl or optionally substituted alkenyl. When a carbamate groups contains an optionally substituted carbamate functional group structure is represented by —O—C(=O)N($R^c$)—, such carbamate groups are additionally comprised of an organic moiety, independently selected from $R^c$, wherein that other organic moiety is as described herein for an organic moiety bonded to an ester functional group, and is bonded to the —O—C(=O)—N($R^c$)— structure, wherein the resulting structure has the formula of organic moiety-O—C(=O)—N($R^c$)— or —O—C(=O)—N($R^c$)-organic moiety. When carbamate is recited as a substituent or variable group of a Markush structure or other organic moiety with which it is associated, the monovalent, singly bonded oxygen atom (O-linked) or monovalent nitrogen atom (N-linked) of the carbamate functional group is attached to a Markush formula with which it is associated. The linkage of the carbamate substituent is either explicitly stated (N- or O-linked) or implicit in the context to which this substituent is referred. O-linked carbamates described herein are exemplary monovalent O-linked moieties, and N-linked carbamates described herein are exemplary N-linked moieties.

"Antibody" as used herein, unless otherwise stated or implied by context, refers to intact monoclonal antibodies, polyclonal antibodies, monospecific antibodies, multispecific antibodies (e.g., bispecific antibodies), and antibody fragments having an antigen binding provided that the antibody or fragment thereof, or a plurality of antibodies or fragments thereof in a collection of such species, which may be deglycosylated or differ from each other in least in part by sequence mutation and/or glycosylation patterns, has the requisite number of sites on the antibody or fragment thereof for covalent attachment to the requisite number of quaternized drug-linker moieties. The native form of an intact antibody is a tetramer and consists of two identical pairs of immunoglobulin chains, each pair having one light chain and one heavy chain. In each pair, the light and heavy chain variable regions (VL and VH) are together primarily responsible for binding to an antigen. The light chain and heavy chain variable domains consist of a framework region interrupted by three hypervariable regions, also called "complementarity determining regions" or "CDRs." The constant regions may be recognized by and interact with the immune system (see, e.g., Janeway et al., (2001), "Immunol. Biology, 5th ed.", Garland Publishing, New York). An antibody can be of any type (e.g., IgG, IgE, IgM, IgD, and IgA), class (e.g., $IgG_1$, $IgG_2$, $IgG_3$, $IgG_4$, $IgA_1$ and $IgA_2$) or subclass, but is typically an intact $IgG_1$ or fragment thereof. The antibody can be derived from any suitable species. In some aspects, the antibody is of human or murine origin or is a human, humanized or chimeric antibody. An antibody or antibody fragment thereof capable of antigen binding, is an exemplary targeting agent that corresponds to or is incorporated into a Ligand Drug Conjugate of the present invention as a Ligand Unit, which in these instances is sometimes referred to as an antibody Ligand Unit. In some aspects, an antibody or antigen-binding fragment thereof has a reactive functional group for attachment to a Linker Unit of a Drug Linker compound and in other aspects is modified to have a reactive functional group for attachment to that Linker Unit. Both of those aspects are encompassed by the definition of an antibody. An exemplary modification is reduction of interchain disulfide bonds in the hinge region of an antibody to provide for a reduced antibody having free cysteines thiol functional groups that are reactive towards a maleimide functional group in the Linker Unit of a Drug Linker compound.

In some aspects, an antibody selectively and specifically binds to an epitope on hyper-proliferating or hyper-stimulated mammalian cells, which are abnormal cells, wherein the epitope is preferentially displayed by or is more characteristic of targeted abnormal cells in contrast to normal cells that are not intended to be targeted, or is preferentially displayed within, and is peculiar to, the vicinity of the abnormal cells, or is more characteristic of targeted normal cells in the vicinity of abnormal cells in contrast to normal cells that are not intended to be targeted, which typically are not localized to the abnormal cells. In those aspects, the mammalian cells are typically human cells.

"Monoclonal antibody" as used herein, unless otherwise stated or implied by context, refers to an antibody obtained from a population of substantially homogeneous antibodies, i.e., the individual antibodies comprising the population are identical except for possible naturally-occurring mutations that may be present in minor amounts or differences in glycosylation patterns. A monoclonal antibody (mAb) is highly specific, being directed against a single antigenic site. The modifier "monoclonal" indicates the character of the antibody as being obtained from a substantially homogeneous population of antibodies, and is not to be construed as requiring production of the antibody by any particular method.

"Antibody fragment" as used herein, unless otherwise stated or implied by context, refers to a portion of an intact antibody that is comprised of the antigen-binding site or variable region of the intact antibody and remains capable of binding to the cognate antigen of the intact antibody. Examples of antibody fragments include Fab, Fab', F(ab')$_2$, and Fv fragments, diabodies, triabodies, tetrabodies, linear antibodies, single-chain antibody molecules, scFv, scFv-Fc, multispecific antibody fragments formed from antibody fragment(s), a fragment(s) produced by a Fab expression library, or an epitope-binding fragments of any of the above which immunospecifically binds to a target antigen (e.g., a cancer cell antigen, an immune cell antigen, a viral antigen or a microbial antigen).

"Cytotoxic drug" as used herein, unless otherwise stated or implied by context, refers to compound or a metabolite derived from a Ligand Drug Conjugate that exerts an anti-survival effect on hyper-proliferating cells, hyper-activated immune cells or other abnormal cells. In some aspects, the cytotoxic drug acts directly upon those cells or indirectly by acting upon the abnormal vasculature that supports the survival and/or growth of the hyper-proliferating or other abnormal cells, or the cytotoxic drug acts within sites of infiltrating hyper-activated immune cells. Typically, the abnormal cells acted upon by the cytotoxic drug are mammalian cells, more typically human cells. Cytotoxic activity of a cytotoxic drug may be expressed as an $IC_{50}$ value, which is the effective concentration, typically molar amount per unit volume, at which half the cancer cells in an in vitro cell model system survive exposure to the cytotoxic agent. Thus, an $IC_{50}$ value is model-dependent. Typically, a cytotoxic agent incorporated into a Ligand Drug Conjugate will have an $IC_{50}$ value in an in vitro cell model comprised of hyper-proliferating cells of between 100 nM to 0.1 pM or more typically about 10 nM to 1 pM. A highly toxic cytotoxic drug typically has an $IC_{50}$ value in such models of about 100 pM or lower. Although compounds that reverse resistance to cytotoxic or cytostatic drugs in abnormal cells having the MDR phenotype are not cytotoxic in their own right, they are sometimes included as cytotoxic drugs or cytostatic drugs, which exert an anti-proliferative effect that is not dependent on cell killing but whose effect remains due to inhibition of cell division of hyper-proliferating cells, hyper-stimulated immune cells or other abnormal cells. As unconjugated free drugs, NAMPTi compounds typically exhibit steep dose-response curves indicating that a threshold amount of $NAD^+$ depletion is necessary for cytotoxicity. Furthermore, for maximal cytotoxicity, a sustained exposure to the NAMPTi compound may be necessary in order to deplete intracellular ATP to an amount from which there is no escape from cell death as would occur if $NAD^+$ levels were allowed to rebound.

"Selective binding" and "selectively binds" as the terms are used herein, unless otherwise stated or implied by context, refers to an antibody, a fragment thereof, or an antibody Ligand Unit as the targeting moiety in a Ligand Drug Conjugate that is capable of binding in an immunologically selective and specific manner with its corresponding targeted antigen and not with a multitude of other antigens. Typically, the antibody or fragment thereof binds its targeted antigen with an affinity of at least about $1 \times 10^{-7}$ M, and preferably about $1 \times 10^{-8}$ M to $1 \times 10^{-9}$ M, $1 \times 10^{-10}$ M, or $1 \times 10^{-11}$ M and binds to that predetermined antigen with an affinity that is at least two-fold greater than its affinity for binding to a non-specific antigen (e.g., BSA, casein) other than for a closely-related antigen, wherein said affinities are substantially retained when incorporated into a Ligand Drug Conjugate as an antibody Ligand Unit.

"Ligand-Drug Conjugate" as the term is used herein, unless otherwise stated or implied by context, refers to a compound, or a collection of such compounds comprised of a Ligand (L) Unit corresponding to or incorporating a targeting agent, a quaternized NAMPT Drug ($D^+$) Unit, which upon release from a Ligand Drug Conjugate compound provides a NAMPTi compound, wherein the targeting Ligand Unit of the Ligand Drug Conjugate selectively binds to its cognate targeted moiety and a Linker Unit (LU), which interconnects the L and $D^+$. In some instances, a collection of Ligand Drug Conjugate compounds is referred to as a Ligand Drug Conjugate composition in which the individual Ligand Drug Conjugate compounds differ primarily by the number of quaternized NAMPT Drug Units or quaternized drug linker moieties bonded to each Ligand Unit and/or the locations on the Ligand Unit at which the quaternized NAMPT Drug Units or quaternized drug linker moieties are bound. In other instances, the term Ligand Drug Conjugate applies to an individual member (i.e., a Ligand Drug Conjugate compound) of the composition. When conjugation is to cysteine thiols from fully reduced interchain antibody disulfides using a molar excess of Drug Linker compound, the antibody drug conjugate composition so obtained typically has a uniform or near uniform collection of antibody drug conjugate compounds in which many of the Conjugate compounds have a drug linker loading of 8 and thus the composition may contain minor or negligible amounts of lower loaded species.

"Targeting agent" as used herein, unless otherwise stated or implied by context, refers to an agent that that is capable of selective binding to a targeted moiety and which substantially retains that capability when it is incorporated into a Ligand Drug Conjugate as a Ligand Unit, or when the Ligand Unit of a Ligand Drug Conjugate corresponds in structure to the targeting agent or incorporates the structure of the targeting agent, so that the Ligand Unit is the targeting moeity of the Conjugate. In some aspects the targeting agent is an antibody or fragment thereof that is capable of binding in an immunologically selective and specific manner to an accessible antigen that is characteristic of an abnormal cell or is present in higher copy number in comparison to normal cells or is an accessible antigen that is particular to the surrounding environment in which these cells are found to an extent that reduces the number and/or severity of adverse events typically associated with administration of an equimolar amount of free drug, which is expected to provide for a desired therapeutic index. In other aspects, the targeting agent is a receptor ligand that selectively binds to an accessible receptor characteristic of, or in greater abundance on, abnormal cells or other unwanted cells, or to an accessible receptor that is peculiar to cells of the surrounding environment in which abnormal cells are found. Typically, a targeting agent is an antibody as defined herein that binds in an immunologically selective and specific manner to a targeted moiety of an abnormal mammalian cell, more typically a targeted moiety of an abnormal human cell.

"Targeted moiety" as defined herein is a moiety to be specifically recognized by a targeting agent or a targeting moeity of a Ligand Drug Conjugate, which is its Ligand Unit that corresponds to or incorporates the targeting agent. In some aspects, a targeted moiety is present on, within, or in the vicinity of abnormal cells and is typically present in greater abundance or copy number on those cells in comparison to normal cells not intended to be targeted, or in comparison to the environment of such cells in which abnormal cells are typically not present. That difference in targeted moiety abundance should be in sufficient degree so as to provide for reduction in the number or severity of adverse events typically associated with administration of an equimolar amount of free NAMPT inhibitor compound, which is expected to provide for a desired therapeutic index.

In some aspects, the targeted moiety is an antigen accessible to binding in an immunologically selective and specific manner by an antibody, which is an exemplary targeting agent that is incorporated as or corresponds to an antibody Ligand Unit in a Ligand Drug Conjugate composition or compound thereof. In other aspects, the targeting moiety is that of a ligand for an extracellularly accessible cell membrane receptor, which may be internalized upon binding of the cognate targeting moiety provided by the Ligand Unit of a Ligand Drug Conjugate or compound thereof that incorporates or corresponds in structure to the receptor ligand, or is capable of passive or facilitative transport of a Ligand Drug Conjugate compound subsequent to binding of the cell-surface receptor. In some aspects, the targeted moiety is present on abnormal mammalian cells or on mammalian cells characteristic of the environment of such abnormal cells. In some aspects, the targeted moiety is an antigen of an abnormal mammalian cell, more typically a targeted moiety of an abnormal human cell.

"Target cells", "targeted cells", or like terms as used herein, unless otherwise stated or implied by context, are the intended cells to which Ligand Drug Conjugate is designed to interact in order to inhibit the proliferation or other unwanted activity of that cell. In some aspects, the targeted cells are hyper-proliferating cells or hyper-activated immune cells, which are exemplary abnormal cells. Typically, those abnormal cells are mammalian cells and more typically are human cells. In other aspects, the targeted cells are within the vicinity of the abnormal cells so that action of the Ligand Drug Conjugate on the nearby cells has an intended effect on the abnormal cells. For example, the nearby cells may be epithelial cells that are characteristic of the abnormal vasculature of a tumor. Targeting of those vascular cells by a Ligand Drug Conjugate composition or compound thereof will either have a cytotoxic or a cytostatic effect on these cells, which is believed to result in inhibition of nutrient delivery to the nearby abnormal cells of the tumor. Such inhibition indirectly has a cytotoxic or cytostatic effect on the abnormal cells and may also have a direct cytotoxic or cytostatic effect on the nearby abnormal cells by releasing its quaternized cytotoxic drug payload, such as a quaternized NAMPT Drug Unit as a NAMPTi compound, in the vicinity of these cells.

"Antigen" as the term is used herein, unless otherwise stated or implied by context, is a moiety that is capable of specific binding by an unconjugated antibody or an antigen-binding fragment thereof or to an Antibody Drug Conjugate compound, which is comprised of an antibody Ligand Unit that incorporates or corresponds in structure to the unconjugated antibody. In some aspects, the antigen is an extracellularly-accessible cell-surface protein, glycoprotein, or carbohydrate preferentially, typically a protein or glycoprotein, displayed by abnormal cells in comparison to normal cells distant from the site of the abnormal cells. In some instances, the abnormal cells displaying the antigen are hyper-proliferating cells, which includes cancer cells, in a mammal. In other instances, the abnormal cells displaying the antigen are hyper-activated immune cells in a mammal. In other aspects, the antigen to be specifically bound by an antibody Ligand Unit of an Antibody Drug Conjugate compound having a quaternized cytotoxic or cytostatic Drug Unit, including a quaternized NAMPT Drug Unit, is present in the particular environment of hyper-proliferating cells or hyper-activated immune cells in a mammal in contrast to the environment typically experienced by normal cells in the absence of such abnormal cells. In still other aspects, the cell-surface antigen is capable of internalization upon selective binding by a Conjugate compound of an Antibody Drug Conjugate composition having a quaternized cytotoxic or cytostatic Drug Unit, inclusive of a quaternized NAMPT Drug Unit. Subsequent to internalization, intracellular processing of a Linker Unit of an Antibody Drug Conjugate compound of the composition releases its quaternized Drug Unit as a non-quaternized cytotoxic or cytostatic compound, which is inclusive of release of a quaternized NAMPT Drug Unit as a NAMPTi compound. Antigens associated with hyper-proliferating cells that are cell-surface accessible to an Antibody Drug Conjugate include by way of example and not limitation CD19, CD70, CD30, and CD33.

"Antibody Drug Conjugate" as the term is used herein, unless otherwise stated or implied by context, refers to a Ligand Drug Conjugate wherein the targeting moiety of the Conjugate is that of an antibody, wherein the antibody in the form of an antibody Ligand Unit that is covalently associated with a quaternized NAMPT Drug Unit (D+), through an intervening Linker Unit. In some aspects, the term refers to a collection (i.e., population or plurality) of Conjugate compounds having substantially the same antibody Ligand Unit with respect to its protein sequence, but having variable loading, characterized by a distribution, of the quaternized drug linker moieties for each of the Conjugate compounds and/or variable location of the attached quaternized Drug Unit (as for example when the number of quaternized NAMPT Drug Units in any two Antibody Drug Conjugate compounds in a plurality of such compound is the same but the location of their sites of attachment to the targeting agent in the form of a Ligand Unit differ) and otherwise have substantially the same structure with respect to the Ligand Unit, which allows for variations in glycosylation and mutational differences in peptide sequences of the targeting agent carried forward into the antibody Ligand Unit in those instances when the targeting agent is a monoclonal antibody, and allows for other differences in glycosylation patterns and protein sequences normally expected for a polyclonal antibody as the targeting agent. In those aspects, an Antibody Drug Conjugate is described by the averaged quaternized drug linker or quaternized NAMPT Drug Unit loading per antibody Ligand Unit of the Conjugate compounds of the Antibody Drug Conjugate composition, depending on the presence or absence, respectively, of branching within the Linker Units of the drug linkers moieties. An Antibody Drug Conjugate composition obtained from the methods described herein have the general formula of Ab-$(L_R$-$L_O$-$D^+)_p$, wherein Ab is an antibody Ligand Unit, $D^+$ is a quaternized NAMPT Drug Unit, subscript p is the average number of quaternized drug linker moieties or quaternized NAMPT Drug Units connected to the antibody Ligand Unit through its Linker Unit(s) and $L_R$-$L_O$ defines the Linker Unit(s), wherein $L_R$ is a primary linker, and is so named because that component is required to be present in a Linker Unit of an Antibody Drug Conjugate, and wherein $L_O$ is an optional secondary linker that is present and is susceptible to enzymatic (e.g., protease or glycosidase) action or non-enzymatic action (e.g., reduction under hypoxic conditions or hydrolysis by lower pH) to effect release of the quaternized NAMPT Drug Unit as a NAMPTi compound. In some aspects, that cleavage is enhanced in the environment of abnormal cells or occurs subsequent to cellular internalization of an Antibody Drug Conjugate compound of the composition on binding of its targeting antibody Ligand Unit to its cognate antigen present on the abnormal cells.

In some aspects subscript p is a number ranging from about 2 to about 20, or about 2 to about 16, or about 2 to about 12, or about 2 to about 10, and in some aspects is about 2, about 4, or about 8. An Antibody Drug Conjugate compound of the composition is described by the same general formula in which subscript p is replaced by p', wherein p' is an integer ranging 2 to 20, 2 to 16, 2 to 12 or 2 to 10 and in some aspects is 2, 4, or 8. The average number of quaternized NAMPT Drugs Units or quaternized drug linker moieties per Ligand Unit in a preparation from a conjugation reaction may be characterized by conventional means such as mass spectroscopy, ELISA assay, HIC and/or HPLC. In some instances, separation, purification, and characterization of homogeneous Ligand-Drug Conjugates, where p is a certain value (i.e., p essentially becomes p') from a collection of Ligand Drug Conjugate compounds in a Ligand Drug Conjugate composition with other drug loadings may be achieved by means such as reverse phase HPLC or electrophoresis.

"Ligand Unit" as the term is used herein, unless otherwise stated or implied by context, refers to a targeting moiety of a Ligand Drug Conjugate composition or compound that is capable of binding selectively to its cognate targeted moiety and incorporates or corresponds to the structure of a targeting agent. A Ligand Unit (L) includes without limitation those from receptor ligands, antibodies to cell-surface antigens, and transporter substrates. In some aspects, the receptor, antigen or transporter to be bound by a Conjugate compound of a Ligand Drug Conjugate composition is present in greater abundance on abnormal cells in contrast to normal cells so as to effect reduction in number and/or severity of adverse events, which is expected to achieve a desired therapeutic index. In other aspects, the receptor, antigen or transporter to be bound by a Ligand Drug Conjugate compound of the composition is present in greater abundance on normal cells in the vicinity of abnormal cells in contrast to normal cells that are distant from the site of the abnormal cells, so as to selectively expose the nearby abnormal cells to the released NAMPTi compound. Various aspects of Ligand Units, including antibody Ligand Units, are further described by embodiments of the invention.

"Linker Unit" as the term is used herein, unless otherwise stated or implied by context, refers to an organic moiety in a Ligand Drug Conjugate intervening between and covalently attached to a quaternized NAMPT Drug Unit ($D^+$) and a Ligand Unit (L) as these terms are defined herein. A Linker Unit (LU) is comprised of a primary linker ($L_R$), which is a required component of that Unit, and an optional secondary linker ($L_O$) that is present and intervenes between $L_R$ and $D^+$ within a quaternized drug linker moiety of a Ligand Drug Conjugate compound or between $D^+$ and $L_{R'}$, which is capable of conversion to $L_R$ and therefore is sometimes described as a precursor of $L_R$, of a Drug Linker compound. In some aspects, $L_R$ is comprised of a succinimide ($M^2$) or succinic acid amide ($M^3$) moiety and is sometimes further comprised of a Basic Unit (acyclic or cyclic) within a Linker Unit of a Ligand Drug Conjugate compound, and in other aspects a primary linker is comprised of a maleimide ($M^1$) moiety in a Drug Linker compound and is sometimes represented as $L_{R'}$ to indicate that it can be a precursor to $L_R$ of a Ligand Drug Conjugate and is further comprised of a Basic Unit (acyclic or cyclic), either in protected or protonated from.

As a Drug Linker compound as described herein is sometimes comprised of a maleimide ($M^1$) moiety, attachment of a targeting agent, which is thus converted to a Ligand Unit, occurs to such a Drug Linker compound through a reactive thiol functional group of the targeting agent by way of Michael addition of a sulfur atom from that reactive thiol functional group to the maleimide ring system of $M^1$. When the targeting agent is an antibody, the reactive thiol in some aspects is provided by a cysteine thiol of the antibody resulting from disulfide bond reduction and/or other chemical modification of a native antibody amino acid residue and/or by introduction through genetic engineering. As a result of that addition, a Linker Unit of a Ligand Drug Conjugate compound contains a succinimide ($M^2$) moiety having a thio-substituted succinimide ring system. Subsequent hydrolysis of that ring system under controlled conditions due to the presence of an acyclic or cyclic Basic Unit as part of a self-stabilizing linker ($L_{SS}$), in which $L_R$ within a Ligand Drug Conjugate is $L_{SS}$, results in a succinic acid-amide ($M^3$) moiety, which is a component of self-stabilized linker ($L_S$), as further described herein. As a result, $L_{SS}$ in a Ligand Drug Conjugate compound is hydrolyzed so that $L_{SS}$ as $L_R$ becomes $L_S$. That hydrolysis is controllable due to the protonation state of the Basic Unit (BU), as further described herein, being in appropriate proximity to the succinimide ring system. If no Basic Unit is present in $L_R$, hydrolysis of the succinimide moeity may still occur, but may do so in an uncontrolled manner.

"Primary linker" as the term is used herein, unless otherwise stated or implied by context, refers to a required component of Linker Unit (LU), and for Ligand Drug Conjugates and Drug Linker compounds of the present invention are in some aspects a self-stabilizing ($L_{SS}$) linker or for a Ligand Drug Conjugate is a self-stabilized ($L_S$) linker, as further described herein. A $L_{SS}$ primary linker in a Drug Linker compound or a Ligand Drug Conjugate is characterized by a maleimide ($M^1$) or succinimide ($M^2$) moiety, respectively, while a $L_S$ primary linker in a Ligand Drug Conjugate composition or compound thereof is characterized by a succinic acid amide ($M^3$) moiety. An $L_{SS}$ or $L_S$ primary linker of the present invention is also characterized by a $C_1$-$C_{12}$ alkylene moiety bonded to the imide nitrogen of the maleimide or succinimide ring system of $M^1$ or $M^2$, respectively, or the amide nitrogen of $M^3$, wherein the alkylene moiety in some aspects is substituted by an acyclic Basic Unit and may be further substituted by optional substituents or in other aspects incorporates a cyclic Basic Unit and is optionally substituted. Drug Linker compounds having a $L_{SS}$ primary linker are typically represented in general as $L_{SS}$-$L_O$-$D^+$ while Ligand Drug Conjugates having a $L_{SS}$ primary linker are typically represented in general as L-($L_{SS}$-$L_O$-$D^+$)$_p$ and those having a $L_S$ primary linker are typically represented in general as L-($L_S$-$L_O$-$D^+$)$_p$ in which the variable groups are as previously defined herein.

"Secondary linker" as used herein, unless otherwise stated or implied by context, refers to an organic moiety in a Linker Unit (LU), wherein the secondary linker ($L_O$) is an optional component of that Unit that is present and interconnects a quaternized cytotoxic or cytostatic Drug Unit, such as a quaternized NAMPT Drug Unit, and a primary linker ($L_R$), which is some aspects is a self-stabilizing ($L_{SS}$) linker of a Drug Linker compound or of a Ligand Drug Conjugate, or is a self-stabilized ($L_S$) linker of a Ligand Drug Conjugate upon hydrolysis of $L_{SS}$. Typically, $L_R$ is attached to $L_O$ through a heteroatom or functional group shared between the two Linker Unit components in which $L_O$ is comprised of a self-immolative Spacer Unit (Y) having a PAB or PAB-type moiety, and a Peptide Cleavable Unit. In those aspects W, Y and $D^+$ are arranged in a linear configuration, as represented by —W—Y-$D^+$, wherein W is the Peptide Cleavable Unit and Y bonded to $D^+$ is the PAB or PAB-type self-immolative Spacer Unit. In other aspects, $L_O$ is comprised of a Glucuronide Unit, in which the self-immolative Spacer Unit having the PAB or PAB-type self-immolative moiety is attached to a carbohydrate moiety (Su) through a glycoside cleavable bond in which the carbohydrate moiety and the glycosidic heteroatom (E') that attaches Su to Y is referred to as W' so that W', Y and $D^+$ are arranged in an orthogonal configuration, as represented by —Y(W')-$D^+$, wherein Y bonded to W' and $D^+$ is the PAB or PAB-type self-immolative Spacer Unit.

In either of those aspects, a secondary linker may be further comprised of a first optional Stretcher Unit (A), and/or a Branching Unit (B) when LU is attached to more than one quaternized Drug Unit. When present, the first optional Stretcher Unit, connects $L_R$, which in some aspects is $L_{SS}$ or $L_S$, optionally through intermediacy of B depending on its presence or absence, to the remainder of the secondary linker, or optionally by way of $A_O$, which is an second optional Stretcher Unit that is a component of $L_R$, through —W—Y— or —Y(W')— of the secondary linker, wherein Y, covalently attached to W or W', is a self-immolative Spacer Unit having a PAB or PAB-type moiety.

Since W as a Peptide Cleavable Unit or W' of a Glucuronide Unit is attached to a self-immolative Spacer Unit, enzymatic action on W/W' results in fragmentation of the self-immolative Spacer Unit with concomitant release of $D^+$ as a NAMPTi compound. That fragmentation of the self-immolative Spacer Unit occurs by a 1,4- or 1,6-elimination of $D^+$ from the Spacer Unit's PAB or PAB-type moiety as described herein.

A secondary linker ($L_O$) bonded to $D^+$ in a Linker Unit, as exemplified when only one quaternized NAMPT Drug Unit is attached to LU, is typically represented by structure s1 or structure s2:

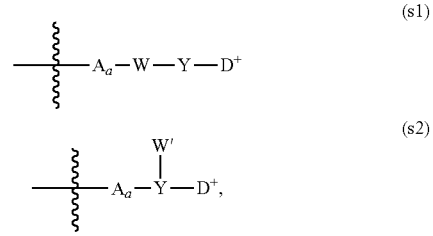

wherein the variable groups are as defined herein. In structure s1, Y is a self-immolative Spacer Unit (Y) as described herein, wherein its PAB or PAB-type moiety is bonded to $D^+$ and W is a Peptide Cleavable Unit. In structure s2, Y is a self-immolative Spacer Unit (Y) as described herein, wherein its PAB or PAB-type moiety is substituted with W' of a Glucuronide Unit and $D^+$, and in a Ligand Drug Conjugate is further substituted with -$L_R$-$A_a$- with $L_R$ bonded to a Ligand Unit (L), or in a Drug Linker compound is further substituted with $L_R$-$A_a$-.

Typically, secondary linkers with structure s1 in which subscripts a is 0 or 1, are represented by:

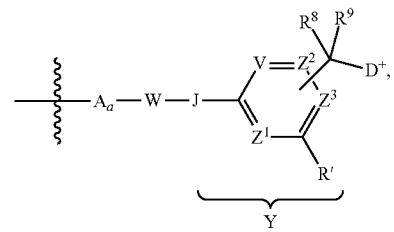

and secondary linkers with structure s2 in which subscripts a is 0 or 1 are represented by:

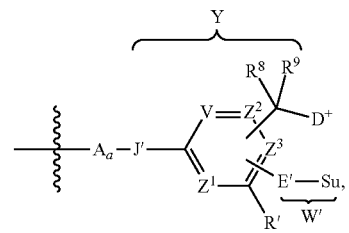

wherein J/J',V, $Z^1$, $Z^2$, $Z^3$, R', $R^8$ and $R^9$ are as defined in embodiments for PAB or PAB-type self-immolative Spacer Units, and E' and Su are as defined in embodiments for Glucuronide Units of formula —Y(W')—, wherein the $A_a$-W-J'- and —C($R^8$)($R^9$)-$D^+$ substituents on the central (hetero)arylene in a secondary linker of structure s1 are ortho or para to each other, or the -E'-Su (i.e., W') and —C($R^8$)($R^9$)-$D^+$ substituents on the central (hetero)arylene in secondary linker of structure s2 are ortho or para to each other.

"Maleimide moiety" as used herein, unless otherwise stated or implied by context, refers to a component of a primary linker of a Drug Linker compound, sometimes represented as $L_R$, and in some aspects is a self-stabilizing linker, sometimes represented as $L_{SS}'$, to indicate that it can be a precursor to $L_R/L_{SS}$ of a Ligand Drug conjugate. A maleimide moiety ($M^1$) is capable of participating in Michael addition (i.e., 1,4-conjugate addition) by a sulfur atom of a reactive thiol functional group of a targeting agent to provide a thio-substituted succinimide ($M^2$) moiety, wherein the thio substituent is a Ligand Unit that incorporates or correspond to the structure of the targeting agent as described herein in a Ligand Drug Conjugate composition or compound thereof. An $M^1$ moiety of a Drug Linker compound is attached to the remainder of the primary linker, through its imide nitrogen. Other than the imide nitrogen, an $M^1$ moiety is typically unsubstituted, but may be asymmetrically substituted at the cyclic double bond of its maleimide ring system. Such substitution can result in regiochemically preferred conjugate addition of a sulfur atom of reactive thiol functional group of a targeting agent to the less hindered or more electronically deficient double bonded carbon atom (dependent on the more dominant contribution) of the maleimide ring system. That conjugate addition results in a succinimide ($M^2$) moiety, which is thio-substituted by a Ligand Unit though a sulfur atom from a thiol functional group provided by the targeting agent. The component of $L_R$ in a Drug Linker compound that is a substituent of the imide nitrogen of $M^1$ and which attaches $L_R$ to the remainder of the Linker Unit is $A_R$, which is a required Stretcher Unit as further described herein.

"Succinimide moiety" as used herein, unless otherwise stated or implied by context, refers to a component of one type of primary linker, which in turn is a component of a Linker Unit of a Ligand Drug Conjugate and results from Michael addition of sulfur tom of a reactive thiol functional group of a targeting agent to the maleimide ring system of a maleimide moiety ($M^1$) in a Drug Linker compound. A succinimide ($M^2$) moiety is therefore comprised of a thio-substituted succinimide ring system that has its imide nitrogen atom substituted with the remainder of the primary linker through its optionally substituted $C_1$-$C_{12}$ alkylene moiety. When the primary linker is a self-stabilizing linker, that moiety incorporates a cyclic Basic Unit or is substituted by an acyclic Basic Unit as described elsewhere, and is optionally substituted with substituent(s) at its succinimide ring system that may have been present on the $M^1$ precursor. In some aspects, those optional substituents on the succinimide ring system are not present and in other aspects the $C_1$-$C_{12}$ alkylene moiety is substituted by $A_O$, which is an second optional Stretcher Unit and when present is a component of the primary linker, at a position distal to its attachment site to the imide nitrogen atom. In turn, the $C_1$-$C_{12}$ alkylene moiety is either covalently attached directly to the secondary linker or indirectly through $A_O$.

When present in a self-stabilizing linker ($L_{SS}$) in a Ligand Drug Conjugate compound, hydrolysis of the succinimide ring system of the thio-substituted succinimide ($M^2$) moiety, which is pH controllable due to the nearby presence of the acyclic or cyclic Basic Unit, can provide regiochemical isomers of succinic acid-amide ($M^3$) moieties in a self-stabilized linker ($L_S$) due to its asymmetric substitution by the thio substituent. The relative amounts of those isomers will be due at least in part to differences in reactivity of the two carbonyl carbons of $M^2$, which can be partially attributed to any substituent(s) that were present in the $M^1$ precursor. Hydrolysis is also expected to occur to some extent when $L_R$ having a $M^2$ moeity that does not contain a Basic Unit, but is highly variable in comparison to the controlled hydrolysis provided by the Basic Unit.

"Succinic acid-amide moiety" as used herein, unless otherwise stated or implied by context, refers to component of a self-stabilized linker ($L_S$) of a Linker Unit within a Ligand Drug Conjugate and has the structure of a succinic amide hemi-acid, which is sometimes referred to as a succinic acid amide, with substitution of its amide nitrogen by another component of $L_S$ wherein that component is an optionally substituted $C_1$-$C_{12}$ alkylene moiety, which in some aspects incorporates cyclic Basic Unit and/or is optionally substituted by $A_O$, or in other aspects is substituted by an acyclic Basic Unit and/or optionally substituted by $A_O$, and wherein the succinic acid-amide ($M^3$) moiety is further substitution by L-S—, wherein L is Ligand Unit incorporating a targeting agent and S is a sulfur atom from that targeting moiety. A succinic acid-amide ($M^3$) moiety results from the thio-substituted succinimide ring system of a succinimide ($M^2$) moiety in self-stabilizing primary linker having undergone breakage of one of its carbonyl-nitrogen bonds by hydrolysis, which is assisted by the Basic Unit. Thus, a succinic acid-amide moiety has a free carboxylic acid functional group and an amide functional group whose nitrogen heteroatom is attached to the remainder of the primary linker, and is substituted by L-S— at the carbon that is alpha to that carboxylic acid or amide functional group, depending on the site of hydrolysis of its $M^2$ precursor. Without being bound by theory, it is believed the aforementioned hydrolysis resulting in the succinic acid-amide ($M^3$) moiety provides a Linker Unit in a Ligand Drug Conjugate that is less likely to suffer premature loss from the Conjugate of its targeting Ligand Unit through elimination of the thio substituent.

"Self-stabilizing linker" as used herein, unless otherwise stated or implied by context, refers to a $M^2$-containing component in a primary linker of a Linker Unit in a Ligand Drug Conjugate or to a $M^1$-containing component of a Linker Unit in a Drug Linker compound, wherein that component may be designated as $L_{SS}'$ to indicate that it is a precursor to the $M^2$-containing component of $L_{SS}$ in a Ligand Drug Conjugate, and which subsequently undergoes conversion under controlled hydrolysis conditions to the corresponding self-stabilized linker ($L_S$). That hydrolysis is facilitated by the Basic Unit component of $L_{SS}$, such that a Ligand Drug Conjugate initially comprised of $L_{SS}$ becomes more resistant to premature loss of its Ligand Unit by virtue of its Linker Unit (LU) now being comprised of $L_S$. The $L_{SS}$ moiety, in addition to its $M^1$ or $M^2$ moiety, is comprised of $A_R$, which is a required Stretcher Unit as further described herein.

In the context of the present invention, $L_{SS}$ of a Drug Linker compound, sometimes shown as $L_{SS}'$ to indicate that it can be a precursor of $L_{SS}$ in a Ligand Drug Conjugate, contains a required Stretcher Unit $A_R$ and a maleimide ($M^1$) moiety through which a targeting agent is to be attached as a Ligand Unit. In some aspects, the $C_1$-$C_{12}$ alkylene moiety of $A_R$ is attached to the imide nitrogen of the maleimide ring system of $M^1$ in a Drug Linker compound and to the remainder of the Linker Unit, the latter of which optionally occurs through $A_O$ of $L_{SS}$, wherein $A_O$ is an optional substituent of the $C_1$-$C_{12}$ alkylene moiety. In some of those aspects, $A_O$ consists or is comprised of an optionally substituted electron withdrawing heteroatom or functional group, referred herein as a Hydrolysis-Enhancing (HE) Unit, which in some aspects in addition to BU may enhance the hydrolysis rate of the $M^2$ moiety in the corresponding $L_{SS}$ moiety to a self-stabilized ($L_S$) moiety, as further described herein, of a Ligand Drug Conjugate compound. After incorporation of the Drug Linker compound into a Ligand Drug Conjugate compound, $L_{SS}$ now contains a succinimide ($M^2$) moiety that is thio-substituted by the Ligand Unit (i.e., Ligand Unit attachment occurs through Michael addition of a sulfur atom of a targeting agent's reactive thiol functional group to the maleimide ring system of $M^1$).

In some aspects, a cyclized Basic unit (cBU) corresponds in structure to an acyclic Basic Unit through formal cyclisation to the basic nitrogen of that Unit so that the cyclic Basic Unit structure is incorporated into $A_R$ as an optionally substituted spiro $C_4$-$C_{12}$ heterocyclo. In such constructs the spiro carbon is attached to the maleimide imide nitrogen of $M^1$, and hence to that nitrogen in $M^2$, and is further attached to the remainder of the Linker Unit optionally through $A_O$, which in some aspects is or is comprised of a Hydrolysis-enhancing (HE) Unit. In that aspect, a cyclic BU assists in the hydrolysis of the succinimide moiety of $M^2$ to its corresponding ring-opened form(s) represented by $M^3$ in qualitatively similar manner to that of an acyclic Basic Unit, which may also be enhanced by HE.

In some aspects, a $L_{SS}$ moiety in a Drug Linker compound, sometimes shown as $L_{SS}'$ to indicate that it can be precursor to $L_{SS}$, of a Ligand Drug Conjugate, according to the present invention, is represented by the general formula of $M^1$-$A_R$(BU)-$A_O$- or -$M^{2-}A_R$(BU)-$A_O$-, respectively, wherein $A_R$(BU) is a required Stretcher Unit ($A_R$) incorporating a cyclic Basic Unit or substituted by an acyclic Basic Unit, $M^1$ and $M^2$ are maleimide and succinimide moieties, respectively, and $A_O$ is an second optional Stretcher Unit, which in some aspects consists or is comprised of HE.

Exemplary, but non-limiting $L_{SS}$ structures for some Ligand Drug Conjugates compounds is represented by:

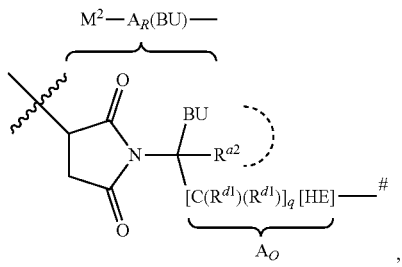

wherein the wavy line indicates the site of covalent attachment to a Ligand Unit, the pound sign (#) indicates the site of covalent attachment to $L_O$, the dotted curved line indicates optional cyclization so that when present BU is a cyclic Basic Unit or when absent BU is an acyclic Basic Unit, the $[C(R^{d1})R^{d1})]_q$—[HE] moiety is $A_O$ of $L_{SS}$ in which $A_O$ is present, wherein HE is an optional Hydrolysis-enhancing Unit, subscript q is 0 or an integer ranging from 1 to 6; each $R^{d1}$ is independently selected from the group consisting of hydrogen and optionally substituted $C_1$-$C_6$ alkyl, or two of $R^{d1}$, the carbon atom(s) to which they are attached and any intervening carbon atoms define an optionally substituted $C_3$-$C_8$ carbocyclo, and the remaining $R^{d1}$, if any, are independently hydrogen or optionally substituted $C_1$-$C_6$; and $R^{a2}$ is an optionally substituted $C_1$-$C_{12}$ alkyl, which in a cyclic Basic Unit along with the carbon atom to which BU and $R^{a2}$ are attached define an optionally substituted spiro $C_4$-$C_{12}$ heterocyclo having a skeletal secondary or tertiary basic nitrogen atom, such that the cyclic Basic Unit is capable of increasing the rate of hydrolysis of the shown succinimide ($M^2$) moiety to provide a succinic acid amide ($M^3$) moiety at a suitable pH in comparison to the corresponding Conjugate in which $R^{a2}$ is hydrogen and BU is replaced by hydrogen, and/or substantially retains the increase in the rate of hydrolysis of the corresponding Conjugate in which in which $R^{a2}$ is hydrogen and BU is an acyclic BU over the aforementioned Conjugate in which $R^{a2}$ is hydrogen and BU is replaced by hydrogen.

Other exemplary $L_{SS}'$ structures, which are present in Drug Linker compounds typically used as intermediates in the preparation of Ligand Drug Conjugate compositions, are represented by:

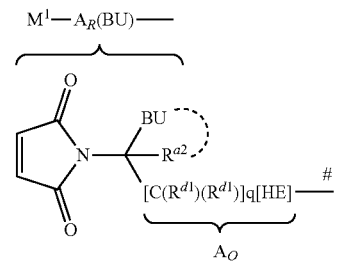

wherein BU and the other variable groups are as defined above for $L_{SS}$ structures in Ligand Drug Conjugates and in the embodiments for that and other exemplary $L_{SS}$ structures. When a Drug Linker compound having a self-stabilizing linker precursor ($L_{SS}'$), which is comprised of a maleimide moiety, is used in the preparation of a Ligand Drug Conjugate, that $L_{SS}'$ moiety is converted into a $L_{SS}$ moiety having a succinimide moiety.

"Self-stabilized linker" is an organic moiety derived from a $M^2$-containing moiety of a self-stabilizing linker ($L_{SS}$) in a Ligand Drug Conjugate that has undergone hydrolysis under controlled conditions so as to provide a corresponding $M^3$-moiety of a self-stabilized linker ($L_S$) wherein that LU component is less likely to reverse the condensation reaction of a targeting moiety with a $M^1$-containing moiety that provided the original $M^2$-containing $L_{SS}$ moiety. In addition to the $M^3$ moiety, a self-stabilized linker ($L_S$) is comprised of $A_R$ incorporating a cyclic Basic Unit or substituted by an acyclic Basic Unit wherein $A_R$ is covalently attached to $M^3$ and the remainder of the Linker Unit in which $L_S$ is a component. The $M^3$ moiety is obtained from conversion of a succinimide moiety ($M^2$) of $L_{SS}$ in a Ligand Drug Conjugate, wherein the $M^2$ moiety has a thio-substituted succinimide ring system resulting from Michael addition of a sulfur atom of a reactive thiol functional group of a targeting moiety to the maleimide ring system of $M^1$ of a $L_{SS}$ moiety in a Drug Linker compound, wherein that $M^2$-derived moiety has reduced reactivity for elimination of its thio-substituent in comparison to the corresponding substituent in $M^2$. In those aspects, the $M^2$-derived moiety has the structure of a succinic acid-amide ($M^3$) moiety corresponding to $M^2$ wherein $M^2$ has undergone hydrolysis of one of its carbonyl-nitrogen bonds of its succinimide ring system, which is assisted by the basic functional group of BU due to its appropriate proximity as a result of that attachment. The product of that hydrolysis therefore has a carboxylic acid functional group and an amide functional group substituted at its amide nitrogen, which corresponds to the imide nitrogen in the $M^2$-containing $L_{SS}$ precursor to $L_S$, with the remainder of LU. In some aspects, the basic functional group is a primary, secondary or tertiary amine of an acyclic Basic Unit, secondary or tertiary amine of a cyclic Basic Unit. In other aspects, the basic nitrogen of BU is a heteroatom of an optionally substituted basic functional group as in a guanidino moeity. In either aspect, the reactivity of the basic functional group of BU for base-catalyzed hydrolysis is controlled by pH by reducing the protonation state of the basic nitrogen, which increases that reactivity.

Thus, a self-stabilized linker ($L_S$) typically has the structure of an $M^3$ moiety covalently bonded to $A_R$ incorporating a cyclic Basic Unit or substituted by an acyclic Basic Unit, wherein $A_R$ in turn is covalently bonded, optionally through $A_O$, to the secondary linker $L_O$. $L_S$ with its $M^3$, $A_R$, $A_O$ and BU components and $L_O$ arranged in the manner so indicated is represented by the formula of $M^3$-$A_R$(BU)-$A_O$-$L_O$- or $M^3$-$A_R$(BU)-$A_O$-$L_O$-, wherein BU represents either type of Basic Unit (cyclic or acyclic).

Exemplary non-limiting structures of $L_{SS}$ and $L_S$ moieties with $M^2$ or $M^3$; and $A_R$(BU), $A_O$ and $L_O$ arranged in the manner indicated above in which BU is acyclic is shown by way of example but not limitation by:

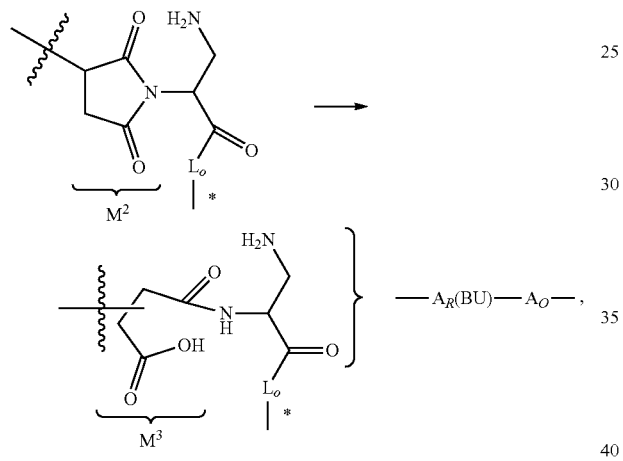

wherein the indicated —CH(CH$_2$NH$_2$)C(=O)— moiety is -$A_R$(BU)-$A_O$-, wherein BU is an acyclic Basic Unit in which $A_R$ is covalently bonded to the imide or amide nitrogen of $M^2$ or $M^3$, respectively, and is substituted by the acyclic Basic Unit, —CH$_2$NH$_2$, and wherein $A_O$ consists of [HE], which is bonded to $L_O$, wherein [HE] is —C(=O)—. Those exemplary structures contain a succinimide ($M^2$) moiety or a succinic acid-amide ($M^3$) moiety from succinimide ring hydrolysis of $M^2$ in the conversion of $L_{SS}$ to $L_S$.

Exemplary structures of $L_{SS}$ and $L_S$ moieties with $M^2$ or $M^3$ and $A_R$(BU) and $A_O$ components bonded to $L_O$ in the manner indicated above in which BU is incorporated into $A_R$ as a cyclic Basic Unit is shown by way of example but not limitation by:

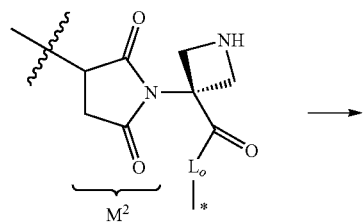

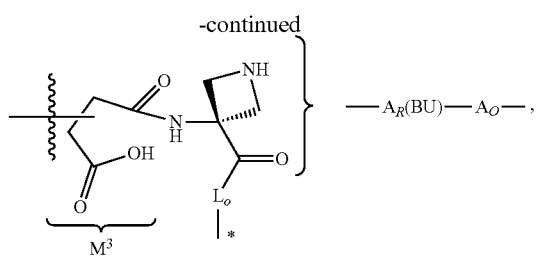

wherein in these $A_R$(BU)-$A_O$ moieties, BU is a heterocyclo cyclic Basic Unit, the structure of which corresponds to the aminoalkyl of an acyclic Basic Unit in an $A_R$(BU) moiety in which the basic nitrogen of the acyclic Basic Unit has been formally cyclized, at least in part, back through $R^{a2}$ to the carbon atom that is alpha to the succinimide nitrogen of $M^2$ to which the acyclic Basic Unit is attached. The wavy line in each of the above $L_{SS}$ and $L_S$ structures indicates the site of covalent attachment of a sulfur atom of a Ligand Unit derived from a reactive thiol functional group of a targeting agent upon Michael addition of that sulfur atom to the maleimide ring system of an $M^1$ moiety in a corresponding Drug Linker compound. The asterisk (*) in each of the above structures indicates the site of covalent attachment of a Drug Unit to the -$L_{SS}$-$L_O$- and -$L_S$-$L_O$-structures of formula -$M^2$/$M^3$-$A_R$(BU)-$A_O$-$L_O$- in which BU is cyclic or acyclic. Since the succinimide ring system of $M^2$ is asymmetrically substituted due to its thio substituent, regiochemical isomers of succinic acid-amide ($M^3$) moieties as defined herein differing in position relative to the liberated carboxylic acid group may result on $M^2$ hydrolysis. In the above structures, the carbonyl functional group attached to $L_O$ exemplifies a hydrolysis enhancer [HE] as defined herein in which [HE] is the indicated $A_O$ component of $L_{SS}$ or $L_S$ that is covalently attached to -$A_R$(BU) and $L_O$.

The -$M^3$-$A_R$(BU)— moieties, wherein BU is acyclic or cyclic Basic Unit, represent exemplary structures of self-stabilized linker ($L_S$) moieties, so named because these structures are less likely to eliminate the thio substituent of the Ligand Unit, and thus cause premature loss of that targeting moiety, in comparison to the corresponding $L_{SS}$ moieties of formula $M^2$-$A_R$(BU). Without being bound by theory, it is believed the increased stability results from the greater conformational flexibility in $M^3$ in comparison to $M^2$, which no longer constrains the thio substituent in a conformation favorable for E2 elimination.

"Basic Unit" as used herein, unless otherwise stated or implied by context, refers to an organic moiety within a self-stabilizing linker ($L_{SS}$) moiety, as described herein, which is carried forward into a corresponding $L_S$ moiety by BU participating in base catalyzed hydrolysis of the succinimide ring system within a $M^2$ moiety comprising $L_{SS}$ (i.e., catalyzes addition of a water molecule to one of the succinimide carbonyl-nitrogen bonds). In some aspects, the base-catalyzed hydrolysis is initiated under controlled conditions tolerable by the targeting Ligand Unit attached to $L_{SS}$. In other aspects the base-catalyzed hydrolysis is initiated on contact of the Drug Linker compound comprised of $L_{SS}$ with a targeting agent in which Michael addition of a sulfur atom of a reactive thiol functional group of the targeting agent effectively competes with hydrolysis of the $L_{SS}$ $M^1$ moeity of the Drug Linker compound. Without being bound by theory, the following aspects describe various considerations for design of a suitable Basic Unit. In one such aspect, the basic functional group of an acyclic Basic Unit and its relative position in $L_{SS}$ with respect to its $M^2$ component are selected for the ability of BU to hydrogen bond to a carbonyl group of $M^2$, which effectively increases its electrophilicity and hence its susceptibility to water attack. In another such aspect, those selections are made so that a water molecule, whose nucleophilicity is increased by hydrogen bonding to the basic functional group of BU, is directed to an $M^2$ carbonyl group. In a third such aspect, those selections are made so the basic nitrogen on protonation does not increase the electrophilicity of the succinimide carbonyls by inductive electron withdrawal to an extent that would promote premature hydrolysis requiring compensation from an undesired excess of Drug Linker compound. In a final such aspect, some combination of those mechanistic effects contributes to catalysis for controlled hydrolysis of $L_{SS}$ to $L_S$.

Typically, an acyclic Basic Unit, which may act through any of the above mechanistic aspects, is comprised of 1 carbon atom or 2 to 6 contiguous carbon atoms, more typically of 1 carbon atom or 2 or 3 contiguous carbon atoms, wherein the carbon atom(s) connect the basic amino functional group of the acyclic Basic Unit to the remainder of the $L_{SS}$ moiety to which it is attached. In order for that basic amine nitrogen to be in the required proximity to assist in the hydrolysis of a succinimide ($M^2$) moiety to its corresponding ring-opened succinic acid amide ($M^3$) moiety, the amine-bearing carbon chain of an acyclic Basic Unit is typically attached to $A_R$ of $L_{SS}$ at the alpha carbon of that moiety relative to the site of attachment of $A_R$ to the succinimide nitrogen of $M^2$ (and hence to the maleimide nitrogen of its corresponding $M^1$-$A_R$ structure). Typically, that alpha carbon in an acyclic Basic Unit has the (S)-stereochemical configuration or the configuration corresponding to that of the alpha carbon of L-amino acids.

As previously described, BU in acyclic form or BU in cyclized form is typically connected to $M^1$ or $M^2$ of $L_{SS}$ or $M^3$ of $L_S$ through an optionally substituted $C_1$-$C_{12}$ alkylene moiety in which that moiety incorporates the cyclized Basic Unit or is substituted by the acyclic Basic Unit and is bonded to the maleimide or succinimide nitrogen of $M^1$ or $M^2$, respectively, or the amide nitrogen of $M^3$. In some aspects, the $C_1$-$C_{12}$ alkylene moiety incorporating the cyclic Basic Unit is covalently bonded to $L_O$ and typically occurs through intermediacy of an ether, ester, carbonate, urea, disulfide, amide carbamate or other functional group, more typically through an ether, amide or carbamate functional group, of $A_O$. Likewise, BU in acyclic form is typically connected to $M^1$ or $M^2$ of $L_{SS}$ or $M^3$ of $L_S$ through an optionally substituted $C_1$-$C_{12}$ alkylene moiety, including optional substitution by $A_O$, wherein the alkylene moeity is substituted by the acyclic Basic unit at the same carbon of the $C_1$-$C_{12}$ alkylene moiety that is attached to the imino nitrogen atom of the maleimide or succinimide ring system of $M^1$ or $M^2$ or the amide nitrogen of $M^3$ subsequent to hydrolysis of the succinimide ring system of $M^2$.

In some aspects, a cyclic Basic Unit incorporates the structure of an acyclic BU by formally cyclizing an acyclic Basic Unit to an optionally substituted $C_1$-$C_{12}$ alkyl ($R^{a2}$) and bonded to the same alpha carbon as the acyclic Basic Unit, thus forming a spirocyclic ring system so that a cyclic Basic Unit is incorporated into the structure of $A_R$ rather than being a substituent of $A_R$ as when BU is acyclic. In those aspects, the formal cyclization is to the basic amine nitrogen of an acyclic Basic Unit thus providing a cyclic Basic Unit as an optionally substituted symmetrical or asymmetrical spiro $C_4$-$C_{12}$ heterocyclo, depending on the relative carbon chain lengths in the two alpha carbon substituents and the sites therein of formal cyclization, in which the basic nitrogen is now a basic skeletal heteroatom. In order for that cyclization to substantially retain the basic properties of the acyclic Basic Unit in a cyclic Basic Unit, the basic nitrogen atom of the acyclic Basic Unit nitrogen should be that of a primary or secondary amine and not a tertiary amine since that would result in a quaternized skeletal nitrogen in the heterocyclo of the cyclic Basic Unit. In that aspect of formal cyclization of an acyclic Basic Unit to a cyclic Basic Unit, in order to substantially retain the ability of the basic nitrogen to assist in hydrolysis of $M^2$ to $M^3$ in conversion of $L_{SS}$ to $L_S$, the resulting structure of the cyclic Basic Unit in these primary linkers will typically have its basic nitrogen located so that no more than three, and typically one or two, intervening carbon atoms are between the basic nitrogen atom and the spiro alpha carbon of the $A_R$ component. Cyclic Basic Units incorporated into $A_R$ and the $L_{SS}$ and $L_S$ moieties having those as components are further described by the embodiments of the invention.

"Hydrolysis-enhancing Unit" as used herein, unless otherwise stated or implied by context, refers to is electron withdrawing group or moiety that is an optional substituent of an $L_{SS}$ moiety and its hydrolysis product $L_S$. A Hydrolysis-enhancing [HE] Unit is a second optional Stretcher Unit ($A_O$) or subunit thereof that when present is a substituent of $A_R$ and thus is another component of $L_{SS}$, wherein $A_R$ is bonded to the imide nitrogen of an $M^2$ moiety, so that the electron withdrawing effect of HE can increase the electrophilicity of the succinimide carbonyl groups in that moiety for its conversion to a $M^3$ moiety of $L_S$. With $A_R$ incorporating or substituted by a cyclic Basic Unit or an acyclic Basic Unit, respectively, the potential effect of HE on the carbonyl groups of $M^2$ for increasing the hydrolysis rate to $M^3$ by induction and the aforementioned effect(s) of either type of BU, are adjusted so that premature hydrolysis of $M^1$ does not occur to an appreciable extent during preparation of a Ligand Drug Conjugate from a Drug Linker compound comprised of the structure of $M^1$-$A_R$(BU)—[HE]—. Instead, the combined effects of BU and [HE] to promote hydrolysis (i.e., conversion of an -$M^2$-$A_R$(BU)—[HE]— moiety of a Ligand Drug Conjugate compound to its corresponding -$M^3$-$A_R$(BU)—[HE]— moiety) under controlled conditions (as when pH is purposely increased so as to decrease protonation of the Basic Unit) are such that an undue molar excess of Drug Linker compound to compensate for hydrolysis of its $M^1$ moiety is not required. Therefore, Michael addition of the sulfur atom of a reactive thiol functional group of the targeting agent to the maleimide ring system of $M^1$, which provides a targeting Ligand Unit attached to a succinimide ring system of $M^2$, typically occurs at a rate that effectively competes with $M^1$ hydrolysis. Without being bound by theory, it is believed that at low pH, as for example when the basic amine of BU is in the form of a TFA salt, premature hydrolysis of $M^1$ in a Drug Linker product is much slower than when the pH is raised to that suitable for base catalysis using an appropriate buffering agent and that an acceptable molar excess of Drug Linker compound can adequately compensate for any loss due to premature $M^1$ hydrolysis that does occur during the time course for completion or near completion of the Michael addition of a sulfur atom of a targeting agent's reactive thiol functional group to a Drug Linker compound's $M^1$ moiety.

As previously discussed, enhancement of carbonyl hydrolysis by either type of Basic Unit is dependent on the basicity of its functional group and the distance of that basic functional group in relation to the $M^1$/$M^2$ carbonyl groups. Typically, the HE Unit is a carbonyl moiety (i.e., ketone or —C(=O)—) or other carbonyl-containing functional group located distal to the end of $A_R$ that is bonded to $M^2$, or $M^3$ derived therefrom, and that also provides for covalent attachment of $L_{SS}$ or $L_S$ to the secondary linker ($L_O$). Carbonyl-containing functional groups other than ketone include esters, carbamates, carbonates and ureas. When HE is a carbonyl-containing functional group other than ketone, the carbonyl moiety of that functional group, which $A_O$ is comprised or consists of and is shared with $L_O$, is typically bonded $A_R$. In some aspects, the HE Unit may be sufficiently distant within $A_R$ from the imide nitrogen to which $A_R$ is also covalently bonded so that no discernable or minor effect on hydrolytic sensitivity of the succinimide carbonyl-nitrogen bonds of an $M^2$-containing moiety is observable, but instead is driven primarily by BU.

"Stretcher Unit" as used herein, unless otherwise stated or implied by context, refers to an organic moiety in a primary or secondary linker of a Linker Unit that physically separates the targeting Ligand Unit from other intervening components of the Linker Unit that are more proximal to the Drug Unit. An $A_R$ Stretcher Unit is a required component in a $L_{SS}$ or $L_S$ primary linker since it provides the Basic Unit, although corresponding structures to which there is no BU attached or incorporated therein are sometimes indicate as $A_R$. The presence of a first optional Stretcher Unit (A) of $L_O$ and/or second optional Stretcher Unit ($A_O$) of $L_{SS}/L_S$ may be required when there is insufficient steric relief from the Ligand Unit provided by an $L_{SS}$ primary linker absent one or both of those optional Stretcher Units to allow for efficient processing of a Linker Unit in a quaternized drug linker moiety of a Ligand Drug Conjugate for release of its quaternized cytotoxic or cytostatic Drug Unit, such as the release of a quaternized NAMPT Drug Unit as a NAMPTi compound. Alternatively, or in addition to steric relief, those optional components may be included for synthetic ease in preparing a Drug Linker compound. A first or second optional Stretcher Unit (A or $A_O$) can each be independently a single distinct unit or can contain multiple subunits. Typically, A or $A_O$ is one distinct unit or has 2 to 4 distinct subunits. In some aspects A or $A_O$, or a subunit of either one, has the formula of -$L^P$(PEG)- whose variable groups are defined elsewhere.

In some aspects, in addition to covalent attachment to $M^1$ of a Drug Linker compound or $M^2/M^3$ of a Ligand Drug Conjugate compound, $A_R$ is bonded to a secondary linker optionally through $A_O$ wherein $A_O$, as a substituent of $A_R$ and thus a component of $L_{SS}/L_S$, is comprised or consists of a carbonyl-containing functional group, which can serve as a Hydrolysis-enhancing (HE) Unit for improving the rate of conversion of $L_{SS}$ to $L_S$, which is catalyzed by an cyclic Basic Unit as incorporated into $A_R$ or by an acyclic Basic Unit as a substituent of $A_R$. In some of those aspects, $A_R$ in which $A_O$ is absent, or $A_R$-$A_O$ in which $A_O$ is present, is bonded to a secondary linker ($L_O$) through a Branching Unit of $L_O$, if in Formula 1, Formula 1a, Formula 1b, Formula I, Formula Ia, or Formula Ib, subscript n is 2 or more, which requires that subscript b is 1. In other aspects, if subscript n is 1, which requires that subscript b is 0, then $A_R$ is bonded to a secondary linker ($L_O$) optionally through a second optional Stretcher Unit ($A_O$) of $L_{SS}$ or $L_S$, or $A_R$ or $A_O$ is bonded to $L_O$ through a first optional Stretcher Unit (A) of $L_O$, when subscript a is 1, or through W when subscript a is 0 and components W, Y and $D^+$ are arranged linearly (i.e., arranged as —W—Y-$D^+$), wherein W is a Peptide Cleavable Unit. In still other aspects, $A_R$ in which $A_O$ is absent, or $A_R$-$A_O$ in which $A_O$ is present of $L_{SS}$ or $L_S$ is bonded to Y in a Glucuronide Unit of formula —Y(W')—, so that W, Y and $D^+$ are arranged orthogonally (i.e., arranged as —Y(W')-$D^+$), when subscript a is 0, or is bonded to A of $L_O$ when subscript a is 1.

Some Linker Units in an Ligand Drug Conjugate or Drug Linker compound contain the formula of -$L^P$(PEG)-W—Y—, in which subscript a is 1 and A, or a subunit thereof, in Formula 1, Formula 1a, Formula 1b, Formula I, Formula Ia, or Formula Ib is -$L^P$(PEG)-, and wherein W is a Peptide Cleavable Unit, or contain the formula -$L^P$(PEG)-Y(W')-in which subscript a is 1 and A, or a subunit thereof, in Formula 1, Formula 1a, Formula 1b, Formula I, Formula Ia, or Formula Ib is -$L^P$(PEG)-, wherein —Y(W')— is a Glucuronide Unit in which L is a Parallel Connecter Unit and PEG is a PEG Unit.

Typically, when subscript a is 1, a first optional Stretcher Unit (A) is present and contains one carbon atom or two to six contiguous carbon atoms that connects A to $A_R$ or to a second optional Stretcher Unit ($A_O$), depending on the absence or presence of $A_O$, respectively, of the primary linker, when subscript b is 0 or to B when subscript b is 1, through one functional group and connects A to W, wherein W is a Peptide Cleavable Unit, or to Y of a Glucuronide Unit, within the secondary linker through another functional group. In some aspects of Formula 1, Formula 1a, Formula 1b, Formula I, Formula Ia or Formula Ib, subscript a is 0, so that no first Stretcher Unit is present, or subscript a is 1 wherein A is an α-amino acid, a β-amino acid or other amine-containing acid residue so that A is bonded to $A_R$ in which $A_O$ is absent, or $A_R$-$A_O$ in which $A_O$ is present or to B, and to W or Y of —Y(W')— through amide functional groups. In other aspects, A is bonded to $A_O$ of $A_R$, when $A_O$ is present and consists or is comprised of a Hydrolysis-enhancing Unit (HE).

"Branching Unit" as used herein, unless otherwise stated or implied by context, refers to a tri-functional or multi-functional organic moiety that is an optional component of a Linker Unit (LU). A Branching Unit (B) may be a single distinct unit or may be comprised of multiple subunits to provide the required sites of covalent attachment when more than one quaternized cytotoxic or cytostatic Drug Units, inclusive of quaternized NAMPT Drug ($D^+$) Units, typically 2, 3 or 4, are attached to a Linker Unit (LU) of a quaternized drug linker moiety in a Ligand Drug Conjugate compound or Drug Linker compound. In a Ligand Drug Conjugate of Formula 1, Formula 1a, Formula 1b, or a Drug Linker compound of Formula I, Formula Ia or Formula Ib, the presence of a Branching Unit is indicated when subscript b of $B_b$ is 1, which occurs when subscript n greater than 1 in any one of these structural formulae. A Branching Unit is at least trifunctional in order to be incorporated into a secondary linker unit ($L_O$) having 2 attached quaternized Drug Units. In aspects where n is 1, a Branching Unit is not present, as indicated when subscript b is 0. Drug Linker or Ligand Drug Conjugate compounds with a Branching Unit due to multiple $D^+$ units per LU have Linker Units containing the formula —B-$A_a$-W—Y—, wherein subscripts a is 0 or 1 and W is a Peptide Cleavable Unit, or have Linker Units containing formula —B-$A_a$-Y(W')—, wherein subscript a is 0 or 1, wherein —Y(W') within that formula is a Glucuronide Unit. As A can contain formula -$L^P$(PEG)-, in those instances Linker Units can contain formula -$L^P$(PEG)-W—Y— or -$L^P$(PEG)-Y(W')— when subscript b is 0 or formula —B-$L^P$(PEG)-W—Y— or —B-$L^P$(PEG)-Y(W')— when subscript b is 1.

In some aspects, a natural or un-natural amino acid or other amine-containing acid compound having a functionalized side chain serves as a Branching Unit or subunit thereof. In some aspects B is a lysine, glutamic acid or aspartic acid moiety in the L- or D-configuration in which the epsilon-amino, gamma-carboxylic acid or beta-carboxylic acid functional group, respectively, along with their amino and carboxylic acid termini, interconnects B within the remainder of LU and to two of $D^+$.

"Cleavable Unit" as used herein, unless otherwise stated or implied by context, refers to an organic moiety that provides for a reactive site within a Linker Unit wherein reactivity towards that site is greater within or surrounding an abnormal cell such as a hyper-proliferating cell or hyper-stimulated immune cell, which in some aspects is due to a greater amount of enzymatic or non-enzymatic activity in these locations sufficient to result in reduced number and/or severity of adverse events typically associated with administration of equimolar amount of free drug, which is expected to provide a desired therapeutic index, in comparison to normal cells that typically are not present at the site or are distant from the site of the abnormal cells such that action upon the reactive site of the Linker Unit results in preferential exposure of the abnormal cells to a cytotoxic or cytostatic compound such as NAMPTi compound released from a Ligand Drug Conjugate compound having that Linker Unit. The exposure from release of the NAMPTi compound is initiated by enzymatic or non-enzymatic action on the Linker Unit having that Cleavable Unit. In some aspects of the invention, a Cleavable Unit contains a reactive site cleavable by an enzyme whose activity or abundance is greater within or surrounding the hyper-proliferating, immune-stimulating or other abnormal cells compared to normal cells or the vicinity of normal cells that are distant from the site of the abnormal cells, which results in the reduced number and/or severity of adverse events typically associated with administration of equimolar amount of free drug. In some of those aspects of the invention, the Cleavable Unit is a substrate for a protease so that W in Formula 1, Formula 1a, Formula 1b, Formula I, Formula Ia or Formula Ib is a Peptide Cleavable Unit, which in some aspects is a substrate for a regulatory protease. In other aspects, the Cleavable Unit is a Glucuronide Unit of formula —Y(W')— replacing W in Formula 1, Formula 1a, Formula 1b, Formula I, Formula Ia or Formula Ib wherein the Glucuronide Unit is a substrate for a glycosidase. In either of those aspects, the protease, or glycosidase is sometimes located intracellularly in targeted cells (i.e., the reactive site of the Cleavable Unit is a peptide bond or glycoside bond, respectively, cleavable by the protease or glycosidase), or the peptide or glycoside bond of the Cleavable Unit and is capable of selective cleavage by an intracellular regulatory protease, hydrolase or glycosidase. In some of those aspects, the reactive site is more likely operated upon enzymatically subsequent to cellular internalization of a Ligand Drug Conjugate compound into a targeted abnormal cell in comparison to enzymatic action by serum proteases, hydrolases, or glycosidases.

Functional groups that provide for cleavable bonds include, by way of example and not limitation, carboxylic acid or amino groups that form an amide bond, as in peptide bonds that are susceptible to enzymatic cleavage by proteases produced or excreted preferentially by abnormal cells in comparison to normal cells distant from the site of the abnormal cells or by a regulatory protease within a targeted cell. Other functional groups that provide for cleavable bonds are found in sugars or carbohydrates having a glycosidic linkage that are substrates for glycosides, which sometimes may be produced preferentially by abnormal cells in comparison to normal cells. Alternatively, the protease or glycosidase enzyme required for processing of the Linker Unit to release a quaternized NAMPT Drug Unit as a NAMPTi compound need not be produced preferentially by abnormal cells in comparison to normal cells provided the processing enzyme is not excreted by normal cells to an extent that would cause undesired side effects from premature release of $D^+$ as the NAMPTi compound. In other instances, the required protease or glycosidase enzyme may be excreted, but to avoid undesired premature release of drug, some aspects of the invention typically require the processing enzyme be excreted in the vicinity of abnormal cells and remain localized to that environment, whether produced by abnormal cells or nearby normal cells in response to the abnormal environment caused by the abnormal cells. In that respect, W as a Peptide Cleavable Unit or W' of a Glucuronide Unit is selected to be preferentially acted upon by a protease or glycosidase, respectively, in or within the environment of abnormal cells in contrast to freely circulating enzymes. In those instances, a Ligand Drug Conjugate compound is less likely to release $D^+$ as a NAMPTi compound in the vicinity of unintended normal cells, nor would it be internalized to any appreciable extent into normal cells that do intracellularly produce but do not excrete the enzyme intended to be acted upon by the internalized Ligand Drug Conjugate compound since such cells are less likely to display a targeted moiety required for entry by that compound or have sufficient copy number of that targeted moiety.

In some aspects, a Peptide Cleavable Unit (W) of Formula 1, Formula 1a, Formula 1b, Formula I, Formula Ia or Formula Ib is comprised of an amino acid or is comprised or consists of one or more non-sequential sequences of amino acids that provide a substrate for a protease present within abnormal cells or a protease localized to the environment of these abnormal cells. Thus, W may be comprised or consist of a dipeptide, tripeptide, tetrapeptide, pentapeptide, hexapeptide, heptapeptide, octapeptide, nonapeptide, decapeptide, undecapeptide or dodecapeptide moiety incorporated into a Linker Unit through an amide bond to a PAB or PAB-type moiety of a self-immolative Spacer Unit (Y) wherein the peptide moiety provides a recognition sequence for that protease. In other aspects, W of Formula 1, Formula 1a, Formula 1b, Formula I, Formula Ia or Formula Ib is replaced by —Y(W')—, sometimes referred to as a Glucuronide Unit, wherein W' is a carbohydrate moiety (Su) attached to a PAB or PAB-type moiety of the Glucuronide Unit's self-immolative Spacer Unit (Y) by a glycosidic bond through an optionally substituted heteroatom (E') that is cleavable by a glycosidase preferentially produced by abnormal cells, or is found in such cells to which an Ligand Drug Conjugate compound having that Spacer Unit and carbohydrate moiety has selective entry due to the presence of the targeted moiety on the abnormal cells.

"Spacer Unit" as used herein, unless otherwise stated or implied by context, refers to a component in a secondary linker ($L_O$) within a Linker Unit of a Ligand Drug Conjugate or Drug Linker compound that is covalently bonded to a quaternized NAMPT Drug Unit ($D^+$), and in some aspects is also covalently bonded to a first optional Stretcher Unit (A) if subscript b is 0 in Formula 1, Formula 1a, Formula 1b, Formula I, Formula Ia or Formula Ib or to a Branching Unit (B) if subscript b is 1 in any one of these formulae or to a second optional Stretcher Unit ($A_O$), if A and B are absent (i.e., subscripts a and b are both 0), or to $A_R$ if none of these other Linker Unit components are present. In some aspects, Y is covalently bonded to W and $D^+$, wherein W is a Peptide Cleavable Unit and Y is capable self-immolation so that Y is a self-immolative Spacer Unit. In other aspects, Y is a component of a Glucuronide Unit of formula —Y(W'), wherein Y bonded to W' is a self-immolative Spacer Unit in order for $D^+$ to be released as a NAMPTi compound subsequent to cleavage of the glycosidic bond between W' and Y.

Typically, in one configuration W, Y, and $D^+$ are arranged linearly with $D^+$ bonded to Y in Formula 1, Formula 1a, Formula 1b, Formula I, Formula Ia or Formula Ib, wherein W is a Peptide Cleavable Unit, so that protease action upon W initiates release $D^+$ as a NAMPTi compound. Typically, in another configuration in which a Ligand Drug Conjugate contains a Glucuronide Unit of formula —Y(W')—, in which W within a secondary linker ($L_O$) of Formula 1, Formula 1a, Formula 1b, Formula I, Formula Ia or Formula Ib is replaced by that Unit, wherein W' of the Glucuronide Unit and $D^+$ are covalently bonded to Y, wherein Y is a self-immolative Spacer Unit, and Y in turn is also bonded to A, B, $A_O$ or $L_R$, depending on the presence or absence of A, B and/or $A_O$, so that W' is orthogonal to the remainder of $L_O$. As before, glycosidase action is followed by self-immolation of Y to release $D^+$ as a free cytotoxic or cytostatic drug, such as a NAMPTi compound, comprised of a nitrogen-containing heteroaryl in which the skeletal nitrogen is no longer quaternized. In either configuration, Y may also serve to separate the cleavage site of the Peptide Cleavable Unit or Glucuronide from $D^+$ to avoid steric interactions from that Unit that would interfere with cleavage of W/W'.

Typically, a self-immolative Spacer Unit is comprised or consists of a PAB or PAB-type moiety bonded to a NAMPT Drug Unit ($D^+$) as defined herein so that enzymatic processing of the Peptide Cleavable Unit or Glucuronide activates the self-immolative PAB or PAB-type moiety for self-destruction thus initiating release of the quaternized NAMPT Drug Unit as NAMPTi compound. In some aspects, a PAB or PAB-type moiety of a self-immolative Spacer Unit is covalently bonded to $D^+$ and to W as a Peptide Cleavable Unit through an amide (or anilide) functional group cleavable by a protease, whereas in other aspects the PAB or PAB-type moiety is covalently bonded to $D^+$ and to W' of a Glucuronide Unit through a glycosidic bond cleavable by a glycosidase.

In either of those aspects, a quaternized NAMPT Drug Unit is directly attached to the PAB or PAB-type moiety of the self-immolative Spacer Unit through a quaternized skeletal nitrogen atom of a nitrogen-containing partially unsaturated heterocyclic or heteroaromatic component of that Unit wherein that component corresponds to or is a bioisostere of the pyridinyl moiety of nicotinamide and remains capable of interacting with enzymatically competent NAMPT homodimer at its nicotinamide binding site when the quaternized NAMPT Drug Unit is released from a Ligand Drug Conjugate compound of the composition as a NAMPT inhibitor (NAMPTi) compound. Typically, the nitrogen-containing partially unsaturated heterocyclic or heteroaromatic component whose nitrogen atom is quaternized is that of a NAMPT Head ($H_N$) Unit, wherein that Unit is capable of interacting with enzymatically competent NAMPT homodimer at the binding site occupied by the pyridine heterocycle of nicotinamide when the quaternized NAMPT Drug Unit is released from a Ligand Drug Conjugate compound as a NAMPTi compound. In some of those aspects, the quaternized nitrogen is that of a 5- or 6-membered partially unsaturated heterocyclic or heteroaromatic ring system that comprises $H_N$ in a NAMPTi compound of general structure $H_N$-DA-$I_N$-$T_N$.

In any one of the above aspects in which W is a peptide Cleavable Unit, the PAB or PAB-type moiety of a self-immolative Spacer Unit (Y) is attached to a quaternized NAMPT Drug Unit ($D^+$) and to W by an amide or anilide functional group, and enzymatic action upon that functional group results in release of $D^+$ due to spontaneous self-destruction of the PAB or PAB-type moiety of Y to provide a NAMPTi compound, which sometimes has the formula of $H_N$-DA-$I_N$-$T_N$, wherein $T_N$, $I_N$, DA and $H_N$ are as defined herein for NAMPTi compounds or quaternized NAMPT Drug Units. In other aspects, the PAB or PAB-type moiety of a self-immolative Spacer Unit (Y) is attached to a quaternized NAMPT Drug Unit ($D^+$) and W' of a Glucuronide Unit through a glycosidic bond so that enzymatic cleavage of that bond initiates release of $D^+$ due to spontaneous self-destruction of the PAB or PAB-type moiety of Y to provide a NAMPTi compound, which sometimes has the formula of $H_N$-DA-$I_N$-$T_N$, wherein $H_N$, DA, $I_N$ and $T_N$ are as defined herein. In those instances, in which the site of quaternization is a skeletal nitrogen atom of a 5- or 6-membered partially unsaturated heterocyclic ring system, release of $D^+$ results in aromatization of that ring system so that the NAMPTi compound from that release has a NAMPTi Head Unit having a 5- or 6-membered aromatic ring system whose skeletal nitrogen atom is no longer quaternized.

"Self-immolating moiety" as used herein refers to a bifunctional moiety within a Spacer Unit (Y) wherein the self-immolative moiety is covalently attached to $D^+$ through a quaternized skeletal nitrogen of a partially unsaturated nitrogen-containing heterocyclic or heteroaromatic component of that quaternized Drug Unit, wherein that component corresponds to the pyridinyl moiety of nicotinamide and is capable of interacting with enzymatically competent NAMPT homodimer at its nicotinamide binding site when the quaternized NAMPT Drug Unit is released from a Ligand Drug Conjugate compound of the composition as a NAMPT inhibitor (NAMPTi) compound, and is also covalently attached to an amino acid residue of W wherein W is a Peptide Cleavable Unit through an optionally substituted heteroatom (J), or to a optionally substituted heteroatom glycosidic heteroatom (E'), bonded to the carbohydrate moiety (Su) of W' of a Glucuronide Unit of formula —Y(W')— so that the self-immolative moiety incorporates these quaternized drug linker components into a normally stable tripartite molecule unless activated, where such substitution of J or E' is permitted provide that such substitution is consistent with the electron-donating properties required for self-immolation as described herein on activation.

On activation, the covalent bond to W in which W is a Peptide Cleavable Unit or the glycosidic bond of W' in a Glucuronide Unit of formula —Y(W')— replacing W is cleaved so that $D^+$ spontaneously separates from the tripartite molecule by self-destruction of the PAB or PAB-type moiety of the self-immolative Spacer Unit resulting in release a NAMPTi compound, which no longer has a quaternized nitrogen. In either of those aspects, self-destruction of Y occurs in some instances after cellular internalization of a Ligand Drug Conjugate compound comprised of a quaternized NAMPT Drug Unit ($D^+$) and a Linker Unit having a self-immolative Spacer Unit in which its PAB or PAB-type moiety is bonded $D^+$.

In some aspects, a component of a PAB or PAB-type moiety of a self-immolative Spacer Unit intervening between $D^+$ and the optionally substituted heteroatom J of Y, wherein J is bonded to W as a Peptide Cleavable Unit, has the formula of —$C_6$-$C_{24}$ arylene-C($R^8$)($R^9$)—, —$C_5$-$C_{24}$ heteroarylene-C($R^8$)($R^9$)—, —$C_6$-$C_{24}$ arylene-C($R^8$)=C ($R^9$)— or —$C_5$-$C_{24}$ heteroarylene-C($R^8$)=C($R^9$)—, in which the (hetero)arylene is optionally substituted, wherein $R^8$ and $R^9$ are as described by the embodiments of the invention, and typically is $C_6$-$C_{10}$ arylene-$CH_2$— or $C_5$-$C_{10}$ heteroarylene-$CH_2$—, in which the (hetero)arylene is optionally substituted with an electron donating group.

In other aspects, a component of a PAB or PAB-type moiety of a self-immolative Spacer Unit (Y) in a Glucuronide Unit of formula —Y(W')— replacing W and intervening between $D^+$ and the optionally substituted heteroatom E' in W' has the formula of —$C_6$-$C_{24}$ arylene-C($R^8$)($R^9$)—, —$C_5$-$C_{24}$ heteroarylene-C($R^8$)($R^9$)—, —$C_6$-$C_{24}$ arylene-C($R^8$)=C($R^9$)— or —$C_5$-$C_{24}$ heteroarylene-C($R^8$)=C($R^9$)—, in which the (hetero)arylene is optionally substituted, and typically is $C_6$-$C_{10}$ arylene-$CH_2$— or $C_5$-$C_{10}$ heteroarylene-$CH_2$— in which the (hetero)arylene is optionally substituted with an electron withdrawing group, wherein $R^8$ and $R^9$ are as described by the embodiments of the invention, in which the central (hetero)arylene of the intervening component is also substituted with -$A_a$-$L_R$ in a Drug Linker compound, or -$A_a$-$L_R$- in a Ligand Drug Conjugate compound, having a Glucuronide-based Linker Unit and is otherwise optionally substituted, wherein A is a first optional Stretcher Unit, subscript a is 0 or 1 and $L_R$ is a primary linker. In those aspects -$A_a$-$L_R$- is bonded to the central (hetero)arylene through an optionally substituted heteroatom (J') or functional group comprised of J', which is independently selected from E'.

In either aspect, the intervening component of the PAB or PAB-type moiety of a self-immolative Spacer Unit is capable of undergoing fragmentation to form a iminoquinone methide or related structure by 1,4 or 1,6-elimination with concomitant release of $D^+$ on cleavage of the protease cleavable bond between J and W or on cleavage of the glycosidase cleavable bond of W'. In some aspects, a self-immolative Spacer Unit having the aforementioned central (hetero)arylene component bonded to J, or to W' and -$A_a$-$L_R$-, is exemplified by an optionally substituted p-aminobenzyl alcohol (PAB) moiety, ortho or para-aminobenzylacetal moiety, or residues of other aromatic compounds that are electronically similar to the PAB group (i.e., PAB-type) such as 2-aminoimidazol-5-methanol derivatives (see, e.g., Hay et al., 1999, *Bioorg. Med. Chem. Lett.* 9:2237) or those in which the phenyl group of the p-aminobenzyl alcohol (PAB) moiety is replaced by a heteroarylene.

In a Glucuronide Unit, the central (hetero)arylene to which W' and —C($R^8$)($R^9$)-$D^+$ or —C($R^8$)=C($R^9$)-$D^+$ are bound is sometimes substituted with an electron withdrawing group, which sometimes can increase the rate of glycosidic cleavage, but may decrease the rate of fragmentation of the self-immolative moiety Spacer Unit to release $D^+$ as a NAMPTi compound due to destabilization of the quinone-methide intermediate produced as an obligatory by-product of that fragmentation.

Without being bound by theory, an aromatic carbon of the central arylene or heteroarylene group of a PAB or PAB-type moiety of a self-immolative Spacer Unit in a Peptide Cleavable-based Linker Unit is substituted by J, wherein the electron-donating heteroatom of J is attached to the cleavage site of W in a Peptide Cleavable-based Linker Unit so that the electron-donating capacity of that heteroatom is attenuated (i.e., EDG ability is masked by incorporation of a PAB or PAB-type moiety of a Self-immolative Spacer Unit into the Peptide Cleavable-based Linker Unit). The other required substituent of the hetero(arylene) is an optionally substituted benzylic carbon that is attached to the quaternized NAMPT Drug Unit ($D^+$), wherein the benzylic carbon is attached to another aromatic carbon atom of the central (hetero)arylene, wherein the aromatic carbon bearing the attenuated electron-donating heteroatom is adjacent to (i.e., 1,2-relationship), or two additional positions removed (i.e., 1,4-relationship) from that other aromatic carbon atom.

Likewise, in a Glucuronide-based Linker Unit, the central (hetero)arylene group of a PAB or PAB-type moiety of its self-immolative Spacer Unit is substituted by W' through a glycosidic bond wherein the electron-donating ability of the optionally substituted heteroatom (E') of that bond is attenuated (i.e., EDG ability is masked by incorporation of the PAB or PAB-type moiety of a Self-immolative Spacer Unit into a Glucuronide-based Linker Unit). The other required substituents of the hetero(arylene) are (1) the remainder of the Linker Unit of formula -$A_a$-$L_R$ in a Drug Linker compound or -$A_a$-$L_R$- in Ligand Drug Conjugate compound, wherein the remainder of the Linker Unit is attached to a second aromatic carbon atom of the central (hetero)arylene and (2) a benzylic carbon that is attached to the quaternized NAMPT Drug Unit ($D^+$), wherein the benzylic carbon is attached to a third aromatic carbon atom of the central (hetero)arylene, wherein the aromatic carbon bearing the attenuated electron-donating heteroatom is adjacent to (i.e., 1,2-relationship), or two additional positions removed (i.e., 1,4-relationship) from that third aromatic carbon atom.

In either type of Linker Unit, the EDG heteroatom is chosen so that upon processing of the cleavage site of W as a Peptide Cleavable Unit or W' of a Glucuronide Unit replacing W, the electron-donating capacity of the masked heteroatom is restored thus triggering a 1,4- or 1,6-elimination to expel -$D^+$ as a NAMPTi compound from the benzylic substituent. Exemplary, but non-limiting, self-immolative moieties and self-immolative Spacer Unit having those self-immolative moieties are exemplified by the embodiments of the invention.

"NAMPTi compound" as used herein, unless otherwise stated or implied by context, refers to a compound capable of exerting a therapeutic effect by inhibition of intracellular nicotinamide phosphoribosyltransferase (NAMPT), which is present in its enzymatically active form as a homodimer. A NAMPTi compound or its derivative typically binds to a narrow tunnel (15×6 angstroms) in the interface between the two monomers of the enzymatically competent NAMPT dimer in which the amino acid sequences of the monomers are arranged anti-parallel to each other, and is sometimes divided into four components: a NAMPT Head Unit ($H_N$), a Donor-Acceptor Unit (DA), an Interconnecting Unit ($I_N$) and a Tail Unit ($T_N$) arranged in the order as given. Typically, a NAMPTi compound of formula $H_N$-DA-$I_N$-$T_N$ is incorporated into or corresponds in structure to a quaternized NAMPT Drug Unit of formula $H_{N'}$-DA-$I_N$-$T_N$ by having a quaternized skeletal nitrogen atom of a nitrogen-containing partially unsaturated heterocyclic or heteroaromatic ring system comprising $H_{N'}$.

NAMPTi compounds useful for practicing the invention include those described in Roulston, A. and Shore, G. C. (2016) "New Strategies to maximize therapeutic opportunities for NAMPT inhibitors in oncology" *Mol. Cell. Oncol.* 3(1): e1052180; Sampath, D. eta 1. (2015) "Inhibition of nicotinamide phosphoribosyl-transferase (NAMPT) as a therapeutic strategy" *Pharmacol Ther.* 151: 16-31; Zak, M. et al. (2015) "Identification of nicotinamide phosphoribosyltransferase (NAMPT) transferase inhibitors with no evidence of CYP3A4 time-dependent inhibition and improved aqueous solubility" *Bioorg. Med. Chem. Lett.* 25: 529-541; Giannetti, A. M. et al. (2014) "Fragment-based identification of amides derived from trans-2-(pyridin-3-yl)cyclopropane carboxylic acid as potent inhibitors of human nicotinamide phosphoribosyltransferase (NAMPT)" *J. Med. Chem.* 57: 770-792; Christensen, M. K. et al. (2013) "Nicotinamide phosphoribosyltransferase inhibitors, design, preparation, and structure-activity relationships" *J. Med. Chem.* 56: 9071-9088; Dragovich, P. S. et al. "Fragment-based design of 3-aminopyridine-derived amides as potent inhibitors of human nicotinamide phosphoribosyltransferase (NAMPT)" *Bioorg. Med. Chem. Lett.* 24: 954-962; Zheng, X. (2013) "Structure-based discovery of novel amide-containing nicotinamide phosphoribosyltransferase (NAMPT) inhibitors" *J. Med. Chem.* 56: 6413-6433; Galli, U. et al. (2013) "Medicinal chemistry of nicotinamide phosphoribosyltransferase (NAMPT) inhibitors" *J. Med. Chem.* 56: 6279-6296; Gunzner-Toste, J. et al. (2013) "Discovery of potent and efficacious urea-containing nicotinamide phosphoribosyltransferase (NAMPT) inhibitors with reduced CYP2C9 inhibition properties" *Bioorg. Med. Chem. Lett.* 23: 3531-3538; You, H. et al. (2011) "Design, synthesis and X-ray crystallographic study of NAmPRTase inhibitors as anti-cancer agents" *Eur. J. Med. Chem.* 46: 1153-1164; Lockman, J. W. et al. (2010) "Analogues of 4-[(7-bromo-2-methyl-4-oxo-3H-quinazolin-6-yl)methylprop-2-ynylamino]-N-(3-pyridylmethyl)benzamide (CB-30865) as potent inhibitors of nicotinamide phosphoribosyltransferase (NAMPT)" *J. Med. Chem.* 53: 8734-8746; Colombano, G. et al. "A novel potent nicotinamide phosphoribosyltransferase inhibitor synthesized by click chemistry" *J. Med. Chem.* 53: 616-623; Galli, U. et al. (2008) "Synthesis and biological evaluation of isosteric analogues of FK866, an inhibitor of NAD salvage" *ChemMedChem* 3: 771-779, the structure of which are specifically incorporated by reference herein.

"Quaternized NAMPT Drug Unit" as used herein, unless otherwise stated or implied by context, refers to a component of a Ligand Drug Conjugate or Drug Linker compound that is covalently attached to a Linker Unit of the Ligand Drug Conjugate or Drug Linker compound through a quaternary nitrogen atom of the quaternized NAMPT Drug Unit ($D^+$) and is released from that Ligand Drug Conjugate or Drug Linker compound as a NAMPTi compound subsequent to the requisite enzymatic or non-enzymatic action on the Linker Unit for activation of its self-immolative Spacer Unit so that the nitrogen atom is no longer quaternized.

"NAMPT Head Unit" as used herein, unless otherwise stated or implied by context, refers to a component of NAMPTi compound that is covalently attached to or incorporates, at least in part, the Donor Acceptor Unit of that compound and is capable of interacting with the binding site of enzymatically competent NAMPT normally occupied by nicotinamide prior to its enzymatic conversion to nicotinamide mononucleotide (NMN) and is typically a $C_5$-$C_{24}$ heteroaryl or a partially unsaturated or partially aromatic $C_8$-$C_{24}$ heterocyclyl, optionally substituted, wherein both are comprised of an optionally substituted 5- or 6-membered nitrogen-containing heteroaromatic ring system, a skeletal nitrogen atom of which in some aspects is the site of quaternization for a quaternized NAMPT Drug Unit, which incorporates or corresponds to the NAMPTi compound.

In those aspects in which the NAMPT Head ($H_N$) Unit incorporates at least part of the Donor Acceptor (DA) Unit, such incorporation typically takes the form of a 5- or 6-membered heteroaromatic or partially aromatic or partially unsaturated exocyclic ring system fused to an optionally substituted 5- or 6-membered nitrogen-containing heteroaromatic ring system of $H_N$ in which the DA Unit is formally cyclized at least in part back to an adjacent skeletal carbon atom of that ring system so as to define a $H_N$-DA Unit. Typically, in such instances when $H_N$ is an optionally substituted 6-membered nitrogen-containing heteroaromatic ring system, cyclization of DA back to that ring system provides a $H_N$-DA moeity in the form of a partially or fully aromatic 6,5- or 6,6-fused ring system.

In some aspects, the $H_N$ Unit is capable of interacting with Phe 193 on one monomer of NAMPT and/or Tyr 18' of the other monomer when these monomers form an enzymatically competent NAMPT homodimer and wherein each NAMPT monomer has the amino acid sequence of NCBI Reference Sequence NP_005737.1. That interaction typically occurs by a π-π offset stacking interaction with one or both aromatic side chains of those two amino acid residues. The nitrogen-containing $C_5$-$C_{24}$ heteroaryl or partially unsaturated $C_9$-$C_{24}$ heterocyclyl typically is weakly basic or remains uncharged under normal physiological conditions. Accordingly, a $H_N$ Unit typically has a pKa ranging from about −2 to about 7 and includes a pyridine mimetic as described herein. Those and other $H_N$ Units are further described by the embodiments of the invention.

"Quaternized NAMPT Head Unit" as used herein, unless otherwise stated or implied by context, refers to a component of quaternized NAMPT Drug Unit that is covalently attached to or incorporates at least in part the Donor Acceptor Unit of that compound and upon release from a Drug Linker or Ligand Drug Conjugate compound is converted to a NAMPT Head Unit of a NAMPTi compound capable of interacting with the binding site of enzymatically competent NAMPT homodimer normally occupied by nicotinamide prior to its enzymatic conversion to nicotinamide mononucleotide (NMN). In some aspects, quaternization of a skeletal nitrogen atom of the 5- or 6-membered nitrogen-containing heteroaromatic ring system of $H_N$ or $H_N$-DA- results in $H_{N^+}$ or $H_{N^+}$-DA- in which the aromaticity of that heteroaromatic ring system is retained. In other aspects, that quaternization, which results in a quaternized NAMPT Heat Unit ($H_{N^+}$), disrupts the aromaticity of $H_N$ so as to form a partially unsaturated heterocyclic ring system, but on release from a Drug Linker or Ligand Drug Conjugate compound that aromaticity is restored. In still other aspects, the weakly basic skeletal nitrogen atom of the pyridine moeity of a pyridine mimetic is the site of quaternization of a quaternized NAMPT Drug Unit.

"Pyridine mimetic" as used herein, unless otherwise stated or implied by context, refers to a NAMPT Head Unit ($H_N$) in which the optionally substituted $C_5$-$C_{24}$ heteroaryl or partially aromatic or unsaturated $C_8$-$C_{24}$ heterocyclyl of that Unit has a skeletal aromatic nitrogen atom with a pKa of between about −2 to about 7 and no other nitrogen atoms with a pKa greater than 7, and is therefore weakly basic, and is capable of interacting with the nicotinamide binding site of enzymatically competent NAMPT homodimer by interactions that include those engaged by the pyridine moeity of nicotinamide. Pyridine mimetics as $H_N$ Units include pyridin-3-yl and pyridin-4-yl, optionally substituted and/or optionally fused to an optionally substituted $C_5$ heteroaryl or a $C_6$ hetero(aryl) where appropriate, wherein the pyridinyl is attached to the Donor Acceptor (DA) Unit by a skeletal aromatic carbon atom of that moeity, with optional cyclization back to an adjacent skeletal aromatic carbon atom. Those and other pyridine mimetics and their related quaternized NAMPT Drug Units are further described by the embodiments of the invention.

In some aspects, DA is optionally cyclized back to the pyridine mimetic, which is typically comprised of an aromatic 6-membered nitrogen-containing ring system, at an adjacent skeletal carbon atom of that ring system formally through a heteroatom of DA, or through an oxygen, sulfur or nitrogen heteroatom, optionally substituted, that is introduced between $H_N$ and DA. In either instance, as a result of that formal cyclization, at least part of the Donor Acceptor (DA) Unit is incorporated into $H_N$ typically in the form of an optionally substituted 5-membered heteroaromatic ring system or an optionally substituted 6-membered non-aromatic ring system so as to define $H_N$-DA typically having a fully aromatic 6,5-fused ring system or partially aromatic 6,6-fused ring system, optionally substituted. In those instances, an optionally substituted heteroatom introduced for that formal cyclization includes —O—, $S(=O)_{0-2}$ and those of formula —N(R)—, wherein R is hydrogen, optionally substituted alkyl, optionally substituted $C_6$-$C_{24}$ aryl and optionally substituted $C_5$-$C_{24}$ heteroaryl. In other aspects, that Unit is optionally cyclized back formally to the pyridine mimetic, which typically is comprised an optionally substituted 6-membered nitrogen-containing heteroaromatic ring system, at an adjacent skeletal carbon atom of that ring system through an optionally substituted methylene introduced between $H_N$ and DA. That formal cyclization also results in partial incorporation of the Donor Acceptor (DA) Unit into $H_N$ but does so typically in the form of an optionally substituted non-aromatic 5-membered ring system so as to define a $H_N$-DA moiety typically having an optionally substituted, partially aromatic 6,5 fused ring system.

"NAMPT Donor-Acceptor Unit" as used herein, unless otherwise stated or implied by context, refers to a component of a NAMPTi compound or a quaternized NAMPT Drug ($D^+$) Unit that is bonded to or is incorporated at least in part into that compound's NAMPT Head ($H_N$) Unit or quaternized NAMPT Head ($H_{N^+}$) Unit of $D^+$ and is also bonded to an interconnecting Unit ($I_N$). Combinations of $H_N/H_{N^+}$ and DA with or without said incorporation by formal cyclization is represented by the formula of $H_N$-DA or $H_{N^+}$-DA. A Donor-Acceptor (DA) Unit is comprised of an optionally substituted hydrogen bond donor or acceptor functional group, wherein a heteroatom of that functional group is attached to $H_N/H_{N^+}$, or DA is an organic moiety comprised of that functional group, wherein a carbon atom of that organic moiety is covalently bonded to $H_N/H_{N^+}$, which in some aspects is the carbon atom to which the hydrogen bond donor or acceptor functional group is attached. In those aspects, the attachment of the heteroatom or carbon atom of DA is to a skeletal aromatic carbon atom at position 2 or 3 of a 5-membered nitrogen-containing heteroaromatic ring system comprising $H_N/H_{N^+}$, or at position 3 or 4 of a 6-membered nitrogen-containing heteroaromatic ring system of which $H_N$ is comprised, or at position 3 or 4 of the 6-membered quaternized nitrogen-containing heteroaromatic ring system of which $H_{N^+}$ is comprised.

In some aspects, aromatization of the heteroaromatic ring system of which $H_N$ is comprised is retained on quaternization, with optional formal cyclization of the Donor-Acceptor (DA) Unit back to an adjacent skeletal carbon atom of either nitrogen-containing heteroaromatic ring system of which $H_N/H_{N^+}$ is comprised through a heteroatom of DA or through an optionally substituted non-aromatic carbon atom or an introduced optionally substituted nitrogen, oxygen or sulfur atom, or at position 3 or 4 of the 6-membered quaternized nitrogen-containing partially unsaturated heterocyclic ring system of which $H_{N^+}$ is comprised. In other aspects in which there is formal cyclization of the Donor-Acceptor (DA) Unit, aromatization of the heteroaromatic ring system of $H_N$ is disrupted on quaternization.

In either aspect, said formal cyclization typically is to an optionally substituted 6-membered nitrogen-containing ring system of which $H_N/H_{N^+}$ is comprised to define a $H_N$-DA or $H_{N^+}$-DA moiety typically having an optionally substituted, partially aromatic or fully aromatic fused 6,5- or 6,6-ring system. In those aspects, said bonding of DA to $H_N$-DA is in relation to a skeletal nitrogen atom of the 5- or 6-membered nitrogen-containing aromatic ring system and wherein said optional cyclization of DA to $H_N$-DA is typically to the adjacent carbon atom of the 6-membered nitrogen-containing heteroaromatic ring system. In any of the above aspects of formal cyclization of DA to $H_N$-DA said formal cyclization occurs to substantially retain the hydrogen bonding ability of the donor or acceptor functional group of DA existing prior to that cyclization.

In some aspects, the hydrogen bond donor or acceptor functional group is or is comprised of an optionally substituted amide functional group so that DA is capable of interacting at the nicotinamide binding site with one or more of the same interactions as the amide functional group of nicotinamide and is thus capable of interacting with Ser 275 of an NAMPT monomer of an enzymatically competent NAMPT homodimer wherein each NAMPT monomer has the amino acid sequence of NCBI Reference Sequence NP_005737.1. That interaction typically occurs with the hydroxyl side chain of that amino acid residue through hydrogen bonding, and/or is capable of interacting with one or more amino acid residues selected from the group consisting of Asp 219, Ser 241, and Val 242 either directly by hydrogen bonding or indirectly through hydrogen bonding network(s) involving the intermediacy of water molecule(s). Those and other DA Units are further described by the embodiments of the invention.

"Acrylamide Donor-Acceptor" as used herein, unless otherwise stated or implied by context, refers to a subset of Donor Acceptor (DA) Units within a NAMPTi compound, or a quaternized NAMPT Drug ($D^+$) Unit incorporating or corresponding to that NAMPTi compound, having an optionally substituted $C_2$-$C_{20}$ alkenylene in which one of the $sp^2$ carbons defining it as an alkenylene moiety is bonded to the carbonyl carbon of an optionally substituted amide functional group, the nitrogen atom of which is the site of attachment to the NAMPT Interconnecting ($I_N$) Unit, and in which another $sp^2$ carbon of the alkenylene moiety which is distal to the amide functional group is the site of covalent attachment of that DA Unit to the optionally substituted 5- or 6-membered nitrogen-containing heteroaromatic ring system of which $H_N/H_{N^+}$ is comprised and in which aromaticity of $H_N$ is retained on quaternization, or to the optionally substituted 6-membered quaternized nitrogen-containing partially unsaturated or aromatic ring system of which $H_{N^+}$ is comprised and in which aromaticity of $H_N$ is disrupted on quaternization.

When an acrylamide DA Unit is formally cyclized at least in part back to an adjacent skeletal carbon atom of the optionally substituted nitrogen-containing heteroaromatic ring system of $H_N$ it typically does so to a 6-membered heteroaromatic ring system of which $H_N$ is comprised through the $sp^2$ carbon atom of the alkenylene moiety proximal to the amide functional group through an oxygen, sulfur or nitrogen heteroatom, optionally substituted, introduced between that proximal $sp^2$ carbon atom and the adjacent carbon atom so as to define a 5-membered heteroaromatic ring system fused to the 6-membered nitrogen-containing heteroaromatic ring system of $H_N$. Bioisosteres of such Donor Acceptor Units are included in the definition of an acrylamide Donor-Acceptor Unit and is an organic moiety that is sterically and functionally equivalent to that type of DA Unit by joining together the $H_N/H_{N^+}$ and $I_N$ Units while retaining a plurality of interactions attributable to the amide functional group of the parent structure within the interface of an enzymatically competent NAMPT homodimer.

"Nicotinamide mimetic" as used herein, unless otherwise stated or implied by context, refers to $H_N$-DA- of a NAMPTi compound, or $H_{N^+}$-DA- of a quaternized NAMPT Drug ($D^+$) Unit incorporating or corresponding to that compound, in which DA is bonded to an a Interconnecting Unit of that compound and in which $H_N$ is a pyridine mimetic and $H_{N^+}$ is the quaternized version thereof, and DA is bonded to position 3 relative to a weakly basic skeletal nitrogen atom of the pyridine mimetic, which in some aspects is the site of quaternization in a quaternized NAMPT Drug Unit, and wherein the pyridine mimetic of $H_N$ and the hydrogen bond donor or acceptor functional group of DA in the released NAMPTi compound is capable of interacting at the nicotinamide binding site of an enzymatically competent NAMPT homodimer with one or more of the same interactions as the pyridine and amide functional groups of nicotinamide as previously described when $D^+$ is released as a NAMPTi compound.

"NAMPT Tail Unit" as used herein, unless otherwise stated or implied by context, refers to a component of a NAMPTi compound or quaternized NAMPT Drug ($D^+$) Unit incorporating or corresponding to that compound, that is bonded to that compound's Interconnecting ($I_N$) Unit. $T_N$ in some aspects is or is comprised of an optionally substituted amino-alcohol residue or an optionally substituted carboxylic acid-alcohol residue, the amino nitrogen or carbonyl carbon atom of which is bonded to $I_N$ or to the remainder of $T_N$ that is bonded to $I_N$. In other aspects, $T_N$ is or is comprised of an optionally substituted benzamide moiety, the amide nitrogen atom of which is bonded to $I_N$ or to the remainder of $T_N$ that is bonded to $I_N$, with optional cyclization of that atom back to $I_N$ or to the remainder of $T_N$ in which either optional cyclization is included within the formula of $I_N$-$T_N$. In still other aspects, $T_N$ is or is comprised of an aryl or biaryl moiety. $T_N$ aryl moieties include those having either a $C_6$-$C_{24}$ arylene or a $C_5$-$C_{24}$ heteroarylene and $T_N$ biaryl moieties include those having independently selected $C_6$-$C_{24}$ arylenes or $C_5$-$C_{24}$ heteroarylenes or a combination thereof. In any of the above aspects in which a remainder of $T_N$ is bonded to $I_N$ that remainder is typically an optionally substituted $C_2$-$C_{20}$ heteroalkylene or an optionally substituted $C_3$-$C_{20}$ heterocyclo or a combination thereof, more typically a $C_2$-$C_7$ heteroalkylene or a $C_5$-$C_6$ heterocyclo or a combination thereof. In those aspects, the $C_3$-$C_{20}$ heterocyclo or $C_5$-$C_6$ heterocyclo is typically saturated or partially unsaturated. In some aspect $T_N$ is substituted with a polar functional group such as —OH or —$NH_2$ that projects out towards solvent-accessible space and in some instance may engage in hydrogen bonding within the binding pocket of enzymatically competent NAMPT homodimer.

In some aspects, $T_N$ or —$I_N$-$T_N$ is capable of engaging in one or more interactions with a hydrophobic cleft region formed by Ile 309, Pro 307, Val 350, Ile 378 and Ala 379 and/or is capable of interacting with one or more amino acid residues selected from the group consisting of Tyr 188, Lys 189, Ala 379, Asn 377, Glu 376, Val 350, Arg 349 and Pro 307 of an NAMPT monomer of an enzymatically competent NAMPT homodimer wherein each NAMPT monomer has the amino acid sequence of NCBI Reference Sequence NP_005737.1. Those and other $T_N$ Units are further described by the embodiments of the invention.

"NAMPT Interconnecting Unit" as used herein, unless otherwise stated or implied by context, refers to a component of a NAMPTi compound or derivative thereof, or of a quaternized NAMPT Drug Unit of that compound or derivative, that interconnects its Donor Acceptor (DA) and Tail ($T_N$) Units. In some aspects, $I_N$ typically engages in Van der Waals interactions with hydrophobic side amino acid side chains that line the tunnel in the region between the DA and Tail Units and allows for the Tail Unit to engage in one or more of the aforementioned interactions to anchor the NAMPTi compound into the dimer interface. Typically, the length of the Interconnecting Unit is also selected to allow projection of $T_N$ towards solvent accessible space on binding of a NAMPTi compound to an enzymatically competent NAMPT homodimer. For that purpose, $I_N$ typically has or is comprised of a hydrophobic residue selected from the group consisting of $C_1$-$C_8$ alkylene, $C_6$-$C_{24}$ arylene or a combination thereof, in which the terminus of the hydrophobic residue distal to the site of attachment to $H_N$-DA is optionally functionalized for attachment to $T_N$ Unit. Those functionalities include —O—, —S(=O)$_{1,2}$, and —C(=O)—. In other aspects, $I_N$ is additionally comprised of an optionally substituted $C_2$-$C_{12}$ heteroalkylene or an optionally substituted $C_5$-$C_{20}$ heterocyclo, which in some aspects is optionally functionalized for covalent attachment to $T_N$. Although the hydrophobic residue of $I_N$ may be capable of hydrophobic interactions in the enzymatically competent dimer interface between two NAMPT monomers, those interactions may not contribute meaningfully to binding of an NAMPTi compound to the enzyme, therefore the capability of $I_N$ in a released quaternized NAMPT Drug Unit for those interactions in some aspects is considered optional. $I_N$ Units are further described by the embodiments of the invention.

"Hematological malignancy" as used herein, unless otherwise stated or implied by context, refers to a blood cell tumor that originates from cells of lymphoid or myeloid origin and is synonymous with the term "liquid tumor". Hematological malignancies may be categorized as indolent, moderately aggressive or highly aggressive.

"Lymphoma" as used herein, unless otherwise stated or implied by context, refers to is hematological malignancy that usually develops from hyper-proliferating cells of lymphoid origin. Lymphomas are sometimes classified into two major types: Hodgkin lymphoma (HL) and non-Hodgkin lymphoma (NHL). Lymphomas may also be classified according to the normal cell type that most resemble the cancer cells in accordance with phenotypic, molecular or cytogenic markers. Lymphoma subtypes under that classification include without limitation mature B-cell neoplasms, mature T cell and natural killer (NK) cell neoplasms, Hodgkin lymphoma and immunodeficiency-associated lymphoproliferative disorders. Lymphoma subtypes include precursor T-cell lymphoblastic lymphoma (sometimes referred to as a lymphoblastic leukemia since the T-cell lymphoblasts are produced in the bone marrow), follicular lymphoma, diffuse large B cell lymphoma, mantle cell lymphoma, B-cell chronic lymphocytic lymphoma (sometimes referred to as a leukemia due to peripheral blood involvement), MALT lymphoma, Burkitt's lymphoma, mycosis fungoides and its more aggressive variant Sezary's disease, peripheral T-cell lymphomas not otherwise specified, nodular sclerosis of Hodgkin lymphoma, and mixed-cellularity subtype of Hodgkin lymphoma.

"Leukemia" as used herein, unless otherwise stated or implied by context, refers to a hematological malignancy that usually develops from hyper-proliferating cells of myeloid origin, and include without limitation, acute lymphoblastic leukemia (ALL), acute myelogenous leukemia (AML), chronic lymphocytic leukemia (CLL), chronic myelogenous leukemia (CML) and acute monocytic leukemia (AMoL). Other leukemias include hairy cell leukemia (HCL), T-cell lymphatic leukemia (T-PLL), large granular lymphocytic leukemia and adult T-cell leukemia.

"Hyper-proliferating cells" as used herein, unless otherwise stated or implied by context, refer to abnormal cells that are characterized by unwanted cellular proliferation or an abnormally high rate or persistent state of cell division or other cellular activity that is unrelated or uncoordinated with that of the surrounding normal tissues. In some aspects, hyper-proliferating cells are hyper-proliferating mammalian cells. In other aspects, hyper-proliferating cells are hyper-stimulated immune cells as defined herein whose persistent state of cell division or activation occurs after the cessation of the stimulus that may have initially evoked the change to their persistent cell division r activation. In other aspects, the hyper-proliferating cells are transformed normal cells or cancer cells and their uncontrolled and progressive state of cell proliferation may result in a tumor that is benign, potentially malignant (premalignant) or frankly malignant. Hyperproliferation conditions resulting from transformed normal cells or cancer cells include, but are not limited to, those characterized as a precancer, hyperplasia, dysplasia, adenoma, sarcoma, blastoma, carcinoma, lymphoma, leukemia or papilloma. Precancers are usually defined as lesions that exhibit histological changes and are associated with an increased risk of cancer development and sometimes have some, but not all, of the molecular and phenotypic properties that characterize the cancer. Hormone associated or hormone sensitive precancers include without limitation, prostatic intraepithelial neoplasia (PIN), particularly high-grade PIN (HGPIN), atypical small acinar proliferation (ASAP), cervical dysplasia and ductal carcinoma in situ. Hyperplasias generally refers to the proliferation of cells within an organ or tissue beyond that which is ordinarily seen that may result in the gross enlargement of an organ or in the formation of a benign tumor or growth. Hyperplasias include, but are not limited to, endometrial hyperplasia (endometriosis), benign prostatic hyperplasia and ductal hyperplasia.

"Normal cells" as used herein, unless otherwise stated or implied by context, refer to cells undergoing coordinated cell division related to maintenance of cellular integrity of normal tissue or replenishment of circulating lymphatic or blood cells that is required by regulated cellular turnover, or tissue repair necessitated by injury, or to a regulated immune or inflammatory response resulting from pathogen exposure or other cellular insult, where the provoked cell division or immune response terminates on completion of the necessary maintenance, replenishment or pathogen clearance. Normal cells include normally proliferating cells, normal quiescent cells and normally activated immune cells.

"Normal quiescent cells" as used herein, unless otherwise stated or implied by context, refer to are noncancerous cells in their resting $G_o$ state and have not been stimulated by stress or a mitogen or are immune cells that are normally inactive or have not been activated by pro-inflammatory cytokine exposure.

"Hyper-stimulated immune cells" as used herein, unless otherwise stated or implied by context, refer to cells involved in innate or adaptive immunity characterized by an abnormally persistent proliferation or inappropriate state of stimulation that occurs after the cessation of the stimulus that may have initially evoked the change in proliferation or stimulation or that occurs in the absence of any external insult. Oftentimes, the persistent proliferation or inappropriate state of stimulation results in a chronic state of inflammation characteristic of a disease state or condition. In some instances, the stimulus that may have initially evoked the change in proliferation or stimulation is not attributable to an external insult but is internally derived as in an autoimmune disease. In some aspects, a hyper-stimulated immune cell is a pro-inflammatory immune cell that has been hyper-activated through chronic pro-inflammatory cytokine exposure.

In some aspects of the invention, a Ligand Drug Conjugate compound of an LDC composition binds to an antigen preferentially displayed by pro-inflammatory immune cells that are abnormally proliferating or are inappropriately or persistently activated. Those immune cells include classically activated macrophages or Type 1 T helper (Th1) cells, which produce interferon-gamma (INF-γ), interleukin-2 (IL-2), interleukin-10 (IL-10), and tumor necrosis factor-beta (TNF-β), which are cytokines that are involved in macrophage and CD8$^+$ T cell activation.

"Glycosidase" as used herein, unless otherwise stated or implied by context, refers to a protein capable of enzymatic cleavage of a glycosidic bond. Typically, the glycosidic bond to be cleaved is present in a Glucuronide Unit as the Cleavable Unit of Ligand Drug Conjugate or Drug Linker compound. Sometimes the glycosidase acting upon a Ligand Drug Conjugate is present intracellularly in hyper-proliferating cells, hyper-activated immune cells or other abnormal cells to which the Ligand Drug Conjugate has preferential access in comparison to normal cells, which is attributable to the targeting capability of its Ligand Unit. Sometimes the glycosidase is more specific to the abnormal or unwanted cells or is preferentially excreted by abnormal or unwanted cells in comparison to normal cells or is present in greater amount in the vicinity of abnormal cells in comparison to amounts of the glycosidase typically found in serum of an intended subject to whom the Ligand Drug Conjugate is to be administered. Typically, the glycosidic bond within a Glucuronide Unit, which has the formula of —W' (Y)—, connects the anomeric carbon in α- or β-configuration, of a carbohydrate moiety (Su) to a self-immolative Stretcher Unit (Y) through an optionally substituted heteroatom (E') so that W' is Su-E'- and is acted upon by a glycosidase. In some aspects E', which forms the glycosidic bond to the carbohydrate moiety (Su), is a phenolic oxygen atom of a self-immolating moiety in a self-immolative Stretcher Unit (Y) such that glycosidic cleavage of that bond triggers 1,4- or 1,6-elimination of D$^+$ as a NAMPTi compound.

"Glucuronide Unit" as used herein, unless otherwise stated or implied by context, refers to a component of a glucuronide-based Linker Unit of a Ligand Drug Conjugae or a Drug Linker compound that when acted upon by a glycosidase releases the quaternized Drug Unit (D$^+$) attached thereto as free NAMPTi compound and is represented by the general formula of —Y(W'), wherein Y is a self-immolative Spacer Unit to which D$^+$ is attached and W' is a carbohydrate moiety covalently attached to Y through a glycosidic bond, which is the site of cleavage of the glycosidase.

In some aspects, Drug Linker compounds containing a Glucuronide Unit are represented by formula $L_{SS}$-$B_b$-($A_a$-$Y_y$(W')-D$^+$)$_n$ in which $L_{SS}$ is M$^1$-$A_R$(BU)-$A_O$- and Ligand Drug Conjugates are represented by L-($L_{SS}$-$B_b$-($A_a$-Y(W')-D$^+$)$_n$)$_p$ or L-($L_S$-$B_b$-($A_a$-Y(W')-D$^+$)$_n$)$_p$, in which $L_{SS}$ is M$^2$-$A_R$(BU)-$A_O$ and $L_S$ is M$^3$-$A_R$(BU)-$A_O$-, wherein $A_O$ is an second optional Stretcher Unit, which in some aspects serves as least in part as Hydrolysis-enhancing (HE) Unit and A is a first optional Stretcher Unit, wherein in some aspects A or a subunit thereof has the formula of -L$^P$(PEG)-, wherein -L$^P$ and PEG are as defined herein for parallel connector units and PEG Units, respectively; BU represents an acyclic or cyclic Basic Unit, and subscripts a and b are independently 0 or 1, and subscript n is 1, 2, 3 or 4, wherein B is a Branching Unit, and is present when subscript n is 2, 3 or 4 so that subscript b is 1 and wherein A is a first Stretcher Unit, when subscript a is 1.

In some of those aspects, —Y(W')— is of the formula (Su-O')—Y—, wherein Su is a carbohydrate moiety, Y is a self-immolative Spacer Unit having a PAB or PAB-type self-immolative moiety with glycosidic bonding to Su, wherein O' as E' represents the oxygen atom of the glycosidic bond cleavable by a glycosidase, wherein a quaternized NAMPT Drug (D$^+$) Unit is bonded directly to the self-immolative moiety of Y through its quaternary amine nitrogen, wherein Su-O'— is attached to the optionally substituted (hetero)arylene of the self-immolative moiety of Y, and D$^+$ is attached to that (hetero)arylene through an optionally substituted benzylic carbon such that self-immolation for release of D$^+$ is initiated, thereby providing free NAMPTi compound. Although such —Y(W')— moieties are referred to as Glucuronide Units, Su of W' is not limited to a glucuronic acid residue.

Typically, a Glucuronide Unit having the formula of (Su-O'—Y)— (in which —O'— represents the oxygen of the glycosidic bond and Su is a carbohydrate moiety) is represented by a structure described herein for a self-immolating Spacer Unit (Y) in which E' bonded to the central (hetero)arylene moiety of a PAB or PAB-type moiety of Y is an oxygen atom with that heteroatom bonded to the carbohydrate moiety (Su) through that moiety's anomeric carbon atom.

In some aspects, such moieties attached to D$^+$ include those of formula —(Su-O')—Y-D$^+$ having the structure of:

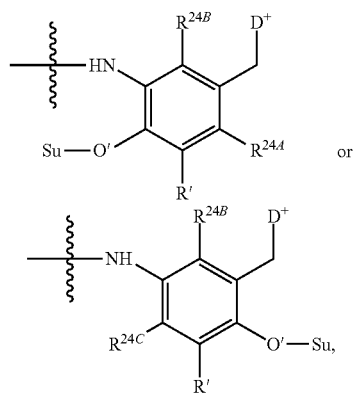

wherein R$^{24A}$, R$^{24B}$ and R$^{24C}$ are independently selected from the group consisting of hydrogen, C$_1$-C$_6$ alkyl, C$_1$-C$_6$ alkoxy, other electron donating groups (EDGs), and halogen, nitro and other electron withdrawing groups (EWGs) or R$^{24A}$ and R' in the left-hand structure or R$^{24C}$ and R' in the right-hand structure together with the aromatic carbons to which they are attached define an benzo-fused C$_5$-C$_6$ carbocycle, and are selected so that the electron donating ability of the phenolic —OH released from the glycosidic bond by enzymatic action of a glycosidase, the sensitivity to selective cleavage by the glycosidase, and the stability of the imino-quinone methide intermediate resulting from fragmentation by 1,4- or 1,6-elimination are balanced with the leaving ability of D$^+$ in order for a suitably efficient release of a NAMPTi compound or derivative to occur. The (Su-O')—Y— moieties in the above structures are representative Glucuronide Units of formula —Y(W')—. When the glycosidic bond is to a glucuronic acid and the glycosidase capable of enzymatic cleavage of that glycosidic bond is a glucuronidase.

In some of those aspects —(Su-O')—Y-D$^+$ has the structure of:

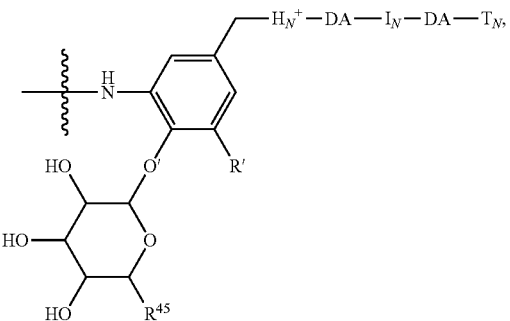

wherein H$_{N^+}$ is the site of quaternization and corresponds to or incorporates H$_N$ of a corresponding or incorporated NAMPTi compound of formula H$_N$-DA-I$_N$-T$_N$; R$^{45}$ is —OH or —CO$_2$H and the remaining variable groups are as defined for NAMPTi compounds and quaternized NAMPT Drug Units. Further descriptions of those and other Glucuronide Units are provided by the embodiments of the invention.

"Carbohydrate moiety" as used herein, unless otherwise stated or implied by context, refers to a monovalent radical of a monosaccharide having the empirical formula of C$_m$(H$_2$O)$_n$, wherein n is equal to m, containing an aldehyde moiety in its hemiacetal form or a derivative thereof in which a CH$_2$OH moiety within that formula has been oxidized to a carboxylic acid (e.g., glucuronic acid from oxidation of the CH$_2$OH group in glucose). Typically, a carbohydrate moiety (Su) is a monovalent radical of cyclic hexose, such as a pyranose, or a cyclic pentose, such as a furanose. Usually, the pyranose is a glucuronide or hexose in the β-D conformation. In some instances, the pyranose is a β-D-glucuronide moiety (i.e., β-D-glucuronic acid linked to the self-immolative moiety of a self-immolative Spacer Unit via a glycosidic bond that is cleavable by β-glucuronidase). Sometimes, the carbohydrate moiety is unsubstituted (e.g., is a naturally occurring cyclic hexose or cyclic pentose). Other times, the carbohydrate moiety can be a β-D-glucuronide derivative, e.g., glucuronic acid in which one or more, typically 1 or 2 of its hydroxyl moieties are independently replaced with moieties selected from the group consisting of halogen and C$_1$-C$_4$ alkoxy.

"Protease" as used herein, unless otherwise stated or implied by context, refers to a protein capable of enzymatic cleavage of a carbonyl-nitrogen bond such as an amide bond typically found in a peptide. Proteases are classified into major six classes: serine proteases, threonine proteases, cysteine proteases, glutamic acid proteases, aspartic acid proteases and metalloproteases so named for the catalytic residue in the active site that is primarily responsible for cleaving the carbonyl-nitrogen bond of its substrate. Proteases are characterized by various specificities, which are dependent of identities of the residues at the N-terminal and/or C-terminal side of the carbonyl-nitrogen bond.

When W is a Peptide Cleavable Unit bonded to a self-immolative Spacer (Y) in Formula 1, Formula 1a, Formula 1b, Formula I, Formula Ia or Formula Ib, through an amide or other carbonyl-nitrogen containing functional group cleavable by a protease that cleavage site is oftentimes limited to those recognized by proteases that are found in abnormal cells, which includes hyper-proliferating cells and hyper-stimulated immune cells, or within cells particular to the environment in which these abnormal cells are present. In those instances, the protease may or may not be preferentially present or found in greater abundance within cells targeted by a Ligand Drug Conjugate having that Peptide Cleavable Unit since it will have poorer access to cells that do not have the targeted moiety or have insufficient copy number of the targeted moiety to which its Ligand Unit is directed to have an adverse effect due to immunologically specific uptake of the Conjugate. Other times, the protease is preferentially excreted by abnormal cells or by cells in the environment in which those abnormal cells are found in comparison to normal cells or in comparison to typical environments in which those normal cells are found in the absence of abnormal cells. Thus, in those instances where the protease is excreted, the protease is typically required to be preferentially present or found in greater abundance in the vicinity of cells targeted by the Ligand Drug Conjugate in comparison to that of normal cells distant from the site of the abnormal cells.

When incorporated into a Ligand Drug Conjugate composition, a peptide that comprises W as a Peptide Cleavable Unit and which is bonded to Y through a carbon-nitrogen bond will present a recognition sequence to a protease that cleaves that bond resulting in fragmentation of the Linker Unit whereby release of a NAMPTi compound from a Conjugate compound of the composition occurs. Sometimes, the recognition sequence is selectively recognized for the purpose of appropriately delivering a NAMPTi compound to the desired site of action by an intracellular protease present in abnormal cells to which the Ligand Drug Conjugate has preferred access in comparison to normal cells due to targeting of the abnormal cells by its Ligand Unit, or is preferentially produced by abnormal cells in comparison to normal cells distant from the vicinity of the abnormal cells. In some aspects, the peptide is resistant to circulating proteases in order to minimize premature release of $D^+$ as a NAMPTi compound and thus mitigates unwanted systemic exposure to the compound so released. In some of those aspects, the peptide will have one or more unnatural or non-classical amino acids in its sequence order to have that resistance. In that and other aspects, the amide bond that is specifically cleaved by a protease is produced by or present within an abnormal cell and is sometimes an anilide bond wherein the nitrogen of that anilide is a nascent electron-donating heteroatom (i.e., J) of a self-immolative moiety having one the previously defined structures for such moieties. Thus, protease action on such a peptide sequence in a Peptide Cleavable Unit results in release of a quaternized NAMPT Drug Unit as a NAMPTi compound from Linker Unit fragmentation occurring by 1,4- or 1,6-elimination through the central (hetero)arylene moiety of a PAB or PAB-type self-immolative Spacer Unit.

Regulatory proteases are typically located intracellularly and are required for the regulation of cellular activities, including cellular maintenance, proliferation or other intracellular activity, that sometimes becomes aberrant or dysregulated in abnormal cells. In some instances, when W is directed to a protease preferentially present intracellularly in comparison its extracellularly presence, that protease is typically a regulatory protease. In some instances, those proteases include cathepsins. Cathepsins include the serine proteases, Cathepsin A, Cathepsin G, aspartic acid proteases Cathepsin D, Cathepsin E and the cysteine proteases, Cathepsin B, Cathepsin C, Cathepsin F, Cathepsin H, Cathepsin K, Cathepsin L1, Cathepsin L2, Cathepsin O, Cathepsin S, Cathepsin W and Cathepsin Z.

In other instances, when W is a Peptide Cleavable Unit directed to a protease that is preferentially distributed extracellularly in the vicinity of abnormal cells, such as hyper-proliferating or hyper-stimulated immune cells, in comparison to normal cells distant from the abnormal cells, that distribution is due to preferential excretion by the abnormal cells or by neighboring cells whose excretion of the protease is peculiar to the environment of hyper-proliferating or hyper-stimulated immune cells. In some of those instances, the protease is a metalloprotease. Typically, those proteases are involved in tissue remodeling, which aids in the invasiveness of hyper-proliferating cells or undesired accumulation of hyper-activated immune cells, which often results in further recruitment of such cells.

"Intracellularly cleaved", "intracellular cleavage" and like terms used herein refer to a metabolic process or reaction within a targeted cell occurring upon a Ligand Drug Conjugate or the like, whereby covalent attachment through its Linker Unit between the quaternized NAMPT Drug Unit and the Ligand Unit of the Conjugate is broken, resulting in release of $D^+$ as a NAMPTi compound within the targeted cell.

"Bioavailability" unless otherwise stated or implied by context, refers to the systemic availability (i.e., blood/plasma levels) of a given amount of a drug administered to a patient. Bioavailability is an absolute term that indicates measurement of both the time (rate) and total amount (extent) of drug that reaches the general circulation from an administered dosage form.

"Subject" unless otherwise stated or implied by context, refers to a human, non-human primate or mammal having a hyper-proliferation, inflammatory or immune disorder or other disorder attributable to abnormal cells or is prone to such a disorder who would benefit from administering an effective amount of a Ligand Drug Conjugate. Non-limiting examples of a subject include human, rat, mouse, guinea pig, monkey, pig, goat, cow, horse, dog, cat, bird and fowl. Typically, the subject is a human, non-human primate, rat, mouse or dog.

"Inhibit", "inhibition of" and like terms, unless otherwise stated or implied by context, means to reduce by a measurable amount, or to prevent entirely an undesired activity or outcome. In some aspects, the undesired outcome or activity is related to abnormal cells and includes hyper-proliferation, or hyper-stimulation or other dysregulated cellular activity underlying a disease state. Inhibition of such a dysregulated cellular activity by a Ligand Drug Conjugate is typically determined relative to untreated cells (sham treated with vehicle) in a suitable test system as in cell culture (in vitro) or in a xenograft model (in vivo). Typically, as a negative control, a Ligand Drug Conjugate is used that targets an antigen not present or has low copy number on the abnormal cells of interest or has a protein-base Ligand Unit, such as an antibody, that is genetically engineered to not be recognized any known antigen.

The term "therapeutically effective amount" unless otherwise stated or implied by context, refers to an amount of NAMPTi compound or Ligand Drug Conjugate having a quaternized NAMPT Drug Unit effective to treat a disease or disorder in a mammal. In the case of cancer, the therapeutically effective amount of the NAMPTi compound or Ligand Drug Conjugate may reduce the number of cancer cells; reduce the tumor size, inhibit (i.e., slow to some extent and preferably stop) cancer cell infiltration into peripheral organs, inhibit (i.e., slow to some extent and preferably stop) tumor metastasis, inhibit, to some extent, tumor growth, and/or relieve to some extent one or more of the symptoms associated with the cancer. To the extent the NAMPTi compound or Ligand Drug Conjugate may inhibit growth and/or kill existing cancer cells, it may be cytostatic or cytotoxic. For cancer therapy, efficacy can, for example, be measured by assessing the time to disease progression (TTP), determining the response rate (RR) and/or overall survival (OS).

In the case of immune disorders resulting from hyper-stimulated immune cells, a therapeutically effective amount of the drug may reduce the number of hyper-stimulated immune cells, the extent of their stimulation and/or infiltration into otherwise normal tissue and/or relieve to some extent one or more of the symptoms associated with a dysregulated immune system due to hyper-stimulated immune cells. For immune disorders due to hyper-stimulated immune cells, efficacy can, for example, be measured by assessing one or more inflammatory surrogates, including one or more cytokines levels such as those for IL-1β, TNFα, INFγ and MCP-1, or numbers of classically activated macrophages.

In some aspects of the invention, a Ligand Drug Conjugate compound associates with an antigen on the surface of a targeted cell (i.e., an abnormal cell such as a hyper-proliferating cell or a hyper-stimulated immune cell), and the Conjugate compound is then taken up inside the targeted cell through receptor-mediated endocytosis. Once inside the cell, one or more Cleavage Units within a Linker Unit of the Conjugate are cleaved, resulting in release of the quaternized NAMPT Drug Unit (D$^+$) as a NAMPTi compound. The compound so released is then free to migrate within the cytosol and induce cytotoxic or cytostatic activities, or in the case of hyper-stimulated immune cells may alternatively inhibit pro-inflammatory signal transduction. In another aspect of the invention, the quaternized NAMPT Drug Unit (D$^+$) is released from a Ligand Drug Conjugate compound outside the targeted cell but within the vicinity of the targeted cell so that the resulting NAMPTi compound from that release is able to subsequently penetrate the cell rather than being prematurely released at distal sites.

"Carrier" unless otherwise stated or implied by context refers to a diluent, adjuvant or excipient, with which a compound is administered. Such pharmaceutical carriers can be liquids, such as water and oils, including those of petroleum, animal, vegetable or synthetic origin, such as peanut oil, soybean oil, mineral oil, sesame oil. The carriers can be saline, gum acacia, gelatin, starch paste, talc, keratin, colloidal silica, urea. In addition, auxiliary, stabilizing, thickening, lubricating and coloring agents can be used. In one embodiment, when administered to a subject, the compound or compositions and pharmaceutically acceptable carriers are sterile. Water is an exemplary carrier when the compounds are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. The present compositions, if desired, can also contain minor amounts of wetting or emulsifying agents, or pH buffering agents.

"Treat", "treatment," and like terms, unless otherwise indicated by context, refer to therapeutic treatment or prophylactic measures to prevent or reduce the potential for relapse, wherein the object is to inhibit or slow down (lessen) an undesired physiological change or disorder, such as the development or spread of cancer or tissue damage from chronic inflammation. Typically, beneficial or desired clinical results of such therapeutic treatments include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. The term can also mean prolonging survival or quality of like of a subject as compared to expected survival or quality of life for a subject not receiving treatment. Those in need of treatment include those already having the condition or disorder as well as those prone to have the condition or disorder.

In the context of cancer or a disease state related to chronic inflammation, the term includes any or all of inhibiting growth of tumor cells, cancer cells, or of a tumor, inhibiting replication of tumor cells or cancer cells, inhibiting dissemination of tumor cells or cancer cell, lessening overall tumor burden or decreasing the number of cancerous cells, inhibiting replication or stimulation of pro-inflammatory immune cells, inhibiting or decreasing the chronic inflammatory state of a dysregulated immune system or decreasing the frequency and/or intensity of flares experienced by subjects having an autoimmune condition or disease or ameliorating one or more symptoms associated with cancer or a hyper-immune stimulated disease or condition.

"Salt form" as used herein, unless otherwise indicated by context, refers to a charged compound in ionic association with a countercation(s) and/or counteranions so as to form an overall neutral species. Accordingly, salt forms include a protonated form of a compound in ionic association with a counteranion. Such a salt forms may result from interaction of a basic functional group and an acid functional group within the same compound or involve inclusion of a negatively charged molecule such as an acetate ion, a succinate ion or other counteranion. In some aspects, a salt form of a compound occurs through interaction of the parent compound's basic or acid functional group with an external acid or base, respectively. In other aspects the charged atom of the compound that is associated with a counteranion is permanent in the sense that spontaneous disassociation to a neural species cannot occur without altering the structural integrity of the parent compound as when a nitrogen atom is quaternized as exemplified by a quaternized Drug Unit. The counterion may be any charged organic or inorganic moiety that stabilizes an opposite charge on the parent compound. Furthermore, a compound in salt form may have more than one charged atoms in its structure. In instances where multiple charged atoms of the parent compound are part of the salt form, that salt from of the compound can have multiple counter ions. Hence, a salt form of a compound can have one or more charged atoms and/or one or more counterions.

A salt form of a compound not involving a quaternized nitrogen atom is typically obtained when a basic functional group of a compound, such as a primary, secondary or tertiary amine or other basic amine functional group interacts with an organic or inorganic acid of suitable pKa for protonation of the basic functional group, or when an acid functional group of a compound with a suitable $pK_a$, such as a carboxylic acid, interacts with a hydroxide salt, such as NaOH or KOH, or an organic base of suitable strength, such as triethylamine, for deprotonation of the acid functional group. In some aspects, a compound in salt form contains at least one basic amine functional group, and accordingly acid addition salts can be formed with this amine group, which includes the basic amine functional group of a cyclic or acyclic Basic Unit.

"Pharmaceutically acceptable salt" as used herein, unless otherwise indicated by context, refers to a salt form of a compound in which its counterion is acceptable for administration of the salt form to an intended subject and include inorganic and organic countercations and counteranions. Exemplary pharmaceutically acceptable counteranions for basic amine functional groups, such as those in cyclic or acyclic Basic Units, include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, mesylate, besylate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

Typically, a pharmaceutically acceptable salt is selected from those described in P. H. Stahl and C. G. Wermuth, editors, *Handbook of Pharmaceutical Salts: Properties, Selection and Use*, Weinheim/Zürich:Wiley-VCH/VHCA, 2002. Salt selection is dependent on properties the drug product must exhibit, including adequate aqueous solubility at various pH values, depending upon the intended route(s) of administration, crystallinity with flow characteristics and low hygroscopicity (i.e., water absorption versus relative humidity) suitable for handling and required shelf life by determining chemical and solid-state stability as when in a lyophilized formulation under accelerated conditions (i.e., for determining degradation or solid-state changes when stored at 40° C. and 75% relative humidity).

"Loading", "drug loading", "payload loading" and like terms as used herein, unless otherwise indicated by context, refer to the average number of payloads ("payload" and "drug" is used interchangeable herein with "biologically active compound or its derivative") in a population of Ligand Drug Conjugate compounds of a Ligand Drug Conjugate composition. The drug loading of that composition, which can also include species lacking conjugated drug, is characterized by a distribution of attached $D^+$ Units or quaternized drug linker moieties per Ligand Unit. Other species may include those Conjugate compounds having the same number of quaternized NAMPT Drug Units or quaternized drug linker moieties per Ligand Unit but differ by the attachment sites of their respective quaternized drug linker moieties to the Linker Unit, but otherwise have substantially the same structure with respect to the Ligand Unit, which for antibody Ligand Units allows for variations in glycosylation and mutational differences in peptide sequences as previously described. Drug loading may range from 1 to 24 quaternized NAMPT Drug Units ($D^+$) or quaternized drug linker moieties, comprising 1 to 4 $D^+$, per Ligand Unit and is sometimes referred to as the DAR, or drug to targeting moiety ratio, wherein the targeting moiety of a Ligand Drug Conjugate is its Ligand Unit.

Ligand Drug Conjugate compositions described herein typically have DAR values ranging from 1 to 24, and in some aspects range from 1 to about 10, from about 2 to about 8, from about 2 to about 6, from about 2 to about 5 or from about 2 to about 4. Typically, DAR values are about 2, about 4, about 6, about 8 or about 10. The average number of conjugated drugs per Ligand Unit, or DAR value, of a Ligand Drug Conjugate composition may be characterized by conventional means such as UV/visible spectroscopy, mass spectrometry, ELISA assay, and HPLC. A quantitative DAR value may also be determined. In some instances, separation, purification, and characterization of homogeneous Ligand Drug Conjugate compounds having a particular DAR value may be achieved by methods using reverse phase HPLC or electrophoresis. DAR may be limited by the number of attachment sites on a targeting agent that is to be incorporated into a Ligand Drug Conjugate as its Ligand Unit.

For example, when the targeting agent is an antibody and the attachment site is the sulfur atom of a cysteine thiol functional group, the antibody may have only one or several that are sufficiently reactive towards the maleimide ring system of a $M^1$-$A_R$(BU)-containing moiety, such as a Drug Linker compound, so as to undergo Michael addition. Sometimes, the cysteine thiol functional group is from of a cysteine residue that participated in an interchain disulfide bond of an antibody prior to reduction of that disulfide bond. Other times, the cysteine thiol functional group is that of a cysteine residue that did not participate in an interchain disulfide bond, but was introduced through genetic engineering. Sometimes, less than the theoretical maximum of quaternized NAMPT Drug Units or quaternized drug linker moieties having these Units is conjugated to an antibody during a conjugation reaction.

I. EMBODIMENTS

Provided herein are Ligand Drug Conjugate compositions and compounds, and their Drug Linker compound precursors and Intermediates thereof, wherein a Ligand Drug Conjugate compound of the composition is capable of preferential delivery of a NAMPTi compound to hyperproliferating cells, hyper-activated immune cells or other abnormal cells or is capable of preferential delivery of that compound to the vicinity of such abnormal cells including preferential delivery to nearby normal cells in comparison to normal cells or the vicinity of normal cells that are distant from these abnormal cells and are thus useful for treating diseases and conditions characterized by these abnormal cells.

1.1 General:

A Ligand Drug Conjugate has three major components: (1) a Ligand Unit, which incorporates or corresponds to a targeting agent that selectively binds to a targeted moiety present on, within or in the vicinity of abnormal cells in comparison to other moieties present on, within, or in the vicinity of normal cells where these abnormal cells are typically not present, or the targeted moiety is present on, within, or in the vicinity of abnormal cells in greater copy number in comparison to normal cells or the environment of normal cells where abnormal cells are typically not present, (2) a quaternized Drug Unit ($D^+$) incorporating or corresponding to the structure of a NAMPTi compound and having a quaternary skeletal nitrogen atom in a 5- or 6-membered nitrogen-containing partially unsaturated heterocyclic or heteroaromatic ring system as the site of quaternized nitrogen atom, and (3) a Linker Unit, which interconnects $D^+$ and the Ligand Unit and is capable of conditionally releasing $D^+$ as a NAMPTi compound, wherein said release is preferably within or in the vicinity of abnormal cells or within or in the vicinity of targeted normal cells that are peculiar to the environment of the abnormal cells as opposed to normal cells distant from the site of the abnormal cells in order to achieve a desired therapeutic index.

A NAMPTi compound to be used in the present invention is one that primarily or selectively exerts its biological effect (e.g., cytotoxic or cytostatic effect) on mammalian cells by inhibiting intracellular NAMPT. In some embodiments, the NAMPT compound competes competitively with nicotinamide at its binding site of enzymatically competent NAMPT homodimer and in these instances may or may not undergo phospho-ribosylation by the enzyme to form a mononucleotide. Without being bound by theory, the mononucleotide metabolite so formed may also be more slowly released from NAMPT than nicotinamide mononucleotide (NMN), thus causing product inhibition of the enzyme and/or when released may inhibit nicotinamide mononucleotide adenylyl transferase (NMNAT) in its conversion of NMN to NAD. The inhibition at either of those steps of the NAD salvage pathway may be more prolonged due to intracellular trapping of the mononucleotide metabolite due to its 5'-phosphate group, which inhibits efflux from the cell targeted by a Ligand Drug Conjugate compound having a quaternized NAMPT Drug Unit that incorporates or corresponds to the NAMPTi compound.

In some aspects, the targeted moiety, which is recognized by the targeting Ligand Unit of the Conjugate, is an epitope of an extracellular displayed membrane protein and is preferentially found on abnormal cells in comparison to normal cells. Specificity towards the abnormal (i.e., the targeted cells) results from the Ligand (L) Unit of the Ligand Drug Conjugate. In some embodiments, the Ligand Unit is that of an antibody (an exemplary but non-limiting targeting agent), wherein the Ligand Unit substantially retains the antibody's ability to recognize the abnormal mammalian cells. Such a Ligand Unit is sometimes referred to as an antibody Ligand Unit.

In some embodiments, it is preferred that the membrane protein targeted by the Ligand Unit have sufficient copy number and be internalized upon binding of a Ligand Drug Conjugate compound through its Ligand Unit in order to intracellularly deliver an effective amount of the NAMPTi compound to exert a cytotoxic, cytostatic, immune-suppressive or anti-inflammatory effect.

A NAMPTi compound to be incorporated or which corresponds to a quaternized NAMPT Drug Unit may exhibit adverse peripheral effects when administered in unconjugated form. Due to selective delivery when in the form of quaternized NAMPT Drug Unit in a Ligand Drug Conjugate, such compounds may be better tolerated. For that purpose, the Linker Unit of a Ligand Drug Conjugate is not merely a passive structure that serves as a bridge between a targeting Ligand Unit and a quaternized NAMPT Drug Unit but must be carefully engineered to have sufficient stability from the site of administration of the Ligand Drug Conjugate until its delivery to the targeted site to prevent premature release of the quaternized NAMPT Drug Unit and then should efficiently release it as the free NAMPTi compound. To accomplish that task, a targeting agent having a reactive sulfur atom of a thiol or thiol-containing functional group is preferably reacted with a $L_{SS}$-containing moiety of a Drug Linker compound having the formula $M_1-A_R(BU)-A_O-$ to form a $L_{SS}$-containing moiety having the formula of $M^2-A_R(BU)-A_O-$ within a Ligand Drug Conjugate, which under controlled hydrolysis conditions is convertible to a $L_S$-containing moiety having the formula $M^3-A_R(BU)-A_O-$, wherein BU is a cyclic or acyclic Basic Unit, $M^1$, $M^2$ and $M^3$ are a maleimide, succinimide and succinic acid amide moiety, respectively, and $A_R$ is a required Stretcher Unit and $A_O$ is a second optional Stretcher Unit. Thus, preferred Ligand Drug Conjugate are comprised of a targeting Ligand Unit, a quaternized NAMPT Drug Unit ($D^+$) and an intervening Linker Unit (LU) having $L_{SS}$ or $L_S$ as a primary linker ($L_R$), in which $L_R$ is bonded to the Ligand Unit and to $D^+$ through a secondary linker ($L_O$) so that one component of $L_O$ is attached to $L_R$ and the same or different component of $L_O$ is attached to $D^+$.

1.1 Primary Linker ($L_R$) with Basic Unit (BU):

A primary linker ($L_R$) is a component of a Linker Unit of a Ligand Drug Conjugate, a Drug Linker compound, or other Intermediate and preferably has a cyclic or acyclic Basic Unit, thus defining $L_R$ as a self-stabilizing linker ($L_{SS}$) or self-stabilized linker ($L_S$). In such Ligand Drug Conjugates, $L_R$ is attached to a Ligand Unit through a succinimide ($M^2$) moiety when $L_R$ is $L_{SS}$ or through a succinic acid amide ($M^3$) moiety when $L_R$ is $L_S$, in which the latter primary linker is obtained from hydrolysis of the $M^2$ moiety mediated by its Basic Unit (BU), or $L_R$ is capable of that attachment through interaction of a sulfur atom of a reactive thiol functional group of a targeting agent with a maleimide ($M^1$) moiety of $L_{SS}$ as $L_R$ in a Drug Linker compound or other Intermediate.

1.1.1 Acyclic Basic Unit

In some embodiments, $L_R$- is a $L_{SS}$ primary linker in a Drug Linker compound that has the formula $M^1-A_R(BU)-A_O-$, wherein BU is an acyclic Basic Unit. Exemplary $L_{SS}$ primary linkers of that formula in which $A_O$ is a Hydrolysis-enhancing (HE) Unit are represented by the substructure in Formula I in which $L_R$ is replaced by $L_{SS}$ of:

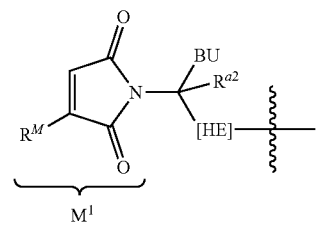

wherein the indicated $M^1$ moiety is a maleimide moiety, BU is acyclic Basic Unit, the wavy line indicates covalent binding to $-L_O-D^+$, $R^M$ is hydrogen or optionally substituted $C_1-C_6$ alkyl, HE is an optional Hydrolysis-enhancing Unit, and $R^{a2}$ is hydrogen or an optionally substituted $C_1-C_8$ alkyl. An acyclic Basic Unit is in some embodiments is comprised of an optionally substituted $C_1-C_6$ alkylene in which one of its radical centers is bonded to the same carbon as $R^{a2}$, wherein that carbon is in the alpha position relative to the imide nitrogen of the $M^1$ moiety, and the other radical center is bonded to a basic amine functional group of BU. To avoid premature hydrolysis of the maleimide ring system by base catalysis, the basic nitrogen of the basic amine functional group is typically protonated as a salt form, or the basic amine of the basic amine functional group is protected with an acid labile protecting group so that deprotection results in a protonated BU. For the former strategy to preclude premature hydrolysis, the basic amine of the basic functional group may be a primary, secondary or tertiary amine, while for the latter strategy, the basic amine of the basic functional group may be a primary or secondary amine.

On interaction with a reactive thiol functional group of a targeting agent, the $L_{SS}$ primary linker of formula $M^1$-$A_R$(BU)— in a Drug Linker compound is converted to a L-$L_{SS}$- substructure of formula L-$M^2$-$A_R$(BU)-$A_O$- in a quaternized drug linker moiety bonded to L of a Ligand Drug Conjugate of Formula 1a or Formula 1b in which L-($L_R$- of Formula 1 is replaced by L-($L_{SS}$- as exemplified by substructures:

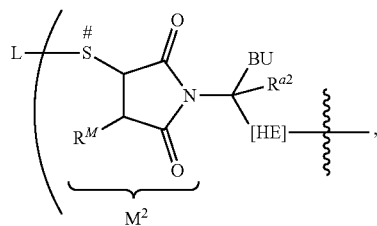

wherein HE as $A_O$ in a Hydrolysis-enhancing Unit, and the indicated $M^2$ moiety is a succinimide moiety, wherein that moiety is thio-substituted with L-S—; and wherein L is a Ligand Unit incorporating or corresponding to the targeting agent and the indicated (#) sulfur atom is derived from a reactive thiol or thiol-containing functional group of the targeting agent; the wavy line indicates the site of covalent attachment to $L_O$; BU is an acyclic Basic Unit, and the remaining variable groups are as defined for the corresponding $M^1$-$A_R$(BU)— substructure above in which BU is an acyclic Basic Unit, On controlled hydrolysis of the succinimide ring system mediated by the acyclic Basic Unit, the L-$L_{SS}$- moiety having the above L-$M^2$-$A_R$(BU)-$A_O$- substructure is converted to one having a $L_S$ primary linker for a Ligand Unit bonded to a quaternized drug linker moiety as exemplified by substructure(s):

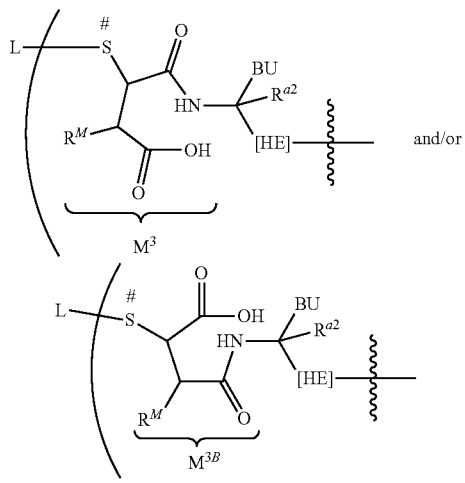

wherein the drug linker moieties of Conjugate compounds of the Ligand Drug Conjugate composition of Formula 1a or Formula 1b in which L-($L_R$- of Formula 1 is replaced by L-($L_S$-may be represented as having a single one of the above $L_S$ primary linkers bonded to L or as having a mixture of both, collectively referred to as L-($M^3$-$A_R$(BU)-$A_O$-, wherein BU is an acyclic Basic Unit and the remaining variable groups are as previously defined for their $M^2$-containing precursor, wherein the indicated $M^{3A}$ and $M^{3B}$ moieties are succinic acid amide ($M^3$) moieties thio-substituted by L-S—, and wherein the contribution of the above L-($M^{3A}$-$A_R$(BU)-$A_O$- and L-($M^{3B}$-$A_R$(BU)-$A_O$- constituents to the Conjugate compound mixture is dependent on the relative reactivity of the two carbonyl carbons of the succinimide ring system of the succinic acid ($M^2$) moiety of the L-($M^2$-$A_R$(BU)-$A_O$- precursor to base catalyzed hydrolysis.

In preferred embodiments, $R^{a2}$ in any one of the above $M^1$-$A_R$(BU)-$A_O$-, L-($M^2$-$A_R$(BU)-$A_O$- and L-($M^3$-$A_R$(BU)-$A_O$- substructures is —H, —$CH_3$, —$CH_2CH_3$, or —$CH_2CH_2CH_3$. In other preferred embodiments, [HE] as $A_O$ in any one of those structures is —C(=O)—. In any one of those embodiments, BU preferably has the formula of —[C($R^{a1}$)($R^{a1}$)]—[C($R^{a1}$)($R^{a1}$)]$_x$—N($R^{a3}$)($R^{a3}$), wherein subscript x is 0, 1, 2 or 3, each $R^{a1}$ independently is independently selected from the group consisting of hydrogen and $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, and ($C_5$-$C_{10}$ heteroaryl)-$C_1$-$C_4$ alkyl-, optionally substituted, or two $R^{a1}$ together with the carbon(s) to which they are attached and any intervening carbons define an optionally substituted $C_3$-$C_6$ carbocyclo; $R^{a3}$ independently are hydrogen, optionally substituted $C_1$-$C_6$ alkyl or a nitrogen protecting group, or together with the nitrogen atom to which they are attached define a optionally substituted $C_3$-$C_6$ heterocyclo or both $R^{a3}$ together define a nitrogen protecting group.

In more preferred embodiments, an acyclic BU is of formula —$(CH_2)_xNH_2$, —$(CH_2)_xNHR^{a3}$, or —$(CH_2)_xN(R^{a3})_2$, wherein subscript x is an integer ranging from 1 to 4, with 1 or 2 particularly preferred; and $R^{a3}$, at each instance, is independently hydrogen, —$CH_3$ or —$CH_2CH_3$, or both $R^{a3}$ together with the nitrogen to which they are attached define an azetidinyl, pyrrolidinyl or piperidinyl heterocyclyl, in which a basic primary, secondary or tertiary amine so defined is optionally protonated or is in a salt form, preferably as a pharmaceutically acceptable salt form.

In some of those more preferred embodiments, $R^{a2}$ is hydrogen and in this, and any one of the above embodiments an acyclic BU having the structure of —$CH_2$—$NH_2$ or —$CH_2CH_2$—$NH_2$ is particularly preferred. A Ligand Drug Conjugate of Formula 1a or Formula 1b, wherein $R^{a2}$ is hydrogen and the acyclic Basic Unit is —$CH_2$—$NH_2$ may be used as a comparator to a corresponding Conjugate in which BU is a cyclic Basic Unit, the structure of which is incorporated into that of $A_R$ and is formally derived by cyclization of an acyclic BU to $R^{a2}$ in any one of the above $L_{SS}$ or $L_S$ structures, wherein $R^2$ is other than hydrogen, as described herein. In any one of those more preferred embodiments, $R^M$ is preferably hydrogen or $C_1$-$C_4$ alkyl, more preferably hydrogen.

In particularly preferred embodiments, $L_{SS}$ primary linkers of a Drug Linker compound within Formula I, Formula Ia or Formula Ib in which $L_R$ of Formula I is replaced by $L_{SS}$ having an acyclic Basic Unit, or of a quaternized drug linker moiety bonded to a Ligand Unit of a Ligand Drug Conjugate compound of Formula 1a or Formula 1b in which L-($L_R$- of Formula 1, is replaced by L-($L_{SS}$ having an acyclic Basic Unit are represented, respectively, by substructures:

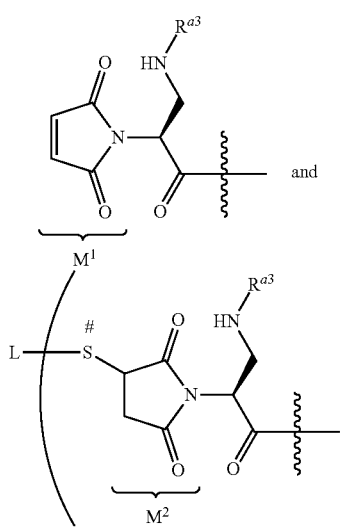

wherein $R^{a3}$ is preferably hydrogen, $C_1$-$C_4$ alkyl or a nitrogen protecting group and wherein the basic nitrogen atom to which $R^{a3}$ is attached is optionally protonated or in pharmaceutically acceptable salt form when $R^{a3}$ is hydrogen or $C_1$-$C_4$ alkyl.

$L_S$ primary linkers are derived from assisted hydrolysis by the acyclic Basic Unit under controlled conditions of those $L_{SS}$ primary linkers. Exemplary but non-limiting substructure(s) of Formula 1a or Formula 1b from that hydrolysis in which a Ligand Unit is bonded to a quaternized drug linker moiety in which L-($L_R$- of Formula 1 is replaced by L-($L_S$- are represented by:

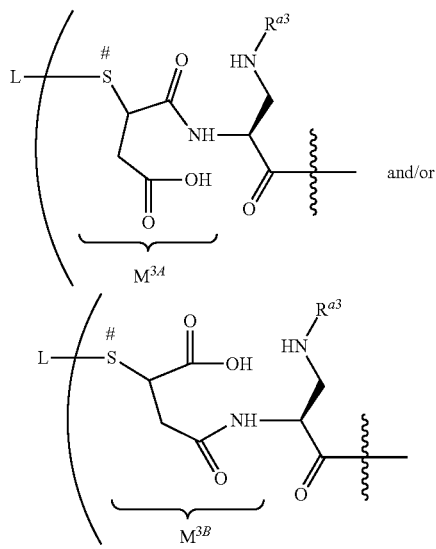

wherein the thio substituent L-S— is bonded to the carbon alpha to the carboxylic acid functional group or the amide functional group of the succinic acid ($M^3$) amide moiety or is a mixture of the two regioisomers and wherein $R^{a3}$ is hydrogen, $C_1$-$C_4$ alkyl or a nitrogen protecting group and wherein the basic nitrogen atom to which $R^{a3}$ is attached is optionally protonated or in pharmaceutically acceptable salt form when $R^{a3}$ is hydrogen or $C_1$-$C_4$ alkyl.

In particularly preferred embodiments $R^{a3}$ is hydrogen, wherein the basic nitrogen atom to which $R^{a3}$ is attached is protonated or in a pharmaceutically acceptable salt form, or $R^{a3}$ is —C(=O)O-t-Bu (BOC).

1.1.2 Cyclic Basic Unit

As mentioned above, a $L_{SS}$ moiety or L-($L_{SS}$ substructure having a cyclic Basic Unit will, in some embodiments, corresponds to any one of the above $M^1$-$A_R$(BU)-$A_O$-, L- and $M^2$-$A_R$(BU)-$A_O$- formulae in which $R^2$ is an optionally substituted $C_1$-$C_6$ alkyl, as exemplified by substructures of:

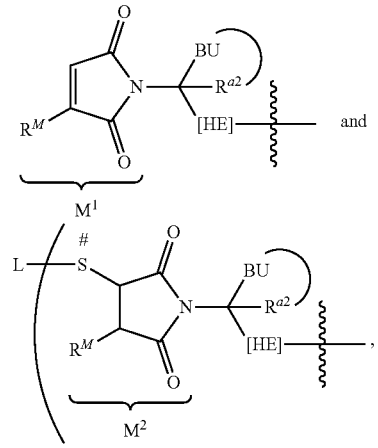

respectively, within a Drug Linker compound of Formula Ia in which $L_R$ of Formula I is replaced by $L_{SS}$, or within a drug linker moiety bonded to L within Formula 1a or Formula 1b in which L-($L_R$- of Formula 1 is replaced by L-($L_S$- corresponding to any one of the above L-($M^3$-$A_R$(BU)-$A_O$- formulae in which $R^{a2}$ is an optionally substituted $C_1$-$C_6$ alkyl, as exemplified by substructure(s) of:

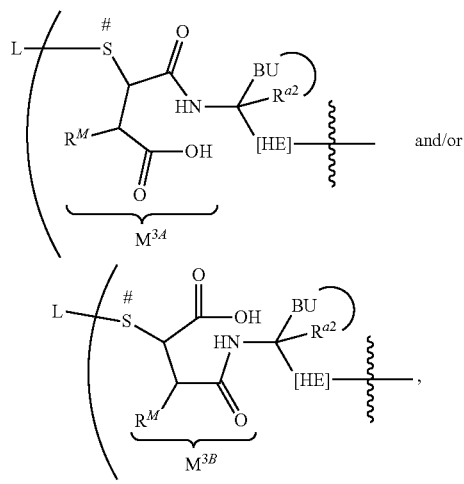

wherein BU is formally cyclized onto $R^{a2}$ so as to provide a cyclic Basic Unit, as indicated by the solid curved line, and the remaining variable groups are as defined in the corresponding $L_{SS}$ and $L_S$ moieties in which BU is acyclic.

Preferably, the basic nitrogen of a cyclic BU is capable of increasing the rate of hydrolysis of the succinimide ($M^2$)

moiety of Formula 1a or Formula 1b in which L-($L_R$- of Formula 1 is replaced by L-($L_{SS}$- to provide the shown succinic acid amide ($M^3$) moiety(ies) of Formula 1a or Formula 1b, respectively, wherein L-($L_R$- of Formula 1 is replaced by L-($L_S$-, at a suitable pH in comparison to a corresponding Conjugate in which $R^{a2}$ is hydrogen and BU is absent. More preferably, the enhancement of hydrolysis provided by a corresponding Conjugate in which BU is an acyclic Basic Unit is substantially retained by the Conjugate having an acyclic Basic Unit formally derived from that acyclic BU.

Formally, a cyclic Basic Unit in one group of embodiments includes those derived from removing a hydrogen atom from a basic nitrogen atom of a primary or secondary basic amine functional group of an acyclic Basic Unit and by removing a hydrogen atom from a carbon in the optionally substituted $C_1$-$C_{12}$ alkyl carbon chain of $R^{a2}$ to form an alkylene moiety and then combining the basic amino and alkylene moieties at their radical centers so as to form a corresponding spiro $C_4$-$C_{12}$ heterocyclo in which the radical nitrogen atom becomes a basic skeletal heteroatom of the heterocyclo, thereby resulting in a basic secondary or tertiary amine.

Preferably, the basic skeletal nitrogen atom of the spiro $C_4$-$C_{12}$ heterocyclo is one or two carbon atoms removed from the imide nitrogen of $M^1/M^2$ and is thus preferably removed from the corresponding amide nitrogen of $M^3$ by the same number of carbon atoms subsequent to controlled hydrolysis of $M^2$.

$L_{SS}$ primary linkers of a Drug Linker compound of Formula Ia or $L_{SS}$ primary linkers of a quaternized drug linker moiety bonded to a Ligand Unit of Formula 1a in which $L_R$ of Formula I is replaced by $L_{SS}$', which is the precursor to $L_{SS}$ in a Ligand Drug Conjugate of Formula 1a, or in which L-($L_R$- of Formula 1 is replaced by L-($L_{SS}$-, wherein in each formula BU is cyclic Basic Unit having a spiro heterocyclo in which the basic nitrogen atom of the basic amine functional group of BU is a skeletal atom are exemplified by substructures of:

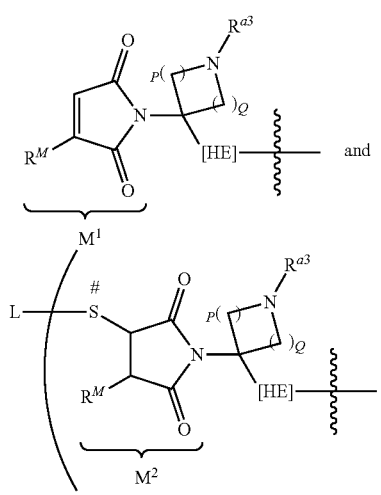

respectively, and $L_S$ primary linkers for a quaternized drug linker moiety bonded to a Ligand Unit of Formula 1b, in which L-($L_R$- of Formula 1 is replaced by L-($L_S$- and BU is cyclic Basic Unit, each having a spiro heterocyclo in which the basic nitrogen of the basic amine functional group is a skeletal atom are exemplified by substructures of:

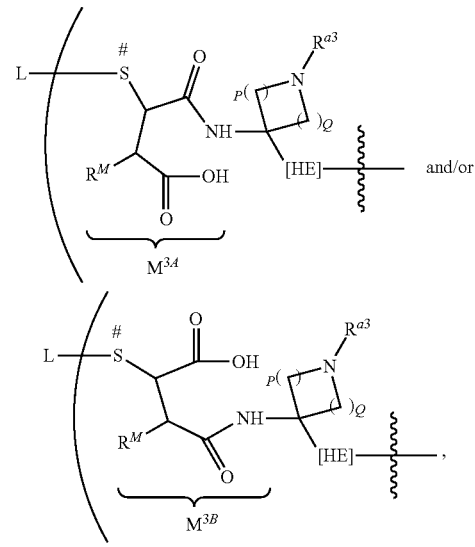

wherein $R^M$ is hydrogen or optionally substituted $C_1$-$C_6$ alkyl; subscript P is 1 or 2; subscript Q ranges from 1 to 6; and wherein $R^{a3}$ is —H, optionally substituted $C_1$-$C_6$ alkyl, optionally substituted —$C_1$-$C_4$ alkylene-($C_6$-$C_{10}$ aryl), or —$R^{PEG1}$—O—(CH$_2$CH$_2$O)$_{1-36}$—$R^{PEG2}$, wherein $R^{PEG1}$ is $C_1$-$C_4$ alkylene, $R^{PEG2}$ is —H or $C_1$-$C_4$ alkylene, wherein the basic nitrogen bonded to $R^3$ is optionally protonated or is in a salt form, preferably a pharmaceutically acceptable salt form, or $R^{a3}$ is a nitrogen protecting group such as a suitable acid-labile protecting group, and the remaining variable groups are as previously defined for $L_{SS}$ and $L_S$ primary linkers having the corresponding acyclic Basic Units. In preferred embodiments, subscript P is 1 and subscript Q is 1, 2 or 3 or subscript P is 2 and subscript Q is 1 or 2.

A suitable acid-labile protecting group for a basic amine nitrogen of a primary or secondary amine include an alkyloxy carbonyl group such as —C(═O)O-t-Bu (BOC). In any one of the above structures in which BU is a cyclic basic Unit, [HE] is preferably —C(═O)—. In any one of those preferred embodiments, $R^M$ is preferably hydrogen or $C_1$-$C_4$ alkyl, more preferably hydrogen.

In more preferred embodiments $L_{SS}$ primary linkers of a Drug Linker compound of Formula Ia in which $L_R$ of Formula I is replaced by $L_{SS}$ and having a cyclic Basic Unit and $L_{SS}$ primary linkers of a quaternized drug linker moiety bonded to a Ligand Unit of Formula 1a in which L-($L_R$- of Formula 1 is replaced by L-($L_{SS}$- and having a cyclic Basic Unit, are exemplified, respectively, by substructures of:

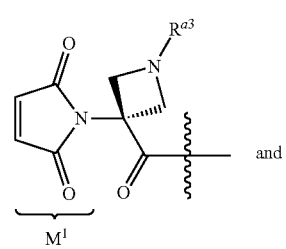

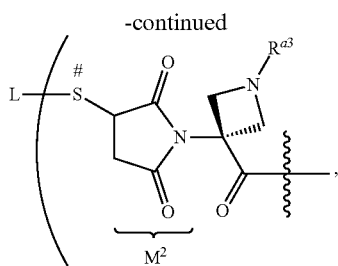

wherein $R^{a3}$ is —C(=O)O-t-Bu (BOC) or is hydrogen, wherein in the latter embodiment the nitrogen atom bonded to $R^{a3}$ is optionally protonated or is in a salt form, preferably in a pharmaceutically acceptable salt form.

In more preferred embodiments, $L_S$ primary linkers of a quaternized drug linker moiety bonded to a Ligand Unit in a Ligand Drug Conjugate of Formula 1b in which L-($L_R$- of Formula 1 is replaced by L-($L_S$- derived from controlled hydrolysis by the cyclic Basic Unit of the above $L_{SS}$ primary linker for a Ligand Drug Conjugate is exemplified by substructures of:

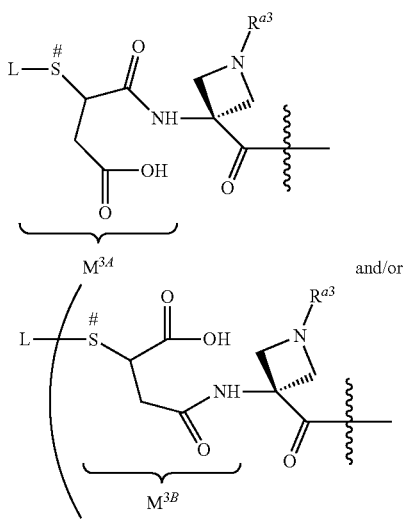

wherein the thio substituent L-(S— thio-substituent is bonded to the carbon alpha to the carboxylic acid functional group or the amide functional group of the succinic acid ($M^3$) amide moiety or is a mixture of the two regioisomers, and $R^3$ is —C(=O)O-t-Bu (BOC) or is hydrogen, wherein in the latter embodiment the nitrogen atom bonded to $R^{a3}$ is optionally protonated or is in a salt form, preferably in pharmaceutically acceptable salt form.

1.2 Secondary Linkers ($L_O$):

Secondary linkers in a Linker Unit of Ligand Drug Conjugate or a Drug Linker compound or an Intermediate thereof, is an organic moiety situated between a primary linker ($L_R$) and a quaternized NAMPT Drug Unit ($D^+$). A secondary linker ($L_O$) is subject to enzymatic or non-enzymatic processing so as to release $D^+$ as a NAMPTi compound. In those embodiments, a Cleavable Unit is present in $L_O$ to allow for that processing. In some embodiments of Ligand Drug Conjugates of Formula 1, Formula 1a or Formula Ia, or Drug Linker compounds of Formula I or Formula Ia, W is a Peptide Cleavable Unit so that $L_O$ presents a cleavage site for enzymatic processing by a protease to initiate release of $D^+$ as a NAMPTi compound. In those embodiments, a self-immolative Spacer Unit (Y) intervenes between W and the quaternized NAMPT Drug Unit, wherein the PAB or PAB-type moeity of Y is attached to W and $D^+$. In embodiments of Formula 1, Formula 1a Formula I or Formula Ia, enzymatic processing of the $L_O$ occurs at a Glucuronide Unit of formula —Y(W')—, replacing W in these formulae, wherein W' is a carbohydrate moiety (Su) bonded to a self-immolative Spacer Unit (Y) through an optionally substituted heteroatom (E') within a glycosidic bond, wherein that bond allows for enzymatic processing of $L_O$ by a glycosidase to initiate release of $D^+$ as a NAMPTi compound.

In some embodiments, the Peptide Cleavable Unit (W) provides a substrate for a protease present within or in the vicinity of hyper-proliferating cells, hyper-activated immune cells or other abnormal cells. Preferred are Peptide Cleavable Units that are not recognized or are poorly recognized by proteases that may be excreted by normal cells distant from the site of the targeted abnormal cells. Other preferred Peptide Cleavable Units are not recognized or are poorly recognized by proteases having systemic circulation so as to minimize non-targeted release of a quaternized Drug Unit from its Ligand Drug Conjugate that would result in undesired systemic exposure of a NAMPTi compound that was conjugated as that quaternized Drug Unit. More preferred are those Peptide Cleavable Units that are recognized as substrates by proteases that are regulatory proteases or proteases found in lysosomes, which are cellular compartments to which a Ligand Drug Conjugate is sometimes delivered upon internalization of a membrane-surface receptor to which the Ligand Unit of a Ligand Drug Conjugate compound has selectively and specifically bound. Regulatory and lysosomal proteases are exemplary intracellular proteases.

In one embodiment, W is a Peptide Cleavable Unit within a secondary linker of Formula 1, Formula 1a, Formula 1b, Formula I, Formula Ia or Formula Ib is comprised or consists of an amino acid, such as glutamate, or a dipeptide moiety having the structure of:

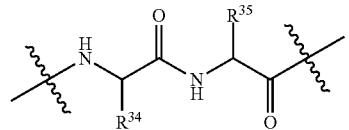

wherein the wavy lines indicate the sites of covalent attachment within a Linker Unit comprised of that secondary linker and $R^{34}$ is benzyl, methyl, isopropyl, isobutyl, sec-butyl, —CH(OH)CH$_3$ or $R^{34}$ has the structure of

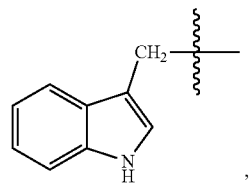 [SMILES: *Cc1c[nH]c2ccccc12]

wherein the wavy line indicates the site of covalent attachment to the dipeptide backbone, and $R^{35}$ is methyl, —$(CH_2)_4$—$NH_2$, —$(CH_2)_3NH(C=O)NH_2$, —$(CH_2)_3NH(C=NH)NH_2$, or —$(CH_2)_2CO_2H$, wherein the dipeptide moiety provides for a recognition site for a protease, preferably a regulatory or lysosomal protease.

In preferred embodiments, the Peptide Cleavable Unit consists or is comprised of a dipeptide. In another embodiment, the Peptide Cleavable Unit is comprised or consists of the dipeptide valine-citrulline (val-cit or vc). In another embodiment, the Peptide Cleavable Unit is comprised or consists of the dipeptide threonine-glutamic acid (thr-glu). In any one of those embodiments, the amino acid or dipeptide moeity is covalently attached to a self-immolative moiety of a self-immolative Spacer Unit (Y) through an amide bond. In some of those embodiments, that amide bond is between the carbonyl carbon of the carboxylic acid functional group of alanine or citrulline and an optionally substituted amine, the nitrogen atom of which is bonded to the optionally substituted central (hetero)arylene of the PAB or PAB-type self-immolative moiety and is sometimes referred to as an anilide bond. In other preferred embodiments, that amide bond is between the carbonyl carbon of the α-carboxylic acid functional group of glutamate and an optionally substituted amine, the nitrogen atom of which is bonded to the central optionally substituted (hetero)arylene in the PAB or PAB-type self-immolative moiety. Thus, in those embodiments, a self-immolative moiety is comprised of an optionally substituted arylamine or heteroarylamine moiety of a self-immolative Spacer Unit to which the aforementioned carboxylic acid functional group of an amino acid or a dipeptide moiety is attached through an anilide bond with the amino nitrogen bonded to that (hetero) arylamine moiety.

In another embodiment, a Glucuronide Unit of formula —Y(W')— replacing W in Formula 1, Formula 1a, Formula 1b, Formula I or Formula Ia within a secondary linker is comprised of a glycoside-bonded carbohydrate moiety (W') having a recognition site for an glycosidase. In preferred embodiments the glycosidase is intracellularly located with cells targeted by a Ligand Drug Conjugate comprised of that Glucuronide Unit. In those embodiments W' is a carbohydrate moiety (Su) bonded to a glycosidic heteroatom (E') in which the bond between Su and E' is a glycosidic bond, wherein Su-E' provides a recognition site for cleavage of that bond by a glycosidase. In those embodiments W' preferably has the structure of

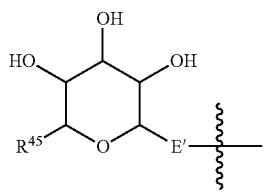

wherein $R^{45}$ is —$CH_2OH$ or —$CO_2H$ and E' is a heteroatom moiety such as —O—, —S— or —NH—, optionally substituted by an optionally substituted $C_1$-$C_6$ alkyl, which is bonded to the carbohydrate moiety (Su) and to a self-immolative moiety of a self-immolative Spacer Unit Y (as indicated by the wavy line) wherein the bond to the carbohydrate moiety provides for a recognition site for a glycosidase. Preferably, that site is recognized by a lysosome glycosidase. In some embodiments, the glycosidase is a glucuronidase so that $R^{45}$ is —$CO_2H$.

In preferred embodiments, $L_O$, in addition to a Peptide Cleavable Unit, is also comprised of a first Stretcher Unit (A). In some of those embodiment, A or a subunit thereof is -$L^P$(PEG)-. In other preferred embodiments, in addition to a Glucuronide Unit, $L_O$ is comprised of a first Stretcher Unit (A). In either of those embodiments A or a subunit thereof is sometimes -$L^P$(PEG)- in which $L^P$ is a parallel connector Unit and PEG is a PEG Unit. When $L_O$ contains a Peptide Cleavable Unit, A, W and Y are arranged in a linear relationship with respect to $D^+$ as represented within -$L_O$-$D^+$ structures of s1. When $L_O$ contains a Glucuronide Unit, which has the formula —Y(W')—, A, W' and Y are arranged in an orthogonal relationship with respect to $D^+$ as represented within -$L_O$-$D^+$ structures of s2.

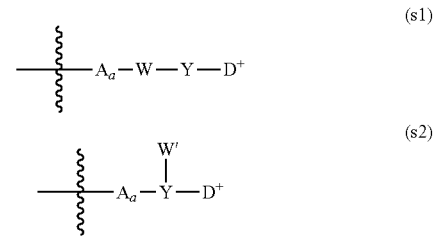

wherein the wavy line in either structure indicates the site of covalent bonding to $L_R$ in a Ligand Drug Conjugate or Drug Linker compound and subscript a is 0 or 1, wherein in both formulae Y is a self-immolative Spacer Unit. When subscript a is 1, the wavy line before A indicates covalent bonding of that $L_O$ subunit to a primary linker ($L_R$) of Formula 1 or Formula I, preferably to $L_{SS}$ of Formula 1a or Formula Ia or to $L_S$ of Formula 1b, replacing $L_R$ of Formula 1 or Formula I. When subscript a is 0 that wavy line indicates covalent binding to $L_R$ in Formula 1 or Formula I, to $L_{SS}$ of Formula 1a or Formula Ia, or $L_S$ or Formula 1b.

In preferred embodiments, subscript a is 1 in structure s1 or s2. In some of those embodiments, -$A_O$ is also present, which is covalently attached to A. In some of those preferred embodiments A or a subunit thereof is -$L^P$(PEG)-. In either one of those preferred embodiments of structure s1 or structure s2, the Spacer Unit (Y) bonded to W or W' is a self-immolative Spacer Unit comprised of a PAB or PAB-type self-immolative moiety.

In those embodiments of structure s1 in a Ligand Drug Conjugate of Formula 1, Formula 1a or Formula 1b, or a Drug Linker compound of Formula I or Formula Ia, $D^+$ is bonded to the Linker Unit through its NAMPT Head Unit so that the NAMPTi compound resulting from protease cleavage of the W—Y bond has the formula of $H_N$-DA-$I_N$-$T_N$, wherein the variable groups $T_N$, $I_N$, DA and $H_N$ are as defined for embodiments of NAMPTi compounds or quaternized NAMPT Drug Units. In those embodiments of structure s2 in a Ligand Drug Conjugate of Formula I, Formula Ia or Formula 1b, or a Drug Linker compound of Formula I or Formula Ia, $D^+$ is bonded to a Glucuronide Unit in a Linker Unit in which W is replaced by —Y(W')— within any one of these formulae through its NAMPT Head Unit so that the NAMPTi compound resulting from glycosidase cleavage of the W'—Y bond has the formula of $H_N$-DA-$I_N$-$T_N$, wherein the variable groups $T_N$, $I_N$, DA and $H_N$ are as defined for embodiments of NAMPTi compounds or quaternized NAMPT Drug Units.

Structures of some exemplary $A/A_O$, W and Y moieties in $L_O$ and their substituents are described in WO 2004/010957, WO 2007/038658, U.S. Pat. Nos. 6,214,345, 7,498,298, 7,968,687 and 8,163,888, and US Pat. Publ. Nos. 2009-0111756, 2009-0018086 and 2009-0274713 and these disclosures are specifically incorporated by reference herein.

In some embodiments A, or subunits thereof, has the structure of

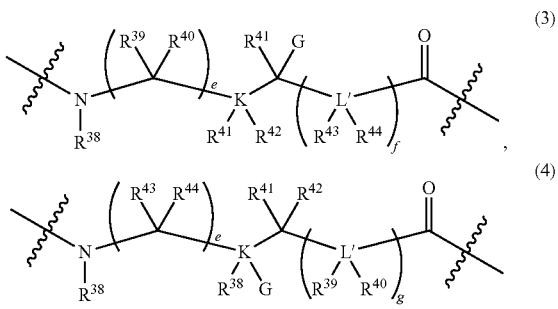

wherein the wavy lines indicate covalent attachments within the remainder of a Linker Unit, and wherein the wavy line to the carbonyl moiety of either structure represents the site of covalent attachment to the amino terminus of a dipeptide moiety comprising W wherein W is a Peptide Cleavable Unit and A W and Y are arranged linearly with respect to $D^+$ or the wavy line to the carbonyl moiety of either structure represents covalent attachment to the PAB or PAB-type moiety of a self-immolative Spacer Unit described herein wherein —(W')Y— is a Glucuronide Unit replacing W in which W' is bonded to Y and A, W' and Y are arranged orthogonally with respect to $D^+$, and wherein the wavy line to the amino moiety of either structures represents the site of covalent attachment to a carbonyl-containing functional group of another subunit of A or to $L_R$ or $L_{SS}$ in a Ligand Drug Conjugate or Drug Linker compound or to $L_S$ of a Ligand Drug Conjugate if A is a single discrete unit, preferably through $A_O$; and wherein K and L' independently are C, N, O or S atoms, provided that when K or L' is O or S, $R^{41}$ and $R^{42}$ to K or $R^{43}$ and $R^{44}$ to L' are absent, and when K or L are N, one of $R^{41}$, $R^{42}$ to K or one of $R^{42}$, $R^{43}$ to L' are absent, and provided that no two adjacent L' are independently selected as N, O, or S atoms;

wherein subscripts e and f are independently selected integers that range from 0 to 12, and subscript g is an integer ranging from 1 to 12:

wherein G is hydrogen, optionally substituted $C_1$-$C_6$ alkyl, —OH, —$OR^{PR}$, —$CO_2H$, $CO_2R^{PR}$, wherein $R^{PR}$ is a suitable protecting, —$N(R^{PR})(R^{PR})$, wherein $R^{PR}$ are independently a protecting group or $R^{PR}$ together form a suitable protecting group, or —$N(R^{45})(R^{46})$, wherein one of $R^{45}$, $R^{46}$ is hydrogen or $R^{PR}$, wherein $R^{PR}$ is a suitable protecting group, and the other is hydrogen or optionally substituted $C_1$-$C_6$ alkyl;

wherein $R^{38}$ is hydrogen or optionally substituted $C_1$-$C_6$ alkyl; $R^{39}$-$R^{44}$ independently are hydrogen, optionally substituted $C_1$-$C_6$ alkyl, optionally substituted aryl, or optionally substituted heteroaryl, or both $R^{39}$, $R^{40}$ together with the carbon to which they are attached comprise a $C_3$-$C_6$ cycloalkyl, or $R^{41}$, $R^{42}$ together with K to which they are attached when K is C, or $R^{43}$, $R^{44}$ together with L' to which they are attached when L' is C comprise a $C_3$-$C_6$ cycloalkyl, or $R^{40}$ and $R^{41}$, or $R^{40}$ and $R^{43}$, or $R^{41}$ and $R^{43}$ to together with the carbon or heteroatom to which they are attached and the atoms intervening between those carbon and/or heteroatoms comprise a 5- or 6-membered carbocyclo or heterocyclo, provided that when K is O or S atom, $R^{41}$ and $R^{42}$ are absent, when K is N, one of $R^{41}$, $R^{42}$ is absent, when L' is O or S atom, $R^{43}$ and $R^{44}$ are absent, and when L' is N, one of $R^{43}$, $R^{44}$ is absent.

In some embodiments $R^{38}$ of formula (3) or formula (4) is hydrogen. In other embodiments, —$K(R^{41})(R^{42})$— is —$(CH_2)$—. In other embodiments when subscript e is not 0, $R^{39}$ and $R^{40}$ are hydrogen in each occurrence. In other embodiments when subscript f is not 0, -$L(R^{43})(R^{44})$— is —$CH_2$— in each occurrence.

In preferred embodiments, G is —$CO_2H$. In other preferred embodiments, K and/or L are C. In other preferred embodiments, subscript e or f is 0. In still other preferred embodiments, subscripts e+f is an integer ranging from 1 to 4.

In some embodiments A, or a subunit thereof has the structure of —NH—$C_1$-$C_{10}$ alkylene-C(=O)—, —NH—$C_1$-$C_{10}$ alkylene-NH—C(=O)—$C_1$-$C_{10}$ alkylene-C(=O)—, —NH—$C_1$-$C_{10}$ alkylene-C(=O)—NH—$C_1$-$C_{10}$ alkylene (C=O)—, —NH—$(CH_2CH_2O)_s$—$CH_2(C=O)$—, —NH—$(C_3$-$C_8$ carbocyclo)(C=O)—, —NH—$(C_6$-$C_{10}$ arylene-)—C(=O)—, and —NH—$(C_3$-$C_8$ heterocyclo-)C(=O).

In other embodiments A, or a subunit thereof, has the structure of

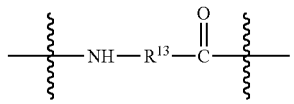

wherein $R^{13}$ is —$C_1$-$C_{10}$ alkylene-, —$C_3$-$C_8$ carbocyclo-, —$C_6$-$C_{10}$ arylene-, —$C_1$-$C_{30}$ heteroalkylene-, —$C_3$-$C_8$ heterocyclo-, —$C_1$-$C_{10}$ alkylene-$C_6$-$C_{10}$ arylene-, —$C_6$-$C_{10}$ arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_1$-$C_{10}$ alkylene-($C_3$-$C_8$ heterocyclo)-, —($C_3$-$C_8$ heterocyclo)-$C_1$-$C_{10}$ alkylene-, —$(CH_2CH_2O)_{1-10}$(—$CH_2)_{1-3}$—, or —$(CH_2CH_2NH)_{1-10}$(—$CH_2)_{1-3}$—. In some embodiments, $R^{13}$ is —$C_1$-$C_{10}$ alkylene- or —$C_1$-$C_{30}$ heteroalkylene-. In some embodiments, $R^{13}$ is —$C_1$-$C_{10}$ alkylene-, —$(CH_2CH_2O)_{1-10}$—$(CH_2)_{1-3}$—, or —$(CH_2CH_2NH)_{1-10}$—$(CH_2)_{1-3}$—. In some embodiments, $R^{13}$ is —$C_1$-$C_{10}$ alkylene-polyethylene glycol, or -polyethyleneimine.

In more preferred embodiments A, or a subunit thereof, corresponds in structure to an alpha-amino acid-, a beta-amino acid moiety, or other amine-containing acid residue. Other embodiments of A as a single unit or having subunits $A_{1-4}$ are described in embodiments for Linker Units of Ligand Drug Conjugate that have the formula of -$L_R$-$L_O$-, -$L_{SS}$-$L_O$-, $L_S$-$L_O$ or Linker Units of Drug Linker compounds that have the formula of $L_R$-$L_O$- or $L_{SS}$-$L_O$-.

In any one of the above embodiments, a self-immolative Spacer Unit of $L_O$ is capable of undergoing a 1,4- or 1,6-elimination reaction subsequent to enzymatic processing of W/W' which results in cleavage of the bond between W/W' and the PAB or PAB-type moiety of a self-immolative Spacer Unit Y. In those embodiments having a Peptide Cleavable Unit, W and Y are arranged linearly within $L_O$ of a Linker Unit of a Ligand Drug Conjugate of Formula 1, Formula 1a or Formula Ib or within $L_O$ of a Linker Unit of a Drug Linker compound of Formula I or Formula Ia with respect to $D^+$ so that $-Y-D^+$ preferably has the structure of:

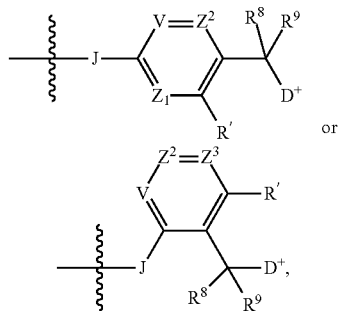

or wherein $D^+$ is a quaternized NAMPT Drug Unit corresponding to or incorporating a NAMPTi compound, J is an optionally substituted heteroatom whose electron donating ability is attenuation due to covalent bonding to W, which ability is restored on cleavage of the W-J bond to permit fragmentation of Y to release $D^+$ as a NAMPTi compound;

V, $Z^1$, $Z^2$ independently are $=N-$ or $=C(R_{24})-$, wherein $R^{24}$ is independently selected from the group consisting of hydrogen, halogen, $-NO_2$, $-CN$, $-OR^{25}$, $-SR^{26}$, $-N(R^{27})(R^{28})$, optionally substituted $C_1-C_6$ alkyl, optionally substituted $C_2-C_6$ heteroalkyl, and $-C(R^{29})=C(R^{30})-R^{31}$, wherein $R^{25}$ is hydrogen, optionally substituted $C_1-C_6$ alkyl, optionally substituted $C_6-C_{10}$ aryl or optionally substituted $C_6-C_{10}$ heteroaryl, $R^{26}$ is optionally substituted $C_1-C_6$ alkyl, optionally substituted $C_6-C_{10}$ aryl or optionally substituted $C_5-C_{10}$ heteroaryl, $R^{27}$ and $R^{28}$ independently are hydrogen, optionally substituted $C_1-C_6$ alkyl, optionally substituted $C_6-C_{10}$ aryl or optionally substituted $C_5-C_{10}$ heteroaryl or both $R^{27}$ and $R^{28}$ together with the nitrogen to which they are attached define an optionally substituted 5- or 6-membered heterocyclyl, $R^{29}$ and $R^{30}$ independently are hydrogen, or optionally substituted $C_1-C_6$ alkyl, and $R^{31}$ is hydrogen, optionally substituted $C_1-C_6$ alkyl, optionally substituted $C_6-C_{10}$ aryl, optionally substituted $C_5-C_{10}$ heteroaryl, $-C(=O)OR^{32}$ or $-C(=O)NR^{32}$, wherein $R^{32}$ is hydrogen, optionally substituted $C_1-C_6$ alkyl, optionally substituted $C_6-C_{24}$ aryl, or optionally substituted $C_5-C_{24}$ heteroaryl, or when V, $Z^2$ or $Z^2$, $Z^3$ are each $-C(R^{24})-$, the adjacent $R^{24}$ substituents together with the aromatic carbon atoms to which they are attached defines a $C_5-C_6$, carbocyclo or heterocyclo ring, optionally substituted, fused to the central (hetero)arylene of Y;

$R^8$ and $R^9$ independently are hydrogen, optionally substituted $C_1-C_6$ alkyl, or together with the benzylic carbon to which they are attached define an optionally substituted $C_3-C_6$ carbocyclo, or one of $R^8$, $R^9$ is hydrogen or optionally substituted $C_1-C_6$ alkyl and the other is optionally substituted $C_5-C_{10}$ aryl or $C_5-C_{10}$ heteroaryl; and R' is hydrogen or $-NO_2$, or other electron withdrawing group or is $-OCH_3$ or other electron donating group or is an optionally substituted $C_1-C_6$ alkyl or optionally substituted $C_2-C_6$ heteroalkyl; and R' is hydrogen, optionally substituted $C_1-C_6$ alkyl, or is halogen, $-NO_2$, $-CN$ or other electron withdrawing group, or is $-OCH_3$ or other electron donating group, or when $Z^1$ or $Z^3$ is $=C(R^{24})-$ in which $R^{24}$ is optionally substituted $C_1-C_6$ alkyl or optionally substituted $C_2-C_6$ heteroalkyl, R' and the adjacent $R^{24}$ substituent together with the aromatic carbon atoms to which they are attached defines a $C_5-C_6$, carbocyclo or heterocyclo ring, optionally substituted, fused to the central (hetero)arylene of Y.

In preferred embodiments, the quaternized NAMPT Drug Unit ($D^+$) is attached to $L_O$ through its quaternized NAMPT Head ($H_{N^+}$) Unit through a quaternized skeletal nitrogen atom of a nitrogen-containing 5- or 6-membered partially unsaturated heterocyclic or heteroaromatic ring system comprising $H_{N^+}$ so that release of $D^+$ provides a NAMPTi compound of formula $H_N$-DA-$I_N$-$T_N$, wherein variable groups $T_N$, $I_N$, DA and $H_N/H_{N^+}$ are as defined for embodiments of NAMPTi compounds or quaternized NAMPT Drug Units, wherein $H_N$ is comprised of a nitrogen-containing 5- or 6-membered heteroaromatic ring system; and V, $Z^1$, $Z^2$ and $Z^3$ independently are $-C(R^{24})=$ or $-N=$;

$R^{24}$ independently selected from the group consisting of hydrogen, halogen, $-NO_2$, and optionally substituted $C_1-C_6$ alkyl, one of $R^8$, $R^9$ is hydrogen or optionally substituted $C_1-C_6$ alkyl and the other is hydrogen; and R' is hydrogen or is $-NO_2$ or other electron withdrawing group or is $-OCH_3$ or other electron donating group; and J is $-N(R^{33})-$, wherein $R^{33}$ is as defined for $R^{32}$, and is preferably hydrogen or methyl, wherein the wavy line to J represents covalent bonding of the nitrogen atom of $-N(R^{33})-$ to W of Formula 1, Formula 1a, Formula 1b, Formula I or Formula Ia so as to inhibit the electron donating ability of J to suitably stabilize the central (hetero)arylene component of the self-immolative Spacer Unit and wherein enzymatic processing of W as a Peptide Cleavable Unit by a protease results in dis-inhibition of that ability, as when J is bonded to the carbonyl moiety of a carbonyl-containing functional group of the Peptide Cleavable Unit. As a result of that processing, release of the aforementioned benzylic substituent of the central (hetero)arylene component (i.e., $D^+$), is initiated to provide a NAMPTi compound, which in preferred embodiments has the formula of $H_N$-DA-$I_N$-$T_N$, wherein variable groups $T_N$, $I_N$, DA and $H_N$ are as described for NAMPTi compounds or quaternized NAMPT Drug Units.

In other preferred embodiments, no more than two of $R^{24}$ are other than hydrogen. In other preferred embodiments one or both of $R^8$ and $R^9$ are hydrogen or J is $-NH-$. In still other preferred embodiments V, $Z^1$, $Z^2$ and $Z^3$ are each $=CH-$, or one of V, $Z^1$, $Z^2$ or one of V, $Z^1$, $Z^3$ is $=C(R^{24})$, wherein $R^{24}$ is an electron withdrawing group and the remainder are $=CH-$. In more preferred embodiments, V, $Z^1$, $Z^2/Z^3$ are each $=CH-$; and $R^8$ and $R^9$ are each hydrogen. In other more preferred embodiments, V, $Z^1$, $Z^2/Z^3$ are each $=CH-$ and $R^8$ and $R^9$ are each hydrogen and J' is $-NH-$.

In embodiments having a Glucuronide Unit of formula $-Y(W')-$, in which W of Formula 1, Formula 1a, Formula 1b, Formula I or Formula Ia is replace with that Glucuronide Unit, W' and Y are arranged orthogonally within $L_O$ of the Linker Unit with respect to $-D^+$, wherein Y is self-immolative Spacer Unit having its PAB or PAB-type moiety bonded to a glycoside-bonded carbohydrate (Su) moiety through an optionally substituted heteroatom (E') so as to display a recognition site for a glycosidase. In those embodiments the orthogonal arrangement of Y and W' with respect to $-D^+$ is represented by the structure of:

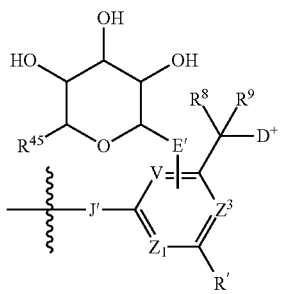

wherein J' and E' are independently selected from the group consisting of —O—, S—, and optionally substituted NH, including —N($R^{33}$)—, wherein $R^{33}$ is as defined for $R^{32}$, preferably hydrogen or methyl;

V, $Z^1$ and $Z^3$ independently are —C($R^{24}$)= or =N—; $R^{24}$ independently are selected from the group consisting of hydrogen, halogen, —$NO_2$, —CN, —$OR^{25}$, —$SR^{26}$, —N($R^{27}$)($R^{28}$), —C($R^{29}$)=C($R^{30}$)—$R^{31}$, W', optionally substituted $C_1$-$C_6$ alkyl and optionally substituted $C_2$-$C_6$ heteroalkyl;

provided that E' of W' is bonded to one of V, $Z^1$, $Z^3$, in which that variable group is defined as =C($R^{24}$)— (i.e., one of $R^{24}$ is W'— of formula Su-E'—) so that W' and the —C($R^8$)($R^9$)-$D^+$ moiety are in a 1,2 or 1,4 relationship and provided and the other V, $Z^1$, $Z^2$ is defined by =N— or =C($R^{24}$)— wherein $R^{24}$ is other than W'; and $R^{45}$ is —$CH_2OH$ or —$CO_2H$; and wherein $R^{25}$ is hydrogen, optionally substituted $C_1$-$C_6$ alkyl, optionally substituted $C_6$-$C_{10}$ aryl or optionally substituted $C_5$-$C_{10}$ heteroaryl; $R^{26}$ is optionally substituted $C_1$-$C_6$ alkyl, optionally substituted $C_6$-$C_{10}$ aryl or optionally substituted $C_5$-$C_{10}$ heteroaryl, and $R^{27}$ and $R^{28}$ independently are hydrogen, optionally substituted $C_1$-$C_6$ alkyl, optionally substituted $C_6$-$C_{10}$ aryl or optionally substituted $C_5$-$C_{10}$ heteroaryl or both $R^{27}$ and $R^{28}$ together with the nitrogen to which they are attached define an optionally substituted 5- or 6-membered heterocyclyl, $R^{29}$ and $R^{30}$ independently are hydrogen, or optionally substituted $C_1$-$C_6$ alkyl, and $R^{31}$ is hydrogen, optionally substituted $C_1$-$C_6$ alkyl, optionally substituted $C_6$-$C_{10}$ aryl, optionally substituted $C_5$-$C_{10}$ heteroaryl, —CN, —C(=O)$OR^{32}$ or —C(=O)$NR^{32}$; wherein $R^{32}$ is hydrogen, optionally substituted $C_1$-$C_6$ alkyl, optionally substituted a $C_6$-$C_{10}$ aryl, or optionally substituted $C_6$-$C_{10}$ heteroaryl;

$R^8$ and $R^9$ independently are hydrogen or optionally substituted $C_1$-$C_6$ alkyl or together with the benzylic carbon to which both are attached define an optionally substituted $C_3$-$C_6$ carbocyclo or one of $R^8$, $R^9$ is hydrogen or optionally substituted $C_1$-$C_6$ alkyl and the other is optionally substituted $C_6$-$C_{10}$ aryl or optionally substituted $C_5$-$C_{10}$ heteroaryl; $R^{45}$ is —$CH_2OH$ or —$CO_2H$;

R' is hydrogen, optionally substituted $C_1$-$C_6$ alkyl, or is —$NO_2$, or other electron withdrawing group, or is —$OCH_3$ or other electron donating group, or when $Z^1$ or $Z^3$ is =C($R^{24}$)— in which $R^{24}$ is optionally substituted $C_1$-$C_6$ alkyl or optionally substituted $C_2$-$C_6$ heteroalkyl, R' and the adjacent $R^{24}$ substituent together with the aromatic carbon atoms to which they are attached defines a $C_5$-$C_6$, carbocyclo or heterocyclo ring, optionally substituted, fused to the central (hetero) arylene of Y; and the wavy line to J' represents covalent bonding of J' to a functional group of A if subscript a is 1 or to $A_O$ if subscript a is 0 and $A_O$ is present (e.g., when J' is bonded to the carbonyl moiety of a carbonyl-containing functional group of A of $L_O$ or $A_O$ of $L_R$), or to $A_R$ if A and $A_O$ are both absent;

and wherein enzymatic processing of W'-E' by a glycosidase results in dis-inhibition of the ability of E' as an electron donating group to trigger 1,4- or 1,6-elimination of the benzylic substituent from the central (hetero) arylene of the PAB or PAB-type self-immolative Spacer Unit Y. As a result, releases of that processing, release of $D^+$ as a NAMPTi compound is initiated, which in preferred embodiments has the formula of $H_N$-DA-$I_N$-$T_N$, wherein variable groups $T_N$, $I_N$, DA and $H_N$ are as described for NAMPTi compounds or quaternized NAMPT Drug Units.

In preferred embodiments, at least one of $R^{24}$ not replaced by a bond to W' is an electron withdrawing group, preferably halogen, or one of $V^1$, $Z^2$, $Z^3$ is =N— and the remainder are =C($R^{24}$) in which one of the $R^{24}$ substituents is replaced by a bond to W'. In other preferred embodiments R' is an electron withdrawing group, preferably —$NO_2$.

In other preferred embodiments, the orthogonal arrangement involving the self-immolative moiety of Y bonded to W' and $D^+$ is represented by the structure of:

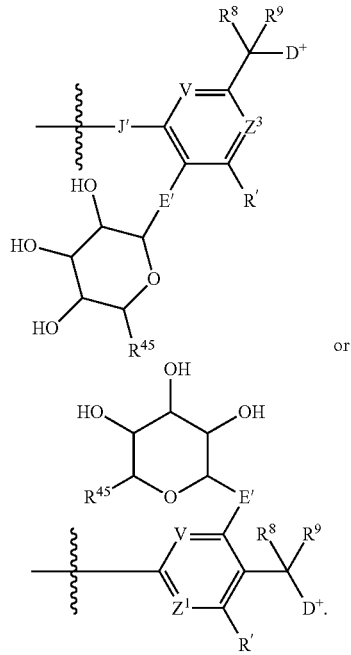

wherein the variable group are as previously described. In more preferred embodiments of the above orthogonal arrangement, -E'- is —O— or —NH—, wherein oxygen as the glycosidic bonded heteroatom is represented by O', and V and $Z^3/Z^1$ are each =C($R^{24}$), wherein $R^{24}$ independently is hydrogen or an electron withdrawing group. In other preferred embodiments $R^8$ and $R^9$ are hydrogen and one of V and $Z^1$ or one of V and $Z^3$ is =CH— and the other is =C($R^{24}$)—, wherein $R^{24}$ is an electron withdrawing group, preferably halogen. In other preferred embodiments, E' is 0' and J' is —NH, V, $Z^1/Z^2$ are each =CH— and R' is hydrogen or an electron withdrawing group, preferably-$NO_2$.

In particularly preferred embodiments, —Y(W')-D⁺ has the structure of:

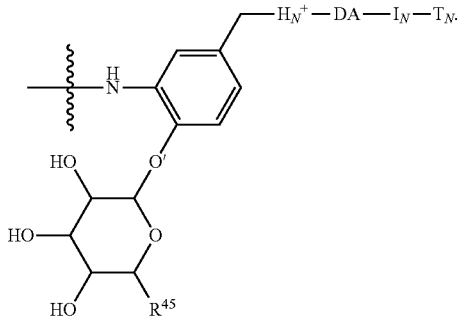

1.3 L_R-L_O Linker Units

In one group of embodiments of -L_R-L_O-, -L_SS-L_O-, or -L_S-L_O- Linker Units of a Ligand Drug Conjugate or L_R-L_O- or L_SS-L_O- Linker Unit of Drug Linker compounds, which are sometimes indicated as L_R'-L_O- or L_SS'-L_O- to indicate they are precursors to a Ligand Drug Conjugate's Linker Units, a quaternized NAMPT Drug Unit (D⁺) in any of the —W—Y-D⁺ or —Y(W')-D⁺ structures disclosed herein represents a NAMPTi compound in which a heteroaryl nitrogen atom of its NAMPT Head (H_N) Unit is quaternized by covalently attachment to a self-immolative Spacer Unit as H_N⁺, in which said attachment either retains the aromaticity of the heteroaryl or disrupts by forming a partially unsaturated heterocyclic ring system having a quaternized skeletal nitrogen atom. In the later instance, release of D⁺ as a NAMPTi compound restores the aromaticity of the heteroaryl with the skeletal nitrogen atom no longer being quaternized. In preferred embodiments, the nitrogen atom so quaternized is that of an optionally substituted 6-membered heteroaromatic ring system comprising a pyrimidine mimetic or nicotinamide mimetic represented by H_N or H_N-DA-, respectively so that quaternization of a skeletal nitrogen atom of the heteroaromatic ring system provides H_N⁺ as a quaternized pyrimidine mimetic or H_N⁺-DA- as a quaternized nicotinamide mimetic that retains its aromaticity.

In some of those embodiments, in which L_O is of structure s1 and having an acyclic or cyclic Basic Unit, -L_SS-L_O-D⁺ of a quaternized drug linker moiety within a Ligand Drug Conjugate compound of Formula 1a and its hydrolysis product -L_S-L_O-D⁺ in Formula 1b in which subscript p is replaced by p' whose formation in preferred embodiments is catalyzed by an acyclic or cyclic Basic Unit, have the structures of:

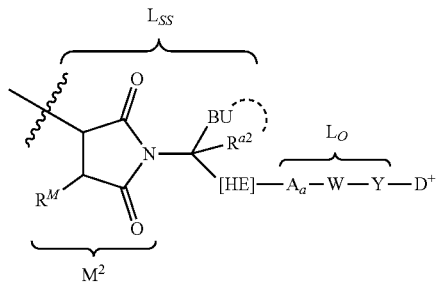

and

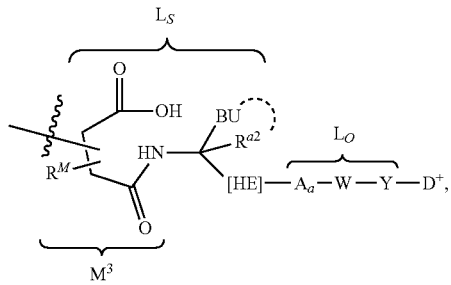

respectively, and corresponding Drug Linker Compounds of Formula Ia have the structure of:

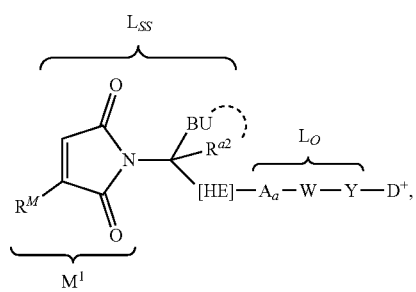

respectively, wherein protease action on W as a Peptide Cleavable Unit initiates release of D⁺ as a NAMPTi compound, the wavy line indicates covalent bonding of a Ligand Unit, which for the M³ moiety in L_S is to the carbon atom that is adjacent to its acid or amide functional group with R^M bonded to the carbon adjacent to the remaining functional group; the dotted curved line indicates optional cyclization so that when absent BU is an acyclic Basic Unit and R² is optionally substituted $C_1$-$C_6$ alkyl, and when present BU and R^{a2} together with the carbon atom to which both are attached define a cyclic Basic Unit; A is an optional first Stretcher Unit; subscript a is 0 or 1, indicating the absence or presence of A, respectively; [HE] is an optional Hydrolysis-enhancing Unit; R^M is hydrogen or $C_1$-$C_4$ alkyl; Y is a PAB or PAB-type self-immolative Spacer Unit as described herein for secondary linkers; and D⁺ is a quaternized NAMPT Drug Unit.

In preferred embodiments, -L_SS-L_O-D⁺ and -L_S-L_O-D⁺ in which L_O is of structure s1 in a Ligand Drug Conjugate compound of Formula 1a or Formula 1b in which subscript p is replaced by p' and having an acyclic or cyclic Basic Unit and Y is a PAB or PAB-type self-immolative Spacer Unit have structures of:

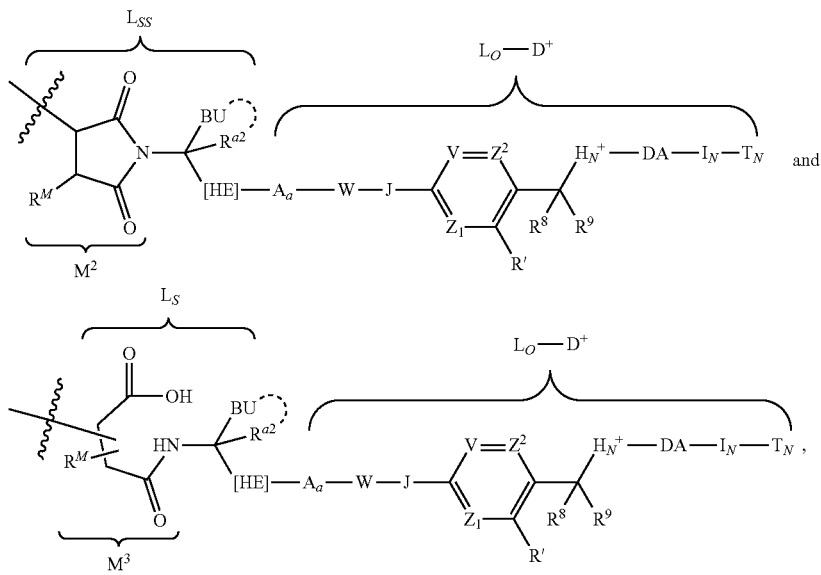

respectively, and corresponding Drug Linker Compounds of Formula Ia have the structure of:

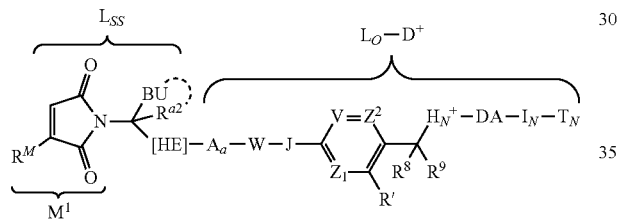

in which the indicated $M^1$ residue represents a maleimide moiety, wherein protease action on W as a Peptide Cleavable Unit initiates release of $D^+$ as a NAMPTi compound of formula $H_N$-DA-$I_N$-$T_N$, wherein $H_N$ is a NAMPT Head Unit and $H_{N^+}$ is the quaternized NAMPT Head Unit in which a skeletal nitrogen atom of the nitrogen-containing 5- or 6-membered partially unsaturated heterocyclic or heteroaromatic ring system comprising $H_{N^+}$ is quaternized, DA is a NAMPT Donor Acceptor Unit having optional cyclization back to $H_{N^+}$, $I_N$ is a NAMPT Interconnection Unit, $T_N$ is a NAMPT Tail Unit having optional cyclization back to itself or to $I_N$, the wavy line indicates covalent bonding of a Ligand Unit, which for the $M^3$ moiety in $L_S$ is to the carbon atom that is adjacent to its acid or amide functional group with $R^M$ bonded to the carbon adjacent to the remaining functional group; the dotted curved line indicates optional cyclization so that when absent BU is an acyclic Basic Unit and $R^2$ is optionally substituted $C_1$-$C_6$ alkyl, and when present BU and $R^{a2}$ together with the carbon atom to which both are attached define a cyclic Basic Unit; A is an optional first Stretcher Unit; subscript a is 0 or 1, indicating the absence or presence of A, respectively; [HE] is an optional Hydrolysis-enhancing Unit; $R^M$ is hydrogen or $C_1$-$C_4$ alkyl; V, $Z^1$ and $Z^2$ are independently =N— or =C($R^{24}$)—, wherein $R^{24}$, independently selected, is hydrogen, optionally substituted $C_1$-$C_6$ alkyl, an electron donating group or an electron withdrawing group; R' is hydrogen, an electron donating group or an electron withdrawing group; $R^8$ and $R^9$ independently are hydrogen, optionally substituted $C_1$-$C_6$ alkyl or together with the benzylic carbon to which they are attached define an optionally substituted $C_3$-$C_6$ carbocyclo, or one of $R^8$, $R^9$ is hydrogen or optionally substituted $C_1$-$C_6$ alkyl and the other is optionally substituted $C_6$-$C_{10}$ aryl or optionally substituted $C_5$-$C_{10}$ heteroaryl; J is an optionally substituted heteroatom, such as —O— or optionally substituted —NH—, which includes —N($R^{33}$), wherein $R^{33}$ is hydrogen or optionally substituted $C_1$-$C_6$ alkyl; and In preferred embodiments, two of V, $Z^1$, $Z^2$ are =CH— and the remainder is =N— or =C($R^{24}$)—, wherein $R^{24}$ is hydrogen, an electron donating group or an electron withdrawing group; R' is an electron donating group or an electron withdrawing group and $R^8$ and $R^9$ are independently hydrogen or $C_1$-$C_4$ alkyl. In other preferred embodiments, two of V, $Z^1$, $Z^2$ are =CH— and the remainder is =N— or =C($R^{24}$)—, wherein $R^{24}$ is an electron donating group or an electron withdrawing group, R' hydrogen and $R^8$ and $R^9$ are independently hydrogen, $C_1$-$C_4$ alkyl or optionally substituted phenyl. In other preferred embodiments, J is —NH— and two of V, $Z^1$, $Z^2$ are =CH— and the remainder is =C($R^{24}$)—, wherein $R^{24}$ is an electron donating group, preferably a $C_1$-$C_6$ alkoxy, or an electron withdrawing group, preferably —NO$_2$, and R' is hydrogen, and $R^8$ and $R^9$ are independently selected from the group consisting of hydrogen, —CH$_3$, and —CH$_2$CH$_3$. In other preferred embodiments, V, $Z^1$, $Z^2$ are each =CH— and $R^8$ and $R^9$ are independently selected from the group consisting of hydrogen, —CH$_3$, and —CH$_2$CH$_3$, J' is —NH— and R' is hydrogen. In those embodiments, the indicated $M^2$ and $M^3$ residues represent a succinimide moiety and a succinic acid amide moiety, respectively.

In any one of the forgoing embodiments, preferably two of V, $Z^1$, $Z^2$ are =CH— and the remainder is =N— or =C($R^{24}$)—, wherein $R^{24}$ is hydrogen, an electron donating group or an electron withdrawing group; R' is hydrogen, an electron donating group or an electron withdrawing group and $R^8$ and $R^9$ are independently hydrogen or $C_1$-$C_4$ alkyl. In other preferred embodiments, two of V, $Z^1$, $Z^2$ are =CH— and the remainder is =N— or =C($R^{24}$)—, wherein $R^{24}$ is an electron donating group or an electron withdrawing group, R' hydrogen and $R^8$ and $R^9$ are independently hydrogen, $C_1$-$C_4$ alkyl or optionally substituted phenyl. In other preferred embodiments, J is —NH— and two of V, $Z^1$, $Z^2$ are =CH— and the remainder is =C($R^{24}$)—, wherein $R^{24}$ is an electron donating group, preferably a $C_1$-$C_6$ alkoxy, or an electron withdrawing group and R' is hydrogen, and $R^8$ and $R^9$ are independently selected from the group consisting of hydrogen, —$CH_3$, and —$CH_2CH_3$. In still other preferred embodiments V, $Z^1$, $Z^2$ are each =CH— and $R^8$ and $R^9$ are independently selected from the group consisting of hydrogen, —$CH_3$, and —$CH_2CH_3$, J is —NH— and R' is an electron donating group or an electron withdrawing group In other preferred embodiments, in any one of the foregoing embodiments of formula $L_{SS}$-$L_O$-$D^+$ of a Drug Linker compound of Formula Ia, or of formula -$L_{SS}$-$L_O$-$D^+$ or -$L_S$-$L_O$-$D^+$ of a Ligand Drug Conjugate of Formula 1a or Formula 1b, respectively, preferably $R^8$ and $R^9$ are each hydrogen, [HE] is —C(=O)—, and one of V, $Z^1$, $Z^2$ is =C($R^{24}$), wherein $R^{24}$ is an electron donating group or an electron withdrawing group and the remainder are =CH— and R' is hydrogen, or $R^8$ and $R^9$ are each hydrogen, [HE] is —C(=O)—, and V, $Z^1$, $Z^2$ are each =CH—, and R' is an electron withdrawing group or an electron donating group. In more preferred embodiments, each of V, $Z^1$, $Z^2$ is =CH— and $R^8$ and $R^9$ are each hydrogen, J is —NH— and R' is hydrogen.

In other preferred embodiments, -$L_{SS}$-$L_O$-$D^+$ of a quaternized drug linker moiety within a Ligand Drug Conjugate compound of Formula Ia and its hydrolysis product -$L_S$-$L_O$-$D^+$ in Formula 1b in both of which subscript p is replaced by p' and $L_O$ is of structure is so that A, W and Y are in a linear configuration with respect to $D^+$, are represented by:

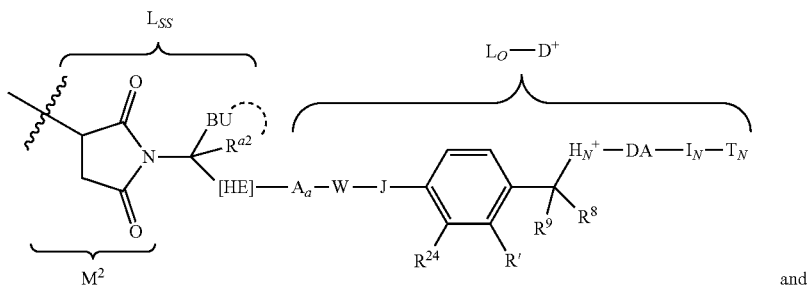

and

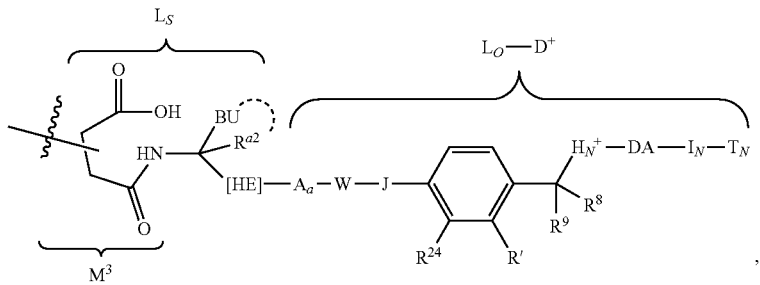

, respectively, and corresponding Drug Linker compounds of Formula Ia are represented by:

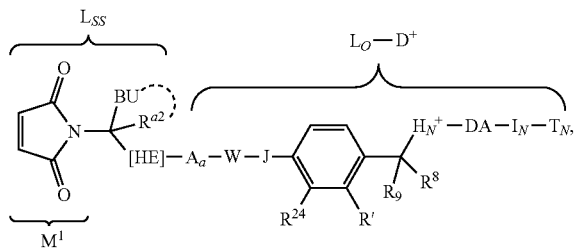

wherein -D$^+$ has the formula of —H$_{N'}$-DA-I$_N$-T$_N$ and protease action on W as a Peptide Cleavable Unit initiates release of D$^+$ as a NAMPTi compound of formula H$_N$-DA-I$_N$-T$_N$, R$^{24}$ is an electron donating group or an electron withdrawing group and R' is hydrogen, or R$^{24}$ is hydrogen and R' is an electron donating group or an electron withdrawing group, or R$^{24}$ and R' are both hydrogen; and W is a Peptide Cleavable Unit, and the dotted curved line and other variable groups are as previously described for quaternized drug linker moieties in Ligand Drug Conjugates having an acyclic or cyclic Basic Unit in peptide-cleavable secondary linkers.

In those quaternized drug linker moieties and Drug Linker compounds, preferably J is —NH—. In more preferred embodiments in which A, W and Y in L$_O$ are in a linear configuration with respect to D$^+$, a quaternized drug linker moiety within a Ligand Drug Conjugate compound of Formula 1a in which subscript p is replaced by p' is of formula -L$_{SS}$-L$_O$-D$^+$ or is its hydrolysis product of formula -L$_S$-L$_O$-D$^+$ in Formula 1b, in both of which subscript p is replaced by p' and wherein D$^+$ has the formula of —H$_{N'}$-DA-I$_N$-T$_N$, have the structures of:

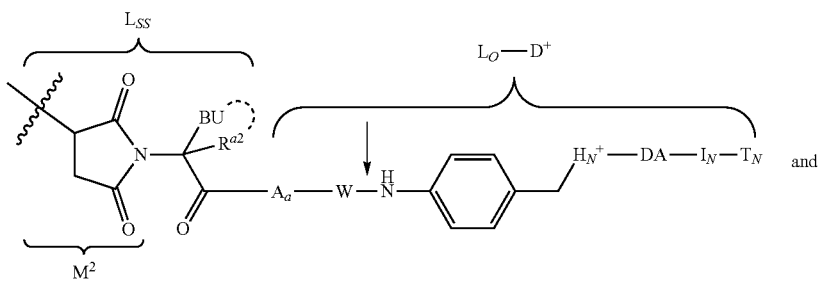

and

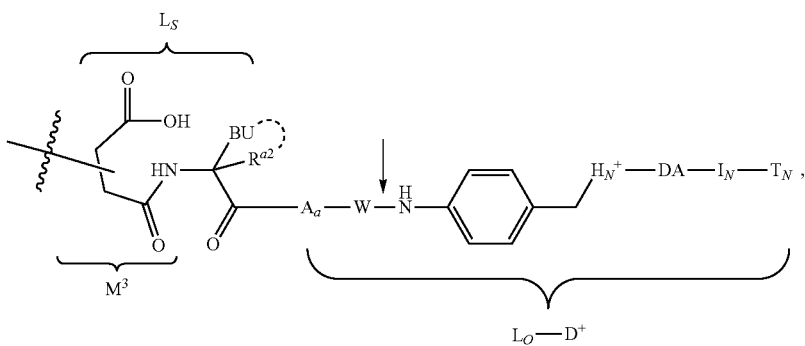

respectively, and corresponding Drug Linker compounds of formula $L_{SS}$-$L_O$-$D^+$ in Formula Ia have the structure of:

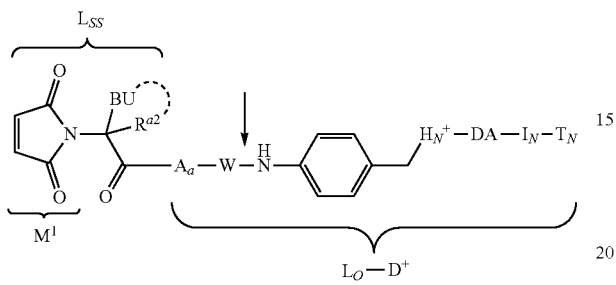

wherein —$H_{N^+}$-DA-$I_N$-$T_N$ represents -$D^+$; wherein protease cleavage of the indicated W—N bond initiates release of $D^+$ as a NAMPTi compound of formula $H_N$-DA-$I_N$-$T_N$ and wherein in any one of the above -$L_O$-$D^+$ substructures W is a Peptide Cleavable Unit that consists or is comprised of an amino acid or a dipeptide, wherein the amino acid or dipeptide moiety is at the distal end of W and the indicated bond is an amide bond specifically cleavable by an intracellular protease in comparison to freely circulating serum proteases and wherein the remaining variable groups are as previously defined for quaternized drug linker moieties in Ligand Drug Conjugates and Drug Linker compounds having an acyclic or cyclic Basic Unit and a peptide cleavable secondary linker.

In other embodiments, in which $L_O$ is of structure s1 and not having a Basic Unit, -$L_R$-$L_O$-$D^+$ of a quaternized drug linker moiety within a Ligand Drug Conjugate composition or compound thereof in which subscript p is replaced by p' of Formula 1, has the structure of:

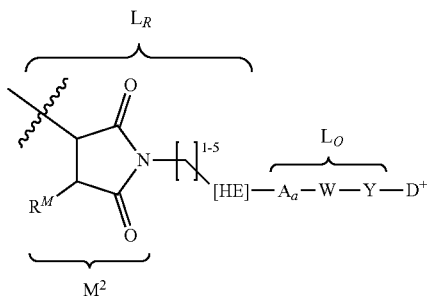

and and corresponding Drug Linker Compounds of Formula I have the structure of:

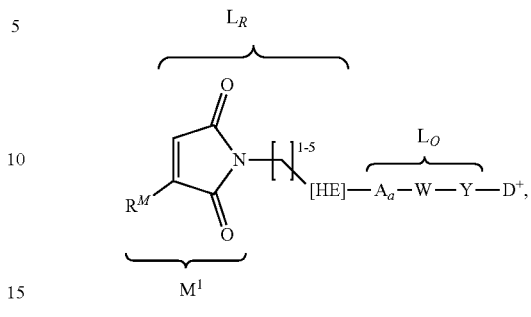

respectively, wherein protease action on W as a Peptide Cleavable Unit initiates release of $D^+$ as a NAMPTi compound, the wavy line indicates covalent bonding of a Ligand Unit; A is an optional first Stretcher Unit; subscript a is 0 or 1, indicating the absence or presence of A, respectively; [HE] is an optional Hydrolysis-enhancing Unit; $R^M$ is hydrogen or $C_1$-$C_4$ alkyl; Y is a PAB or PAB-type self-immolative Spacer Unit as described herein for secondary linkers; and $D^+$ is a quaternized NAMPT Drug Unit.

In preferred embodiments, -$L_R$-$L_O$-$D^+$ in which $L_O$ is of structure s1 in a Ligand Drug Conjugate composition or compound thereof in which subscript p is replaced by p' of Formula 1 and not having a Basic Unit and Y is a PAB or PAB-type self-immolative Spacer Unit has the structure of:

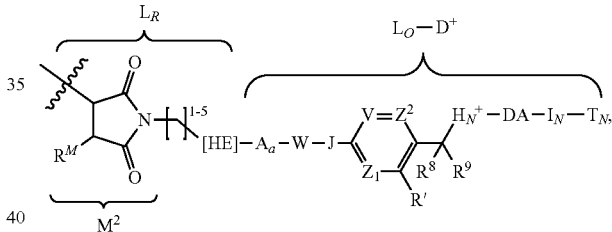

and corresponding Drug Linker Compounds of Formula I have the structure of:

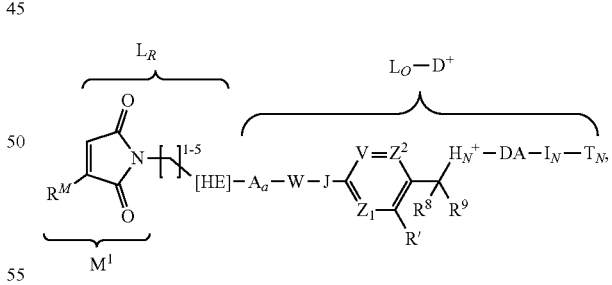

wherein protease action on W as a Peptide Cleavable Unit initiates release of $D^+$ as a NAMPTi compound of formula $H_N$-DA-$I_N$-$T_N$, wherein $H_N$ is a NAMPT Head Unit and $H_{N^+}$ is the quaternized NAMPT Head Unit in which a skeletal nitrogen atom of the nitrogen-containing 5- or 6-membered partially unsaturated heterocyclic or heteroaromatic ring system comprising $H_{N^+}$ is quaternized, DA is a NAMPT Donor Acceptor Unit having optional cyclization back to $H_{N^+}$, $I_N$ is a NAMPT Interconnection Unit, $T_N$ is a NAMPT Tail Unit having optional cyclization back to itself or to $I_N$, the wavy line indicates covalent bonding of a Ligand Unit; A is an optional first Stretcher Unit; subscript a is 0 or 1, indicating the absence or presence of A, respectively; [HE] is an optional Hydrolysis-enhancing Unit; $R^M$ is hydrogen or $C_1$-$C_4$ alkyl; V, $Z^1$ and $Z^2$ are independently =N— or =C($R^{24}$)—, wherein $R^{24}$, independently selected, is hydrogen, optionally substituted $C_1$-$C_6$ alkyl, an electron donating group or an electron withdrawing group; R' is hydrogen, an electron donating group or an electron withdrawing group; $R^8$ and $R^9$ independently are hydrogen, optionally substituted $C_1$-$C_6$ alkyl or together with the benzylic carbon to which they are attached define an optionally substituted $C_3$-$C_6$ carbocyclo, or one of $R^8$, $R^9$ is hydrogen or optionally substituted $C_1$-$C_6$ alkyl and the other is optionally substituted $C_6$-$C_{10}$ aryl or optionally substituted $C_5$-$C_{10}$ heteroaryl; J is an optionally substituted heteroatom, such as —O— or optionally substituted —NH-consistent with the requirement of J for initiating self-immolation on cleavage of the W—N bond, which includes —N($R^{33}$), wherein $R^{33}$ is hydrogen or optionally substituted $C_1$-$C_6$ alkyl.

In preferred embodiments, two of V, $Z^1$, $Z^2$ are =CH— and the remainder is =N— or =C($R^{24}$)—, wherein $R^{24}$ is hydrogen, an electron donating group or an electron withdrawing group; R' is an electron donating group or an electron withdrawing group and $R^8$ and $R^9$ are independently hydrogen or $C_1$-$C_4$ alkyl. In other preferred embodiments, two of V, $Z^1$, $Z^2$ are =CH— and the remainder is =N— or =C($R^{24}$)—, wherein $R^{24}$ is an electron donating group or an electron withdrawing group, R' hydrogen and $R^8$ and $R^9$ are independently hydrogen, $C_1$-$C_4$ alkyl or optionally substituted phenyl. In other preferred embodiments, J is —NH— and two of V, $Z^1$, $Z^2$ are =CH— and the remainder is =C($R^{24}$)—, wherein $R^{24}$ is an electron donating group, preferably a $C_1$-$C_6$ alkoxy, or an electron withdrawing group, preferably —$NO_2$, and R' is hydrogen, and $R^8$ and $R^9$ are independently selected from the group consisting of hydrogen, —$CH_3$, and —$CH_2CH_3$. In other preferred embodiments V, $Z^1$, $Z^2$ are each =CH— and $R^8$ and $R^9$ are independently selected from the group consisting of hydrogen, —$CH_3$, and —$CH_2CH_3$, J is —NH— and R' is hydrogen. In those embodiments, the indicated $M^2$ residue represents a succinimide moiety.

In other preferred embodiments, -$L_R$-$L_O$-$D^+$ of a quaternized drug linker moiety in a Ligand Drug Conjugate composition or compound thereof in which subscript p is replaced by p' of Formula 1 not having a Basic Unit within a Ligand Drug Conjugate composition or compound thereof in which $L_O$ of structure s1 so that A, W and Y are in a linear configuration with respect to $D^+$, is represented by:

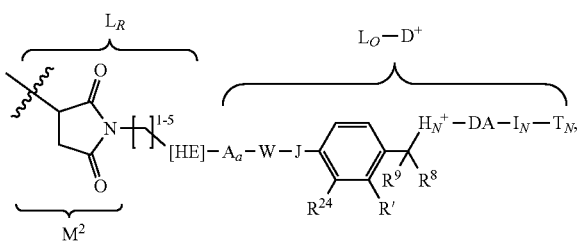

and corresponding Drug Linker compounds of Formula I are represented by:

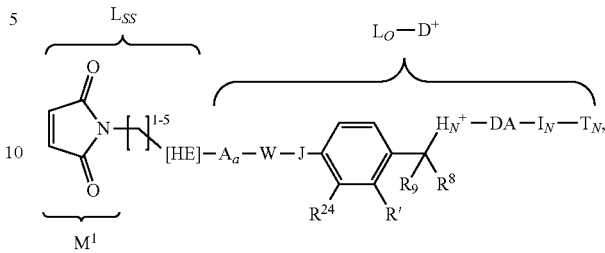

wherein -$D^+$ has the formula of —$H_{N'}$-DA-$I_N$-$T_N$ and protease action on W as a Peptide Cleavable Unit initiates release of $D^+$ as a NAMPTi compound of formula $H_N$-DA-$I_N$-$T_N$, $R^{24}$ is an electron donating group or an electron withdrawing group and R' is hydrogen, or $R^{24}$ is hydrogen and R' is an electron donating group or an electron withdrawing group, or $R^{24}$ and R' are both hydrogen; and the dotted curved line and other variable groups are as previously described for quaternized drug linker moieties in Ligand Drug Conjugates having an acyclic or cyclic Basic Unit in peptide-cleavable secondary linkers.

In those quaternized drug linker moieties and Drug Linker compounds, preferably J is —NH—. In more preferred embodiments in which A, W and Y in $L_O$ are in a linear configuration with respect to $D^+$, a quaternized drug linker moiety of formula -$L_R$-$L_O$-$D^+$ within a Ligand Drug Conjugate composition or compound thereof in which subscript p is replaced by p' of Formula 1, wherein $D^+$ has the formula of —$H_{N'}$-DA-$I_N$-$T_N$, has the structure of:

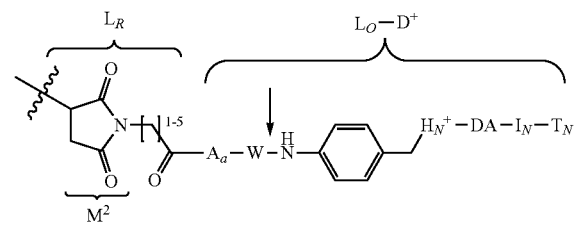

and corresponding Drug Linker compounds of formula $L_R$-$L_O$-D of Formula I have the structure of:

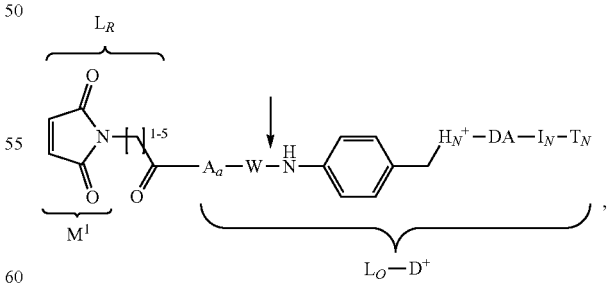

wherein —$H_{N'}$-DA-$I_N$-$T_N$ represents -$D^+$; wherein protease cleavage of the indicated W—N bond initiates release of $D^+$ as a NAMPTi compound of formula $H_N$-DA-$I_N$-$T_N$ and wherein in any one of the above -$L_O$-$D^+$ substructures W consists or is comprised of an amino acid or a dipeptide wherein the amino acid or dipeptide moeity is at the distal end of W and the indicated bond is an amide bond specifically cleavable by an intracellular protease in comparison to freely circulating serum proteases and wherein the remaining variable groups are as previously defined for quaternized drug linker moieties in Ligand Drug Conjugates and Drug Linker compounds having an acyclic or cyclic Basic Unit and a peptide cleavable secondary linker.

In any one of the above embodiments in which W is a Peptide Cleavable Unit comprised of a dipeptide that dipeptide is recognized by an intracellular protease. Preferably, that protease is a cathepsin protease in which preferred dipeptides recognized by the cathepsin protease have the structure of

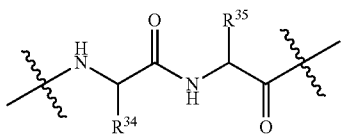

wherein R$^{34}$ is benzyl, methyl, isopropyl, isobutyl, sec-butyl, —CH(OH)CH$_3$ or has the structure of

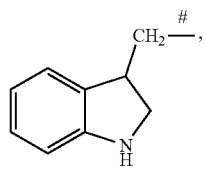

wherein the pound sign (#) indicates the site of covalent attachment to the dipeptide backbone and R$^{35}$ is methyl, —(CH$_2$)$_4$—NH$_2$, —(CH$_2$)$_3$NH(C=O)NH$_2$, (CH$_2$)$_3$NH(C=NH)NH$_2$, or —(CH$_2$)$_2$CO$_2$H, wherein the wavy line at the dipeptide N-terminal indicates the site of covalent binding to A or A$_O$ or to L$_{SS}$ or L$_S$, depending on the presence or absence of A and/or A$_O$, and the wavy line at the dipeptide C-terminal indicates the site of covalent binding to J or —NH— as J.

In other L$_R$-L$_O$ embodiments, a quaternized drug linker moiety of formula -L$_{SS}$-L$_O$-D$^+$ of a Ligand Drug Conjugate composition or compound thereof in which subscript p is replaced by p' of Formula 1 in which L$_O$ contains a Glucuronide Unit of formula —Y(W')— so that L$_O$ is of structure s2, which has A, W' and Y in an orthogonal configuration with respect to D$^+$, has the structure of:

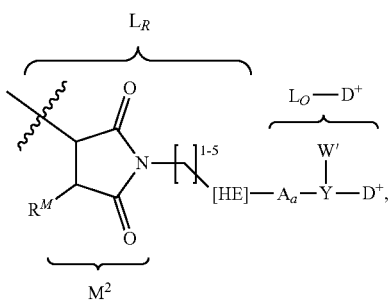

and corresponding Drug Linker Compounds of Formula I have the structure of:

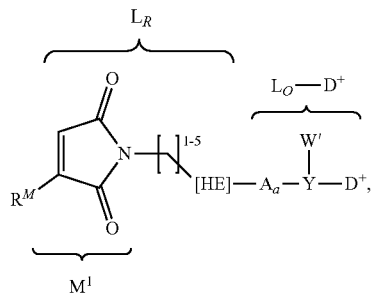

wherein the wavy line indicates covalent bonding of a Ligand Unit; A is an optional first Stretcher Unit; subscript a is 0 or 1, indicating the absence or presence of A, respectively; [HE] is an optional Hydrolysis Enhancer Unit; R$^M$ is hydrogen or C$_1$-C$_4$ alkyl, W' represents a glycoside-bonded carbohydrate (Su) moiety through an optionally substituted heteroatom (E') bonded to Y so as to display a recognition site for a glycosidase and consistent with the requirement that E' initiates self-immolation on cleavage of the W'-E' bond, wherein Y is a PAB or PAB-type self-immolative Spacer Unit as described above for secondary linkers, and D$^+$ is a quaternized NAMPT Drug Unit, wherein glycosidase action on the glycoside bond of W' initiates release of D$^+$ as a NAMPTi compound of formula H$_N$-DA-I$_N$-T$_N$.

In preferred embodiments, -L$_R$-L$_O$-D$^+$ in a Ligand Drug Conjugate composition or compound thereof in which subscript p is replaced by p' of Formula 1 in which W is replaced by a Glucuronide Unit of formula —Y(W)— so that L$_O$ is of structure s2 and not having an acyclic or cyclic Basic Unit and Y is a PAB or PAB-type self-immolative Spacer Unit has structure of:

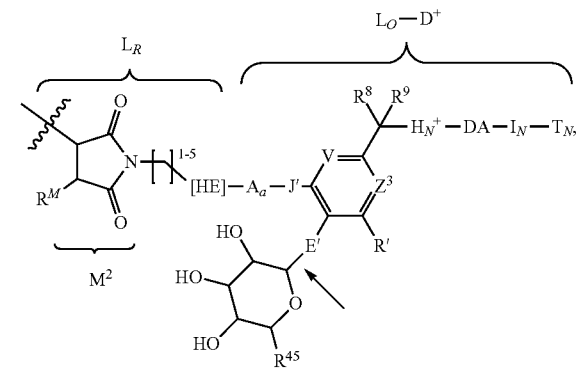

and corresponding Drug Linker Compounds of Formula I have the structure of:

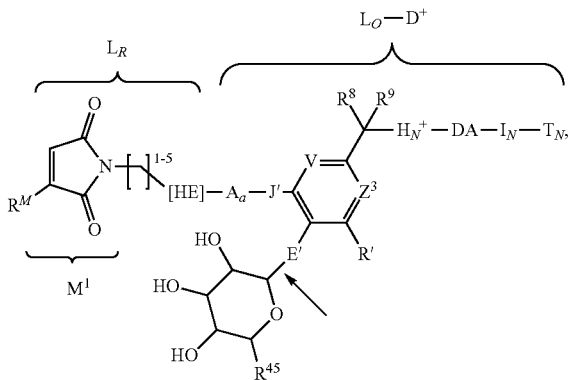

wherein glycosidase action on the indicated glycoside bond initiates release of a NAMPTi compound of formula $H_N$-DA-$I_N$-$T_N$ wherein $H_N$ is a NAMPT Head Unit, $H_{N^+}$ is the quaternized NAMPT Head Unit having a skeletal nitrogen atom of a heteroaryl or partially unsaturated or partially aromatic heterocyclyl comprising that Unit as the site of quaternization, DA is a NAMPT Donor Acceptor Unit having optional cyclization back to $H_{N^+}$, $I_N$ is a NAMPT Interconnection Unit, $T_N$ is a NAMPT Tail Unit having optional cyclization back to itself or to $I_N$, V and $Z^3$ are independently =N— or =C($R^{24}$)—, wherein $R^{24}$, independently selected, is hydrogen, optionally substituted $C_1$-$C_6$ alkyl or an electron donating or electron withdrawing group; $R^8$ and $R^9$ independently are hydrogen or optionally substituted $C_1$-$C_6$ alkyl or together with the benzylic carbon to which both are attached define an optionally substituted $C_3$-$C_6$ carbocyclo, or one of $R^8$, $R^9$ is hydrogen or optionally substituted $C_1$-$C_6$ alkyl and the other is optionally substituted $C_6$-$C_{10}$ aryl or optionally substituted $C_5$-$C_{10}$ heteroaryl; J' and E' are independently selected optionally substituted heteroatoms, such as —O— or optionally substituted —NH— consistent with the requirement of E' for initiating self-immolation on cleavage of the W'—N bond, which includes —N($R^{33}$), wherein each $R^{33}$ is independently hydrogen or optionally substituted $C_1$-$C_6$ alkyl; $R^{45}$ is —$CH_2OH$ or —$CO_2H$; and the wavy line indicates covalent bonding of a Ligand Unit; and the remaining variable groups are as previously defined above.

In preferred embodiments, $R^8$ and $R^9$ are independently hydrogen or $C_1$-$C_4$ alkyl. In other preferred embodiments, J' is —NH—. In more preferred embodiments, one of V and $Z^3$ is =N— or =C($R^{24}$), wherein $R^{24}$ is an electron withdrawing group and the other is =CH—; R' is hydrogen or an electron withdrawing group; $R^8$ and $R^9$ are independently selected from the group consisting of hydrogen, —$CH_3$ and —$CH_2CH_3$; and J' is —NH—. In other more preferred embodiments, V and $Z^3$ are each =CH— and R' is hydrogen; $R^8$ and $R^9$ are independently selected from the group consisting of hydrogen, —$CH_3$ and —$CH_2CH_3$; and J' is —NH—. In any one of those embodiments the indicated $M^2$ and $M^3$ residues represent a succinimide moiety and a succinic acid amide moiety, respectively.

In more preferred embodiments, -$L_R$-$L_O$-$D^+$ in which W is a Glucuronide Unit of formula —Y(W')— replacing W in a Ligand Drug Conjugate composition or compound thereof in which subscript p is replaced by p' of Formula 1 so that $L_O$ is of structure s2 in which A, W' and Y are in an orthogonal configuration with respect to $D^+$, wherein $D^+$ has the formula of —$H_{N^+}$-DA-$I_N$-$T_N$, and are represented by:

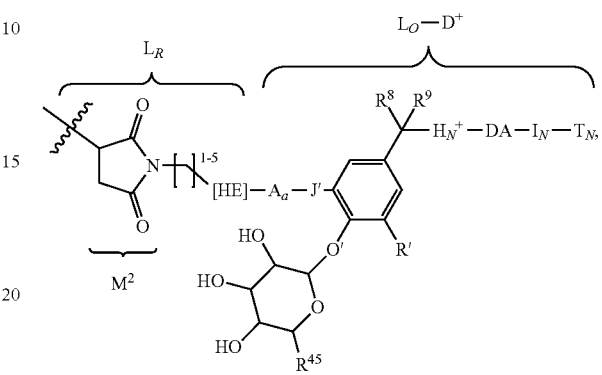

and corresponding Drug Linker compounds of Formula I are represented by:

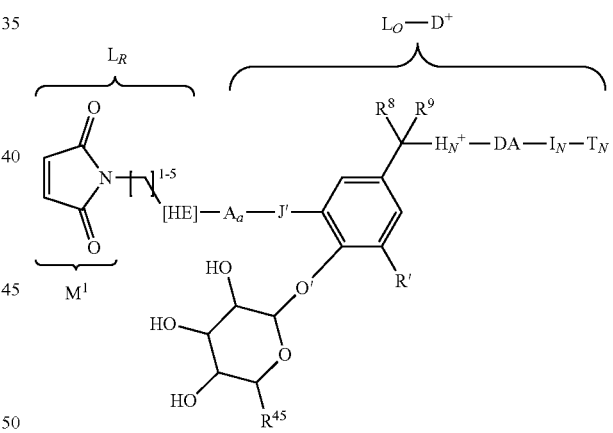

wherein O' represents a glycosidic-bonded oxygen atom, the bond to which is cleavable by a glycosidase to initiate release of $D^+$ as a NAMPTi compound of formula $H_N$-DA-$I_N$-$T_N$, and wherein the variable groups are as previously described for Glucuronide-based quaternized drug linker moieties in Ligand Drug Conjugates or Drug Linker compounds.

In those quaternized drug linker moieties and Drug Linker compounds, preferably one of $R^8$, $R^9$ is hydrogen and the other is hydrogen, $C_1$-$C_4$ alkyl or optionally substituted phenyl. In other such embodiments preferably J' is —O—, —S— or —N($R^{33}$), wherein $R^{33}$ is hydrogen or $C_1$-$C_4$ alkyl and/or R' is hydrogen or an electron withdrawing group. In more preferred embodiments J' is —NH— and R' is hydrogen.

In more preferred embodiments in which A, W' and Y in $L_O$ are in an orthogonal configuration with respect to $D^+$, a quaternized drug linker moiety of formula $-L_R-L_O-D^+$ in a Formula 1a Ligand Drug Conjugate composition or compound thereof in which subscript p is replaced by p', wherein $D^+$ has the formula of $—H_{N^+}-DA-I_{N'}-T_N$, is represented by:

and corresponding Drug Linker compounds of Formula I are represented by:

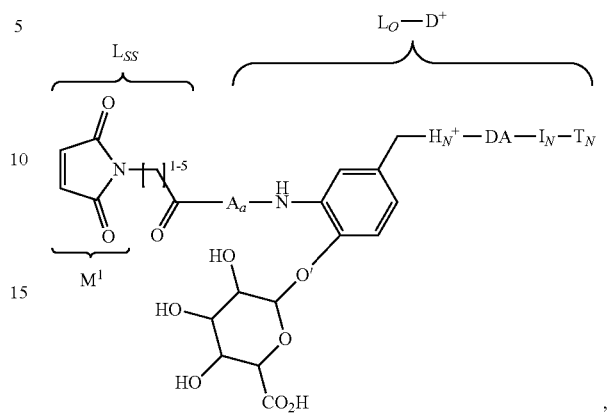

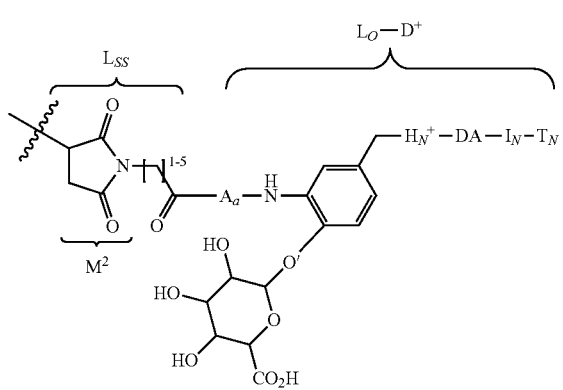

wherein O' represents a glycosidic-bonded oxygen atom, the bond to which is cleavable by a glycosidase to initiate release of $D^+$ as a NAMPTi compound of formula $H_{N'}-DA-I_{N'}-T_N$, and the other variable groups are as previously described for Glucuronide-based quaternized drug linker moieties in Ligand Drug Conjugates or Drug Linker compounds.

In preferred embodiments in which W as a Peptide Cleavable Unit and having a heterocyclo cyclic Basic Unit, the $-L_{SS}$ and $-L_S$ containing quaternized drug linker moieties of a Ligand Drug Conjugate compound of Formula 1a or Formula 1b in which subscript p is replaced by p' and having $L_O$ of structure s1 are represented by:

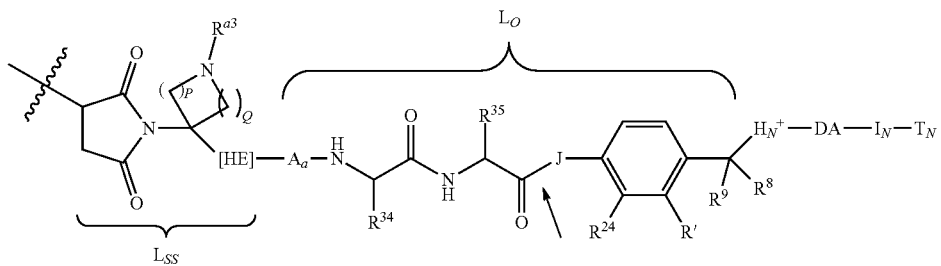

and

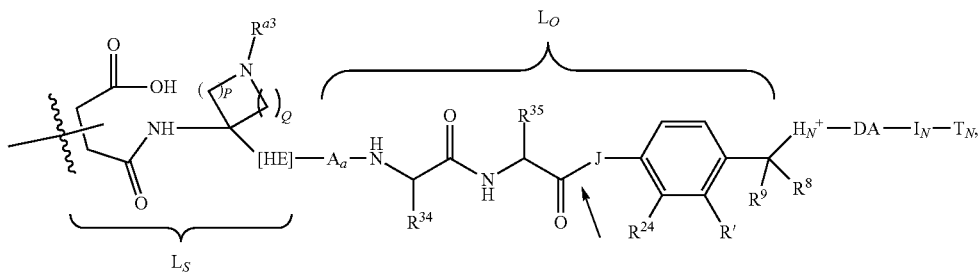

respectively, and corresponding Drug Linker compounds of Formula Ia are represented by:

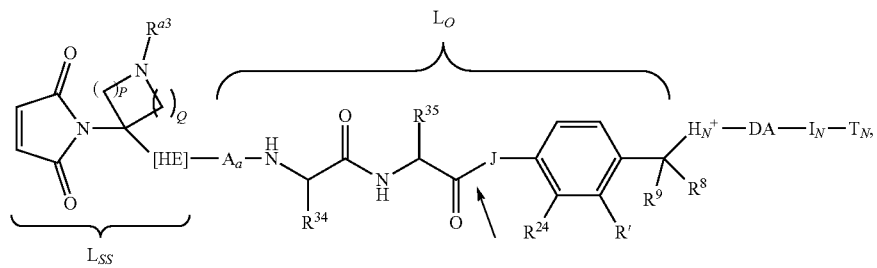

wherein subscript P is 1 or 2; subscript Q ranges from 1 to 6; and wherein $R^{a3}$ is —H, optionally substituted $C_1$-$C_6$ alkyl, optionally substituted —$C_1$-$C_4$ alkylene-($C_6$-$C_{10}$ aryl), or —$R^{PEG1}$—O—$(CH_2CH_2O)_{1-36}$—$R^{PEG2}$, wherein $R^{PEG1}$ is $C_1$-$C_4$ alkylene, $R^{PEG2}$ is —H or $C_1$-$C_4$ alkylene, wherein the basic nitrogen bonded to $R^3$ is optionally protonated or is in a salt form, preferably in a pharmaceutically acceptable salt form, or $R^3$ is a nitrogen protecting group such as a suitable acid-labile protecting group, and J' is —N($R^{33}$)—, O or S, wherein $R^{33}$ is hydrogen or $C_1$-$C_4$ alkyl; and $L_{SS}$ and -$L_S$ containing quaternized drug linker moieties of a Ligand Drug Conjugate compound of Formula 1a or Formula 1b having $L_O$ of formula s1 in which W is a Peptide Cleavable Unit and having an acyclic Basic Unit are represented by:

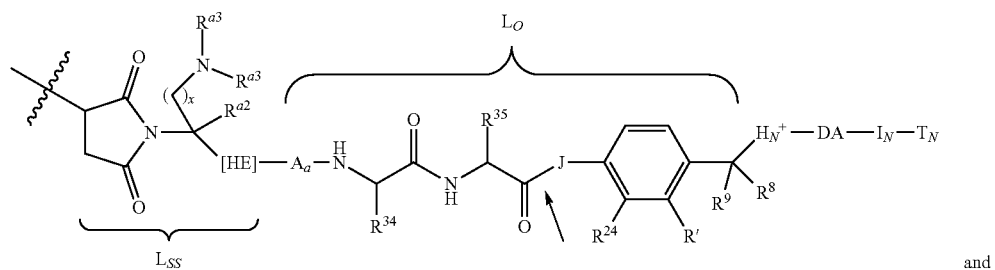

and

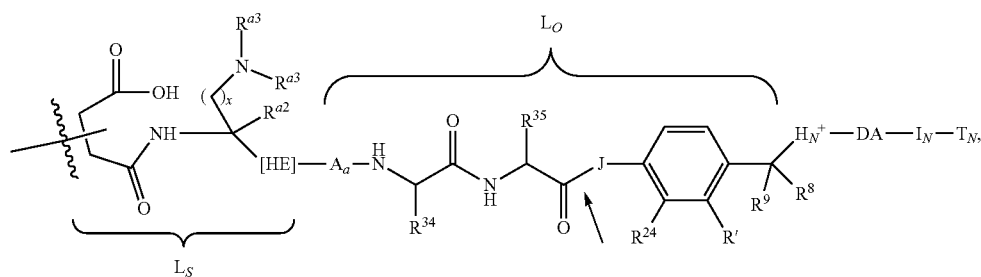

respectively, and corresponding Drug Linker compounds of Formula Ia are represented by:

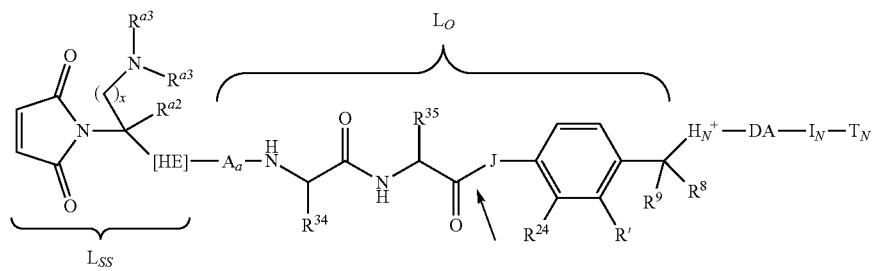

wherein cleavage of the indicated W-J bond within $L_O$ initiates release of an NAMPTi compound of formula $H_N$-DA-$I_N$-$T_N$, HE is an optional Hydrolysis Enhancing Unit, A is an optional first Stretcher Unit, subscript a is 0 or 1, indicating the absence or presence of A, respectively; subscript x is 1 or 2, $R^{a2}$ is hydrogen or —$CH_3$ or —$CH_2CH_3$; $R^{a3}$, at each instance, is independently hydrogen, —$CH_3$ or —$CH_2CH_3$, or both $R^{a3}$ together with the nitrogen to which they are attached define an azetidinyl, pyrrolidinyl or piperidinyl heterocyclyl, in which a basic primary, secondary or tertiary amine so defined is optionally protonated or is in a salt form, preferably in a pharmaceutically acceptable salt form;

$R^{34}$ and $R^{35}$ are as previously defined for Peptide Cleavable Units and the remaining variable groups are as previously defined for drug linker moieties and Drug Linker compounds comprised of these Peptide Cleavable Units.

In more preferred embodiments, the -$L_{SS}$ or -$L_S$ containing quaternized drug linker moieties of a Ligand Drug Conjugate compound having $L_O$ of structure s1 in Formula 1a or Formula 1b, in which subscript p is replaced by p' and W is a Peptide Cleavable Unit and having a heterocyclo cyclic Basic Unit are represented by:

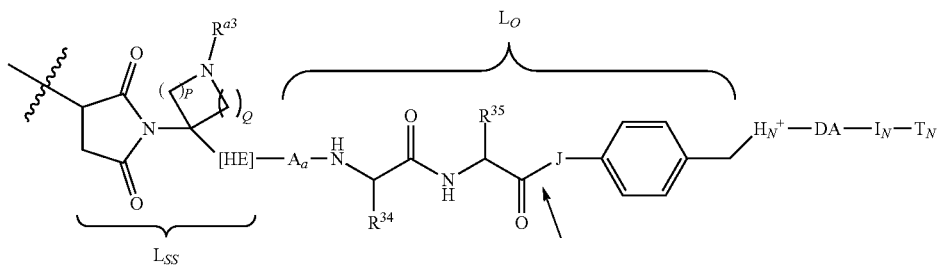

and

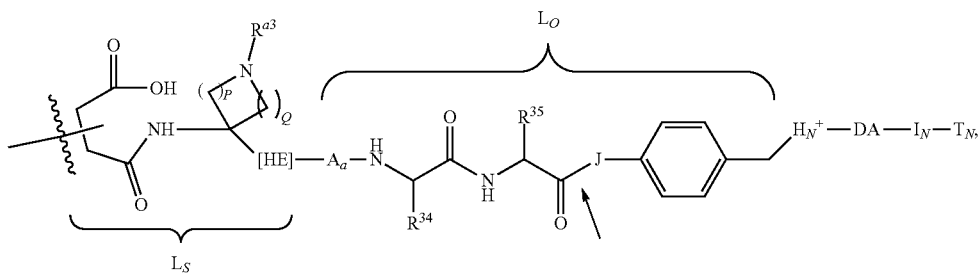

respectively, and corresponding Drug Linker compounds of Formula Ia are represented by:

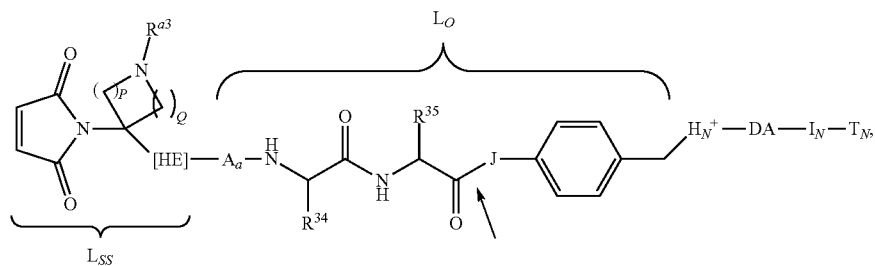

and -L$_{SS}$ and -L$_S$ containing quaternized drug linker moieties in a Ligand Drug Conjugate compound of Formula 1a or Formula 1b in which subscript p is replaced by p' and having L$_O$ of structure s1 in which W is a Peptide Cleavable Unit and having an acyclic Basic Unit are represented by:

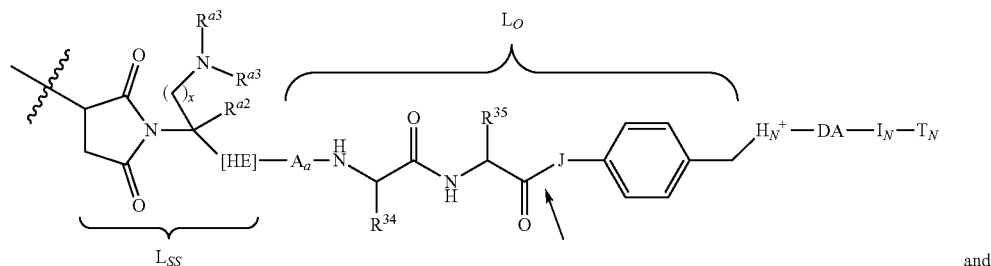

and

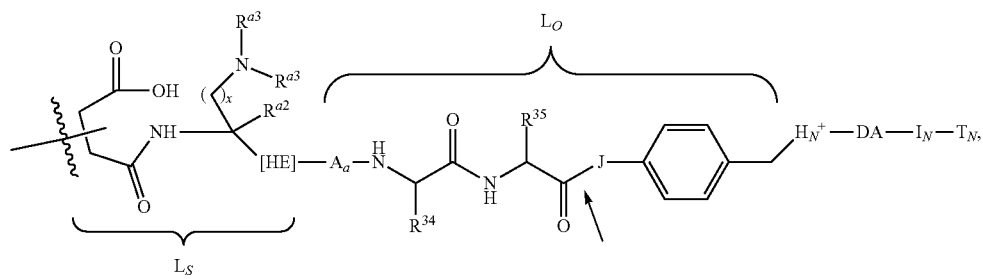

respectively, and corresponding Drug Linker compounds of Formula Ia are represented by:

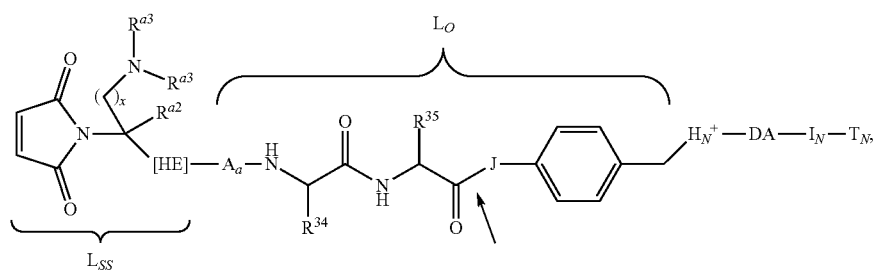

wherein protease cleavage of the indicated anilide bond within $L_O$ initiates releases of $D^+$ as a NAMPTi compound or its derivative having the formula $H_N\text{-}DA\text{-}I_N\text{-}T_N$, wherein $T_N$, $I_N$, DA and $H_N/H_{N^+}$ are as defined for NAMPTi compounds and quaternized NAMPT Drug Units, the basic nitrogen to which $R^{a3}$ is bonded is optionally protonated when $R^{a3}$ is other than a nitrogen protecting group, and $R^{34}$ and $R^{35}$ are as previously defined for Peptide Cleavable Units and the remaining variable groups are as previously defined for quaternized drug linker moieties and Drug Linker compounds having a peptide cleavage secondary linker.

In other preferred embodiments, the $L_{SS}$- and $L_S$-containing quaternized drug linker moieties having a Glucuronide Unit replacing W in a Ligand Drug Conjugate compound of Formula 1a or Formula 1b in which subscript p is replaced by p' and $L_O$ is of structure s2, and a heterocyclo cyclic Basic Unit within a Ligand Drug Conjugate compound have the structures of:

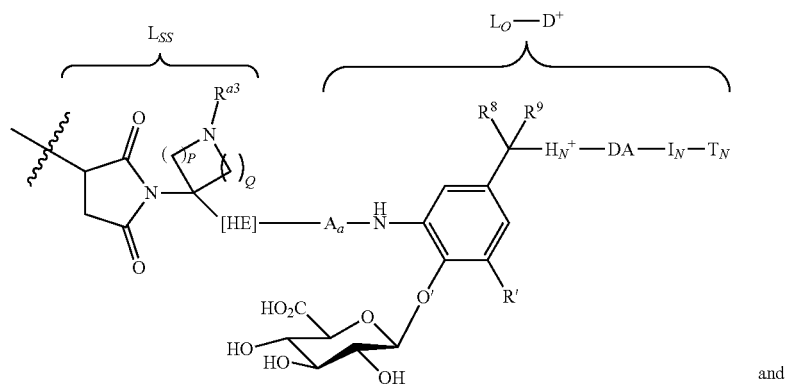

and

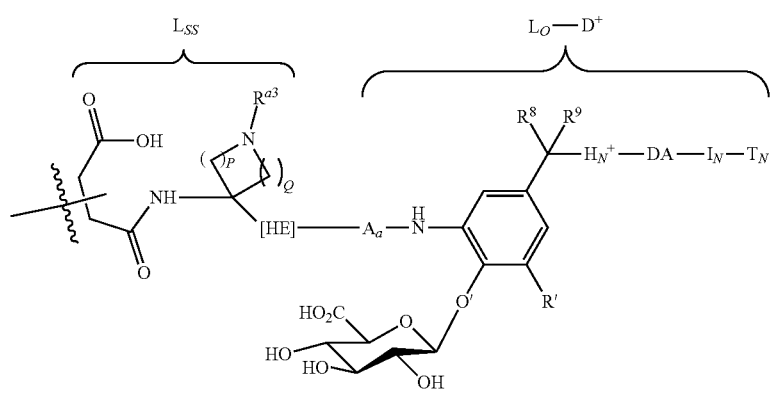

, respectively, and corresponding Drug Linker compounds of Formula Ia are represented by:

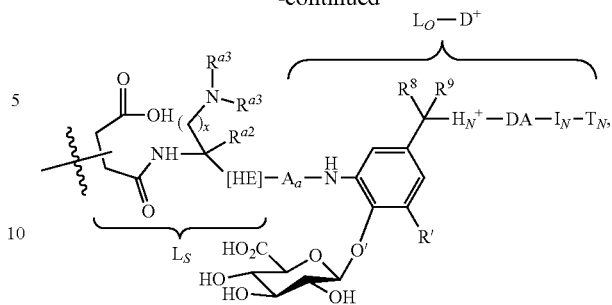

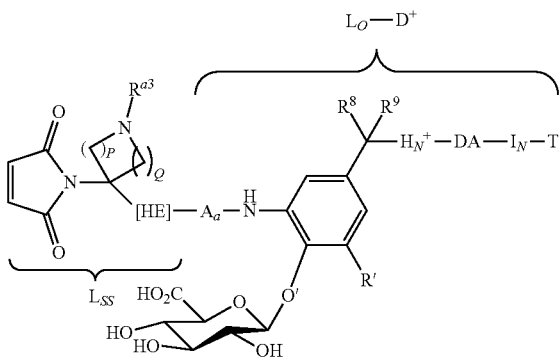

and $L_{SS}$- and $L_S$-containing quaternized drug linker moieties having a Glucuronide Unit in which $L_O$ is of structure s2, and an acyclic Basic Unit within a Ligand Drug Conjugate compound of Formula 1a or Formula 1b in which subscript p is replaced by p' have the structures of:

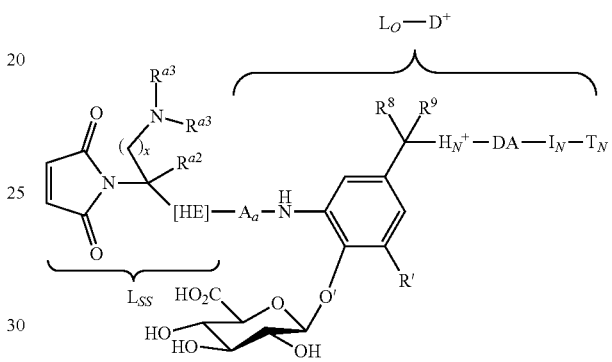

wherein $D^+$ is $-H_{N'}$-DA-$I_N$-$T_N$ and O' represents a glycosidic-bonded oxygen atom, the bond to which is cleavable by a glycosidase to initiate release of $D^+$ as a NAMPTi compound of formula $H_N$-DA-$I_N$-$T_N$, subscript x is 1 or 2, $R^{a2}$ is hydrogen or $-CH_3$ or $-CH_2CH_3$; $R^{a3}$, at each instance, is independently hydrogen, $-CH_3$ or $-CH_2CH_3$, or both $R^3$ together with the nitrogen to which they are attached define an azetidinyl, pyrrolidinyl or piperidinyl heterocyclyl, wherein the basic primary, secondary or tertiary amine so defined is optionally protonated or is in a salt form, preferably in a pharmaceutically acceptable salt form, and wherein O' represents a glycosidic-bonded oxygen, the bond to which is cleavable by a glycosidase; and the other variable groups are as previously described for Glucuronide-based quaternized drug linker moieties in Ligand Drug Conjugates and Drug Linker compounds.

In more preferred embodiments, the -$L_{SS}$ containing quaternized drug linker moieties within a Ligand Drug Conjugate compound of Formula 1a in which subscript p is replaced by p' and having $L_O$ of structure s1, wherein W is a Peptide Cleavable Unit and having a heterocyclo cyclic Basic Unit or an acyclic Basic Unit are represented by:

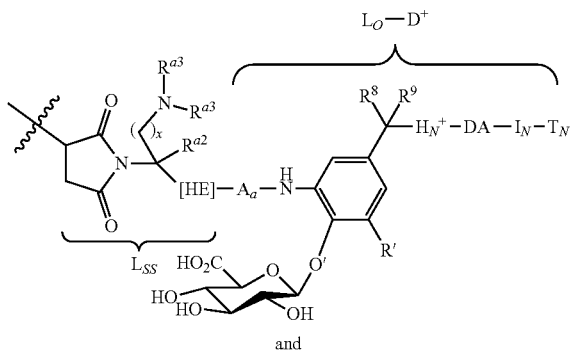

and

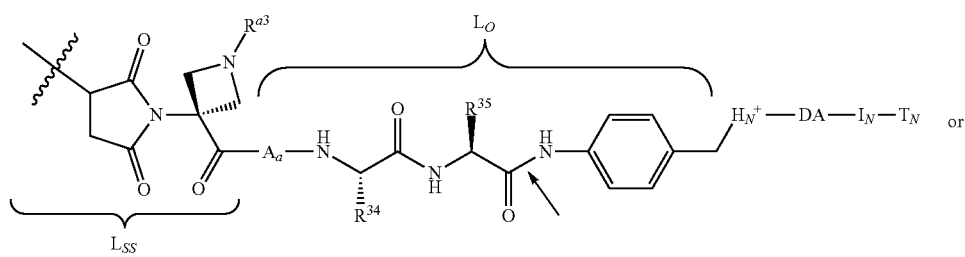

or

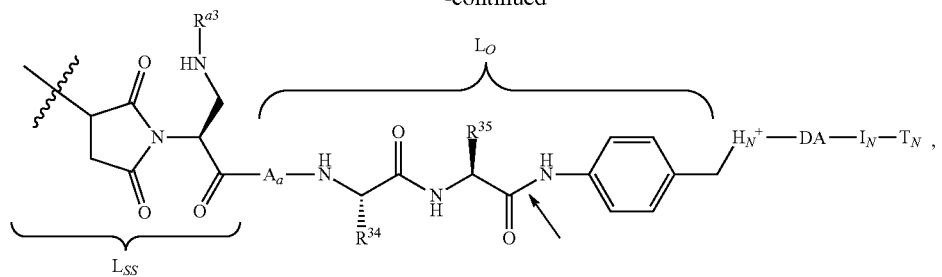
and more preferred $L_S$-containing drug linker moieties within a Ligand Drug Conjugate compound of Formula 1b in which subscript p is replaced by p' from controlled hydrolysis of the quaternized above drug linker moieties are represented by:
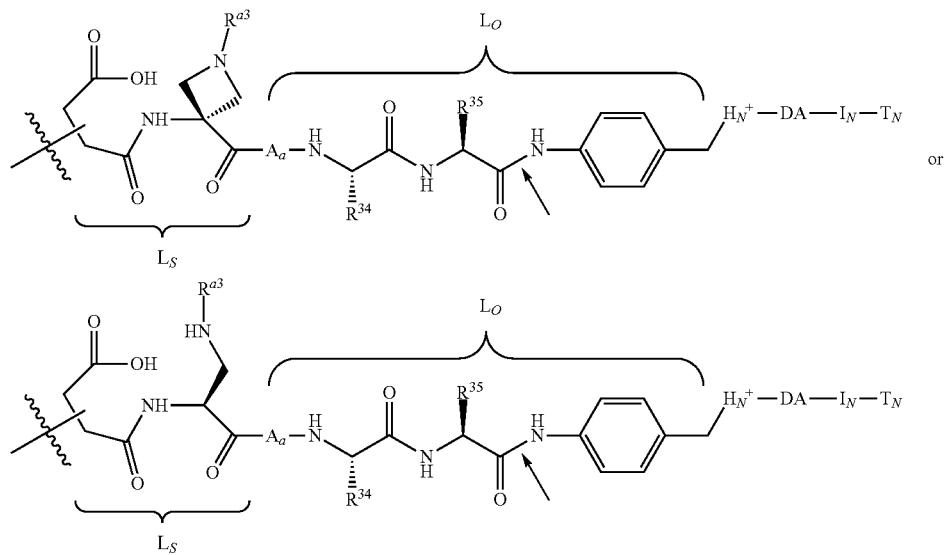
and corresponding more preferred Drug Linker compounds of Formula Ia are represented by:
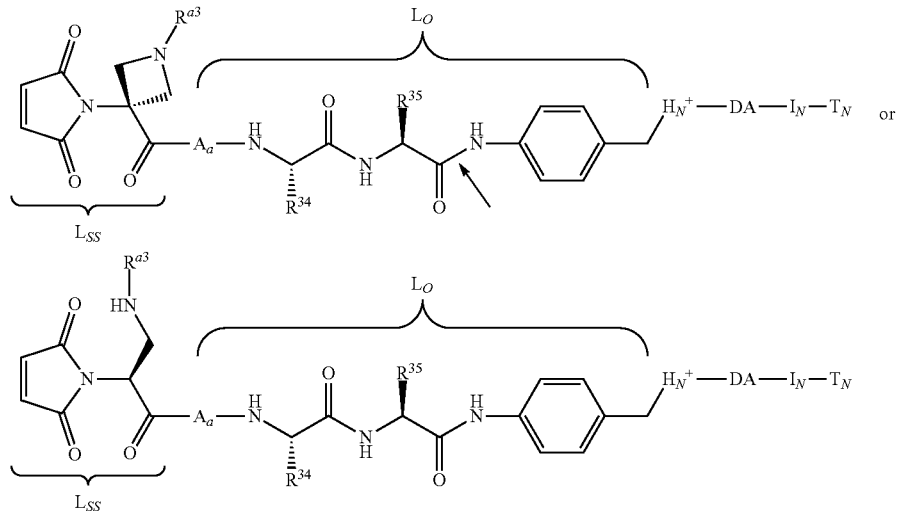

wherein D⁺ is —H$_{N^+}$-DA-I$_N$-T$_N$ and protease cleavage of the indicated anilide bond initiate release of D⁺ as a NAMPTi compound of formula H$_N$-DA-I$_N$-T$_N$, wherein the variable groups are as previously described for quaternized drug linker moieties and Drug Linker compounds having a heterocyclo cyclic Basic Unit or an acyclic Basic Unit and a peptide cleavable secondary linker in Ligand Drug Conjugates and Drug Linker compounds and wherein the nitrogen atom to which R$^{a3}$ is bonded is optionally protonated or in a salt form, preferably in a pharmaceutically acceptable salt from, when R$^{a3}$ is other than a nitrogen protecting group.

In other more preferred embodiments the -L$_{SS}$ containing quaternized drug linker moieties having a Glucuronide Unit in which L$_O$ is of structure s2 and having a heterocyclo cyclic Basic Unit or an acyclic Basic Unit within a Ligand Drug Conjugate compound of Formula 1a in which subscript p is replaced by p' are represented by:

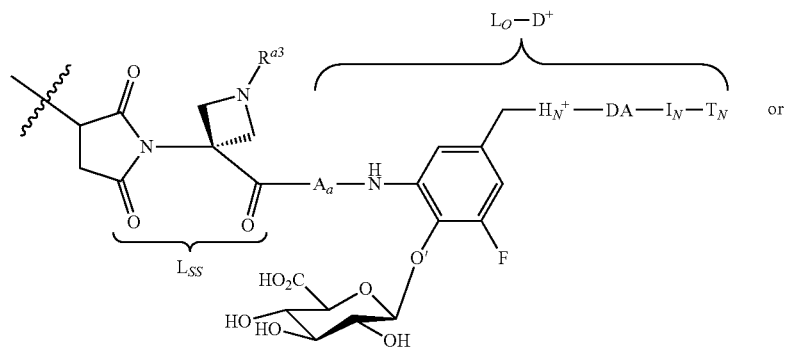

or

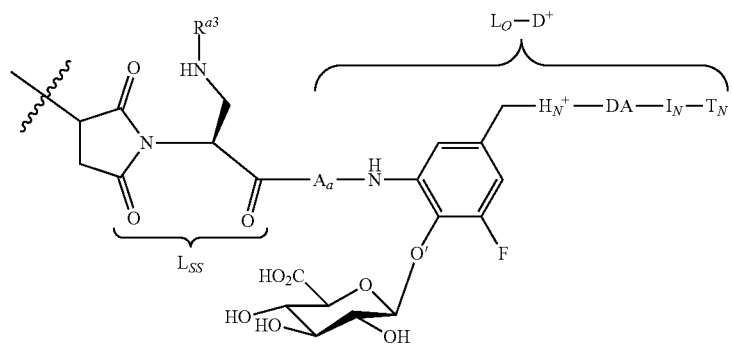

117 and the $L_S$-containing quaternized drug linker moieties from controlled hydrolysis of the above $L_{SS}$-containing drug linker moieties in a Ligand Drug Conjugate compound of Formula 1b in which subscript p is replaced by p' have the structures of:

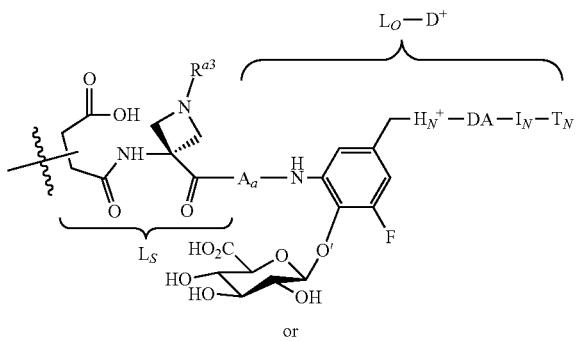

or

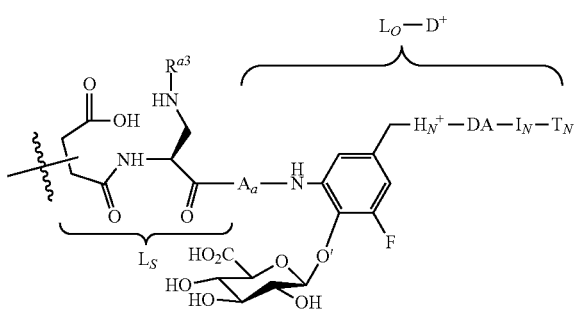

and corresponding Drug Linker compounds of Formula Ia are represented by:

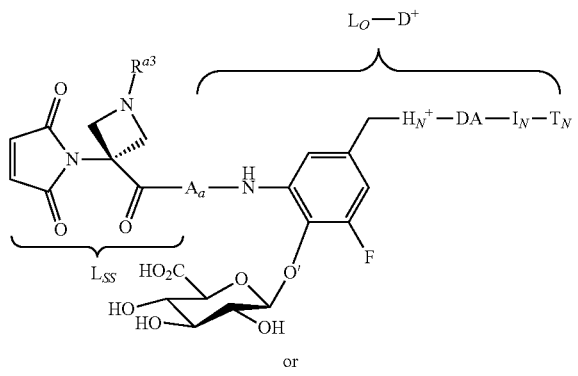

or

118

-continued

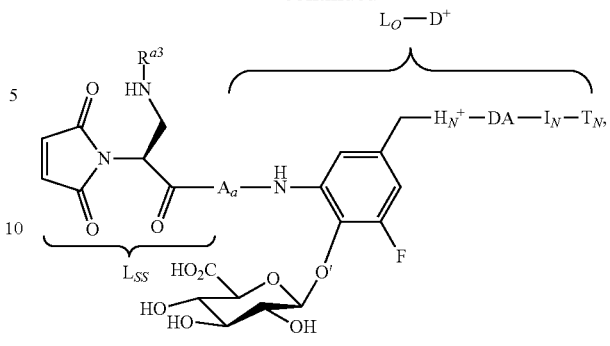

wherein $D^+$ is —$H_{N^+}$-DA-$I_{N'}$-$T_N$ and O' represent a glycosidic bonded oxygen atom, the bond to which is cleavable by a glycosidase to initiate release of $D^+$ as a NAMPTi compound of formula $H_N$-DA-$I_{N'}$-$T_N$, and the other variable groups are as previously described for drug linker moieties and Drug Linker compounds having a heterocyclo cyclic Basic Unit or an acyclic Basic Unit and a Glucuronide-based secondary linker in Ligand Drug Conjugates and Drug Linker compounds and wherein the nitrogen atom to which $R^{a3}$ is bonded is optionally protonated or in a salt form, preferably in a pharmaceutically acceptable salt from, when $R^{a3}$ is other than a nitrogen protecting group.

In the above preferred and more preferred embodiments, the $L_{SS}$ and $L_S$ components within a quaternized drug linker moiety of a Ligand Drug Conjugate composition or compound thereof exemplify the general formula of $M^2$-$A_R$(BU)-$A_O$- and $M^3$-$A_R$(BU)-$A_O$-, respectively, wherein BU is a cyclic Basic Unit and in which [HE] as $A_O$ is —C(=O)—, wherein $M^2$ is succinimide moiety and $M^3$ is succinic acid amide moiety, and $L_{SS}$ of a Drug Linker compound exemplify the general formula of $M^1$-$A_R$(BU)-$A_O$-, wherein BU is a cyclic Basic Unit which is a precursor to representative $L_{SS}$ moieties of a Ligand Drug Conjugates comprised of a cyclic Basic Unit, wherein $M^1$ is a maleimide moiety and [HE] as $A_O$ is —C(=O)—.

In some of the above embodiments when subscript a is 1, A, or a subunit thereof, and is bonded to $A_O$ in any one of the above $L_R$-$L_O$-$D^+$ structures in which $L_R$ is either $L_{SS}$ or $L_S$, preferably has a structure corresponding to an independently selected amine-containing acid (e.g., an amino acid residue) wherein the carboxylic acid terminus of the amine-containing acid is bonded to W as an ester or amide, preferably as an amide, and its N-terminus is bonded to $L_{SS}$ of formulae $M^1$-$A_R$(BU)-$A_O$- or $M^2$-$A_R$(BU)-$A_O$- or $L_S$ of formula $M^3$-$A_R$(BU)-$A_O$-, wherein BU is a cyclic Basic Unit, through a carbonyl-containing functional group. In several of those embodiments $A_O$ is [HE] or is comprised of [HE], wherein HE is a carbonyl-containing functional group so that its carbonyl carbon is bonded to the N-terminus of W, when subscript a is 0 or to the N-terminus of A or a subunit thereof when subscript a is 1.

In preferred embodiments in which W is a Peptide Cleavable Unit and not having a Basic Unit, the $L_R$-containing quaternized drug linker moieties of a Ligand Drug Conjugate compound of Formula 1 in which subscript p is replaced by p' and having $L_O$ of structure s are represented by:

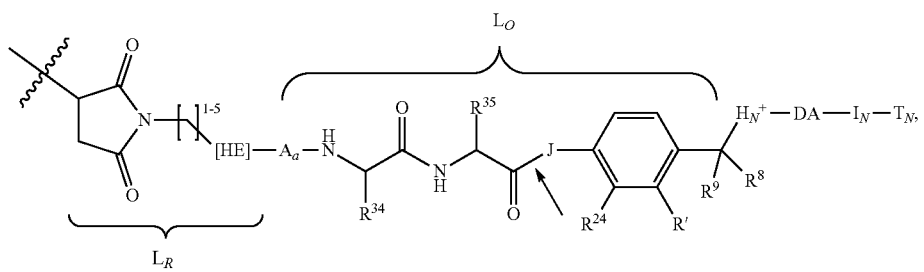

and corresponding Drug Linker compounds of Formula I are represented by:

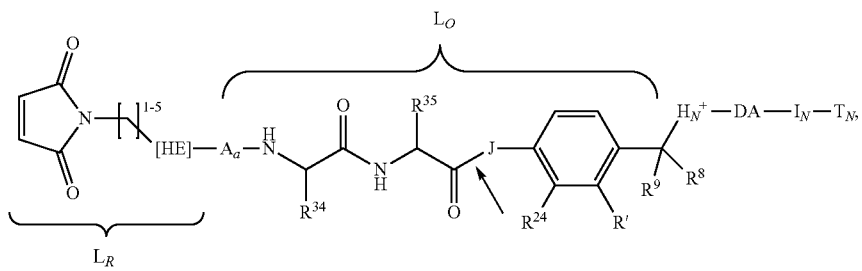

wherein J is —N($R^{33}$)—, O or S, wherein $R^{33}$ is hydrogen or $C_1$-$C_4$ alkyl; and cleavage of the indicated W-J bond within $L_O$ initiates release of an NAMPTi compound of formula $H_N$-DA-$I_N$-$T_N$, HE is an optional Hydrolysis Enhancing Unit, A is an optional first Stretcher Unit, subscript a is 0 or 1, indicating the absence or presence of A, respectively; and $R^{34}$ and $R^{35}$ are as previously defined for Peptide Cleavable Units and the remaining variable groups are as previously defined for drug linker moieties and Drug Linker compounds comprised of these Peptide Cleavable Units.

In more preferred embodiments, the -$L_R$ containing quaternized drug linker moieties of a Ligand Drug Conjugate compound of Formula 1 in which subscript p is replaced by p' and having $L_O$ of structure s1 in which W is a Peptide Cleavable Unit and having a heterocyclo cyclic Basic Unit are represented by:

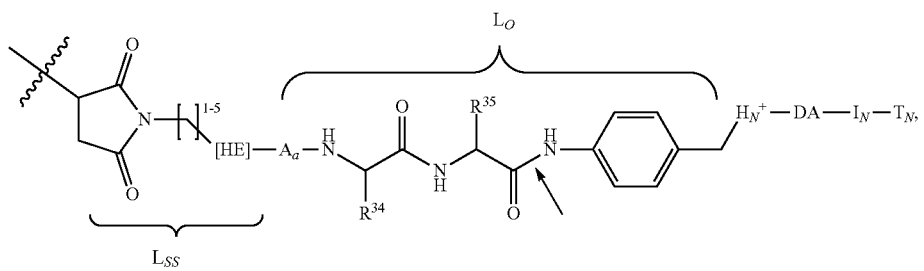

and corresponding Drug Linker compounds of Formula I are represented by:

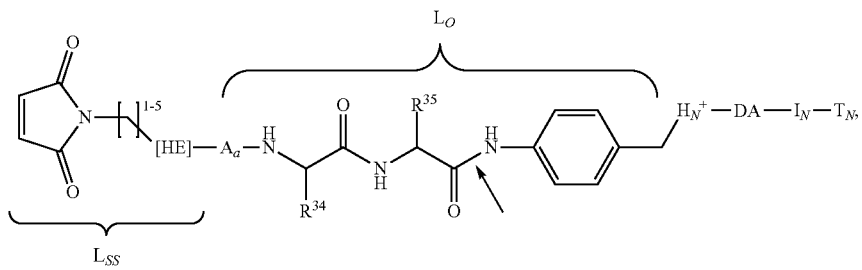

wherein protease cleavage of the indicated anilide bond within $L_O$ initiates releases of a NAMPTi compound or its derivative having the formula $H_{N'}$-DA-$I_N$-$T_N$, wherein $T_N$, $I_N$, DA and $H_N/H_{N'}$ are as defined for NAMPTi compounds and quaternized NAMPT Drug Units, the basic nitrogen to which $R^{a3}$ is bonded is optionally protonated when $R^{a3}$ is other than a nitrogen protecting group, and $R^{34}$ and $R^{35}$ are as previously defined for Peptide Cleavable Units and the remaining variable groups are as previously defined for quaternized drug linker moieties and Drug Linker compounds having a peptide cleavage secondary linker.

In other preferred embodiments the -$L_R$ containing quaternized drug linker moieties having a Glucuronide Unit of formula —Y(W)— replacing W in a Ligand Drug Conjugate of Formula 1 in which subscript p is replaced by p' and $L_O$ is of structure s2 and not having a Basic Unit have the structure of:

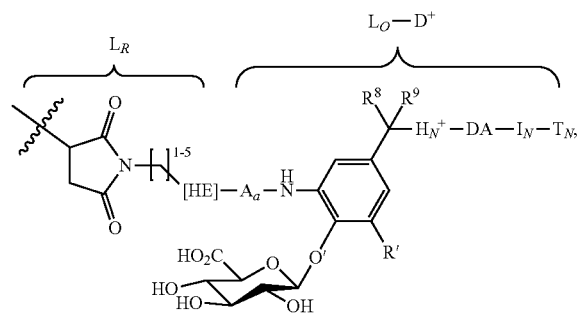

and corresponding Drug Linker compounds of Formula I are represented by:

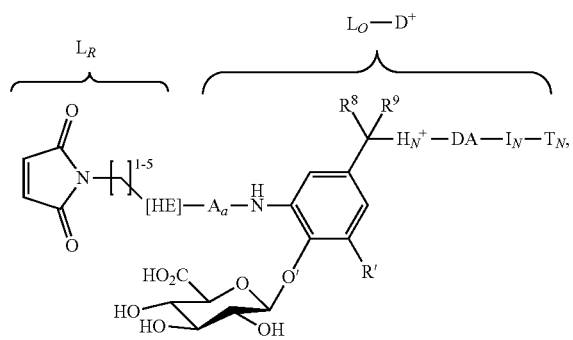

wherein $D^+$ is —$H_{N'}$-DA-$I_N$-$T_N$, wherein O' represents a glycosidic-bonded oxygen, the bond to which is cleavable by a glycosidase to initiate release of $D^+$ as a NAMPTi compound of formula $H_N$-DA-$I_N$-$T_N$; and the other variable groups are as previously described for Glucuronide-based quaternized drug linker moieties in Ligand Drug Conjugates and Drug Linker compounds.

In more preferred embodiments, the -$L_R$ containing quaternized drug linker moieties within a Ligand Drug Conjugate compound of Formula 1a in which subscript p is replaced by p' and having $L_O$ of structure s1, wherein W is a Peptide Cleavable Unit and not having a Basic Unit are represented by:

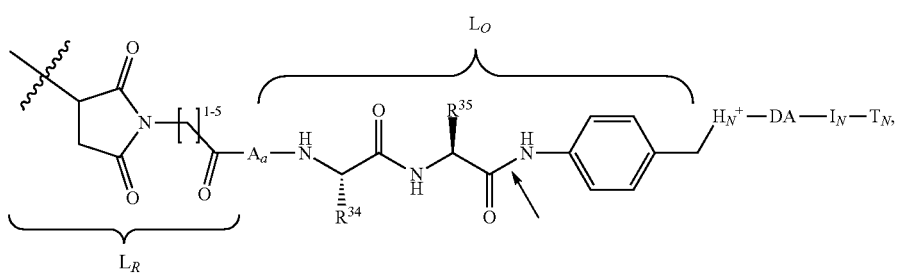

and corresponding more preferred Drug Linker compounds of Formula I are represented by:

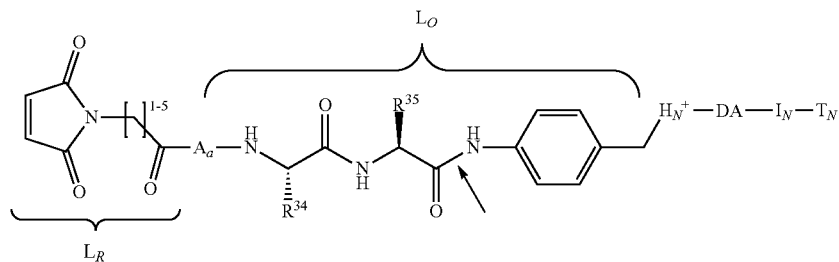

or
wherein D⁺ is —$H_N^+$-DA-$I_N$-$T_N$ and protease cleavage of the indicated anilide bond initiate release of D⁺ as a NAMPTi compound of formula $H_N$-DA-$I_N$-$T_N$, wherein the variable groups are as previously described for quaternized drug linker moieties and Drug Linker compounds having a peptide cleavable secondary linker in Ligand Drug Conjugates and Drug Linker compounds.

In other more preferred embodiments the -$L_R$ containing quaternized drug linker moieties having a Glucuronide Unit in which $L_O$ is of structure s2 and not having a Basic Unit within a Ligand Drug Conjugate compound of Formula 1 in which subscript p is replaced by p' are represented by:

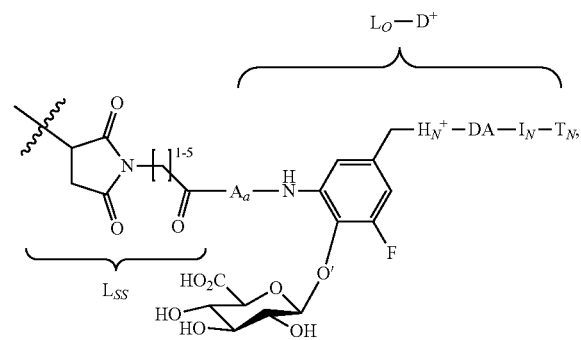

and corresponding Drug Linker compounds of Formula I are represented by:

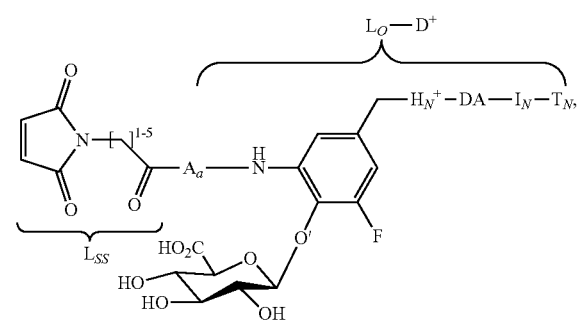

wherein D⁺ is —$H_N^+$-DA-$I_N$-$T_N$ and O' represent a glycosidic bonded oxygen atom, the bond to which is cleavable by a glycosidase to initiate release of D⁺ as a NAMPTi compound of formula $H_N$-DA-$I_N$-$T_N$, and the other variable groups are as previously described for drug linker moieties and Drug Linker compounds having a Glucuronide-based secondary linker in Ligand Drug Conjugates and Drug Linker compounds.

In the above preferred and more preferred embodiments, the $L_R$ components not having a Basic Unit within a quaternized drug linker moiety of a Ligand Drug Conjugate exemplify the general formula of $M^2$-$A_R$-$A_O$- and $M^3$-$A_R$-$A_O$-, respectively, in which [HE] as $A_O$ is —C(=O)—, wherein $M^2$ is succinimide moiety, and $L_R$ of a Drug Linker compound exemplify the general formula of $M^1$-$A_R$-$A_O$-, which is a precursor to representative $L_R$ moieties of a Ligand Drug Conjugates not having a Basic Unit, wherein $M^1$ is a maleimide moiety and [HE] as $A_O$ is —C(=O)—.

In some of the above embodiments when subscript a is 1, A, when present as a single unit, is bonded to $A_O$ in any one of the above -$L_R$-$L_O$-D⁺, -$L_{SS}$-$L_O$-D⁺ or -$L_S$-$L_O$-D⁺ structures in a Ligand Drug Conjugate composition of Formula 1, Formula 1a or Formula 1b or a compound thereof of either one of these formulae in which subscript p is replaced by p' or one of the above $L_R$-$L_O$-D⁺ or $L_{SS}$-$L_O$-D⁺ Drug Linker compound structures of Formula I, Formula Ia or Formula Ib, preferably has a structure corresponding to an independently selected amine-containing acid (e.g., an amino acid residue) wherein the carboxylic acid terminus of the amine-containing acid is bonded to W as an ester or amide, preferably as an amide, and its N-terminus is bonded to $L_R$ of formula $M^1$-$A_R$-$A_O$- or $M^2$-$A_R$-$A_O$-, $L_{SS}$ of formulae $M^1$-$A_R$(BU)-$A_O$- or $M^2$-$A_R$(BU)-$A_O$-, or $L_S$ of formula $M^3$-$A_R$(BU)-$A_O$-, wherein unit and BU is a cyclic Basic Unit, through a carbonyl-containing functional group. In several of those embodiments $A_O$ is [HE] or is comprised of [HE], wherein HE is a carbonyl-containing functional group so that its carbonyl carbon is bonded to the N-terminus of W, when W is a Peptide Cleavable Unit or to the N-terminus of A, when W is a Glucuronide Unit of formula —Y(W)—.

In other of the above embodiments when subscript a is 1, A, when present as two or more distinct subunits corresponding to independently selected amine-containing acids (e.g., an amino acid residues), the proximal subunit of A is bonded to a carbonyl-containing functional group of $A_O$ through the amine functional group of the subunit and the carboxylic acid terminus of the distal subunit of A is bonded to W as an ester or amide. In several of those embodiments $A_O$ is [HE] or is comprised of [HE], wherein HE is a carbonyl-containing functional group so that its carbonyl carbon is bonded to the N-terminus of W, when W is a Peptide Cleavable Unit or to the N-terminus of A or subunit thereof, when W is a Glucuronide Unit.

In other embodiments A, or a subunit thereof, has the formula of -$L^P$(PEG)-, wherein L' is a Parallel Connector Unit and PEG is a PEG Unit. In those embodiments, the PEG Unit contains a total of 2 to 36 ethyleneoxy monomer units and $L^P$ is comprised of an amine-containing acid residue, preferably an amino acid residue, covalently attached to W. In more preferred embodiments, the covalent attachment of $L^P$ within the Linker Unit of a drug linker moiety of Ligand Drug Conjugate or of a Drug Linker compound is through amide functional groups. In other more preferred embodiments, the PEG Unit contains a total of 4 to 24 contiguous ethyleneoxy monomer units.

In any one of the above -$L_R$-$L_O$-$D^+$ Ligand Drug Conjugate substructures not having a Basic Unit, -$L_{SS}$-$L_O$-$D^+$ and -$L_S$-$L_O$-$D^+$ Ligand Drug Conjugate substructures having a heterocyclo cyclic Basic Unit or acyclic Basic Unit, $L_R$-$L_O$-$D^+$ Drug Linker compound structures not having a Basic Unit, and $L_{SS}$-$L_O$-$D^+$ Drug Linker compound structures having a heterocyclo cyclic Basic Unit or a acyclic Basic Unit; and having a protease cleavable Peptide Cleavable Unit, preferably $R^{34}$ is methyl, isopropyl or —CH(OH)CH$_3$ and $R^{35}$ is methyl, —(CH$_2$)$_3$NH(C=O)NH$_2$ or —(CH$_2$)$_2$CO$_2$H.

In any one of the above -$L_R$-$L_O$-$D^+$ Ligand Drug Conjugate substructures not having a Basic Unit, -$L_{SS}$-$L_O$-$D^+$ and -$L_S$-$L_O$-$D^+$ Ligand Drug Conjugate substructures having a heterocyclo cyclic Basic Unit or an acyclic Basic Unit, $L_R$-$L_O$-$D^+$ Drug Linker compound structures not having a Basic Unit, and $L_{SS}$-$L_O$-$D^+$ Drug Linker compound structures having a heterocyclo cyclic Basic Unit or an acyclic Basic Unit; and having a glycosidase cleavable Glucuronide Unit preferably $R^{45}$ is —CO$_2$H.

In preferred embodiments in which A, W', Y are in an orthogonal configuration with respect to $D^+$, a first Stretcher Unit (A) is present that is a single unit or is of 2 or more subunits, preferably 2, wherein the single Unit or each subunit independently has the structure previously defined for formula (3) or formula (4) or has the structure of formula (3a) or formula (4a):

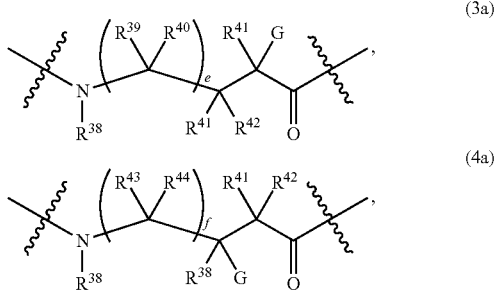

wherein subscript e or f is 0 or 1 and G and $R^{39}$-$R^{44}$ are as previously defined and the wavy line to the carbonyl moiety of any one of the formula (3), (3a), (4) and (4a) structures represents the site of attachment of A to J' preferably through an amide functional group and wherein the wavy line to the amino moiety of either one of these structures represents the site of attachment to a carbonyl-containing functional group of a second Stretcher Unit $A_O$ or to the carbonyl carbon of [HE] as $A_O$. In preferred embodiments of formula (3) or formula (4) L' is absent (i.e., subscript q is 0) and G is hydrogen, —CO$_2$H or —NH$_2$ or the side chain of a naturally occurring amino acid such as aspartic acid, glutamic acid or lysine. In other preferred embodiments, L' and K are carbon and $R^{41}$, $R^{42}$, $R^{43}$ and $R^4$ in each occurrence is hydrogen. In other preferred embodiments $R^{38}$-$R^{44}$ in each occurrence is hydrogen. Other preferred embodiments have formula (3) wherein K is nitrogen and one of $R^{41}$, $R^{42}$ is absent and the other is hydrogen. Other preferred embodiments have formula (4) wherein subscript r is 1, K is nitrogen and one of $R^{41}$, $R^{42}$ is absent and the other is hydrogen. In other preferred embodiments subscripts p and q of structure (3) are both 0 or subscripts q and r of structure (4) are both 0. Other preferred embodiments have structure (3) wherein subscripts p and q are both 0 and K together with $R^{41}$ and $R^{42}$ is —C(=O)—. Other preferred embodiments have structure (4) wherein subscript q is 1 and L' together with $R^{43}$ and $R^{44}$ is —C(=O)—.

In preferred embodiments in which A, W, Y are in a linear configuration with respect to $D^+$, a first Stretcher Unit (A) is present having the same variable group preferences as described above for preferred embodiments in which W', Y and $D^+$ are in an orthogonal configuration. In such preferred embodiments, the wavy line to the carbonyl moiety of any one of the formula (3), (3a), (4) and (4a) structures represents the site of attachment of A, when A is a single unit, or of the distal subunit thereof, when A has multiple subunits, to the N-terminus of W as the Peptide Cleavable Unit, and the wavy line to the amino moiety of either one of these structures represents the site of attachment to a carbonyl-containing functional group of the proximal subunit of A, when A has multiple subunits or to the carbonyl carbon of [HE] as $A_O$, when A is a single discrete unit.

In other preferred embodiments, A and $A_O$ are both present and A or its subunits are independently selected from the group consisting of formula (3), (3a), (4) and (4a). In more preferred embodiments, A or a subunit thereof is an alpha-amino, beta-amino or other amine-containing acid residue. In more preferred embodiments, A or a subunit thereof is an alpha-amino, beta-amino or other amine-containing acid residue.

In any one of the above -$L_R$-$L_O$-$D^+$ Ligand Drug Conjugate substructures not having a Basic Unit, -$L_{SS}$-$L_O$-$D^+$ and -$L_S$-$L_O$-$D^+$ Ligand Drug Conjugate substructures having a heterocyclo cyclic Basic Unit or acyclic Basic Unit, $L_R$-$L_O$-$D^+$ Drug Linker compound structures not having a Basic Unit, and $L_{SS}$-$L_O$-$D^+$ Drug Linker compound structures having a heterocyclo cyclic Basic Unit or a acyclic Basic Unit in which a first optional Stretcher Unit is present, preferred amine-containing acid residues that correspond to A or a subunit thereof have the structure of —NH—X$^1$—C(=O)— wherein X$^1$ is an optionally substituted $C_1$-$C_6$-alkylene.

Particularly preferred Ligand Drug Conjugates are represented by any one of the above -$L_R$-$L_O$-$D^+$, -$L_{SS}$-$L_O$-$D^+$ and -$L_S$-$L_O$-$D^+$ Ligand Drug Conjugate sub-structures bonded to L in which L is an antibody Ligand Unit bonded to the $L_R$, $L_{SS}$ or $L_S$ moiety.

1.3.1 Ligand Unit

In some embodiments of the invention, a Ligand Unit is present. The Ligand Unit (L) is a targeting moiety of a Ligand Drug Conjugate that specifically binds to a targeted moiety. The Ligand Unit can selectively and specifically bind to a cell component, which serves as the targeted moiety, or to other targeted molecules of interest. The Ligand Unit acts to target and present the quaternized Drug ($D^+$) Unit of the Ligand Drug Conjugate to the particular target cell population with which the Ligand Unit interacts in order to selectively release $D^+$ as a NAMPTi compound. Targeting agents that provide for Ligand Units include, but are not limited to, proteins, polypeptides and peptides.

Exemplary Ligand Units include, but are not limited to, those provided by proteins, polypeptides and peptides such as antibodies, e.g., full-length antibodies and antigen binding fragments thereof, interferons, lymphokines, hormones, growth factors and colony-stimulating factors. Other suitable Ligand Units are those from vitamins, nutrient-transport molecules, or any other cell binding molecule or substance. In some embodiments a Ligand Unit is from non-antibody protein targeting agent. In other embodiments, a Ligand Unit is from a protein targeting agent such as an antibody. Preferred targeting agents are larger molecular weight proteins, e.g., having a molecular weight of at least about 80 Kd.

A targeting agent reacts with a $L_R$ moeity not having a Basic Unit, or a $L_{SS}$ moiety of a Drug Linker compound, which contains cyclic or acyclic Basic Unit to form a Ligand Unit covalently attached to quaternized drug-linker moiety, wherein the quaternized drug-linker moiety has the formula $-L_R-L_O-D^+$ or $-L_{SS}-L_O-D^+$. The targeting agent has or is modified to have the appropriate number of attachment sites to accommodate the requisite number of drug-linker moieties, defined by subscript p, whether they be naturally occurring or non-naturally occurring (e.g., engineered). For example, in order for the value of subscript p to be from 6 to 14, a targeting agent has to be capable of forming a bond to 6 to 14 drug-linker moieties.

A targeting agent is capable of forming a bond to the $L_R$ or $L_{SS}$ moiety of the Linker Unit of a Drug Linker compound via a reactive or activateable heteroatom or a heteroatom-containing functional group of the targeting agent. Reactive or activateable heteroatoms or a heteroatom-containing functional groups that may be present on a targeting agent include sulfur (in one embodiment, from a thiol functional group of a targeting agent), C=O (in one embodiment, from a carbonyl or carboxyl group of a targeting agent) and nitrogen (in one embodiment, from a primary or secondary amino group of a targeting agent). In some embodiments the reactive or activateable heteroatoms are be present on the targeting agent in the targeting agent's natural state, for example in a naturally-occurring antibody, or in other embodiments are introduced into the targeting agent via chemical modification or genetic engineering.

In one embodiment, a targeting agent has a thiol functional group and the Ligand Unit derived therefrom is attached to a quaternized drug linker moiety of a Ligand Drug Conjugate compound via the thiol functional group's sulfur atom.

In another embodiment, the targeting agent has lysine residues that react with an activated ester, including but are not limited to, N-hydroxysuccinimide, pentafluorophenyl, and p-nitrophenyl esters), of $L_R$ not having a Basic Unit thus resulting in an amide bond between the nitrogen atom from the Ligand Unit and the C=O functional group from the Linker Unit of the Drug Linker compound.

In yet another embodiment, the targeting agent has one or more lysine residues that can be chemically modified to introduce one or more thiol functional groups. The Ligand Unit from that targeting agent is attached to the Linker Unit via the introduced thiol functional group's sulfur atom. Reagents that are used to modify lysines include, but are not limited to, N-succinimidyl S-acetylthioacetate (SATA) and 2-Iminothiolane hydrochloride (Traut's Reagent).

In another embodiment, the targeting agent has one or more carbohydrate groups that is chemically modified to have one or more reactive thiol functional groups. The Ligand Unit from that targeting agent is attached to the Linker Unit via the introduced thiol functional group's sulfur atom, or the targeting agent has one or more carbohydrate groups that are oxidized to provide an aldehyde (—CHO) group (see, e.g., Laguzza, et al., 1989, *J. Med. Chem.* 32(3):548-55). The corresponding aldehyde is then capable of reacting react with a $L_R$ moiety of a Drug Linker compound having a nucleophillic nitrogen atom. Other reactive sites on $L_R$ capable of reacting with a carbonyl group on a targeting agent include, but are not limited to, hydrazine and hydroxylamine. Other protocols for the modification of proteins for the attachment of drug linker moieties are described in Coligan et al., *Current Protocols in Protein Science*, vol. 2, John Wiley & Sons (2002) (incorporated herein by reference).

In preferred embodiments, the reactive group of $L_R$ or $L_{SS}$, sometimes indicated as $L_R'$ or $L_{SS}'$ to indicate that it is a precursor to $L_R$ or $L_{SS}$, respectively, of a Drug Linker compound is a maleimide ($M^1$) moiety and covalent attachment of L to $L_R$ or $L_{SS}$ of a drug linker moiety is accomplished through a sulfur atom of a reactive thiol functional group of a targeting agent so that a thio-substituted succinimide ($M^2$) moiety is formed through Michael addition. In some embodiments the reactive thiol functional group is present on the targeting agent in the targeting agent's natural state, for example, a naturally-occurring residue, or in other embodiments is introduced into the targeting agent via chemical modification and/or genetic engineering.

It has been observed for bioconjugates that the site of drug conjugation can affect a number of parameters including ease of conjugation, drug-linker stability, effects on biophysical properties of the resulting bioconjugates, and in-vitro cytotoxicity. With respect to quaternized drug-linker stability, the site of conjugation of a quaternized drug-linker moeity to a targeting agent to provide a Ligand Drug Conjugate composition or compound thereof sometimes influences the ability of the conjugated quaternized drug-linker moiety to undergo an elimination reaction and for the quaternized drug linker moiety to be transferred from the Ligand Unit of a Ligand Drug Conjugate compound to an alternative reactive thiol functional group present in the milieu of the Ligand Drug Conjugate, such as, for example, a sulfur atom of reactive cysteine thiol in albumin, free cysteine, or glutathione when in plasma. The sites for covalent attachment to a drug linker moeity include, for example, from reduced interchain disulfides as well as select cysteine engineered sites. In some embodiments, the Ligand Drug Conjugates described herein are conjugated to thiol residues at sites that are less susceptible to the elimination reaction (e.g., positions 239 according to the EU index as set forth in Kabat) and in other embodiments these less susceptible site are used addition to other sites to achieve a desired quaternized drug loading.

In yet another embodiment, the targeting agent is that of an antibody and the reactive thiol functional group is chemically introduced into the antibody, for example by introduction of a cysteine residue. Accordingly, in some embodiments, the Linker Unit of a Ligand Drug Conjugate compound is conjugated to a quaternized drug linker moiety through a sulfur atom of an introduced cysteine residue.

Thus, in more preferred embodiments, the targeting agent is an antibody and the reactive thiol functional group is generated by reduction of an interchain disulfide, so that the Linker Unit is conjugated to cysteine residue(s) of the reduced interchain disulfides of the Ligand Unit. In other more preferred embodiments, the targeting agent is an antibody and the reactive thiol functional group is from cysteine residue(s) of reduced interchain disulfides of the Ligand Unit and cysteine residue(s) introduced by genetic engineering.

When the conjugates comprise non-immunoreactive protein, polypeptide, or peptide ligands instead of an antibody, useful non-immunoreactive protein, polypeptide, or peptide ligands include, but are not limited to, transferrin, epidermal growth factors ("EGF"), bombesin, gastrin, gastrin-releasing peptide, platelet-derived growth factor, IL-2, IL-6, transforming growth factors ("TGF"), such as TGF-α and TGF-β, vaccinia growth factor ("VGF"), insulin and insulin-like growth factors I and II, somatostatin, lectins and apoprotein from low density lipoprotein.

Particularly preferred targeting agents are antibodies, including intact antibodies. In fact, in any of the embodiments described herein, the Ligand Unit can be that of an antibody. Useful polyclonal antibodies are heterogeneous populations of antibody molecules derived from the sera of immunized animals. Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest is prepared by using any technique known in the art, which in some embodiments provides for the production of antibody molecules by continuous cell lines in culture.

Useful monoclonal antibodies include, but are not limited to, human monoclonal antibodies, humanized monoclonal antibodies, or chimeric human-mouse (or other species) monoclonal antibodies. The antibodies include full-length antibodies and antigen binding fragments thereof. Human monoclonal antibodies may be made by any one of the numerous techniques known in the art (e.g., Teng et al., 1983, Proc. Natl. Acad. Sci. USA. 80:7308-7312; Kozbor et al., 1983, Immunology Today 4:72-79; and Olsson et al., 1982, Meth. Enzymol. 92:3-16).

In some embodiments, the antibody is a functionally active fragment, derivative or analog of an antibody that immunospecifically binds to target cells (e.g., cancer cell antigens, viral antigens, or microbial antigens) or other antibodies bound to tumor cells or matrix. In this regard, "functionally active" means that the fragment, derivative or analog is able to immunospecifically binds to targeted cells. To determine which CDR sequences bind the antigen, synthetic peptides containing the CDR sequences is sometimes used in binding assays with the antigen by any binding assay method known in the art (e.g., the BIA core assay) (See, e.g., Kabat et al., 1991, Sequences of Proteins of Immunological Interest, Fifth Edition, National Institute of Health, Bethesda, Md.; Kabat E et al., 1980, J. Immunology 125(3): 961-969).

Other useful antibodies include fragments of antibodies such as, but not limited to, F(ab')$_2$ fragments, Fab fragments, Fvs, single chain antibodies, diabodies, triabodies, tetrabodies, scFv, scFv-FV, or any other molecule with the same specificity as the antibody.

Additionally, recombinant antibodies, such as chimeric and humanized monoclonal antibodies, comprising both human and non-human portions, which in some embodiments are made using standard recombinant DNA techniques, are useful antibodies. A chimeric antibody is a molecule in which different portions are derived from different animal species, such as for example, those having a variable region derived from a murine monoclonal and human immunoglobulin constant regions. (See, e.g., U.S. Pat. Nos. 4,816,567; and 4,816,397, which are incorporated herein by reference in their entirety). Humanized antibodies are antibody molecules from non-human species having one or more complementarity determining regions (CDRs) from the non-human species and a framework region from a human immunoglobulin molecule. (See, e.g., U.S. Pat. No. 5,585,089, which is incorporated herein by reference in its entirety). Such chimeric and humanized monoclonal antibodies may be produced by any one of the recombinant DNA techniques known in the art, for example using methods, each of which is specifically incorporated herein by reference, as described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., Science (1988) 240:1041-1043; Liu et al., Proc. Natl. Acad. Sci. (USA) (1987) 84:3439-3443; Liu et al., J. Immunol. (1987) 139: 3521-3526; Sun et al. Proc. Natl. Acad. Sci. (USA) (1987) 84:214-218; Nishimura et al. Cancer. Res. (1987) 47:999-1005; Wood et al., Nature (1985) 314:446-449; Shaw et al., J. Natl. Cancer Inst. (1988) 80:1553-1559; Morrison, Science (1985) 229:1202-1207; Oi et al. BioTechniques (1986) 4:214; U.S. Pat. No. 5,225,539; Jones et al., Nature 1986) (321:552-525; Verhoeyan et al., Science (1988) 239:1534; and Beidler et al., J. Immunol. (1988)141:4053-4060.

Completely human antibodies are particularly preferred and in some embodiments is produced using transgenic mice that are incapable of expressing endogenous immunoglobulin heavy and light chains genes, but which can express human heavy and light chain genes.

Antibodies include analogs and derivatives that are either modified, i.e., by the covalent attachment of any type of molecule as long as such covalent attachment permits the antibody to retain its antigen binding immunospecificity. For example, but not by limitation, derivatives and analogs of the antibodies include those that have been further modified, e.g., by glycosylation, acetylation, PEGylation, phosphorylation, amidation, derivitization by known protecting/blocking groups, proteolytic cleavage, linkage to a cellular antibody unit or other protein, etc. Any one of the numerous chemical modifications by known techniques may be used including, but not limited to, specific chemical cleavage, acetylation, formylation, metabolic synthesis in the presence of tunicamycin, etc. Additionally, in some embodiments the analog or derivative contains one or more unnatural amino acids.

In some embodiments antibodies have modifications (e.g., substitutions, deletions or additions) in amino acid residues that interact with Fc receptors. In particular, such antibodies have modifications in amino acid residues identified as involved in the interaction between the anti-Fc domain and the FcRn receptor (see, e.g., International Publication No. WO 97/34631, which is incorporated herein by reference in its entirety).

In some preferred embodiments, known antibodies for the treatment of cancer can be used. In another specific embodiment, antibodies for the treatment of an autoimmune disease are used in accordance with the compositions and methods of the invention.

In certain embodiments, useful antibodies are capable of binding to a receptor or a receptor complex expressed on an activated lymphocyte. In some of those embodiments, the receptor or receptor complex comprises an immunoglobulin gene superfamily member, a TNF receptor superfamily member, an integrin, a cytokine receptor, a chemokine receptor, a major histocompatibility protein, a lectin, or a complement control protein.

In some embodiments, the antibody will specifically bind to CD19, CD30, CD33, CD70 or Liv-1.

The antibody can be a humanized anti-CD33 antibody (US 2013/0309223 incorporated by reference herein in its entirety and for all purposes), a humanized anti-Beta6 antibody (see, e.g., WO 2013/123152 incorporated by reference herein in its entirety and for all purposes), a humanized anti-Liv-1 antibody (see, e.g., US 2013/0259860 incorporated by reference herein in its entirety and for all purposes), or a humanized AC10 (hAC10) antibody (see, e.g., U.S. Pat. No. 8,257,706, incorporated by reference herein in its entirety and for all purposes). Exemplary attachment of the Linker Unit to the antibody Ligand Unit is via thioether linkages. The thioether linkages are formed subsequent to interchain disulfide bond reduction(s), introduced cysteines resides, and combinations thereof.

1.3.2 Parallel Connector Unit

In some embodiments A or $A_O$ is a Parallel Connector Unit (L) having the structure of Formula A or Formula B:

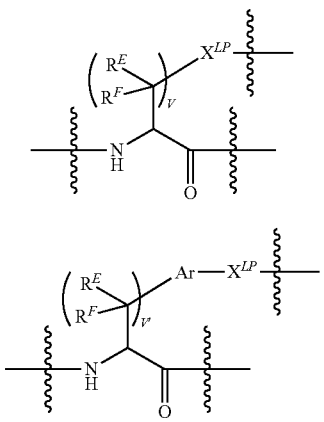

(Formula A)

(Formula B)

wherein subscript v is an integer ranging from 1 to 4; subscript v' is an integer ranging from 0 to 4; $X^{LP}$ is provided by a natural or un-natural amino acid side chain or is selected from the group consisting of —O—, —NR$^{LP}$—, —S—, —S(=O)—, —S(=O)$_2$—, —C(=O)—, —C(=O)N(R$^{LP}$)—, —N(R$^{LP}$)C(=O)N (R$^{LP}$)—, and —N(R$^{LP}$)C(=NR$^{LP}$)N(R$^{LP}$)—, or heterocyclo wherein each R$^{LP}$ is independently selected from the group consisting of hydrogen and optionally substituted $C_1$-$C_{12}$ alkyl, preferably hydrogen and optionally substituted $C_1$-$C_6$ alkyl or two of R$^{LP}$ together along with their intervening atoms define an optionally substituted $C_3$-$C_{20}$ heterocyclyl, preferably optionally substituted $C_3$-$C_6$ heterocyclyl and any remaining R$^{LP}$ are as previously defined; Ar is an optionally substituted $C_6$-$C_{24}$ arylene or optionally substituted $C_5$-$C_{24}$ heteroarylene, preferably optionally substituted phenylene; each R$^E$ and R$^F$ is independently selected from the group consisting of —H, optionally substituted $C_1$-$C_{12}$ alkyl, optionally substituted $C_6$-$C_{24}$ aryl and optionally substituted $C_5$-$C_{24}$ heteroaryl, preferably from the group consisting of hydrogen and optionally substituted phenyl, or R$^E$ and R$^F$ together with the same carbon to which they are attached, or R$^E$ and R$^F$ from adjacent carbons together with these carbons, defines a optionally substituted $C_3$-$C_{20}$ carbocyclo, preferably optionally substituted $C_3$-$C_6$ carbocyclo with any remaining R$^E$ and R$^F$ substituents as previously defined; and wherein the wavy lines indicates covalent attachment of the Formula A or Formula B structure within a Ligand Drug Conjugate or Drug Linker compound structure.

In some embodiments, -L$^P$(PEG)- has the structure of Formula A1 or A2:

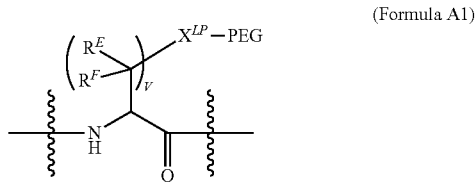

(Formula A1)

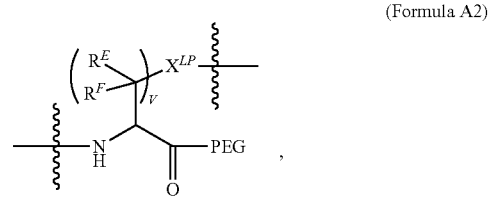

(Formula A2)

wherein the variable groups are as defined in Formula A.

In preferred embodiments, L$^P$ has the structure of Formula A1 wherein X$^{LP}$ is provided by a natural or un-natural amino acid side chain.

In preferred embodiments of Formula A, Formula A1, Formula A2 or Formula B, R$^E$ and R$^F$ are independently selected from the group consisting of —H, and —$C_1$-$C_4$ alkyl. In preferred embodiments of Formula A, Formula A1 or Formula A2, X$^{LP}$ is selected from the group consisting of —O—, —NH, —S— and —C(=O)—.

In some embodiments, L$^P$ is selected from the group consisting of lysine, glutamic acid, aspartic acid, cysteine, penicillamine, serine and threonine each of which is in D- or L-stereochemical configuration.

In other embodiments, L$^P$ is selected from the group consisting of lysine, glutamic acid, aspartic acid, cysteine, and penicillamine each of which is in D- or L-stereochemical configuration.

In other embodiments, L$^P$ is a thiol containing amino acid residue in the D- or L-stereochemical configuration. The thiol containing amino acid is preferably cysteine, homocysteine, or penicillamine.

In other embodiments, L$^P$ is an aminoalkanedioic acid residue. Preferred aminoalkanedioic acids are N-alkylaminoalkanedioic acids, 2-aminohexanedioic acid, 2-aminoheptanedioic acid and 2-aminooctanedioic acid (H-Asu-OH).

In other embodiments, L$^P$ is a diaminoalkanoic acid residue. Preferred diaminoalkanoic acids are N-alkyl-diamino-alkanoic acids, N,N-dialkylamino-alkanoic acids, α,γ-diaminobutyric acid (H-Dab-OH), and α,β-diaminopropionic acid.

In preferred embodiments lysine, cysteine or penicillamine amino acid residues for $L^P$ are shown below:

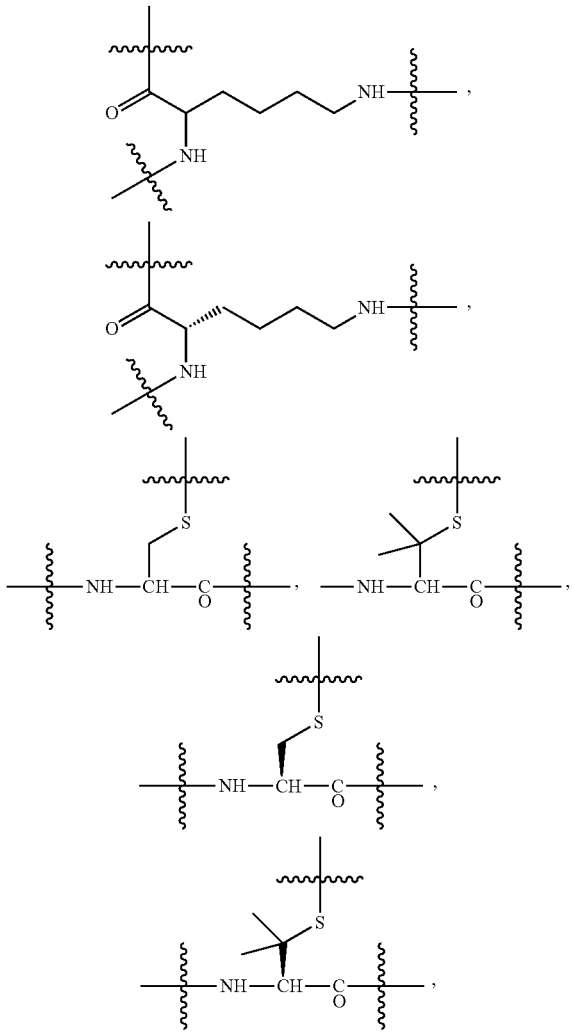

wherein the wavy lines indicate the points of covalent attachment to PEG and L of $L^P$(PEG)- within a Linker Unit of a drug linker moiety or a Drug Linker compound.

Preferred Ligand-Drug Conjugates having lysine as the $L^P$ unit are shown below wherein L, $L_S$, A, $A_O$, W, W', Y, $D^+$, PEG, and subscripts a and p are as described herein. (R)- and (S)-stereoisomers at the indicated (*) position are suitable for use herein.

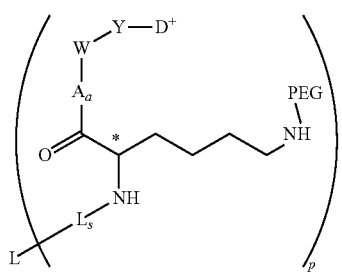

-continued

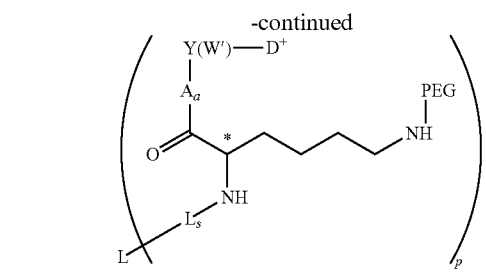

1.3.3 PEG Unit

The PEG Units as taught herein are designed to impart a suitable level of hydrophobicity masking of hydrophobic quaternized NAMPT Drug Units(s) and other hydrophobic components of a quaternized drug-linker moiety within a Ligand Drug Conjugate. For that reason, the incorporation of PEG Unit as taught herein is particularly suitable for hydrophobic quaternized NAMPT Drug Units that negatively impact the pharmacokinetics of the resultant Ligand Drug Conjugate as compared to the unconjugated targeting agent that corresponds to or is incorporated into its Ligand Unit. Those poorer pharmokinetics include greater plasma clearance, which is sometimes attributable to the hydrophobicity of a hydrophobic NAMPTi compound or derivative thereof incorporated into or corresponding to the quaternized NAMPT Drug Unit of the Ligand Drug Conjugate. Thus, Ligand Drug Conjugates having a hydrophobic quaternized NAMPT Drug Unit that display significantly greater plasma clearance and correspondingly lower plasma exposure relative to the unconjugated targeting agent will benefit by a Linker Unit to which that hydrophobic quaternized NAMPT Drug Unit is attached having a Stretcher Unit or subunit thereof of formula -$L^P$(PEG)-, wherein $L^P$ is a Parallel Connector Unit and PEG is a PEG Unit. Ligand-Drug Conjugates whose Linker Units are comprised of such Stretcher Units will have those more favorable pharmokinetic properties due to the parallel orientation within a hydrophobic quaternized drug-linker moiety of a hydrophobic quaternized NAMPT Drug Unit and the PEG Unit attached to $L^P$ whereby the negative impact of hydrophobicity of the hydrophobic quaternized NAMPT Drug Unit, which may be further aggravated by other hydrophobic components of the drug-linker moiety, on plasma clearance is sufficiently reduced or is essentially eliminated (i.e., hydrophobicity of a drug-linker moiety is masked).

The PEG Unit will be directly attached to the Ligand-Drug Conjugate (or Intermediate thereof) at the Parallel Connector Unit. The other terminus (or termini) of the PEG Unit will be free and untethered and may take the form of a methoxy, carboxylic acid, alcohol or other suitable functional group. The methoxy, carboxylic acid, alcohol or other suitable functional group acts as a cap for the terminal PEG subunit, referred to as a PEG Capping Unit, of the PEG Unit. The skilled artisan will understand that the PEG Unit in addition to comprising repeating polyethylene glycol subunits may also contain non-PEG material (e.g., to facilitate coupling of multiple PEG chains to each other or to facilitate coupling to the Parallel Connector Unit). Non-PEG material refers to the atoms in the PEG Unit that are not part of the repeating —$CH_2CH_2O$— subunits. In some embodiments, the PEG Unit comprises two monomeric PEG chains linked to each other via non-PEG elements.

Thus, in some embodiments, the PEG Unit is covalently bound to an amino acid residue of L via a reactive functional group of $L^{P'}$, which is the precursor to $L^P$. Reactive functional groups are those to which an activated PEG molecule may be bound (e.g., a free amino or carboxyl group). For example, N-terminal amino acid residues and lysine (K) residues have a free amino group; and C-terminal amino acid residues have a free carboxyl group. Sulfhydryl groups (e.g., as found on cysteine residues) may also be used as a reactive functional group of $L^{P'}$ for attachment of a PEG Unit to $L^P$. In addition, enzyme-assisted methods for introducing activated groups (e.g., hydrazide, aldehyde, and aromatic-amino groups) specifically at the C-terminus of a polypeptide have been described (see Schwarz, et al. (1990) *Methods Enzymol.* 184:160; Rose, et al. (1991) *Bioconjugate Chem.* 2:154; and Gaertner et al. (1994) *J. Biol. Chem.* 269:7224].

The attachment of the PEG Unit may have two potential impacts upon the pharmacokinetics of the resulting Ligand-Drug Conjugate. The desired impact is the decrease in clearance (and consequent in increase in exposure) that arises from the reduction in non-specific interactions induced by the exposed hydrophobic elements of the drug-linker. The second impact may be undesired and is dues to the decrease in volume and rate of distribution that may arise from the increase in the molecular weight of the Ligand Drug Conjugate compound having a -$L^P$(PEG)- moeity in the Linker Units of its quaternized drug linker moieties. Increasing the number of PEG subunits increases the hydrodynamic radius of a conjugate, resulting in decreased diffusivity. In turn, decreased diffusivity may diminish the ability of the Ligand-Drug Conjugate to penetrate into a tumor (Schmidt and Wittrup, *Mol. Cancer Ther.* (2009) 8:2861-2871). Because of these two competing pharmacokinetic effects, it is desirable to have a PEG Unit that is sufficiently large to decrease the clearance of the Ligand Drug Conjugate compounds of an administered Ligand Drug Conjugate composition thus increasing plasma exposure, but not so large as to greatly diminish its diffusivity, which may reduce the ability of the Ligand-Drug Conjugate compound to reach the intended targeted cell population.

In preferred embodiments, the PEG Unit is a derivitized linear single PEG chain having from 2 to 72, 2 to 60, 2 to 48, 2 to 36 or 2 to 24 subunits, or from 4 to 72, 4 to 60, 4 to 48, 4 to 36 or 4 to 24 subunits or from 6 to 72, 6 to 60, 6 to 48, 6 to 36 or 6 to 24 subunits, or from 8 to 72, 8 to 60, 8 to 48, 8 to 36 or 8 to 24 subunits, or from 12 to 72, 12 to 60, 12 to 48, 12 to 36 or 12 to 24 subunits, or from 8 to 36, 8 to 24 or 8 to 12 subunits.

Preferred linear PEG Units for use in any of the embodiments provided herein are as follows:

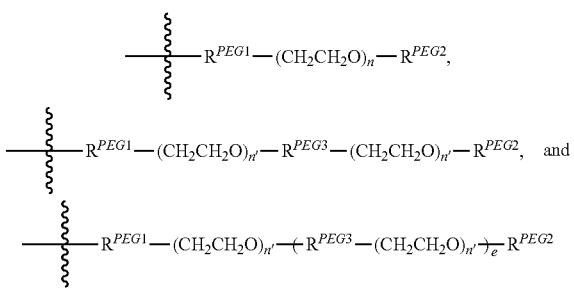

wherein the wavy line indicates site of attachment to the Parallel Connector Unit to $L^P$; $R^{PEG1}$ is a PEG Attachment Unit, $R^{PEG2}$ is a PEG Capping Unit; $R^{PEG3}$ is an PEG Coupling Unit (i.e., for coupling multiple PEG subunit chains together), subscript n is selected from 2 to 72, preferably from 4 to 72, more preferably from 6 to 72, from 8 to 72, from 10 to 72, from 12 to 72, from 6 to 24 or from 8 to 24, with 8 to 12 particularly preferred; subscript e is 2 to 5; and each subscript n' is independently selected from 1 to 72.

In more preferred embodiments, there are no more than 72 or 36 PEG subunits in a PEG Unit. In other more preferred embodiments, subscript n is 8 or about 8, 12 or about 12, or 24 or about 24.

The PEG Attachment Unit ($R^{PEG1}$) is part of a PEG Unit and acts to connect the PEG Unit to the Parallel Connector Unit ($L^P$) through a functional group of the PEG Unit. Functional groups for attachment of the PEG Unit to $L^P$ include sulfhydryl groups to form disulfide bonds or thioether bonds, aldehyde, ketone, or hydrazine groups to form hydrazone bonds, hydroxylamine to form oxime bonds, carboxylic or amino groups to form peptide bonds, carboxylic or hydroxy groups to form ester bonds, sulfonic acids to form sulfonamide bonds, alcohols to form carbamate bonds, and amines to form sulfonamide bonds or carbamate bonds or amide bonds. Accordingly, the PEG Unit in some embodiment is attached to $L^P$ via disulfide, thioether, hydrazone, oxime, peptide, ester, sulfonamide, carbamate, or amide bonds.

In some embodiments, $R^{PEG1}$ is —C(O)—, —O—, —S—, —S(O)—, —NH—, —C(O)O—, —C(O)C$_1$-C$_{10}$alkyl, —C(O)C$_1$-C$_{10}$alkyl-O—, —C(O)C$_1$-C$_{10}$alkyl-CO$_2$—, —C(O)C$_1$-C$_{10}$alkyl-NH—, —C(O)C$_1$-C$_{10}$alkyl-S—, —C(O)C$_1$-C$_{10}$alkyl-C(O)—NH—, —C(O)C$_1$-C$_{10}$alkyl-NH—C(O)—, —C$_1$-C$_{10}$alkyl, —C$_1$-C$_{10}$alkyl-O—, —C$_1$-C$_{10}$alkyl-CO$_2$—, —C$_1$-C$_{10}$alkyl-NH—, —C$_1$-C$_{10}$alkyl-S—, —C$_1$-C$_{10}$ alkyl-C(O)—NH—, —C$_1$-C$_{10}$ alkyl-NH—C(O)—, —CH$_2$CH$_2$SO$_2$—C$_1$-C$_{10}$alkyl-, —CH$_2$C(O)—C$_1$-C$_{10}$ alkyl-, =N—(O or NH)—C$_1$-C$_{10}$ alkyl-O—, =N—(O or NH)—C$_1$-C$_{10}$ alkyl-NH—, =N—(O or NH)—C$_1$-C$_{10}$alkyl-CO$_2$—, =N—(O or NH)—C$_1$-C$_{10}$alkyl-S—,

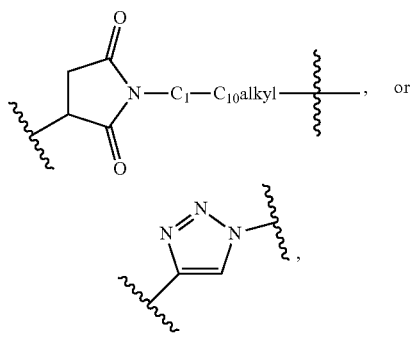

wherein in each instance C$_1$-C$_{10}$ is optionally substituted

In preferred embodiments, $R^{PEG1}$ is —NH—, —C(=O)—, triazole-linked groups, or —S—, or maleimido-linked groups such as

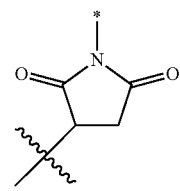 [SMILES: *C1CC(=O)N(*)C1=O]

wherein the wavy line indicates the site of attachment to $L^P$ and the asterisk indicates the site of attachment within the PEG Unit.

The PEG Capping Unit ($R^{PEG2}$) is part of the PEG Unit and acts to terminate a PEG Unit at its untethered end, which is distal to the tethered end of the PEG Unit.

In exemplary embodiments, $R^{PEG2}$ is independently —$C_1$-$C_{10}$ alkyl, —$C_2$-$C_{10}$ alkyl-$CO_2H$, —$C_2$-$C_{10}$ alkyl-OH, —$C_2$-$C_{10}$ alkyl-$NH_2$, —$C_2$-$C_{10}$ alkyl-NH($C_1$-$C_3$ alkyl), or —$C_2$-$C_{10}$ alkyl-N($C_1$-$C_3$ alkyl)$_2$, wherein each $C_1$-$C_3$ alkyl is independently selected and wherein $C_1$-$C_{10}$, $C_2$-$C_{10}$ and $C_1$-$C_3$ are optionally substituted.

$R^{PEG3}$ is part of a PEG Unit when there two linear sequences of contiguous PEG subunits contained within the PEG Unit and acts to join these sequences together into a single linear chain. In exemplary embodiments, $R^{PEG3}$ is —$C_1$-$C_{10}$ alkyl-C(O)—NH—, —$C_1$-$C_{10}$ alkyl-NH—C(O)—, —$C_2$-$C_{10}$ alkyl-NH—, —$C_2$-$C_{10}$ alkyl-O—, —$C_1$-$C_{10}$ alkyl-S—, or —$C_2$-$C_{10}$ alkyl-NH—, wherein $C_1$-$C_{10}$ alkyl and $C_2$-$C_{10}$ alkyl are optionally substituted.

Preferred linear PEG Units that can be used in any of the embodiments provided herein are as follows:

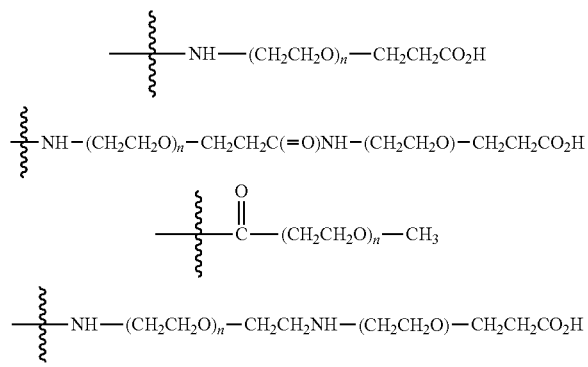

wherein the wavy line indicates site of covalent attachment to $L^P$, and each subscript n is independently selected from 4 to 72, 6 to 72, 8 to 72, 10 to 72, 12 to 72, 6 to 24, or 8 to 24. In some aspects, subscript n is about 8, about 12, or about 24.

It will be appreciated that when referring to PEG subunits, and depending on context, the number of subunits can represent an average number, e.g., when referring to a population of Ligand-Drug Conjugates or Intermediate Compounds (e.g., Drug Linker compounds), and/or when using polydisperse PEGs.

1.3.4 Cleavable Unit

A Cleavable Unit is a component of a secondary linker within a drug linker moiety of a Ligand Drug Conjugate or is a component of a Linker Unit of a Drug Linker compound wherein the Cleavable Unit provides for a reactive site that when acted upon enzymatically or non-enzymatically results in breaking of a covalent bond within the secondary linker to initiate release of a quaternized NAMPT Drug ($D^+$) as a NAMPTi compound. In some embodiments, reactivity to that site is greater within or surrounding a hyper-proliferating cell or a hyper-stimulated immune cell, which are exemplary abnormal cells, in comparison to a normal cell such that action upon that site results in preferential exposure to the abnormal cell of the NAMPTi compound on release $D^+$ as that compound from a drug linker moiety of a Ligand Drug Conjugate compound. In some of those embodiments, a Cleavable Unit contains a reactive site cleavable by an enzyme whose activity or abundance is greater within or surrounding the hyper-proliferating, immune-stimulating or other abnormal or unwanted cell compared to normal cells or whose activity or abundance is greater the vicinity of normal cells that are distant from the site of the abnormal or unwanted cells. In preferred embodiments W or W' provides for an enzyme substrate, wherein W is in the form of a Peptide Cleavable Unit and W' is a glycosidic bonded carbohydrate moeity in those instances in which W is placed by a Glucuronide Unit of formula —Y(W'), wherein Y is a self-immolative Spacer Unit. In some of those embodiments, W or W' is more likely operated upon enzymatically subsequent to cellular internalization of a Ligand Drug Conjugate compound into a targeted abnormal cell. That internalization more likely occurs in those cells in comparison to normal cells due to greater presentation of the targeted moiety recognized by the targeting moiety (i.e., the Ligand Unit) of the Ligand Drug Conjugate compound on the cellular membrane of the targeted abnormal cells. Therefore, the targeted cells will more likely be exposed intracellularly to a NAMPTi compound liberated from the Ligand Drug Conjugate compound on release of its quaternized NAMPT Drug Unit. The Cleavable Unit in some embodiments comprise one or multiple sites susceptible to cleavage under conditions of the targeted site or within the targeted cells, and in other embodiments has only one such site.

A Peptide Cleavable Unit is a substrate for a protease, preferably a regulatory protease, and W' is a substrate for a glycosidase, wherein the protease or glycosidase is located intracellularly in targeted cells (i.e., the reactive site of W or W' is a peptide bond or glycoside bond, respectively, cleavable by the protease or glycosidase). In those embodiments the peptide or glycoside bond of W/W' is capable of selective cleavage by an intracellular regulatory protease or glycosidase in comparison to serum proteases or glycosidases. Those intracellular regulatory proteases or glycosidases in more preferred embodiments are more specific to the targeted abnormal cells in comparison to normal cells distant from the site of the abnormal cells. In other embodiments, W/W' is a substrate for a protease or glycosidase excreted in greater amounts by the targeted abnormal cells in comparison to normal cells distant from the site of the abnormal cells so that W or W' is capable of selective cleavage by the excreted protease or glycosidase, respectively. In still other embodiments W/W' is a substrate for a protease or glycosidase, present within or preferentially excreted by normal cells that are peculiar to the environment of the abnormal cells in comparison to other normal cells in the periphery.

In other embodiments, a Ligand Drug Conjugate compound is preferentially internalized into targeted normal cells that are peculiar to the environment of abnormal cells in comparison to normal cells in the periphery such that enzymatic action W/W' of the Conjugate compound will release a quaternized NAMPT Drug Unit as a NAMPTi compound thereby preferentially exposing the nearby abnormal cells to that NAMPTi compound.

In any one of those embodiments, W or W' in a Drug Linker or a quaternized drug linker moiety of a Ligand Drug Conjugate compound is covalently attached to a Spacer Unit (Y) that is comprised or consists of a self-immolating moiety such that enzymatic action W or W' triggers self-destruction of that Unit within Y-$D^+$ of —W—Y-$D^+$ or —Y(W')-$D^+$, of that Drug Linker or Ligand Drug Conjugate compound's quaternized drug linker moiety to release $D^+$ as a NAMPTi compound in which the skeletal nitrogen atom of the heterocyclyl or heteroaryl of the quaternized NMAPT Head Unit is no longer quaternized, wherein W represents a Peptide Cleavable Unit and —Y(W')— is a Glucuronide Unit replacing W.

The protease or glycosidase enzyme required for processing of the Linker Unit to release $D^+$ as a NAMPTi compound need not be produced preferentially by targeted abnormal cells in comparison to normal cells provided the processing enzyme is not excreted by normal cells to an entent that would cause undesired side effects from premature release of the drug compound or moeity. In other instances, the required protease or glycosidase enzyme may be excreted, but to avoid undesired premature release of the quaternised NAMPT Drug Unit, it is preferred that the processing enzyme be excreted in the vicinity of abnormal cells and remain localized to that environment, whether produced by abnormal cells or nearby normal cells in response to the abnormal environment caused by the abnormal cells. In that respect W as a Peptide Cleavable Unit or W' of a Glucuronide Unit in which W is replace by —Y(W')— is selected to be preferentially acted upon by a protease or glycosidase in or within the environment of abnormal cells in contrast to freely circulating enzymes. In those instances, a Ligand Drug Conjugate compound is less likely to release its quaternized NAMPT Drug Unit as a NAMPTi compound in the vicinity of unintended normal cells nor would it be internalized into normal cells that do intracellularly produce but do not excrete the enzyme intended for action upon the Ligand Drug Conjugate compound since such cells are less likely to display a targeted moiety required for entry by the Ligand Drug Conjugate compound.

In some embodiments, W as a Peptide Cleavable Unit is comprised of an amino acid or is comprised or consists of one or more sequences of amino acids that provide a substrate for a protease present within abnormal cells or a protease localized to the environment of these abnormal cells. Thus, a Peptide Cleavable Unit may be comprised or consist of a dipeptide, tripeptide, tetrapeptide, pentapeptide, hexapeptide, heptapeptide, octapeptide, nonapeptide, decapeptide, undecapeptide or dodecapeptide moiety incorporated into a Linker Unit through an amide bond to a self-immolative moiety of a self-immolative Y wherein that moiety is a recognition sequence for that protease. In other aspects, W' in a Glucuronide Unit of formula —Y(W')— replacing W, wherein W' is a carbohydrate moiety (Su) having a glycosidic bond to an optionally substituted heteroatom (E'), in which the heteroatom may be optionally substituted where permitted as described herein, attached to a self-immolative moiety of the Glucuronide's self-immolative Spacer Unit (Y) that is cleavable by a glycosidase preferentially produced by abnormal cells or in nearby normal cells peculiar to the environment of the abnormal cells, or found within such cells to which a Ligand Drug Conjugate having that self-immolative Spacer Unit and carbohydrate moiety, has selective entry due to the greater presence of the targeted moiety on the targeted cells in comparison to unintended normal cells.

1.3.4 Spacer Units

A secondary linker ($L_O$) when bonded to a quaternized NAMPT Drug Unit ($D^+$) in a Linker Unit attached to only one such Drug Unit and having a PAB or PAB-related self-immolative Spacer Unit is represented by the structure of s1 or s2:

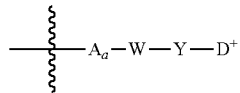

(s1)

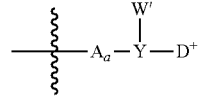

(s2)

wherein in structure s1 W is a Peptide Cleavable Unit, Y is the PAB or PAB-type self-immolative Spacer Unit and wherein a peptide bond of the Peptide Cleavable Unit, preferably between W and Y, is cleavable by a protease to initiate release of $D^+$ as a NAMPTi compound and wherein structure s2 is related to structure s1 by replacing W—Y with a Glucuronide Unit of formula —Y(W')—, wherein Y is the PAB or PAB-type Spacer Unit and W' is glycosidic-bonded carbohydrate wherein the glycosidic bond between W' and Y is cleavable by a glycosidase to initiate release of $D^+$ as a NAMPTi compound, and wherein in either formula A is an optional first Stretcher Unit and subscript a is 0 or 1 indicating the absence or presence of A, respectively.

Exemplary PAB or PAB-related self-immolative moieties when present in a secondary linker bonded to -$D^+$ have a central arylene or heteroarylene substituted by a masked electron donating group (EDG) and a benzylic carbon bonded directly to $D^+$ wherein the masked EDG and benzylic carbon substituents are ortho or para to each other (i.e., 1,2 or 1,4 substitution pattern). Exemplary, but non-limiting, structures of self-immolative Spacer Units having a PAB or PAB-related self-immolative moiety bonded directly to $D^+$ and to a Peptide Cleavable Unit in which the central (hetero) arylene has the requisite 1,2 or 1,4 substitution pattern that allows for 1,4- or 1,6-fragmentation to release $D^+$ as a NAMPTi compound are represented by:

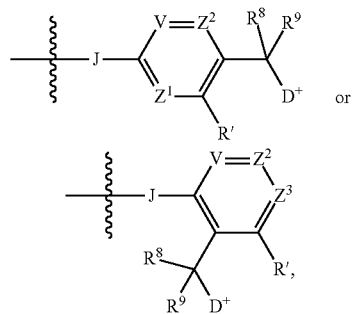

wherein the wavy line to J indicates the site of covalent attachment to a Peptide Cleavable Unit through J or through a functional group comprising J, wherein J is a heteroatom, optionally substituted where permitted as described herein (as in certain optionally substituted —NH— moieties), $D^+$ is a quaternized NAMPT Drug Unit, and wherein V, $Z^1$, $Z^2$, $Z^3$ are independently =N or =C($R^{24}$)—, wherein each $R^{24}$ is independently selected from the group consisting of hydrogen and $C_1$-$C_{12}$ alkyl, $C_2$-$C_{12}$ alkenyl, $C_2$-$C_{12}$ alkynyl, $C_6$-$C_{24}$ aryl, ($C_6$-$C_{24}$ aryl)-$C_1$-$C_{12}$ alkyl-, $C_5$-$C_{24}$ heteroaryl and ($C_5$-$C_{24}$ heteroaryl)-$C_1$-$C_{12}$ alkyl-, optionally substituted, halogen and other electron withdrawing groups and electron donating groups; R' is hydrogen or $C_1$-$C_{12}$ alkyl, $C_2$-$C_{12}$ alkenyl, $C_2$-$C_{12}$ alkynyl, $C_6$-$C_{24}$ aryl, ($C_6$-$C_{24}$ aryl)-$C_1$-$C_{12}$ alkyl-, $C_5$-$C_{24}$ heteroaryl, or $C_5$-$C_{24}$ heteroaryl)-$C_1$-$C_{12}$ alkyl, optionally substituted, an electron donating group or an electron withdrawing group; and $R^8$ and $R^9$ are independently selected from the group consisting of hydrogen, $C_1$-$C_{12}$ alkyl, $C_2$-$C_{12}$ alkenyl, $C_2$-$C_{12}$ alkynyl, $C_6$-$C_{24}$ aryl and $C_5$-$C_{24}$ heteroaryl, optionally substituted, or both $R^8$ and $R^9$ together with the carbon atom to which they are attached define a optionally substituted $C_3$-$C_{20}$ carbocyclo. In preferred embodiments, one or more of V, $Z^1/Z^3$, $Z^2$ is =CH— and any remainder are —N= or =C($R^{24}$)—, wherein $R^{24}$ is other than hydrogen. In other preferred embodiments R' is hydrogen or an electron donating group, including $C_1$-$C_6$ alkoxy such as —$OCH_3$ and —$OCH_2CH_3$, or one of $R^8$, $R^9$ is hydrogen and the other is hydrogen or $C_1$-$C_4$ alkyl. In more preferred embodiments two or more of V, $Z^1/Z^3$ and $Z^2$ are =CH— and any remainder is —N= or =C($R^{24}$)—, wherein $R^{24}$ is other than hydrogen. In any one of those preferred embodiments, more preferred are those in which $R^8$, $R^9$ and R' are each hydrogen.

In some embodiments, a self-immolative Spacer Unit having a PAB or PAB-type moiety bound to $D^+$ in a Linker Unit comprised of a Peptide Cleavable Unit has the structure of:

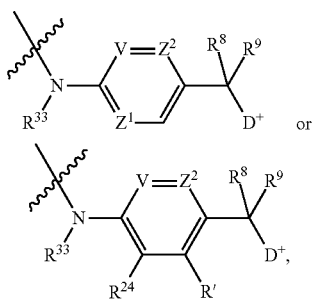

wherein the wavy line adjacent to the nitrogen atom indicates the site of covalent attachment to W, wherein that bond to W is cleavable by a protease, and $R^{33}$ is hydrogen or optionally substituted $C_1$-$C_6$ alkyl so that —N($R^{33}$) is an exemplary optionally substituted heteroatom that is appropriately substituted, preferably hydrogen or $C_1$-$C_4$ alkyl, more preferably hydrogen, —$CH_3$ or —$CH_2CH_3$. In more preferred embodiments, $R^{33}$ is hydrogen so that the nitrogen atom is an unsubstituted heteroatom of the form —NH—, and V, $Z^1$ and $Z^2$ are each =CH— and $R^{24}$ and R' are hydrogen or one of V, $Z^1$ and $Z^2$ is =N— or =C($R^{24}$)—, wherein $R^{24}$ is an electron donating group or an electron donating group or each of V, $Z^1$ and $Z^2$ is =CH— and $R^{24}$ or R' is an electron donating group or an electron withdrawing group. Preferred $R^{24}$ and R' electron donating groups are optionally substituted $C_1$-$C_6$ alkoxy, more preferably, —$OCH_3$ or —$OCH_2CH_3$. In more preferred embodiments each of V, $Z^1$ and $Z^2$ is =CH— and $R^{24}$ and R' are each hydrogen Without being bound by theory, the mechanism of self-immolation of Y in which $R^{33}$ is —H is illustrated for Ligand Drug Conjugates and Drug Linker compounds having a Peptide Cleavable Unit as:

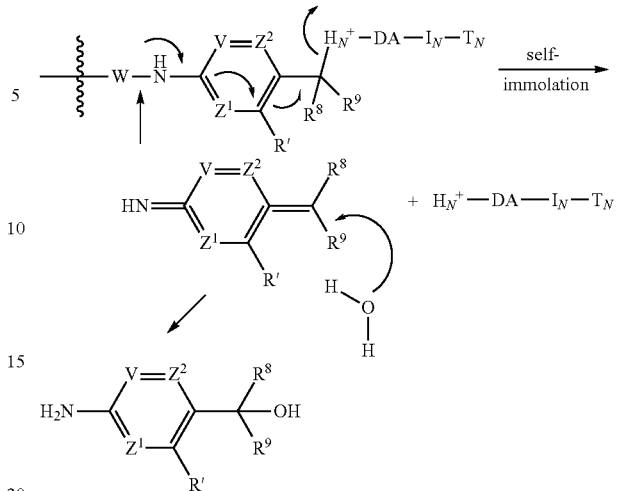

In some embodiments, —Y(W')-$D^+$, as shown in structure s2 in which a Glucuronide Unit of formula —Y(W')—, has the structure of:

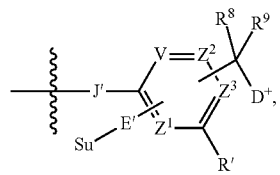

wherein J' is an optionally substituted heteroatom where permitted as described herein, including O, S and optionally substituted —NH—, and the wavy line to J' indicates the site of stable covalent bonding (i.e., is not enzymatically processed or is stable at the targeted site) to $L_R$, which is preferably $L_{SS}$ or $L_S$, or the remainder of the secondary linker through said heteroatom or a functional group comprised of that heteroatom; E', independently selected from J', is an electron donating moiety such as —O—, —S—, or —N($R^{33}$)—, wherein $R^{33}$ is as defined above, wherein the electron donating ability of E' is attenuated by its bonding to the carbohydrate moiety (Su) of W', wherein W' is -E'-Su, wherein Su bonded to E' provides for a cleavage site for a glycosidase, and E' and the benzylic carbon of the —C($R^8$)($R^9$)-$D^+$ moiety are bonded to the central (hetero)arylene at positions defined by V, $Z^1$, $Z^2$ or $Z^3$, requiring at least two of V, $Z^1$, $Z^2$, $Z^3$ to be =C($R^{24}$)-in which one $R^{24}$ substituent is the —C($R^8$)($R^9$)-$D^+$ moiety and the other is W', such that W' and the —C($R^8$)($R^9$)-$D^+$ moiety are in a 1,2 or 1,4 relationship so as to permit the 1,4- or 1,6-fragmention on cleavage to release $D^+$ as a NAMPTi compound; and the remaining variable groups are as previously defined for PAB or PAB-related self-immolative Spacer Units that are bonded to a Peptide Cleavable Unit. In preferred embodiments, J' is —O—, —N($R^{33}$)— wherein $R^{33}$ is preferably hydrogen or $C_1$-$C_4$ alkyl, wherein the bond to J' and the remainder of the quaternized drug linker moiety is not intended to be cleavable. In other preferred embodiments, one or both of the remaining V, $Z^1$, $Z^2$, $Z^3$ variable groups not bonded to W' and —C($R^8$)($R^9$)-$D^+$ is =CH—. In still other preferred embodiments, R' is hydrogen or an electron withdrawing group, including —NO$_2$, or one of R$^8$, R$^9$ is hydrogen and the other is hydrogen or C$_1$-C$_4$ alkyl. In more preferred embodiments both remaining variable groups from V, Z$^1$, Z$^2$, Z$^3$ are =CH—.

In some embodiments, for a secondary linker-D$^+$ moiety of structure s2, a self-immolative Spacer Unit having a PAB or PAB-type moiety bound to D$^+$ has the structure of:

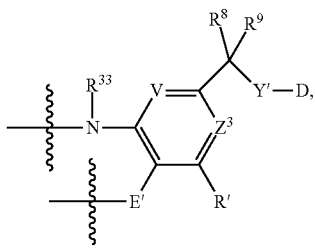

wherein the variable groups are as previously defined. In preferred embodiments, both of V, Z$^3$ are =CH—. In other preferred embodiments R$^{33}$ is hydrogen. In still other more preferred embodiments, R$^8$ and R$^9$ are each hydrogen and R' is hydrogen.

The central (hetero)arylene of a self-immolative moiety may be further substituted to affect the kinetics of the 1,2- or 1,4-elimination in order to modulate the release of D$^+$, to improve the physiochemical properties of the Ligand Drug Conjugate (e.g., reduce hydrophobicity) into which it is incorporated and/or increase the sensitivity of the bond to protease or glycosidase cleavage. For example, when E' of W' is an oxygen atom of a glycosidic bond within a Glucuronide Unit that by definition is cleavable by a glycosidase to increase sensitivity to glycosidase cleavage R' can be an electron withdrawing group intended to increase sensitivity to glycosidase cleavage Exemplary and non-limiting examples of self-immolative structures are provided by Alouane et al. "Self-immolative spacers: Kinetic aspects, structure-property relationships, and applications" *Angew. Chem. Int. Ed.* (2015): 54: 7492-7509; Blencowe et al. "Self-immolative linkers in polymeric delivery systems" *Polym. Chem.* (2011) 2: 773-790; Greenwald et al. "Drug delivery systems employing 1,4- or 1,6-elimination: poly(ethylene glycol) prodrugs of amine-containing compounds" *J. Med. Chem.* (1999) 42: 3657-3667; and in U.S. Pat. Nos. 7,091,186; 7,754,681; 7,553,816; and 7,989,434, all of which are incorporated by reference herein in their entireties with the structures and variable groups provided therein specifically incorporated by reference.

1.4 Quaternized NAMPT Drug Unit

A quaternized NAMPT Drug Unit (D$^+$) is covalently attached to L$_O$ of a Linker Unit of a Formula 1, Formula 1a or Formula 1b Ligand Drug Conjugate compound in which subscript p is replaced by p', or the Linker Unit of a Drug Linker compound of Formula I or Formula Ia preferably through its quaternized NAMPT Head (H$_{N^+}$) Unit, whereupon release from the Ligand Drug Conjugate compound or Drug Linker compound that Unit becomes a NAMPT Head Unit (H$_N$) of a NAMPTi compound that is capable of interacting with enzymatically competent NAMPT homodimer at its nicotinamide binding site. That release occurs subsequent to enzymatic processing in a secondary linker (L$_O$) of the Linker Unit of the Conjugate compound or Drug Linker compound. In Formula 1a and Formula Ia, W is a Peptide Cleavable Unit, which is capable of being processed by a protease, preferably by cleavage of a peptide bond to Y, wherein Y is a self-immolative Spacer Unit, and in Formula 1b and Formula Ib, W is replaced by —Y(W'), which is a Glucuronide Unit, wherein Y is a self-immolative Spacer Unit and W' is attached to that Spacer Unit through a glycosidic bond is capable of cleavage by a glycosidase.

In preferred embodiments, a quaternized NAMPT Drug (D$^+$) Unit has the general formula of:

in suitable salt form, preferably one that is pharmaceutically acceptable, wherein the pound sign (#) indicates the site of covalent attachment to L$_O$ through a quaternized nitrogen of H$_{N^+}$ in Formula 1, Formula 1a, Formula 1b, Formula I or Formula Ia; H$_{N^+}$ is a quaternized NAMPT Head Unit, DA is a NAMPT Donor-Acceptor Unit, I$_N$ is a NAMPT Interconnecting Unit and T$_N$ is a NAMPT Tail Unit.

In those embodiments, H$_{N^+}$ incorporates or corresponds to H$_N$ of a NAMPTi compound or derivative thereof and is formally derived from quaternization of H$_N$ through attachment to L$_O$ through a skeletal nitrogen atom of a heteroaryl comprising H$_N$ in which aromaticity of the heteroaryl is either maintained or disrupted within H$_{N^+}$. That formal quaternization is not limiting to the identity of the quaternized NAMPT Drug Unit since it makes no inference as to the manner of preparation of such compounds as the remainder of the quaternized NAMPT Drug Unit can be constructed subsequent to covalent attachment of H$_N$ or H$_N$-DA so as to provide —H$_{N^+}$ or —H$_{N^+}$-DA. Furthermore, the quaternized nitrogen may be that of a precursor to H$_{N^+}$, as for example when H$_{N^+}$ is comprised of a partially unsaturated heterocyclic ring system having a skeletal nitrogen atom that is quaternized, which is then fully aromatized.

In one embodiment, initiation of release of D$^+$ as a NAMPTi compound of formula H$_N$-DA-I$_N$-T$_N$, wherein H$_N$ is a NAMPT Head Unit and the other variable groups are as described for quaternized NAMPT Drug Units, occurs from protease cleavage of a Peptide Cleavable Unit in a secondary linker of the Ligand Unit. In another embodiment, initiation of D$^+$ release occurs with glycosidase cleavage of a Glucuronide Unit in the secondary linker to provide a NAMPTi compound of formula H$_N$-DA-I$_N$-T$_N$. In preferred embodiments, the covalent bond of W-D$^+$ in which W is a peptide Cleavable Unit is cleaved by the protease. In another embodiment, initiation of release of D$^+$ as a NAMPTi compound occurs from glycosidase cleavage of a Glucuronide Unit of formula —Y(W')—, which replaces W in Formula 1, Formula 1a, Formula 1b, Formula I or Formula Ia in which Y is a self-immolative Unit. In either of those embodiment in which H$_{N^+}$ is comprised of a partially unsaturated heterocyclic ring system release of D$^+$ results in a NAMPTi compound so that the heterocyclic ring system is converted to a heteroaromatic ring system comprising H$_N$.

Particularly preferred NAMPTi compounds provided by combinations of NAMPT Head (H$_N$), NAMPT Donor Acceptor (DA), NAMPT Interconnecting (I$_N$) and NAMPT Tail (T$_N$) Units have the structures of:

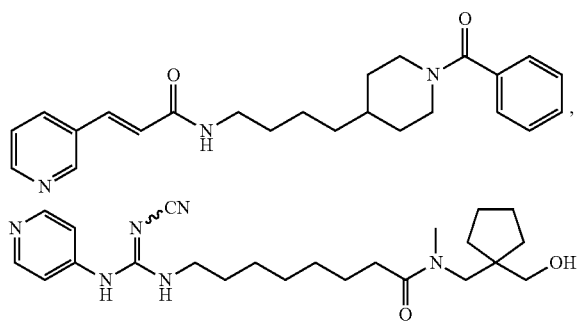

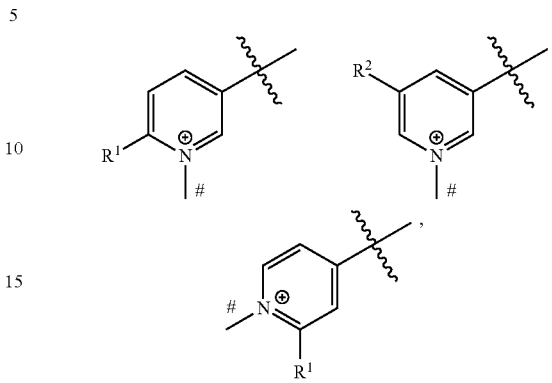

and salt thereof, including but not limited to pharmaceutically acceptable salts.

1.4.1 Quaternized NAMPT Head Unit

A quaternized NAMPT Head ($H_{N^+}$) Unit is a component of a quaternized NAMPT Drug ($D^+$) Unit of formula —$H_{N^+}$-DA-$I_{N}$-$T_N$ in which $H_{N^+}$ is covalently attached to or incorporates in whole or in part the NAMPT Donor Acceptor (DA) Unit of $D^+$ and is capable of interacting with the binding site of NAMPT normally occupied by the pyridine moiety of nicotinamide prior to its enzymatic conversion to nicotinamide mononucleotide (NMN) upon release as $H_N$ in a NAMPTi compound of formula $H_N$-DA-$I_N$-$T_N$. In some embodiments the quaternized NAMPT Head ($H_{N^+}$) Unit, or a $H_{N^+}$-DA moiety in which $H_{N^+}$ incorporates the DA Unit at least in part, is a $C_5$-$C_{24}$ heteroaryl or partially unsaturated or partially aromatic $C_8$-$C_{24}$ heterocyclyl, optionally substituted, either one of which is comprised of an optionally substituted 5- or 6-membered nitrogen-containing partially unsaturated heterocyclic or heteroaromatic ring system. In those embodiments in which the $H_{N^+}$ Unit incorporates the DA Unit at least in part, such incorporation preferably takes the form of a an optionally substituted 5- or 6-membered aromatic or non-aromatic ring system in which the DA Unit attached to $H_{N^+}$ through a carbon skeletal of an optionally substituted 6-membered nitrogen heteroaromatic ring system comprising $H_{N^+}$ is formally cyclized to that ring system in the manner described herein, so as to define a $H_{N^+}$-DA moiety having a partially unsaturated, partially aromatic or fully aromatic 6,5- or 6,6 fused ring system.

In preferred embodiments, $H_{N^+}$ is that of a pyridine mimetic in which a skeletal nitrogen atom of the mimetic is quaternized by $L_O$ of a Ligand Drug Conjugate compound or Drug Linker compound, wherein the optionally substituted $C_5$-$C_{24}$ heteroaryl or partially aromatic $C_8$-$C_{24}$ heterocyclyl of the pyridine mimetic prior to quaternization has a pKa of between about −2 to about 7, with no other skeletal nitrogen atoms having a pKa greater than 7 and is therefore weakly basic, or remains essentially uncharged under normal physiological conditions, and is capable of interacting with the nicotinamide binding site of enzymatically competent NAMPT dimer by one or more interactions engaged by the pyridine moiety of nicotinamide when $D^+$ is released as a NAMPTi compound such that $H_{N^+}$ is converted to $H_N$.

In some preferred embodiments, a pyridine mimetic is comprised of a 6-membered optionally substituted nitrogen-containing heteroaromatic ring system, a skeletal nitrogen atom of which is quaternized to provide $H_{N^+}$ and is more preferably pyridin-3-yl or pyridin-4-yl, optionally substituted and/or optionally fused to an optionally substituted $C_5$ or $C_6$ heterocycle, where appropriate, wherein the pyridinyl moiety is attached by an aromatic carbon atom to the Donor Acceptor (DA) Unit. Accordingly, more preferred $H_{N^+}$ from quaternized pyridine mimetics those having one of the structures of:

or a salt thereof, preferably a pharmaceutically acceptable salt, wherein $R^1$ is hydrogen, an electron donating group or an electron withdrawing group, preferably hydrogen, —$NH_2$ or chloro; $R^2$ is halogen, preferably fluoro; the pound sign indicates the site of attachment of $L_O$ of a Drug Linker compound or of a quaternized drug linker moiety of a Ligand Drug Conjugate compound; and the wavy line indicates the site of covalent attachment to DA and an adjacent aromatic carbon atom thereto is the site of formal optional cyclization by DA to provide $H_{N^+}$-DA in which $H_{N^+}$ incorporates at least part of DA.

In other preferred embodiments, a pyridine mimetic is comprised of a 5,6-fused optionally substituted nitrogen-containing heteroaromatic ring system, a skeletal nitrogen atom of which is quaternized to provide $H_{N^+}$.

In some more preferred embodiments, DA is covalently attached to $H_{N^+}$ wherein that Unit is a quaternized pyridine mimetic comprised of an optionally substituted 6-membered nitrogen-containing heteroaromatic ring system wherein that attachment to a skeletal aromatic carbon atom of that ring system occurs without cyclization back to $H_{N^+}$.

In other more preferred embodiments, DA is formally cyclized at least in part back to a quaternized pyridine mimetic having an optionally substituted 6-membered nitrogen-containing heteroaromatic ring system at an adjacent skeletal aromatic carbon of that ring system to form a $H_{N^+}$-DA moiety in which DA is at least partially incorporated into $H_{N^+}$. In some of those preferred embodiments, formal cyclization occurs through a heteroatom of DA or through an oxygen, sulfur or nitrogen heteroatom, optionally substituted, introduced between $H_{N^+}$ and DA, which in either instance incorporates at least part the Donor Acceptor (DA) Unit into $H_{N^+}$ in the form of a 5-membered aromatic ring system so as to define a $H_{N^+}$-DA moiety having a fully aromatic or partially aromatic 6,5-fused ring system.

In other preferred embodiments in which DA is formally cyclized at least in part back to the quaternized pyridine mimetic at an adjacent skeletal aromatic carbon to form a $H_{N^+}$-DA moiety in which $H_{N^+}$ incorporates at least in part DA, DA cyclized to that adjacent skeletal carbon atom through an optionally substituted methylene introduced between $H_{N^+}$ and DA in the form of a non-aromatic 5-membered ring so as to define a $H_{N^+}$-DA moiety having a partially aromatic 6,5-fused ring system. Those embodiments defining $H_{N^+}$-DA moieties are sometimes collectively referred to as quaternized nicotinamide moieties and result in a partially unsaturated or partially or fully aromatic quaternized nicotinamide mimetic when $D^+$ having that $H_{N^+}$-DA moeity is released as a NAMPTi compound of formula $H_N$-DA-$I_N$-$T_N$.

In any one of the aforementioned embodiments, more preferably $H_N$ as a pyridine mimetic or $H_N$-DA as a nicotinamide mimetic corresponds to or is incorporated into a quaternized NAMPT Drug ($D^+$) Unit as $H_{N^+}$ and $H_{N^+}$-DA, respectively, and is capable on release of $D^+$ as an NAMPTi compound from a Drug Linker compound, or a quaternized drug linker moiety of a Ligand Drug Conjugate compound, of interacting with Phe 193 on one monomer of NAMPT and/or Tyr 18' of the other monomer when these monomers form an enzymatically competent NAMPT homodimer and wherein each NAMPT monomer has the amino acid sequence of NCBI Reference Sequence NP_005737.1. Without being bound by theory those interactions may occur by a π-π offset stacking with one or both aromatic side chains of those two amino acid residues.

1.4.2 NAMPT Donor Acceptor Unit

A NAMPT Donor-Acceptor (DA) Unit is a component of a NAMPTi compound or a quaternized NAMPT Drug Unit that is bonded to or is incorporated at least in part into the NAMPT Head ($H_N$) Unit as a $H_N$-DA moiety or into the quaternized NAMPT Head ($H_{N^+}$) Unit and is also bonded to the NAMPT Interconnecting ($I_N$) Unit of that compound or quaternized Unit. A Donor-Acceptor (DA) Unit is comprised of a hydrogen bond donor or acceptor functional group, wherein a heteroatom of that functional group is attached to $H_N/H_{N^+}$, or DA is an organic moiety comprised of that functional group wherein a carbon atom of the organic moiety is attached to $H_N/H_{N^+}$, which in some embodiments is the carbon atom to which the hydrogen bond donor or acceptor functional group is attached, wherein in some embodiments attachment of the functional group heteroatom or carbon atom of the organic moiety of DA is to a carbon skeletal atom at position 2 or 3 of a 5-membered nitrogen-containing heteroaromatic ring system of $H_N/H_{N^+}$.

In other embodiments, attachment of the functional group heteroatom or carbon atom of the organic moiety of DA is at position 3 or 4 of the 6-membered nitrogen-containing heteroaromatic ring system of $H_N$, or the 6-membered nitrogen-containing partially unsaturated heterocyclic ring system of $H_{N^+}$ with optional cyclization of DA Unit formally back to an adjacent skeletal carbon atom of either nitrogen-containing ring system through a heteroatom of DA or through an introduced optionally substituted non-aromatic carbon atom or an aromatic optionally substituted nitrogen, oxygen or sulfur atom resulting in a $H_N$-DA moiety having an optionally substituted, partially aromatic or fully aromatic fused ring system, or a $H_{N^+}$-DA moiety having an optionally substituted partially unsaturated, partially aromatic or fully aromatic ring system.

In either embodiment, said bonding of DA is in relation to a skeletal nitrogen atom of the 5- or 6-membered nitrogen-containing aromatic ring system of $H_N$ or the partially unsaturated or partially of fully aromatic heterocyclic ring system of $H_{N^+}$ and wherein said formal optional cyclization to the adjacent skeletal carbon atom of the nitrogen-containing heteroaromatic or heterocyclic ring system substantially retains the hydrogen bonding ability of the donor or acceptor functional group of DA prior to the formal cyclization.

In preferred embodiments, $H_N$ is a pyrimidine mimetic so that the $H_N$-DA-moiety with or without formal cyclization of DA back to the pyridine mimetic is a nicotinamide mimetic. In those embodiments in which DA is formally cyclized at least in part back to the pyridine moiety, it does so to form a partially aromatic or fully aromatic 6,5- or 6,6-fused ring system, which incorporates at least in part the DA Unit. Thus, in preferred embodiments of $H_{N^+}$ and $H_{N^+}$-DA-, a quaternized pyridine or nicotinamide mimetic without formal cyclization of DA is a 5- or 6-membered heteroaryl in which a skeletal nitrogen atom is quaternized and to which DA is bonded. In those embodiments in which DA is formally cyclized at least in part to $H_{N^+}$, $H_{N^+}$-DA- is a partially unsaturated or partially aromatic heterocyclyl having a 6,5- or 6,6-fused ring system in which a skeletal nitrogen atom of its 6-membered partially unsaturated or aromatic ring system is quaternized and which incorporates at least in part the DA Unit or is a 6,5-fused heteroaryl in which a skeletal nitrogen atom of the of its 6-membered aromatic ring system is quaternized and which incorporates at least in part the DA Unit.

In other preferred embodiments, DA is comprised of an optionally substituted amide functional group, which is the hydrogen bond donor or acceptor functional group of DA, and is capable of interacting at the nicotinamide binding site with one or more of the same interactions as the amide functional group of nicotinamide. DA in a quaternized NAMPT Drug Unit in some embodiments is thus capable of interacting with Ser 275 of an NAMPT monomer of an enzymatically competent NAMPT homodimer when released from a Ligand Drug Conjugate compound or Drug Linker compound, wherein each NAMPT monomer has the amino acid sequence of NCBI Reference Sequence NP_005737.1. In some of those embodiments, the amide functional group of DA is capable of interacting with Ser 275 at the hydroxyl side chain of that amino acid residue through hydrogen bonding, and/or is also capable of interacting with one or more amino acid residues selected from the group consisting of Asp 219, Ser 241, and Val 242 either directly by hydrogen bonding or indirectly through hydrogen bonding network(s) involving the intermediacy of water molecule(s).

In more preferred embodiments, DA is an acrylamide Donor Acceptor Unit characterized by an optionally substituted amide functional group, which serves as the hydrogen bond donor or acceptor, and an optionally substituted $C_2$-$C_{20}$ alkenylene and in which one of the $sp^2$ carbons of the alkenylene is bonded to the carbonyl carbon of the amide functional group, the nitrogen atom of which is the site of attachment to the NAMPT Interconnecting ($I_N$) Unit, and in which another $sp^2$ carbon of the alkenylene not attached to the amide functional group is the site of covalent attachment of that DA Unit to the optionally substituted 5- or 6-membered nitrogen-containing heteroaromatic ring system of $H_N$ or the 5- or 6-membered partially unsaturated heterocyclic or heteroaromatic ring system of $H_{N^+}$. In other more preferred embodiments, DA is a bioisostere of that acrylamide Donor Acceptor Unit. An acrylamide bioisostere of an acrylamide DA Unit is an organic moiety that is sterically and functionally equivalent to that type of DA Unit by joining together the $H_N/H_{N^+}$ and $I_N$ Units while retaining a plurality of interactions attributable to the parent compound within the interface of an enzymatically competent NAMPT dimer.

Preferred acrylamide DA and amide bioisostere DA Units have or are comprised, respectively, of the structures of:

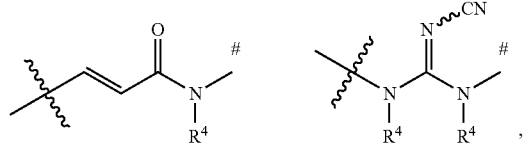

and salts, thereof, including but not limited to pharmaceutically acceptable salts, wherein the pound sign (#) indicates the site of covalent attachment of DA to $I_N$; the wavy line indicates the site of covalent attachment to $H_N/H_{N^+}$ or the remainder of DA, which is bonded to $H_N/H_{N^+}$, and the distal carbon atom of the acrylamide DA Unit is the site of said formal optional cyclization to $H_N/H_{N^+}$; and each $R^4$ is independently selected from the group consisting of hydrogen and optionally substituted $C_1$-$C_4$ alkyl, preferably from the group consisting of hydrogen, methyl and ethyl, more preferably each $R^4$ is hydrogen.

When an acrylamide DA Unit is formally cyclized at least in part back to an adjacent skeletal carbon atom of the optionally substituted nitrogen-containing heteroaromatic ring system of $H_N$ or when an acrylamide DA Unit is formally cyclized at least in part back to an adjacent skeletal carbon atom of the optionally substituted nitrogen-containing partially unsaturated heterocyclic or heteroaromatic ring system of $H_{N^+}$, it does so in particularly preferred embodiments to a 6-membered optionally substituted nitrogen-containing heteroaromatic ring system of $H_N$ or through a 6-membered optionally substituted nitrogen-containing partially unsaturated heterocyclic or heteroaromatic ring system of $H_{N^+}$ through the $sp^2$ carbon atom of the alkenylene moiety proximal to the amide functional group through an oxygen, sulfur or nitrogen heteroatom, optionally substituted, introduced between that proximal $sp^2$ carbon atom and the adjacent carbon atom so as to define a 5-membered heteroaromatic ring system fused to the 6-membered nitrogen-containing heteroaromatic ring system of $H_N$ or the 6-membered nitrogen-containing partially unsaturated heterocyclic or heteroaromatic ring system of $H_{N+}$. When the 6-membered optionally substituted nitrogen-containing heteroaromatic ring system is a pyridine mimetic and DA bonded thereto is an acrylamide DA Unit, the $H_N$-DA moiety in which DA is optionally cyclized back to $H_N$ in the formal manner so described is sometimes referred to as a nicotinamide mimetic. When the 6-membered optionally substituted nitrogen-containing partially unsaturated heterocyclic or heteroaromatic ring system is that of a quaternized pyridine mimetic and DA bonded thereto is an acrylamide DA Unit, the $H_{N^+}$-DA moiety in which DA is optionally cyclized back to $H_{N^+}$ in the formal manner so described is sometimes referred to as a quaternized nicotinamide mimetic. Other $H_N$-DA or $H_{N^+}$-DA moieties or nicotinamide or quaternized nicotinamide mimetics have or are comprised of an amide functional group or a bioisostere thereof as described above, with optional formal cyclization back to $H_N$ or $H_{N^+}$ in those embodiments in which $H_N$ or $H_{N^+}$ prior to that formal cyclization is a pyridine or quaternized pyridine mimetic, respectively, where sterically permitted.

Particularly preferred $H_N$-DA moieties or nicotinamide mimetics in which DA is not cyclized back to $H_N$ have the structure of:

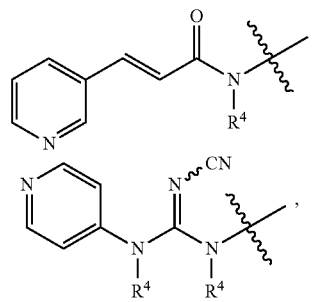

or salts thereof, preferably a pharmaceutically acceptable salt, and particularly preferred $H_{N^+}$-DA moieties or quaternized nicotinamide mimetics in which DA is not cyclized back to $H_{N^+}$ have the structure of:

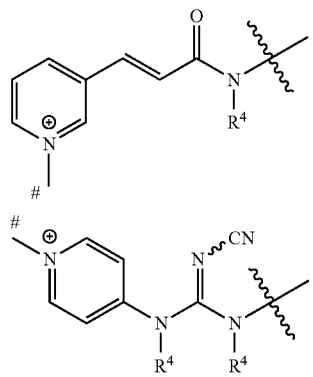

in salt form, preferably in pharmaceutically acceptable salt form, wherein each $R^4$ is independently selected from the group consisting of hydrogen and optionally substituted $C_1$-$C_4$ alkyl, preferably from the group consisting of hydrogen, methyl and ethyl, more preferably each $R^4$ is hydrogen; the wavy line indicates the site of covalent attachment to $I_N$; and the pound sign (#) indicates the site of covalent attachment to $L_O$ of a Drug Conjugate compound or a drug linker moeity of a Ligand Drug Conjugate compound.

Other $H_N$-DA or nicotinamide mimetics and other $H_{N^+}$-DA or nicotinamide mimetics not specifically enumerated above, which are formally derivable by various combinations of $H_N/H_{N^+}$ and DA Units described herein with or without formal cyclization of DA back to $H_N/H_{N^+}$ are contemplated with preferred combinations of $H_N$ and DA having a distance between the weakly basic or uncharged nitrogen that is not bonded to DA of the 5- or 6-membered nitrogen heteroaromatic ring system of $H_N$ and the atom of DA most distal from that nitrogen atom in a range of about 7.0 to about 7.3 angstroms, more preferably from about 7.1 to about 7.2 angstroms, when the NAMPTi compound or derivative thereof is in its MM2 minimized conformation. Accordingly preferred combinations of $H_{N^+}$ and DA are formally derivable from quaternization of the weakly basic or essentially uncharged nitrogen of $H_N$ in $H_N$-DA or of the nicotinamide mimetic. In other preferred combinations the distance between the atom of $H_N/H_{N^+}$ bonded to DA and the atom of the NAMPT Interconnecting ($I_N$) Unit to which the NAMPT Tail ($T_N$) Unit is attached in that minimized conformation is in the range from about 8.0 angstroms to about 9.5 angstroms, more preferably from about 8.3 angstroms to about 9.2 angstroms.

1.4.3 NAMPT Interconnector Unit

A NAMPT Interconnector ($I_N$) Unit is a component of a NAMPTi compound or a quaternized NAMPT Drug Unit that interconnects its Donor Acceptor (DA) and Tail ($T_N$) Units. In some embodiments, $I_N$ is capable of engaging in Van der Waals interactions with hydrophobic side amino acid side chains that line the tunnel in the region between the DA and Tail Units in an enzymatically competent NAMPT homodimer and allows for the Tail Unit to engage in one or more of the aforementioned interactions to anchor the NAMPTi compound into the dimer interface. Typically, the length of the Interconnecting Unit is also selected to allow projection of $T_N$ towards solvent accessible space on binding of a NAMPTi compound resulting from release of $D^+$ from a Drug Linker or Ligand Drug Conjugate compound. For that purpose, preferred embodiments of $I_N$ are comprised of a hydrophobic residue selected from the group consisting of optionally substituted $C_1$-$C_5$ alkylene, optionally substituted $C_6$-$C_{24}$ arylene, optionally substituted $C_5$-$C_6$ heteroarylene, or a combination thereof, in which the terminus of the hydrophobic residue distal to site of attachment to $H_N$-DA or $H_{N'}$-DA is optionally functionalized for attachment to the NAMPT Tail ($T_N$) Unit or $I_N$ is comprised of or additionally contains an optionally substituted $C_2$-$C_{12}$ heteroalkylene, an optionally substituted $C_5$-$C_{20}$ heterocyclo or an optionally substituted —$C_6$-$C_{20}$ aryl-($C_1$-$C_4$) alkyl- in which the terminus of $I_N$ distal to its site of its attachment to $H_N$-DA or $H_{N'}$-DA is optionally functionalized for attachment to the NAMPT Tail ($T_N$) Unit. In some non-limiting embodiments, the optional functionalization is provided by —S(=O)$_2$—, —C(=O)—, —O— or —NH— or —C(=O)NH—, optionally substituted.

In preferred combinations of $H_N$/$H_{N'}$, DA and $I_N$ in NAMPTi compounds and quaternized NAMPT Drug Units, $I_N$ or $I_N$-$T_N$ of the NAMPTi compound from release of that quaternized Drug Unit from a Ligand Drug Conjugate compound or Drug Linker compound is capable of interacting with one or more, preferably two or more, amino acid residues of a NAMPT monomer of an enzymatically competent NAMPT homodimer selected from the group consisting of Val 242, Ile 309, Ile 351, and His 191 of NAMPT, wherein the NAMPT monomer has the amino acid sequence of NCBI Reference Sequence NP_005737.1.

In other preferred embodiments, an $I_N$ Unit is or is comprised of —$X^1$—[C(=O)]$_{0,1}$—, —$X^1$—S(=O)$_{1,2}$—, —$X^2$—$C_6$-$C_{24}$ arylene-[C(=O)]$_{0,1}$—, —$X^2$—$C_6$-$C_{24}$ arylene-[S(=O)$_{1,2}$]$_{0,1}$—, —$X^2$—$C_6$-$C_{24}$ arylene-O—, —$X^2$—$C_5$-$C_{24}$ heteroarylene-[C(=O)$_{0,1}$]—, —$X^2$—$C_5$-$C_{24}$ heteroarylene-[S(=O)$_{1,2}$]$_{0,1}$—, —$X^2$—$C_5$-$C_{24}$ heteroarylene-O— or —$X^2$—$C_3$-$C_{20}$ heterocyclo-[C(=O)$_{0,1}$]—, wherein the arylene, heteroarylene and heterocyclo are optionally substituted, wherein $X^1$ is optionally substituted $C_5$-$C_7$ alkylene and $X^2$ is absent or is an optionally substituted $C_1$-$C_4$ alkylene. In more preferred embodiments, $I_N$ is —CH$_2$—(CH$_2$)$_{3-7}$—CH$_2$—, —CH$_2$—(CH$_2$)$_{3-7}$—CH$_2$—O—, —CH$_2$—(CH$_2$)$_{3-7}$—C(=O)—, —CH$_2$—(CH$_2$)$_{3-7}$—S(=O)$_2$— or —CH$_2$—(CH$_2$)$_{3-7}$—S(=O)—. In some of those embodiments a carbon atom of $X_1$ or $X_2$ is the site of optional cyclization of $T_N$ back to $I_N$.

In other more preferred embodiments, $I_N$ has or is comprised of the structure of:

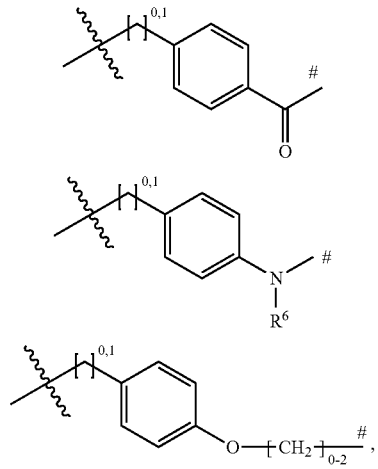

wherein the wavy line indicates the site of covalent attachment to DA or the remainder of $I_N$, which is bonded to DA and the pound sign (#) indicates the site of covalent attachment to $T_N$; and $R^6$ is hydrogen or optionally substituted saturated or unsaturated $C_1$-$C_6$ alkyl, preferably $C_1$-$C_4$ alkyl, —CH$_2$CH=C(CH$_3$)$_2$, or —CH$_2$—C≡CH.

In other more preferred embodiments $I_N$ has or is comprised of the structure of:

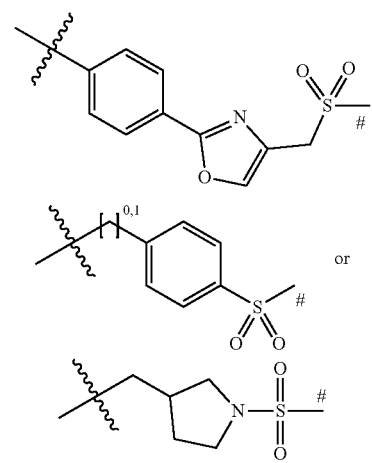

1.4.4 NAMPT Tail Unit

A NAMPT Tail ($T_N$) Unit is a component of a NAMPTi compound or a quaternized NAMPT Drug Unit that is bonded to its Interconnecting ($I_N$) Unit. In some embodiments, a NAMPT Tail ($T_N$) Unit is comprised of an optionally substituted amino-alcohol residue or an optionally substituted carboxylic acid-alcohol residue, the amino nitrogen or carbonyl carbon atom of which is bonded to $I_N$ or the remainder of $T_N$ that is bonded $I_N$.

In other embodiments, $T_N$ is comprised of an optionally substituted benzamide moiety, the amide nitrogen atom of which is bonded to $I_N$ or the remainder of $T_N$ that is bonded to $I_N$, with formal optional cyclization of that atom back to $I_N$ or the remainder of $T_N$ wherein said cyclization is included within the formula of $I_N$-$T_N$. In some embodiments, that optional cyclization is to a carbon atom of $X^1$ or $X^2$ of $I_N$ as defined herein. In either instance, the aromatic ring of the benzamide moiety is optionally substituted with hydroxyl, thiol or an amino residue preferably at position 3 or 4 relative to the site at which the amide carbonyl carbon atom of the benzamide moiety is attached.

In other embodiments, $T_N$ is or is comprised of a optionally substituted $C_5$-$C_{24}$ aryl, $C_5$-$C_{24}$ heteroaryl or a combination thereof independently selected in the form of a biaryl, an aromatic atom of which is bonded to $I_N$ or the remainder of $T_N$ that is bonded to $I_N$, wherein the aromatic ring(s) is(are) optionally substituted independently with one or substituents selected from the group consisting of hydroxyl, thiol and amino residues, optionally substituted, and halogen or $T_N$ is or is comprised of a nitrogen-containing $C_5$-$C_{20}$ heterocyclyl, a skeletal nitrogen atom of which is covalently attached to $I_N$.

In any one of the above preferred groups of embodiments of $T_N$, a remainder of $T_N$ for bonding to $I_N$ is preferably an optionally substituted $C_2$-$C_4$ heteroalkylene or an optionally substituted $C_3$-$C_{20}$ heterocyclo or a combination thereof.

More preferred $T_N$ Units are or are comprised of amino alcohol residues having the structures of:

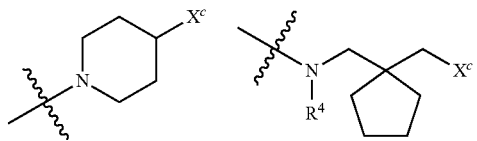

and salts thereof, including but not limited to pharmaceutically acceptable salts, wherein $X^C$ is hydrogen, halogen, —OH or $C_1$-$C_4$ alkoxy; $R^4$ is hydrogen or optionally substituted $C_1$-$C_4$ alkyl, preferably hydrogen or methyl; and the wavy line indicates the site of covalent attachment to the remainder of $T_N$, which is bonded to $I_N$ or to $I_N$.

Other preferred embodiments $T_N$ Units are or are comprised of an optionally substituted benzamide moieties having or comprised of the following structure:

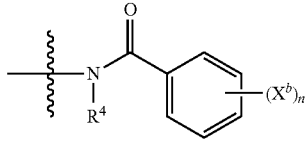

wherein subscript n is 0, 1 or 2; $X^b$ if present is selected from the group consisting of $NH_2$, —OH, $C_1$-$C_4$ alkoxy, $C_1$-$C_4$ alkyl, optionally substituted, and halogen, provided that when subscript n is 2 one of $X^b$ is $NH_2$, —OH, $C_1$-$C_4$ alkoxy or $C_1$-$C_4$ alkyl, optionally substituted, or halogen and the other $C_1$-$C_4$ alkoxy or $C_1$-$C_4$ alkyl, optionally substituted, or halogen and wherein the phenyl optionally substituted by $X^b$ is optionally fused to a 5- or 6-membered heterocyclic or heteroaromatic ring system; $R^4$ is hydrogen or optionally substituted $C_1$-$C_4$ alkyl, preferably hydrogen, methyl or ethyl; and the wavy line indicates the site of covalent attachment to $I_N$ or the remainder of $T_N$ that is bonded to $I_N$, and the amide nitrogen atom of the benzamide moiety is the site of formal optional cyclization of $T_N$ to $I_N$ or the remainder of $T_N$ that is bonded to $I_N$ so that $R^4$ attached to that nitrogen atom is replaced by a bond.

In more preferred embodiments $T_N$ Units are optionally substituted benzamide moieties having the following structures:

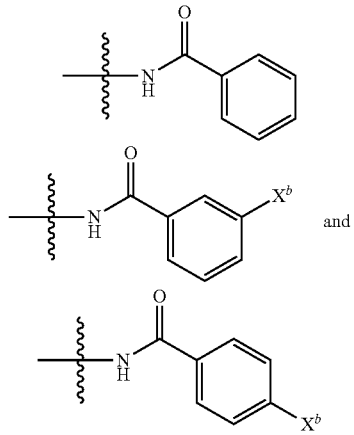

wherein $X^b$ is optionally substituted —$NH_2$, —OH, $C_1$-$C_4$ alkoxy or $C_1$-$C_4$ alkyl, optionally substituted, or halogen, preferably —$NH_2$, —$N(CH_3)_2$, —$N(CH_2CH_3)_2$, —F, —Cl, —OH, —$OCH_3$, —$OCH_2CH_3$ or —$CH_3$, more preferably —F or —$C_1$; and the wavy line indicates the site of covalent attachment to $I_N$ or the remainder of $T_N$ that is bonded to $I_N$, and the amide nitrogen atom of the benzamide moiety is the site of optional cyclization of $T_N$ to $I_N$ so that the hydrogen atom attached to that amide nitrogen is replaced by a bond.

In still other preferred embodiments, $T_N$ Units are or are comprised of an aryl or heteroaryl moiety having the structure of:

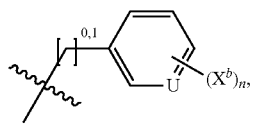

wherein U is =$C(R^{24})$— or =N— subscript n is 0, 1 or 2, with optionally fusion of the aryl to a 5- or 6-membered heterocyclic or heteroaromatic ring system, and salts thereof, including but not limited to pharmaceutically acceptable salts, wherein subscript n is 0, 1 or 2; wherein $R^{24}$ is hydrogen or $X^b$ wherein each $X^b$ is independently selected from the group consisting of $NH_2$, —OH, $C_1$-$C_4$ alkoxy and $C_1$-$C_4$ alkyl, optionally substituted, and halogen, and the wavy line indicates the site of covalent attachment to $I_N$ or the remainder of $T_N$ that is bonded to $I_N$. In some of those embodiments, subscript n is 0 and $R^{24}$ is hydrogen. In other embodiments, subscript n is 0 and $R^{24}$ is halogen or optionally substituted $C_1$-$C_4$ alkyl, such as —$CH_3$ or —$CF_3$. In other embodiments subscript n is 1, $R^{24}$ is hydrogen or halogen, preferably —$C_1$ or —F when halogen, and $X^b$ is independently halogen, optionally substituted $C_1$-$C_4$ alkoxy, such as —$OCH^3$ or —$OCF_3$.

Non-limiting examples of $T_N$ Units comprised of an aryl or heteroaryl moiety have the structure of:

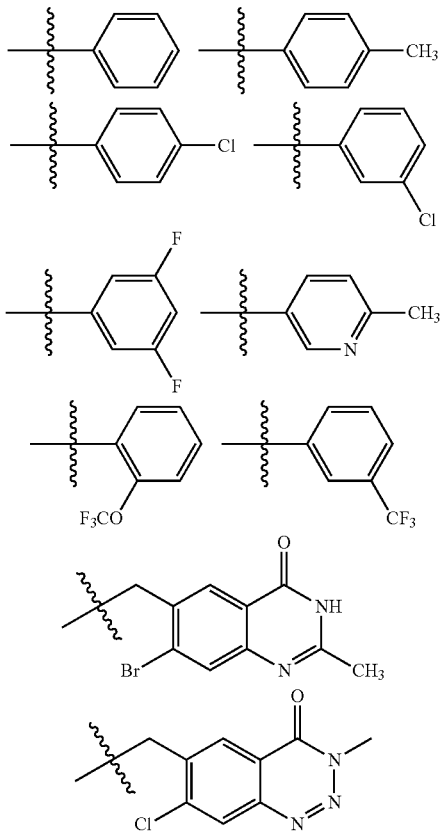

or are or are comprised of a biaryl or heteroaryl moeity, an aromatic skeletal atom of which is bonded to $I_N$ as exemplified by non-limiting examples of:

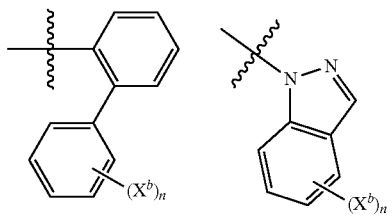

and salts thereof, including but not limited to pharmaceutically acceptable salts, wherein subscript n and $X^b$ are as previously defined for $T_N$ Units having an aryl moeity.

Preferred combinations of $T_N$ and $I_N$ Units (i.e., —$I_N$-$T_N$) have structures of:

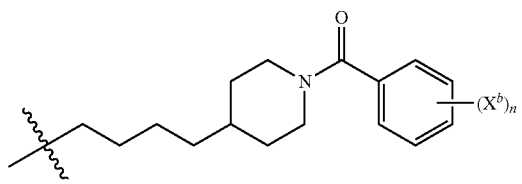

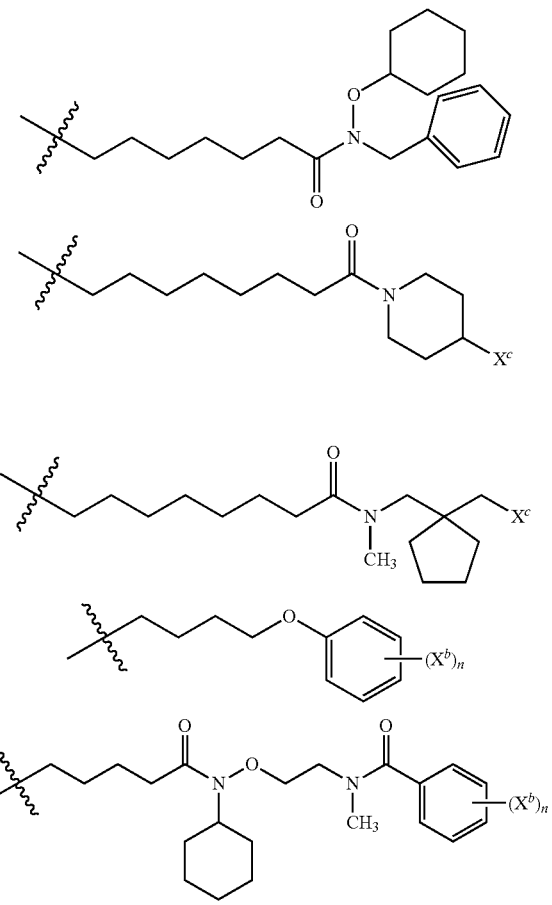

wherein $X^b$ and subscript n is as previously defined for NAMPT Tail Units for NAMPTi compounds or quaternized NAMPT Drug Units and the wavy line indicates the site of covalent attachment to DA. Preferably, when subscript n is 1 or 2, $X^b$ independently are halogen more preferably selected from the group consisting of —F and —Cl Other preferred $I_N$-$T_N$ moieties have structures of:

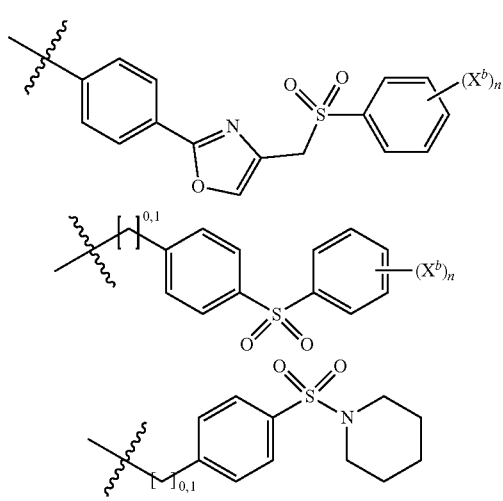

-continued

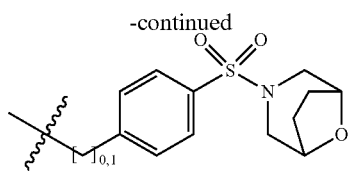

wherein $X^b$, subscript n and the wavy line is as previously defined for NAMPT Tail Units for NAMPTi compounds or quaternized NAMPT Drug Units. In preferred embodiments, subscript n is 1 and $X^b$ is —$CH_3$, —Cl, —F or —$OCF_3$ or subscript n is 2 and $X^b$ are independently selected from the group consisting of Cl and F $T_N$ Units in combination with any one of the above $H_N/H_{N'}$, DA and $I_N$ Units not specifically enumerated are also contemplated. In preferred combinations, $T_N$ of a released quaternized NAMPT Drug Unit from a Ligand Drug Conjugate compound or Drug Linker compound as a NAMPTI compound is capable of interacting with one or more, preferably two or more and more preferably three or more, amino acid residues of a NAMPT monomer of an enzymatically competent NAMPT homodimer selected from the group consisting of Ile 309, Pro 307, Val 350, Ile 378 and Ala 379, wherein the NAMPT monomer has the amino acid sequence of NCBI Reference Sequence NP_005737.1. Other preferred embodiments of $T_N$ are those of a released quaternized NAMPT Drug Unit as a NAMPTI compound from a Ligand Drug Conjugate compound or Drug Linker compound in which $T_N$ or $I_N$-$T_N$ is capable of interacting with one or more, preferably two or more and more preferably three or more, amino acid residues of a NAMPT monomer of an enzymatically competent NAMPT homodimer selected from the group consisting of Tyr 188, Lys 189, Ala 379, Asn 377, Glu 376, Val 350, Arg 349 and Pro 307, wherein the NAMPT monomers have the amino acid sequence of NCBI Reference Sequence NP_005737.1.

Other $T_N$ Units in a NAMPTi compound or derivative thereof or in a NAMPT Drug Unit of that compound or derivative in a Ligand Drug Conjugate compound or Drug Linker compound not specifically enumerated above preferably have a distance from the heteroatom that serves as the conjugation site of that compound or derivative, or from the site of conjugation of its corresponding quaternized NAMPT Drug Unit, to the atom of $T_N$ that is attached to $I_N$ when the NAMPTi compound or derivative thereof is in its MM2 minimized conformation in a range from about 5.5 to about 7.0 angstroms or more preferably at about 5.9 angstroms.

1.5 Treatment of Hyper-Proliferating Conditions

In some embodiments, the Ligand-Drug Conjugates described herein are useful for treating hyper-proliferation conditions, including treating of a cancer in a subject or patient by inhibiting the multiplication of a tumor cell or cancer cell, causing apoptosis in a tumor or cancer cell, including treating cancer in the subject or patient. Thus, the Ligand-Drug Conjugates are used accordingly in a variety of settings for the treatment of cancers. For that purpose, the Ligand-Drug Conjugates are used to deliver a NAMPTi compound to a tumor cell or cancer cell or to the vicinity of such cells, including the delivery to nearby normal cells that are peculiar to the environment of the abnormal cells. Without being bound by theory, in one embodiment, the Ligand Unit of a Ligand-Drug Conjugate compound binds to or associates with a cell-surface antigen epitope of a cancer-cell or other tumor-associated cell antigen or receptor, and upon that binding or association of the Ligand-Drug Conjugate is capable of being taken up (internalized) into the targeted cells through antigen- or receptor-mediated endocytosis or other internalization mechanism. In some preferred embodiments, the antigen is attached to a tumor cell or cancer cell or is an extracellular matrix protein associated with the tumor cell or cancer cell. In other preferred embodiment, the antigen is that of nearby normal cells that are peculiar to the environment of the abnormal cells. Once inside the targeted cell, via an enzymatic or non-enzymatic cleavable mechanism, depending upon the components of the Linker Unit, the quaternized NAMPT Drug Unit is released within the cell as a NAMPTi compound. In an alternative embodiment, the quaternized NAMPT Drug Unit is cleaved from the Ligand-Drug Conjugate within the vicinity of the tumor cell or cancer cell, and the NAMPTi compound from release of $D^+$ subsequently penetrates the cell.

The Ligand-Drug Conjugates therefore provide conjugation-specific tumor or cancer targeting of a NAMPTi compound, thus reducing general toxicity of that drug.

In some embodiments, the Linker Units stabilize the Ligand-Drug Conjugates in blood, yet are capable of liberating NAMPTi compound once inside the cell.

In one embodiment, the Ligand Unit binds to a tumor cell or cancer cell.

In another embodiment, the Ligand Unit is an antibody Ligand Unit binds to an epitope of a tumor cell or cancer cell antigen that is on the surface of the tumor cell or cancer cell.

In another embodiment, the Ligand Unit is an antibody Ligand Unit that binds to an epitope associated with a tumor cell or cancer cell antigen that is of an extracellular matrix protein associated with the tumor cell or cancer cell.

The specificity of the Ligand Unit for a particular tumor cell or cancer cell is an important consideration for determining those tumors or cancers that are most effectively treated and having a desired therapeutic index. For example, a Ligand Drug conjugate having a BR96 antibody Ligand unit is sometimes useful for treating antigen positive carcinomas including those of the lung, breast, colon, ovaries, and pancreas. As another non-limiting example, a Ligand-Drug Conjugates having an anti-CD30 or an anti-CD70 binding antibody Ligand unit is sometimes useful for treating hematologic malignancies.

Preferred types of cancers that are treatable with a Ligand Drug Conjugates are solid tumors and blood-borne cancers, such as acute and chronic leukemias, and lymphomas.

Solid tumors for treatment by a Ligand Drug Conjugate, are exemplified, but not limited to, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Blood-borne cancers for treatment by a Ligand Drug Conjugate, are exemplified, but not limited to, acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", hairy cell leukemia, and multiple myeloma.

Acute and chronic are inclusive of lymphoblastic, myelogenous, lymphocytic, and myelocytic leukemias.

Lymphomas are inclusive of Hodgkin's disease, non-Hodgkin's Lymphoma, Multiple myeloma, Waldenström's macroglobulinemia, Heavy chain disease, and Polycythemia vera.

Cancers are inclusive of those from a tumor, metastasis, or other diseases or disorders characterized by hyper-proliferating cells, which are treatable or its progression inhibited by administration of an Antibody Drug Conjugate composition.

In other embodiments, methods for treating cancer are provided, by preferably administering to a subject or patient in need thereof an effective amount of a Ligand Drug Conjugate composition and a chemotherapeutic agent. In one embodiment the cancer to be treated with a chemotherapeutic agent in combination with a Ligand Drug Conjugate has not been found to be refractory to the chemotherapeutic agent. In another embodiment, the cancer to be treated with a chemotherapeutic in combination with a Ligand Drug Conjugate is refractory to the chemotherapeutic agent. The Ligand Drug Conjugate compositions can be administered to a subject or patient that has also undergone surgery as treatment for the cancer.

In some embodiments, the subject or patient also receives an additional treatment, such as radiation therapy. In a specific embodiment, the Ligand-Drug Conjugate is administered concurrently with another chemotherapeutic agent, which may or may not be another Ligand Drug Conjugate having a different targeting Ligand Unit, or with radiation therapy. In another specific embodiment, a non-targeted chemotherapeutic agent or radiation therapy is administered prior or subsequent to administration of a Ligand Drug Conjugate.

In some embodiments, a chemotherapeutic agent used in combination with a Ligand Drug Conjugate is administered over a series of sessions. Any one or a combination of the chemotherapeutic agents, such a standard of care chemotherapeutic agent(s), can be administered.

Additionally, methods of treatment of cancer with a Ligand Drug Conjugate are provided as an alternative to chemotherapy or radiation therapy where the chemotherapy or the radiation therapy has proven or can prove to be too toxic, e.g., results in unacceptable or unbearable side effects, for the subject or patient being treated. The subject or patient being treated can, optionally, be treated with another cancer treatment such as surgery, radiation therapy or chemotherapy, depending on which treatment is found to be acceptable or bearable.

1.6 Pharmaceutical Compositions Comprising an LDC

The present invention provides pharmaceutical compositions comprising a Ligand Drug Conjugate composition described herein and a pharmaceutically acceptable carrier. The pharmaceutical compositions are in any form that allows for a Ligand Drug Conjugate to be administered to a subject or patient in need thereof for treatment of a disorder associated with expression of the antigen to which the Ligand Unit binds. For example, and without limitation, the pharmaceutical composition is in the form of a liquid or a lyophilized solid. The preferred route of administration of Antibody Drug Conjugates is parenteral. Parenteral administration of a Ligand Drug Conjugate is inclusive of subcutaneous injections, intravenous, intramuscular, and intrasternal injection or infusion techniques. In other preferred embodiments, a pharmaceutical composition comprising a Ligand Drug Conjugate is administered intravenously in the form of a pharmaceutically acceptable liquid solution.

Pharmaceutical compositions are formulated so as to allow a compound to be bioavailable upon administration of the composition to a patient. Such compositions may take the form of one or more dosage units, where for example, a lyophilized solid may provide a single dosage unit when reconstituted as a solution or suspension on addition of a suitable liquid carrier.

Materials used in preparing the pharmaceutical compositions are preferably non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the pharmaceutical composition, the manner of administration, and the Ligand Drug Conjugate composition employed.

In some embodiments, the pharmaceutical composition is in the form of a liquid. In preferred embodiments, the liquid is useful for delivery by injection. In a composition for administration by injection, one or more of a surfactant, preservative, wetting agent, dispersing agent, suspending agent, buffer, stabilizer and isotonic agent is preferably included.

The liquid compositions, whether they are solutions, suspensions or other like form, preferably comprise one or more of the following excipients: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as amino acids, acetates, citrates or phosphates; detergents, such as nonionic surfactants, polyols; and agents for the adjustment of tonicity such as sodium chloride or dextrose. In some embodiments of a parenteral composition, that composition is enclosed in ampoule, a disposable syringe or a multiple-dose vial made of glass, plastic or other material. Physiological saline is an exemplary adjuvant. An injectable pharmaceutical composition is preferably sterile and is comprised of one or more of the above excipient in pharmaceutically acceptable form.

The amount of the Ligand Drug Conjugate that is effective in the treatment of a particular disorder or condition will depend on the nature of the disorder or condition, which is preferably determined by a standard clinical technique. In addition, in vitro or in vivo assays are optionally employed to help identify optimal dosage ranges. The precise dose to be employed in the compositions will also depend on the route of administration, and the seriousness of the disease or disorder, and should be decided according to the judgment of the practitioner and each subject's or patient's circumstances.

The pharmaceutical composition comprises an effective amount of an LDC composition such that a suitable dosage will be obtained for administration to a subject in need thereof for treating the intended Hyperproliferation disease or condition. Typically, this amount is at least about 0.01% by weight of the pharmaceutical composition.

For intravenous administration, the pharmaceutical composition preferably comprises from about 0.01 to about 100 mg of a Ligand Drug Conjugate composition per kg of the animal's body weight. In one such embodiment, the pharmaceutical composition includes from about 1 to about 100 mg of a Ligand Drug Conjugate composition per kg of the subject's or patient's body weight. In preferred embodiments, the amount administered is in the range from about 0.1 to about 25 mg/kg of body weight of a Ligand Drug Conjugate composition.

Generally, the dosage of a Ligand Drug Conjugate composition administered to a patient range from about 0.01 mg/kg to about 100 mg/kg of the subject's or patient's body weight. In some embodiments, the dosage administered to a subject or patient is between about 0.01 mg/kg to about 15 mg/kg of the subject's or patient's body weight. In some embodiments, the dosage administered to a subject or patient ranges from between about 0.1 mg/kg and about 15 mg/kg of the subject's or patient's body weight. In some embodiments, the dosage administered to a subject or patient ranges from between about 0.1 mg/kg to about 20 mg/kg of the subject's or patient's body weight. In some embodiments, the dosage administered ranges from between about 0.1 mg/kg to about 5 mg/kg or about 0.1 mg/kg to about 10 mg/kg of the subject's or patient's body weight. In some embodiments, the dosage administered ranges from between about 1 mg/kg to about 15 mg/kg of the subject's or patient's body weight. In some embodiments, the dosage administered ranges from between about 1 mg/kg to about 10 mg/kg of the subject's or patient's body weight. In some embodiments, the dosage administered ranges from between about 0.1 to 4 mg/kg, preferably 0.1 to 3.2 mg/kg, or more preferably 0.1 to 2.7 mg/kg of the subject's or patient's body weight over a treatment cycle.

A Ligand Drug Conjugate is administered by any convenient route, for example by infusion or bolus injection, by absorption through epithelial or mucocutaneous linings (e.g., oral mucosa, rectal and intestinal mucosa). Administration is systemic or local. Various delivery systems are known, e.g., encapsulation in liposomes, microparticles, microcapsules, capsules, and may be used to administer a compound to a subject or patient in need thereof. In certain embodiments, more than one Ligand Drug Conjugate compound or composition is administered to a subject or patient.

In one embodiment, a Ligand Drug Conjugate is formulated in accordance with routine procedures as a pharmaceutical composition adapted for intravenous administration to subject, particularly to patients, which are human beings. Typically, the carriers or vehicles for intravenous administration are sterile isotonic aqueous buffer solutions. Where necessary, the compositions also include a solubilizing agent. Compositions for intravenous administration optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent.

When a Ligand Drug Conjugate is administered by infusion, it will be dispensed, for example, with an infusion bottle containing sterile pharmaceutical grade water or saline. Where the Ligand Drug Conjugate is administered by injection, an ampoule of sterile water for injection or saline may be provided so that the ingredients can be mixed prior to administration.

The pharmaceutical compositions are generally formulated as sterile, substantially isotonic and in full compliance with all Good Manufacturing Practice (GMP) regulations of the U.S. Food and Drug Administration.

1.7 Numbered Embodiments

The following numbered embodiments describe further aspects of the invention and are not intended to limit it in any way.

1. A Ligand Drug Conjugate composition represented by Formula 1:

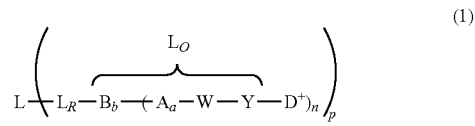

in salt form, particularly in pharmaceutically acceptable salt form, wherein L is a Ligand Unit; W is a Peptide Cleavable Unit, or W—Y is replaced by a Glucuronide Unit of formula —Y(W'), wherein W' represents a carbohydrate moiety with glycosidic bonding to Y through an optionally substituted heteroatom; and Y is a self-immolative Spacer Unit comprised of a PAB or PAB-type moeity; $D^+$ is a quaternized NAMPT Drug Unit ($D^+$) covalently attached to the remainder of the Formula 1 composition structure through a quaternized skeletal aromatic nitrogen atom of an optionally substituted $C_5$-$C_{24}$ heteroaryl, or a quaternized skeletal non-aromatic nitrogen atom of a partially unsaturated or partially aromatic optionally substituted $C_9$-$C_{24}$ heterocyclyl, wherein non-enzymatic or enzymatic action on W/W' of a drug linker moiety of a Ligand Drug Conjugate compound of the composition is capable of initiating release of the quaternized NAMPT Drug ($D^+$) Unit as a NAMPTi compound comprised of an optionally substituted $C_5$-$C_{24}$ or $C_9$-$C_{24}$ heteroaryl having the previously quaternized skeletal nitrogen atom;

wherein the Ligand Drug Conjugate compound is represented by Formula 1 in which subscript p is replaced by p'; $L_R$ is a primary linker that interconnects the Ligand Unit and Drug Unit through $L_O$, wherein $L_O$ is an optional secondary linker that is present; subscripts a and b independently are 0 or 1, indicating the absence or presence, respectively, of A or B; subscript n is 1, 2, 3 or 4; A is a first optional Stretcher; B is a Branching Unit, when subscript b is 1 and subscript n is 2, 3 or 4, or B is absent, so that subscript b is 0, when subscript n is 1, wherein each of A and B is an independently selected single unit or is optionally comprised or consists of two, three or four independently selected subunits; and subscript p is a number ranging from 1 to 24 and subscript p' is an integer ranging from 1 to 24.

2. The Ligand Drug Conjugate composition of embodiment 1 wherein the quaternized NAMPT Drug Unit is represented by the general structure of:

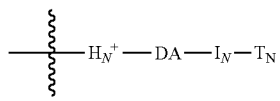

in salt form, particularly in pharmaceutically acceptable salt form, wherein $H_{N^+}$ is a quaternized NAMPT Head Unit as the quaternized component of $D^+$ wherein the optionally substituted $C_5$-$C_{24}$ heteroaryl or partially unsaturated or partially aromatic optionally substituted $C_9$-$C_{24}$ heterocyclyl of that component is comprised of a 5- or 6-membered nitrogen-containing partially unsaturated or heteroaromatic ring system, a skeletal nitrogen atom of which is the site of quaternization to $L_O$, as indicated by the wavy line to $H_{N^+}$;

DA is a Donor-Acceptor Unit wherein the Donor-Acceptor Unit is or is comprised of a hydrogen bond donor or acceptor functional group and is bonded to a carbon skeletal atom at position 2 or 3 of the 5-membered nitrogen-containing partially unsaturated or heteroaromatic ring system or at position 3 or 4 of the 6-membered nitrogen-containing partially unsaturated or heteroaromatic ring system, with optional formal cyclization of DA back to an adjacent skeletal carbon atom of the 6-membered nitrogen-containing ring system through an introduced optionally substituted non-aromatic carbon atom or an optionally substituted nitrogen, oxygen or sulfur atom resulting in a partially unsaturated, partially aromatic or fully aromatic 6,5- or 6,6-fused ring system, wherein said bonding of DA is in relation to a skeletal nitrogen atom of the 5- or 6-membered nitrogen-containing partially unsaturated or heteroaromatic ring system and wherein said formal cyclization to the adjacent carbon atom of the 6-membered nitrogen-containing partially unsaturated or heteroaromatic ring system substantially retains the hydrogen bonding ability of the donor or acceptor functional group of DA in absence of said cyclization;

$I_N$ is an Interconnecting Unit, wherein the Interconnecting Unit is or is comprised of $-X^1-[C(=O)]_{0,1}-$, $-X^1-S(=O)_{1,2}-$, $-X^2-C_6-C_{24}$ arylene-$[C(=O)]_{0,1}-$, $-X^2-C_6-C_{24}$ arylene-$[S(=O)_{1,2}]_{0,1}$, $-X^2-C_6-C_{24}$ arylene-$O-$, $-X^2-C_5-C_{24}$ heteroarylene-$[C(=O)_{0,1}]-$, $-X^2-C_5-C_{24}$ heteroarylene-$[S(=O)_{1,2}]_{0,1}$, $-X^2-C_5-C_{24}$ heteroarylene-$O-$ or $-X^2-C_3-C_{20}$ heterocyclo-$[C(=O)_{0,1}]-$, wherein the arylene, heteroarylene and heterocyclo are optionally substituted; $X^1$ is optionally substituted $C_5$-$C_7$ alkylene; $X^2$ is absent or is an optionally substituted $C_1$-$C_4$ alkylene;

$T_N$ is a NAMPT Tail Unit, wherein the NAMPT Tail Unit is or is comprised of an optionally substituted amino-alcohol residue or a carboxylic acid-alcohol residue, the amino nitrogen or carbonyl carbon of which is bonded to $I_N$, or $T_N$ is or is comprised of an optionally substituted benzamide moiety or a bioisostere thereof, the amide nitrogen atom of which is bonded to $I_N$ with optional cyclization of that atom back to $I_N$ or to the remainder of $T_N$, or $T_N$ is or is comprised of an optionally substituted $C_6$-$C_{24}$ aryl, $C_5$-$C_{24}$ heteroaryl or a combination thereof independently selected in the form of a biaryl, an aromatic atom of which is bonded to $I_N$ or the remainder of $T_N$; and wherein $T_N$ or the remainder thereof is bond to $I_N$, wherein said remainder is an optionally substituted $C_2$-$C_7$ heteroalkylene or an optionally substituted $C_5$-$C_6$ heterocyclo, and wherein enzymatic action on W/W' of a drug linker moiety of a Ligand Drug Conjugate compound of the composition is capable of initiating release of the quaternized NAMPT Drug ($D^+$) Unit as a NAMPTi compound of formula $H_N$-DA-$I_N$-$T_N$, wherein $H_N$ is a NAMPT Head Unit that is a fully aromatic $C_5$-$C_{24}$ or $C_9$-$C_{24}$ heteroaryl, optionally substituted, comprised of a 5- or 6-membered nitrogen-containing heteroaromatic ring system having the previously quaternized skeletal nitrogen atom, and the other variable groups are as previously defined, wherein $H_N-$ or $H_N$-DA- of the NAMPTi compound is capable of interacting with enzymatically competent NAMPT homodimer at its nicotinamide binding site.

3. The Ligand Drug Conjugate composition of embodiment 2 wherein the NAMPT Head ($H_N$) Unit is a pyridine mimetic and $H_{N^+}$ is that Unit in which a skeletal aromatic nitrogen atom of the pyridine mimetic is quaternized.

4. The Ligand Drug Conjugate composition of embodiment 2 or 3 wherein the Donor Acceptor (DA) Unit is comprised of an optionally substituted amide functional group or bioisostere thereof.

5. The Ligand Drug Conjugate composition of embodiment 2 wherein $H_N$-DA is a nicotinamide mimetic and $H_{N^+}$-DA is that mimetic in which a skeletal nitrogen atom of the 5- or 6-membered nitrogen-containing partially unsaturated or heteroaromatic ring system of $H_{N^+}$ is quaternized.

6. The Ligand Drug Conjugate composition of embodiment 2 wherein the 6-membered nitrogen-containing heteroaromatic ring system of the NAMPT Head ($H_N$) Unit is that of pyridine with optional cyclization of DA back to the pyridine aromatic ring system through an introduced aromatic oxygen, sulfur or an optionally substituted nitrogen atom so that $H_N$ contains a 6-5 fused aromatic ring system and $H_{N^+}$ is that Unit in which the pyridine aromatic ring system is quaternized at its skeletal nitrogen atom.

7. The Ligand Drug Conjugate composition of any one of embodiments 2 to 6 wherein $H_N$ from release of the quaternized NAMPT Drug ($D^+$) Unit is capable of interacting with Phe 193 on one monomer of an enzymatically competent NAMPT homodimer and/or Tyr 18' of the other monomer, wherein the NAMPT monomers have the amino acid sequence of NCBI Reference Sequence NP_005737.1.

8. The Ligand Drug Conjugate composition of embodiment 7 wherein said NAMPT Head Unit interaction(s) is through π-π stacking with the aromatic side chain(s) of Phe 193 and/or Tyr 18'.

9. The Ligand Drug Conjugate composition of embodiment 2 wherein the NAMPT Head ($H_N$) Unit has the structure of:

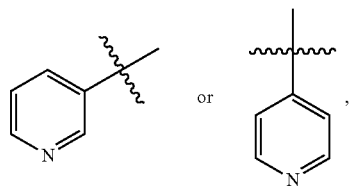 [SMILES: *c1cccnc1 ; *c1ccncc1]

or a salt thereof, in particular a pharmaceutically acceptable salt, and H_{N^+} has the structure of

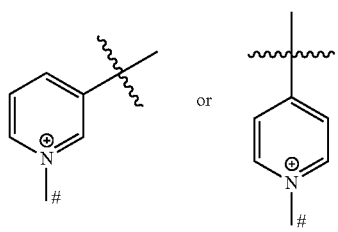

in salt form, in particular in pharmaceutically acceptable salt form, wherein the pound sign (#) indicates the point of covalent attachment to L_O; the wavy line indicates the site of covalent attachment to DA and an adjacent aromatic carbon atom thereto is the site of said optional formal cyclization by DA to H_N/H_{N^+}.

10. The Ligand Drug Conjugate composition of any one of embodiments 2 to 9 wherein the Donor Acceptor (DA) Unit is an acrylamide DA Unit, optionally cyclized to an adjacent skeletal carbon atom of the nitrogen-containing aromatic ring system of H_N/H_{N^+} to which it is attached, or is an amide bioisostere.

11. The Ligand Drug Conjugate composition of any one of embodiments 2 to 10 wherein the Donor Acceptor (DA) Unit of the released NAMPT Drug Unit is capable of interacting with one or more amino acid residues of an NAMPT monomer of an enzymatically competent NAMPT homodimer selected from the group consisting of Asp 219, Ser 241, Val 242 and Ser 275, wherein the NAMPT monomer has the amino acid sequence of NCBI Reference Sequence NP_005737.1.

12. The Ligand Drug Conjugate composition of embodiment 11 wherein said DA interaction(s) is hydrogen bonding either directly or indirectly through hydrogen bonding network(s) involving the intermediacy of water molecule(s).

13. The Ligand Drug Conjugate composition of any one of embodiments 2 to 11 wherein the Donor-Acceptor (DA) Unit is an acrylamide DA Unit or an amide bioisostere having the structures of:

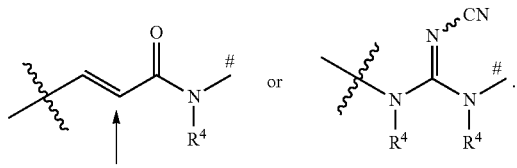

respectively, or salts thereof, in particular pharmaceutical acceptable salts, wherein each $R^4$ is independently selected from the group consisting of hydrogen and optionally substituted $C_1$-$C_4$ alkyl; DA is optionally cyclized to H_N/H_{N^+}, wherein said cyclization is to the sp² carbon atom of the acrylamide DA Unit proximal to the carbonyl carbon (as indicated) through an introduced optionally substituted non-aromatic carbon atom or an optionally substituted aromatic heteroatom; the wavy line indicates the site of covalent attachment to H_N/H_{N^+}, and the indicated carbon atom adjacent thereto is the site of said optional cyclization by the acrylamide DA; and the pound sign (#) indicates the site of covalent attachment to I_N.

14. The Ligand Drug Conjugate composition of embodiment 2 wherein H_N-DA- is a nicotinamide mimetic having the structure of:

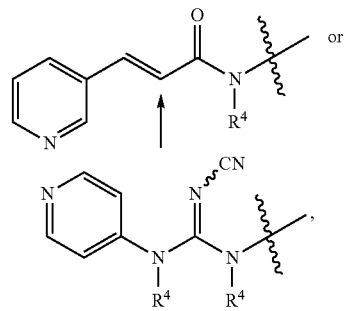

or a salt thereof, in particular, a pharmaceutically acceptable salt, and H_{N^+}-DA has the structure of:

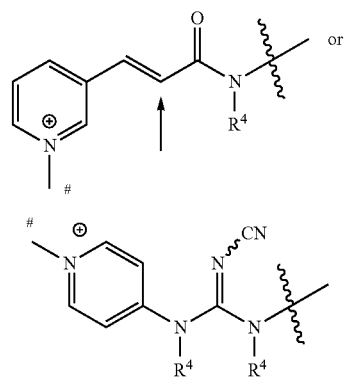

in salt form, in particular, in pharmaceutically acceptable salt form, wherein $R^4$ is independently selected from the group consisting of hydrogen and optionally substituted $C_1$-$C_4$ alkyl; the pound sign (#) indicates the point of covalent attachment to L_O; and the wavy line indicates the site of covalent attachment to I_N, and wherein the sp² carbon atom proximal to the carbonyl carbon is the site (as indicated) of optional cyclization to H_N/H_{N^+} through an introduced optionally substituted non-aromatic carbon atom or an optionally substituted aromatic heteroatom.

15. The Ligand Drug Conjugate composition of any one of embodiments 2 to 14, wherein the NAMPT Tail (T_N) Unit or —I_N-T_N- of the quaternized NAMPT Drug Unit on release as a NAMPTi compound is capable of interacting with one or more amino acid residues of a NAMPT monomer of an enzymatically competent NAMPT homodimer selected from the group consisting of Ile 309, Pro 307, Val 350, Ile 378 and Ala 379, wherein the NAMPT monomer has the amino acid sequence of NCBI Reference Sequence NP_005737.1.

16. The Ligand Drug Conjugate composition of any one of embodiment 2 to 14, wherein T_N or —I_N-T_N- of the quaternized NAMPT Drug Unit on release as a NAMPTi compound is capable of interacting with one or more amino acid residues of a NAMPT monomer of an enzymatically competent NAMPT homodimer selected from the group consisting of Tyr 188, Lys 189, Ala 379, Asn 377, Glu 376, Val 350, Arg 349 and Pro 307, wherein the NAMPT monomer has the amino acid sequence of NCBI Reference Sequence NP_005737.1.

17. The Ligand Drug Conjugate composition of any one of embodiments 2 to 14 wherein the NAMPT Tail ($T_N$) Unit is an amino alcohol moiety having the structure of:

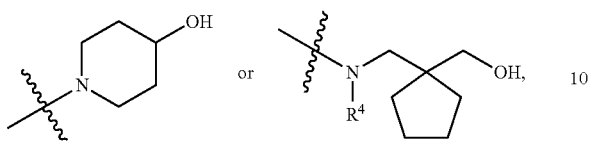

wherein $R^4$ is hydrogen or optionally substituted $C_1$-$C_4$ alkyl; and the wavy line indicates the site of covalent attachment to $I_N$.

18. The Ligand Drug Conjugate composition of any one of embodiments 2 to 14 wherein the Tail ($T_N$) Unit is or is comprised of an optionally substituted benzamide moeity covalently attached to $I_N$ or the remainder of $T_N$, through it amide nitrogen atom.

19. The Ligand Drug Conjugate composition of embodiment 18 wherein the benzamide moiety has the structure of:

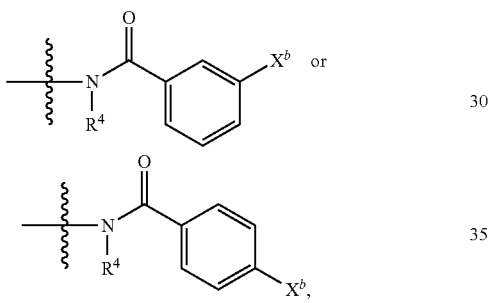

wherein $X^b$ is —H, halogen, —OH, optionally substituted $C_1$-$C_4$ alkoxy, optionally substituted $C_1$-$C_4$ alkyl or —NH$_2$, optionally substituted; $R^4$ is hydrogen or optionally substituted $C_1$-$C_4$ alkyl; and the wavy line indicates the site of covalent attachment to $I_N$; and wherein the benzamide moeity is optionally cyclized to $I_N$ wherein the amide nitrogen of the benzamide moiety is the site of said cyclization so that $R^4$ is replaced by a covalent bond.

20. The Ligand Drug Conjugate composition of embodiment 19 wherein the benzamide moiety has the structure of:

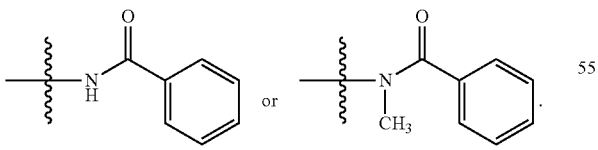

21. The Ligand Drug Conjugate composition of any one of embodiments 2 to 14 wherein the NAMPT Tail ($T_N$) Unit is or is comprised of an optionally substituted (hetero)aryl or biaryl moiety.

22. The Ligand Drug Conjugate composition of embodiment 21 wherein the NAMPT Tail ($T_N$) Unit is an aryl, heteroaryl or biaryl moiety having a having the structure of:

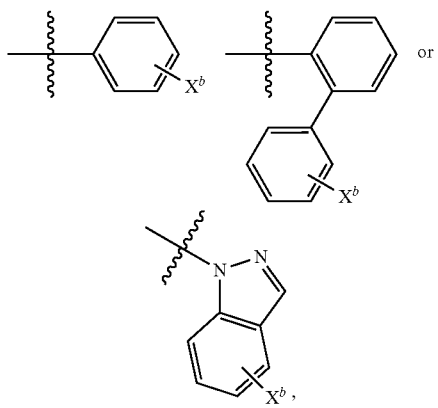

respectively, wherein $X^b$ is —H, halogen, —OH, optionally substituted $C_1$-$C_4$ alkoxy, optionally substituted $C_1$-$C_4$ alkyl or —NH$_2$, optionally substituted; and the wavy line indicates the site of covalent attachment to $I_N$.

23. The Ligand Drug Conjugate composition of any one of embodiments 2 to 22 wherein $I_N$ of the quaternized NAMPT Drug Unit (D$^+$) on release as a NAMPTi compound is capable of interacting with one or more amino acids of a NAMPT monomer of an enzymatically competent NAMPT homodimer selected from the group consisting of Val 242, Ile 309, Ile 351, and His 191 of NAMPT, wherein the NAMPT monomer has the amino acid sequence of NCBI Reference Sequence NP_005737.1

24. The Ligand Drug Conjugate composition of any one of embodiments 2 to 22 wherein $I_N$ is —CH$_2$—(CH$_2$)$_{3-7}$—CH$_2$—, —CH$_2$—(CH$_2$)$_{3-7}$—CH$_2$—O—, —CH$_2$—(CH$_2$)$_{3-7}$—C(=O)—, —CH$_2$—(CH$_2$)$_{3-7}$—S(=O)$_2$— or —CH$_2$—(CH$_2$)$_{3-7}$—S(=O)—.

25. The Ligand Drug Conjugate composition of any one of embodiments 2 to 22 wherein $I_N$ has the structure of:

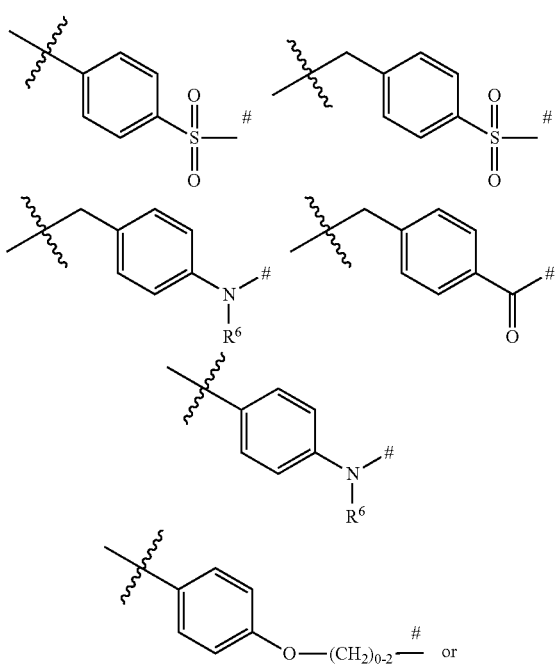

-continued

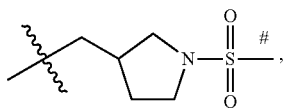

wherein the wavy line indicates the site of covalent attachment to DA and the pound sign (#) indicates the site of covalent attachment to $T_N$; and $R^6$ is hydrogen, $C_1$-$C_4$ alkyl, —$CH_2CH$=$C(CH_3)_2$, or —$CH_2$—$C$≡$CH$.

26. The Ligand Drug Conjugate composition of any one of embodiments 2 to 14, wherein —$I_N$-$T_N$ has the structure of:

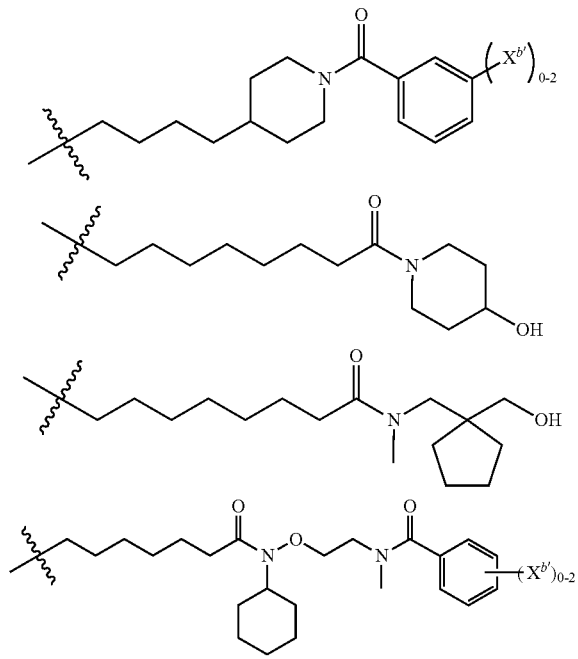

wherein $X^{b'}$ when present is independently selected from the group consisting of halogen, —OH, optionally substituted $C_1$-$C_4$ alkoxy, optionally substituted $C_1$-$C_4$ alkyl and —$NH_2$, optionally substituted; and the wavy line indicates the site of covalent attachment to DA.

27. The Ligand Drug Conjugate composition of any one of embodiments 2 to 14, wherein —$I_N$-$T_N$ has the structure of:

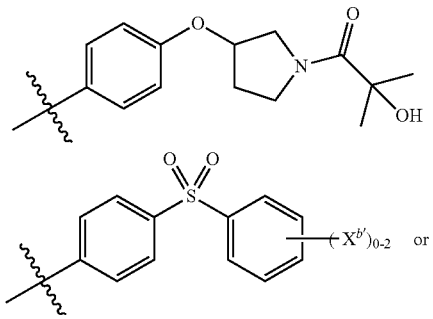

-continued

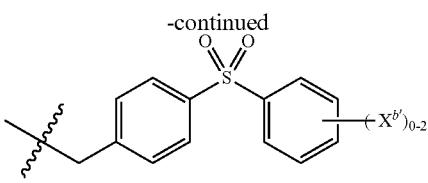

wherein $X^{b'}$ if present is selected from the group consisting of, —OH and $NH_2$, optionally substituted, and halogen, provided that when subscript n is 2 one of $X^b$ is —OH or —$NH_2$, optionally substituted, or halogen and the other is halogen; and the wavy line indicates the site of covalent attachment to DA.

28. The Ligand Drug Conjugate composition of embodiment 1 wherein the quaternized NAMPT Drug ($D^+$) Unit has the structure of:

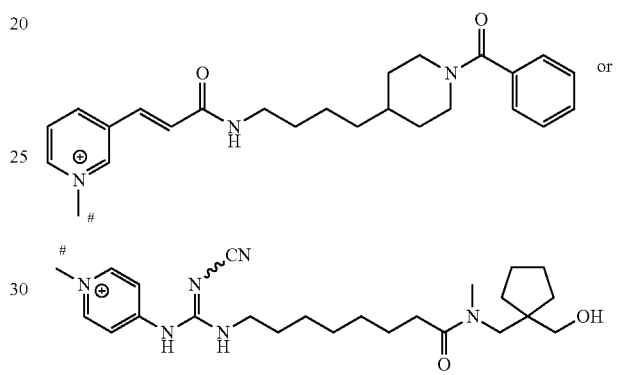

in salt form, in particular in pharmaceutically acceptable salt form, wherein the pound sign (#) indicates the site of quaternization by $L_O$.

29. The Ligand Drug Conjugate composition of any one of embodiments 1 to 28 wherein L-($L_R$- has the structure of:

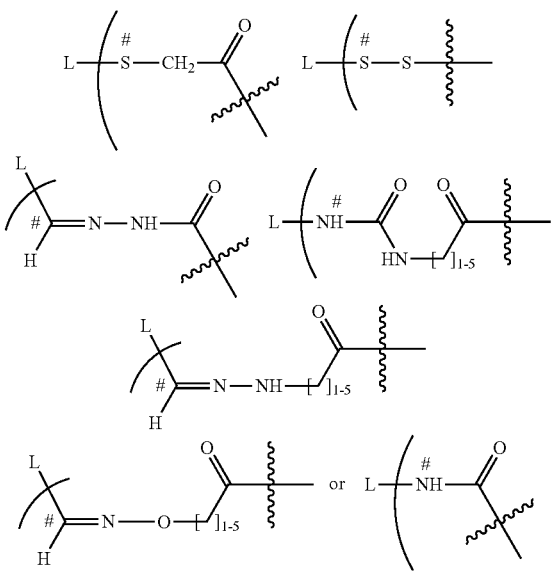

or a salt thereof, in particular a pharmaceutically acceptable salt, wherein L is a Ligand Unit and the indicated (#) atom is from the Ligand Unit; and wherein the wavy line indicates the site of covalent attachment to the remainder of the Conjugate structure.

30. The Ligand Drug Conjugate composition of any one of embodiments 1 to 28 wherein L-($L_R$- has the structure of:

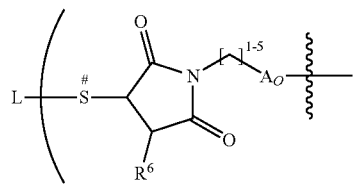

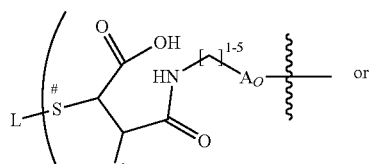

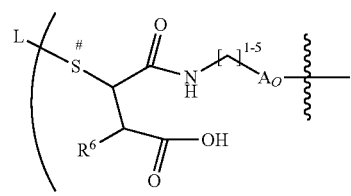

or a salt thereof, in particular a pharmaceutically acceptable salt, wherein L is a Ligand Unit and the indicated (#) sulfur atom is from the Ligand Unit; $R^6$ is hydrogen or an optionally substituted $C_1$-$C_6$ alkyl; $A_O$ is a second optional Stretcher Unit; and the wavy line indicates the site of covalent attachment to the remainder of the Conjugate structure.

31. The Ligand Drug Conjugate composition of any one of embodiments 1 to 28 wherein L-($L_R$- has the structure of:

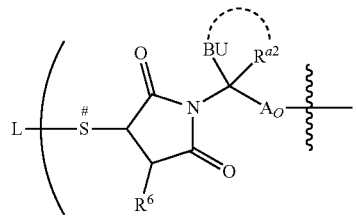

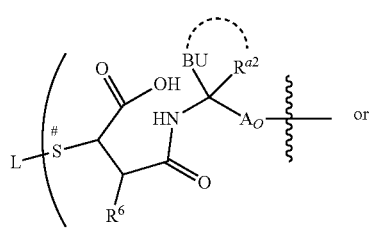

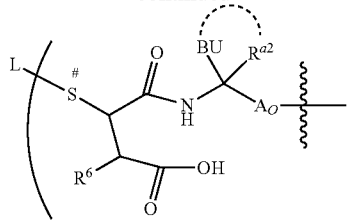

or a salt thereof, in particular a pharmaceutically acceptable salt, wherein L is a Ligand Unit and the indicated (#) sulfur atom is from the Ligand Unit; and $R^6$ is hydrogen or an optionally substituted $C_1$-$C_6$ alkyl; $A_O$ is a second optional Stretcher Unit; BU is a Basic Unit; $R^{a2}$ is optionally substituted $C_1$-$C_{12}$ alkyl; the dotted curved line indicates optional cyclization so that in the absence of said cyclization BU is an acyclic Basic Unit or in the presence of said cyclization BU is a cyclized Basic Unit in which $R^{a2}$ and BU together with the carbon atom to which both are attached, define an optionally substituted spiro $C_3$-$C_{20}$ heterocyclo containing a skeletal basic nitrogen atom of a secondary or tertiary amine functional group of BU, wherein the basic nitrogen atom of the acyclic Basic Unit or cyclic Basic Unit is optionally suitably protected by a nitrogen protecting group, dependent on the degree of substitution of the basic nitrogen atom, or is optionally protonated; and the wavy line indicates the site of covalent attachment to the remainder of the Conjugate structure.

32. The Ligand Drug Conjugate composition of embodiment 30 wherein L-($L_R$- has the structure of:

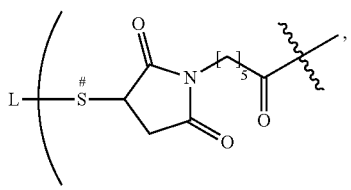

or salt thereof, in particular a pharmaceutically acceptable salt.

33. The Ligand Drug Conjugate composition of embodiment 31 wherein L-($L_R$- has the structure of:

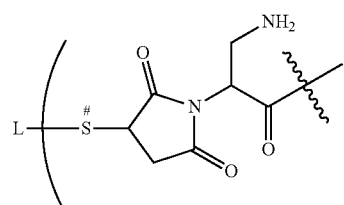

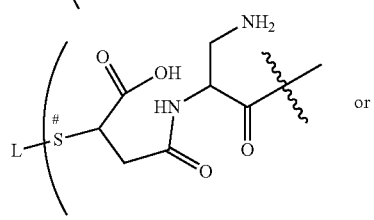

-continued

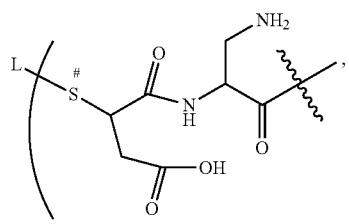

or a salt thereof, in particular pharmaceutically acceptable salt.

34. The Ligand Drug Conjugate composition of embodiment 31 wherein L-(L$_R$- has the structure of:

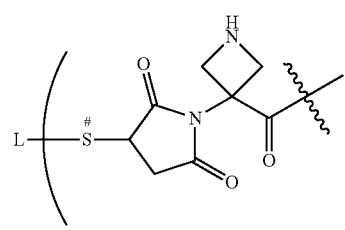

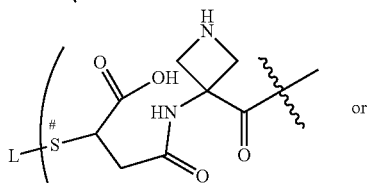

or

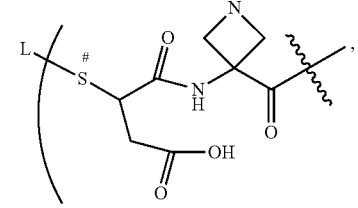

or a salt thereof, in particular a pharmaceutically acceptable salt.

35. The Ligand Drug Conjugate composition of any one of embodiments 1 to 28 wherein the composition is represented by the structure(s) of Formula 1a and/or Formula 1b or is represented by the structure(s) of Formula 1c and/or Formula 1d:

(1a)

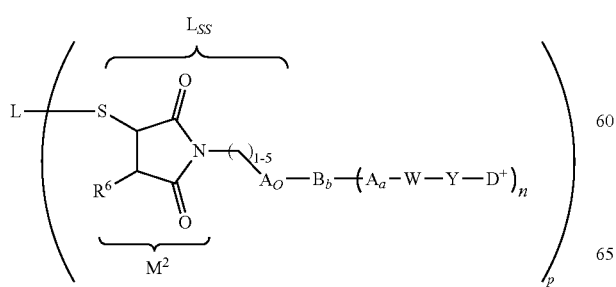

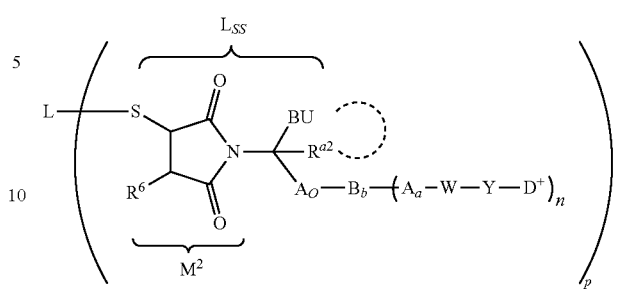
(1b)

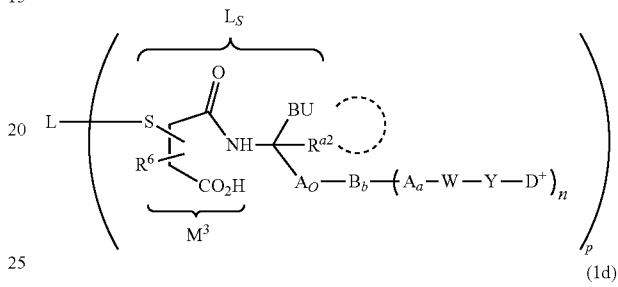
(1c)

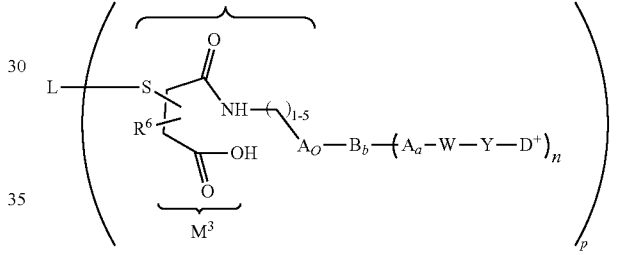
(1d)

in salt form(s), in particular pharmaceutically acceptable salt form(s), wherein L is a Ligand Unit; S is a sulfur atom of the Ligand Unit, which in Formula 1b or Formula 1d is bonded to the carbon atom α or β to the carboxylic acid functional group of the indicated succinic acid amide ($M^3$) moiety; $R^6$ is hydrogen or an optionally substituted $C_1$-$C_6$ alkyl, which in Formula 1b or Formula 1d is bonded to the saturated carbon atom adjacent to the carbon substituted by L-S—; $A_O$ is a second optional Stretcher Unit; and W is a Peptide Cleavable Unit, or W—Y is replaced by a Glucuronide Unit of formula —Y(W')—, wherein W' represents a carbohydrate moiety with glycosidic bonding to Y through an optionally substituted heteroatom; Y is a self-immolative Spacer Unit comprised of a PAB or PAB-type moeity;

BU is a Basic Unit and $R^{a2}$ is optionally substituted $C_1$-$C_{12}$ alkyl; and the dotted curved line indicates optional cyclization so that in the absence of said cyclization BU is an acyclic Basic Unit or in the presence of said cyclization BU is a cyclized Basic Unit in which $R^{a2}$ and BU together with the carbon atom to which both are attached, define an optionally substituted spiro $C_3$-$C_{20}$ heterocyclo containing a skeletal basic nitrogen atom of a secondary or tertiary amine functional group of BU, wherein the basic nitrogen atom of the acyclic Basic Unit or cyclic Basic Unit is optionally suitably protected by a nitrogen protecting group, dependent on the degree of substitution of the basic nitrogen atom, or is optionally protonated, and wherein enzymatic action upon W/W' of a drug linker moiety of a Ligand Drug Conjugate compound of the composition initiates release of the quaternized NAMPT Drug ($D^+$) Unit as a NAMPTi compound, and wherein the Ligand Drug Conjugate compound is represented by Formula 1a, Formula 1b, Formula 1c or Formula 1d in which subscript p is replaced by p'.

36. The Ligand Drug Conjugate composition of embodiment 35, wherein the composition is represented by the structure(s) of:

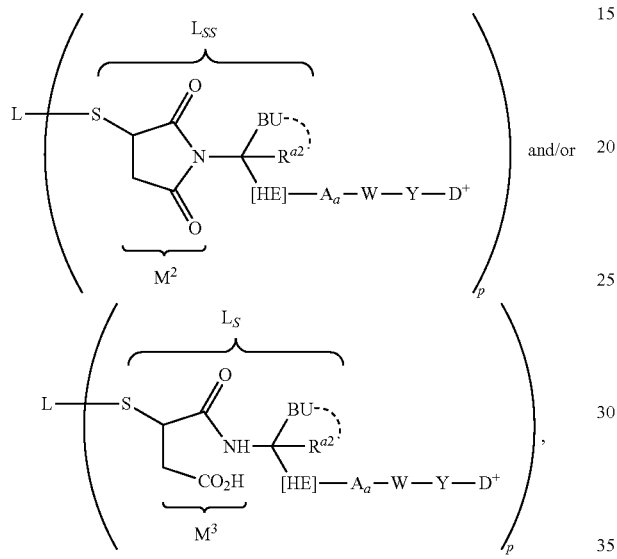

in salt form(s), in particular in pharmaceutically acceptable salt form(s), wherein [HE] as $A_O$ is an optional Hydrolysis Enhancing Unit; W is Peptide Cleavable Unit, and Y is a self-immolative Spacer Unit comprised of a PAB or PAB-type moeity, wherein protease action on the Peptide Cleavable Unit is capable of cleaving the W-J' bond within a drug linker moiety of a Ligand Drug Conjugate compound of the composition to initiate release of the quaternized NAMPT Drug ($D^+$) Unit as NAMPTi compound from that Ligand Drug Conjugate compound, or W—Y is replaced by a Glucuronide Unit of formula —Y(W')— having the structure of:

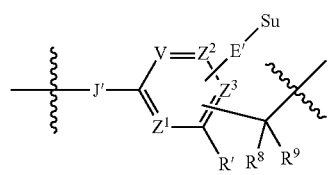

wherein Su is a carbohydrate moiety and -E'- represents an optionally substituted heteroatom of an glycosidic bond cleavable by a glycosidase so that Su-E' is W' and the remainder of the Glucuronide Unit structure is a self-immolative Spacer Unit bonded to W'; J' is an independently selected heteroatom, optionally substituted; V, $Z^1$, $Z^2$ and $Z^3$ are independently =N— or =C($R^{24}$)—, wherein each $R^{24}$ is independently selected from the group consisting of hydrogen and $C_1$-$C_{12}$ alkyl, $C_2$-$C_{12}$ alkenyl and $C_2$-$C_{12}$ alkynyl, optionally substituted, and halogen, an electron withdrawing group, an electron donating group, -E'-Su, and —C($R^8$)($R^9$)—, provided that one and only one —C($R^8$)($R^9$)-moiety and one and only one -E'-Su moiety is present, wherein one of V, $Z^1$, $Z^2$ and $Z^3$ is =C($R^{24}$)— in which $R^{24}$ is —C($R^8$)($R^9$)— and another of V, $Z^1$, $Z^2$ and $Z^3$ is =C($R^{24}$)— in which $R^{24}$ is -E'-Su, provided the —C($R^8$)($R^9$)— and -E'-Su moieties are ortho or para to each other;

$R^8$ and $R^9$ independently are hydrogen, or $C_1$-$C_{12}$ alkyl, $C_2$-$C_{12}$ alkenyl or $C_2$-$C_{12}$ alkynyl, optionally substituted, or $C_6$-$C_{20}$ aryl or $C_5$-$C_{20}$ heteroaryl, optionally substituted, or $R^8$ and $R^9$ together with the carbon atom to which both are attached define an optionally substituted $C_5$-$C_{20}$ carbocyclo; and R' is hydrogen or —$NO_2$, or other electron withdrawing group or —$OC_1$-$C_6$ alkyl, or other electron donating group; and wherein the wavy line adjacent to J' indicates the site of covalent attachment of the Glucuronide Unit to A when subscript a is 1 or to the indicated $L_{SS}$ or $L_S$ primary linker when subscript a is 0; and the wavy line adjacent to the —C($R^8$)($R^9$)— moiety indicates the site of covalent attachment of the Glucuronide Unit to $D^+$; and wherein glycosidase action on the Glucuronide Unit is capable of cleaving its glycosidic bond to initiate release of the quaternized NAMPT Drug ($D^+$) Unit as NAMPTi compound from a drug linker moiety of a Ligand Drug Conjugate compound of the composition; and wherein the Ligand Drug Conjugate compound is of corresponding structure to the composition in which subscript p is replaced by p'.

37. The Ligand Drug Conjugate composition of embodiment 35, wherein the composition is represented by the structure(s) of:

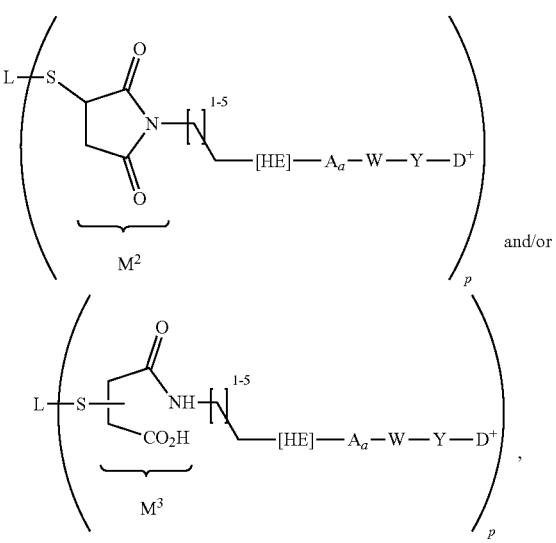

in salt form(s), in particular in pharmaceutically acceptable salt form(s), wherein [HE] as $A_O$ is an optional Hydrolysis Enhancing Unit; W is Peptide Cleavable Unit, and Y is a self-immolative Spacer Unit comprised of a PAB or PAB-type moeity, wherein protease action on the Peptide Cleavable Unit is capable of cleaving the W-J' bond within a drug linker moiety of a Ligand Drug Conjugate compound of the composition to initiate release of the quaternized NAMPT Drug ($D^+$) Unit as NAMPTi compound from that Ligand Drug Conjugate compound, or W—Y is replaced by a Glucuronide Unit of formula —Y(W')— having the structure of:

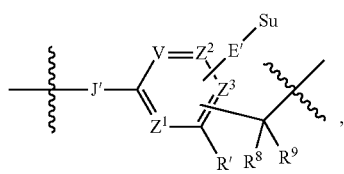

wherein Su is a carbohydrate moiety and -E'- represents an optionally substituted heteroatom of an glycosidic bond cleavable by a glycosidase so that Su-E' is W' and the remainder of the Glucuronide Unit structure is a self-immolative Spacer Unit bonded to W'; J' is an independently selected heteroatom, optionally substituted; V, $Z^1$, $Z^2$ and $Z^3$ are independently =N— or =C($R^{24}$)—, wherein each $R^{24}$ is independently selected from the group consisting of hydrogen and $C_1$-$C_{12}$ alkyl, $C_2$-$C_{12}$ alkenyl and $C_2$-$C_{12}$ alkynyl, optionally substituted, and halogen, an electron withdrawing group, an electron donating group, -E'-Su, and —C($R^8$)($R^9$)—, provided that one and only one —C($R^8$)($R^9$)-moiety and one and only one -E'-Su moiety is present, wherein one of V, $Z^1$, $Z^2$ and $Z^3$ is =C($R^{24}$)— in which $R^{24}$ is —C($R^8$)($R^9$)— and another of V, $Z^1$, $Z^2$ and $Z^3$ is =C($R^{24}$)— in which $R^{24}$ is -E'-Su, provided the —C($R^8$)($R^9$)— and -E'-Su moieties are ortho or para to each other;

$R^8$ and $R^9$ independently are hydrogen, or $C_1$-$C_{12}$ alkyl, $C_2$-$C_{12}$ alkenyl or $C_2$-$C_{12}$ alkynyl, optionally substituted, or $C_6$-$C_{20}$ aryl or $C_5$-$C_{20}$ heteroaryl, optionally substituted, or $R^8$ and $R^9$ together with the carbon atom to which both are attached define an optionally substituted $C_5$-$C_{20}$ carbocyclo; and R' is hydrogen or —$NO_2$, or other electron withdrawing group or —$OC_1$-$C_6$ alkyl, or other electron donating group; and wherein glycosidase action on the Glucuronide Unit is capable of cleaving its glycosidic bond to initiate release of the quaternized NAMPT Drug ($D^+$) Unit as NAMPTi compound from a drug linker moiety of a Ligand Drug Conjugate compound of the composition; and wherein the Ligand Drug Conjugate compound is of corresponding structure to the composition in which subscript p is replaced by p'.

38. The Ligand-Drug Conjugate composition of embodiment 35, 36 or 37 wherein W—Y is replaced by a Glucuronide Unit of formula —Y(W')— for which —Y(W')-$D^+$ has the structure of:

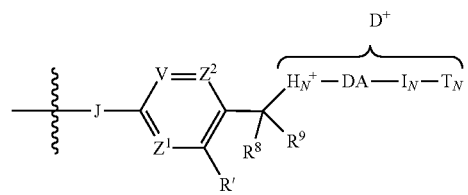

in salt form, in particular in pharmaceutically acceptable salt form, wherein R' is hydrogen or —$NO_2$ or other electron withdrawing group; $R^{45}$ is —$CH_2OH$ or —$CO_2H$; wherein —O'— represents the oxygen heteroatom of an O-glycosidic bond cleavable by a glycosidase, wherein said cleavage within a compound of the Ligand Drug Conjugate composition initiates release of the quaternized NAMPT Drug ($D^+$) Unit as a NAMPTi compound from a drug linker moiety of that Ligand Drug Conjugate compound.

39. The Ligand-Drug Conjugate composition of embodiment 35, 36 or 37, wherein W is a Peptide Cleavable Unit for which —Y-$D^+$ has the structure of:

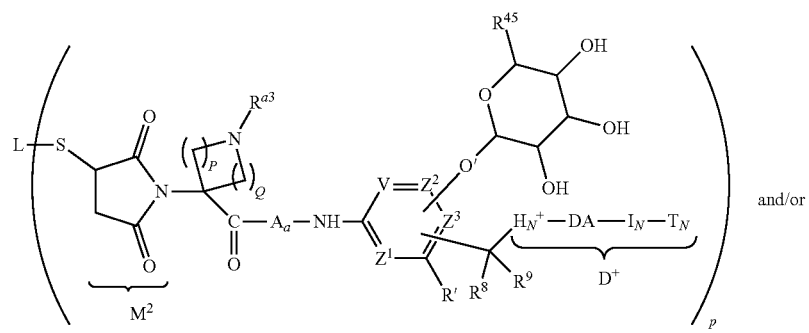

in salt form, in particular in pharmaceutical acceptable salt form, wherein R' is hydrogen or —$OC_1$-$C_6$ alkyl or other electron donating group;

J is an optionally substituted heteroatom bonded to W as indicated by the wavy line, wherein cleavage of that bond within a drug linker moiety of a Ligand Drug Conjugate compound of the composition by a protease initiates release of the quaternized NAMPT Drug ($D^+$) Unit as a NAMPTi compound from that Ligand Drug Conjugate compound.

40. The Ligand Drug Conjugate composition or compound of embodiment 36, wherein the composition is represented by the structure(s) of:

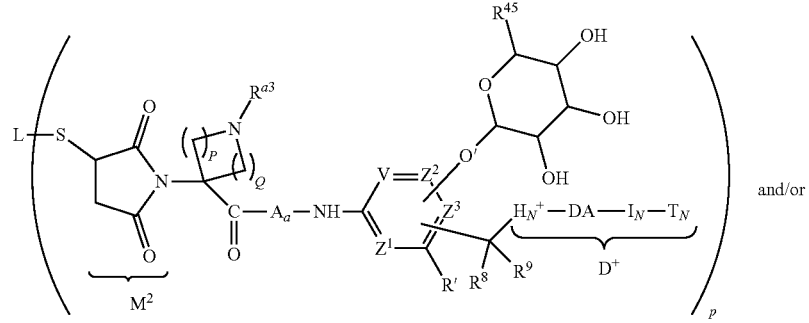

and/or

-continued

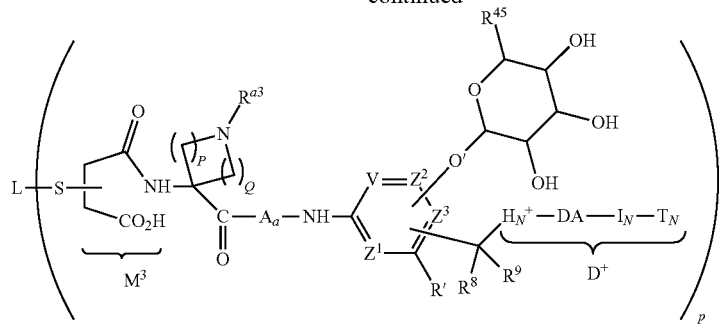

in salt form(s), in particular in pharmaceutical acceptable salt form(s), wherein subscript P is 1, 2 or 3; subscript Q ranges from 1 to 6; cR' is hydrogen or —$NO_2$ or other electron withdrawing group; $cR^{45}$ is —$CH_2OH$ or —$CO_2H$; $R^{a3}$ is —H, or optionally substituted $C_1$-$C_6$ alkyl, optionally substituted —$C_1$-$C_4$ alkylene-($C_6$-$C_{10}$ aryl), or —$R^{PEG1}$—O—$(CH_2CH_2O)_{1-36}$—$R^{PEG2}$, wherein $R^{PEG1}$ is $C_1$-$C_4$ alkylene, and $R^{PEG2}$ is —H or $C_1$-$C_4$ alkyl; and wherein the basic nitrogen atom bonded to $R^3$ is optionally protonated, and wherein —O'— represents the oxygen heteroatom of an O-glycosidic bond cleavable by a glycosidase, wherein said cleavage within a drug linker moiety of a Ligand Drug Conjugate compound of the composition initiates release of the quaternized NAMPT Drug ($D^+$) Unit as a NAMPTi compound from that Ligand Drug Conjugate compound, wherein the Ligand Drug Conjugate compound is of corresponding structure to the composition in which subscript p is replaced by p'.

41. The Ligand Drug Conjugate composition of embodiment 36, wherein the composition or compound is represented by the structure(s) of:

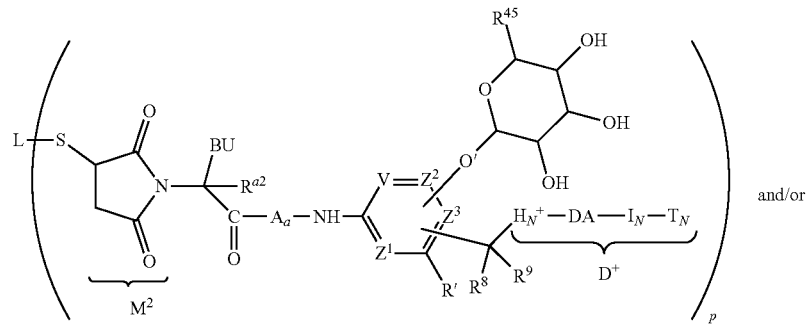 and/or

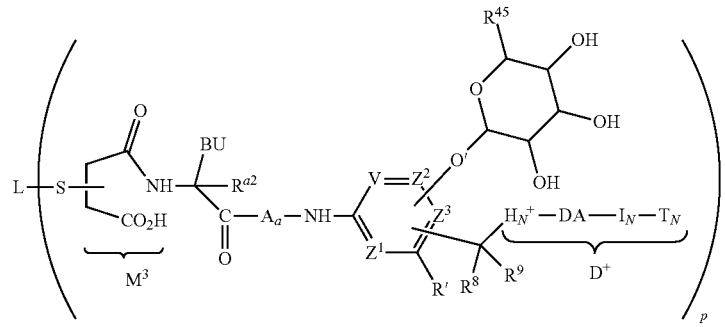

in salt form(s), in particular in pharmaceutical acceptable salt form(s), wherein R' is hydrogen or —NO$_2$ or other electron withdrawing group; R$^{45}$ is —CH$_2$OH or —CO$_2$H; R$^{a2}$ is hydrogen or C$_1$-C$_6$ alkyl;

BU has the structure of —[C(R$^{a1}$)(R$^{a1}$)]—[C(R$^{a1}$)(R$^{a1}$)]$_{0-3}$—N(R$^{a3}$)(R$^{a3}$), each R$^{a1}$ independently is hydrogen or C$_1$-C$_4$ alkyl, C$_6$-C$_{10}$ aryl, C$_5$-C$_{10}$ heteroaryl, (C$_6$-C$_{10}$ aryl)-C$_1$-C$_4$ alkyl-, or (C$_5$-C$_{10}$ heteroaryl)-C$_1$-C$_4$ alkyl-, optionally substituted, or two R$^{a1}$ together with the carbon(s) to which they are attached and any intervening carbons define an optionally substituted C$_3$-C$_6$ cycloalkyl; R$^{a3}$ independently are hydrogen, optionally substituted C$_1$-C$_6$ alkyl or R$^{a3}$ together with the nitrogen atom to which both are attached define a C$_3$-C$_6$ heterocyclyl in which the basic nitrogen is a skeletal atom; wherein the basic nitrogen atom of BU bonded to R$^{a3}$ is optionally protonated; and wherein —O'— represents the oxygen atom of an O-glycosidic bond cleavable by a glycosidase, wherein said cleavage within a drug linker moeity of a Ligand Drug Conjugate compound of the composition initiates release of the quaternized NAMPT Drug (D$^+$) Unit as a NAMPTi compound from that Ligand Drug Conjugate compound, wherein the Ligand Drug Conjugate compound is of corresponding structure to the composition in which subscript p is replaced by p'.

42. The Ligand Drug Conjugate composition of embodiment 37, wherein the composition or compound is represented by the structure(s) of:

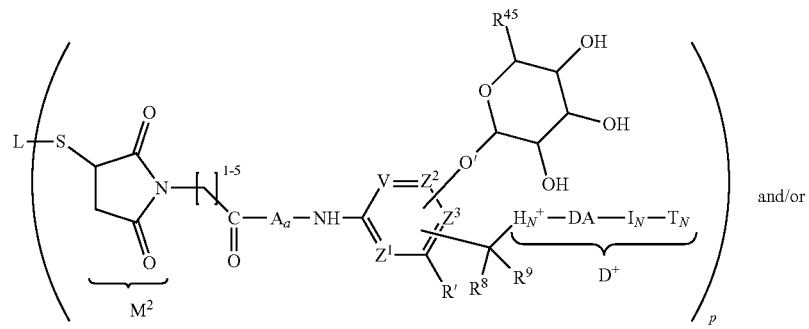

and/or

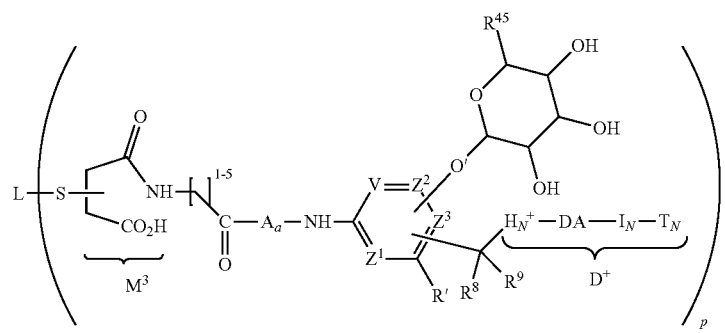

in salt form(s), in particular in pharmaceutical acceptable salt form(s), wherein R' is hydrogen or —$NO_2$ or other electron withdrawing group; $R^{45}$ is —$CH_2OH$ or —$CO_2H$; $R^{a2}$ is hydrogen or $C_1$-$C_6$ alkyl;

and wherein —O'— represents the oxygen atom of an O-glycosidic bond cleavable by a glycosidase, wherein said cleavage within a drug linker moeity of a Ligand Drug Conjugate compound of the composition initiates release of the quaternized NAMPT Drug ($D^+$) Unit as a NAMPTi compound from that Ligand Drug Conjugate compound, wherein the Ligand Drug Conjugate compound is of corresponding structure to the composition in which subscript p is replaced by p'.

43. The Ligand Drug Conjugate composition of embodiment 36, wherein the composition is represented by the structure(s) of:

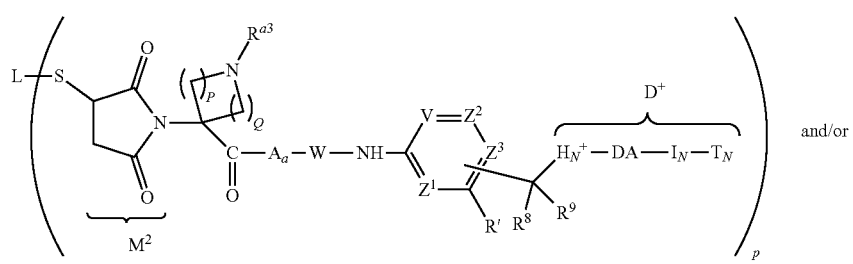

and/or

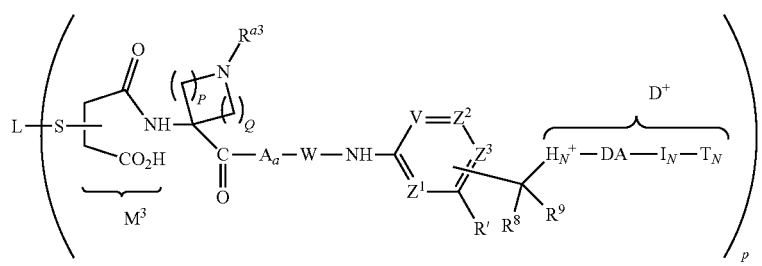

in salt form(s), in particular in pharmaceutical acceptable salt form(s), wherein W is a Peptide Cleavable Unit; subscript P is 1, 2 or 3; subscript Q ranges from 1 to 6; R' is hydrogen or —$OC_1$-$C_6$ alkyl or other electron donating group; $R^{a3}$ is —H, or optionally substituted $C_1$-$C_6$ alkyl, optionally substituted —$C_1$-$C_4$ alkylene-($C_6$-$C_{10}$ aryl), or —$R^{PEG1}$—O—$(CH_2CH_2O)_{1-36}$—$R^{PEG2}$, wherein $R^{PEG1}$ is $C_1$-$C_4$ alkylene, and $R^{PEG2}$ is —H or $C_1$-$C_4$ alkyl; and wherein the basic nitrogen atom bonded to $R^3$ is optionally protonated, and wherein protease action on the Peptide Cleavable Unit is capable of cleaving the W—NH bond, wherein said cleavage within a drug linker moeity of a Ligand Drug Conjugate compound of the composition initiates release of the quaternized NAMPT Drug ($D^+$) Unit as a NAMPTi compound from that Ligand Drug Conjugate compound, wherein the Ligand Drug Conjugate compound is of corresponding structure to the composition in which subscript p is replaced by p'.

44. The Ligand Drug Conjugate composition of embodiment 36, wherein the composition is represented by the structure(s) of:

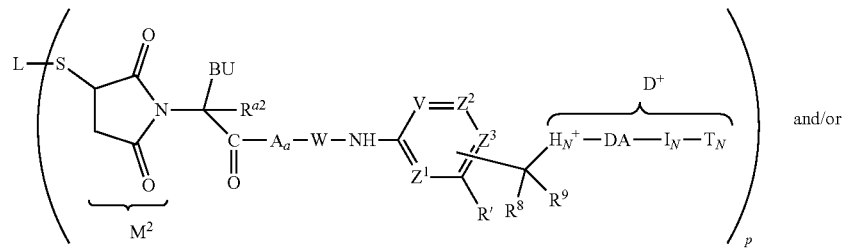

and/or

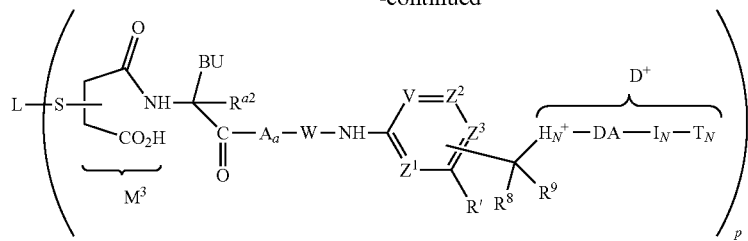

in salt form(s), in particular in pharmaceutical acceptable salt form(s), wherein W is a Peptide Cleavable Unit; R' is hydrogen or —$OC_1$-$C_6$ alkyl or other electron donating group; $R^{a2}$ is hydrogen or $C_1$-$C_6$ alkyl;

BU has the structure of —$[C(R^{a1})(R^{a1})]$—$[C(R^{a1})(R^{a1})]_{0-3}$—$N(R^{a3})(R^{a3})$, each $R^{a1}$ independently is hydrogen or $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, or ($C_5$-$C_{10}$ heteroaryl)-$C_1$-$C_4$ alkyl-, optionally substituted, or two $R^{a1}$ together with the carbon(s) to which they are attached and any intervening carbons define an optionally substituted $C_3$-$C_6$ cycloalkyl; wherein the basic nitrogen atom of BU bonded to $R^{a3}$ is optionally protonated; and wherein protease action on the Peptide Cleavable Unit is capable of cleaving the W—NH bond, wherein said cleavage within a drug linker moeity of a Ligand Drug Conjugate compound of the composition initiates release of the quaternized NAMPT Drug ($D^+$) Unit as a NAMPTi compound from that Ligand Drug Conjugate compound, wherein the Ligand Drug Conjugate compound is of corresponding structure to the composition in which subscript p is replaced by p'.

45. The Ligand Drug Conjugate composition of embodiment 37, wherein the composition is represented by the structure(s) of:

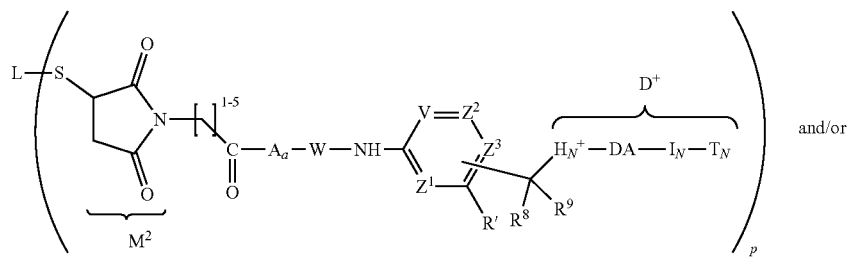

and/or

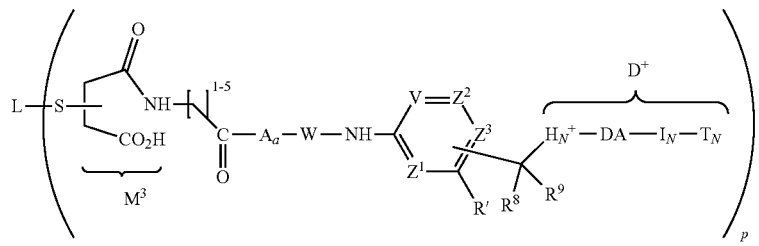

in salt form(s), in particular in pharmaceutical acceptable salt form(s), wherein W is a Peptide Cleavable Unit; R' is hydrogen or —OC$_1$-C$_6$ alkyl or other electron donating group; and R$^{a2}$ is hydrogen or C$_1$-C$_6$ alkyl, wherein protease action on the Peptide Cleavable Unit is capable of cleaving the W—NH bond, wherein said cleavage within a drug linker moeity of a Ligand Drug Conjugate compound of the composition initiates release of the quaternized NAMPT Drug (D$^{+)}$) Unit as a NAMPTi compound from that Ligand Drug Conjugate compound, and wherein the Ligand Drug Conjugate compound is of corresponding structure to the composition in which subscript p is replaced by p'.

46. The Ligand-Drug Conjugate composition of embodiment 36, wherein the composition is represented by the structure(s) of:

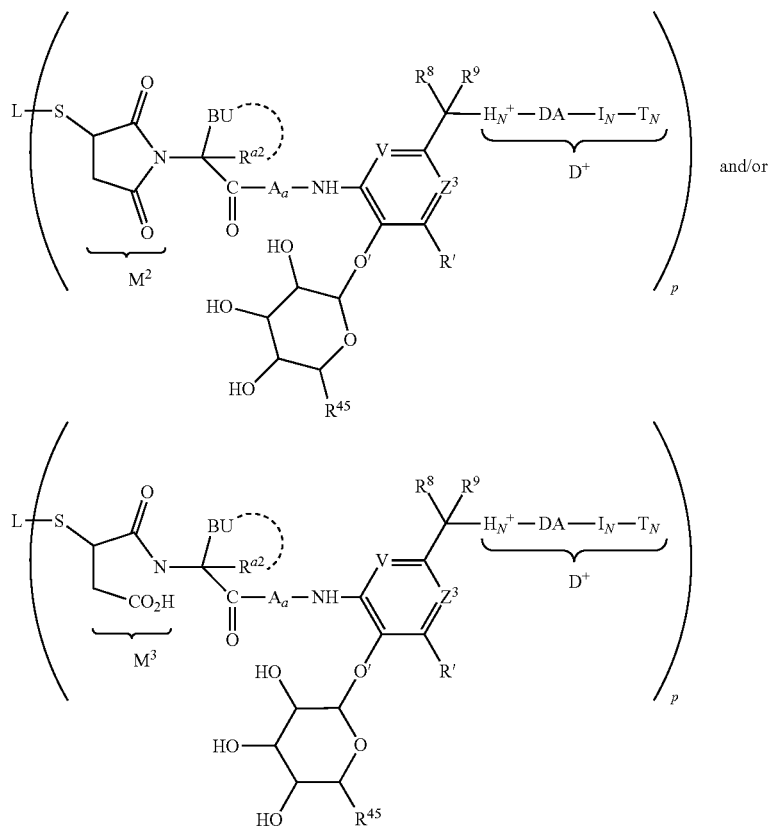

and/or in salt form(s), in particular in pharmaceutical acceptable salt form(s), wherein R' is hydrogen or —NO$_2$ or other electron withdrawing group; R$^{45}$ is —CH$_2$OH or —CO$_2$H;

BU has the structure of —[C(R$^{a1}$)(R$^{a1}$)]—[C(R$^{a1}$)(R$^{a1}$)]$_{0-3}$—N(R$^{a3}$)(R$^{a3}$), each R$^{a1}$ independently is hydrogen or C$_1$-C$_4$ alkyl, C$_6$-C$_{10}$ aryl, C$_5$-C$_{10}$ heteroaryl, (C$_6$-C$_{10}$ aryl)-C$_1$-C$_4$ alkyl-, or (C$_5$-C$_{10}$ heteroaryl)-C$_1$-C$_4$ alkyl-, optionally substituted, or two R$^{a1}$ together with the carbon(s) to which they are attached and any intervening carbons define an optionally substituted C$_3$-C$_6$ cycloalkyl; R$^{a3}$ independently are hydrogen, optionally substituted C$_1$-C$_6$ alkyl or R$^{a3}$ together with the nitrogen atom to which both are attached define a C$_3$-C$_6$ heterocyclyl in which the basic nitrogen is a skeletal atom; R$^{a2}$ is hydrogen or C$_1$-C$_6$ alkyl, optionally cyclized to BU, as indicated by the dotted curved line, wherein one of R$^{a1}$ or one of R$^{a3}$ is replaced with a bond to a carbon atom of R$^{a2}$ when R$^{a2}$ is C$_1$-C$_6$ alkyl; wherein the basic nitrogen atom of BU bonded to R$^{a3}$ is optionally protonated; and wherein —O'— represents the oxygen atom of an O-glycosidic bond cleavable by a glycosidase, wherein said cleavage within a drug linker moeity of a Ligand Drug Conjugate compound of the composition initiates release of the quaternized NAMPT Drug (D$^+$) Unit as a NAMPTi compound from that Ligand Drug Conjugate compound, and wherein the Ligand Drug Conjugate compound is of corresponding structure to the composition in which subscript p is replaced by p'.

47. The Ligand-Drug Conjugate composition of embodiment 36, wherein the composition is represented by the structure(s) of:

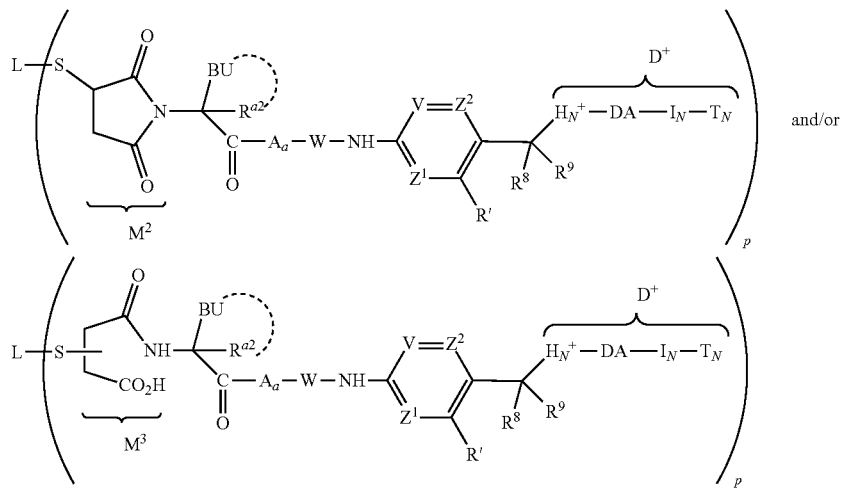

in salt form(s), in particular in pharmaceutical acceptable salt form(s), wherein W is a Peptide Cleavable Unit; R' is hydrogen or —OC$_1$-C$_6$ alkyl or other electron donating group; R$^{45}$ is —CH$_2$OH or —CO$_2$H;

BU has the structure of —[C(R$^{a1}$)(R$^{a1}$)]—[C(R$^{a1}$)(R$^{a1}$)]$_{0-3}$—N(R$^{a3}$)(R$^3$), each R$^{a1}$ independently is hydrogen or C$_1$-C$_4$ alkyl, C$_6$-C$_{10}$ aryl, C$_5$-C$_{10}$ heteroaryl, (C$_6$-C$_{10}$ aryl)-C$_1$-C$_4$ alkyl-, or (C$_5$-C$_{10}$ heteroaryl)-C$_1$-C$_4$ alkyl-, optionally substituted, or two R$^{a1}$ together with the carbon(s) to which they are attached and any intervening carbons define an optionally substituted C$_3$-C$_6$ cycloalkyl; R$^{a3}$ independently are hydrogen, optionally substituted C$_1$-C$_6$ alkyl or R$^{a3}$ together with the nitrogen atom to which both are attached define a C$_3$-C$_6$ heterocyclyl in which the basic nitrogen is a skeletal atom; R$^{a2}$ is hydrogen or C$_1$-C$_6$ alkyl, optionally cyclized to BU, as indicated by the dotted curved line, wherein one of R$^{a1}$ or one of R$^{a3}$ is replaced with a bond to a carbon atom of R$^{a2}$ when R$^2$ is C$_1$-C$_6$ alkyl; wherein the basic nitrogen atom of BU bonded to R$^{a3}$ is optionally protonated; and wherein protease action on the Peptide Cleavable Unit is capable of cleaving the W—NH bond, wherein said cleavage within a drug linker moiety of a Ligand Drug Conjugate compound of the composition initiates release of the quaternized NAMPT Drug (D$^+$) Unit as a NAMPTi compound from that Ligand Drug Conjugate compound, wherein the Ligand Drug Conjugate compound is of corresponding structure to the composition in which subscript p is replaced by p'.

48. The Ligand-Drug Conjugate composition of embodiment 37, wherein the composition is represented by the structure(s) of:

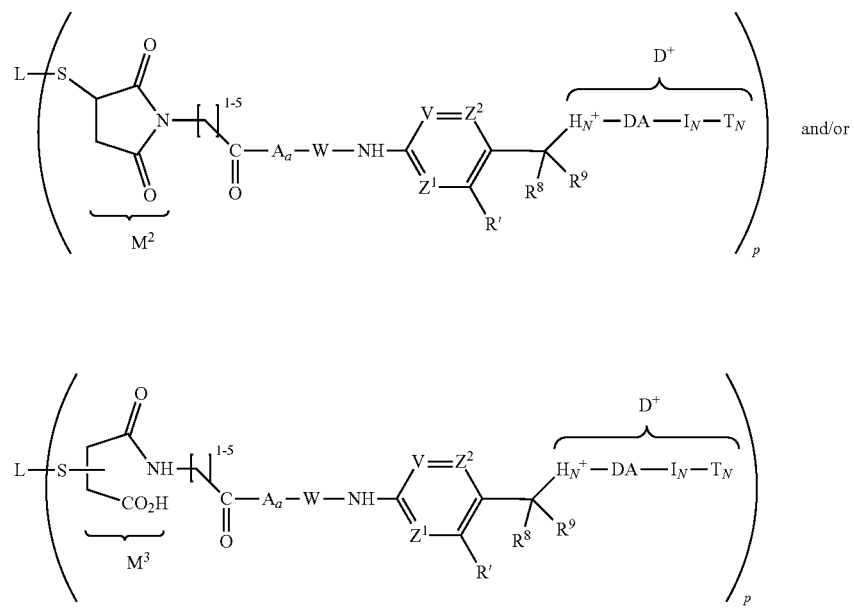

in salt form(s), in particular in pharmaceutical acceptable salt form(s), wherein W is a Peptide Cleavable Unit; R' is hydrogen or —OC$_1$-C$_6$ alkyl or other electron donating group; R$^{45}$ is —CH$_2$OH or —CO$_2$H,
wherein protease action on the Peptide Cleavable Unit is capable of cleaving the W—NH bond, wherein said cleavage within a drug linker moeity of a Ligand Drug Conjugate compound of the composition initiates release of the quaternized NAMPT Drug (D$^+$) Unit as a NAMPTi compound from that Ligand Drug Conjugate compound, wherein the Ligand Drug Conjugate compound is of corresponding structure to the composition in which subscript p is replaced by p'.

49. The Ligand-Drug Conjugate composition of embodiment 36, wherein the composition is represented by the structure(s) of:

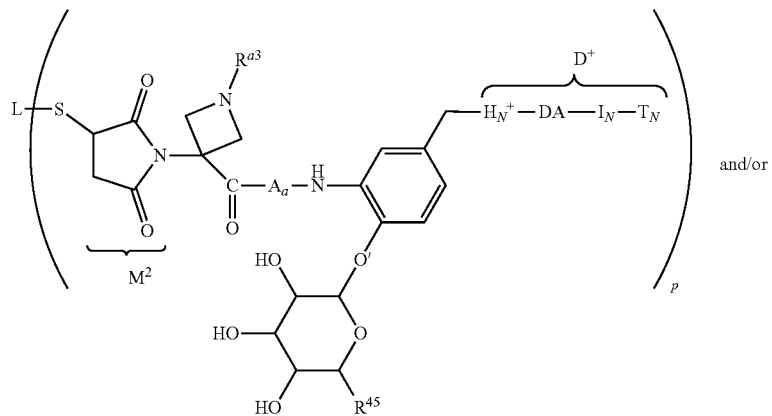

and/or

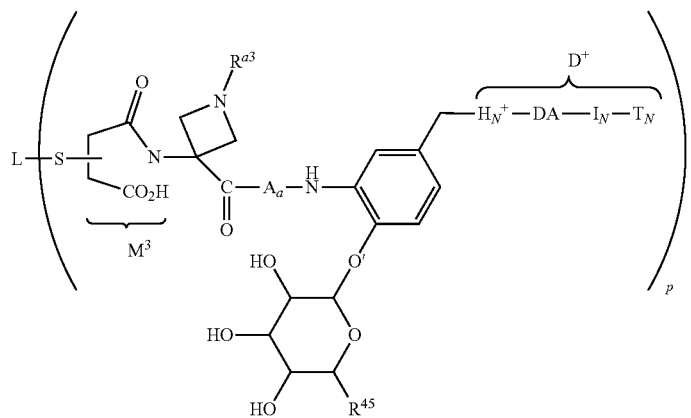

in salt form(s), in particular in pharmaceutical acceptable salt form(s), wherein R$^{45}$ is —CH$_2$OH or —CO$_2$H; R$^3$ is —H, or optionally substituted C$_1$-C$_6$ alkyl, optionally substituted —C$_1$-C$_4$ alkylene-(C$_6$-C$_{10}$ aryl), or —R$^{PEG1}$—O—(CH$_2$CH$_2$O)$_{1-36}$—R$^{PEG2}$ wherein R$^{PEG1}$ is C$_1$-C$_4$ alkylene, and R$^{PEG2}$ is —H or C$_1$-C$_4$ alkyl; and wherein the basic nitrogen atom bonded to R$^3$ is optionally protonated;
—O'— represents the oxygen atom of an O-glycosidic bond cleavable by a glycosidase, wherein said cleavage within a drug linker moeity of a Ligand Drug Conjugate compound of the composition initiates release of the quaternized NAMPT Drug (D$^+$) Unit as a NAMPTi compound from that Ligand Drug Conjugate compound, wherein the Ligand Drug Conjugate compound is of corresponding structure to the composition in which subscript p is replaced by p'.

50. The Ligand-Drug Conjugate composition of embodiment 36, wherein the composition is represented by the structure of:

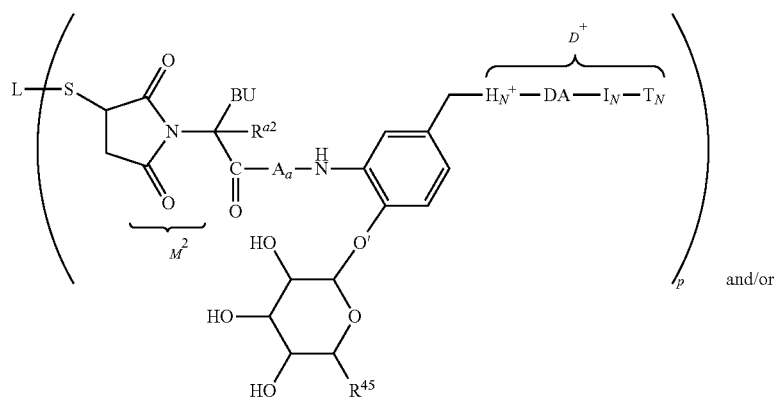

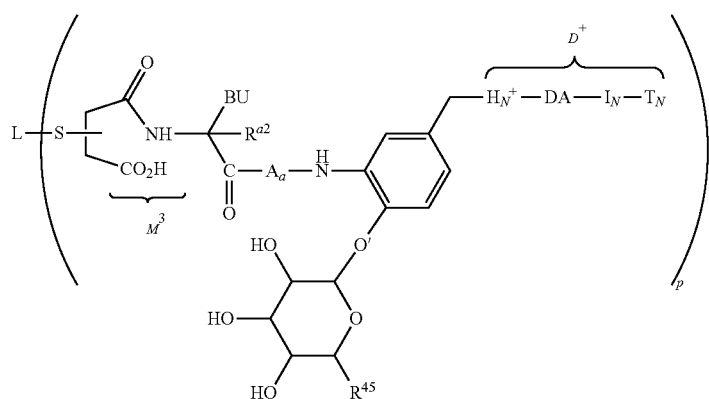

in salt form(s), in particular in pharmaceutical acceptable salt form(s), wherein $R^{45}$ is —$CH_2OH$ or —$CO_2H$; BU is —$CH_2$—$NH_2$, optionally protonated; $R^{a2}$ is hydrogen; and —O'— represents the oxygen atom of an O-glycosidic bond cleavable by a glycosidase, wherein said cleavage within a drug linker moiety of a Ligand Drug Conjugate compound of the composition initiates release of the quaternized NAMPT Drug ($D^+$) Unit as a NAMPTi compound from that Ligand Drug Conjugate compound, wherein the Ligand Drug Conjugate compound is of corresponding structure to the composition in which subscript p is replaced by p'.

51. The Ligand-Drug Conjugate composition of embodiment 37, wherein the composition is represented by the structure of:

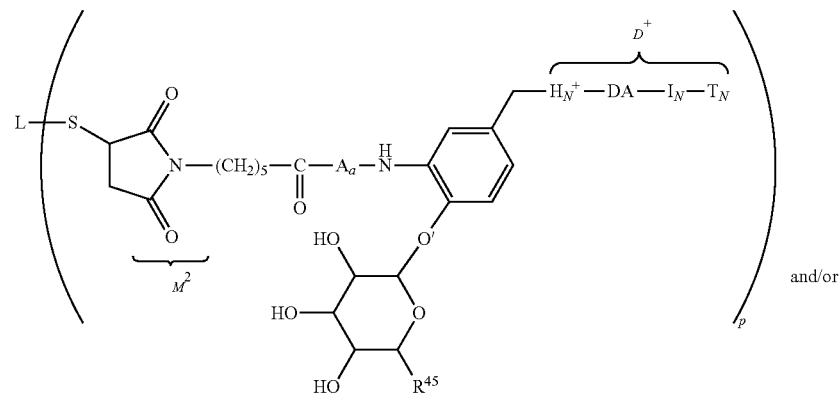

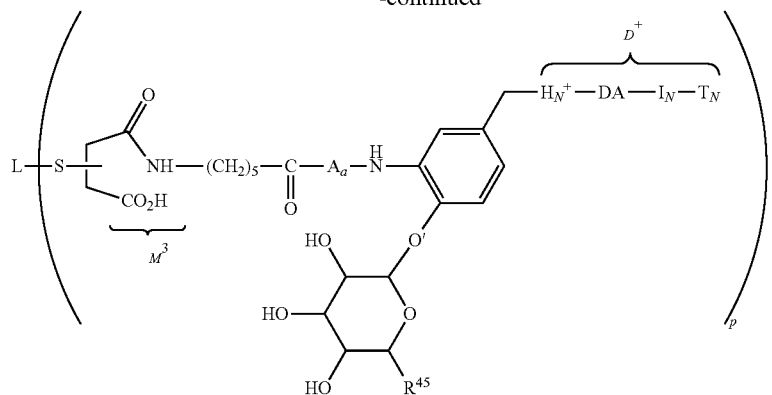

in salt form(s), in particular in pharmaceutical acceptable salt form(s), wherein $R^{45}$ is —$CH_2OH$ or —$CO_2H$; and —O'— represents the oxygen atom of an O-glycosidic bond cleavable by a glycosidase, wherein said cleavage within a drug linker moeity of a Ligand Drug Conjugate compound of the composition initiates release of the quaternized NAMPT Drug ($D^+$) Unit as a NAMPTi compound from that Ligand Drug Conjugate compound, wherein the Ligand Drug Conjugate compound is of corresponding structure to the composition in which subscript p is replaced by p'.

52. The Ligand-Drug Conjugate composition of embodiment 36, wherein the composition is represented by the structure(s) of:

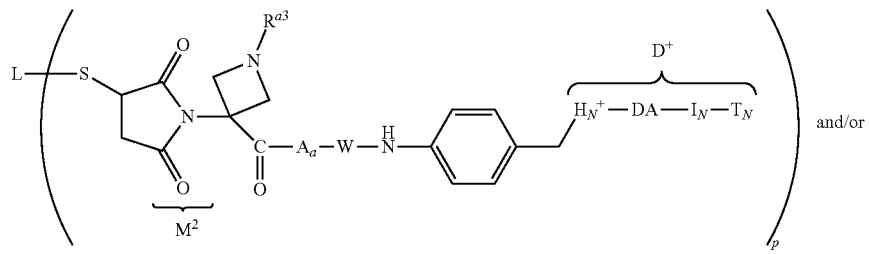

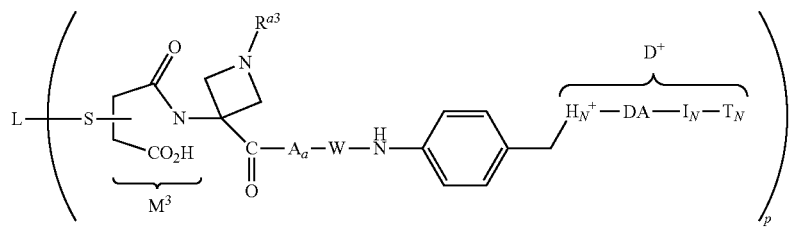

in salt form(s), in particular in pharmaceutical acceptable salt form(s), wherein W is a Peptide Cleavable Unit; $R^{a3}$ is —H, or optionally substituted $C_1$-$C_6$ alkyl, optionally substituted —$C_1$-$C_4$ alkylene-($C_6$-$C_{10}$ aryl), or —$R^{PEG1}$—O—$(CH_2CH_2O)_{1-36}$—$R^{PEG2}$ wherein $R^{PEG1}$ is $C_1$-$C_4$ alkylene, and $R^{PEG2}$ is —H or $C_1$-$C_4$ alkyl; and wherein the basic nitrogen atom bonded to $R^{a3}$ is optionally protonated; and wherein protease action on the Peptide Cleavable Unit is capable of cleaving the W—NH bond, wherein said cleavage within a drug linker moeity of a Ligand Drug Conjugate compound of the composition initiates release of the quaternized NAMPT Drug ($D^+$) Unit as a NAMPTi compound or derivative thereof from that Ligand Drug Conjugate compound, wherein the Ligand Drug Conjugate compound is of corresponding structure to the composition in which subscript p is replaced by p'.

53. The Ligand-Drug Conjugate composition of embodiment 36, wherein the composition is represented by the structure(s) of:

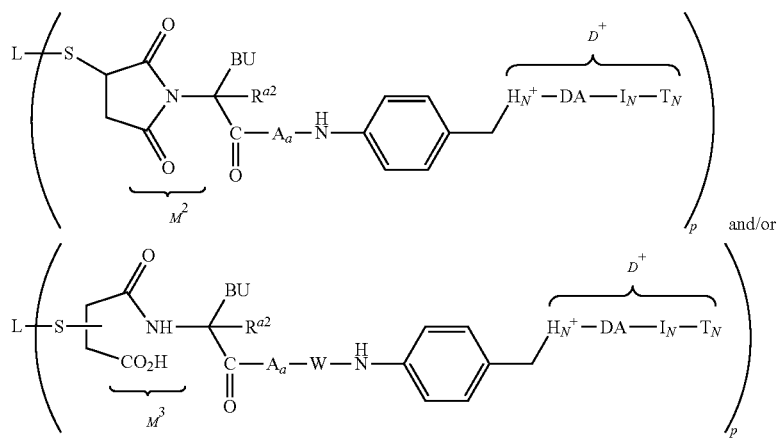

in salt form(s), in particular in pharmaceutical acceptable salt form(s), wherein W is a Peptide Cleavable Unit; BU is —$CH_2$—$NH_2$, optionally protonated; $R^{a2}$ is hydrogen;

and wherein protease action on the Peptide Cleavable Unit is capable of cleaving the W—NH bond, wherein said cleavage within a drug linker moeity of a Ligand Drug Conjugate compound of the composition initiates release of the quaternized NAMPT Drug ($D^+$) Unit as a NAMPTi compound from that Ligand Drug Conjugate compound, wherein the Ligand Drug Conjugate compound is of corresponding structure to the composition in which subscript p is replaced by p'.

54. The Ligand-Drug Conjugate composition of embodiment 37, wherein the composition is represented by the structure(s) of:

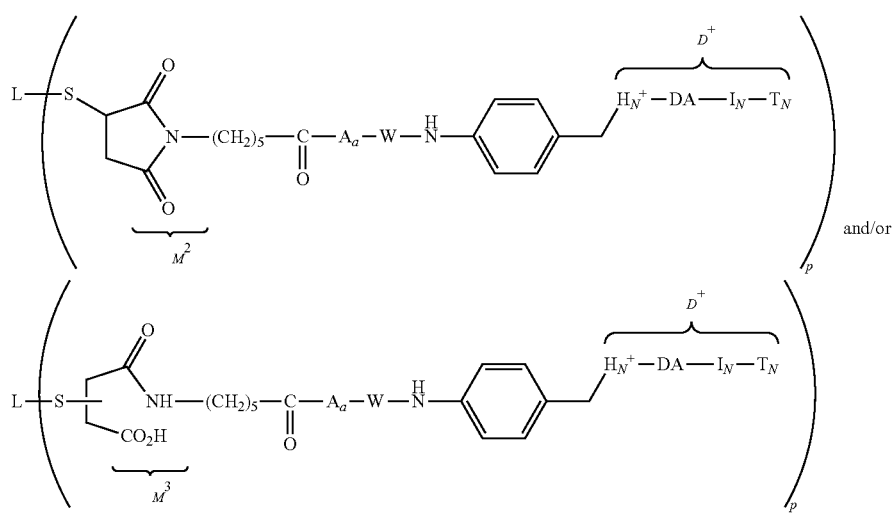

in salt form(s), in particular in pharmaceutical acceptable salt form(s), wherein W is a Peptide Cleavable Unit, wherein protease action on the Peptide Cleavable Unit is capable of cleaving the W—NH bond, wherein said cleavage within a drug linker moeity of a Ligand Drug Conjugate compound of the composition initiates release of the quaternized NAMPT Drug Unit ($D^+$) as a NAMPTi compound from that Ligand Drug Conjugate compound, wherein the Ligand Drug Conjugate compound is of corresponding structure to the composition in which subscript p is replaced by p'.

55. The Ligand-Drug Conjugate composition of any one of the preceding embodiments in which W is a Peptide Cleavable Unit that Unit is comprised of a dipeptide wherein the dipeptide provides for a recognition site for a regulatory or lysosomal protease for cleavage by said protease of the W-J' bond or the W—NH bond when J' is —NH within a drug linker moeity of a Ligand Drug Conjugate compound of the composition so as to initiate release of the quaternized NAMPT Drug Unit (D⁺) as NAMPTi compound from that Ligand Drug Conjugate compound, wherein the Ligand Drug Conjugate compound is of corresponding structure to the composition in which subscript p is replaced by subscript p'.

56. The Ligand-Drug Conjugate composition of embodiment 55 wherein W has or is comprised of the structure of:

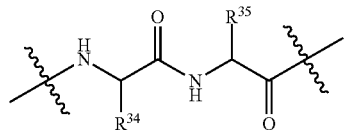

wherein $R^{34}$ is benzyl, methyl, isopropyl, isobutyl, sec-butyl, —CH(OH)CH₃ or has the structure of

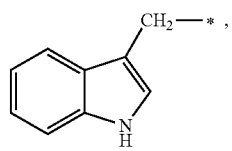

wherein the asterisk indicates the site of covalent attachment to the dipeptide backbone; and $R^{35}$ is methyl, —(CH₂)₄—NH₂, —(CH₂)₃NH(C=O)NH₂, —(CH₂)₃NH(C=NH)NH₂, or —(CH₂)₂CO₂H; wherein the dipeptide provide a recognition site for a protease and wherein the wavy lines indicate the points of covalent attachment of the dipeptide into the structure representing the Ligand-Drug Conjugate composition.

57. The Ligand-Drug Conjugate composition of embodiment 55 wherein the dipeptide is selected from the group consisting of -Phe-Lys-, -Val-Ala-, -Val-Lys-, -Ala-Lys-, -Val-Cit-, -Phe-Cit-, -Leu-Cit-, -Ile-Cit-, -Phe-Arg-, and -Trp-Cit-, wherein Cit is citrulline.

58. The Ligand-Drug Conjugate composition of any one of embodiments 1 to 57, wherein A or a subunit thereof is -L$^P$(PEG)-.

59. The Ligand-Drug Conjugate composition of embodiment 58 wherein -L$^P$- or a subunit thereof is a aminoalkanedioic acid, a diaminoalkanoic acid, a sulfur-substituted alkanedioic acid, a sulfur-substituted aminoalkanoic acid, a diaminoalkanol, an aminoalkanediol, a hydroxyl substituted alkanedioic acid, a hydroxyl substituted aminoalkanoic acid or a sulfur-substituted aminoalkanol residue, optionally substituted, wherein the substituted sulfur is in reduced or oxidized form.

60. The Ligand-Drug Conjugate composition of embodiment 58 wherein -L$^P$- or a subunit thereof is an amino acid residue of lysine, arginine, asparagine, glutamine, ornithine, citrulline, cysteine, homocysteine, penicillamine, threonine, serine, glutamic acid, aspartic acid, tyrosine, histidine or tryptophan, wherein the amino acid is in the D- or L-configuration.

61. The Ligand-Drug Conjugate composition of embodiment 58 wherein L$^P$ or a subunit thereof is selected from the group consisting of lysine, glutamic acid, aspartic acid, cysteine, penicillamine, serine or threonine in its D- or L-stereochemical configuration.

62. The Ligand-Drug Conjugate composition of embodiment 58, wherein -L$^P$-or a subunit thereof has the structure of Formula L$^P$-1 or L$^P$-2:

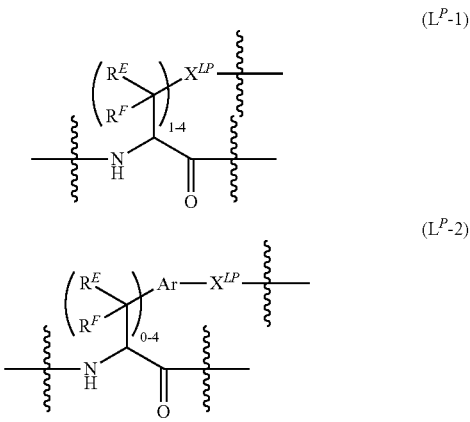

or a salt thereof, in particular a pharmaceutical acceptable salt thereof, wherein X$^{LP}$ is selected from the group consisting of —O—, —NR$^{LP}$—, —S—, —S(=O)—, —S(=O)₂—, —C(=O)—, —C(=O)N(R$^{LP}$)—, —N(R$^{LP}$)C(=O)N(R$^{LP}$)—, —N(R$^{LP}$)C(=NR$^{LP}$)N(R$^{LP}$)—, and C₃-C₈ heterocyclo; wherein each R$^{LP}$ is independently selected from the group consisting of hydrogen and optionally substituted C₁-C₆ alkyl, or two of R$^{LP}$ together along with the carbons atoms to which they are attached and their intervening atoms define a C₅-C₆ heterocyclo and any remaining R$^{LP}$ are as previously defined; Ar is a C₆-C₁₀ arylene or a C₅-C₁₀ heteroarylene, optionally substituted;

each R$^E$ and R$^F$ is independently selected from the group consisting of —H, optionally substituted C₁-C₆ alkyl, optionally substituted C₂-C₆ alkylene, optionally substituted C₆-C₁₀ arylene and optionally substituted C₅-C₁₀ heteroarylene, or R$^E$ and R$^F$ together with the carbon atom to which both are attached defines an optionally substituted spiro C₃-C₆ carbocyclo, or R$^E$ and R$^F$ from adjacent carbon atoms together with these atoms and any intervening carbon atoms defines an optionally substituted C₅-C₆ carbocyclo with any remaining R$^E$ and R$^F$ as previously defined; and wherein one of the wavy lines indicates the site of covalent attachment of a PEG Unit and the other wavy lines indicates covalent attachment of Formula L$^P$-1 or Formula L$^P$-2 within the structure representing the Ligand Drug Conjugate composition.

63. The Ligand-Drug Conjugate composition of embodiment 58 wherein -L(PEG)- has the structure of Formula LE-3 or Formula LE-4:

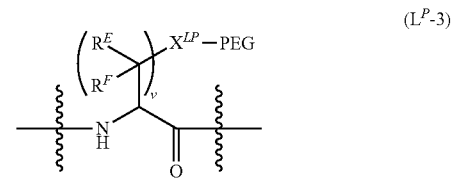

-continued

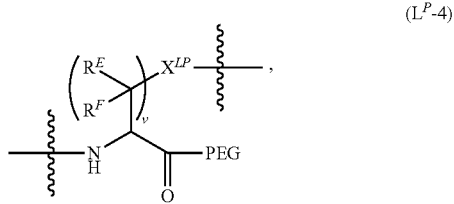
(L$^P$-4)

or a salt thereof, in particular a pharmaceutical acceptable salt thereof, wherein subscript v is an integer ranging from 1 to 4; X$^{LP}$ is selected from the group consisting of —O—, —NR$^{LP}$—, —S—, —S(=O)—, —S(=O)$_2$—, —C(=O)—, —C(=O)N(R$^{LP}$)—, —N(R$^{LP}$)C(=O)N(R$^{LP}$)—, —N(R$^{LP}$)C(=NR$^{LP}$)N(R$^{LP}$)—, and C$_3$-C$_8$ heterocyclo; wherein each R$^{LP}$ is independently selected from the group consisting of hydrogen and optionally substituted C$_1$-C$_6$ alkyl, or two of R$^{LP}$ together along with the carbons atoms to which they are attached and their intervening atoms define a C$_5$-C$_6$ heterocyclo and any remaining R$^{LP}$ are as previously defined; Ar is a C$_6$-C$_{10}$ arylene or a C$_5$-C$_{10}$ heteroarylene, optionally substituted;

each R$^E$ and R$^F$ is independently selected from the group consisting of —H, optionally substituted C$_1$-C$_6$ alkyl, optionally substituted C$_2$-C$_6$ alkylene, optionally substituted C$_6$-C$_{10}$ arylene and optionally substituted C$_5$-C$_{10}$ heteroarylene, or R$^E$ and R$^F$ together with the carbon atom to which both are attached defines an optionally substituted spiro C$_3$-C$_6$ carbocyclo, or R$^E$ and R$^F$ from adjacent carbon atoms together with these atoms and any intervening carbon atoms defines an optionally substituted C$_5$-C$_6$ carbocyclo with any remaining R$^E$ and R$^F$ as previously defined, or wherein the side chain of —[C(R$^E$)(R$^F$)]$_v$—X$^{LP}$— is provided by a natural or un-natural amino acid side chain; and wherein one of the wavy lines indicate the site of covalent attachment of a PEG Unit and the other wavy lines indicates covalent attachment of Formula L$^P$-1 or Formula L$^P$-2 within the structure representing the Ligand Drug Conjugate composition.

64. The Ligand-Drug Conjugate composition of embodiment 62 or 63 wherein R$^E$ and R$^F$ are independently selected from the group consisting of —H, and —C$_1$-C$_4$ alkyl.

65. The Ligand-Drug Conjugate composition of embodiment 62, 63 or 64 wherein X$^{LP}$ is selected from the group consisting of —O—, —NH, —S— and —C(=O)—.

66. The Ligand-Drug Conjugate composition of any one of embodiments 58 to 65 wherein PEG has the structure selected from the group consisting of

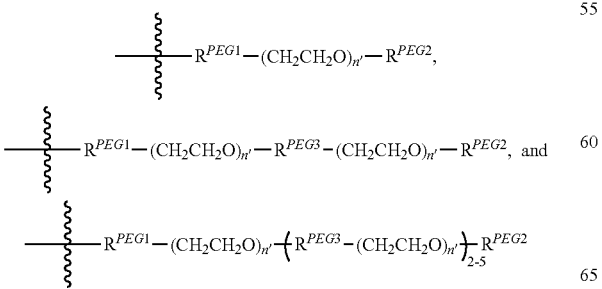

wherein the wavy line indicates site of attachment to X$^{LP}$ of the Parallel Connector Unit (L$^P$); subscript n' independently ranges from 1 to 72; R$^{PEG1}$ is an optional PEG Attachment Unit; R$^{PEG2}$ is a PEG Capping Unit; and R$^{PEG3}$ is an PEG Coupling Unit.

67. The Ligand-Drug Conjugate composition of any one of embodiments 58 to 65 wherein —X$^{LP}$—PEG has the structure of:

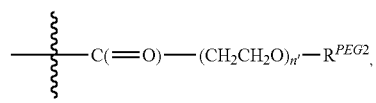

wherein subscript n' is 8, 12 or 24 and R$^{PEG2}$ is H or —CH$_3$.

68. The Ligand-Drug Conjugate composition of any one of embodiments 1 to 67 wherein A or a subunit thereof has the structure of formula (3) or formula (4):

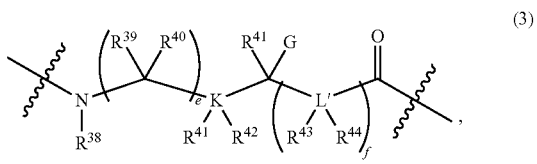
(3)

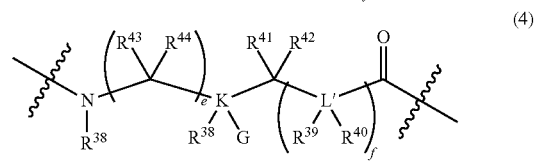
(4)

wherein the wavy lines indicated covalent attachment within the composition structure; wherein K and L' independently are C, N, O or S, provided that when K or L' is O or S, R$^{41}$ and R$^{42}$ to K or R$^{43}$ and R$^{44}$ to L' are absent, and when K or L' are N, one of R$^{41}$, R$^{42}$ to K or one of R$^{42}$, R$^{43}$ to L' are absent, and provided that no two adjacent L' are independently selected as N, O, or S; wherein subscripts e and f are independently selected integers that range from 0 to 12, and subscript g is an integer ranging from 1 to 12;

wherein G is hydrogen, optionally substituted C$_1$-C$_6$ alkyl, —OH, —OR$^{PR}$, —CO$_2$H, CO$_2$R$^{PR}$, wherein R$^{PR}$ is a suitable protecting, or G is —N(R$^{PR}$)(R$^{PR}$), wherein R$^{PR}$ are independently a protecting group or R$^{PR}$ together form a suitable protecting group, or G is —N(R$^{45}$)(R$^{46}$), wherein one of R$^{45}$, R$^{46}$ is hydrogen or R$^{PR}$, wherein R$^{PR}$ is a suitable protecting group, and the other is hydrogen or optionally substituted C$_1$-C$_6$ alkyl; wherein R$^{38}$ is hydrogen or optionally substituted C$_1$-C$_6$ alkyl;

R$^{39}$-R$^{44}$ are independently selected from the group consisting of hydrogen, optionally substituted C$_1$-C$_6$ alkyl, optionally substituted aryl, and optionally substituted heteroaryl, or R$^{39}$, R$^{40}$ together with the carbon atom to which both are attached, or R$^{41}$, R$^{42}$ together with K to which both are attached when K is a carbon atom, define a C$_3$-C$_6$ carbocyclo, and R$^{41}$-R$^{44}$ are as defined herein, or R$^{43}$, R$^4$ together with L' to which both are attached when L' is a carbon atom define a C$_3$-C$_6$ carbocyclo, and R$^{39}$-R$^{42}$ are as defined herein, or R$^{40}$ and R$^{41}$, or R$^{40}$ and R$^{43}$, or R$^{41}$ and R$^{43}$ to together with the carbon atom or heteroatom to which both are attached and the atoms intervening between those carbon atoms and/or heteroatoms define a $C_5$-$C_6$ carbocyclo or a $C_5$-$C_6$ heterocyclo, and $R^{39}$, $R^{44}$ and the remainder of $R^{40}$-$R^{43}$ are as defined herein, provided that when K is O or S, $R^{41}$ and $R^{42}$ are absent, and when K is N, one of $R^{41}$, $R^{42}$ is absent, and when L' is O or S, $R^{43}$ and $R^4$ are absent, and when L' is N, one of $R^{43}$, $R^{44}$ is absent, or A, or a subunit thereof, is an alpha-amino, beta-amino or another amine-containing acid residue.

69. The Ligand-Drug Conjugate composition of embodiment 68 wherein formula (3) or formula (4) has the structure of formula (3a) or formula (4a):

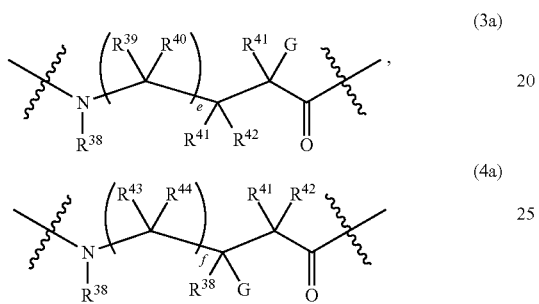

wherein subscript e and f are independently 0 or 1.

70. The Ligand-Drug Conjugate composition of any one of embodiments 1 to 69 wherein the Ligand Unit is an antibody, thereby defining an antibody Ligand Unit of an antibody drug conjugate (ADC), wherein the moiety targeted by the antibody Ligand Unit is an accessible cell-surface antigen of abnormal cells that is capable of cellular internalization when bound to ADC compound of the composition and is present in greater copy number on the abnormal cells in comparison to normal cells distant from the site of the abnormal cells.

71. The Ligand-Drug Conjugate composition of anyone of embodiments 1 to 69 wherein the Ligand Unit is a cognate ligand of an accessible cell-surface receptor on abnormal cell that is capable of cellular internalization when bound to a Ligand Drug Conjugate compound of the composition, and wherein the receptor is present in greater copy number on the abnormal cells in comparison to normal cells.

72. The Ligand-Drug Conjugate composition of any one of embodiments 1 to 69 wherein the Ligand Unit is an antibody, thereby defining an antibody Ligand Unit of an antibody drug conjugate (ADC), wherein the moiety targeted by the antibody Ligand Unit is an accessible cell-surface antigen of a vascular epithelial cell in the vicinity of abnormal cells, wherein said antigen is capable of cellular internalization of bound ADC and is present in greater copy number on said cells in comparison to normal epithelial cells distant from the site of the abnormal cells.

73. The Ligand Drug Conjugate composition of any one of embodiments 1 to 72 wherein subscript p is about 2, about 4, or about 8.

74. The Ligand Drug Conjugate composition of any one of the preceding embodiments in which a succinimide ($M^2$) or succinic acid amide ($M^3$) moeity is present the Ligand Unit is that of an antibody or antigen-binding fragment thereof, thereby defining an antibody Ligand Unit, wherein the sulfur atom of the antibody Ligand Unit bonded to the succinic acid ($M^2$) moiety or succinic acid amide ($M^3$) moiety is that of a cysteine residue of the antibody or antigen-binding fragment thereof.

75. The Ligand Drug Conjugate composition of embodiment 74 wherein the cysteine residue is an introduced cysteine residue in the heavy chain or light chain of the antibody or antigen binding-fragment thereof.

76. The Ligand Drug Conjugate composition of embodiment 1, wherein the composition is represented by the structure(s) of:

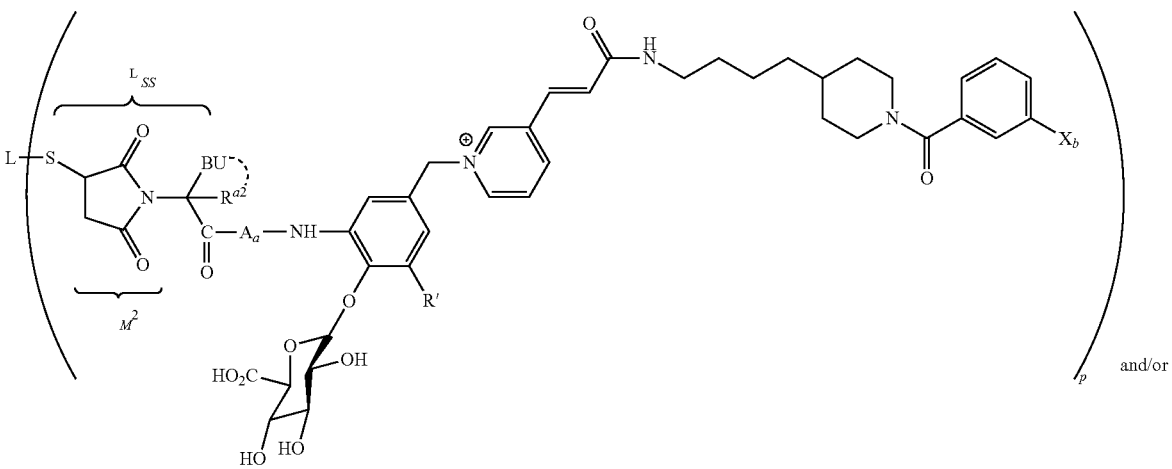

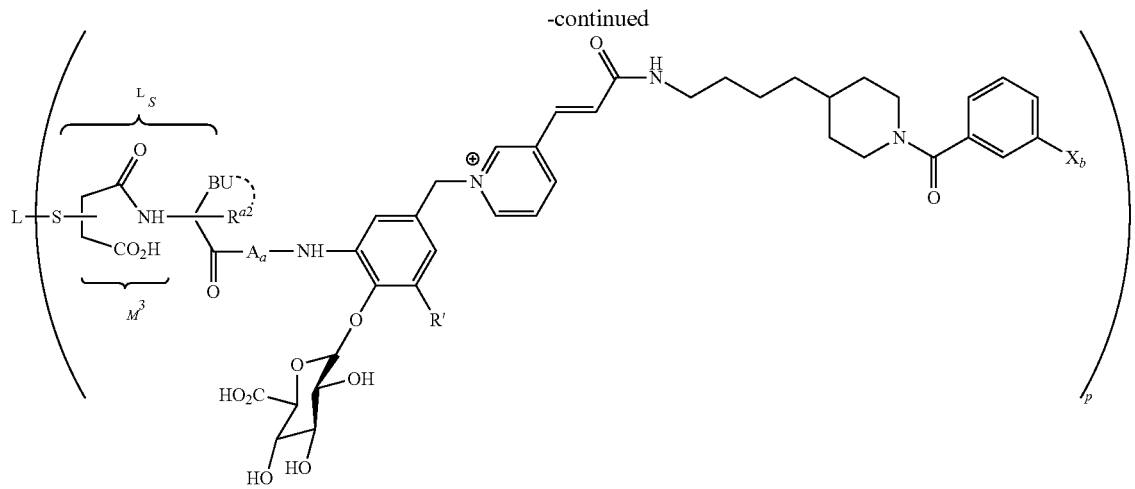

in salt form(s), in particular in pharmaceutical acceptable salt form(s), wherein L is an antibody, thereby defining an antibody Ligand Unit of an antibody drug conjugate (ADC), and S is a sulfur atom of the antibody; subscript a is 1 and A is an amino acid residue; BU is an acyclic Basic Unit so that the dotted curve line is absent, and $R^{a2}$ is hydrogen, or BU together with $R^{a2}$ as $C_1$-$C_6$ alkyl and the carbon atom to which both are attached define a cyclic Basic Unit so that the dotted curved line is present; and R' is hydrogen or $-NO_2$; and $X^b$ is $-H$, $-OH$ or $-NH_2$.

77. The Ligand Drug Conjugate composition of embodiment 1, wherein the composition is represented by the structure(s) of:

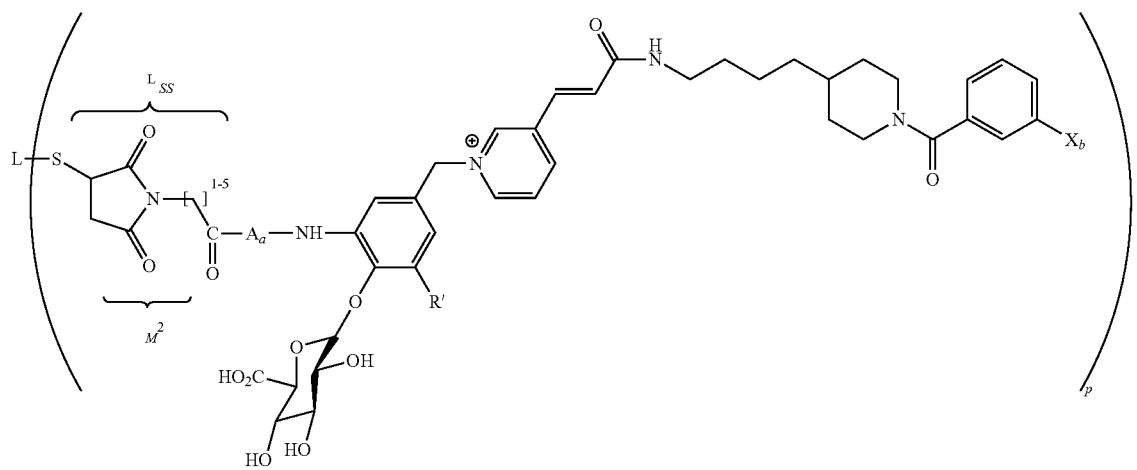

in salt form, in particular in pharmaceutical acceptable salt form, wherein
L is an antibody, thereby defining an antibody Ligand Unit of an antibody drug conjugate (ADC), and S is a sulfur atom of the antibody; subscript a is 1 and A is an amino acid residue; and R' is hydrogen or —NO$_2$; and X$^b$ is —H, —OH or —NH$_2$.

78. The Ligand Drug Conjugate composition of embodiment 76, wherein the composition is represented by the structure(s) of:

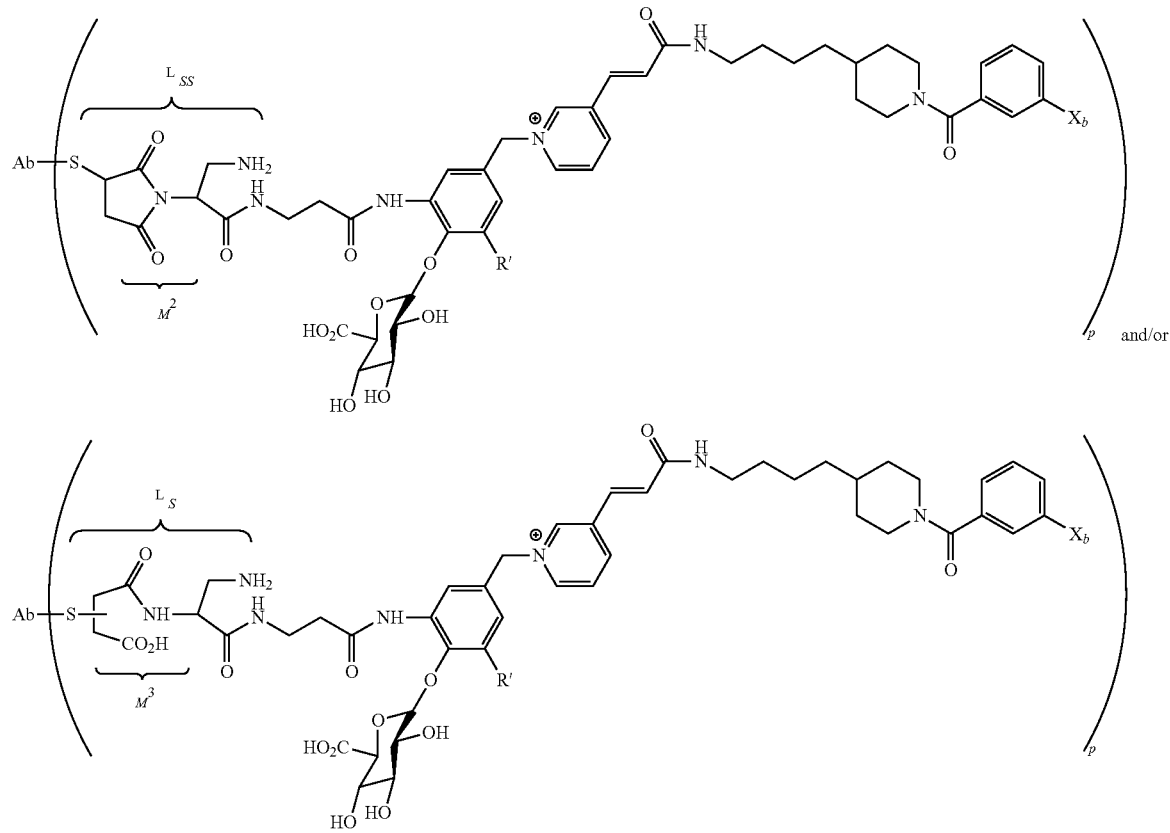

in salt form(s), in particular in pharmaceutical acceptable salt form(s), wherein Ab is an antibody Ligand Unit; S is a sulfur atom of the antibody; and subscript p is about 8.

79. The Ligand Drug Conjugate composition of embodiment 76, wherein the composition is represented by the structure(s) of:

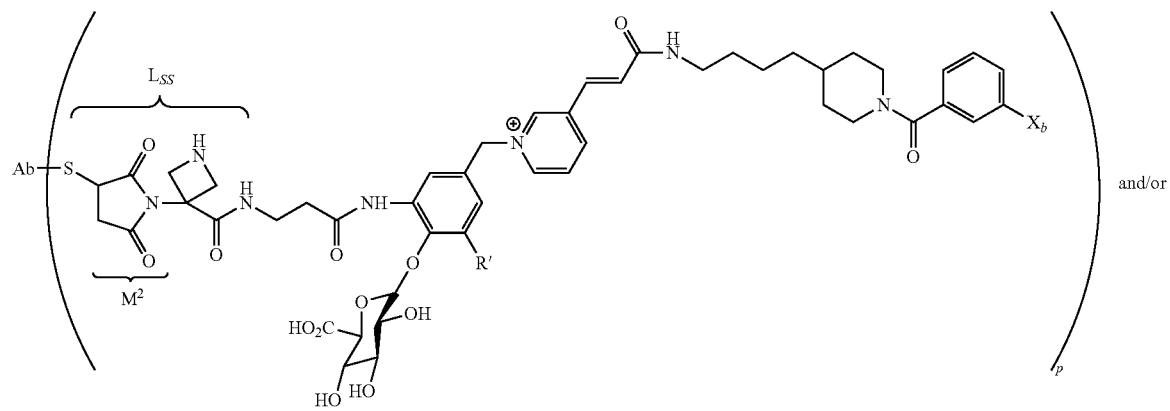

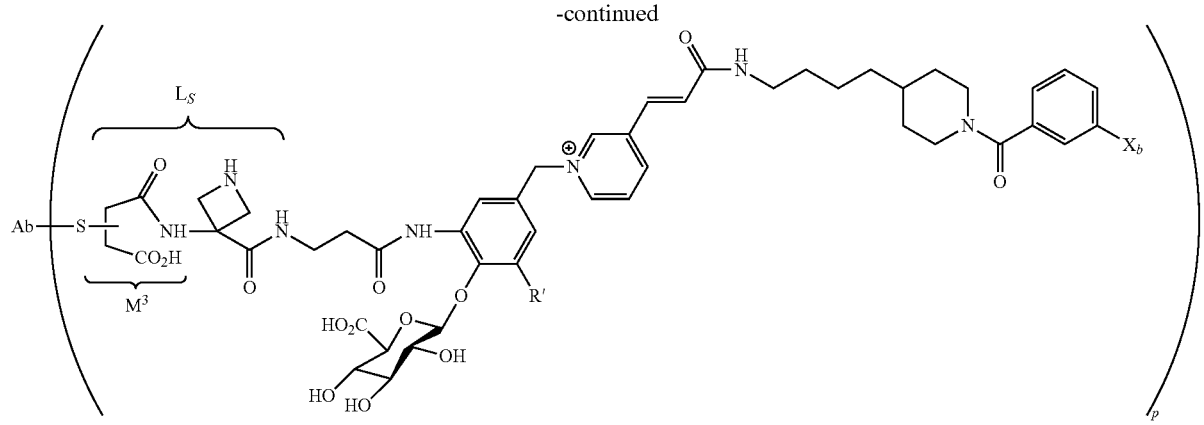
in salt form(s), in particular in pharmaceutical acceptable salt form(s), wherein Ab is an antibody Ligand Unit; S is a sulfur atom of the antibody; and subscript p is about 8.
80. The Ligand Drug Conjugate composition of embodiment 1, wherein the composition is represented by the structure(s) of:
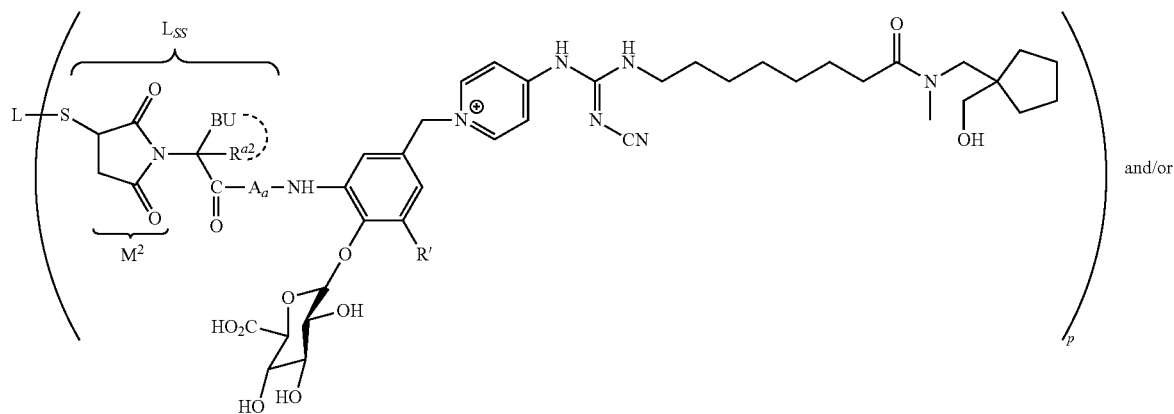
and/or
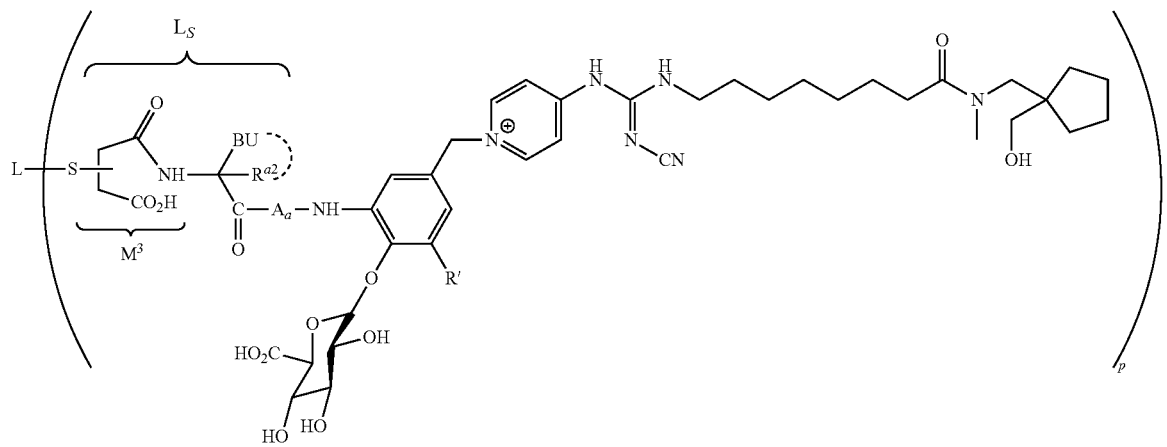

in salt form(s), in particular in pharmaceutical acceptable salt form(s), wherein L is an antibody, thereby defining an antibody Ligand Unit of an antibody drug conjugate (ADC), and S is a sulfur atom of the antibody; subscript a is 1 and A is an amino acid residue;

BU is an acyclic Basic Unit so that the dotted curve line is absent, and $R^{a2}$ is hydrogen, or BU together with $R^{a2}$ as $C_1$-$C_6$ alkyl and the carbon atom to which both are attached define a cyclic Basic Unit so that the dotted curved line is present; and R' is hydrogen or —$NO_2$; and $X^b$ is —H, —OH or —$NH_2$.

81. The Ligand Drug Conjugate composition of embodiment 1, wherein the composition is represented by the structure(s) of:

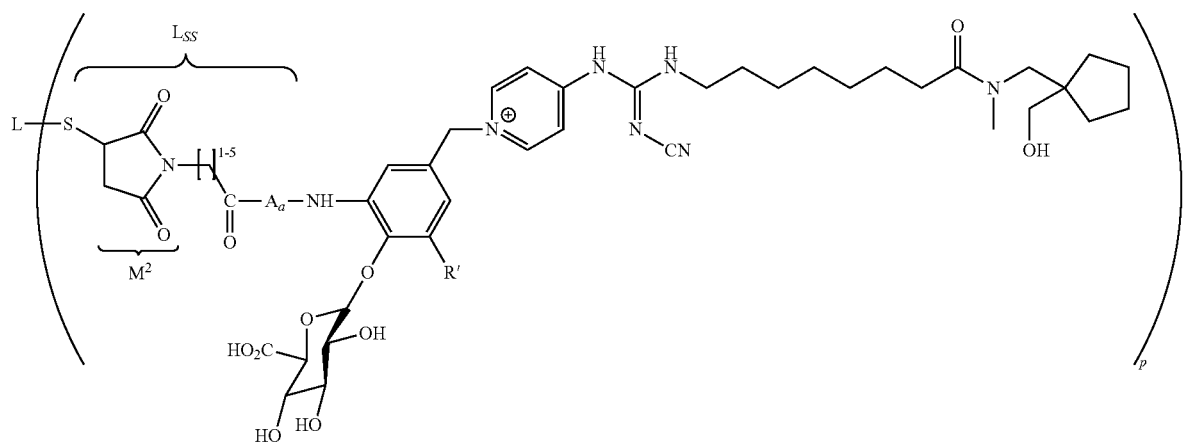

in salt form, in particular in pharmaceutical acceptable salt form, wherein L is an antibody, thereby defining an antibody Ligand Unit of an antibody drug conjugate (ADC), and S is a sulfur atom of the antibody; subscript a is 1 and A is an amino acid residue;

R' is hydrogen or —$NO_2$; and $X^b$ is —H, —OH or —$NH_2$.

82. The Ligand Drug Conjugate composition of embodiment 80, wherein the composition is represented by the structure(s) of:

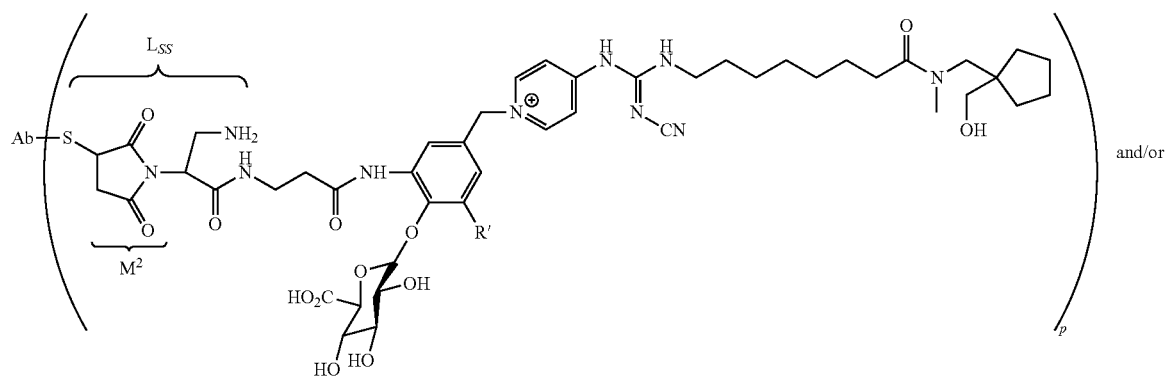

-continued
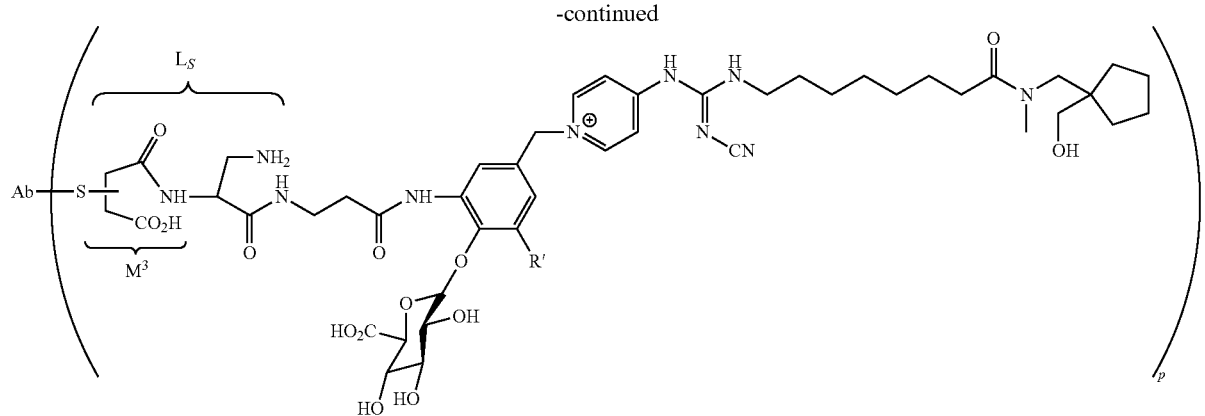
in salt form(s), in particular in pharmaceutical acceptable salt form(s), wherein Ab is an antibody Ligand Unit; S is a sulfur atom of the antibody; and subscript p is about 8.
83. The Ligand Drug Conjugate composition of embodiment 80, wherein the composition is represented by the structure(s) of:
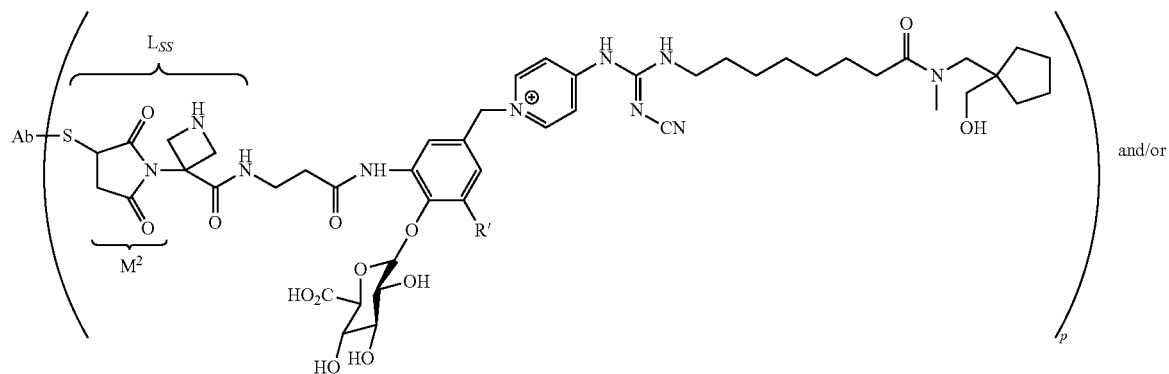
and/or
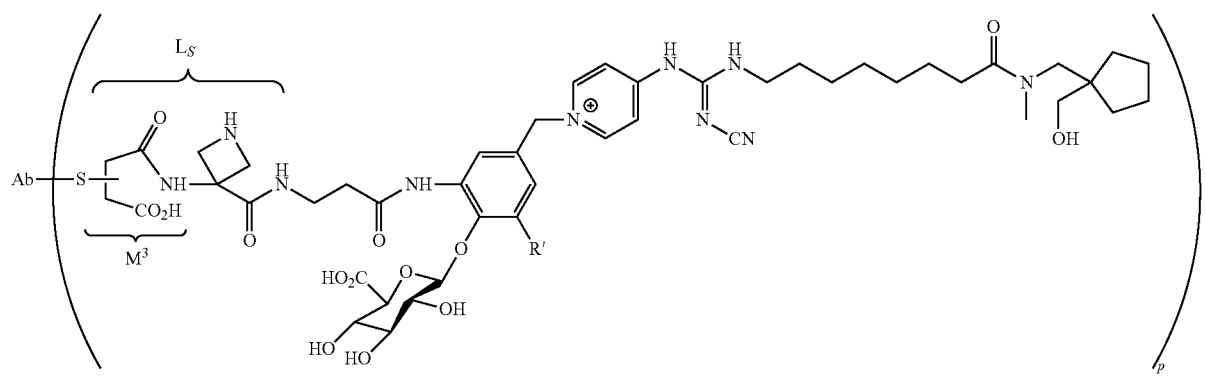

in salt form(s), in particular in pharmaceutical acceptable salt form(s), wherein Ab is an antibody Ligand Unit; S is a sulfur atom of the antibody; and subscript p is about 8.

84. The Ligand Drug Conjugate composition of embodiment 1, wherein the composition is represented by the structure(s) of:

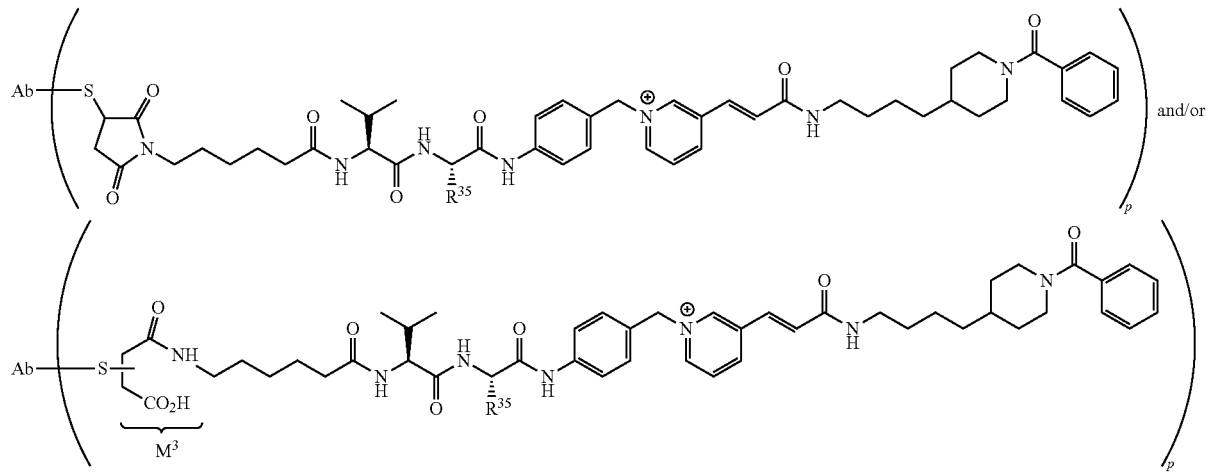

in salt form(s), in particular in pharmaceutical acceptable salt form(s), wherein Ab is an antibody Ligand Unit; S is a sulfur atom of the antibody; and subscript p is about 8.

85. The Ligand Drug Conjugate composition of embodiment 1, wherein the composition is represented by the structure(s) of:

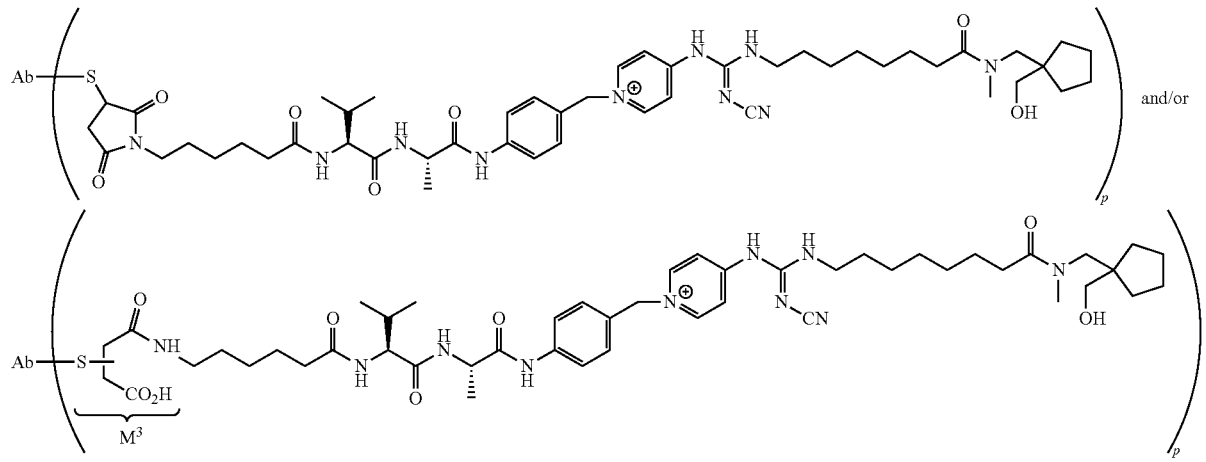

in salt form(s), in particular in pharmaceutical acceptable salt form(s), wherein Ab is an antibody Ligand Unit; S is a sulfur atom of the antibody; and subscript p is about 8.

86. A formulation comprising a Ligand Drug Conjugate or an Antibody Drug Conjugate composition of any one of embodiments 1 to 85 and one, two, three or more excipients.

87. The formulation of embodiment 86 wherein the formulation is a pharmaceutically acceptable formulation or a precursor thereof.

88. The formulation of embodiment 87 wherein the pharmaceutically acceptable formulation precursor is a solid suitable for reconstitution as a solution for intravenous injection to a subject.

89. The formulation of embodiment 87 wherein the pharmaceutically acceptable formulation is a liquid suitable for intravenous injection to a subject.

90. The formulation of claims of any one of embodiments 86 to 89 wherein the Ligand Drug Conjugate or Antibody Drug Conjugate composition is present in the formulation in an effective amount for treatment of a hyperproliferative disease or condition.
91. A method of treating a hyperproliferative disease or condition comprising the step of administering to a patient having said disease or condition an effective amount of a Ligand Drug Conjugate or Antibody Drug Conjugate composition of any one of embodiments 1 to 85.
92. The method of embodiment 91 wherein the hyperproliferative disease or condition is a cancer.
93. The method of embodiment 92 wherein the cancer is a leukemia or lymphoma.
94. A method of inhibiting the multiplication of a tumor cell or cancer cell, or causing apoptosis in a tumor or cancer cell, by exposing said cell with an effective amount of a Ligand Drug Conjugate or Antibody Drug Conjugate composition of any one of embodiments 1 to 85.
95. A Drug Linker Compound represented by Formula I:

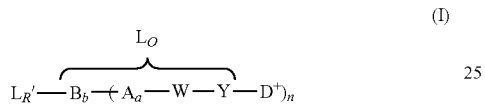
(I)

in salt form, particularly in pharmaceutically acceptable salt form, wherein $L_O$, as indicated, is an optional linker that is present;
W is a Peptide Cleavable Unit, or W—Y is replaced by a Glucuronide Unit of formula —Y(W'), wherein W' represents a carbohydrate moiety with glycosidic bonding to Y through an optionally substituted heteroatom; and Y is a self-immolative Spacer Unit comprised of a PAB or PAB-type moeity; $D^+$ is a quaternized NAMPT Drug Unit ($D^+$) covalently attached to the remainder of the Formula 1 composition structure through a quaternized skeletal aromatic nitrogen atom of an optionally substituted $C_5$-$C_{24}$ heteroaryl, or a quaternized skeletal non-aromatic nitrogen atom of a partially unsaturated or partially aromatic optionally substituted $C_9$-$C_{24}$ heterocyclyl,
wherein non-enzymatic or enzymatic action on W/W' of the Drug Linker compound or of a drug linker moiety of a Ligand Drug Conjugate compound prepared from the Drug Linker compound is capable of initiating release of the quaternized NAMPT Drug ($D^+$) Unit as a NAMPTi compound comprised of an optionally substituted $C_5$-$C_{24}$ or $C_9$-$C_{24}$ heteroaryl having the previously quaternized skeletal nitrogen atom;
$L_{R'}$ is a primary linker having a functional group capable of forming a covalent bond to a targeting moiety that becomes the Ligand Unit of a Ligand Drug Conjugate compound of Formula I in which subscript p is replaced by subscript p', wherein the other variable groups are as defined for that formula;
subscripts a and b independently are 0 or 1, indicating the absence or presence, respectively, of A or B; subscript n is 1, 2, 3 or 4; A is a first optional Stretcher Unit; B is a Branching Unit, when subscript b is 1 and subscript n is 2, 3 or 4, or B is absent, so that subscript b is 0, when subscript n is 1, wherein each of A and B is an independently selected single unit or is optionally comprised or consists of two, three or four independently selected subunits; and subscript p is a number ranging from 1 to 24 and subscript p' is an integer ranging from 1 to 24.
96. The Drug Linker compound of embodiment 95 wherein the quaternized NAMPT Drug Unit ($D^+$) is represented by the general structure of:

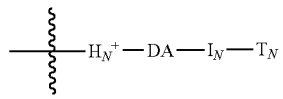

in salt form, particularly in pharmaceutically acceptable salt form,
wherein $H_{N^+}$ is a quaternized NAMPT Head Unit as the quaternized component of $D^+$ wherein the optionally substituted $C_5$-$C_{24}$ heteroaryl or partially unsaturated or partially aromatic optionally substituted $C_9$-$C_{24}$ heterocyclyl of that component is comprised of a 5- or 6-membered nitrogen-containing partially unsaturated or heteroaromatic ring system, a skeletal nitrogen atom of which is the site of quaternization to $L_O$, as indicated by the wavy line to $H_{N^+}$;
DA is a Donor-Acceptor Unit wherein the Donor-Acceptor Unit is or is comprised of a hydrogen bond donor or acceptor functional group and is bonded to a carbon skeletal atom at position 2 or 3 of the 5-membered nitrogen-containing partially unsaturated or heteroaromatic ring system or at position 3 or 4 of the 6-membered nitrogen-containing partially unsaturated or heteroaromatic ring system, with optional formal cyclization of DA back to an adjacent skeletal carbon atom of the 6-membered nitrogen-containing ring system through an introduced optionally substituted non-aromatic carbon atom or an optionally substituted nitrogen, oxygen or sulfur atom resulting in a partially unsaturated, partially aromatic or fully aromatic 6,5- or 6,6-fused ring system,
wherein said bonding of DA is in relation to a skeletal nitrogen atom of the 5- or 6-membered nitrogen-containing partially unsaturated or heteroaromatic ring system and wherein said formal cyclization to the adjacent carbon atom of the 6-membered nitrogen-containing partially unsaturated or heteroaromatic ring system substantially retains the hydrogen bonding ability of the donor or acceptor functional group of DA in absence of said cyclization;
$I_N$ is an Interconnecting Unit, wherein the Interconnecting Unit is or is comprised of —$X^1$—[C(=O)]$_{0,1}$—, —$X^1$—S(=O)$_{1,2}$—, —$X^2$—$C_6$-$C_{24}$ arylene-[C(=O)]$_{0,1}$—, —$X^2$—$C_6$-$C_{24}$ arylene-[S(=O)$_{1,2}$]$_{0,1}$, —$X^2$—$C_6$-$C_{24}$ arylene-O—, —$X^2$—$C_5$-$C_{24}$ heteroarylene-[C(=O)$_{0,1}$]—, —$X^2$—$C_5$-$C_{24}$ heteroarylene-[S(=O)$_{1,2}$]$_{0,1}$, —$X^2$—$C_5$-$C_{24}$ heteroarylene-O— or —$X^2$—$C_3$-$C_{20}$ heterocyclo-[C(=O)$_{0,1}$]-, wherein the arylene, heteroarylene and heterocyclo are optionally substituted; $X^1$ is optionally substituted $C_5$-$C_7$ alkylene; $X^2$ is absent or is an optionally substituted $C_1$-$C_4$alkylene;
$T_N$ is a NAMPT Tail Unit, wherein the NAMPT Tail Unit is or is comprised of an optionally substituted aminoalcohol residue or a carboxylic acid-alcohol residue, the amino nitrogen or carbonyl carbon of which is bonded to $I_N$, or $T_N$ is or is comprised of an optionally substituted benzamide moiety or a bioisostere thereof, the amide nitrogen atom of which is bonded to $I_N$ with optional cyclization of that atom back to $I_N$ or to the remainder of $T_N$, or $T_N$ is or is comprised of an optionally substituted $C_6$-$C_{24}$ aryl, $C_5$-$C_{24}$ heteroaryl or a combination thereof independently selected in the form of a biaryl, an aromatic atom of which is bonded to $I_N$ or the remainder of $T_N$;

and wherein $T_N$ or the remainder thereof is bond to $I_N$, wherein said remainder is an optionally substituted $C_2$-$C_7$ heteroalkylene or an optionally substituted $C_5$-$C_6$ heterocyclo, and wherein enzymatic action on W/W' of the Drug Linker compound or a drug linker moeity of a Ligand Drug Conjugate compound prepared from the Drug Linker compound releases the quaternized NAMPT Drug ($D^+$) Unit as a NAMPTi compound of formula $H_N$-DA-$I_N$-$T_N$, wherein $H_N$ is a NAMPT Head Unit that is a fully aromatic $C_5$-$C_{24}$ or $C_9$-$C_{24}$ heteroaryl, optionally substituted, comprised of a 5- or 6-membered nitrogen-containing heteroaromatic ring system having the previously quaternized skeletal nitrogen atom, and the other variable groups are as previously defined, wherein $H_N$— or $H_N$-DA- of the NAMPTi compound is capable of interacting with enzymatically competent NAMPT homodimer at its nicotinamide binding site.

97. The Drug Linker compound of claim 96 wherein the NAMPT Head ($H_N$) Unit is a pyridine mimetic and $H_{N^+}$ is that Unit in which a skeletal aromatic nitrogen atom of the pyridine mimetic is quaternized.

98. The Drug Linker compound of embodiment 96 or 97 wherein the Donor Acceptor (DA) Unit is comprised of an optionally substituted amide functional group or bioisostere thereof.

99. The Drug Linker compound of embodiment 96 wherein $H_N$-DA- is a nicotinamide mimetic and $H_{N^+}$-DA- is that mimetic in which a skeletal nitrogen atom of the 5- or 6-membered nitrogen-containing partially unsaturated or heteroaromatic ring system of $H_{N^+}$ is quaternized.

100. The Drug Linker compound of embodiment 96 wherein the 6-membered nitrogen-containing heteroaromatic ring system of the NAMPT Head Unit is that of pyridine with optional cyclization of DA back to the pyridine aromatic ring system through an introduced aromatic oxygen, sulfur or an optionally substituted nitrogen atom so that $H_N$ contains a 6-5 fused aromatic ring system and $H_{N^+}$ is that Unit in which the pyridine aromatic ring system is quaternized at its skeletal nitrogen atom.

101. The Drug Linker compound of any one of embodiments 96 to 100 wherein $H_N$ of the quaternized NAMPT Drug Unit released as a NAMPTi compound is capable of interacting with Phe 193 on one monomer of an enzymatically competent NAMPT homodimer and/or Tyr 18' of the other monomer, wherein the NAMPT monomers have the amino acid sequence of NCBI Reference Sequence NP_005737.1.

102. The Drug Linker compound of embodiment 101 wherein said NAMPT Head Unit interaction(s) is through π-π stacking with the aromatic side chain(s) of Phe 193 and/or Tyr 18'.

103. The Drug Linker compound of embodiment 96 wherein the NAMPT Head Unit has the structure of:

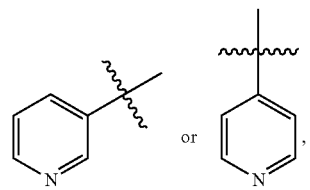 [SMILES: *c1cccnc1 ; *c1ccncc1]

or a salt thereof, in particular, a pharmaceutically acceptable salt thereof, and $H_{N^+}$ has the structure of:

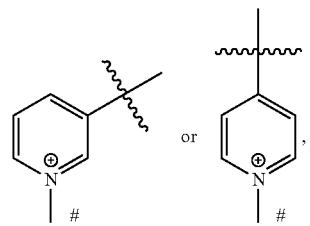

in salt form, particularly in pharmaceutically acceptable salt form, wherein the pound sign (#) indicates the point of covalent attachment to $L_O$; the wavy line indicates the site of covalent attachment to DA and an adjacent aromatic carbon atom thereto is the site of said optional formal cyclization by DA to $H_N/H_{N^+}$.

104. The Drug Linker compound of any one of embodiments 90 to 97 wherein the Donor Acceptor Unit (DA) is an acrylamide DA Unit, optionally cyclized to an adjacent skeletal carbon atom of the nitrogen-containing aromatic ring system of $H_N/H_{N^+}$ to which it is attached.

105. The Drug Linker compound of any one of embodiments 96 to 104 wherein the Donor Acceptor (DA) Unit of the quaternized NAMPT Drug ($D^+$) Unit on release as a NAMPTi compound is capable of interacting with one or more amino acid residues of an NAMPT monomer of an enzymatically competent NAMPT homodimer selected from the group consisting of Asp 219, Ser 241, Val 242 and Ser 275, wherein the NAMPT monomer has the amino acid sequence of NCBI Reference Sequence NP_005737.1.

106. The Drug Linker compound of embodiment 105 wherein said DA interaction(s) is hydrogen bonding either directly or indirectly through hydrogen bonding network(s) involving the intermediacy of water molecule(s).

107. The Drug Linker compound of any one of embodiments 96 to 104 wherein the Donor-Acceptor (DA) Unit has the structure of:

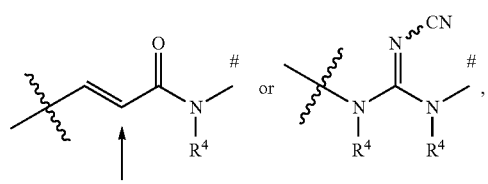

respectively, or a salt thereof, particularly a pharmaceutical acceptable salt thereof, wherein each $R^4$ is independently selected from the group consisting of hydrogen and optionally substituted $C_1$-$C_4$ alkyl; DA is optionally cyclized to $H_N/H_{N^+}$, wherein said cyclization is to the sp² carbon atom of the acrylamide DA Unit proximal to the carbonyl carbon (as indicated) through an introduced optionally substituted non-aromatic carbon atom or an optionally substituted aromatic heteroatom; the wavy line indicates the site of covalent attachment to $H_N/H_{N^+}$, and the indicated carbon atom adjacent thereto is the site of said optional cyclization by the acrylamide DA; and the pound sign (#) indicates the site of covalent attachment to $I_N$.

108. The Drug Linker compound of embodiment 101 wherein $H_N$-DA- has the structure of:

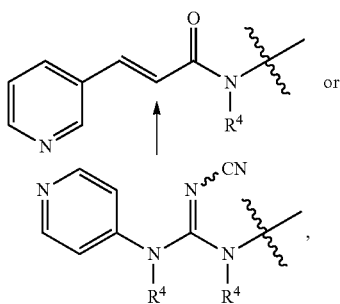

or a salt thereof, in particular, a pharmaceutically acceptable salt thereof, and $H_{N^+}$-DA has the structure of:

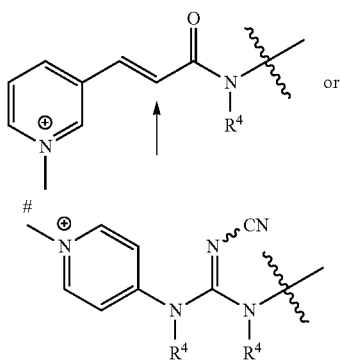

in salt form, in particular, in pharmaceutically acceptable salt form, wherein $R^4$ is independently selected from the group consisting of hydrogen and optionally substituted $C_1$-$C_4$ alkyl; and the pound sign (#) indicates the point of covalent attachment to $L_O$; the wavy line indicates the site of covalent attachment to $I_N$, and wherein the sp² carbon atom proximal to the carbonyl carbon is the site (as indicated) of optional cyclization to $H_N/H_{N^+}$ through an introduced optionally substituted non-aromatic carbon atom or an optionally substituted aromatic heteroatom.

109. The Drug Linker compound of any one of embodiments 96 to 108, wherein the NAMPT Tail ($T_N$) Unit or —$I_N$-$T_{N^-}$ of the quaternized NAMPT Drug ($D^+$) Unit on release as a NAMPTi compound is capable of interacting with one or more amino acid residues of a NAMPT monomer of an enzymatically competent NAMPT homodimer selected from the group consisting of Ile 309, Pro 307, Val 350, Ile 378 and Ala 379, wherein the NAMPT monomer has the amino acid sequence of NCBI Reference Sequence NP_005737.1.

110. The Drug Linker compound of any one of embodiments 96 to 108, wherein $T_N$ or —$I_N$-$T_{N^-}$ of the quaternized NAMPT Drug ($D^+$) Unit on release as a NAMPTi compound is capable of interacting with one or more amino acid residues of a NAMPT monomer of an enzymatically competent NAMPT homodimer selected from the group consisting of Tyr 188, Lys 189, Ala 379, Asn 377, Glu 376, Val 350, Arg 349 and Pro 307, wherein the NAMPT monomer has the amino acid sequence of NCBI Reference Sequence NP_005737.1.

111. The Drug Linker compound of any one of embodiments 96 to 108 wherein the NAMPT Tail ($T_N$) Unit is an amino alcohol moiety having the structure of:

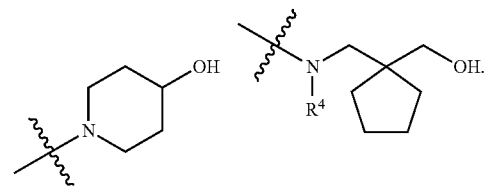

wherein $R^4$ is hydrogen or optionally substituted $C_1$-$C_4$ alkyl; and the wavy line indicates the site of covalent attachment to $I_N$.

112. The Drug Linker compound of any one of embodiments 96 to 108 wherein the NAMPT Tail ($T_N$) Unit is or is comprised of an optionally substituted benzamide covalently attached to $I_N$ or the remainder of $T_N$, through it amide nitrogen atom.

113. The Drug Linker compound of embodiment 112 wherein the NAMPT Tail ($T_N$) Unit is a benzamide moiety having the structure of:

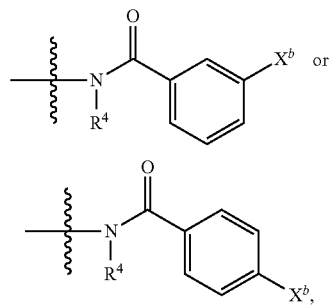

wherein $X^b$ is —H, halogen, —OH, optionally substituted $C_1$-$C_4$ alkoxy, optionally substituted $C_1$-$C_4$ alkyl or —$NH_2$, optionally substituted; $R^4$ is hydrogen or optionally substituted $C_1$-$C_4$ alkyl; the wavy line indicates the site of covalent attachment to $I_N$; and wherein the benzamide moiety is optionally cyclized to $I_N$ wherein the amide nitrogen of the benzamide moiety is the site of said cyclization so that $R^4$ is replaced by a covalent bond.

114. The Drug Linker compound of embodiment 113 wherein the benzamide moiety has the structure of:

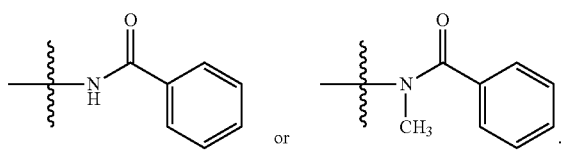 [SMILES: *NC(=O)c1ccccc1 ; *N(C)C(=O)c1ccccc1]

115. The Drug Linker compound of any one of embodiments 96 to 108 wherein the NAMPT Tail ($T_N$) Unit is or is comprised of an optionally substituted (hetero)aryl or biaryl moiety.
116. The Drug Linker compound of embodiment 115 wherein the NAMPT Tail Unit is an aryl, heteroaryl or biaryl moiety having a having the structure of:

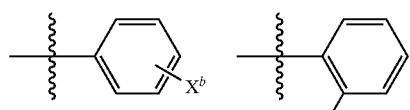

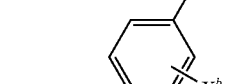

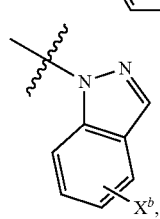

respectively, or a salt thereof, in particular, a pharmaceutically acceptable salt thereof, wherein $X^b$ is —H, halogen, —OH, optionally substituted $C_1$-$C_4$ alkoxy, optionally substituted $C_1$-$C_4$ alkyl or —$NH_2$, optionally substituted; the wavy line indicates the site of covalent attachment to $I_N$.
117. The Drug Linker compound of any one of embodiments 96 to 116 wherein $I_N$ of the quaternized NAMPT Drug ($D^+$) Unit on release as a NAMPTi compound is capable of interacting with one or more amino acids of a NAMPT monomer of an enzymatically competent NAMPT homodimer selected from the group consisting of Val 242, Ile 309, Ile 351, and His 191 of NAMPT, wherein the NAMPT monomer has the amino acid sequence of NCBI Reference Sequence NP_005737.1
118. The Drug Linker compound of any one of embodiments 96 to 116 wherein $I_N$ is —$CH_2$—$(CH_2)_{3-7}$—$CH_2$—, —$CH_2$—$(CH_2)_{3-7}$—$CH_2$—O—, —$CH_2$—$(CH_2)_{3-7}$—C(=O)—, —$CH_2$—$(CH_2)_{3-7}$—S(=O)$_2$— or —$CH_2$—$(CH_2)_{3-7}$—S(=O)—.
119. The Drug Linker compound of any one of embodiments 96 to 116 wherein $I_N$ has the structure of:

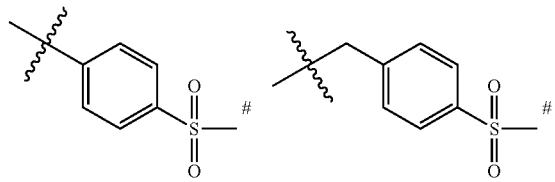

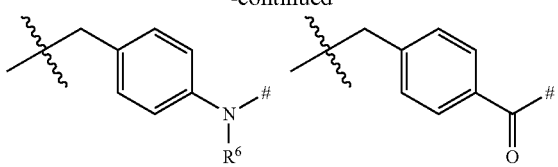

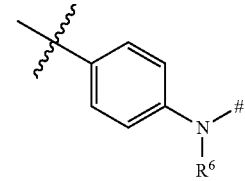

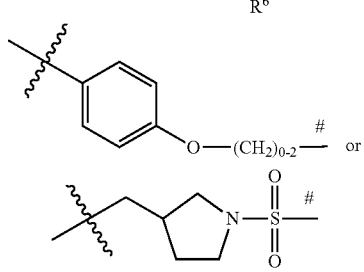

wherein the wavy line indicates the site of covalent attachment to DA and the pound sign (#) indicates the site of covalent attachment to $T_N$; and $R^6$ is hydrogen, $C_1$-$C_4$ alkyl, —$CH_2CH$=$C(CH_3)_2$, or —$CH_2$—C≡CH.
120. The Drug Linker compound of any one of embodiments 96 to 108, wherein —$I_N$-$T_N$ has the structure of:

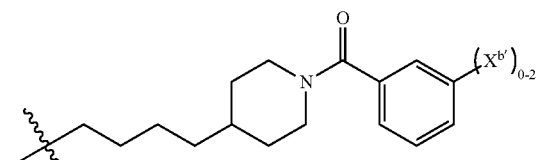

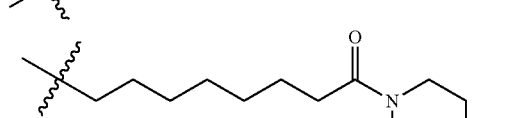

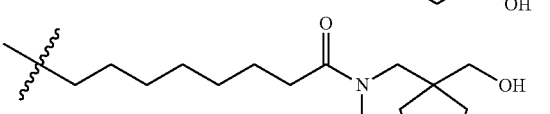

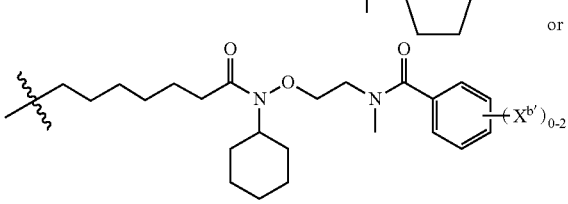

wherein $X^{b'}$ when present is independently selected from the group consisting of halogen, —OH, optionally substituted $C_1$-$C_4$ alkoxy, optionally substituted $C_1$-$C_4$ alkyl and —$NH_2$, optionally substituted; and the wavy line indicates the site of covalent attachment to DA.
121. The Drug Linker compound of any one of embodiments 96 to 108, wherein —$I_N$-$T_N$ has the structure of:

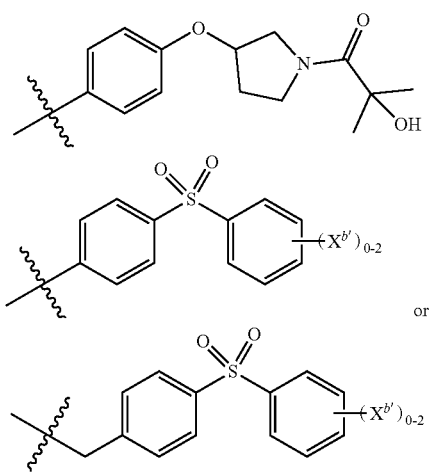

wherein $X^{b'}$ if present is selected from the group consisting of, —OH and NH$_2$, optionally substituted, and halogen, provided that when subscript n is 2 one of $X^b$ is —OH or —NH$_2$, optionally substituted, or halogen and the other is halogen; and the wavy line indicates the site of covalent attachment to DA.

122. The Drug Linker compound of embodiment 96 wherein the quaternized NAMPT Drug (D$^+$) Unit has the structure of:

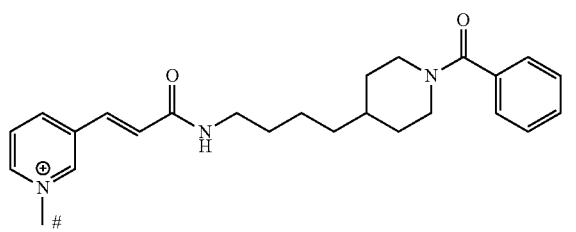 [SMILES: C[n+]1cccc(/C=C/C(=O)NCCCCC2CCN(C(=O)c3ccccc3)CC2)c1]

in salt form, particularly in pharmaceutically acceptable salt form, wherein the pound sign (#) indicates the site of quaternization by $L_O$.

123. The Drug Linker compound of any one of embodiments 95 to 122 wherein $L_{R'}$- has the structure of:

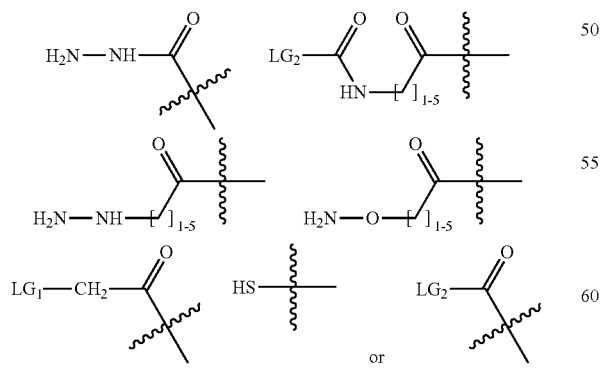

or a salt thereof, in particular, a pharmaceutically acceptable salt thereof, wherein $LG_1$ is a leaving group for nucleophillic displacement by a targeting agent nucleophile; $LG_2$ is a leaving group for amide bond formation to a targeting agent, or —OH to provide an activateable carboxylic acid for amide bond formation to a targeting agent; and the wavy line indicates the site of covalent attachment to the remainder of the Drug Linker compound structure.

124. The Drug Linker compound of any one of embodiments 95 to 122 wherein $L_{R'}$- has the structure of:

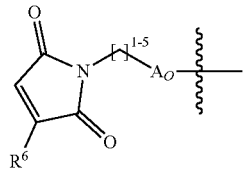

Wherein $R^6$ is hydrogen or an optionally substituted $C_1$-$C_6$ alkyl; $A_O$ is an second optional Stretcher Unit; and the wavy line indicates the site of covalent attachment to the remainder of the Drug Linker compound structure.

125. The Drug Linker compound of any one of embodiments 95 to 122 wherein $L_{R'}$- has the structure of:

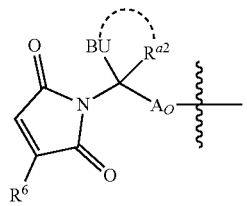

or a salt thereof, wherein L is a Ligand Unit and the indicated (#) sulfur atom is from the Ligand Unit; and $R^6$ is hydrogen or an optionally substituted $C_1$-$C_6$ alkyl; $A_O$ is a second optional Stretcher Unit; BU is a Basic Unit; $R^{a2}$ is optionally substituted $C_1$-$C_{12}$ alkyl; the dotted curved line indicates optional cyclization so that in the absence of said cyclization;

BU is an acyclic Basic Unit or in the presence of said cyclization BU is a cyclized Basic Unit in which $R^2$ and BU together with the carbon atom to which both are attached, define an optionally substituted spiro $C_3$-$C_{20}$ heterocyclo containing a skeletal basic nitrogen atom of a secondary or tertiary amine functional group of BU, wherein the basic nitrogen atom of the acyclic Basic Unit or cyclic Basic Unit is optionally suitably protected by a nitrogen protecting group, dependent on the degree of substitution of the basic nitrogen atom, or is optionally protonated; and the wavy line indicates the site of covalent attachment to the remainder of the Drug Linker compound structure.

126. The Drug Linker compound of embodiment 124 wherein $L_{R'}$- has the structure of:

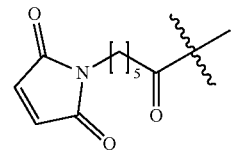

127. The Drug Linker compound of embodiment 125 wherein $L_{R'}$ has the structure of:

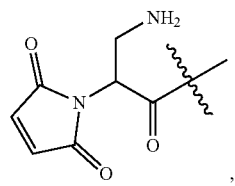 [SMILES: *C(=O)C(CN)N1C(=O)C=CC1=O]

or a salt thereof, in particular, a pharmaceutically acceptable salt thereof.

128. The Drug Linker compound of embodiment 125 wherein $L_{R'}$ has the structure of:

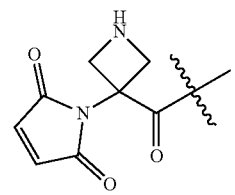 [SMILES: *C(=O)C1(N2C(=O)C=CC2=O)CNC1]

or a salt thereof, in particular, a pharmaceutically acceptable salt thereof.

129. The Drug Linker compound of embodiment 95 wherein the compound is represented by the structure(s) of Formula Ia or Formula Ib:

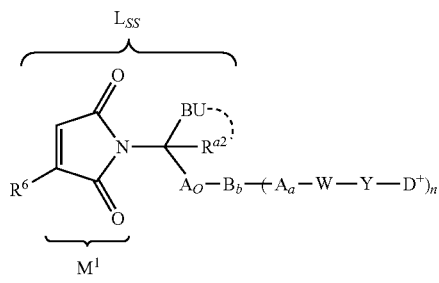
(Formula Ia)

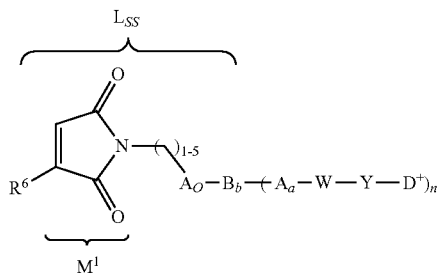
(Formula Ib)

or a salt thereof, in particular, a pharmaceutically acceptable salt thereof, wherein $R^6$ is hydrogen or an optionally substituted $C_1$-$C_6$ alkyl;
$A_O$ is a second optional Stretcher Unit; and
W is a Peptide Cleavable Unit, or
W—Y is replaced by a Glucuronide Unit of formula —Y(W')—, wherein W' represents a carbohydrate moiety with glycosidic bonding to Y through an optionally substituted heteroatom;
Y is a self-immolative Spacer Unit comprised of a PAB or PAB-type moeity;
wherein enzymatic action upon W/W' of the Drug Linker compound or a drug linker moeity of a Ligand Drug Conjugate compound prepared from the Drug Linker compound initiates release of the quaternized NAMPT Drug ($D^+$) Unit as a NAMPTi compound.

130. The Drug Linker compound of embodiment 129, wherein the compound is represented by the structure(s) of:

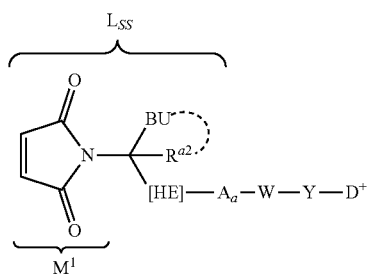

or a salt thereof, in particular, a pharmaceutically acceptable salt thereof, wherein

[HE] as $A_O$ is an optional Hydrolysis Enhancing Unit;
W is Peptide Cleavable Unit, and Y is a self-immolative Spacer Unit comprised of a PAB or PAB-type moeity, wherein protease action on the Peptide Cleavable Unit resulting in cleavage of the W-J' bond within the Drug Linker compound or a drug linker moeity of a Ligand Drug Conjugate compound prepared from the Drug Linker compound initiates release of the quaternized NAMPT Drug Unit ($D^+$) as NAMPTi compound from that Ligand Drug Conjugate compound, or
W—Y is replaced by a Glucuronide Unit of formula —Y(W')— having the structure of:

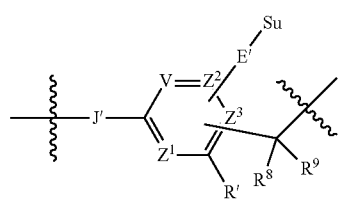

wherein Su is a carbohydrate moiety and -E'- represents an optionally substituted heteroatom of an glycosidic bond cleavable by a glycosidase so that Su-E' is W' and the remainder of the Glucuronide Unit structure is a self-immolative Spacer Unit bonded to W";
J' is an independently selected heteroatom, optionally substituted;
V, $Z^1$, $Z^2$ and $Z^3$ are independently =N— or =C($R^{24}$)—, wherein each $R^{24}$ is independently selected from the group consisting of hydrogen and $C_1$-$C_{12}$ alkyl, $C_2$-$C_{12}$ alkenyl and $C_2$-$C_{12}$ alkynyl, optionally substituted, and halogen, an electron withdrawing group, an electron donating group, -E'-Su, and —C($R^8$)($R^9$)—,
provided that one and only one —C($R^8$)($R^9$)— moiety and one and only one -E'-Su moiety is present,
wherein one of V, $Z^1$, $Z^2$ and $Z^3$ is =C($R^{24}$)— in which $R^{24}$ is —C($R^8$)($R^9$)— and another of V, $Z^1$, $Z^2$ and $Z^3$ is =C($R^{24}$)— in which $R^{24}$ is -E'-Su, provided the —C(R⁸)(R⁹)— and -E'-Su moieties are ortho or para to each other;

R⁸ and R⁹ independently are hydrogen, or $C_1$-$C_{12}$ alkyl, $C_2$-$C_{12}$ alkenyl or $C_2$-$C_{12}$ alkynyl, optionally substituted, or $C_6$-$C_{20}$ aryl or $C_5$-$C_{20}$ heteroaryl, optionally substituted, or R⁸ and R⁹ together with the carbon atom to which both are attached define an optionally substituted $C_5$-$C_{20}$ carbocyclo; and R' is hydrogen or —NO₂, or other electron withdrawing group or —$OC_1$-$C_6$ alkyl, or other electron donating group; and wherein the wavy line adjacent to J' indicates the site of covalent attachment of the Glucuronide Unit to A when subscript a is 1 or to the indicated $L_{SS}$ or $L_S$ primary linker when subscript a is 0; and the wavy line adjacent to the —C(R⁸)(R⁹)— moiety indicates the site of covalent attachment of the Glucuronide Unit to D⁺; and wherein glycosidase action on the Glucuronide Unit resulting in cleavage of its glycosidic bond initiates release of the quaternized NAMPT Drug Unit (D⁺) as NAMPTi compound from the Drug Linker compound or a drug linker moiety of a Ligand Drug Conjugate compound prepared from the Drug Linker compound;

wherein the Ligand Drug Conjugate compound is of corresponding structure to the composition of Formula 1 in which subscript p is replaced by p'; and wherein the basic functional group of BU is optionally protonated, or the basic nitrogen atom thereof is optionally protected.

131. The Drug Linker compound of embodiment 130, wherein the compound is represented by the structure(s) of:

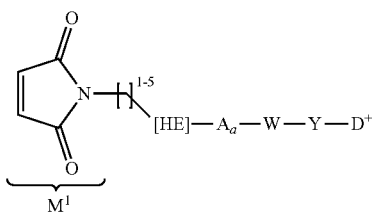

in salt form, in particular, in pharmaceutically acceptable salt form, wherein

[HE] as $A_O$ is an optional Hydrolysis Enhancing Unit;

W is Peptide Cleavable Unit, and Y is a self-immolative Spacer Unit comprised of a PAB or PAB-type moeity, wherein protease action on the Peptide Cleavable Unit resulting in cleavage of the W-J' bond within the Drug Linker compound or a drug linker moiety of a Ligand Drug Conjugate compound prepared from the Drug Linker compound initiates release of the quaternized NAMPT Drug Unit (D⁺) as NAMPTi compound, or W—Y is replaced by a Glucuronide Unit of formula —Y(W')— having the structure of:

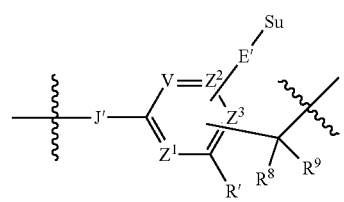

wherein Su is a carbohydrate moiety and -E'- represents an optionally substituted heteroatom of an glycosidic bond cleavable by a glycosidase so that Su-E' is W' and the remainder of the Glucuronide Unit structure is a self-immolative Spacer Unit bonded to W';

J' is an independently selected heteroatom, optionally substituted;

V, $Z^1$, $Z^2$ and $Z^3$ are independently =N— or =C($R^{24}$)—, wherein each $R^{24}$ is independently selected from the group consisting of hydrogen and $C_1$-$C_{12}$ alkyl, $C_2$-$C_{12}$ alkenyl and $C_2$-$C_{12}$ alkynyl, optionally substituted, and halogen, an electron withdrawing group, an electron donating group, -E'-Su, and —C(R⁸)(R⁹)—, provided that one and only one —C(R⁸)(R⁹)— moiety and one and only one -E'-Su moiety is present, wherein one of V, $Z^1$, $Z^2$ and $Z^3$ is =C($R^{24}$)— in which $R^{24}$ is —C(R⁸)(R⁹)— and another of V, $Z^1$, $Z^2$ and $Z^3$ is =C($R^{24}$)— in which $R^{24}$ is -E'-Su, provided the —C(R⁸)(R⁹)— and -E'-Su moieties are ortho or para to each other;

R⁸ and R⁹ independently are hydrogen, or $C_1$-$C_{12}$ alkyl, $C_2$-$C_{12}$ alkenyl or $C_2$-$C_{12}$ alkynyl, optionally substituted, or $C_6$-$C_{20}$ aryl or $C_5$-$C_{20}$ heteroaryl, optionally substituted, or R⁸ and R⁹ together with the carbon atom to which both are attached define an optionally substituted $C_5$-$C_{20}$ carbocyclo; and R' is hydrogen or —NO₂, or other electron withdrawing group or —$OC_1$-$C_6$ alkyl, or other electron donating group; and wherein the wavy line adjacent to J' indicates the site of covalent attachment of the Glucuronide Unit to A when subscript a is 1 or to the indicated $L_{SS}$ or $L_S$ primary linker when subscript a is 0; and the wavy line adjacent to the —C(R⁸)(R⁹)— moiety indicates the site of covalent attachment of the Glucuronide Unit to D⁺; and wherein glycosidase action on the Glucuronide Unit resulting in cleavage of its glycosidic bond within the Drug Linker compound or a drug linker moiety of a Ligand Drug Conjugate compound prepared from the Drug Linker compound initiates release of the quaternized NAMPT Drug (D⁺) Unit as a NAMPTi compound.

132. The Drug Linker compound of any one of embodiment 129 to 131 wherein the quaternized NAMPT Drug Unit (D⁺) is represented by the general structure of:

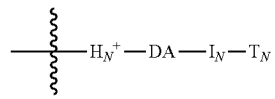

in salt form, particularly in pharmaceutically acceptable salt from, wherein $H_{N^+}$ is a quaternized NAMPT Head Unit as the quaternized component of D⁺ wherein the optionally substituted $C_5$-$C_{24}$ heteroaryl or partially unsaturated or partially aromatic optionally substituted $C_9$-$C_{24}$ heterocyclyl of that component is comprised of a 5- or 6-membered nitrogen-containing partially unsaturated or heteroaromatic ring system, a skeletal nitrogen atom of which is the site of quaternization to $L_O$, as indicated by the wavy line to $H_{N^+}$;

DA is a Donor-Acceptor Unit wherein the Donor-Acceptor Unit is or is comprised of a hydrogen bond donor or acceptor functional group and is bonded to a carbon skeletal atom at position 2 or 3 of the 5-membered nitrogen-containing partially unsaturated or heteroaromatic ring system or at position 3 or 4 of the 6-membered nitrogen-containing partially unsaturated or heteroaromatic ring system, with optional formal cyclization of DA back to an adjacent skeletal carbon atom of the 6-membered nitrogen-containing ring system through an introduced optionally substituted non-aromatic carbon atom or an optionally substituted nitrogen, oxygen or sulfur atom resulting in a partially unsaturated, partially aromatic or fully aromatic 6,5- or 6,6-fused ring system, wherein said bonding of DA is in relation to a skeletal nitrogen atom of the 5- or 6-membered nitrogen-containing partially unsaturated or heteroaromatic ring system and wherein said formal cyclization to the adjacent carbon atom of the 6-membered nitrogen-containing partially unsaturated or heteroaromatic ring system substantially retains the hydrogen bonding ability of the donor or acceptor functional group of DA in absence of said cyclization;

$I_N$ is an Interconnecting Unit, wherein the Interconnecting Unit is or is comprised of —$X^1$—[C(=O)]$_{0,1}$—, —$X^1$—S(=O)$_{1,2}$—, —$X^2$—$C_6$-$C_{24}$ arylene-[C(=O)]$_{0,1}$—, —$X^2$—$C_6$-$C_{24}$ arylene-[S(=O)$_{1,2}$]$_{0,1}$, —$X^2$—$C_6$-$C_{24}$ arylene-O—, —$X^2$—$C_5$-$C_{24}$ heteroarylene-[C(=O)$_{0,1}$]-, —$X^2$—$C_5$-$C_{24}$ heteroarylene-[S(=O)$_{1,2}$]$_{0,1}$, —$X^2$—$C_5$-$C_{24}$ heteroarylene-O— or —$X^2$—$C_3$-$C_{20}$ heterocyclo-[C(=O)$_{0,1}$]-, wherein the arylene, heteroarylene and heterocyclo are optionally substituted;

$X^1$ is optionally substituted $C_5$-$C_7$ alkylene;

$X^2$ is absent or is an optionally substituted $C_1$-$C_4$ alkylene;

$T_N$ is a NAMPT Tail Unit, wherein the NAMPT Tail Unit is or is comprised of an optionally substituted amino-alcohol residue or a carboxylic acid-alcohol residue, the amino nitrogen or carbonyl carbon of which is bonded to $I_N$, or $T_N$ is or is comprised of an optionally substituted benzamide moiety or a bioisostere thereof, the amide nitrogen atom of which is bonded to $I_N$ with optional cyclization of that atom back to $I_N$ or to the remainder of $T_N$, or $T_N$ is or is comprised of an optionally substituted $C_6$-$C_{24}$ aryl, $C_5$-$C_{24}$ heteroaryl or a combination thereof independently selected in the form of a biaryl, an aromatic atom of which is bonded to $I_N$ or the remainder of $T_N$; and wherein $T_N$ or the remainder thereof is bond to $I_N$, wherein said remainder is an optionally substituted $C_2$-$C_7$ heteroalkylene or an optionally substituted $C_5$-$C_6$ heterocyclo, and wherein enzymatic action on W/W' of the Drug Linker compound or a drug linker moiety of a Ligand Drug Conjugate compound prepared from the Drug Linker compound releases the quaternized NAMPT Drug (D$^+$) Unit as a NAMPTi compound of formula H$_N$-DA-I$_N$-T$_N$, wherein H$_N$ is a NAMPT Head Unit that is a fully aromatic $C_5$-$C_{24}$ or $C_9$-$C_{24}$ heteroaryl, optionally substituted, comprised of a 5- or 6-membered nitrogen-containing heteroaromatic ring system having the previously quaternized skeletal nitrogen atom, and the other variable groups are as previously defined, wherein H$_N$— or H$_N$-DA- of the NAMPTi compound is capable of interacting with enzymatically competent NAMPT homodimer at its nicotinamide binding site.

133. The Drug Linker compound of embodiment 132 wherein W—Y is replaced by a Glucuronide Unit of formula —Y(W')— for which —Y(W')-D$^+$ has the structure of:

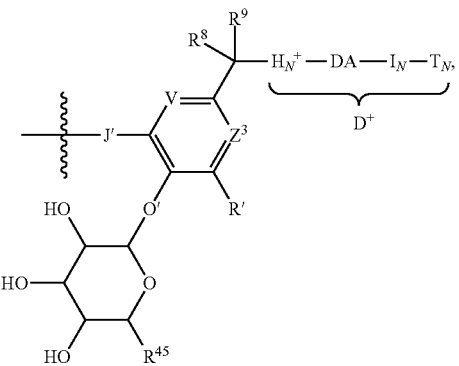

in salt form, particularly in pharmaceutically acceptable salt from, wherein

R' is hydrogen or —NO$_2$ or other electron withdrawing group; and

R$^{45}$ is —CH$_2$OH or —CO$_2$H.

134. The Drug Linker compound of embodiment 132, wherein W is a Peptide Cleavable Unit for which —Y-D$^+$ has the structure of:

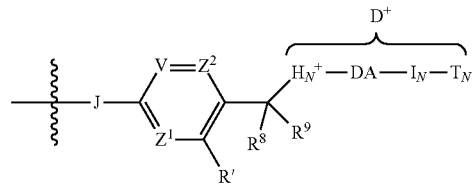

or a pharmaceutical acceptable salt thereof, wherein

R' is hydrogen or —OC$_1$-C$_6$ alkyl or other electron donating group;

J is an optionally substituted heteroatom bonded to W as indicated by the wavy line, wherein cleavage of that bond within the Drug Linker compound or a drug linker moiety of a Ligand Drug Conjugate compound prepared from the Drug Linker compound initiates release of the quaternized NAMPT Drug (D$^+$) Unit as a NAMPTi compound of formula H$_N$-DA-I$_N$-T$_N$.

135. The Drug Linker compound or compound of embodiment 132, wherein the compound is represented by the structure of:

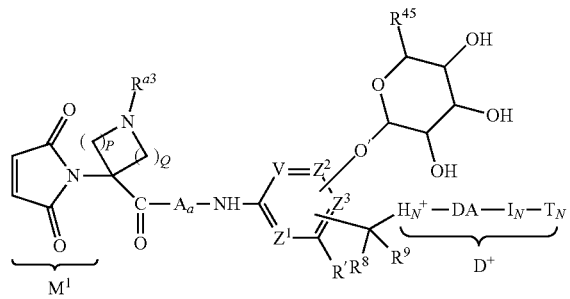

in salt form, particularly in pharmaceutically acceptable salt from, wherein subscript P is 1, 2 or 3;

subscript Q ranges from 1 to 6;

R' is hydrogen or —NO$_2$ or other electron withdrawing group;

R$^{45}$ is —CH$_2$OH or —CO$_2$H;

R$^{a3}$ is —H, or optionally substituted C$_1$-C$_6$ alkyl, optionally substituted —C$_1$-C$_4$ alkylene-(C$_6$-C$_{10}$ aryl), or —R$^{PEG1}$—O—(CH$_2$CH$_2$O)$_{1-36}$—R$^{PEG2}$, wherein R$^{PEG1}$ is C$_1$-C$_4$ alkylene, and R$^{PEG2}$ is —H or C$_1$-C$_4$ alkyl; and wherein the basic nitrogen atom bonded to R$^{a3}$ is optionally protonated, or R$^{a3}$ is a suitable amine protecting group, and wherein —O'— represents the oxygen heteroatom of an O-glycosidic bond cleavable by a glycosidase, wherein said cleavage within the Drug Linker compound or a drug linker moeity of a Ligand Drug Conjugate compound prepared from the Drug Linker compound initiates release of the quaternized NAMPT Drug (D$^+$) Unit as a NAMPTi compound.

136. The Drug Linker compound of embodiment 132, wherein the compound is represented by the structure of:

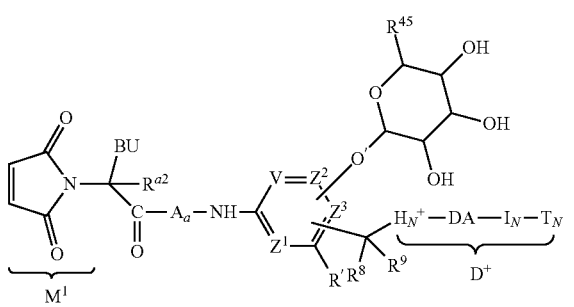

in salt form, particularly in pharmaceutically acceptable salt from, wherein subscript P is 1, 2 or 3;

subscript Q ranges from 1 to 6;

R' is hydrogen or —NO$_2$ or other electron withdrawing group;

R$^{45}$ is —CH$_2$OH or —CO$_2$H;

R$^{a2}$ is hydrogen or C$_1$-C$_6$ alkyl;

BU has the structure of —[C(R$^{a1}$)(R$^{a1}$)]—[C(R$^{a1}$)(R$^{a1}$)]$_{0-3}$—N(R$^{a3}$)(R$^{a3}$), each R$^{a1}$ independently is hydrogen or C$_1$-C$_4$ alkyl, C$_6$-C$_{10}$ aryl, C$_5$-C$_{10}$ heteroaryl, (C$_6$-C$_{10}$ aryl)-C$_1$-C$_4$ alkyl-, or (C$_5$-C$_{10}$ heteroaryl)-C$_1$-C$_4$ alkyl-, optionally substituted, or two R$^{a1}$ together with the carbon(s) to which they are attached and any intervening carbons define an optionally substituted C$_3$-C$_6$ cycloalkyl; R$^{a3}$ independently are hydrogen, optionally substituted C$_1$-C$_6$ alkyl or R$^{a3}$ together with the nitrogen atom to which both are attached define a C$_3$-C$_6$ heterocyclyl in which the basic nitrogen is a skeletal atom;

wherein the basic functional group of BU is optionally protonated, or the basic nitrogen atom thereof is optionally protected; and wherein —O'— represents the oxygen atom of an O-glycosidic bond cleavable by a glycosidase, wherein said cleavage within the Drug Linker compound or a drug linker moeity of a Ligand Drug Conjugate compound prepared from the Drug Linker compound initiates release of the quaternized NAMPT Drug (D$^+$) Unit as a NAMPTi compound.

137. The Drug Linker compound of embodiment 132, wherein the compound is represented by the structure of:

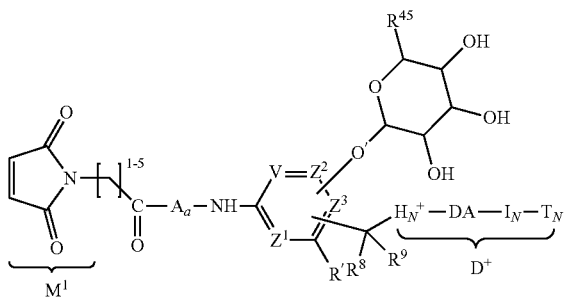

in salt form, particularly in pharmaceutically acceptable salt from, wherein subscript P is 1, 2 or 3;

subscript Q ranges from 1 to 6;

R' is hydrogen or —NO$_2$ or other electron withdrawing group;

R$^{45}$ is —CH$_2$OH or —CO$_2$H;

R$^{a2}$ is hydrogen or C$_1$-C$_6$ alkyl; and wherein —O'— represents the oxygen atom of an O-glycosidic bond cleavable by a glycosidase, wherein said cleavage within the Drug Linker compound or a drug linker moeity of a Ligand Drug Conjugate compound prepared from the Drug Linker compound initiates release of the quaternized NAMPT Drug (D$^+$) Unit as a NAMPTi compound.

138. The Drug Linker embodiment of embodiment 132, wherein the compound is represented by the structure of:

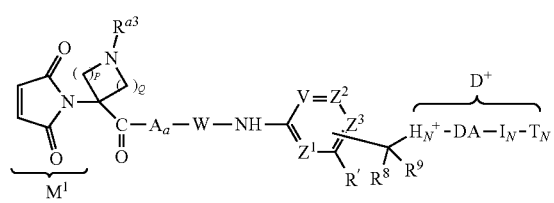

in salt form, particularly in pharmaceutically acceptable salt from, wherein

W is a Peptide Cleavable Unit;

subscript P is 1, 2 or 3;

subscript Q ranges from 1 to 6;

R' is hydrogen or —OC$_1$-C$_6$ alkyl or other electron donating group;

R$^{a3}$ is —H, or optionally substituted C$_1$-C$_6$ alkyl, optionally substituted —C$_1$-C$_4$ alkylene-(C$_6$-C$_{10}$ aryl), or —R$^{PEG1}$—O—(CH$_2$CH$_2$O)$_{1-36}$—R$^{PEG2}$, wherein R$^{PEG1}$ is C$_1$-C$_4$ alkylene, and R$^{PEG2}$ is —H or C$_1$-C$_4$ alkyl; and wherein the basic nitrogen atom bonded to R$^{a3}$ is optionally protonated, or R$^{a3}$ is a suitable amine protecting group, and wherein protease action on the Peptide Cleavable Unit cleaves the W—NH bond, wherein said cleavage within the Drug Linker compound or a drug linker moeity of a Ligand Drug Conjugate compound prepared from the Drug Linker compound initiates release of the quaternized NAMPT Drug (D⁺) Unit as a NAMPTi compound.

139. The Drug Linker compound of embodiment 132, wherein the compound is represented by the structure of:

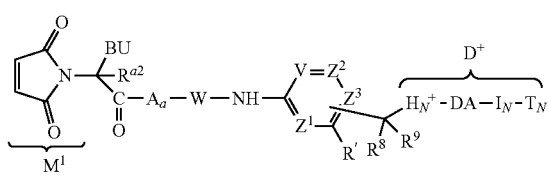

in suitable salt form, wherein
W is a Peptide Cleavable Unit;
subscript P is 1, 2 or 3;
subscript Q ranges from 1 to 6;
R' is hydrogen or —OC$_1$-C$_6$ alkyl or other electron donating group;
R$^{a2}$ is hydrogen or C$_1$-C$_6$ alkyl;
BU has the structure of —[C(R$^{a1}$)(R$^{a1}$)]—[C(R$^{a1}$)(R$^{a1}$)]$_{0-3}$—N(R$^{a3}$)(R$^{a3}$), each R$^{a1}$ independently is hydrogen or C$_1$-C$_4$ alkyl, C$_6$-C$_{10}$ aryl, C$_5$-C$_{10}$ heteroaryl, (C$_6$-C$_{10}$ aryl)-C$_1$-C$_4$ alkyl-, or (C$_5$-C$_{10}$ heteroaryl)-C$_1$-C$_4$ alkyl-, optionally substituted, or two R$^{a1}$ together with the carbon(s) to which they are attached and any intervening carbons define an optionally substituted C$_3$-C$_6$ cycloalkyl;
wherein the basic functional group of BU bonded is optionally protonated, or the basic nitrogen atom thereof is optionally protected; and
wherein protease action on the Peptide Cleavable Unit cleaves the W—NH bond, wherein said cleavage within the Drug Linker compound or a drug linker moiety of a Ligand Drug Conjugate compound prepared from the Drug Linker compound initiates release of the quaternized NAMPT Drug (D⁺) Unit as a NAMPTi compound.

140. The Drug Linker compound of embodiment 132, wherein the compound is represented by the structure of:

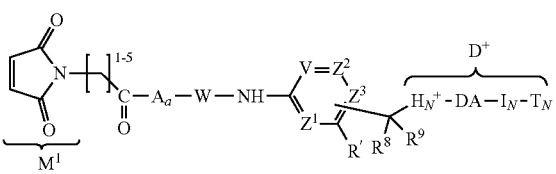

in salt form, particularly in pharmaceutically acceptable salt from, wherein
W is a Peptide Cleavable Unit;
subscript P is 1, 2 or 3;
subscript Q ranges from 1 to 6;
R' is hydrogen or —OC$_1$-C$_6$ alkyl or other electron donating group;
R$^{a2}$ is hydrogen or C$_1$-C$_6$ alkyl,
wherein protease action on the Peptide Cleavable Unit cleaves the W—NH bond, wherein said cleavage within the Drug Linker compound or a drug linker moiety of a Ligand Drug Conjugate compound prepared from the Drug Linker compound initiates release of the quaternized NAMPT Drug (D⁺) Unit as a NAMPTi compound.

141. The Drug Linker compound of embodiment 132, wherein the compound is represented by the structure of:

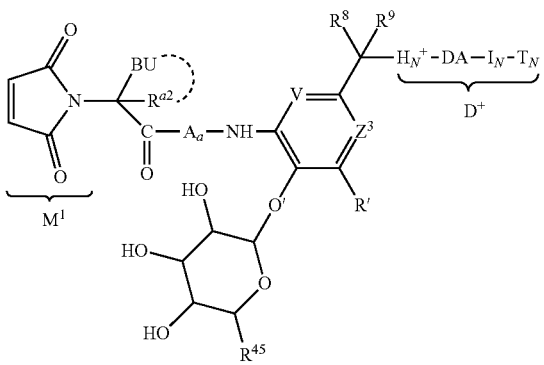

in salt form, particularly in pharmaceutically acceptable salt from, wherein
R' is hydrogen or —NO$_2$ or other electron withdrawing group;
R$^{45}$ is —CH$_2$OH or —CO$_2$H;
BU has the structure of —[C(R$^{a1}$)(R$^{a1}$)]—[C(R$^{a1}$)(R$^{a1}$)]$_{0-3}$—N(R$^{a3}$)(R$^{a3}$), each R$^{a1}$ independently is hydrogen or C$_1$-C$_4$ alkyl, C$_6$-C$_{10}$ aryl, C$_5$-C$_{10}$ heteroaryl, (C$_6$-C$_{10}$ aryl)-C$_1$-C$_4$ alkyl-, or (C$_5$-C$_{10}$ heteroaryl)-C$_1$-C$_4$ alkyl-, optionally substituted, or two R$^{a1}$ together with the carbon(s) to which they are attached and any intervening carbons define an optionally substituted C$_3$-C$_6$ cycloalkyl; R$^3$ independently are hydrogen, optionally substituted C$_1$-C$_6$ alkyl or R$^3$ together with the nitrogen atom to which both are attached define a C$_3$-C$_6$ heterocyclyl in which the basic nitrogen is a skeletal atom;
R$^{a2}$ is hydrogen or C$_1$-C$_6$ alkyl, optionally cyclized to BU, as indicated by the dotted curved line, wherein one of R$^{a1}$ or one of R$^3$ is replaced with a bond to a carbon atom of R$^{a2}$ when R$^{a2}$ is C$_1$-C$_6$ alkyl;
wherein the basic functional group of BU is optionally protonated, or the basic nitrogen atom thereof is optionally protected; and
wherein —O'— represents the oxygen atom of an O-glycosidic bond cleavable by a glycosidase, wherein said cleavage within the Drug Linker compound or a drug linker moiety of a Ligand Drug Conjugate compound prepared from the Drug Linker compound initiates release of the quaternized NAMPT Drug (D⁺) Unit as a NAMPTi compound.

142. The Drug Linker compound of embodiment 132, wherein the compound is represented by the structure of:

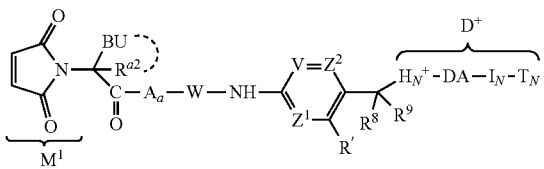

in salt form, particularly in pharmaceutically acceptable salt from, wherein

W is a Peptide Cleavable Unit;

R' is hydrogen or —OC$_1$-C$_6$ alkyl or other electron donating group;

R$^{45}$ is —CH$_2$OH or —CO$_2$H;

BU has the structure of —[C(R$^{a1}$)(R$^{a1}$)]—[C(R$^{a1}$)(R$^{a1}$)]$_{0-3}$—N(R$^{a3}$)(R$^{a3}$), each R$^{a1}$ independently is hydrogen or C$_1$-C$_4$ alkyl, C$_6$-C$_{10}$ aryl, C$_5$-C$_{10}$ heteroaryl, (C$_6$-C$_{10}$ aryl)-C$_1$-C$_4$ alkyl-, or (C$_5$-C$_{10}$ heteroaryl)-C$_1$-C$_4$ alkyl-, optionally substituted, or two R$^{a1}$ together with the carbon(s) to which they are attached and any intervening carbons define an optionally substituted C$_3$-C$_6$ cycloalkyl; R$^{a3}$ independently are hydrogen, optionally substituted C$_1$-C$_6$ alkyl or R$^{a3}$ together with the nitrogen atom to which both are attached define a C$_3$-C$_6$ heterocyclyl in which the basic nitrogen is a skeletal atom;

R$^{a2}$ is hydrogen or C$_1$-C$_6$ alkyl, optionally cyclized to BU, as indicated by the dotted curved line, wherein one of R$^{a1}$ or one of R$^{a3}$ is replaced with a bond to a carbon atom of R$^{a2}$ when R$^2$ is C$_1$-C$_6$ alkyl;

wherein the basic functional group of BU is optionally protonated, or the basic nitrogen atom thereof is optionally protected; and wherein protease action on the Peptide Cleavable Unit cleaves the W—NH bond, wherein said cleavage within the Drug Linker compound or a drug linker moeity of a Ligand Drug Conjugate compound prepared from the Drug Linker compound initiates release of the quaternized NAMPT Drug (D$^+$) Unit as a NAMPTi compound.

143. The Drug Linker compound of claim 132, wherein the compound is represented by the structure of:

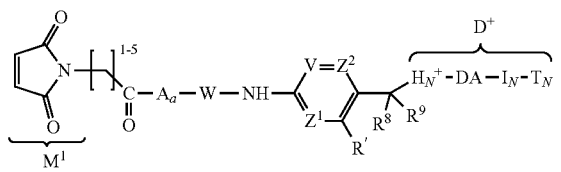

in salt form, particularly in pharmaceutically acceptable salt form, wherein

W is a Peptide Cleavable Unit;

R' is hydrogen or —OC$_1$-C$_6$ alkyl or other electron donating group;

R$^{45}$ is —CH$_2$OH or —CO$_2$H, wherein protease action on the Peptide Cleavable Unit cleaves the W—NH bond, wherein said cleavage within the Drug Linker compound or a drug linker moeity of a Ligand Drug Conjugate compound prepared from the Drug Linker compound initiates release of the quaternized NAMPT Drug (D$^+$) Unit as a NAMPTi compound.

144. The Drug Linker compound of embodiment 132, wherein the compound is represented by the structure of:

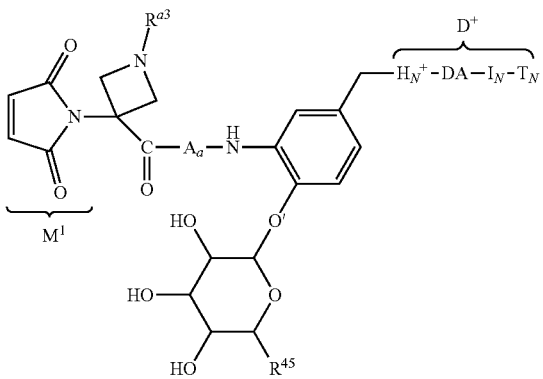

in salt form, particularly in pharmaceutically acceptable salt from, wherein

R$^{45}$ is —CH$_2$OH or —CO$_2$H;

R$^{a3}$ is —H, or optionally substituted C$_1$-C$_6$ alkyl, optionally substituted —C$_1$-C$_4$ alkylene-(C$_6$-C$_{10}$ aryl), or —R$^{PEG1}$—O—(CH$_2$CH$_2$O)$_{1-36}$—R$^{PEG2}$, wherein R$^{PEG1}$ is C$_1$-C$_4$ alkylene, and R$^{PEG2}$ is —H or C$_1$-C$_4$ alkyl; and wherein the basic nitrogen atom bonded to R$^{a3}$ is optionally protonated, or R$^{a3}$ is a suitable amine protecting group;

—O'— represents the oxygen atom of an O-glycosidic bond cleavable by a glycosidase, wherein said cleavage within the Drug Linker compound or a drug linker moeity of a Ligand Drug Conjugate compound prepared from the Drug Linker compound initiates release of the quaternized NAMPT Drug (D$^+$) Unit as a NAMPTi compound.

145. The Drug Linker compound of embodiment 132, wherein the compound is represented by the structure of:

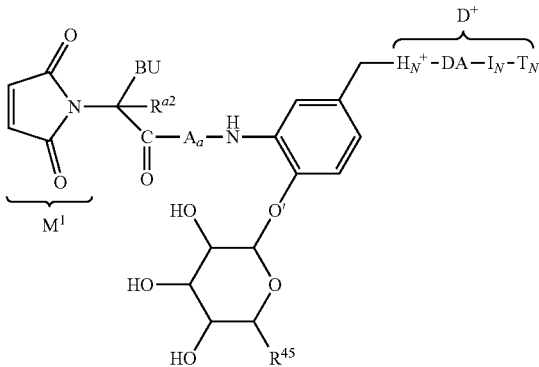

in salt form, particularly in pharmaceutically acceptable salt from, wherein

R$^{45}$ is —CH$_2$OH or —CO$_2$H;

BU is —CH$_2$—NH$_2$, optionally protonated, or the basic nitrogen atom thereof is optionally protected;

R$^{a2}$ is hydrogen; and

—O'— represents the oxygen atom of an O-glycosidic bond cleavable by a glycosidase, wherein said cleavage within the Drug Linker compound or a drug linker moeity of a Ligand Drug Conjugate compound prepared from the Drug Linker compound initiates release of the quaternized NAMPT Drug (D$^+$) Unit as a NAMPTi compound.

146. The Drug Linker compound of embodiment 132, wherein the compound is represented by the structure of:

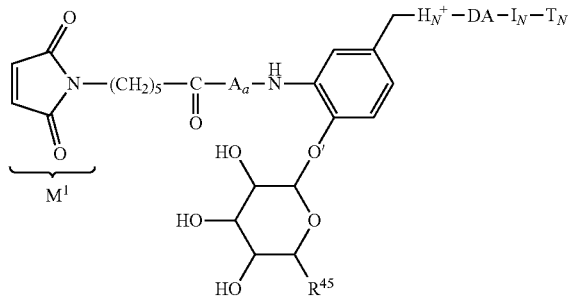

in suitable salt form, wherein
$R^{45}$ is —$CH_2OH$ or —$CO_2H$; and
—O'— represents the oxygen atom of an O-glycosidic bond cleavable by a glycosidase, wherein said cleavage within the Drug Linker compound or a drug linker moiety of a Ligand Drug Conjugate compound prepared from the Drug Linker compound initiates release of the quaternized NAMPT Drug ($D^+$) Unit as a NAMPTi compound.

147. The Drug Linker compound of embodiment 132, wherein the compound is represented by the structure of:

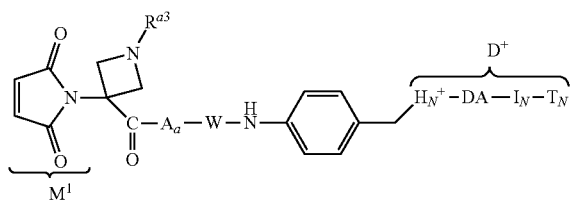

in salt form, particularly in pharmaceutically acceptable salt from, wherein
W is a Peptide Cleavable Unit;
$R^{a3}$ is —H, or optionally substituted $C_1$-$C_6$ alkyl, optionally substituted —$C_1$-$C_4$ alkylene-($C_6$-$C_{10}$ aryl), or —$R^{PEG1}$—O—$(CH_2CH_2O)_{1-36}$—$R^{PEG2}$, wherein $R^{PEG1}$ is $C_1$-$C_4$ alkylene, and $R^{PEG2}$ is —H or $C_1$-$C_4$ alkyl; and
wherein the basic nitrogen atom bonded to $R^{a3}$ is optionally protonated; and
wherein protease action on the Peptide Cleavable Unit cleaves the W—NH bond, wherein said cleavage within the Drug Linker compound or a drug linker moiety of a Ligand Drug Conjugate compound prepared from the Drug Linker compound initiates release of the quaternized NAMPT Drug ($D^+$) Unit as a NAMPTi compound.

148. The Drug Linker compound of embodiment 132, wherein the compound is represented by the structure of:

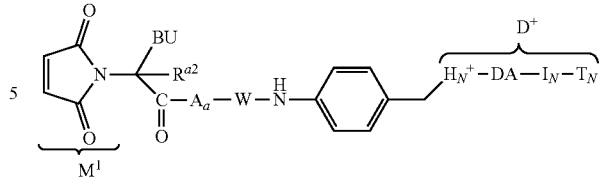

in salt form, particularly in pharmaceutically acceptable salt from, wherein
W is a Peptide Cleavable Unit;
BU is —$CH_2$—$NH_2$, optionally protonated;
$R^{a2}$ is hydrogen; and
wherein protease action on the Peptide Cleavable Unit cleaves the W—NH bond, wherein said cleavage within the Drug Linker compound or a drug linker moiety of a Ligand Drug Conjugate compound prepared from the Drug Linker compound initiates release of the quaternized NAMPT Drug ($D^+$) Unit as a NAMPTi compound.

149. The Drug Linker compound of embodiment 132, wherein the compound is represented by the structure of:

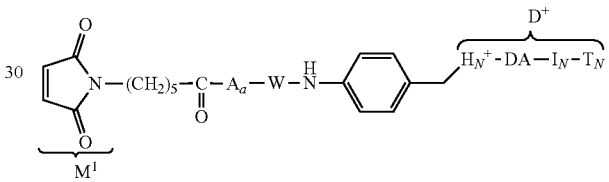

in suitable salt form, wherein
W is a Peptide Cleavable Unit,
wherein protease action on the Peptide Cleavable Unit cleaves the W—NH bond, wherein said cleavage within the Drug Linker compound or a drug linker moiety of a Ligand Drug Conjugate compound prepared from the Drug Linker compound initiates release of the quaternized NAMPT Drug ($D^+$) Unit as a NAMPTi compound.

150. The Drug Linker compound of any one of the preceding Drug Linker compound embodiments in which W is a Peptide Cleavable Unit that Unit is comprised of a dipeptide wherein the dipeptide provides for a recognition site for a regulatory or lysosomal protease for cleavage by said protease of the W-J' bond or the W—NH bond when J' is —NH within the Drug Linker compound or a drug linker moiety of a Ligand Drug Conjugate compound prepared from the Drug Linker compound initiates release of the quaternized NAMPT Drug ($D^+$) Unit as a NAMPTi compound.

151. The Drug Linker compound of embodiment 150 wherein W has the structure of:

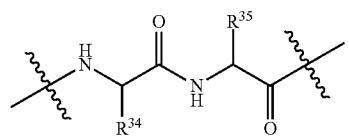

wherein R³⁴ is benzyl, methyl, isopropyl, isobutyl, sec-butyl, —CH(OH)CH₃ or has the structure of H

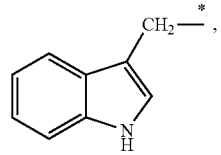

wherein the asterisk indicates the site of covalent attachment to the dipeptide backbone; and R³⁵ is methyl, —(CH₂)₄—NH₂, —(CH₂)₃NH(C=O)NH₂, —(CH₂)₃NH(C=NH)NH₂, or —(CH₂)₂CO₂H; and wherein the wavy lines indicate the points of covalent attachment of the dipeptide into the structure representing the Drug Linker compound.

152. The Drug Linker compound of embodiment 151 wherein W is selected from the group consisting of -Phe-Lys-, -Val-Ala-, -Val-Lys-, -Ala-Lys-, -Val-Cit-, -Phe-Cit-, -Leu-Cit-, -Ile-Cit-, -Phe-Arg-, and -Trp-Cit-, wherein Cit is citrulline.

153. The Drug Linker compound of any one of embodiments 95 to 152, wherein A or a subunit thereof is -L$^P$(PEG)-.

154. The Drug Linker compound of embodiment 153 wherein -L$^P$- or a subunit thereof is a aminoalkanedioic acid, a diaminoalkanoic acid, a sulfur-substituted alkanedioic acid, a sulfur-substituted aminoalkanoic acid, a diaminoalkanol, an aminoalkanediol, a hydroxyl substituted alkanedioic acid, a hydroxyl substituted aminoalkanoic acid or a sulfur-substituted aminoalkanol residue, optionally substituted, wherein the substituted sulfur is in reduced or oxidized form.

155. The Drug Linker compound of embodiment 153 wherein -L$^P$- or a subunit thereof is an amino acid residue of lysine, arginine, asparagine, glutamine, ornithine, citrulline, cysteine, homocysteine, penicillamine, threonine, serine, glutamic acid, aspartic acid, tyrosine, histidine or tryptophan, wherein the amino acid is in the D- or L-configuration.

156. The Drug Linker compound of embodiment 153 wherein L$^P$ or a subunit thereof is selected from the group consisting of lysine, glutamic acid, aspartic acid, cysteine, penicillamine, serine or threonine in its D- or L-stereochemical configuration.

157. The Drug Linker compound of embodiment 153, wherein -L$^P$- or a subunit thereof has the structure of Formula L$^P$-1 or L$^P$-2:

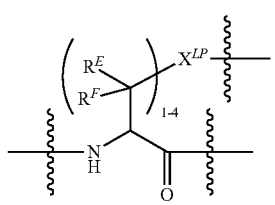

(Formula L$^P$-1)

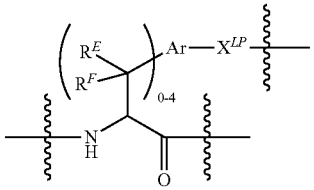

(Formula L$^P$-2)

or a salt thereof, in particular a pharmaceutical acceptable salt thereof, wherein X$^{LP}$ is selected from the group consisting of —O—, —NR$^{LP}$—, —S—, —S(=O)—, —S(=O)₂—, —C(=O)—, —C(=O)N(R$^{LP}$)—, —N(R$^{LP}$)C(=O)N(R$^{LP}$)—, —N(R$^{LP}$)C(=NR$^{LP}$)N(R$^{LP}$)—, and C₃-C₅ heterocyclo;

wherein each R$^{LP}$ is independently selected from the group consisting of hydrogen and optionally substituted C₁-C₆ alkyl, or two of R$^{LP}$ together along with the carbons atoms to which they are attached and their intervening atoms define a C₅-C₆ heterocyclo and any remaining R$^{LP}$ are as previously defined;

Ar is a C₆-C₁₀ arylene or a C₅-C₁₀ heteroarylene, optionally substituted;

each R$^E$ and R$^F$ is independently selected from the group consisting of —H, optionally substituted C₁-C₆ alkyl, optionally substituted C₂-C₆ alkylene, optionally substituted C₆-C₁₀ arylene and optionally substituted C₅-C₁₀ heteroarylene, or R$^E$ and R$^F$ together with the carbon atom to which both are attached defines an optionally substituted spiro C₃-C₆ carbocyclo, or R$^E$ and R$^F$ from adjacent carbon atoms together with these atoms and any intervening carbon atoms defines an optionally substituted C₅-C₆ carbocyclo with any remaining R$^E$ and R$^F$ as previously defined; and wherein one of the wavy lines indicates the site of covalent attachment of a PEG Unit and the other wavy lines indicates covalent attachment of Formula L$^P$-1 or Formula L$^P$-2 within the structure representing the Drug Linker compound.

158. The Drug Linker compound of embodiment 153 wherein -L$^P$(PEG)- has the structure of Formula L$^P$-3 or Formula L$^P$-4:

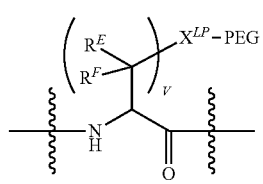

(Formula L$^P$-3)

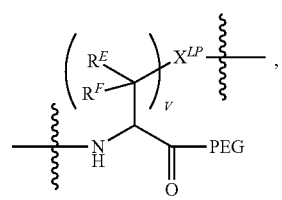

(Formula LP-4)

or a salt thereof, in particular a pharmaceutical acceptable salt thereof, wherein wherein subscript v is an integer ranging from 1 to 4;

$X^{LP}$ is selected from the group consisting of —O—, —NR$^{LP}$—, —S—, —S(=O)—, —S(=O)$_2$—, —C(=O)—, —C(=O)N(R$^{LP}$)—, —N(R$^{LP}$)C(=O)N(R$^{LP}$)—, —N(R$^{LP}$)C(=NR$^{LP}$)N(R$^{LP}$)—, and $C_3$-$C_5$ heterocyclo;

wherein each R$^{LP}$ is independently selected from the group consisting of hydrogen and optionally substituted $C_1$-$C_6$ alkyl, or two of R$^{LP}$ together along with the carbons atoms to which they are attached and their intervening atoms define a $C_5$-$C_6$ heterocyclo and any remaining R$^{LP}$ are as previously defined;

Ar is a $C_6$-$C_{10}$ arylene or a $C_5$-$C_{10}$ heteroarylene, optionally substituted;

each R$^E$ and R$^F$ is independently selected from the group consisting of —H, optionally substituted $C_1$-$C_6$ alkyl, optionally substituted $C_2$-$C_6$ alkylene, optionally substituted $C_6$-$C_{10}$ arylene and optionally substituted $C_5$-$C_{10}$ heteroarylene, or R$^E$ and R$^F$ together with the carbon atom to which both are attached defines an optionally substituted spiro $C_3$-$C_6$ carbocyclo, or R$^E$ and R$^F$ from adjacent carbon atoms together with these atoms and any intervening carbon atoms defines an optionally substituted $C_5$-$C_6$ carbocyclo with any remaining R$^E$ and R$^F$ as previously defined, or wherein the side chain of —[C(R$^E$)(R$^F$)]$_v$—X$^{LP}$— is provided by a natural or un-natural amino acid side chain; and wherein one of the wavy lines indicate the site of covalent attachment of a PEG Unit and the other wavy lines indicates covalent attachment of Formula L$^P$-1 or Formula L$^P$-2 within the structure representing the Drug Linker compound.

159. The Drug Linker compound of embodiment 157 or 158 wherein R$^E$ and R$^F$ are independently selected from the group consisting of —H, and —$C_1$-$C_4$ alkyl.

160. The Drug Linker compound of embodiment 157, 158 or 159 wherein X$^{LP}$ is selected from the group consisting of —O—, —NH, —S— and —C(=O)—.

161. The Drug Linker compound of any one of embodiments 153 to 160 wherein PEG has the structure selected from the group consisting of:

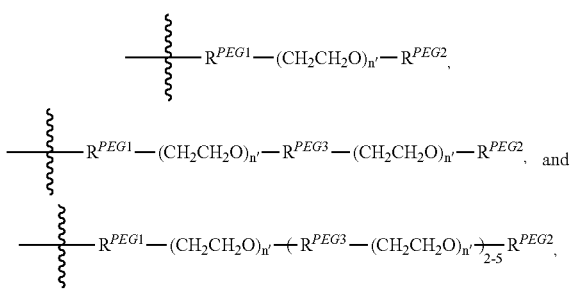

wherein the wavy line indicates site of attachment to X$^{LP}$ of the Parallel Connector Unit (L$^P$);

subscript n' independently ranges from 1 to 72;

R$^{PEG1}$ is an optional PEG Attachment Unit;

R$^{PEG2}$ is a PEG Capping Unit; and

R$^{PEG3}$ is an PEG Coupling Unit.

162. Drug Linker compound of any one of embodiments 157 to 160 wherein —X$^{LP}$-PEG has the structure of:

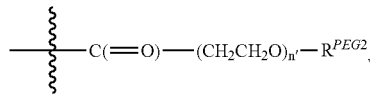

wherein subscript n' is 8, 12 or 24 and R$^{PEG2}$ is H or —CH$_3$.

163. The Drug Linker compound of any one of embodiments 95 to 152 wherein A or a subunit thereof has the structure of formula (3) or formula (4):

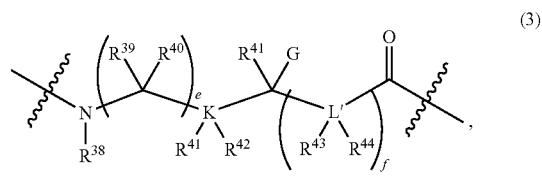

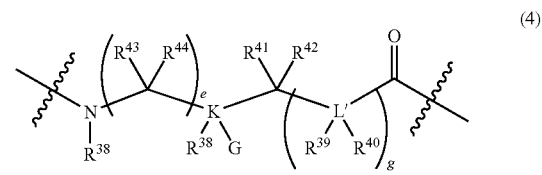

wherein the wavy lines indicated covalent attachment within the composition structure;

wherein K and L' independently are C, N, O or S, provided that when K or L' is O or S, R$^{41}$ and R$^{42}$ to K or R$^{43}$ and R$^{44}$ to L' are absent, and when K or L' are N, one of R$^{41}$, R$^{42}$ to K or one of R$^{42}$, R$^{43}$ to L' are absent, and provided that no two adjacent L' are independently selected as N, O, or S;

wherein subscripts e and f are independently selected integers that range from 0 to 12, and subscript g is an integer ranging from 1 to 12;

wherein G is hydrogen, optionally substituted $C_1$-$C_6$ alkyl, —OH, —OR$^{PR}$, —CO$_2$H, CO$_2$R$^{PR}$, wherein R$^{PR}$ is a suitable protecting, or G is —N(R$^{PR}$)(R$^{PR}$), wherein R$^{PR}$ are independently a protecting group or R$^{PR}$ together form a suitable protecting group, or G is —N(R$^{45}$)(R$^{46}$), wherein one of R$^{45}$, R$^{46}$ is hydrogen or R$^{PR}$, wherein R$^{PR}$ is a suitable protecting group, and the other is hydrogen or optionally substituted $C_1$-$C_6$ alkyl;

wherein R$^{38}$ is hydrogen or optionally substituted $C_1$-$C_6$ alkyl;

R$^{39}$-R$^{44}$ are independently selected from the group consisting of hydrogen, optionally substituted $C_1$-$C_6$ alkyl, optionally substituted aryl, and optionally substituted heteroaryl, or R$^{39}$, R$^{40}$ together with the carbon atom to which both are attached, or R$^{41}$, R$^{42}$ together with K to which both are attached when K is a carbon atom, define a $C_3$-$C_6$ carbocyclo, and R$^{41}$-R$^4$ are as defined herein, or R$^{43}$, R$^{44}$ together with L' to which both are attached when L' is a carbon atom define a $C_3$-$C_6$ carbocyclo, and R$^{39}$-R$^{42}$ are as defined herein, or R$^{40}$ and R$^{41}$, or R$^{40}$ and R$^{43}$, or R$^{41}$ and R$^{43}$ to together with the carbon atom or heteroatom to which both are attached and the atoms intervening between those carbon atoms and/or heteroatoms define a $C_5$-$C_6$ carbocyclo or a $C_5$-$C_6$ heterocyclo, and $R^{39}$, $R^4$ and the remainder of $R^{40}$-$R^{43}$ are as defined herein, provided that when K is O or S, $R^{41}$ and $R^{42}$ are absent, and when K is N, one of $R^{41}$, $R^{42}$ is absent, and when L' is O or S, $R^{43}$ and $R^4$ are absent, and when L' is N, one of $R^{43}$, $R^{44}$ is absent, or A, or a subunit thereof, is an alpha-amino, beta-amino or another amine-containing acid residue.

164. The Drug Linker compound of embodiment 163 wherein formula (3) or formula (4) has the structure of formula (3a) or formula (4a):

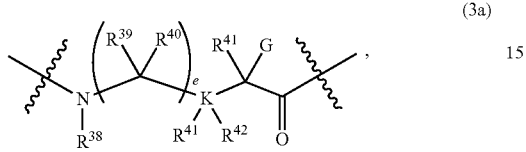
(3a)

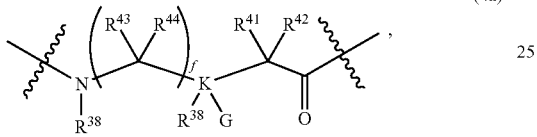
(4a)

wherein subscripts e and f are independently 0 or 1.

165. The Drug Linker compound of embodiment 132, wherein the compound is represented by the structure of:

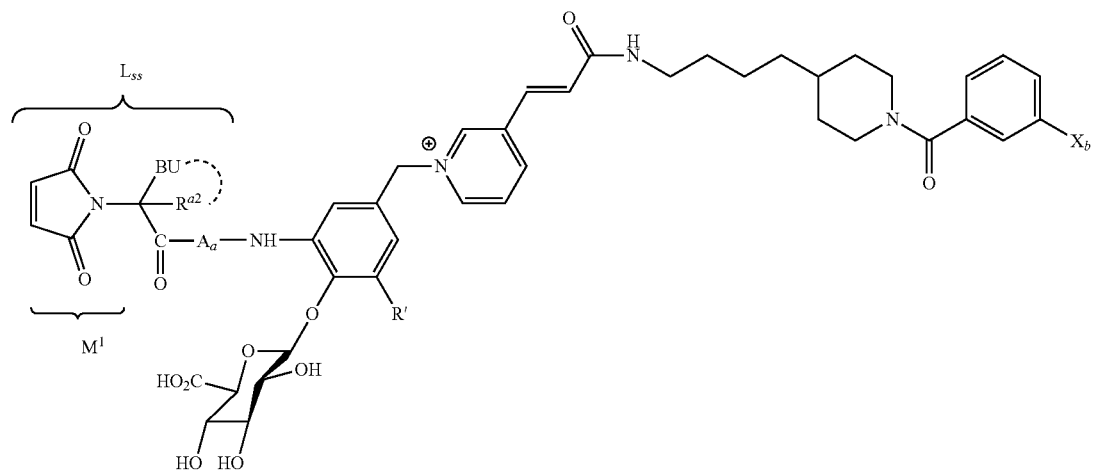

in salt form, in particular in pharmaceutically acceptable salt form, wherein the basic functional group of BU is optionally protonated, or the basic nitrogen atom thereof is optionally protected;

subscript a is 1 and A is an amino acid residue;

BU is an acyclic Basic Unit so that the dotted curve line is absent, and $R^{a2}$ is hydrogen, or BU together with $R^{a2}$ as $C_1$-$C_6$ alkyl and the carbon atom to which both are attached define a cyclic Basic Unit so that the dotted curved line is present; and R' is hydrogen or —$NO_2$; and $X^b$ is —H, —OH or —$NH_2$.

166. The Drug Linker compound of embodiment 132, wherein the compound is represented by the structure of:

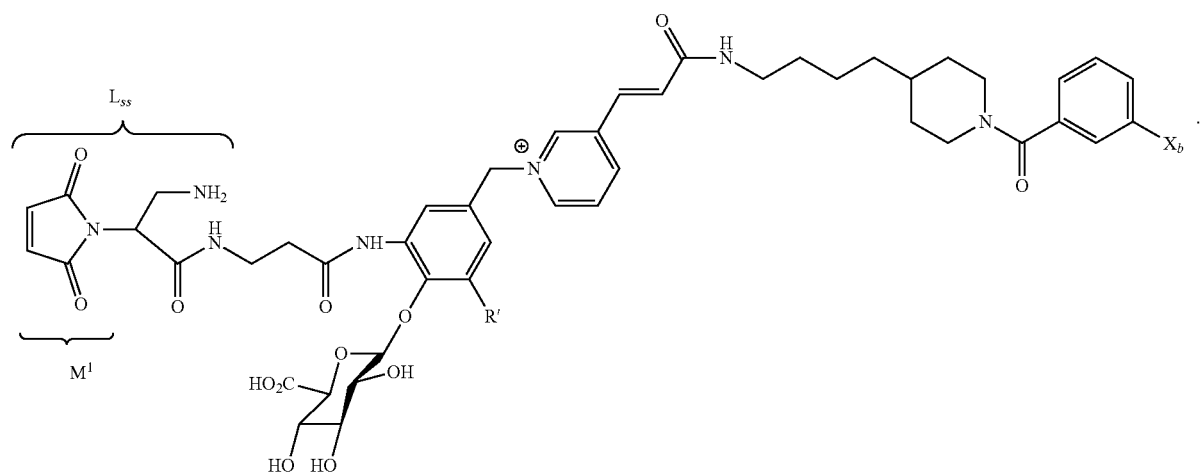

in salt form, in particular in pharmaceutically acceptable salt form, wherein the basic functional group of $L_{SS}$ is optionally protonated, or the basic nitrogen atom thereof is optionally protected.

167. The Drug Linker compound of embodiment 132, wherein the compound is represented by the structure of:

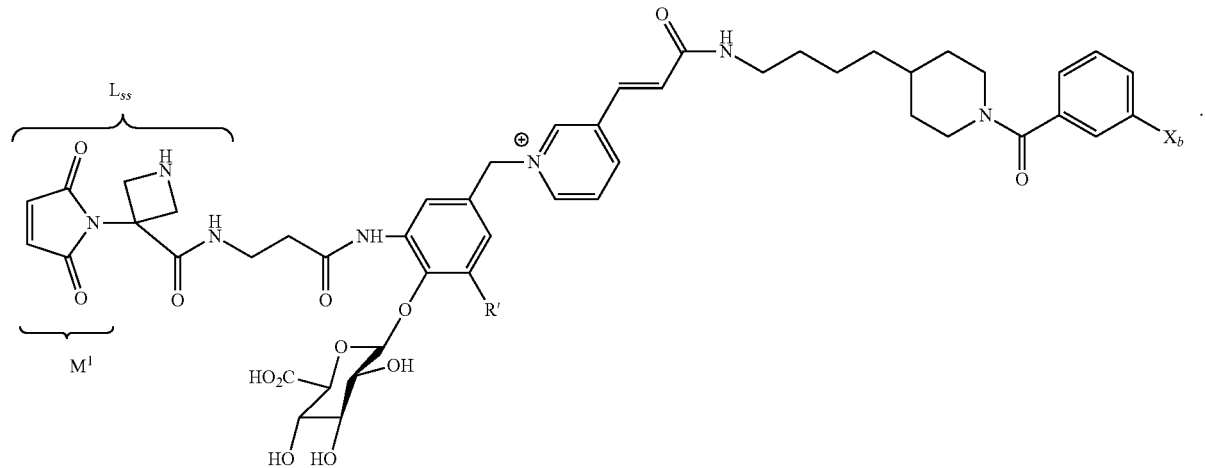

in salt form, in particular in pharmaceutically acceptable salt form, wherein the basic functional group of $L_{SS}$ is optionally protonated, or the basic nitrogen atom thereof is optionally protected.

168. The Drug Linker compound of embodiment 132, wherein the compound is represented by the structure of:

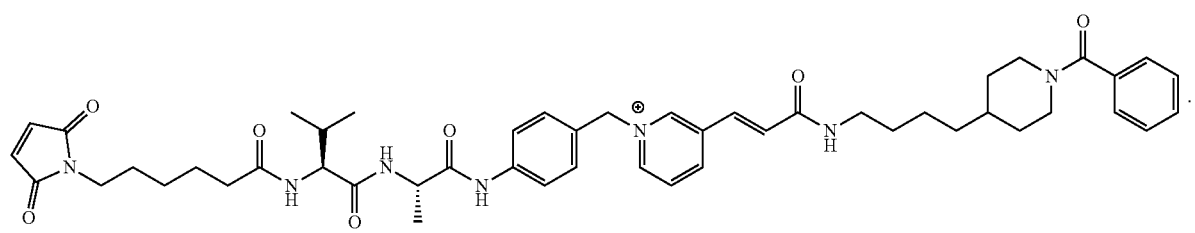 [SMILES: CC(C)[C@H](NC(=O)CCCCCN1C(=O)C=CC1=O)C(=O)N[C@@H](C)C(=O)Nc1ccc(C[n+]2cccc(/C=C/C(=O)NCCCCC3CCN(C(=O)c4ccccc4)CC3)c2)cc1]

in salt form, in particular in pharmaceutically acceptable salt form.

169. The Drug Linker compound of embodiment 132, wherein the compound is represented by the structure of:

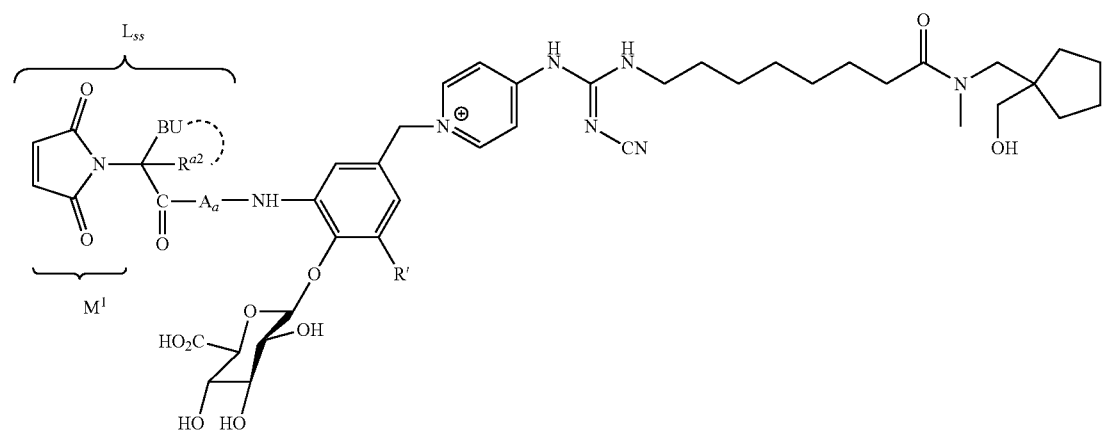

in salt form, wherein the basic functional group of BU is optionally protonated, or the basic nitrogen atom thereof is optionally protected;
subscript a is 1 and A is an amino acid residue;
BU is an acyclic Basic Unit so that the dotted curve line is absent, and $R^{a2}$ is hydrogen, or
BU together with $R^{a2}$ as $C_1$-$C_6$ alkyl and the carbon atom to which both are attached define a cyclic Basic Unit so that the dotted curved line is present; and
R' is hydrogen or —$NO_2$; and
$X^b$ is —H, —OH or —$NH_2$.

170. The Drug Linker compound of embodiment 132, wherein the compound is represented by the structure of:

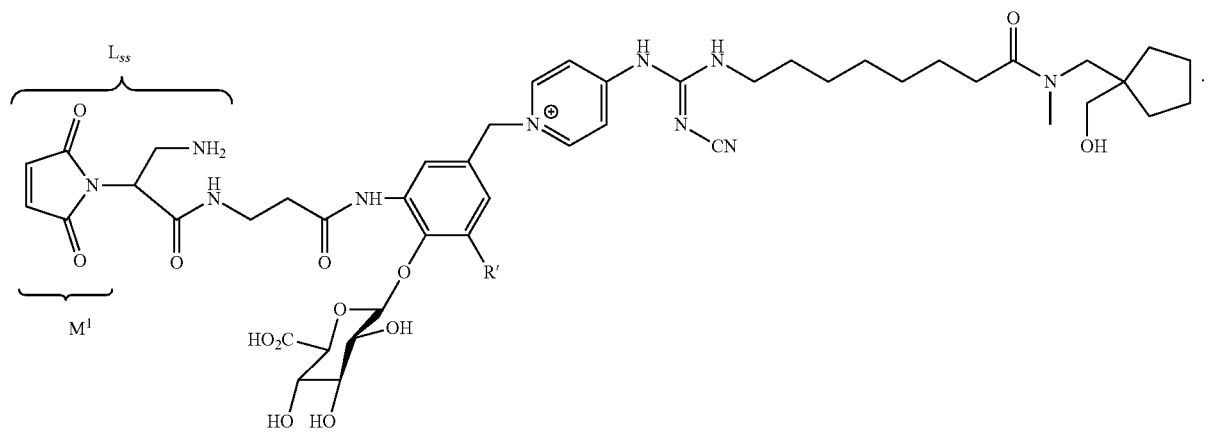

in salt form, in particular in pharmaceutically acceptable salt form, wherein the basic nitrogen atom of $L_{SS}$ is optionally protonated or protected.

171. The Drug Linker compound of embodiment 132, wherein the compound is represented by the structure of:

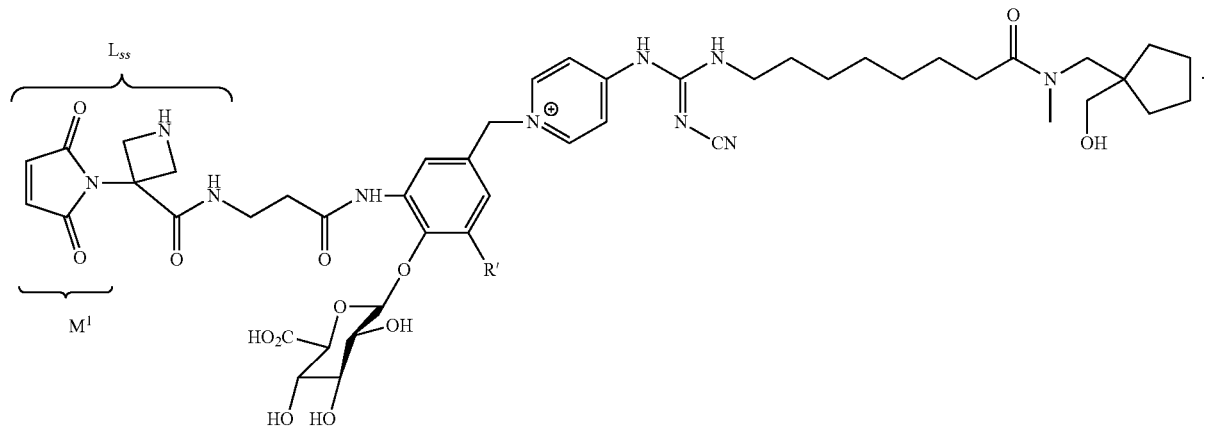

in salt form, in particular in pharmaceutically acceptable salt form, wherein the basic nitrogen atom of $L_{SS}$ is optionally protonated or protected.

172. The Drug Linker compound of embodiment 132, wherein the compound is represented by the structure(s) of:

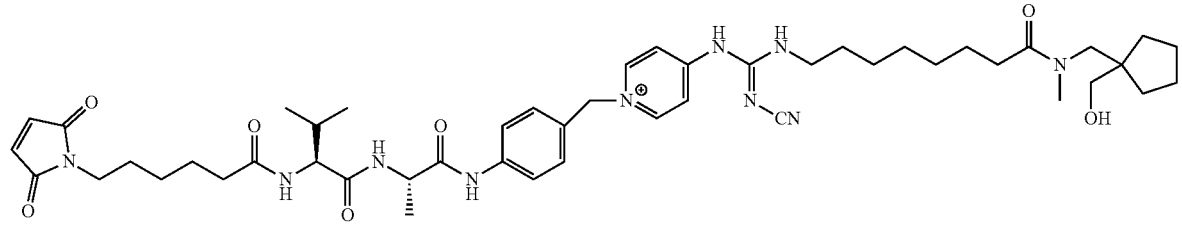 [SMILES: CC(C)[C@H](NC(=O)CCCCCN1C(=O)C=CC1=O)C(=O)N[C@@H](C)C(=O)Nc1ccc(C[n+]2ccc(N/C(=N/C#N)NCCCCCCCC(=O)N(C)CC3(CO)CCCC3)cc2)cc1]

in salt form, in particular in pharmaceutically acceptable salt form.

EXAMPLES

General Information. All commercially available anhydrous solvents were used without further purification. Silica gel chromatography was performed on a Biotage Isolera One flash purification system (Charlotte, NC). UPLC-MS was performed on a Waters Xevo G2 ToF mass spectrometer interfaced to a Waters Acquity H-Class Ultra Performance LC equipped with an Acquity UPLC BEH C18 2.1×50 mm, 1.7 μm reverse phase column. The acidic mobile phase (0.1% formic acid) consisted of a gradient of 3% to 95% acetonitrile in water over 1.43 min (flow rate=0.7 mL/min) with a return to baseline conditions over 0.36 min. Preparative HPLC was carried out on a Waters 2545 solvent delivery system configured with a Waters 2998 PDA detector. Products were purified over a C12 Phenomenex Synergi reverse phase column (10.0-50 mm diameter×250 mm length, 4 m, 80 Å) eluting with 0.05% trifluoroacetic acid in water (solvent A) and 0.05% trifluoroacetic acid in acetonitrile (solvent B). The purification methods generally consisted of linear gradients of solvent A to solvent B, ramping from 5% solvent B to 95% solvent B; flow rate was varied depending on column diameter. NMR spectral data were collected on a Varian Mercury 400 MHz spectrometer. Coupling constants (J) are reported in hertz.

NAMPT enzyme preparation. NAMPT containing a C-terminal 6×His tag was expressed in *E. coli* using the pET28a vector (Novagen). The protein was purified by nickel affinity chromatography, then buffer-exchanged into 50 mM Tris, 100 mM NaCl, pH 7 and flash frozen.

Fluorescence Polarization Assay. A fluorescent probe molecule for use in FP assay was prepared by reaction of (E)-N-(4-(1-(4-(2-hydroxyethoxy)benzoyl)piperidin-4-yl)butyl)-3-(pyridin-3-yl)acrylamide with the diacetate of fluorescein-5-carbonyl azide (via Curtius rearrangement), followed by saponification of the acetate groups as described by Example 20. Assays were run in 384-well plate with 30 μL per well. Assay buffer consisted of 50 mM HEPES, 50 mM KCl, 5 mM MgCl$_2$, 125 μM ATP, 0.5 mM beta-mercaptoethanol, and 0.005% BSA. NAMPT was used at 120 nM and fluorescent probe molecule at 30 nM. Test articles were added as a dilution series from −1000 nM to 0.5 nM. After incubating at room temp for 4 hours, fluorescence polarization was measured on Envision plate reader. Curve fitting was performed in GraphPad Prism using a 4-parameter log(inhibitor concentration) vs response model.

In vitro NAD assays: Cells cultured in log-phase growth were seeded for 24 h in 96-well plates containing 150 μL RPMI 1640 supplemented with 20% FBS. Serial dilutions of free drugs or antibody-drug conjugates in cell culture media were prepared at 4× working concentrations; 50 μL of each dilution was added to the 96-well plates. Following addition of ADC, cells were incubated with test articles for 2-4 d at 37° C. NAD levels were assessed NAD-Glo™ (Promega, Madison, WI) and luminescence was measured on a plate reader. The IC$_{50}$ value is defined here as the concentration that results in a 50% reduction in NAD levels relative to untreated controls.

In vitro cytotoxicity assays: Cells cultured in log-phase growth were seeded for 24 h in 96-well plates containing 150 μL RPMI 1640 supplemented with 20% FBS. Serial dilutions of free drugs or antibody-drug conjugates in cell culture media were prepared at 4× working concentrations; 50 μL of each dilution was added to the 96-well plates. Following addition of ADC, cells were incubated with test articles for 4 d at 37° C. After 96 h, growth inhibition was assessed by CellTiter-Glo™ (Promega, Madison, WI) and luminescence was measured on a plate reader. The IC$_{50}$ value is defined here as the concentration that results in a 50% reduction in cell growth relative to untreated controls.

In vivo xenograft models. All experiments were conducted in concordance with the Animal Care and Use Committee in a facility fully accredited by the Association for Assessment and Accreditation of Laboratory Animal Care. Efficacy experiments were conducted in the L540cy Hodgkin's lymphoma model. Tumor cells, as a cell suspension, were implanted sub-cutaneous in immune-compromised SCID mice. Upon tumor engraftment, mice were randomized to study groups (5 mice per group) when the average tumor volume reached about 100 mm$^3$. The ADC or controls were dosed once via intraperitoneal injection. Tumor volume as a function of time was determined using the formula (L×W$^2$)/2. Animals were euthanized when tumor volumes reached 750 mm$^3$. Mice showing durable regressions were terminated after 10-12 weeks post implant.

Preparation of Quaternized NAMPT Drug Linker Compounds

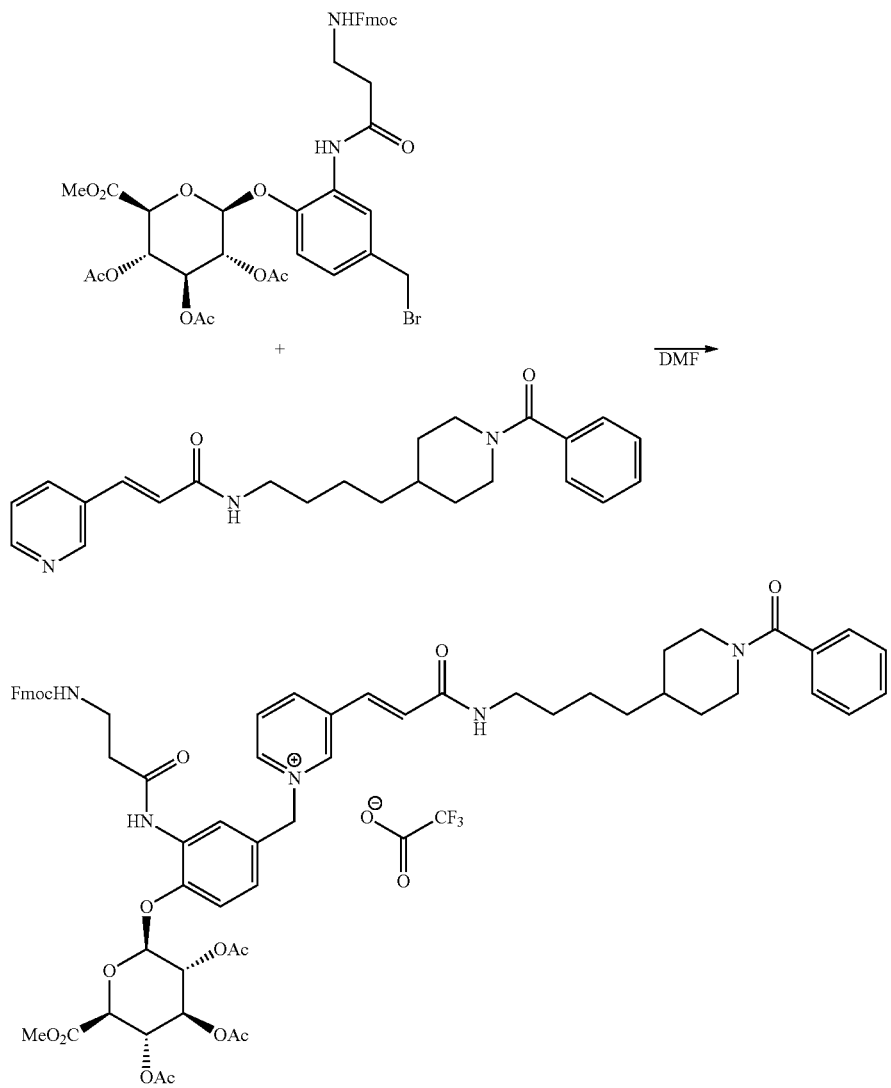

Example 1. 1-(3-(3-((((9H-fluoren-9-yl)methoxy) carbonyl)amino)-propanamido)-4-(((2S,3R,4S,5S, 6S)-3,4,5-triacetoxy-6-(methoxycarbonyl)tetrahydro-2H-pyran-2-yl)oxy)benzyl)-3-((E)-3-((4-(1-benzoylpiperidin-4-yl)butyl)amino)-3-oxoprop-1-en-1-yl)pyridin-1-ium 2,2,2-trifluoroacetate (1)

(2S,3R,4S,5S,6S)-2-(2-(3-((((9H-fluoren-9-yl)methoxy) carbonyl)amino)-propanamido)-4-(bromomethyl)phenoxy)-6-(methoxycarbonyl)tetrahydro-2H-pyran-3,4,5-triyl triacetate (16 mg, 0.02 mmol) and the NAMP inhibitor compound (E)-N-(4-(1-benzoylpiperidin-4-yl)butyl)-3-(pyridin-3-yl)acrylamide (7.7 mg, 0.02 mmol), were dissolved in anhydrous DMF (200 µl) and heated at 55° C. for 4 hours. The benzyl bromide input as the quaternization agent was prepared according to the procedure of *Mol. Cancer Ther.* (2016) 15(5): 938-945, the disclosure for which is specifically incorporated by reference herein. The NAMPT inhibitor compound was prepared according to the procedure of Scheme 1 (R=H) The reaction was cooled to room temperature, diluted with DMSO, and purified by preparative HPLC to provide the title compound (15.0 mg, 0.013 mmol, 68%). LCMS: $t_R$=0.96 min; m/z=953.5 [M]$^+$. $^1$H NMR (400 MHz, DMSO-d$_6$) δ 9.48 (s, 1H), 9.09 (d, J=5.7 Hz, 1H), 8.90 (s, 1H), 8.75 (d, J=8.2 Hz, 1H), 8.40 (t, J=5.6 Hz, 1H), 8.17 (dd, J=8.2, 6.1 Hz, 1H), 8.05 (d, J=2.0 Hz, 1H), 7.89 (dd, J=7.6, 1.1 Hz, 2H), 7.68 (d, J=7.5 Hz, 2H), 7.55 (d, J=15.7 Hz, 1H), 7.46-7.41 (m, 3H), 7.41-7.33 (m, 5H), 7.33-7.26 (m, 2H), 7.15 (d, J=8.5 Hz, 1H), 6.92 (d, J=15.8 Hz, 1H), 5.76 (s, 2H), 5.64 (d, J=7.8 Hz, 1H), 5.49 (t, J=9.7 Hz, 1H), 5.19 (dd, J=9.7, 7.9 Hz, 1H), 5.05 (t, J=9.8 Hz, 1H), 4.74 (d, J=9.9 Hz, 1H), 4.52-4.39 (m, 1H), 4.33-4.25 (m, 2H), 4.21 (t, J=6.9 Hz, 1H), 3.62 (d, J=1.1 Hz, 3H), 3.53 (s, 1H), 3.27 (q, J=6.8 Hz, 2H), 3.19 (q, J=6.6 Hz, 2H), 2.98 (s, 1H), 2.71 (d, J=7.1 Hz, 1H), 2.53 (s, 2H), 2.01 (s, 3H), 2.00 (s, 3H), 1.99 (s, 3H), 1.72 (d, J=12.4 Hz, 1H), 1.58 (s, 1H), 1.51-1.38 (m, 3H), 1.37-1.18 (m, 5H), 1.13-0.93 (m, 2H).

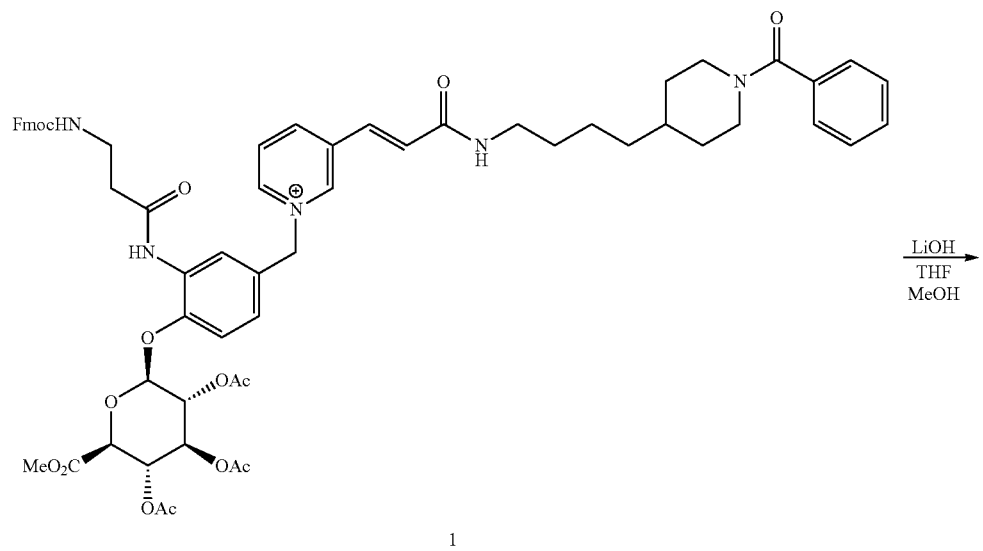
1
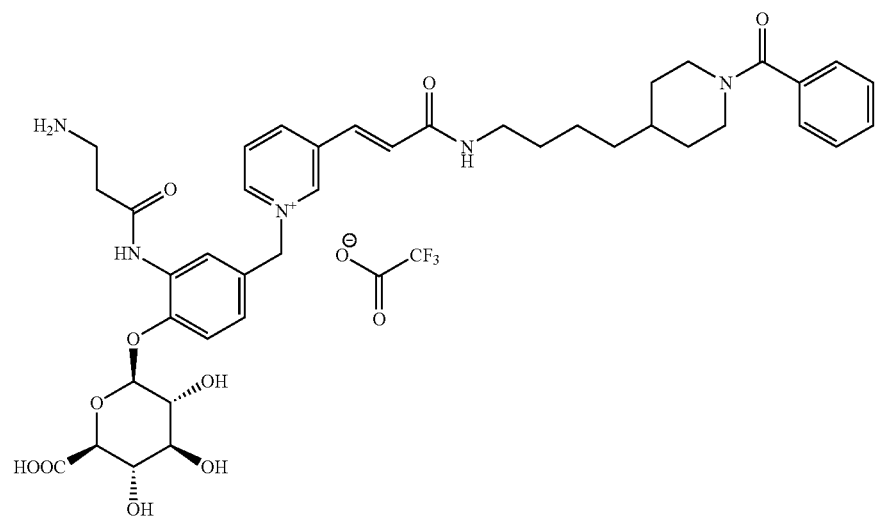
2

Example 2. 1-(3-(3-aminopropanamido)-4-(((2S,3R,4S,5S,6S)-6-carboxy-3,4,5-trihydroxytetrahydro-2H-pyran-2-yl)oxy)benzyl)-3-((E)-3-((4-(1-benzoylpiperidin-4-yl)butyl)amino)-3-oxoprop-1-en-1-yl)pyridin-1-ium 2,2,2-trifluoroacetate (2)

Compound 1 (5.4 mg, 4.8 μmol) was dissolved in a 1:1 mixture of MeOH and THF (400 μL). The solution was cooled on ice prior to addition of a LiOH solution (0.2 M, 240 μL, 48 μmol). The reaction was stirred on ice for 30 min, then warmed to room temperature After 4 hours the reaction was acidified with a drop of acetic acid, then diluted with DMSO and purified by preparative HPLC to provide the title compound (3.6 mg, 4.7 μmol, 98%). LCMS: $t_R$=0.83 min; m/z=760.4 [M]$^+$.

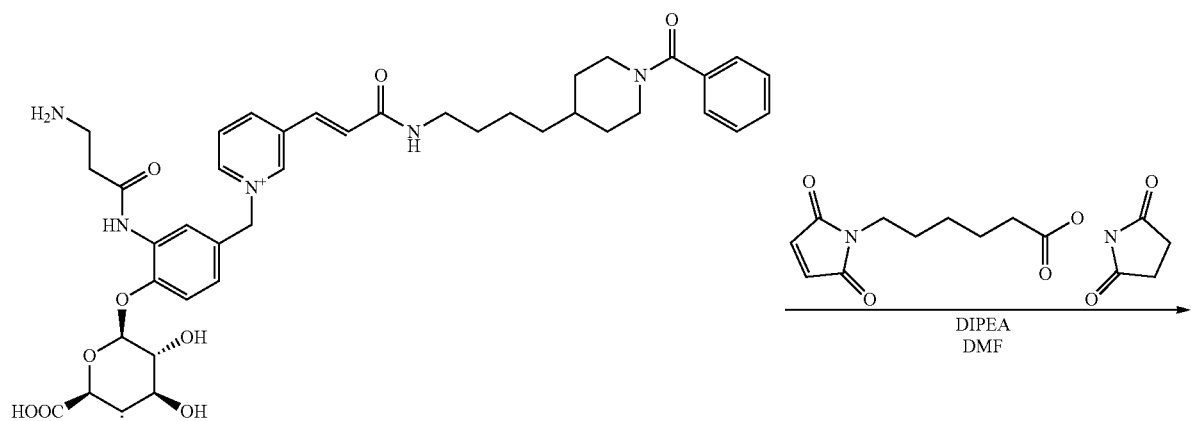

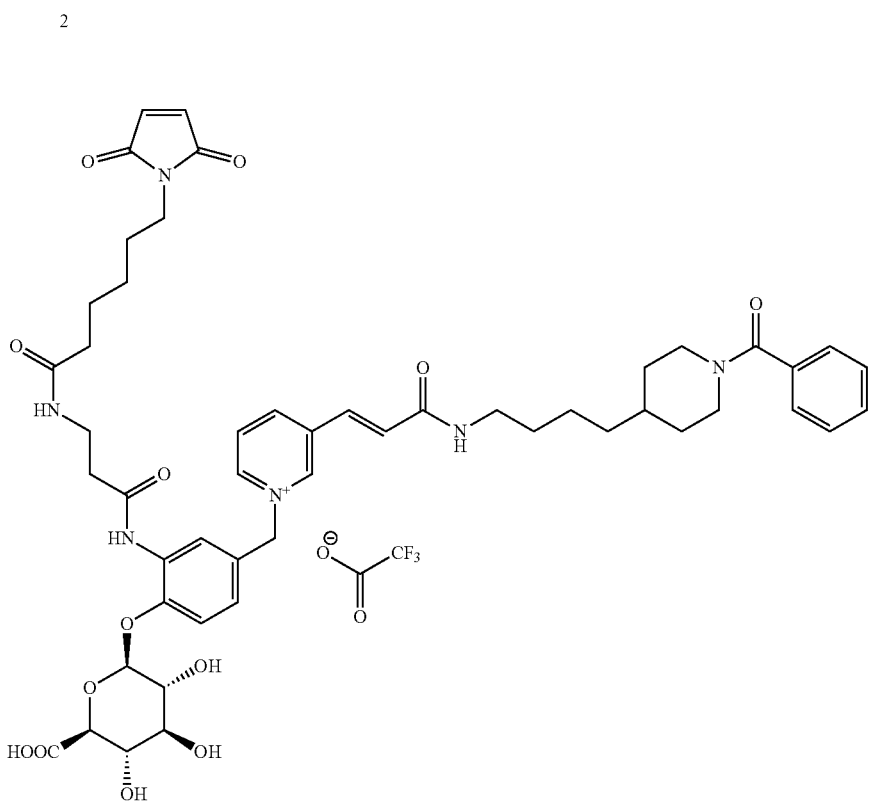

Example 3. 3-((E)-3-((4-(1-benzoylpiperidin-4-yl)butyl)amino)-3-oxoprop-1-en-1-yl)-1-(4-(((2S,3R,4S,5S,6S)-6-carboxy-3,4,5-trihydroxytetrahydro-2H-pyran-2-yl)oxy)-3-(3-(6-(2,5-dioxo-2,5-dihydro-1H-pyrrol-1-yl)hexanamido)propanamido)benzyl)pyridin-1-ium 2,2,2-trifluoroacetate (3)

2,5-Dioxopyrrolidin-1-yl 6-(2,5-dioxo-2,5-dihydro-1H-pyrrol-1-yl)hexanoate (1.6 mg, 5.2 µmol) was dissolved in DMF (100 µL). The resulting solution was added to compound 2 (3.6 mg, 4.7 µmol) followed by addition of DIPEA (2.5 µL, 14 mol). The reaction was mixed vigorously, then incubated at room temperature for 90 minutes. The reaction was diluted with DMSO and purified by preparative HPLC to provide the title compound (2.7 mg, 2.8 µmol, 60%) referred to as mc-GlucQ-FK866. LCMS: $t_R$=0.96 min; m/z=953.5 [M]$^+$.

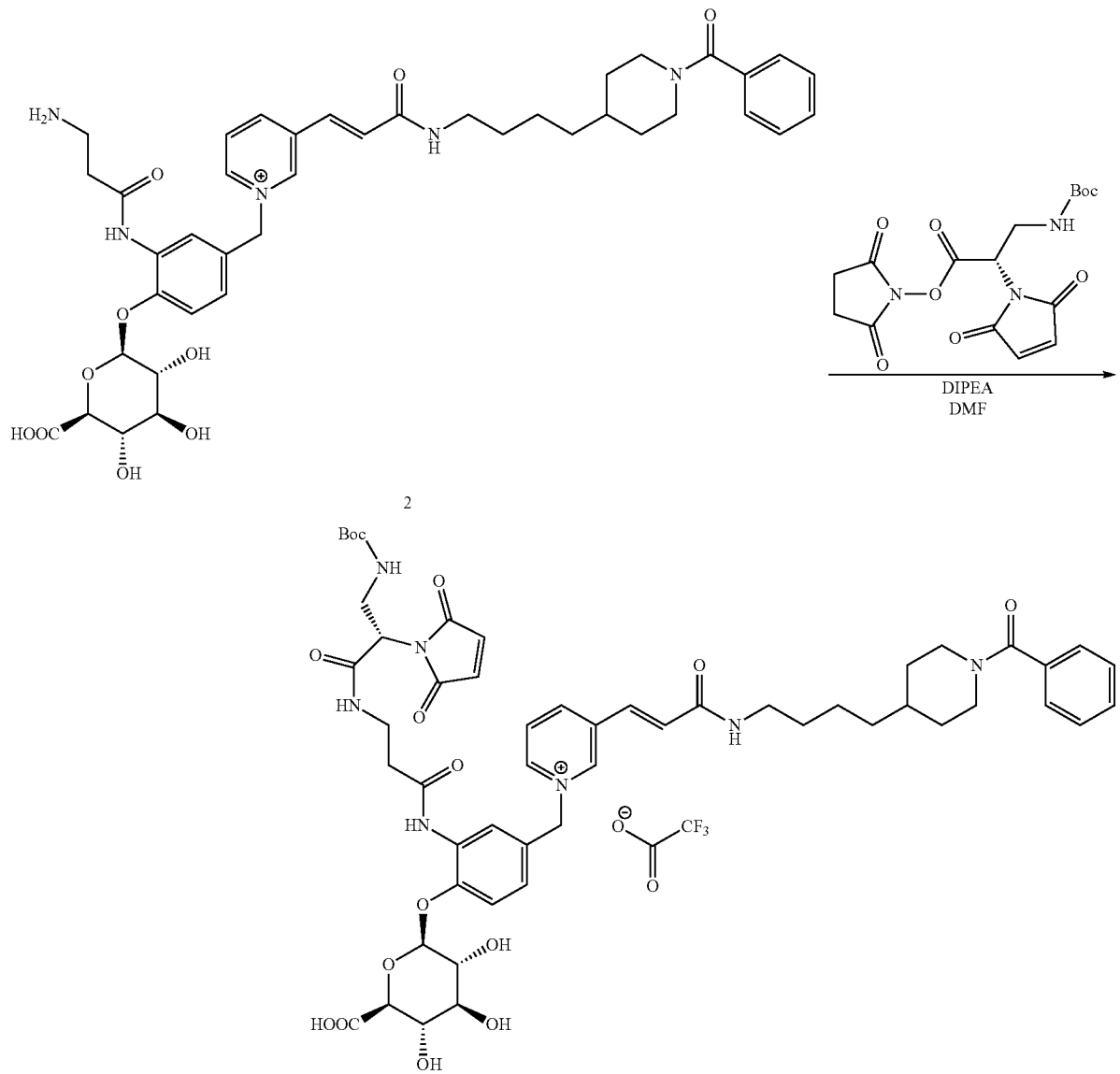

Example 4. 3-((E)-3-((4-(1-benzoylpiperidin-4-yl)butyl)amino)-3-oxoprop-1-en-1-yl)-1-(3-(3-((S)-3-((tert-butoxycarbonyl)amino)-2-(2,5-dioxo-2,5-dihydro-1H-pyrrol-1-yl)propanamido)propanamido)-4-(((2S,3R,4S,5S,6S)-6-carboxy-3,4,5-trihydroxytetrahydro-2H-pyran-2-yl)oxy)benzyl)pyridin-1-ium 2,2,2-trifluoroacetate (4)

Compound 2 (8.9 mg, 0.009 mmol) was dissolved in anhydrous DMF (500 μl) followed by the addition of DIPEA (4.7 μL). 2,5-Dioxopyrrolidin-1-yl (S)-3-((tert-butoxycarbonyl)amino)-2-(2,5-dioxo-2,5-dihydro-1H-pyrrol-1-yl)propanoate (5.2 mg, 0.014 mmol) in anhydrous DMF (100 μL) was then added. The reaction mixture was stirred at room temperature for 2 hours. After 2 hours, the reaction was acidified with HOAc (5 μL), diluted with DMSO/water and purified by prep-HPLC to provide the title compound (8.9 mg, 0.008 mmol, 86.6%). LCMS: $t_R$=1.47 min; m/z=1026.40 [M]$^+$.

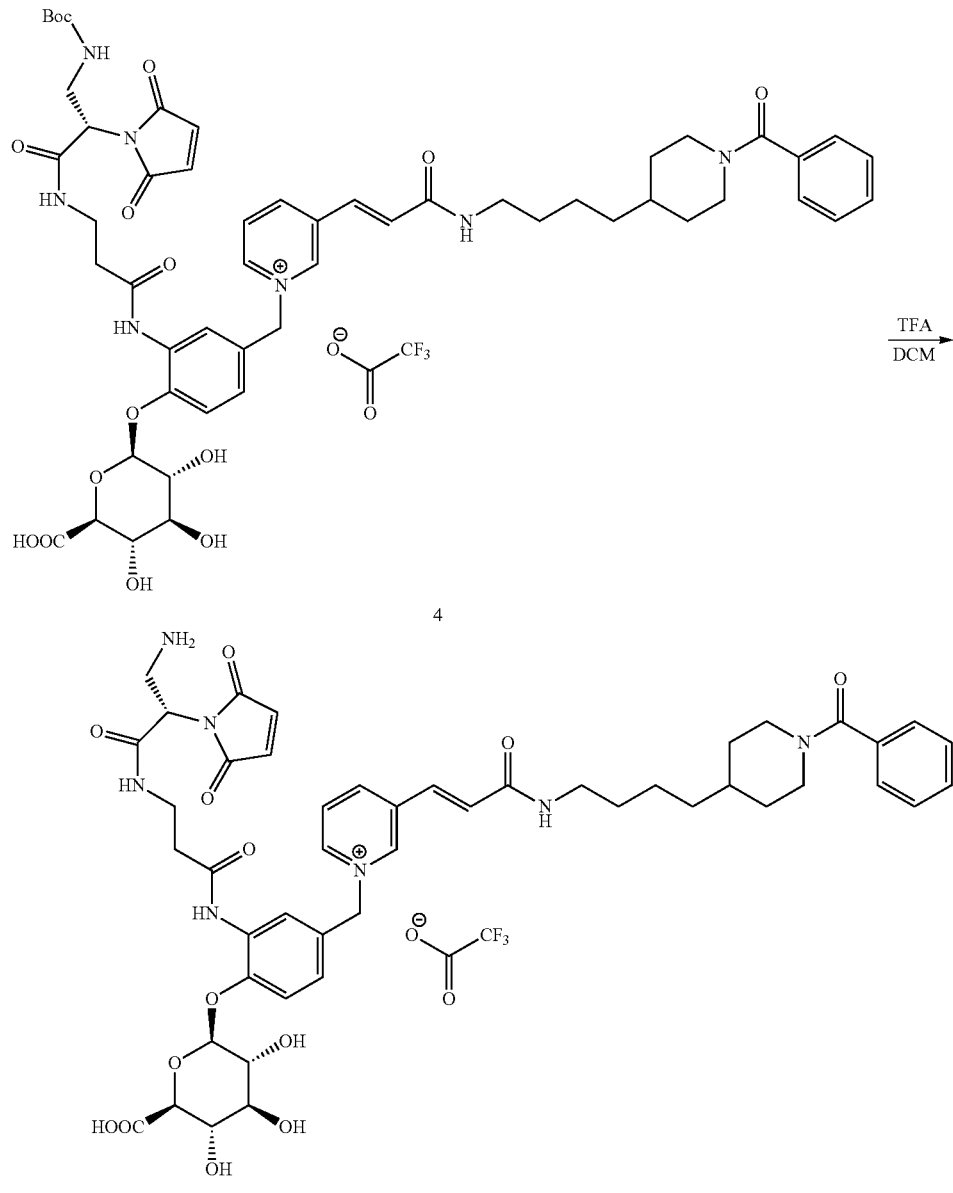

Example 5. 1-(3-(3-((S)-3-amino-2-(2,5-dioxo-2,5-dihydro-1H-pyrrol-1-yl)propanamido)propanamido)-4-(((2S,3R,4S,5S,6S)-6-carboxy-3,4,5-trihydroxy-tetrahydro-2H-pyran-2-yl)oxy)benzyl)-3-((E)-3-((4-(1-benzoylpiperidin-4-yl)butyl)amino)-3-oxoprop-1-en-1-yl)pyridin-1-ium 2,2,2-trifluoroacetate (5)

Compound 4 (8.9 mg, 0.008 mmol) was suspended in DCM (300 μL) and TFA was added (60 μL). The reaction mixture turned homogenous after adding TFA. The reaction was stirred at room temperature for 1 hour. After 1 hour, solvent was removed by vacuum and the crude product was diluted with DMSO/water and purified by prep-HPLC to provide to provide the title compound referred to as MDPr-GlucQ-FK866 (8.9 mg, 0.008 mmol, 98.8%). LCMS: $t_R$=1.16 min; m/z=926.27 [M]$^+$

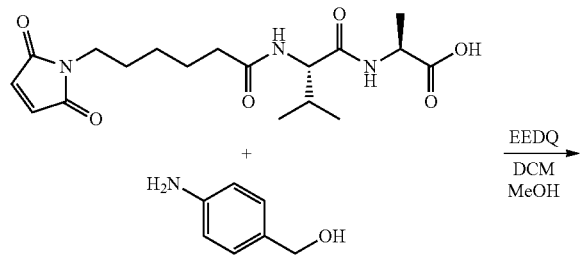

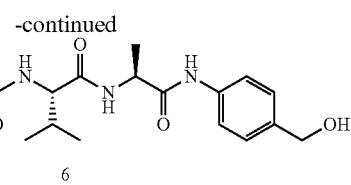

Example 6. 6-(2,5-dioxo-2,5-dihydro-1H-pyrrol-1-yl)-N—((S)-1-(((S)-1-((4-(hydroxymethyl)phenyl)amino)-1-oxopropan-2-yl)amino)-3-methyl-1-oxobutan-2-yl)hexanamide (6)

Added (6-(2,5-dioxo-2,5-dihydro-1H-pyrrol-1-yl)hexanoyl)-L-valyl-L-alanine (500 mg, 1.31 mmol) and (4-aminophenyl)methanol (170 mg, 1.38 mmol) into a round bottom flask. Added anhydrous DCM (5 mL) and anhydrous MeOH (500 μL) and stirred to dissolve solids. EEDQ (357 mg, 1.44 mmol) was added and the reaction stirred at room temperature overnight. Reaction solvents were removed under vacuum and the crude material purified by silica gel chromatography (3-10% MeOH in DCM) to provide the title compound (579 mg, 91%). LCMS: $t_R$=0.95 min; m/z=973.7 [M+H]$^+$. $^1$H NMR (400 MHz, Methanol-d$_4$+CDCl$_3$) δ 7.59-7.51 (m, 2H), 7.33-7.25 (m, 2H), 6.78 (s, 2H), 4.56 (s, 2H), 4.48 (q, J=7.1 Hz, 1H), 4.16 (d, J=7.2 Hz, 1H), 3.48 (t, J=7.1 Hz, 2H), 2.32-2.21 (m, 2H), 2.17-2.00 (m, J=6.7 Hz, 1H), 1.70-1.52 (m, 4H), 1.44 (d, J=7.1 Hz, 3H), 1.37-1.24 (m, 2H), 0.98 (d, J=6.8 Hz, 3H), 0.96 (d, J=6.7 Hz, 3H).

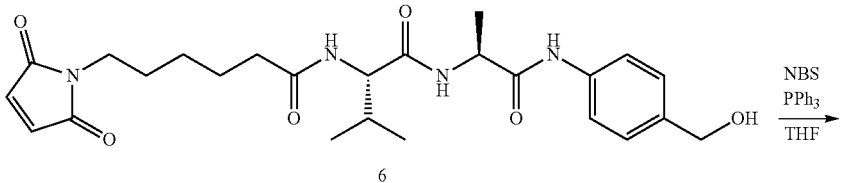

6

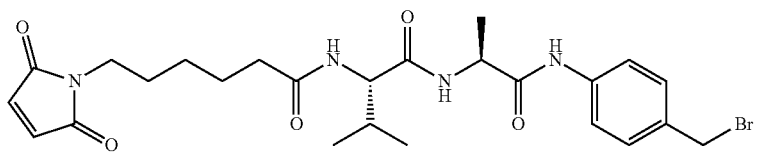

7

Example 7: N—((S)-1-(((S)-1-((4-(bromomethyl) phenyl)amino)-1-oxopropan-2-yl)amino)-3-methyl-1-oxobutan-2-yl)-6-(2,5-dioxo-2,5-dihydro-1H-pyrrol-1-yl)hexanamide (7)

Compound 6 (73.3 mg, 0.15 mmol) and triphenylphosphine (59.3 mg, 0.23 mmol) were suspended in THF (1.5 mL) and briefly sonicated. NBS (40.2 mg, 0.23 mmol) was added and the reaction stirred at room temperature. After 3 hours, additional portions of triphenylphosphine (59.3 mg, 0.23 mmol) and NBS (40.2 mg, 0.23 mmol) were added. After 4 hours, the reaction was purified directly by silica gel chromatography (2-10% MeOH in DCM). Fractions containing compound 7 also showed contaminating triphenylphosphine oxide; these were combined and concentrated to provide an impure preparation of the title compound (63 mg) which was used without further purification.

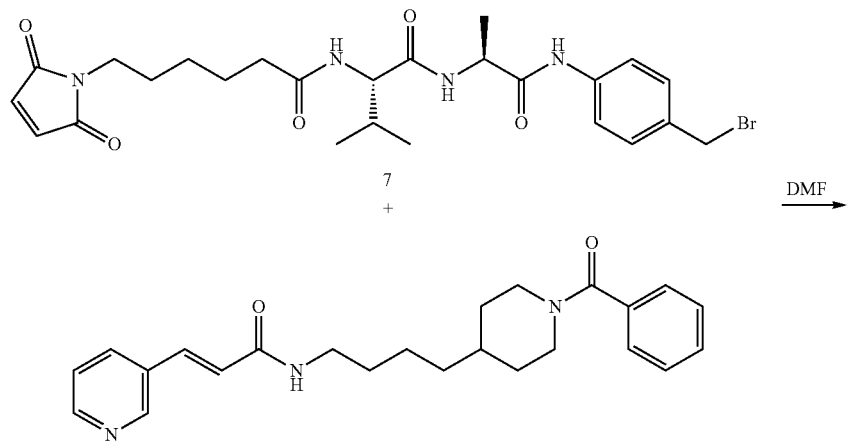

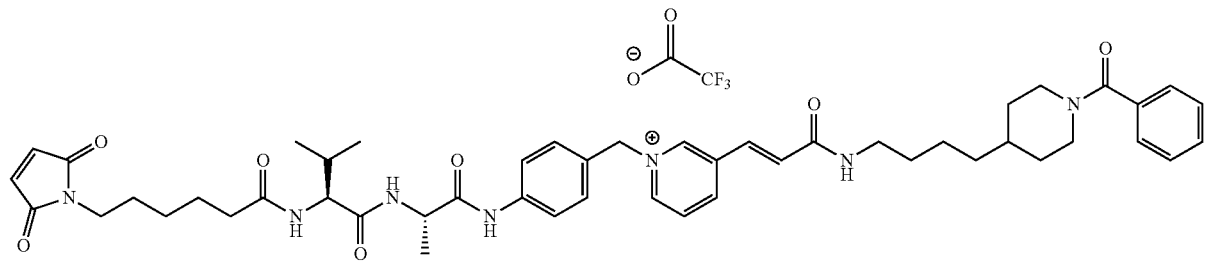

Example 8. 3-((E)-3-((4-(1-benzoylpiperidin-4-yl)butyl)amino)-3-oxoprop-1-en-1-yl)-1-(4-((S)-2-((S)-2-(6-(2,5-dioxo-2,5-dihydro-1H-pyrrol-1-yl)hexanamido)-3-methylbutanamido)propanamido)benzyl)pyridin-1-ium 2,2,2-trifluoroacetate (8)

The impure preparation of compound 7 was prepared as a solution in DMF (20 mg/mL). (E)-N-(4-(1-benzoylpiperidin-4-yl)butyl)-3-(pyridin-3-yl)acrylamide (5.0 mg, 0.013 mmol) was dissolved in anhydrous DMF (150 µL), and 300 µL of solution of compound 7 was added. The reaction was heated at 45° C. After one hour, LCMS showed all compound 7 was consumed while residual pyridine component was detectable. An additional 20 µL of compound 7 solution was added. After 30 min, the reaction was cooled to room temperature, diluted with DMSO, and purified by preparative HPLC to provide the title compound referred to as mc-val-ala-PABQ-FK866 (4.9 mg, 0.006 mmol, 45%). LCMS: $t_R$=1.09 min; m/z=860.5 $[M]^+$.

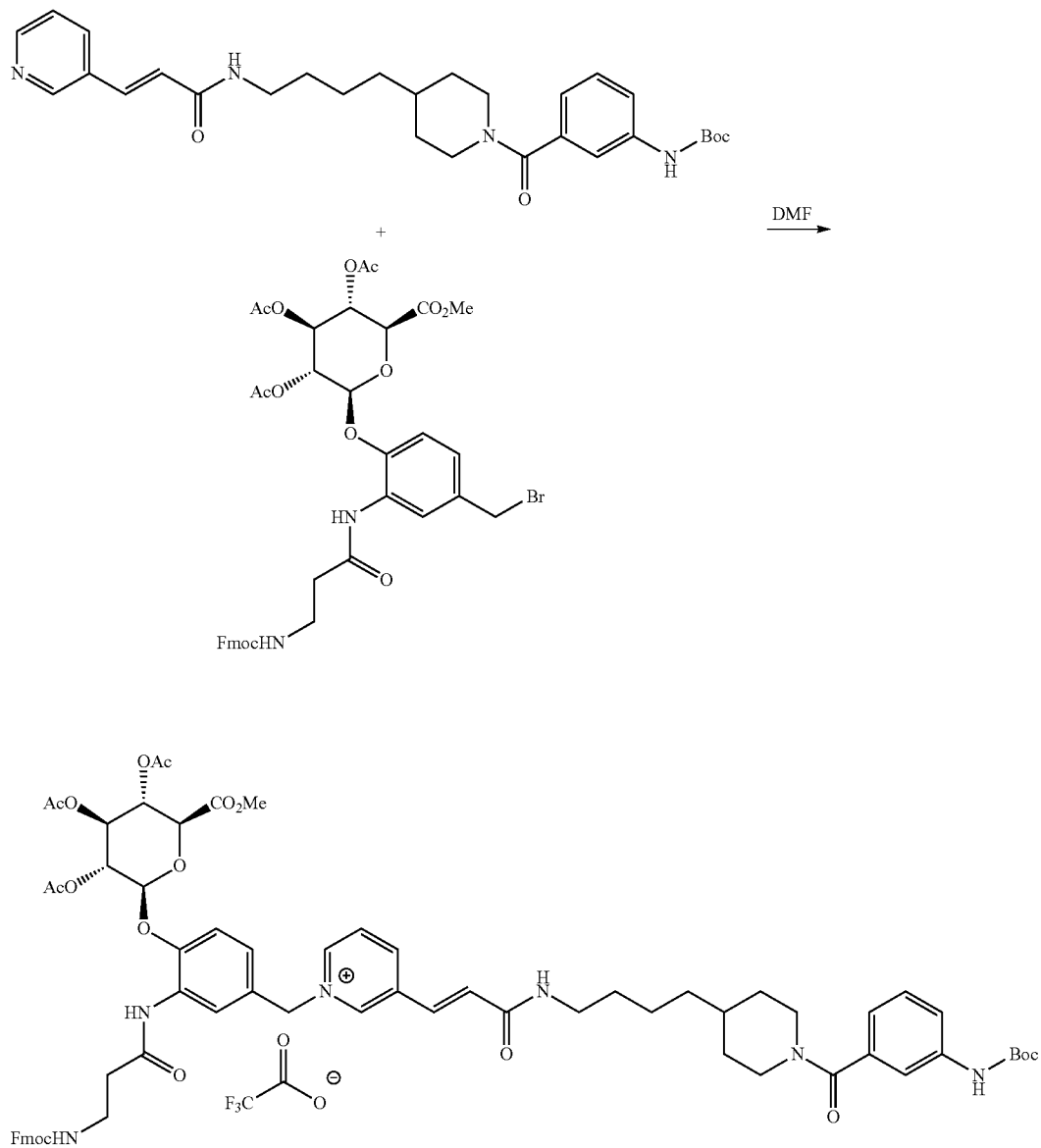

Example 9. 1-(3-(3-((((9H-fluoren-9-yl)methoxy) carbonyl)amino)-propanamido)-4-(((2S,3R,4S,5S, 6S)-3,4,5-triacetoxy-6-(methoxycarbonyl)tetrahydro-2H-pyran-2-yl)oxy)benzyl)-3-((E)-3-((4-(1-(3-((tert-butoxycarbonyl)amino)benzoyl)piperidin-4-yl)butyl) amino)-3-oxoprop-1-en-1-yl)pyridin-1-ium 2,2,2-trifluoroacetate (9)

(2S,3R,4S,5S,6S)-2-(2-(3-((((9H-fluoren-9-yl)methoxy) carbonyl)amino)-propanamido)-4-(bromomethyl)phenoxy)-6-(methoxycarbonyl)tetrahydro-2H-pyran-3,4,5-triyl triacetate (100 mg, 0.123 mmol) and tert-butyl (E)-(3-(4-(4-(3-(pyridin-3-yl)acrylamido)butyl)piperidine-1-carbonyl) phenyl)carbamate (52 mg, 0.103 mmol) was dissolved in anhydrous DMF (800 µL) and the reaction was heated up to 55° C. for 3 hours. The benzyl bromide input as the quaternization agent was prepared according to the procedure of *Mol. Cancer Ther.* (2016) 15(5): 938-945, the disclosure for which is specifically incorporated by reference herein. After 3 hours, the reaction was cooled down to room temperature, diluted with DMSO/water and purified by prep-HPLC to provide the title compound (106.2 mg, 0.079 mmol, 76.6%). LCMS: $t_R$=2.02 min; m/z=1237.82 [M]⁺.

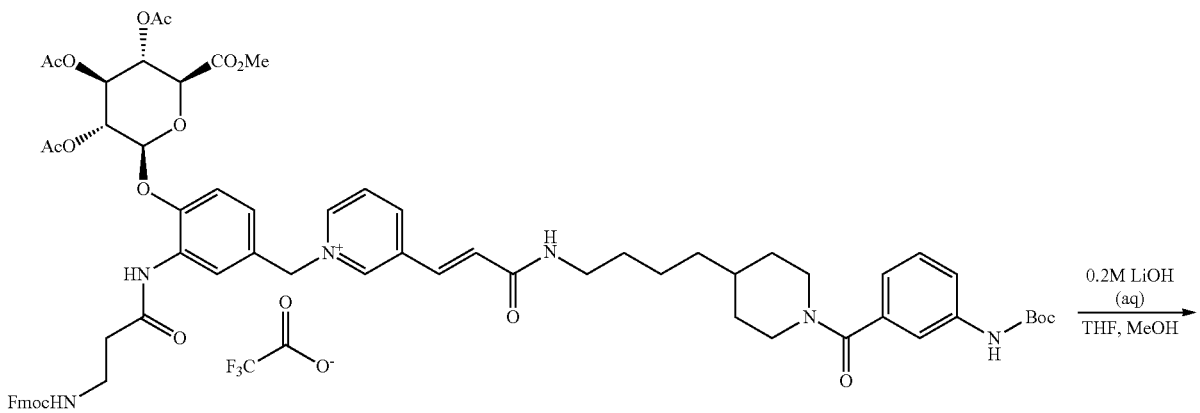

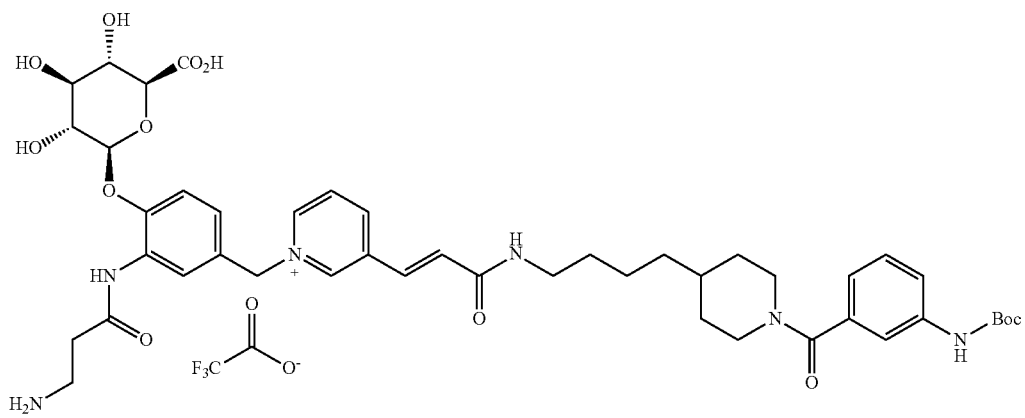

Example 10. 1-(3-(3-aminopropanamido)-4-(((2S, 3R,4S,5S,6S)-6-carboxy-3,4,5-trihydroxytetrahydro-2H-pyran-2-yl)oxy)benzyl)-3-((E)-3-((4-(1-(3-((tert-butoxycarbonyl)amino)benzoyl)piperidin-4-yl)butyl) amino)-3-oxoprop-1-en-1-yl)pyridin-1-ium 2,2,2-trifluoroacetate (10)

Compound 9 (45.5 mg, 0.037 mmol) was dissolved in a 1:1 mixture of MeOH and THF (1.8 mL). The solution was cooled on ice prior to addition of a LiOH solution (0.2 M, 1.8 mL, 0.37 mmol). The reaction was stirred on ice for 40 min, then warmed to room temperature. After 4 hours the reaction was acidified with a drop of acetic acid, then diluted with DMSO and water and purified by preparative HPLC to provide the title compound (19.2 mg, 0.022 mmol, 59.7%). LCMS: $t_R$=1.39 min; m/z=875.43 [M]+.

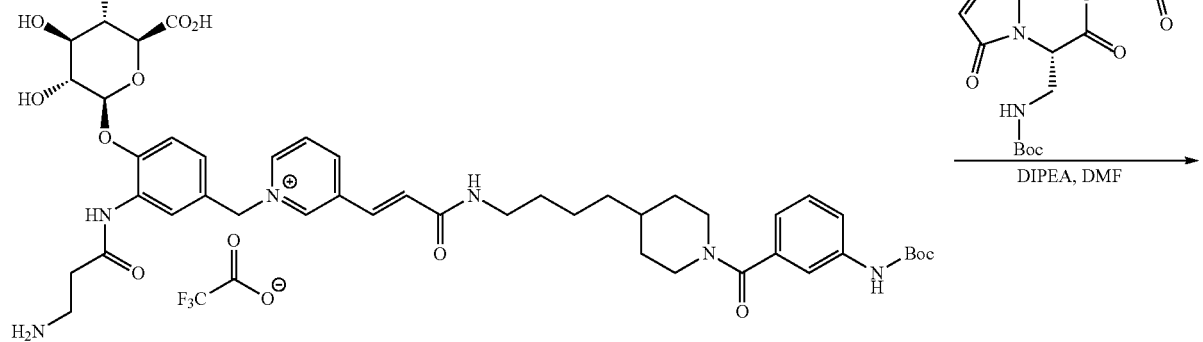

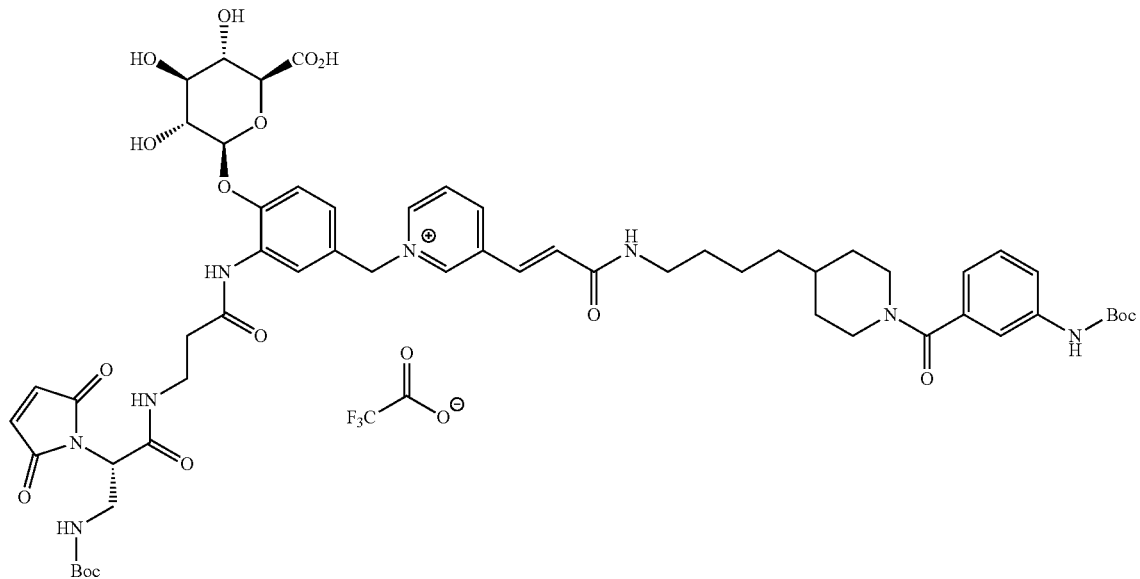

Example 11. 1-(3-(3-((S)-3-((tert-butoxycarbonyl)
amino)-2-(2,5-dioxo-2,5-dihydro-1H-pyrrol-1-yl)
propanamido)propanamido)-4-(((2S,3R,4S,5S,6S)-6-
carboxy-3,4,5-trihydroxytetrahydro-2H-pyran-2-yl)
oxy)benzyl)-3-((E)-3-((4-(1-(3-((tert-
butoxycarbonyl)amino)benzoyl)piperidin-4-yl)butyl)
amino)-3-oxoprop-1-en-1-yl)pyridin-1-ium 2,2,2-
trifluoroacetate (11)

Compound 10 (11.2 mg, 0.011 mmol) was dissolved in anhydrous DMF (600 μL) followed by the addition of DIPEA (5.9 μL). 2,5-Dioxopyrrolidin-1-yl (S)-3-((tert-butoxycarbonyl)amino)-2-(2,5-dioxo-2,5-dihydro-1H-pyrrol-1-yl)propanoate (8.6 mg, 0.023 mmol) in anhydrous DMF (100 μL) was then added. The reaction mixture was stirred at room temperature for 30 min. After 30 min, reaction was acidified with HOAc (5 μL), diluted with DMSO/water and purified by prep-HPLC to provide the title compound (10.4 mg, 0.009 mmol, 80.5%). LCMS: $t_R$=1.61 min; m/z=1141.66 [M]$^+$.

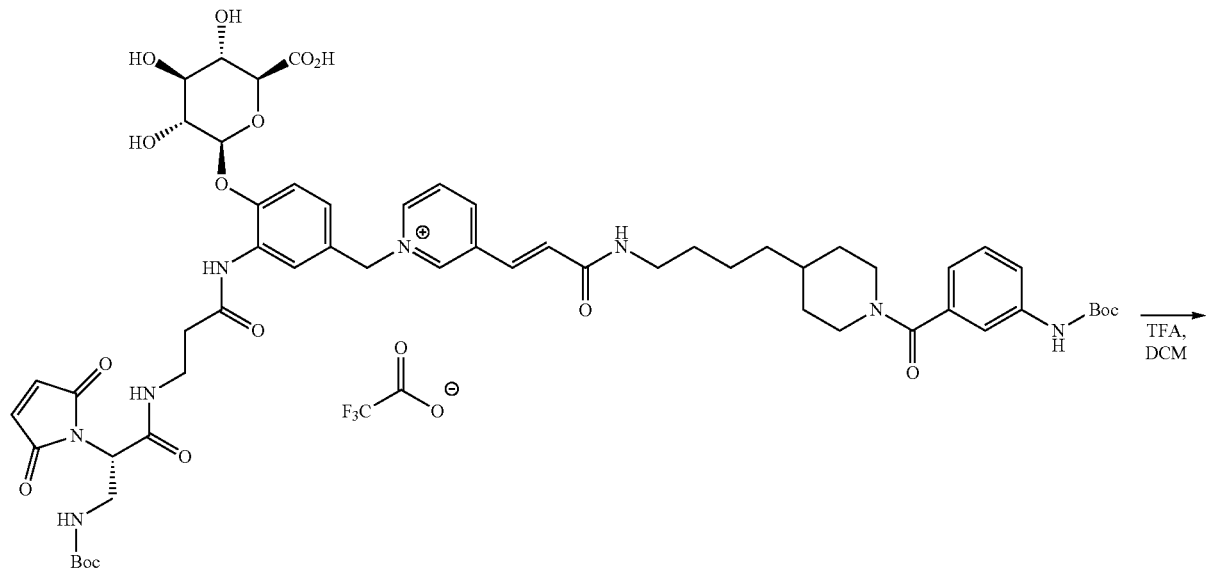

11

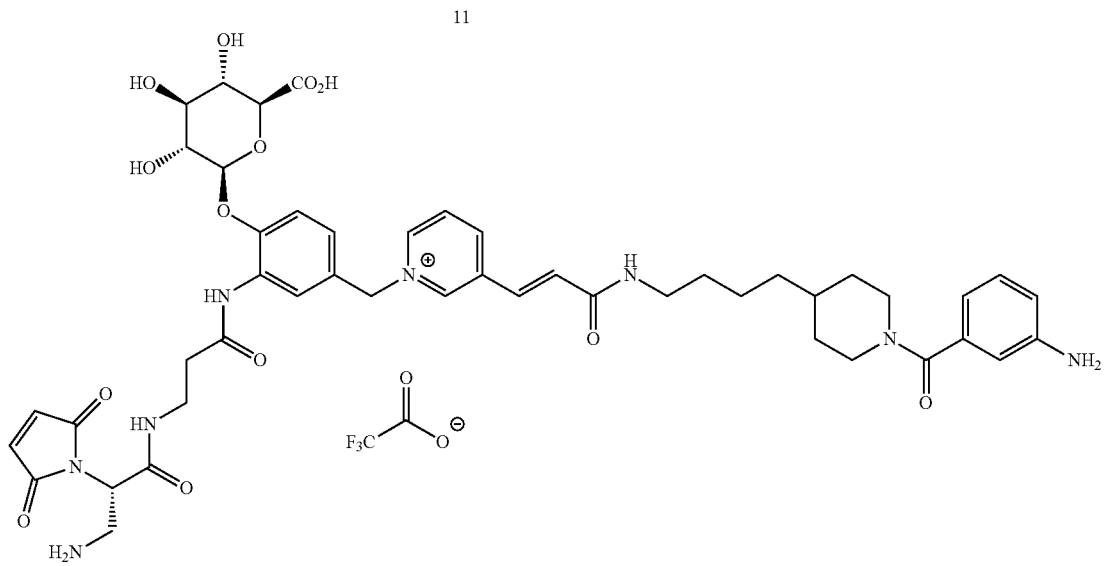

12

Example 12. 1-(3-(3-((S)-3-ammonio-2-(2,5-dioxo-2,5-dihydro-1H-pyrrol-1-yl)propanamido)propanamido)-4-(((2S,3R,4S,5S,6S)-6-carboxy-3,4,5-trihydroxytetrahydro-2H-pyran-2-yl)oxy)benzyl)-3-((E)-3-((4-(1-(3-ammoniobenzoyl)piperidin-4-yl)butyl)amino)-3-oxoprop-1-en-1-yl)pyridin-1-ium 2,2,2-trifluoroacetate (12)

Compound 11 (10.4 mg, 0.008 mmol) was suspended in DCM (240 μL) and TFA (60 μL) was added. The reaction mixture turned homogenous after adding TFA. The reaction was stirred at room temperature for 4 hours. After 4 hours, solvent was removed under vacuum and the crude product was diluted with DMSO/water and purified by prep-HPLC to provide the title compound referred to as MDPr-GlucQ-6050 (8.7 mg, 0.007 mmol, 81.8%). LCMS: $t_R$=0.96 min; m/z=941.21 [M]$^+$.

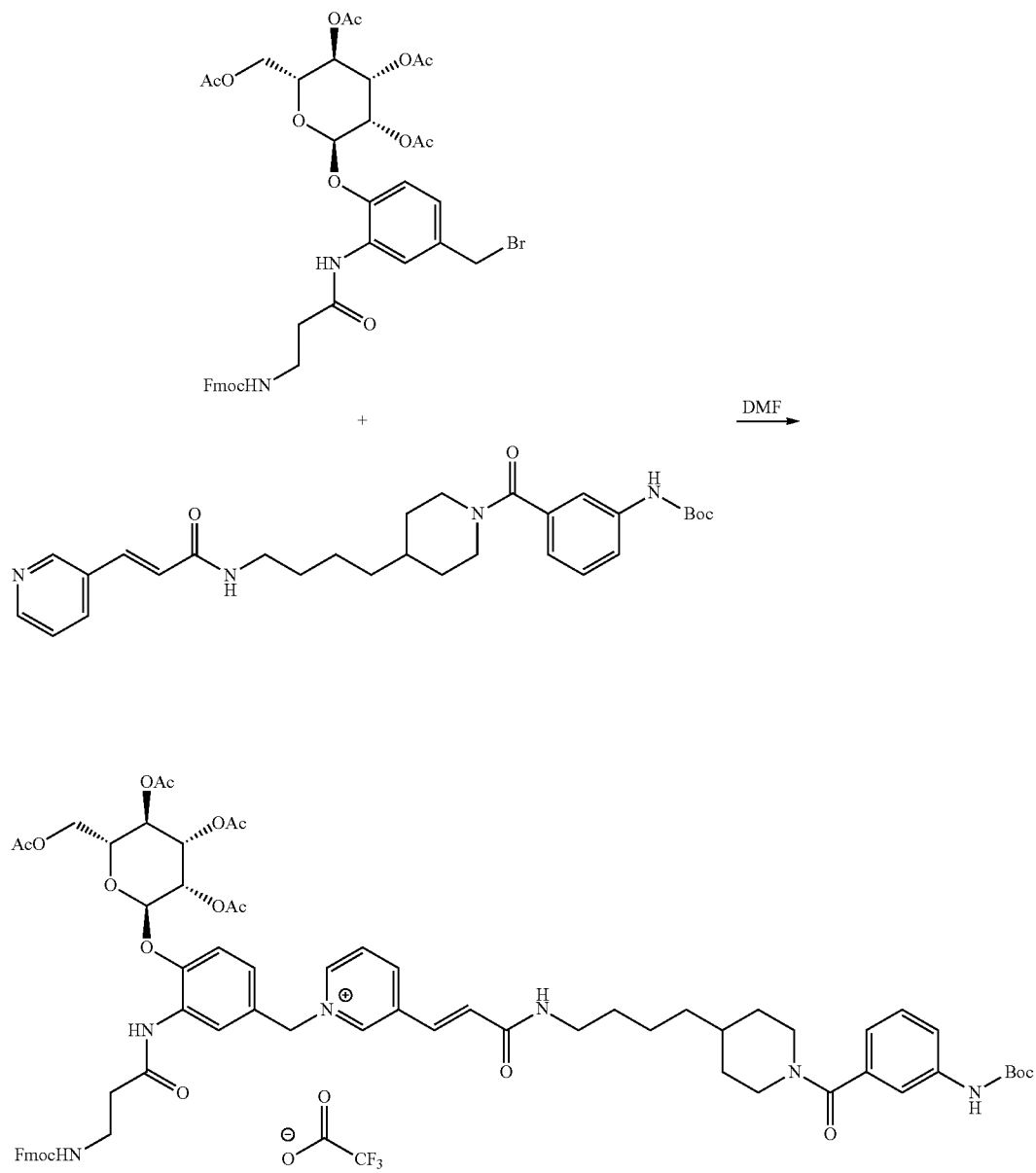

13

Example 13. 1-(3-(3-((((9H-fluoren-9-yl)methoxy)carbonyl)amino)-propanamido)-4-(((2R,3S,4S,5R,6R)-3,4,5-triacetoxy-6-(acetoxymethyl)tetrahydro-2H-pyran-2-yl)oxy)benzyl)-3-((E)-3-((4-(1-(3-((tert-butoxycarbonyl)amino)benzoyl)piperidin-4-yl)butyl)amino)-3-oxoprop-1-en-1-yl)pyridin-1-ium (13)

(2R,3S,4S,5R,6R)-2-(2-(3-((((9H-fluoren-9-yl)methoxy)carbonyl)amino)-propanamido)-4-(bromomethyl)phenoxy)-6-(acetoxymethyl)tetrahydro-2H-pyran-3,4,5-triyl triacetate (109.3 mg, 0.132 mmol) and tert-butyl (E)-(3-(4-(4-(3-(pyridin-3-yl)acrylamido)butyl)piperidine-1-carbonyl)phenyl)carbamate (51.6 mg, 0.102 mmol) were dissolved in anhydrous DMF (800 µL) and heated up to 55° C. for 2 hours. The benzyl bromide input as the quaternization agent was prepared according to the procedure of *Mol. Cancer Ther.* (2016) 15(5): 938-945, the disclosure for which is specifically incorporated by reference herein. The reaction was cooled to room temperature, diluted with DMSO and water, purified by preparative HPLC to provide the title compound (108.2 mg, 0.079 mmol, 77.8%). LCMS: $t_R$=2.00 min; m/z=1251.40 [M]+.

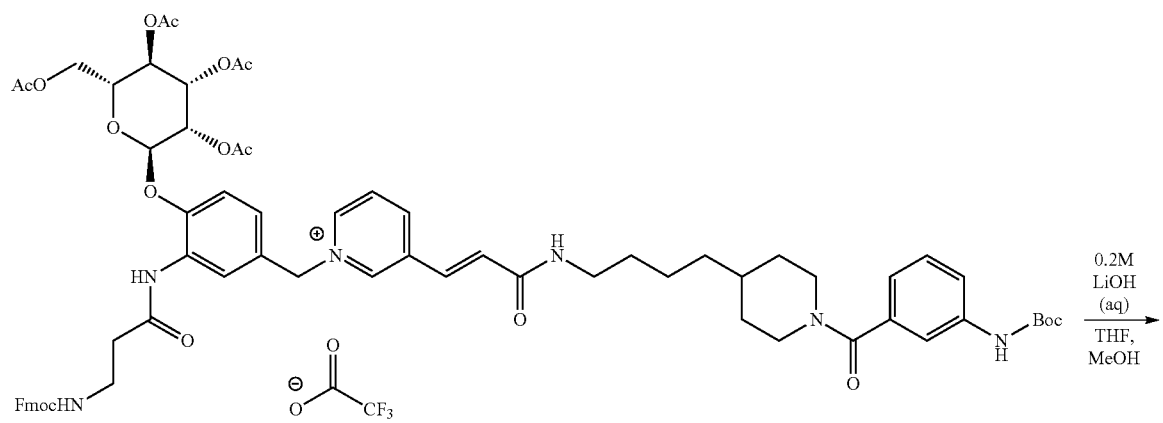

13

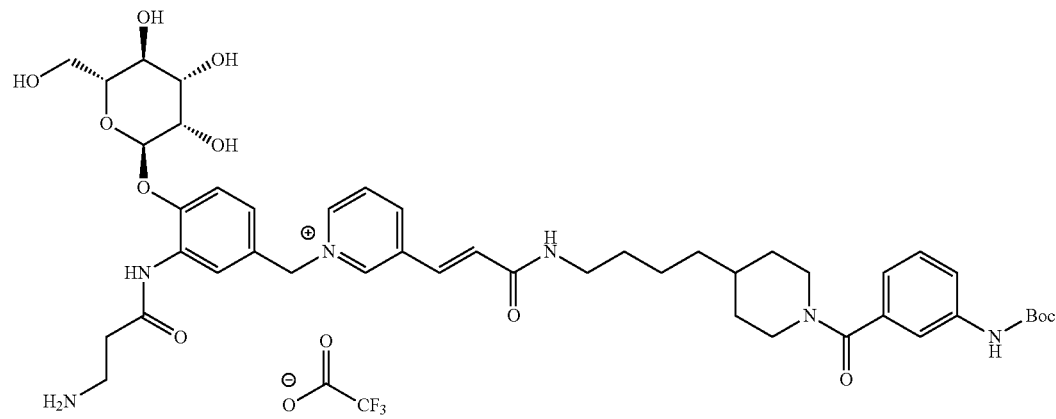

14

Example 14. 1-(3-(3-aminopropanamido)-4-(((2R,3S,4S,5S,6R)-3,4,5-trihydroxy-6-(hydroxymethyl)tetrahydro-2H-pyran-2-yl)oxy)benzyl)-3-((E)-3-((4-(1-(3-((tert-butoxycarbonyl)amino)benzoyl)piperidin-4-yl)butyl)amino)-3-oxoprop-1-en-1-yl)pyridin-1-ium 2,2,2-trifluoroacetate (14)

Compound 13 (50.8 mg, 0.037 mmol) was dissolved in a 1:1 mixture of MeOH and THF (1.8 mL). The solution was cooled on ice prior to the addition of a LiOH solution (0.2 M, 1.86 mL, 0.372 mmol). The reaction was stirred on ice for 30 mins, and then warmed to room temperature. After 3 hours, the reaction was acidified with acetic acid (20 μL), then diluted with DMSO/water and purified by preparative HPLC to provide the title compound (20.6 mg, 0.019 mmol, 50.8%). LCMS: $t_R$=0.84 min; m/z=861.39 [M]$^+$.

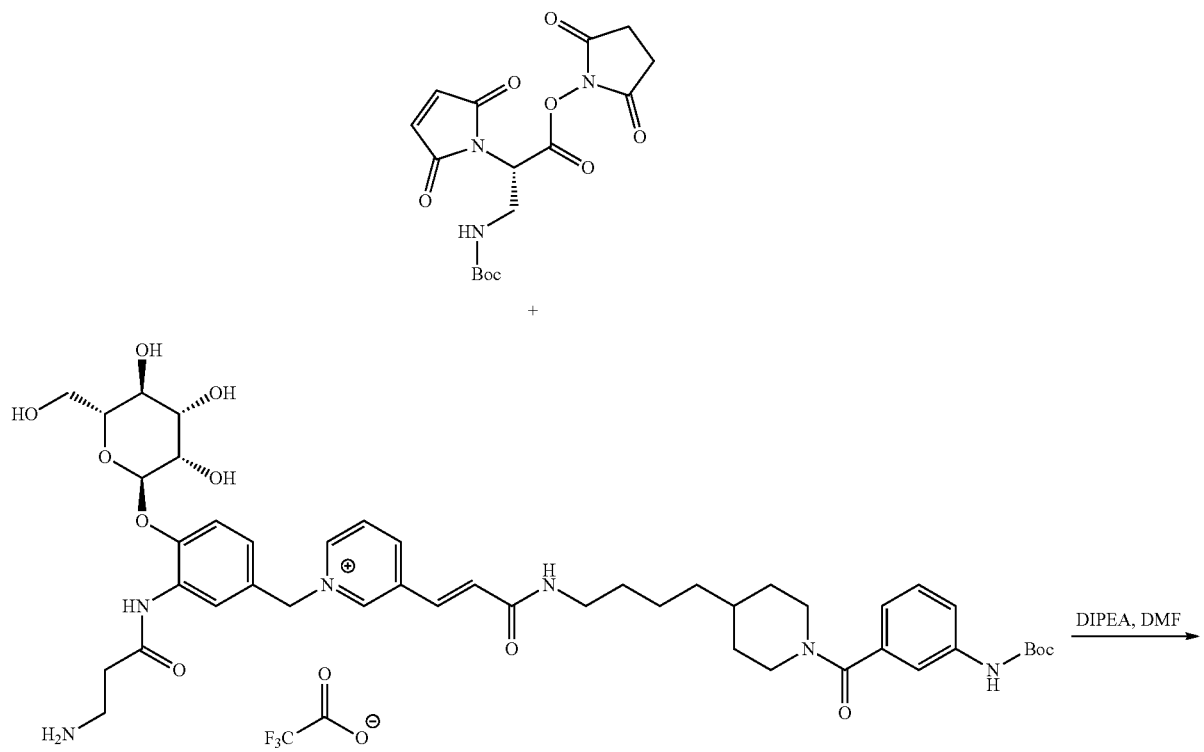

14

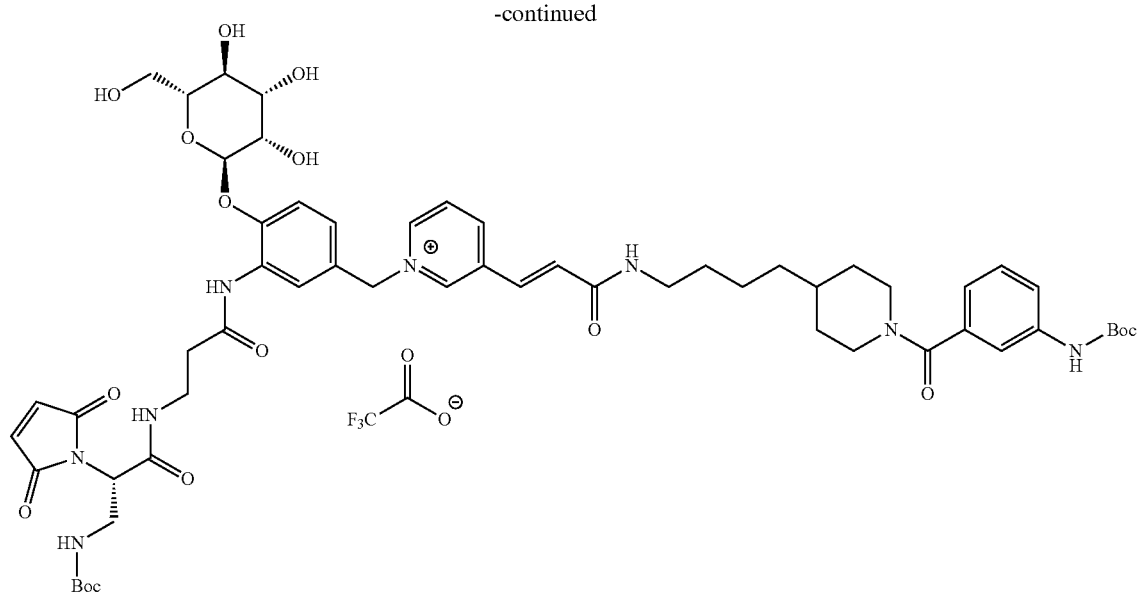

Example 15: 1-(3-(3-((S)-3-((tert-butoxycarbonyl)amino)-2-(2,5-dioxo-2,5-dihydro-1H-pyrrol-1-yl)propanamido)propanamido)-4-(((2R,3S,4S,5S,6R)-3,4,5-trihydroxy-6-(hydroxymethyl)tetrahydro-2H-pyran-2-yl)oxy)benzyl)-3-((E)-3-((4-(1-(3-((tert-butoxycarbonyl)amino)benzoyl)piperidin-4-yl)butyl)amino)-3-oxoprop-1-en-1-yl)pyridin-1-ium 2,2,2-trifluoroacetate (15)

Compound 14 (10.2 mg, 0.011 mmol) was dissolved in anhydrous DMF (300 μL) followed by the addition of DIPEA (9.3 μL). 2,5-Dioxopyrrolidin-1-yl (S)-3-((tert-butoxycarbonyl)amino)-2-(2,5-dioxo-2,5-dihydro-1H-pyrrol-1-yl)propanoate (6.12 mg, 0.016 mmol) in anhydrous DMF (100 μL) was then added. The reaction mixture was stirred at room temperature for 30 min. After 30 min, reaction was acidified with HOAc (10 μL), diluted with DMSO/water and purified by prep-HPLC to provide the title compound (10.3 mg, 0.008 mmol, 77.5%). LCMS: $t_R$=1.58 min; m/z=1127.79 [M]$^+$.

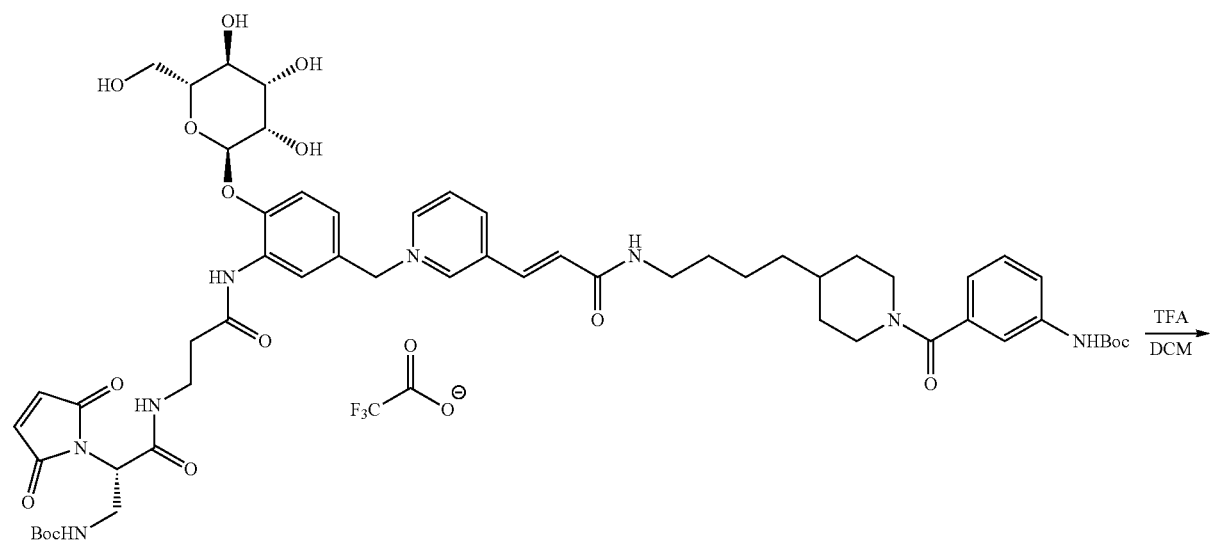

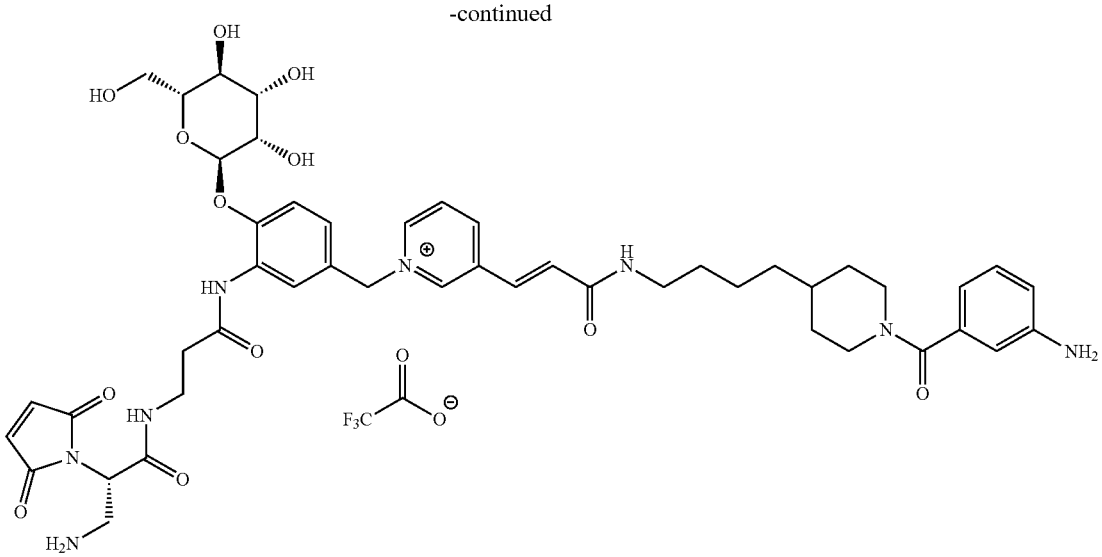

16

Example 16. 1-(3-(3-(((S)-3-ammonio-2-(2,5-dioxo-2,5-dihydro-1H-pyrrol-1-yl)propanamido)propanamido)-4-(((2R,3S,4S,5S,6R)-3,4,5-trihydroxy-6-(hydroxymethyl)tetrahydro-2H-pyran-2-yl)oxy)benzyl)-3-((E)-3-((4-(1-(3-ammoniobenzoyl)piperidin-4-yl)butyl)amino)-3-oxoprop-1-en-1-yl)pyridin-1-ium 2,2,2-trifluoroacetate (16)

Compound 15 (10.3 mg, 0.008 mmol) was suspended in DCM (240 μL) and TFA (60 μL) was added. The reaction mixture turned homogenous after adding TFA. The reaction was stirred at room temperature for 4 hours. After 4 hours, solvent was removed under vacuum and the crude product was diluted with DMSO/water and purified by prep-HPLC to the title compound (5.4 mg, 0.004 mmol, 51.3%) referred to as MDPr-ManQ-6050. LCMS: $t_R$=1.45 min; m/z=1027.46 [M]$^+$.

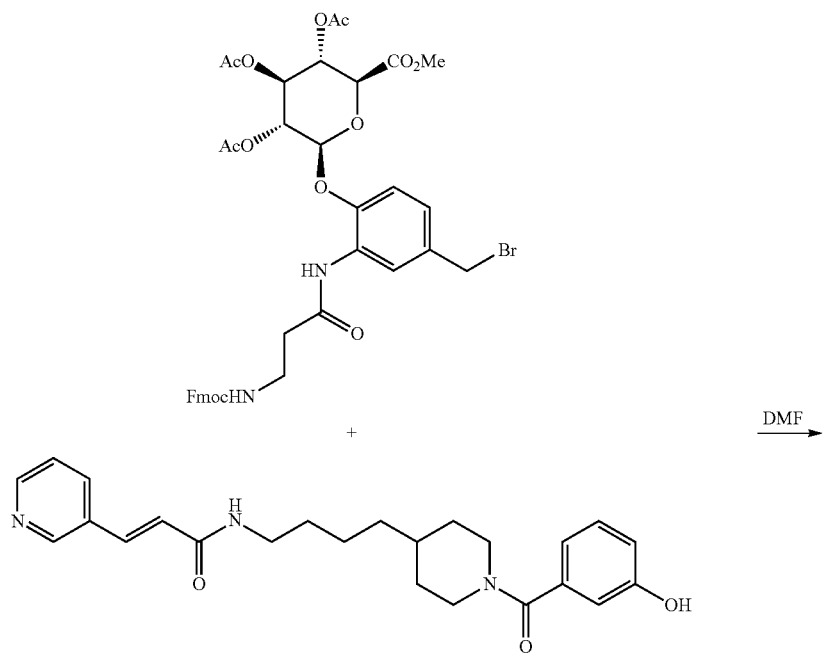

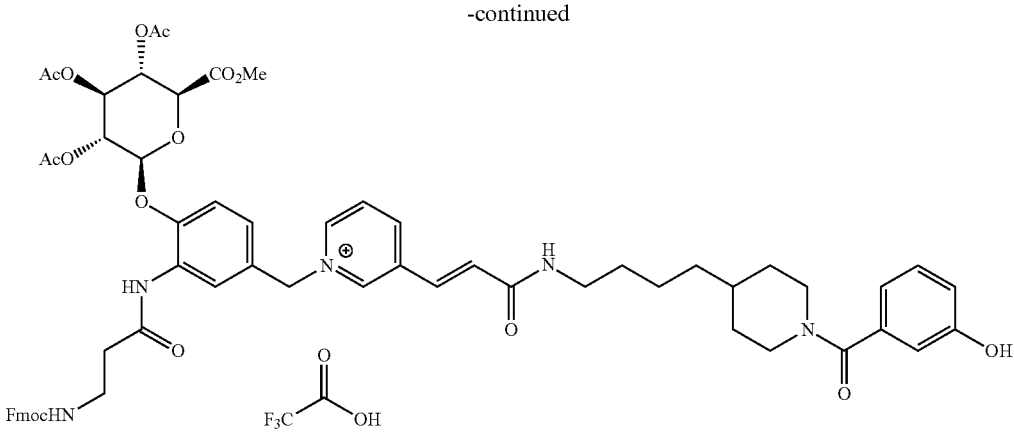

17

Example 17. 1-(3-(3-((((9H-fluoren-9-yl)methoxy)carbonyl)amino)-propanamido)-4-(((2S,3R,4S,5S,6S)-3,4,5-triacetoxy-6-(methoxycarbonyl)tetrahydro-2H-pyran-2-yl)oxy)benzyl)-3-((E)-3-((4-(1-(3-hydroxybenzoyl)piperidin-4-yl)butyl)amino)-3-oxoprop-1-en-1-yl)pyridin-1-ium 2,2,2-trifluoroacetate (17)

(2S,3R,4S,5S,6S)-2-(2-(3-((((9H-fluoren-9-yl)methoxy)carbonyl)amino)-propanamido)-4-(bromomethyl)phenoxy)-6-(methoxycarbonyl)tetrahydro-2H-pyran-3,4,5-triyl triacetate (46.6 mg, 0.057 mmol) and (E)-N-(4-(1-(3-hydroxybenzoyl)piperidin-4-yl)butyl)-3-(pyridin-3-yl) acrylamide (20.0 mg, 0.048 mmol) were dissolved in anhydrous DMF (600 μL). The benzyl bromide input as the quaternization agent was prepared according to the procedure of *Mol. Cancer Ther.* (2016) 15(5): 938-945, the disclosure for which is specifically incorporated by reference herein. The reaction mixture was heated up to 55° C. for 10 hours. After 10 hours, the reaction was cooled down to room temperature and diluted with DMSO/water and purified by prep-HPLC to provide the title compound (60.1 mg, 0.048 mmol, 83.5%). LCMS: $t_R$=1.81 min; m/z=1138.75 [M]$^+$.

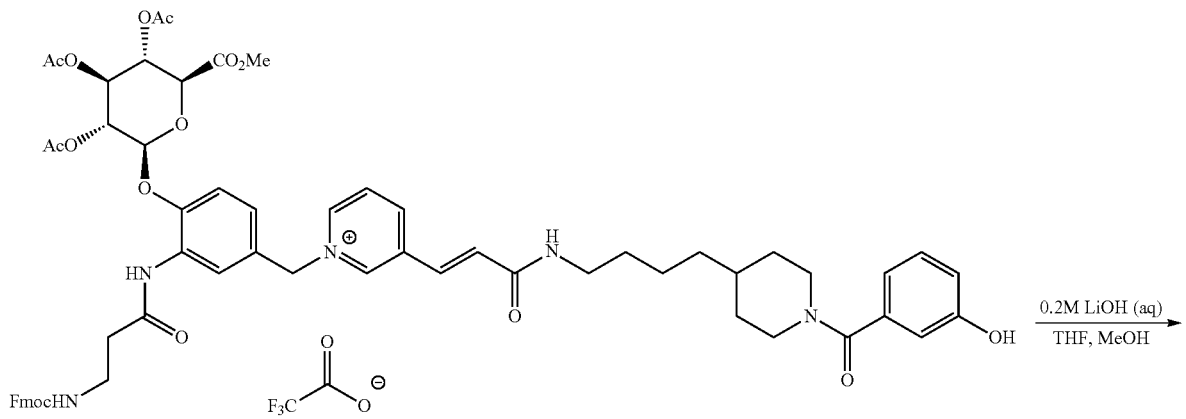

17

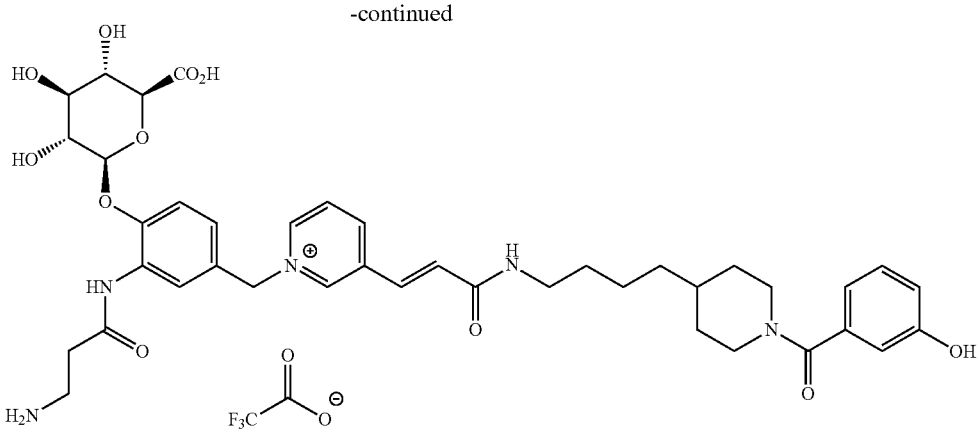

18

Example 18. 1-(3-(3-aminopropanamido)-4-(((2S, 3R,4S,5S,6S)-6-carboxy-3,4,5-trihydroxytetrahydro-2H-pyran-2-yl)oxy)benzyl)-3-((E)-3-((4-(1-(3-hydroxybenzoyl)piperidin-4-yl)butyl)amino)-3-oxoprop-1-en-1-yl)pyridin-1-ium 2,2,2-trifluoroacetate (18)

Compound 17 (60.1 mg, 0.048 mmol) was dissolved in a 1:1 mixture of MeOH and THF (2.4 mL). The solution was cooled on ice prior to addition of a LiOH solution (0.2 M, 2.4 mL, 0.48 mmol). The reaction was stirred on ice for 30 min, then warmed to room temperature. After 4 hours the reaction was acidified with a drop of acetic acid, then diluted with DMSO/water and purified by preparative HPLC to provide the title compound (25.4 mg, 0.025 mmol, 53%). LCMS: $t_R$=1.06 min; m/z=776.18 [M]$^+$.

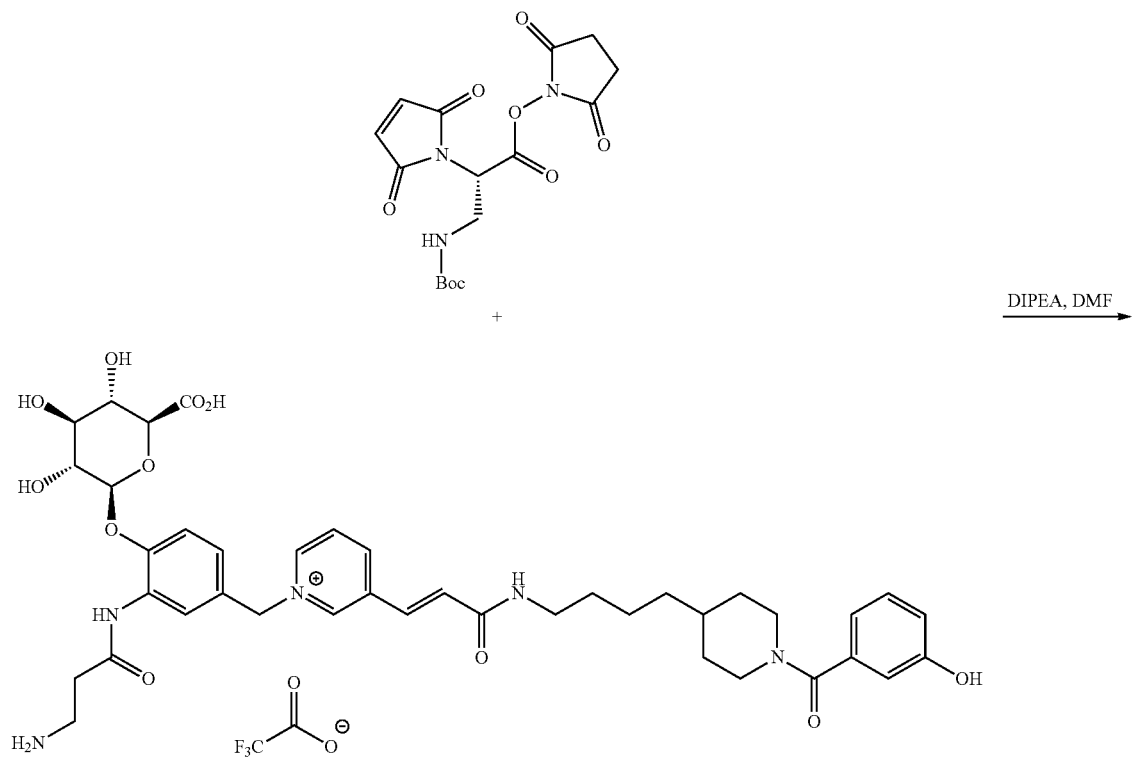

18

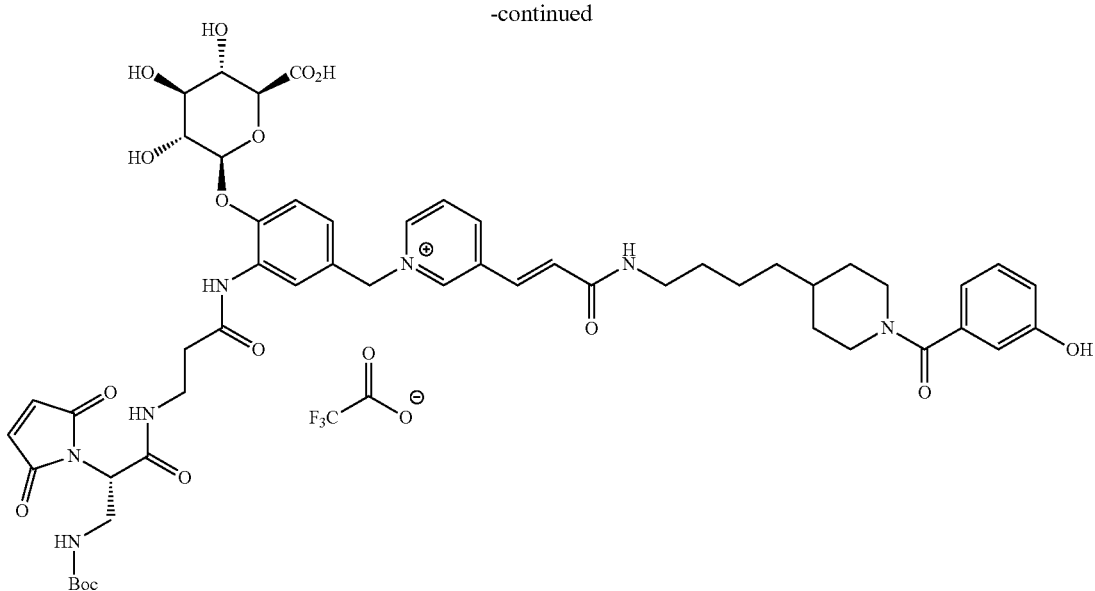

-continued

19

Example 19. 1-(3-(3-((S)-3-((tert-butoxycarbonyl)amino)-2-(2,5-dioxo-2,5-dihydro-1H-pyrrol-1-yl)propanamido)propanamido)-4-(((2S,3R,4S,5S,6S)-6-carboxy-3,4,5-trihydroxytetrahydro-2H-pyran-2-yl)oxy)benzyl)-3-((E)-3-((4-(1-(3-hydroxybenzoyl)piperidin-4-yl)butyl)amino)-3-oxoprop-1-en-1-yl)pyridin-1-ium 2,2,2-trifluoroacetate (19)

Compound 18 (10 mg, 0.01 mmol) was dissolved in anhydrous DMF (400 μL) followed by the addition of DIPEA (5.2 μL). 2,5-Dioxopyrrolidin-1-yl (S)-3-((tert-butoxycarbonyl)amino)-2-(2,5-dioxo-2,5-dihydro-1H-pyrrol-1-yl)propanoate (4.6 mg, 0.012 mmol) in anhydrous DMF (100 μL) was then added. The reaction mixture was stirred at room temperature for 2 hours. After 2 hours, the reaction was acidified with HOAc (5 μL), diluted with DMSO/water and purified by prep-HPLC to provide the title compound (6.3 mg, 0.005 mmol, 54.7%). LCMS: $t_R$=1.34 min; m/z=1142.70 [M]+.

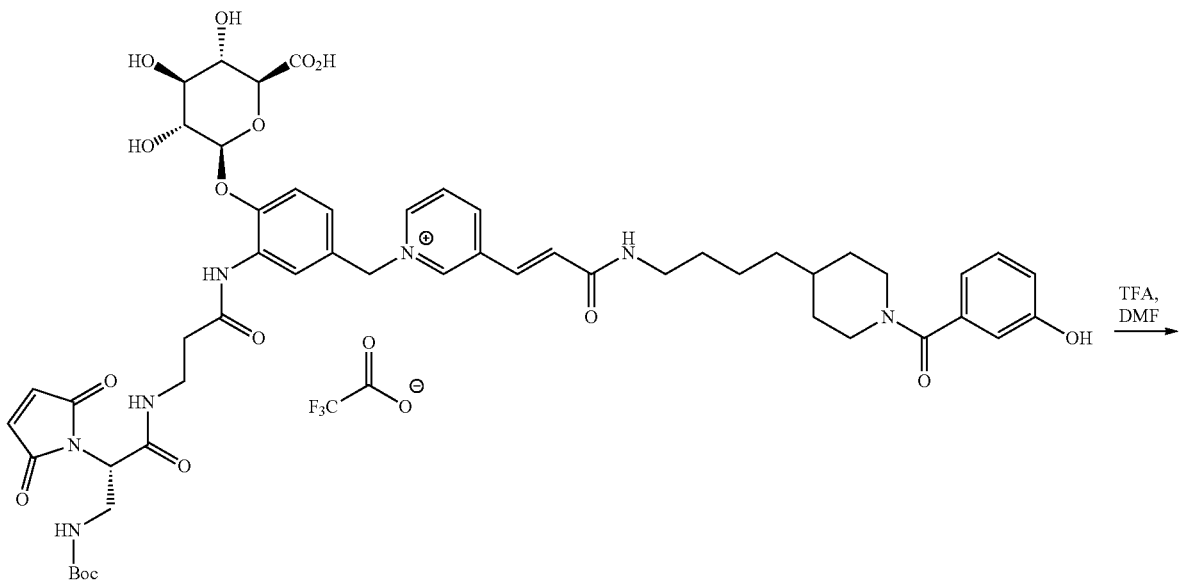

19

293 294
-continued
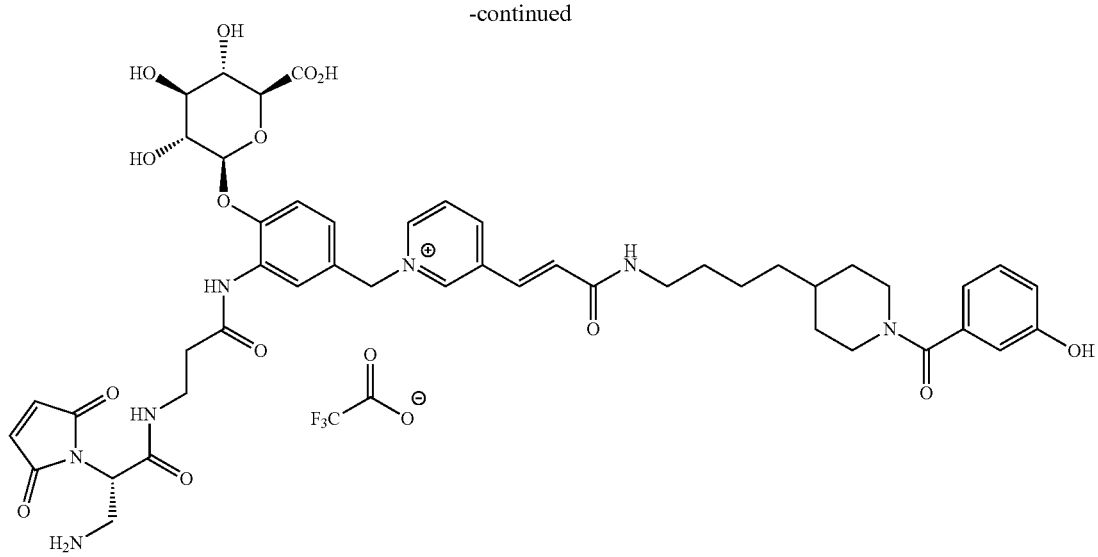
Example 20. Preparation of NAMPTi Fluorophore for Fluorescence Polarization Assay
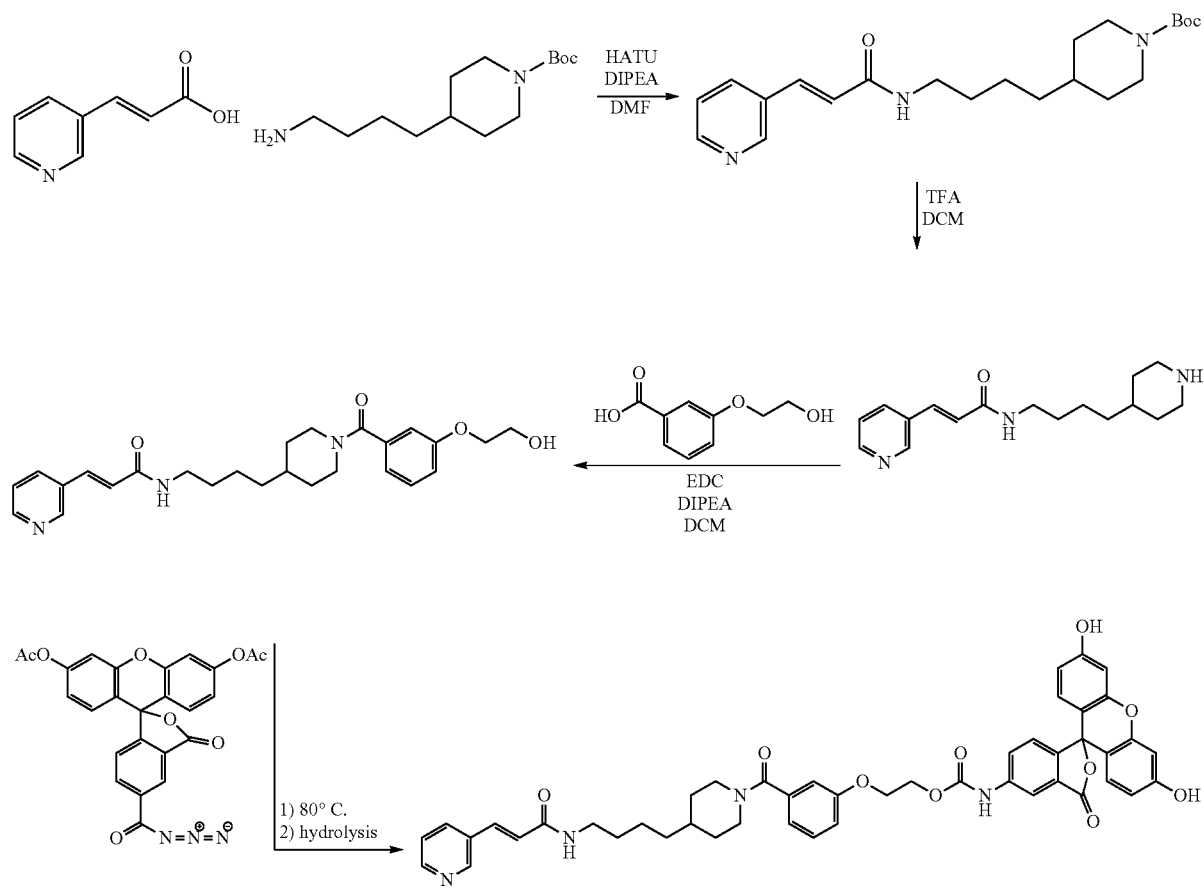

Step 1: (2E)-3-(pyridin-3-yl)prop-2-enoic acid (698 mg, 4.68 mmol) was dissolved in DMF (24 mL) and treated with DIPEA (2 mL, 11.7 mmol) and HATU (1.80 g, 4.68 mmol). After 5 minutes, tert-butyl 4-(4-aminobutyl)piperidine-1-carboxylate (1.00 g, 3.90 mmol) was added as a solution in DMF (8 mL). The reaction was stirred at room temperature overnight. The reaction solvent was removed in vacuo, and the residue re-dissolved in EtOAc then washed once with water, twice with saturated NaHCO$_3$, and once with brine. The organic layer was dried over Na$_2$SO$_4$ and concentrated. The crude product was purified by silica gel chromatography (EtOAc/hexanes) to provide tert-butyl (E)-4-(4-(3-(pyridin-3-yl)acrylamido)butyl)piperidine-1-carboxylate (1.16 g, 3.00 mmol, 77%). LCMS: t$_R$=1.22 min; m/z=388.3 [M+H]$^+$. $^1$H NMR (400 MHz, Chloroform-d) δ 8.78-8.71 (m, 1H), 8.57 (dd, J=4.8, 1.6 Hz, 1H), 7.83-7.75 (m, 1H), 7.62 (d, J=15.7 Hz, 1H), 7.35-7.29 (m, 1H), 6.45 (d, J=15.7 Hz, 1H), 5.68 (t, 1H), 4.18-3.90 (m, 2H), 3.40 (td, J=7.2, 5.9 Hz, 2H), 2.76-2.55 (m, 2H), 1.70-1.51 (m, 4H), 1.45 (s, 9H), 1.43-1.31 (m, 3H), 1.31-1.20 (m, 2H), 1.07 (qd, J=12.5, 4.4 Hz, 2H).

Step 2: tert-butyl (E)-4-(4-(3-(pyridin-3-yl)acrylamido)butyl)piperidine-1-carboxylate from step 1 (1.06 g, 2.75 mmol) was dissolved in dichloromethane (15 mL) and treated with TFA (3 mL) for 90 minutes. The reaction was concentrated in vacuo, re-dissolved in 1:1 MeCN:H$_2$O, and concentrated again to (E)-N-(4-(piperidin-4-yl)butyl)-3-(pyridin-3-yl)acrylamide as the di-TFA salt (1.30 g, 2.69 mmol, 98%). LCMS: t$_R$=0.46 min; m/z=288.2 [M+H]$^+$. $^1$H NMR (400 MHz, Methanol-d$_4$) δ 9.01-8.93 (m, 1H), 8.74 (dd, J=5.5, 1.4 Hz, 1H), 8.60 (dtt, J=8.2, 1.5, 0.6 Hz, 1H), 7.99-7.87 (m, 1H), 7.61 (d, J=15.8 Hz, 1H), 6.88 (d, J=15.8 Hz, 1H), 3.40-3.28 (m, 6H), 2.95 (td, m, 2H), 2.02-1.86 (m, 2H), 1.69-1.53 (m, 3H), 1.50-1.24 (m, 6H).

Step 3: To a reaction vessel containing (E)-N-(4-(piperidin-4-yl)butyl)-3-(pyridin-3-yl)acrylamide TFA salt (30 mg, 0.058 mmol) and 3-(2-hydroxyethoxy)benzoic acid (0.058 mmol) was added a 0.25 M solution of EDC in DCM (350 μL, 0.087 mmol) followed by a 0.25 M solution of DMAP in DCM (350 μL, 0.087 mmol) and DIPEA (51 μL, 0.29 mmol). The reaction was stirred for 3 hours, then concentrated in vacuo. The crude material was re-dissolved in EtOAc and washed twice with water, once with saturated NH$_4$Cl, and once with brine. The organic layer was dried over Na$_2$SO$_4$ and concentrated. The resulting intermediate product was treated with 30% TFA in DCM for 30 minutes, then concentrated in vacuo. Purification by preparative HPLC afforded (E)-N-(4-(1-(3-(2-hydroxyethoxy)benzoyl)piperidin-4-yl)butyl)-3-(pyridin-3-yl)acrylamide LCMS: t$_R$=0.79 min; m/z=452.3 [M+H]$^+$.

Step 4: (E)-N-(4-(1-(4-(2-hydroxyethoxy)benzoyl)piperidin-4-yl)butyl)-3-(pyridin-3-yl)acrylamide was condensed with the diacetate of fluorescein-5-carbonyl azide via Curtius rearrangement followed by hydrolysis of the acetates.

Example 20: 1-(3-(3-((S)-3-ammonio-2-(2,5-dioxo-2,5-dihydro-1H-pyrrol-1-yl)propanamido)propanamido)-4-((((2S,3R,4S,5S,6S)-6-carboxy-3,4,5-trihydroxytetrahydro-2H-pyran-2-yl)oxy)benzyl)-3-((E)-3-((4-(1-(3-hydroxybenzoyl)piperidin-4-yl)butyl)amino)-3-oxoprop-1-en-1-yl)pyridin-1-ium 2,2,2-trifluoroacetate (20)

Compound 19 (6.3 mg, 0.0054 mmol) was suspended in DCM (300 μL) and TFA was added (60 μL). The reaction mixture turned homogenous after adding TFA. The reaction was stirred at room temperature for 1 hour. After 1 hour, solvent was removed under vacuum and the crude product was diluted with DMSO/water and purified by prep-HPLC to provide the title compound (5.9 mg, 0.0050 mmol, 92.5%) referred to as MDPr-GlucQ-6048. LCMS: t$_R$=1.08 min; m/z=942.28 [M]$^+$.

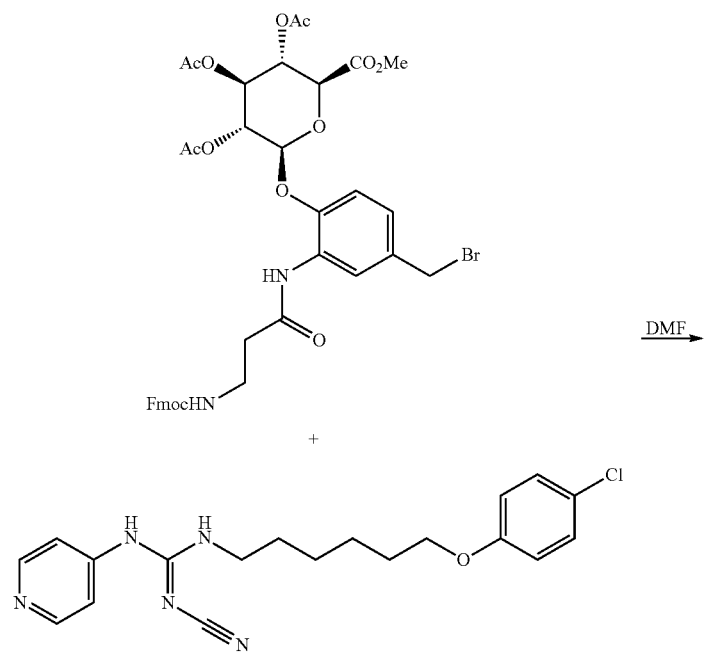

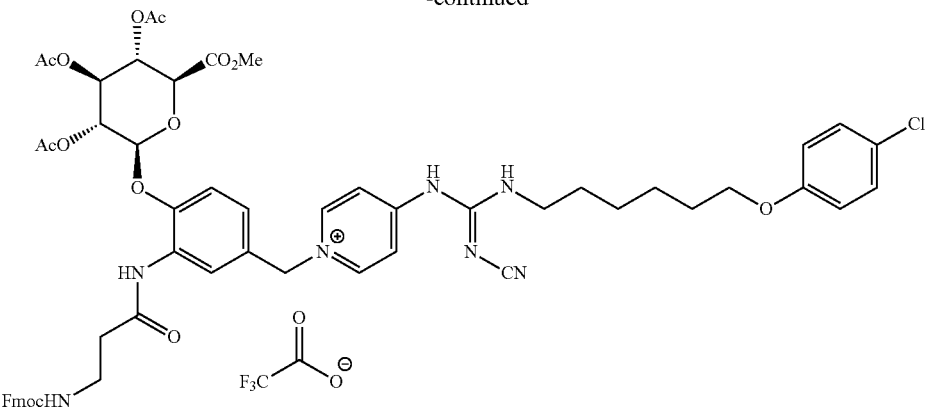

21

Example 21. 1-(3-(3-((((9H-fluoren-9-yl)methoxy)carbonyl)amino)-propanamido)-4-(((2S,3R,4S,5S,6S)-3,4,5-triacetoxy-6-(methoxycarbonyl)tetrahydro-2H-pyran-2-yl)oxy)benzyl)-4-((E)-3-(6-(4-chlorophenoxy)hexyl)-2-cyanoguanidino)-pyridin-1-ium 2,2,2-trifluoroacetate (21)

(2S,3R,4S,5S,6S)-2-(2-(3-((((9H-fluoren-9-yl)methoxy)carbonyl)amino)-propanamido)-4-(bromomethyl)phenoxy)-6-(methoxycarbonyl)tetrahydro-2H-pyran-3,4,5-triyl triacetate (48.1 mg, 0.059 mmol) and (E)-N-(4-(1-(3-hydroxybenzoyl)piperidin-4-yl)butyl)-3-(pyridin-3-yl)acrylamide (14.7 mg, 0.040 mmol) were dissolved in anhydrous DMF (500 μL). The benzyl bromide input as the quaternization agent was prepared according to the procedure of *Mol. Cancer Ther.* (2016) 15(5): 938-945, the disclosure for which is specifically incorporated by reference herein The reaction mixture was heated up to 55° C. for 2 hours. After 2 hours, the reaction was cooled down to room temperature and diluted with DMSO/water and purified by prep-HPLC to provide the title compound (36.8 mg, 0.033 mmol, 84.4%). LCMS: $t_r$=1.47 min; m/z=1102.66 [M]+. 1H NMR (400 MHz, DMSO-d6) δ 11.25 (s, 1H), 8.87 (s, 2H), 8.74 (d, J=6.9 Hz, 2H), 8.00 (d, J=2.1 Hz, 1H), 7.89 (d, J=7.5 Hz, 2H), 7.68 (d, J=7.5 Hz, 2H), 7.54 (s, 2H), 7.46-7.36 (m, 3H), 7.36-7.22 (m, 5H), 7.15 (d, J=8.5 Hz, 1H), 7.01-6.83 (m, 2H), 5.63 (d, J=7.8 Hz, 1H), 5.55 (s, 2H), 5.50 (t, J=9.7 Hz, 1H), 5.19 (dd, J=9.8, 7.8 Hz, 1H), 5.06 (t, J=9.8 Hz, 1H), 4.74 (d, J=10.0 Hz, 1H), 4.34-4.27 (m, 2H), 4.21 (t, J=6.9 Hz, 2H), 3.93 (t, J=6.4 Hz, 2H), 3.62 (s, 3H), 3.39-3.20 (m, 4H), 2.59-2.52 (m, 2H), 2.02 (s, 3H), 2.00 (s, 3H), 1.99 (s, 3H), 1.69 (p, J=6.6 Hz, 2H), 1.56 (p, J=7.3 Hz, 2H), 1.46-1.38 (m, 2H), 1.38-1.29 (m, 2H).

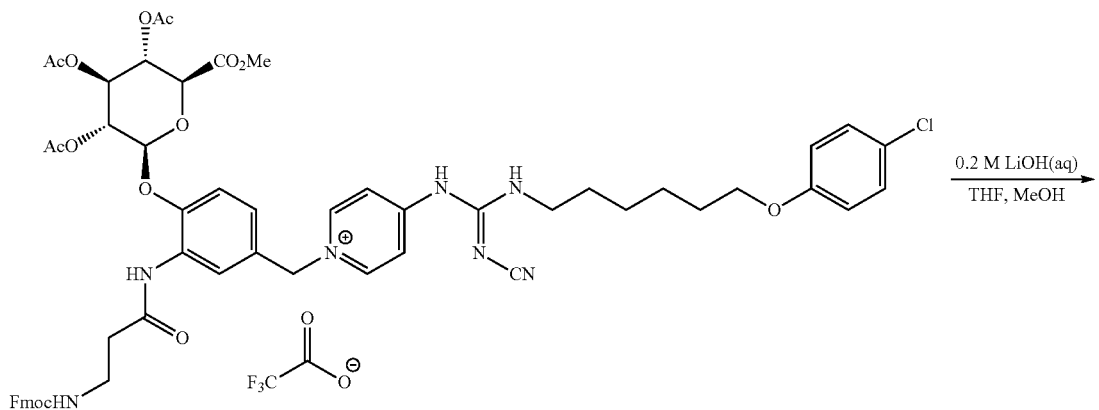

21

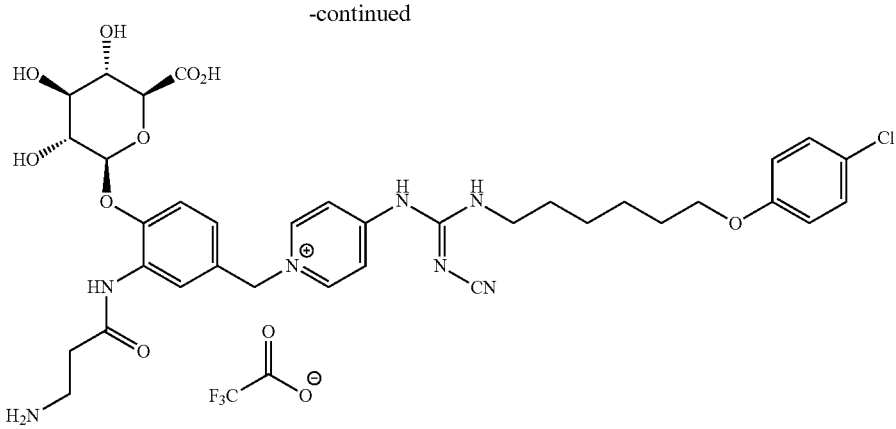

Example 22. 1-(3-(3-ammoniopropanamido)-4-(((2S,3R,4S,5S,6S)-6-carboxy-3,4,5-trihydroxytetrahydro-2H-pyran-2-yl)oxy)benzyl)-4-((E)-3-(6-(4-chlorophenoxy)-hexyl)-2-cyanoguanidino)pyridin-1-ium 2,2,2-trifluoroacetate (22)

Compound 21 (36.8 mg, 0.03 mmol) was dissolved in a 1:1 mixture of MeOH and THF (1.6 mL). The solution was cooled on ice prior to addition of a LiOH solution (0.2 M, 1.51 mL, 0.30 mmol). The reaction was stirred on ice for 30 min, then warmed to room temperature. After 4 hours the reaction was acidified with a drop of acetic acid, then diluted with DMSO/water and purified by preparative HPLC to the title compound (16.0 mg, 0.017 mmol, 54.6%). LCMS: $t_R$=1.51 min; m/z=740.48 [M]$^+$.

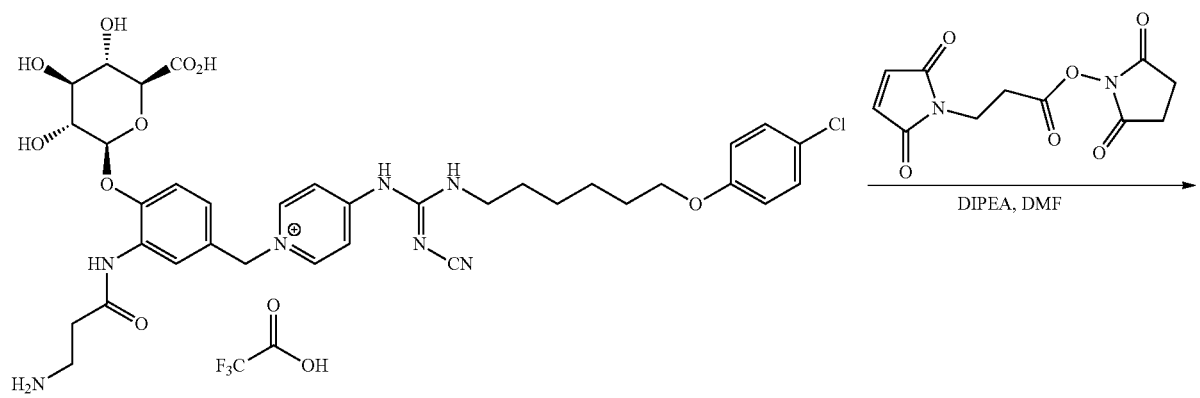

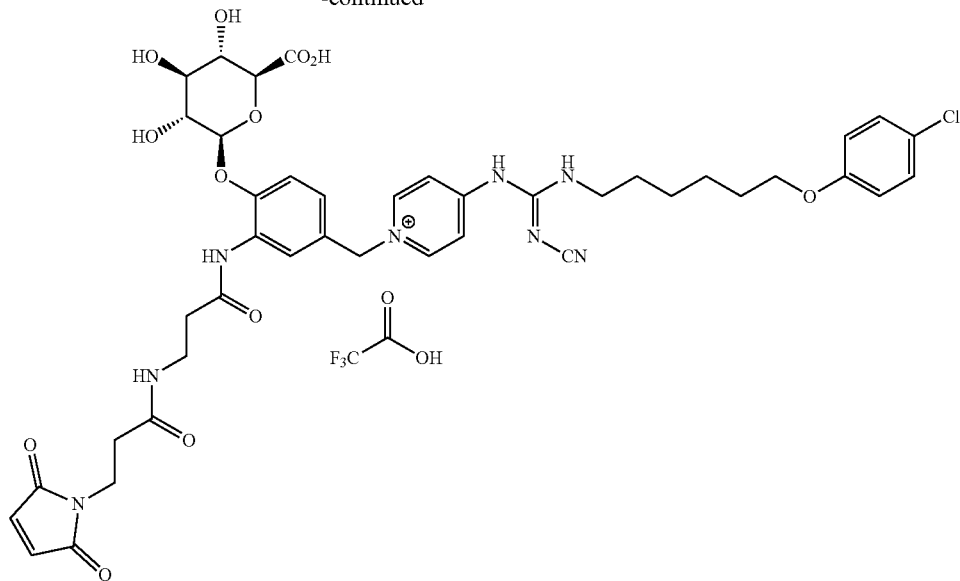

23

Example 23. 1-(4-(((2S,3R,4S,5S,6S)-6-carboxy-3,4,5-trihydroxytetrahydro-2H-pyran-2-yl)oxy)-3-(3-(3-(2,5-dioxo-2,5-dihydro-1H-pyrrol-1-yl)propanamido)-propanamido)benzyl)-4-((E)-3-(6-(4-chlorophenoxy)hexyl)-2-cyanoguanidino)pyridin-1-ium 2,2,2-trifluoroacetate (23)

Compound 22 (16.0 mg, 0.017 mmol) was dissolved in anhydrous DMF (400 µL) followed by the addition of DIPEA (8.6 µL). 2,5-dioxopyrrolidin-1-yl 3-(2,5-dioxo-2,5-dihydro-1H-pyrrol-1-yl)propionate (5.7 mg, 0.021 mmol) in anhydrous DMF (100 µL) was then added. The reaction mixture was stirred at room temperature for 1 hour. After 1 hour, reaction was acidified with HOAc (8 µL), diluted with DMSO/water and purified by prep-HPLC to provide the title compound (9.6 mg, 0.009 mmol, 57.9%) referred to as MDPr-GlucQ-CHS828. LCMS: $t_R$=1.60 min; m/z=891.15 [M]⁺.

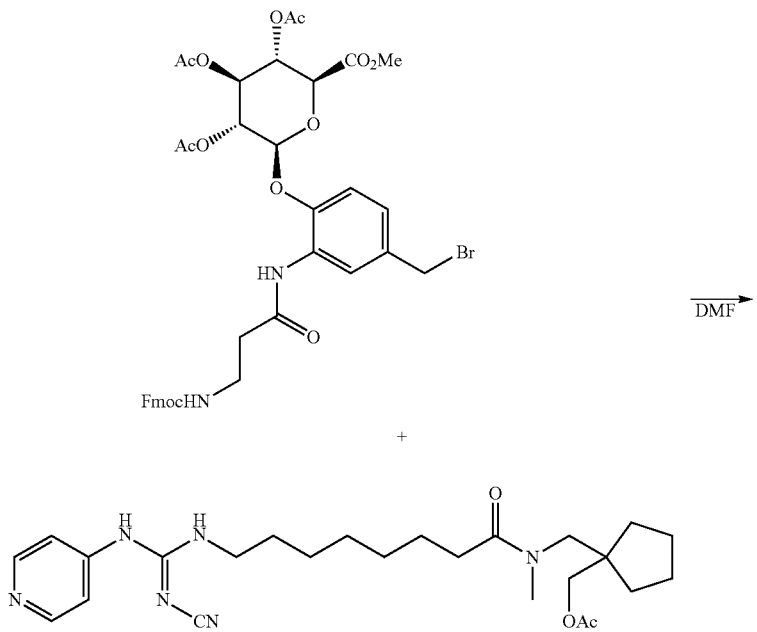

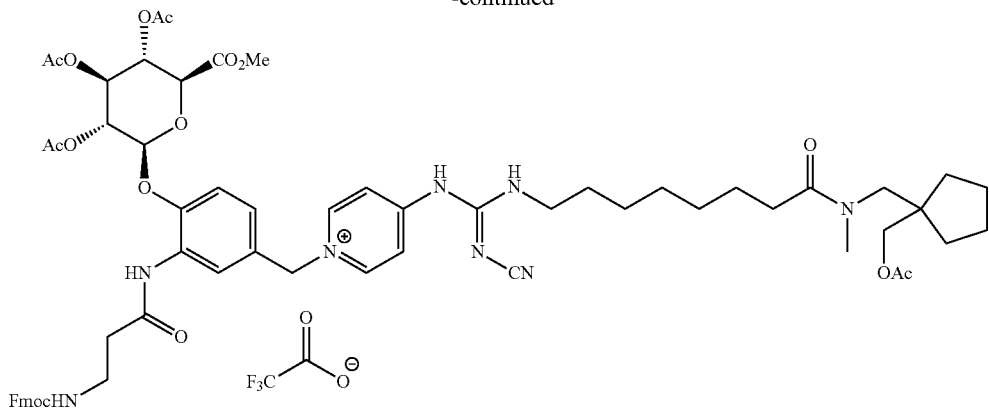

24

Example 24. 1-(3-(3-((((9H-fluoren-9-yl)methoxy)
carbonyl)amino)-propanamido)-4-(((2S,3R,4S,5S,
6S)-3,4,5-triacetoxy-6-(methoxycarbonyl)tetrahydro-
2H-pyran-2-yl)oxy)benzyl)-4-((E)-3-(8-(((1-
(acetoxymethyl)cyclopentyl)methyl)-(methyl)
amino)-8-oxooctyl)-2-cyanoguanidino)pyridin-1-ium
2,2,2-trifluoroacetate (24)

(2S,3R,4S,5S,6S)-2-(2-(3-((((9H-fluoren-9-yl)methoxy)
carbonyl)amino)-propanamido)-4-(bromomethyl)phenoxy)-6-(methoxycarbonyl)tetrahydro-2H-pyran-3,4,5-triyl triacetate (40 mg, 0.05 mmol) and (E)-(1-((8-(2-cyano-3-(pyridin-4-yl)guanidino)-N-methyloctanamido)methyl)cyclopentyl)methyl acetate (19.5 mg, 0.041 mmol) were dissolved in anhydrous DMF (800 μL) and the reaction was heated up to 55° C. for 8 hours. The benzyl bromide input as the quaternization agent was prepared according to the procedure of *Mol. Cancer Ther.* (2016) 15(5): 938-945, the disclosure for which is specifically incorporated by reference herein. After 8 hours, the reaction was cooled down to room temperature, diluted with DMSO/water and purified by prep-HPLC to provide the title compound (34.9 mg, 0.029 mmol, 70.1%). LCMS: $t_R$=2.11 min; m/z=1201.72 [M]$^+$.

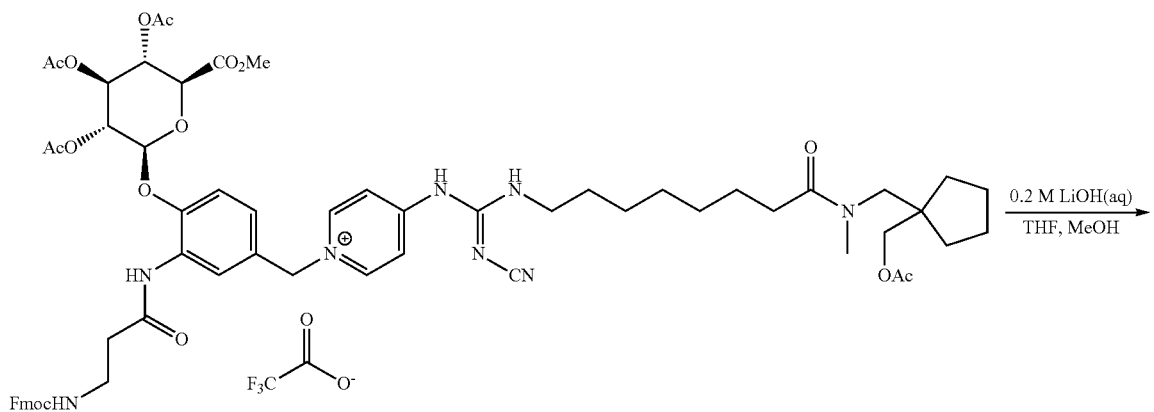

24

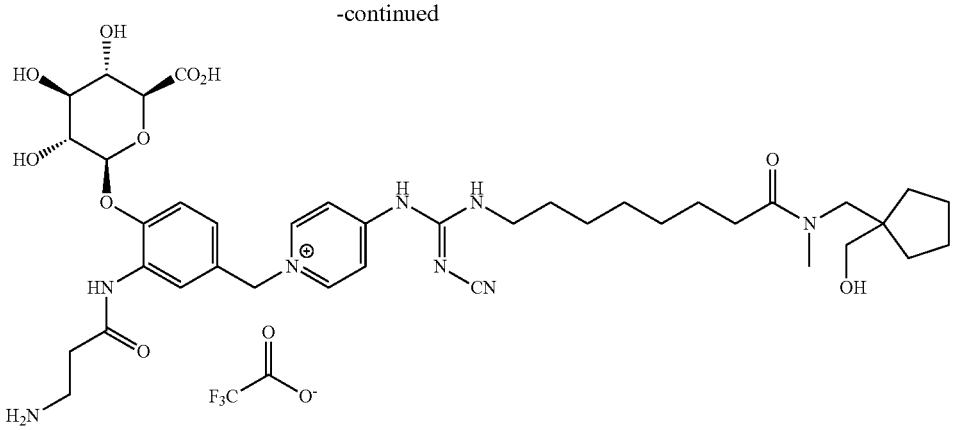

25

Example 25. 1-(3-(3-ammoniopropanamido)-4-(((2S,3R,4S,5S,6S)-6-carboxy-3,4,5-trihydroxytetrahydro-2H-pyran-2-yl)oxy)benzyl)-4-((E)-2-cyano-3-(8-(((1-(hydroxymethyl)cyclopentyl)methyl)(methyl)amino)-8-oxooctyl)guanidino)pyridin-1-ium 2,2,2-trifluoroacetate (25)

Compound 24 (34.9 mg, 0.027 mmol) was dissolved in a 1:1 mixture of MeOH and THF (1.4 mL). The solution was cooled on ice prior to addition of a LiOH solution (0.2 M, 1.3 mL, 0.27 mmol). The reaction was stirred on ice for 30 min, then warmed to room temperature. After 4 hours the reaction was acidified with a drop of acetic acid, then diluted with DMSO and water and purified by preparative HPLC to provide the title compound (18.4 mg, 0.020 mmol, 76.0%). LCMS: $t_R$=1.28 min; m/z=797.43 [M]$^+$.

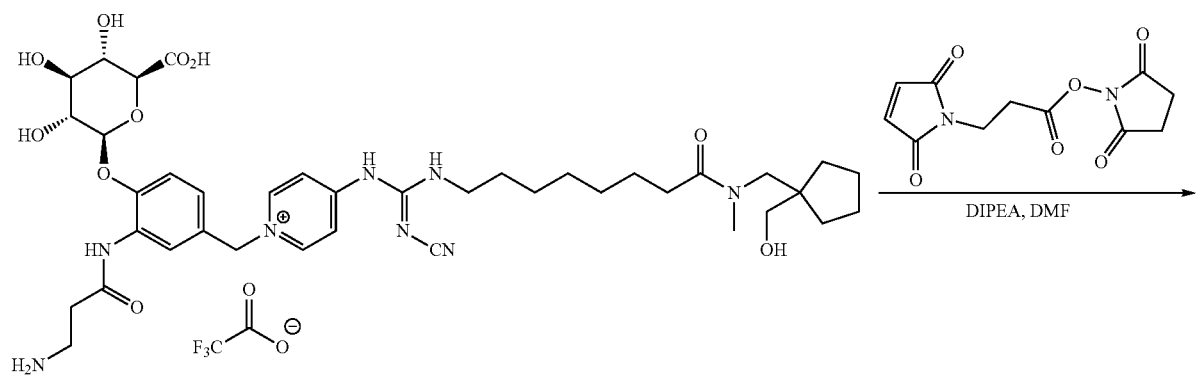

25

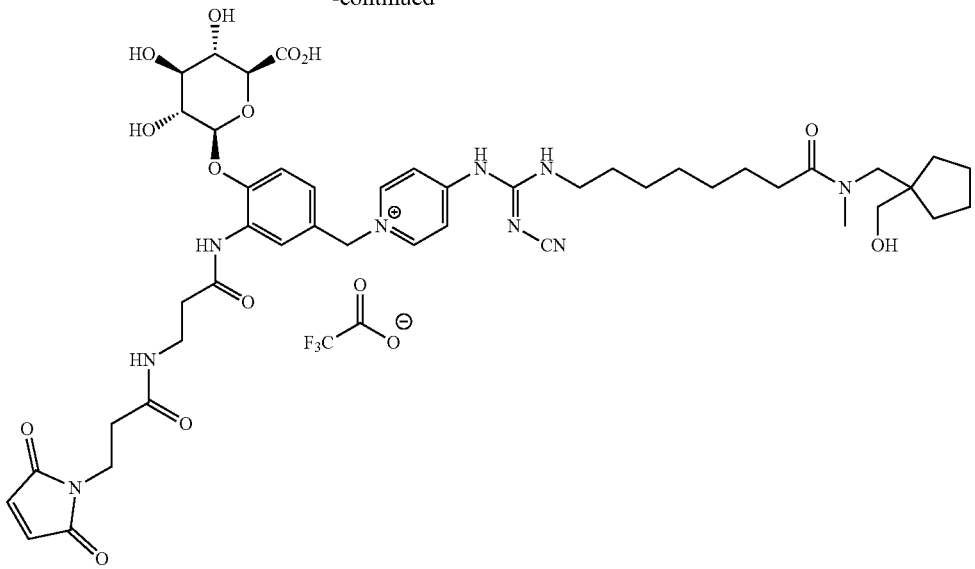

26

Example 26. 1-(4-(((2S,3R,4S,5S,6S)-6-carboxy-3,4,5-trihydroxytetrahydro-2H-pyran-2-yl)oxy)-3-(3-(3-(2,5-dioxo-2,5-dihydro-1H-pyrrol-1-yl)propanamido)-propanamido)benzyl)-4-((E)-2-cyano-3-(8-(((1-(hydroxymethyl)cyclopentyl)methyl)-(methyl)amino)-8-oxooctyl)guanidino)pyridin-1-ium 2,2,2-trifluoroacetate (26)

Compound 25 (16.0 mg, 0.016 mmol) was dissolved in anhydrous DMF (500 uL) followed by the addition of DIPEA (8.2 µL). 2,5-dioxopyrrolidin-1-yl 3-(2,5-dioxo-2,5-dihydro-1H-pyrrol-1-yl)propanoate (5.4 mg, 0.02 mmol) in anhydrous DMF (100 µL) was then added. The reaction mixture was stirred at room temperature for 1 hour. After 1 hour, reaction was acidified with HOAc (8 uL), diluted with DMSO/water and purified by prep-HPLC to provide the title compound (9.6 mg, 0.009 mmol, 57.9%). LCMS: $t_R$=1.36 min; m/z=948.29 [M]$^+$.

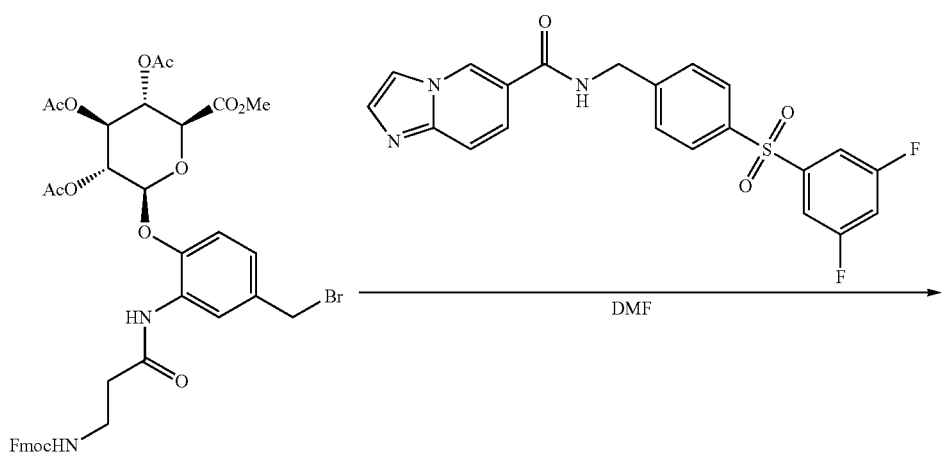

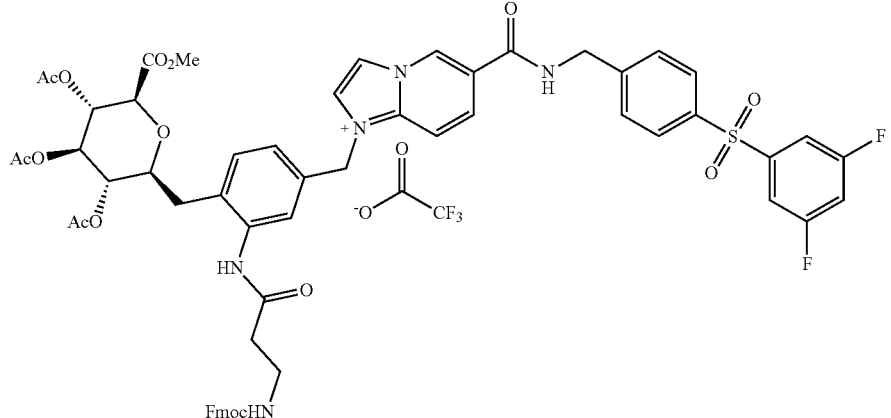

27

Example 27. 1-(3-(3-((((9H-fluoren-9-yl)methoxy)carbonyl)amino)-propanamido)-4-(((2S,3R,4S,5S,6S)-3,4,5-triacetoxy-6-(methoxycarbonyl)tetrahydro-2H-pyran-2-yl)oxy)benzyl)-6-((4-((3,5-difluorophenyl)sulfonyl)benzyl)carbamoyl)-imidazo[1,2-a]pyridin-1-ium 2,2,2-trifluoroacetate (27)

(2S,3R,4S,5S,6S)-2-(2-(3-((((9H-fluoren-9-yl)methoxy)carbonyl)amino)-propanamido)-4-(bromomethyl)phenoxy)-6-(methoxycarbonyl)tetrahydro-2H-pyran-3,4,5-triyl triacetate (22.8 mg, 0.028 mmol) and N-(4-((3,5-difluorophenyl)sulfonyl)benzyl)-imidazo[1,2-a]pyridine-6-carboxamide (10 mg, 0.023 mmol) was dissolved in anhydrous DMF (500 uL) and the reaction was heated up to 55° C. overnight. The reaction was cooled down to room temperature, diluted with DMSO/water and purified by prep-HPLC to provide the title compound (28.1 mg, 0.022 mmol, 78.7%). LCMS: $t_R$=2.05 min; m/z=1158.06 [M]$^+$.

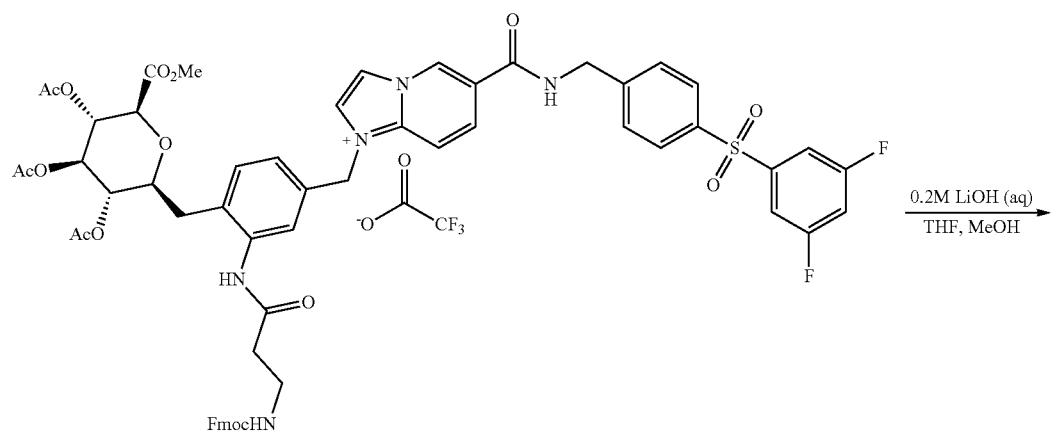

27

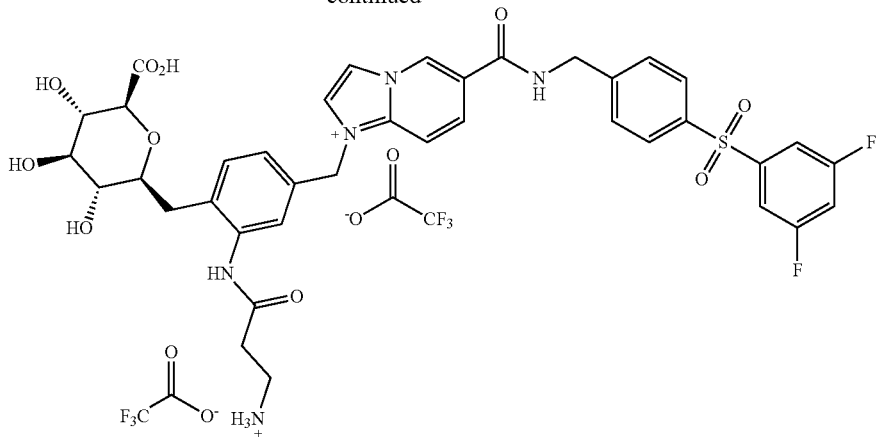

Example 28. 1-(3-(3-ammoniopropanamido)-4-(((2S,3R,4S,5S,6S)-6-carboxy-3,4,5-trihydroxytetrahydro-2H-pyran-2-yl)oxy)benzyl)-6-((4-((3,5-difluorophenyl)-sulfonyl)benzyl)carbamoyl)imidazo[1,2-a]pyridin-1-ium 2,2,2-trifluoroacetate (28)

Compound 27 (28.1 mg, 0.022 mmol) was dissolved in a 1:1 mixture of MeOH and THF (1.2 mL). The solution was cooled on ice prior to addition of a LiOH solution (0.2 M, 1.1 mL, 0.22 mmol). The reaction was stirred on ice for 30 min, then warmed to room temperature. After 3 hours the reaction was acidified with a drop of acetic acid, then diluted with DMSO/water and purified by preparative HPLC to provide the title compound (14.0 mg, 0.014 mmol, 61.9%). LCMS: $t_R$=1.22 min; m/z=796.17 [M]$^+$.

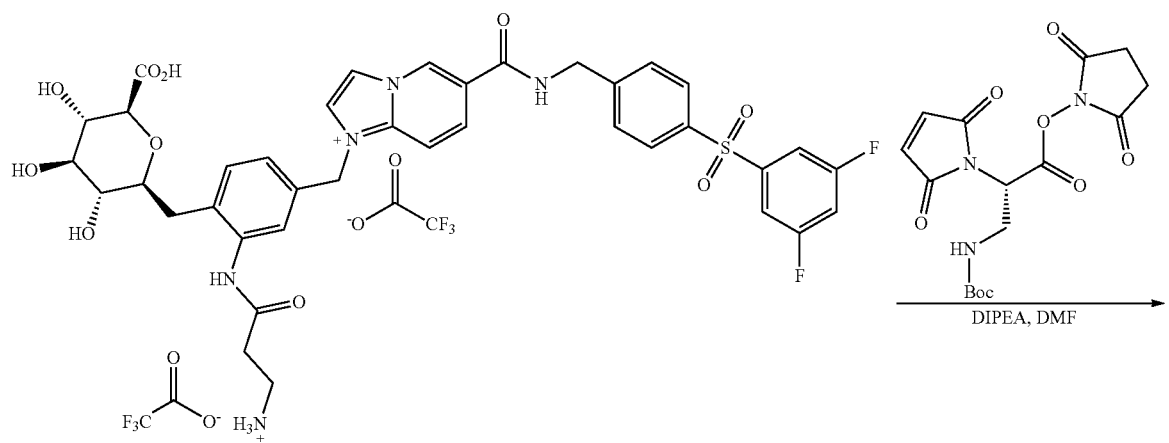

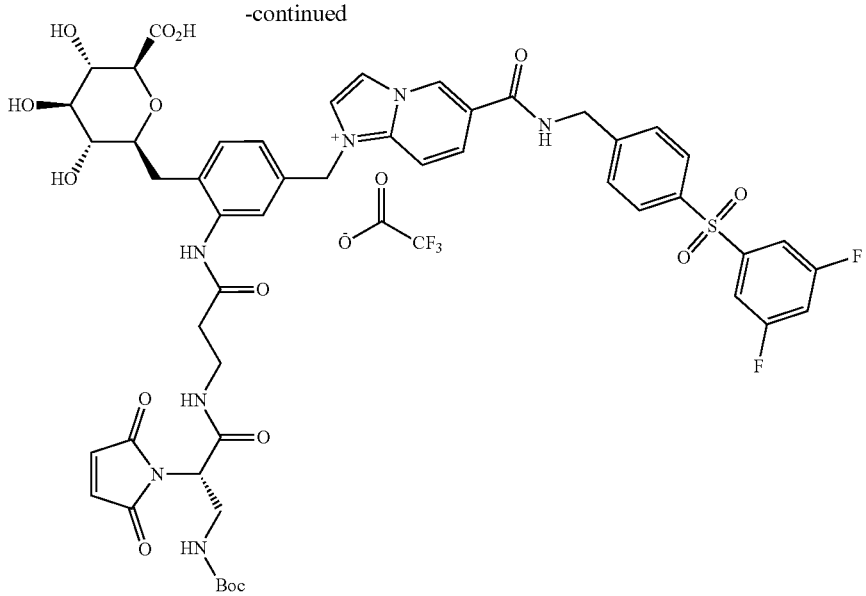

29

Example 29. 1-(3-(3-(((S)-3-((tert-butoxycarbonyl)amino)-2-(2,5-dioxo-2,5-dihydro-1H-pyrrol-1-yl)propanamido)propanamido)-4-(((2S,3R,4S,5S,6S)-6-carboxy-3,4,5-trihydroxytetrahydro-2H-pyran-2-yl)oxy)benzyl)-6-((4-((3,5-difluorophenyl)-sulfonyl)benzyl)carbamoyl)imidazo[1,2-a]pyridin-1-ium 2,2,2-trifluoroacetate (29)

Compound 28 (14 mg, 0.012 mmol) was dissolved in anhydrous DMF (400 uL) followed by the addition of DIPEA (6.3 uL). 2,5-Dioxopyrrolidin-1-yl (S)-3-((tert-butoxycarbonyl)amino)-2-(2,5-dioxo-2,5-dihydro-1H-pyrrol-1-yl)propanoate (6.0 mg, 0.016 mmol) in anhydrous DMF (100 uL) was then added. The reaction mixture was stirred at room temperature for 30 min. After 30 min, reaction was acidified with HOAc (6 uL), diluted with DMSO/water and purified by prep-HPLC to provide the title compound (10.3 mg, 0.009 mmol, 72.8%). LCMS: $t_R$=1.55 min; m/z=1062.10 [M]$^+$.

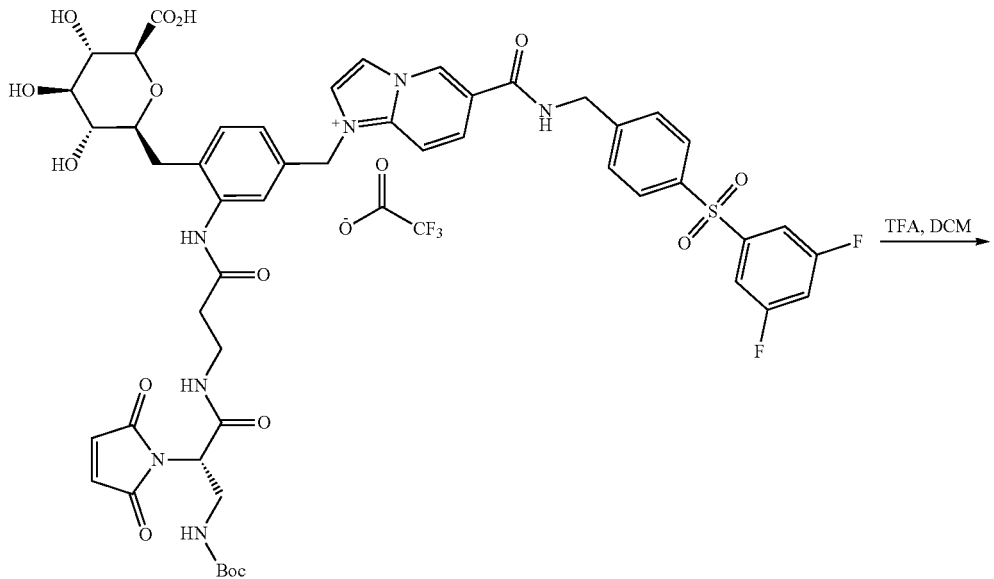

29

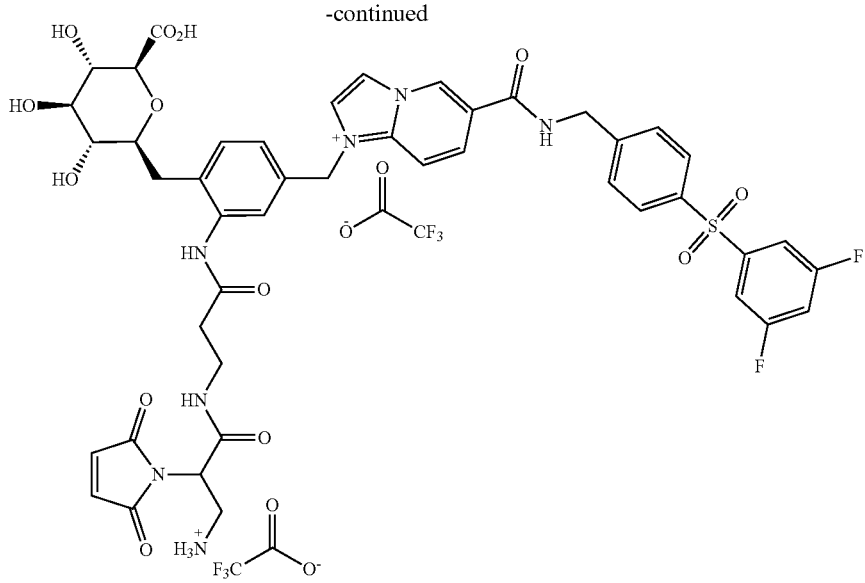

Example 30. 1-(3-(3-((S)-3-ammonio-2-(2,5-dioxo-2,5-dihydro-1H-pyrrol-1-yl)propanamido)propanamido)-4-(((2S,3R,4S,5S,6S)-6-carboxy-3,4,5-trihydroxy-tetrahydro-2H-pyran-2-yl)oxy)benzyl)-6-((4-((3,5-difluorophenyl)sulfonyl)benzyl)-carbamoyl)imidazo[1,2-a]pyridin-1-ium 2,2,2-trifluoroacetate (30)

Compound 29 (10.3 mg, 0.009 mmol) was suspended in DCM (240 uL) and TFA was added (60 uL). The reaction mixture turned homogenous after adding TFA. The reaction was stirred at room temperature for 4 hours. After 4 hours, solvent was removed by vacuum and the crude product was diluted with DMSO/water and purified by prep-HPLC to provide the title compound (9.9 mg, 0.008 mmol, 95%). LCMS: $t_r$=1.24 min; m/z=962.07 [M]+.

Preparation of NAMPT Inhibitor Compounds

Scheme 1: Exemplary preparation of a NAMPTi compound derivative in which $H_N$-DA is a pyridyl-vinylogous amide moiety and the NAMPT Tail Unit is an optionally substituted benzamide moiety.

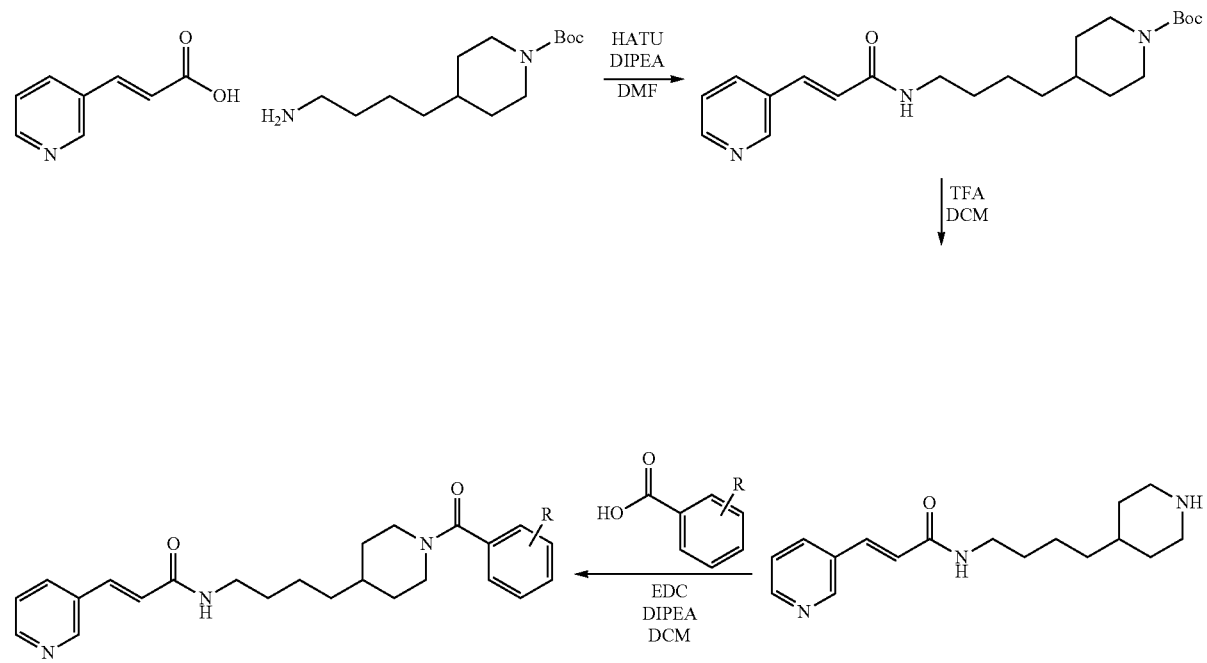

Scheme 2: Exemplary preparation of an NAMPTi derivative compound in which $H_N$-DA is a pyridyl-urea moeity and the NAMPT Tail Unit is an optionally substituted benzamide moeity.
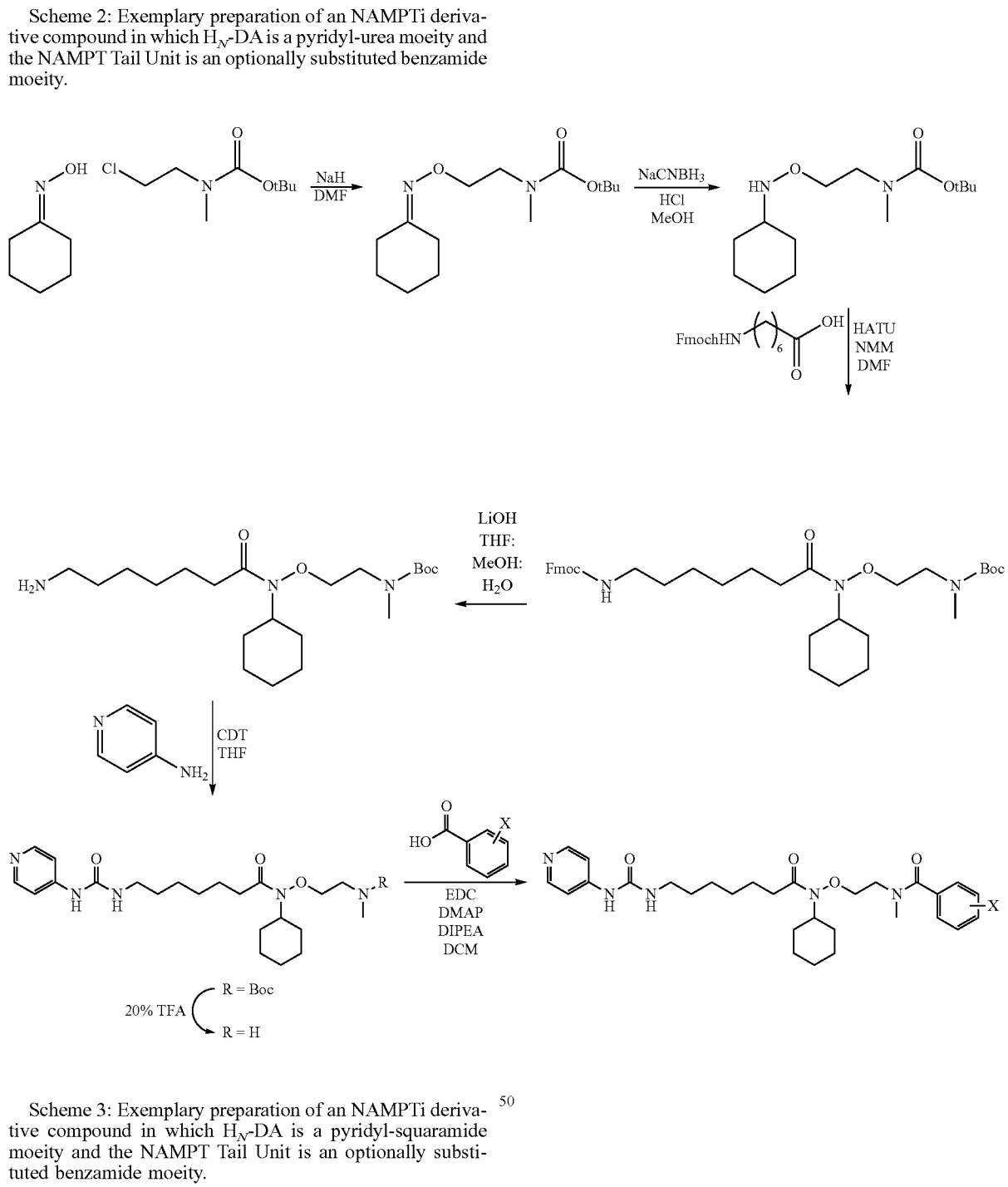
Scheme 3: Exemplary preparation of an NAMPTi derivative compound in which $H_N$-DA is a pyridyl-squaramide moeity and the NAMPT Tail Unit is an optionally substituted benzamide moeity.
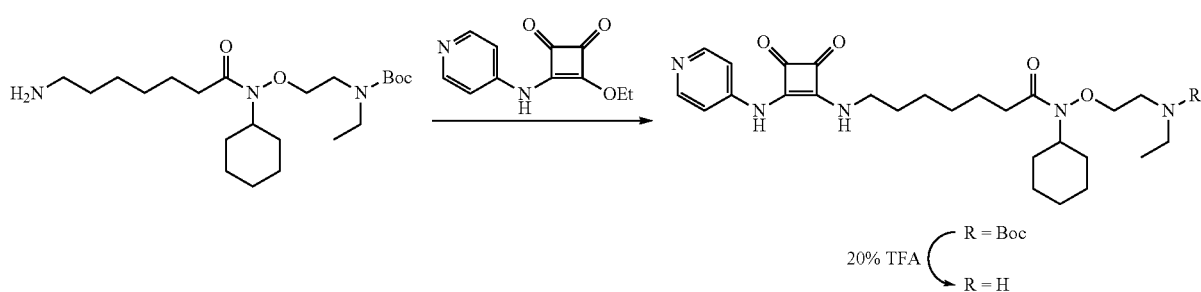

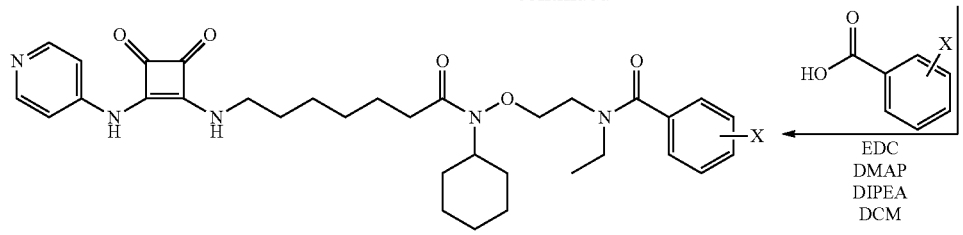
Scheme 4: Alternative exemplary preparation of an NAMPTi derivative compound in which $H_N$-DA is a pyridyl-squaramide moeity and the NAMPT Tail Unit is an optionally substituted benzamide moeity.
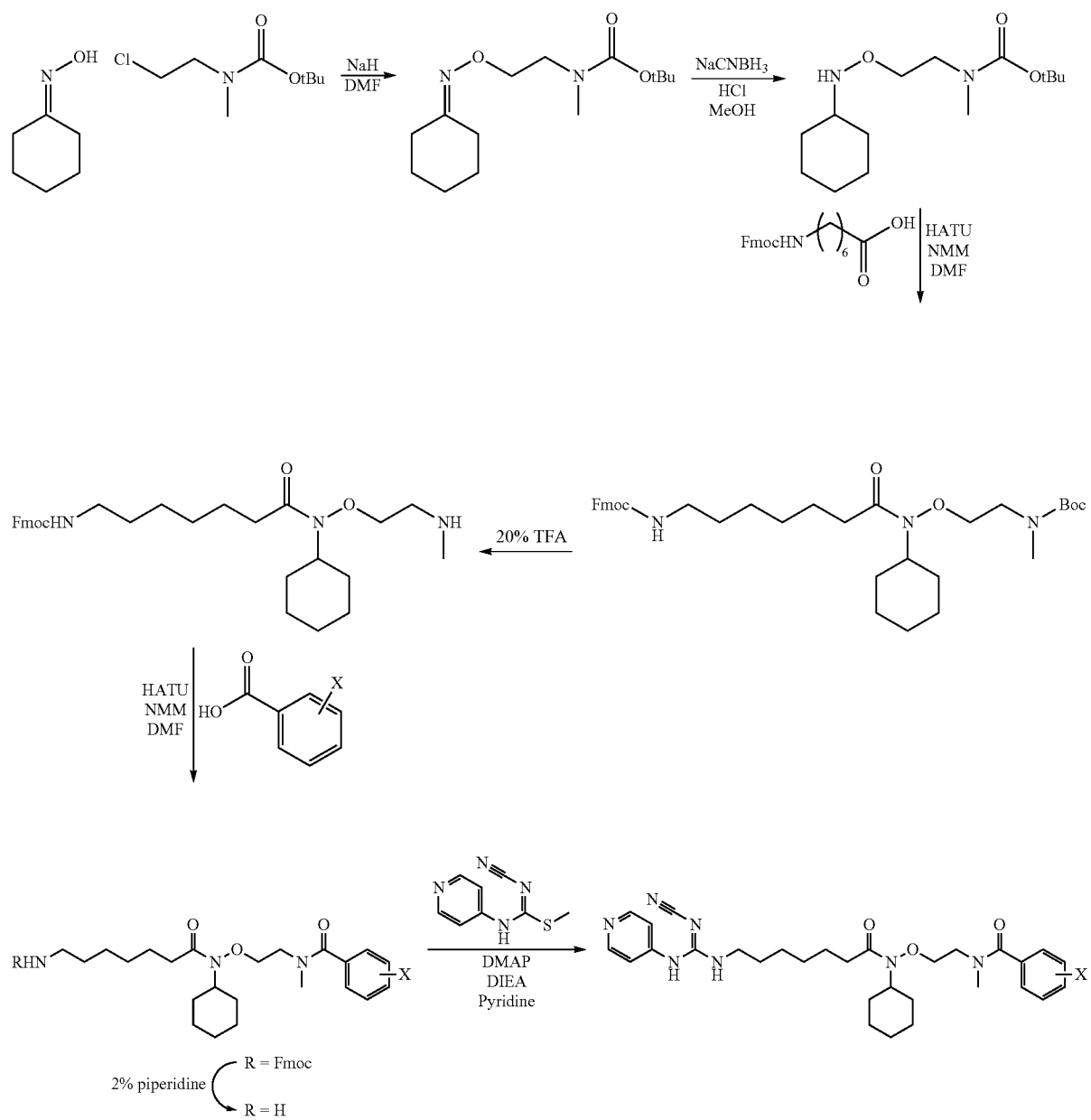

Example 31: tert-butyl (E)-4-(4-(3-(pyridin-3-yl)acrylamido)butyl)piperidine-1-carboxylate (31)

(2E)-3-(pyridin-3-yl)prop-2-enoic acid (698 mg, 4.68 mmol) was dissolved in DMF (24 mL) and treated with DIPEA (2 mL, 11.7 mmol) and HATU (1.80 g, 4.68 mmol). After 5 minutes, tert-butyl 4-(4-aminobutyl)piperidine-1-carboxylate (1.00 g, 3.90 mmol) was added as a solution in DMF (8 mL). The reaction was stirred at room temperature overnight. The reaction solvent was removed in vacuo, and the residue redissolved in EtOAc then washed once with water, twice with saturated NaHCO$_3$, and once with brine. The organic layer was dried over Na$_2$SO$_4$ and concentrated. The crude product was purified by silica gel chromatography (EtOAc/hexanes) to provide the title compound (1.16 g, 3.00 mmol, 77%). LCMS: $t_R$=1.22 min; m/z=388.3 [M+H]$^+$. $^1$H NMR (400 MHz, Chloroform-d) δ 8.78-8.71 (m, 1H), 8.57 (dd, J=4.8, 1.6 Hz, 1H), 7.83-7.75 (m, 1H), 7.62 (d, J=15.7 Hz, 1H), 7.35-7.29 (m, 1H), 6.45 (d, J=15.7 Hz, 1H), 5.68 (t, 1H), 4.18-3.90 (m, 2H), 3.40 (td, J=7.2, 5.9 Hz, 2H), 2.76-2.55 (m, 2H), 1.70-1.51 (m, 4H), 1.45 (s, 9H), 1.43-1.31 (m, 3H), 1.31-1.20 (m, 2H), 1.07 (qd, J=12.5, 4.4 Hz, 2H).

Example 32. (E)-N-(4-(piperidin-4-yl)butyl)-3-(pyridin-3-yl)acrylamide (32)

Compound 31 (1.06 g, 2.75 mmol) was dissolved in dichloromethane (15 mL) and treated with TFA (3 mL) for 90 minutes. The reaction was concentrated in vacuo, redissolved in 1:1 MeCN:H$_2$O, and concentrated again to the title compound as the di-TFA salt (1.30 g, 2.69 mmol, 98%). LCMS: $t_R$=0.46 min; m/z=288.2 [M+H]$^+$. $^1$H NMR (400 MHz, Methanol-d4) δ 9.01-8.93 (m, 1H), 8.74 (dd, J=5.5, 1.4 Hz, 1H), 8.60 (dtt, J=8.2, 1.5, 0.6 Hz, 1H), 7.99-7.87 (m, 1H), 7.61 (d, J=15.8 Hz, 1H), 6.88 (d, J=15.8 Hz, 1H), 3.40-3.28 (m, 6H), 2.95 (td, m, 2H), 2.02-1.86 (m, 2H), 1.69-1.53 (m, 3H), 1.50-1.24 (m, 6H).

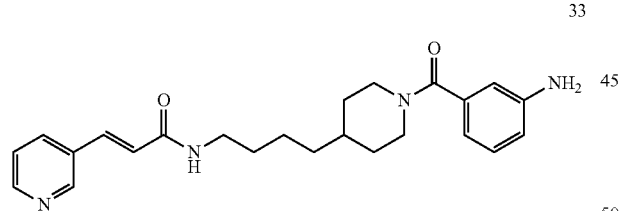

Example 33. (E)-N-(4-(1-(3-aminobenzoyl)piperidin-4-yl)butyl)-3-(pyridin-3-yl)acrylamide (33)

To a reaction vessel containing compound 32 (30 mg, 0.058 mmol) and 3-((tert-butoxycarbonyl)amino)benzoic acid (14 mg, 0.058 mmol) was added a 0.25 M solution of EDC in DCM (350 µL, 0.087 mmol) followed by a 0.25 M solution of DMAP in DCM (350 µL, 0.087 mmol) and DIPEA (51 µL, 0.29 mmol). The reaction was stirred for 3 hours, then concentrated in vacuo. The crude material was redissolved in EtOAc and washed twice with water, once with saturated NH$_4$Cl, and once with brine. The organic layer was dried over Na$_2$SO$_4$ and concentrated. The resulting intermediate product was treated with 30% TFA in DCM for 30 minutes, then concentrated in vacuo. Purification by preparative HPLC afforded the title compound (22.1 mg, 0.042 mmol, 73%). LCMS: $t_R$=0.66 min; m/z=407.3 [M+H]$^+$.

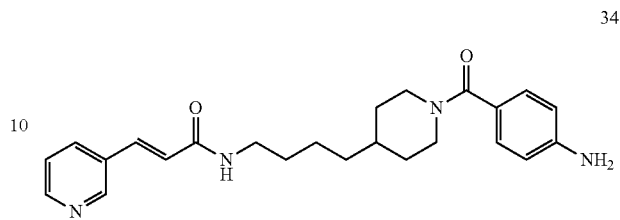

Example 34. (E)-N-(4-(1-(4-aminobenzoyl)piperidin-4-yl)butyl)-3-(pyridin-3-yl)acrylamide (34)

The title compound was prepared according to the methods for compounds 32 and 33 using 4-((tert-butoxycarbonyl)amino)benzoic acid as the starting acid. LCMS: $t_R$=0.67 min; m/z=407.3 [M+H]$^+$.

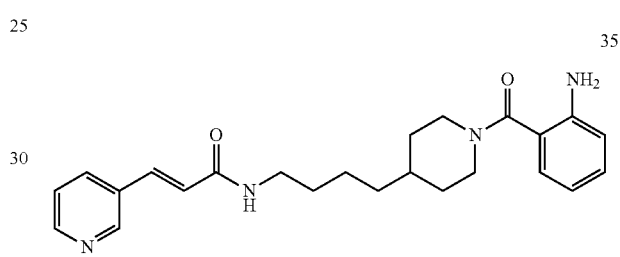

Example 35. (E)-N-(4-(1-(2-aminobenzoyl)piperidin-4-yl)butyl)-3-(pyridin-3-yl)acrylamide (35)

The title compound was prepared according to the methods for compounds 32 and 33 using 2-((tert-butoxycarbonyl)amino)benzoic acid as the starting acid. LCMS: $t_R$=0.88 min; m/z=407.3 [M+H]$^+$.

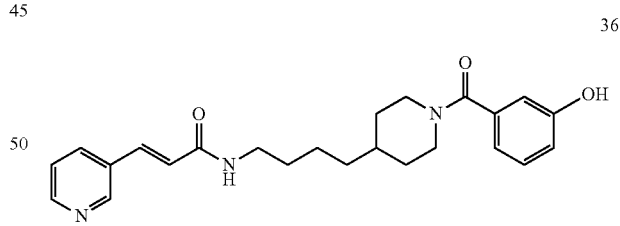

Example 36. (E)-N-(4-(1-(3-hydroxybenzoyl)piperidin-4-yl)butyl)-3-(pyridin-3-yl)acrylamide (36)

To a reaction vessel containing compound 32 (30 mg, 0.058 mmol) and 3-hydroxybenzoic acid (8.0 mg, 0.058 mmol) was added a 0.25 M solution of EDC in DCM (350 µL, 0.087 mmol) followed by a 0.25 M solution of DMAP in DCM (350 µL, 0.087 mmol) and DIPEA (51 µL, 0.29 mmol). The reaction was stirred for 3 hours, then concentrated in vacuo. Purification by preparative HPLC afforded the title compound (12.1 mg, 0.023 mmol, 40%). LCMS: $t_R$=0.79 min; m/z=408.3 [M+H]$^+$.

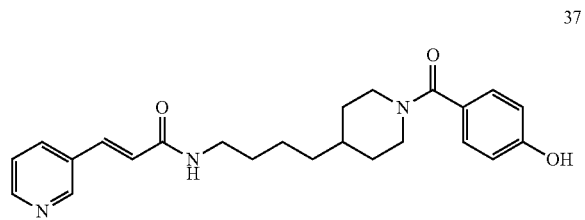 [SMILES: O=C(/C=C/c1cccnc1)NCCCCC1CCN(C(=O)c2ccc(O)cc2)CC1]

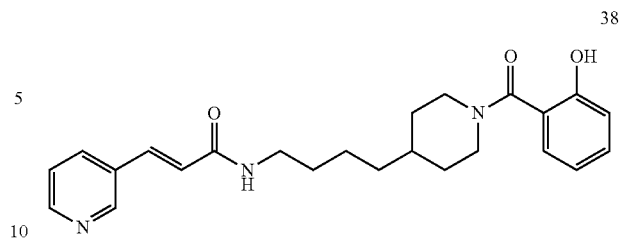

Example 37. (E)-N-(4-(1-(4-hydroxybenzoyl)piperidin-4-yl)butyl)-3-(pyridin-3-yl)acrylamide (37)

The title compound was prepared according to the method for compound 36 using 4-hydroxybenzoic acid as the starting acid. LCMS: $t_R$=0.74 min; m/z=408.3 [M+H]$^+$.

Example 38. (E)-N-(4-(1-(2-hydroxybenzoyl)piperidin-4-yl)butyl)-3-(pyridin-3-yl)acrylamide (38)

The title compound was prepared according to the method of compound 36 using 2-hydroxybenzoic acid as the starting acid. LCMS: $t_R$=1.18 min; m/z=408.2 [M+H]$^+$.

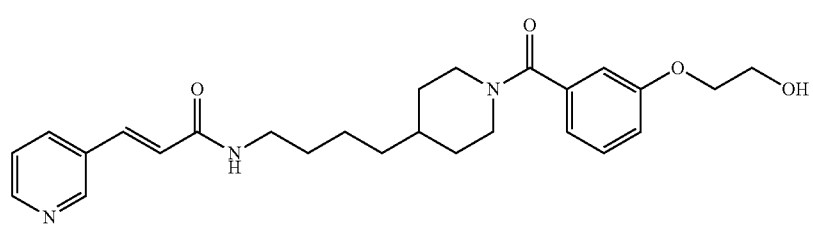

Example 39. (E)-N-(4-(1-(3-(2-hydroxyethoxy)benzoyl)piperidin-4-yl)butyl)-3-(pyridin-3-yl)acrylamide (39)

The title compound was prepared according to the method of compound 36 using 3-(2-hydroxyethoxy)benzoic acid as the starting acid LCMS: $t_R$=0.79 min; m/z=452.3 [M+H]$^+$.

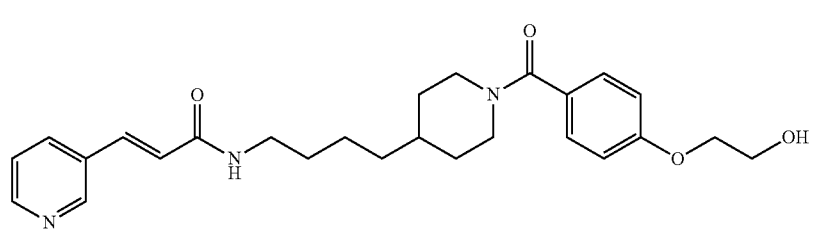

Example 40. (E)-N-(4-(1-(4-(2-hydroxyethoxy)benzoyl)piperidin-4-yl)butyl)-3-(pyridin-3-yl)acrylamide (40)

The title compound was prepared according to the method for compound 36 using 4-(2-hydroxyethoxy)benzoic acid as the starting acid. LCMS: $t_R$=0.74 min; m/z=452.3 [M+H]$^+$.

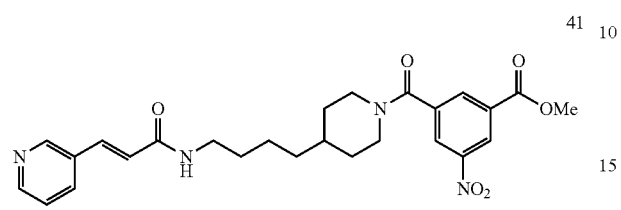

41

Example 41. Methyl (E)-3-nitro-5-(4-(4-(3-(pyridin-3-yl)acrylamido)butyl)-piperidine-1-carbonyl)benzoate (41)

The title compound was prepared according to the method of compound 32 using 3-(methoxycarbonyl)-5-nitrobenzoic acid as the starting acid. LCMS: $t_R$=1.10 min; m/z=495.4 [M+H]$^+$.

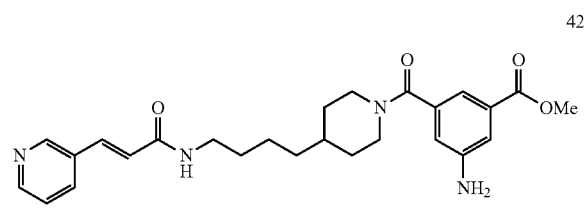 [SMILES: COC(=O)c1cc(N)cc(C(=O)N2CCC(CCCCNC(=O)/C=C/c3cccnc3)CC2)c1]

42

Example 42. Methyl (E)-3-amino-5-(4-(4-(3-(pyridin-3-yl)acrylamido)butyl)-piperidine-1-carbonyl)benzoate (42)

To a stirred solution of 41 (35 mg, 0.057 mmol) in 10:1 MeOH:AcOH was added Zn dust (~40 mg) in portions. After 2 hours, the reaction was filtered through a Celite plug and concentrated in vacuo. The residue was redissolved in DMSO and purified by preparative HPLC to provide the title compound (24 mg, 0.052 mmol, 91%). LCMS: $t_R$=0.89 min; m/z=465.4 [M+H]$^+$.

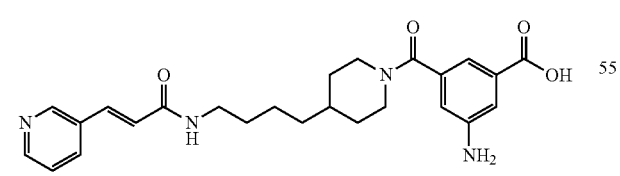

43

Example 43. (E)-3-amino-5-(4-(4-(3-(pyridin-3-yl)acrylamido)butyl)-piperidine-1-carbonyl)benzoic acid (43)

To a stirred solution of 42 (5.0 mg, 0.011 mmol) in 1:1 MeOH:THF (500 μL) was added a 0.2 M solution of LiOH (269 μl, 0.054 mmol). The reaction was stirred at room temperature for 6 hours, then quenched with 1M HCl. The reaction was concentrated in vacuo, then redissolved in DMSO and purified by preparative HPLC to provide the title compound (3.9 mg, 0.007 mmol, 64%). LCMS: $t_R$=0.75 min; m/z=451.4 [M+H]$^+$.

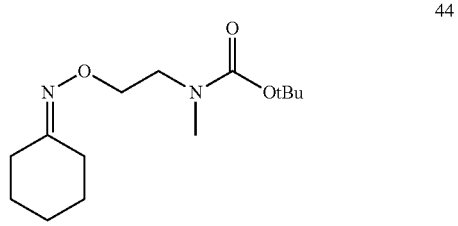 [SMILES: CN(CCON=C1CCCCC1)C(=O)OC(C)(C)C]

44

Example 44. tert-butyl (2-((cyclohexylideneamino)oxy)ethyl)(methyl)-carbamate (44)

Cyclohexanone oxime (478 mg, 4.22 mmol) taken up in 8 mL DMF and chilled in an ice bath. NaH (338 mg, 14.08 mmol, 60% dispersion in mineral oil) added portion-wise, and the reaction mixture stirred at 0° C. for 1 h under argon, after which point tert-butyl (2-chloroethyl)(methyl)carbamate (818 mg, 4.22 mmol) in 2 mL DMF was added, the ice bath removed, and the reaction mixture stirred at room temp 20 h, then heated for 3 h at 60° C. The mixture was cooled, filtered, the filtrate concentrated in vacuo, and the residue partitioned between sat'd NH$_4$Cl and ether. The aqueous extract was extracted an additional time with ether, and the combined organic extracts washed once with 0.5M NaOH, once with brine, dried over MgSO$_4$, filtered, and concentrated in vacuo to provide the title compound (696 mg, 2.57 mmol, 61%). LCMS: $t_R$=1.56 min; m/z=293.2 [M+H]$^+$. $^1$HNMR (400 MHz, CDCl$_3$, δ): 1.46 (s, 9H), 1.56-1.73 (m, 6H), 2.18-2.23 (m, 2H), 2.45 (t, J=6.3 Hz, 2H), 2.91 (s, 3H), 3.40-3.54 (m, 2H), 4.05-4.17 (m, 2H).

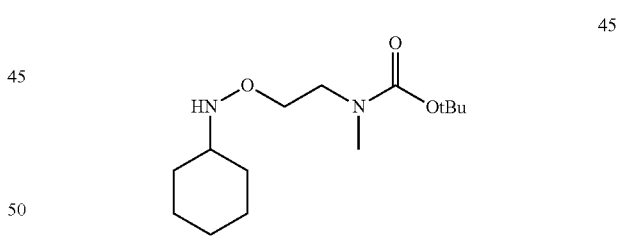

45

Example 45. tert-butyl (2-((cyclohexylamino)oxy)ethyl)(methyl)carbamate (45)

Compound 44 (696 mg, 2.57 mmol) was taken up in 10 mL MeOH and chilled in an ice bath. A small amount of methyl orange was added, then sodium cyanoborohydride (323 mg, 5.15 mmol). To the yellow solution, 2 M HCl in MeOH added until color changed to pink. Stirred 30 min on ice, then ice bath removed and stirred at room temp 4 h. The reaction mixture was concentrated in vacuo, then suspended in water, upon which the pH of mixture was adjusted to 9 with 6 N KOH, diluted with an equal volume of brine, and extracted four times with CH$_2$Cl$_2$. The combined organic extracts were washed with brine, dried over Na$_2$SO$_4$, filtered, and concentrated in vacuo. The crude product was purified by silica gel chromatography (MeOH/CH$_2$Cl$_2$) to provide compound 37 (534 mg, 1.96 mmol, 76%). LCMS: t$_R$=1.56 min; m/z=293.2 [M+H]$^+$. $^1$HNMR (400 MHz, CDCl$_3$, 6): 1.02-1.33 (m, 4H), 1.46 (s, 9H), 1.54-1.68 (m, 2H), 1.74 (dt, J=13.3, 3.9 Hz, 2H), 1.80-1.90 (m, 2H), 2.66-2.85 (m, 1H), 2.88 (s, 3H), 3.30-3.53 (m, 2H), 3.77 (t, J=5.3 Hz, 2H), 5.50 (br s, 1H).

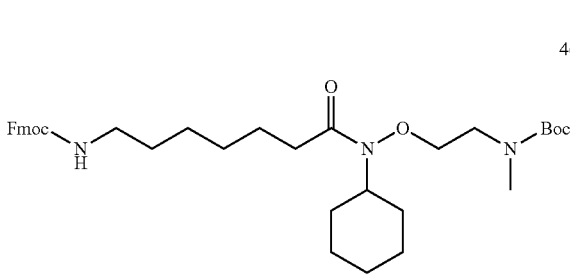

46

Example 46. tert-butyl (12-cyclohexyl-1-(9H-fluoren-9-yl)-3,11-dioxo-2,13-dioxa-4,12-diazapentadecan-15-yl)(methyl)carbamate (46)

A solution of Fmoc-aminoheptanoic acid (720 mg, 1.96 mmol), NMM (0.26 mL, 2.36 mmol), and HATU (894 mg, 2.36 mmol) in 5 mL DMF was added to compound 45 (534 mg, 1.96 mmol) in 5 mL DMF and the reaction mixture stirred at room temp under argon overnight. The reaction mixture was partially concentrated in vacuo, diluted with EtOAc and washed twice with saturated NaHCO$_3$ solution. The aqueous extract was again extracted with EtOAc, and the combined organic extracts washed once with brine, dried over MgSO$_4$, filtered, and concentrated in vacuo. The crude product was purified by silica gel chromatography (MeOH/CH$_2$C$_{12}$) to provide the title compound (339 mg, 0.55 mmol, 28%). LCMS: t$_R$=1.82 min; m/z=621.3 [M+H]$^+$.

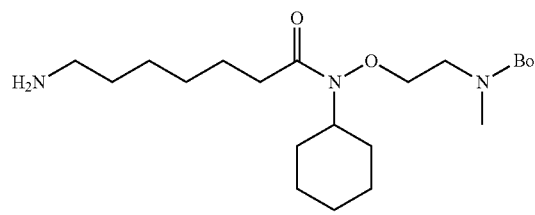

47

Example 47. tert-butyl (2-((7-amino-N-cyclohexyl-heptanamido)oxy)ethyl-(methyl)carbamate (47)

Compound 47 was prepared from compound 46 by the deprotection method of compound 80. LCMS: t$_r$=1.06 min; m/z=400.4 [M+H]$^+$.

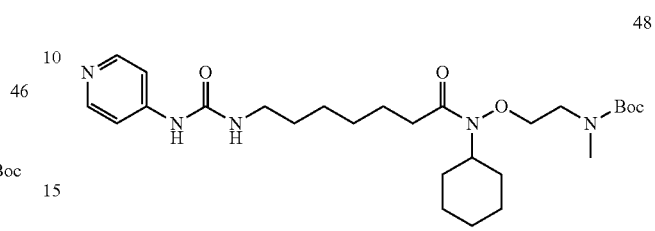

48

Example 48. tert-butyl (2-((N-cyclohexyl-7-(3-(pyridin-4-yl)ureido)-heptanamido)oxy)ethyl)(methyl)carbamate (48)

Carbonyl ditriazole (358 mg, 2.18 mmol) and 4-aminopyridine (68.4 mg, 0.73 mmol) stirred in 15 mL THF at room temperature overnight. The reaction mixture was diluted with EtOAc and washed once with water, dried over Na$_2$SO$_4$, filtered and concentrated in vacuo. The residue was resuspended in 10 mL THF and added to compound 47 in 10 mL THF with DIEA (0.25 mL, 1.45 mmol) and 2 mL DMF for solubility, and the reaction stirred at room temperature under argon 2.5 h and concentrated in vacuo. The crude product was purified by preparative HPLC to give the title compound (183 mg, 0.35 mmol, 49%). LCMS: t$_R$=1.14 min; m/z=520.4 [M+H]$^+$.

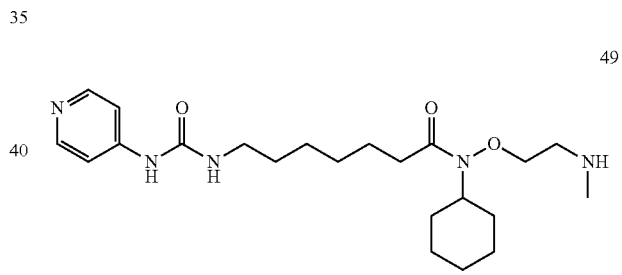

49

Example 49. N-cyclohexyl-N-(2-(methylamino)ethoxy)-7-(3-(pyridin-4-yl)ureido)heptanamide (49)

The title compound was prepared from compound 48 by the method of compound 32. LCMS: t$_R$=0.73 min; m/z=420.4 [M+H]$^+$.

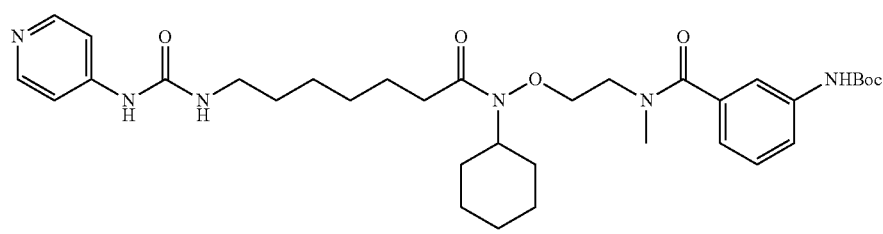

50

Example 50. tert-butyl (3-((2-((N-cyclohexyl-7-(3-(pyridin-4-yl)ureido)-heptanamido)oxy)ethyl)(methyl)carbamoyl)phenyl)carbamate (50)

The title compound was prepared from compound 49 according to the coupling method in the preparation of compound 33 using 3-((tert-butoxycarbonyl)-amino)benzoic acid as the acid component. LCMS: $t_R$=1.17 min; m/z=639.5 [M+H]$^+$.

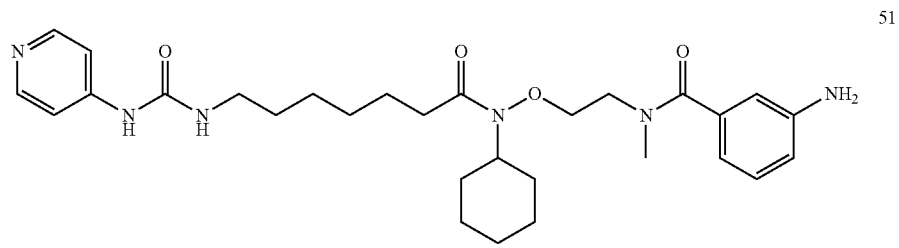 [SMILES: CN(CCON(C(=O)CCCCCCNC(=O)Nc1ccncc1)C1CCCCC1)C(=O)c1cccc(N)c1]

Example 51. 3-amino-N-(2-((N-cyclohexyl-7-(3-(pyridin-4-yl)ureido)-heptanamido)oxy)ethyl)-N-methylbenzamide (51)

The title compound was prepared from 50 by the method of compound 32. LCMS: $t_R$=0.89 min; m/z=539.4 [M+H]$^+$.

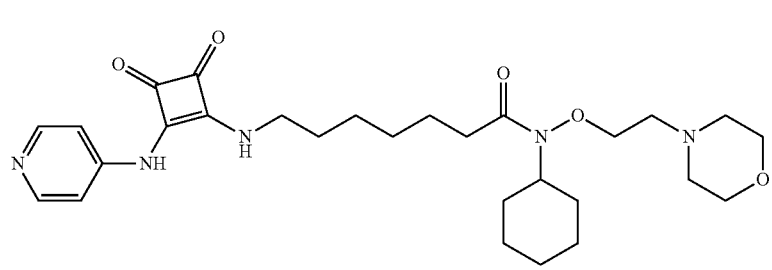

Example 52. N-cyclohexyl-7-((3,4-dioxo-2-(pyridin-4-ylamino)cyclobut-1-en-1-yl)amino)-N-(2-morpholinoethoxy)heptanamide (52)

The title compound was prepared according to WO2010/23307 A1, the procedure for which is specifically incorporated by reference herein.

Example 53. tert-butyl (2-((N-cyclohexyl-7-((3,4-dioxo-2-(pyridin-4-ylamino)cyclobut-1-en-1-yl)amino)heptanamido)oxy)ethyl)(ethyl)carbamate (53)

To a solution of the TFA salt of tert-butyl (2-((7-amino-N-cyclohexyl-heptanamido)oxy)ethyl)(ethyl)carbamate (78.3 mg, 0.15 mmol), which is prepared according to the procedures for compound 47 starting from tert-butyl (2-((cyclohexylideneamino)oxy)ethyl)(ethyl)-carbamate, in 2 mL MeCN was added DIEA (77.5 µL, 0.45 mmol) and 3-ethoxy-4-(pyridin-4-ylamino)cyclobut-3-ene-1,2-dione (32.4 mg, 0.15 mmol) and the reaction stirred at room temp 1 h, then purified by preparative HPLC to give the title compound (49.2 mg, 0.070 mmol, 47%). LCMS: $t_R$=1.35 min; m/z=586.4 [M+H]$^+$.

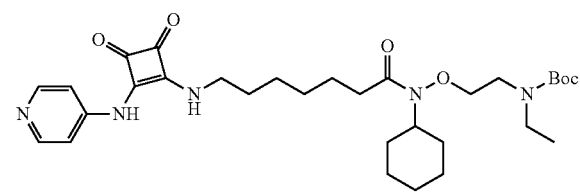

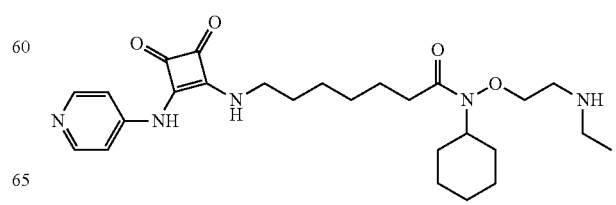

Example 54. N-cyclohexyl-7-((3,4-dioxo-2-(pyridin-4-ylamino)cyclobut-1-en-1-yl)amino)-N-(2-(ethylamino)ethoxy)heptanamide (54)

The title compound was prepared from compound 53 by the method of compound 32. LCMS: $t_R$=0.81 min; m/z=486.3 [M+H]$^+$.

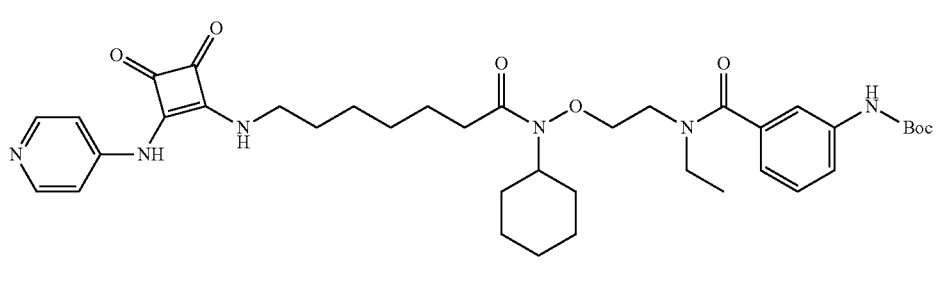

55

Example 55. tert-butyl (3-((2-((N-cyclohexyl-7-((3,4-dioxo-2-(pyridin-4-ylamino)cyclobut-1-en-1-yl)amino)heptanamido)oxy)ethyl)(ethyl)carbamoyl)phenyl)-carbamate (55)

The title compound was prepared from compound 54 according to the coupling method for the preparation of compound 33 using 3-((tert-butoxycarbonyl)-amino)benzoic acid as the starting acid. LCMS: $t_R$=1.36 min; m/z=705.4 [M+H]$^+$.

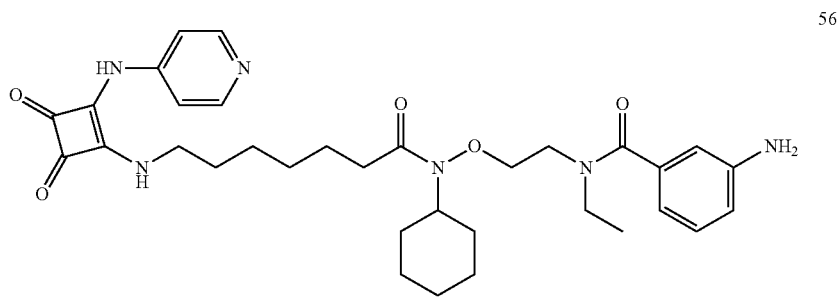 [SMILES: CCN(CCON(C(=O)CCCCCCNc1c(Nc2ccncc2)c(=O)c1=O)C1CCCCC1)C(=O)c1cccc(N)c1]

56

Example 56. 3-amino-N-(2-((N-cyclohexyl-7-((3,4-dioxo-2-(pyridin-4-ylamino)cyclobut-1-en-1-yl)amino)heptanamido)oxy)ethyl)-N-ethylbenzamide (56)

The title compound was prepared from compound 55 according to the deprotection method that provides compound 33. LCMS: $t_R$=1.08 min; m/z=605.4 [M+H]$^+$.

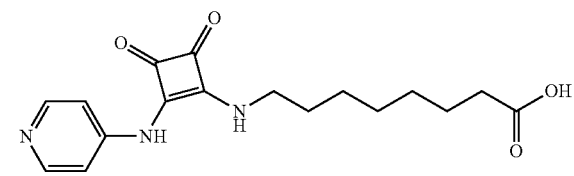

57

Example 57. 8-((3,4-dioxo-2-(pyridin-4-ylamino)cyclobut-1-en-1-yl)amino)octanoic acid (57)

The title compound was prepared by the method of compound 53 using 8-aminooctanoic acid as the starting amine. LCMS: $t_R$=0.68 min; m/z=332.2 [M+H]$^+$.

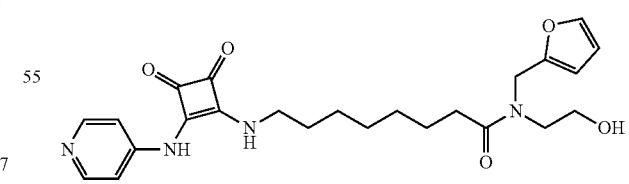

58

Example 58. 8-((3,4-dioxo-2-(pyridin-4-ylamino)cyclobut-1-en-1-yl)amino)-N-(furan-2-ylmethyl)-N-(2-hydroxyethyl)octanamide (58)

The title compound was prepared from compound 57 and 2-((furan-2-ylmethyl)amino)ethan-1-ol by the method of compound 31. LCMS: $t_R$=0.82 min; m/z=455.3 [M+H]$^+$.

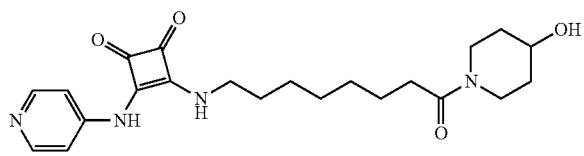

Example 59. 3-((8-(4-hydroxypiperidin-1-yl)-8-oxooctyl)amino)-4-(pyridin-4-ylamino)cyclobut-3-ene-1,2-dione (59)

The title compound was prepared from compound 57 and piperidin-4-ol by the coupling method in the preparation of compound 32. LCMS: $t_R$=0.68 min; m/z=415.3 [M+H]$^+$.

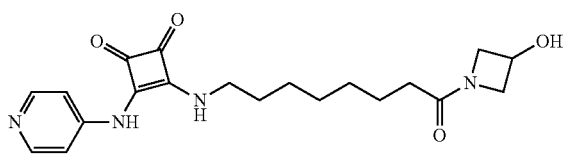

Example 60. 3-((8-(3-hydroxyazetidin-1-yl)-8-oxooctyl)amino)-4-(pyridin-4-ylamino)cyclobut-3-ene-1,2-dione (60)

The title compound was prepared from compound 57 and azetidin-3-ol by the coupling method in the preparation of compound 33. LCMS: $t_R$=0.65 min; m/z=387.2 [M+H]$^+$.

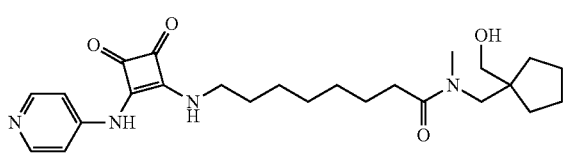

Example 61. 8-((3,4-dioxo-2-(pyridin-4-ylamino)cyclobut-1-en-1-yl)amino)-N-((1-(hydroxymethyl)cyclopentyl)methyl)-N-methyloctanamide (61)

The title compound was prepared from compound 47 and (1-((methylamino)-methyl)cyclopentyl)methanol by the method of compound 31. LCMS: $t_R$=0.98 min; m/z=457.3 [M+H]$^+$.

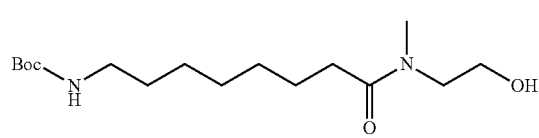

Example 62. tert-butyl (8-((2-hydroxyethyl)(methyl)amino)-8-oxooctyl)-carbamate (62)

The title compound was prepared from 8-((tert-butoxycarbonyl)-amino)octanoic acid and 2-(methylamino)ethan-1-ol according to the coupling method in the preparation of compound 33. LCMS: $t_R$=1.13 min; m/z=339.3

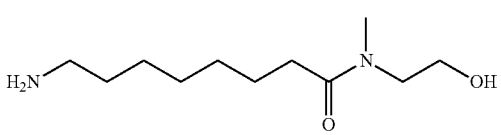

Example 63. 8-amino-N-(2-hydroxyethyl)-N-methyloctanamide (63)

The title compound was prepared from compound 62 according to the deprotection method that provides compound 33. LCMS: $t_R$=0.44 min; m/z=217.3 [M+H]$^+$.

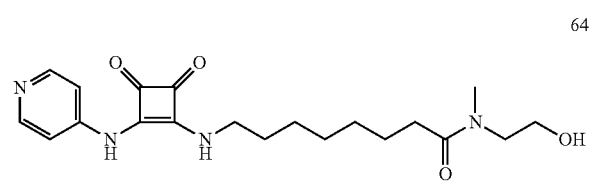 [SMILES: CN(CCO)C(=O)CCCCCCCNc1c(Nc2ccncc2)c(=O)c1=O]

Example 64. 8-((3,4-dioxo-2-(pyridin-4-ylamino)cyclobut-1-en-1-yl)amino)-N-(2-hydroxyethyl)-N-methyloctanamide (64)

The title compound was prepared from compound 63 according to the condensation method for the preparation compound 53. LCMS: $t_R$=0.70 min; m/z=389.4 [M+H]$^+$.

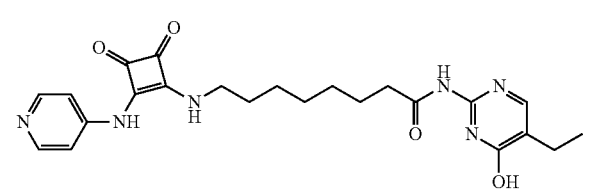

Example 65. 8-((3,4-dioxo-2-(pyridin-4-ylamino)cyclobut-1-en-1-yl)amino)-N-(5-ethyl-4-hydroxypyrimidin-2-yl)octanamide (65)

The title compound was prepared according to the method of compound 31 using compound 57 as the starting acid. LCMS: $t_R$=0.79 min; m/z=453.26 [M+H]$^+$.

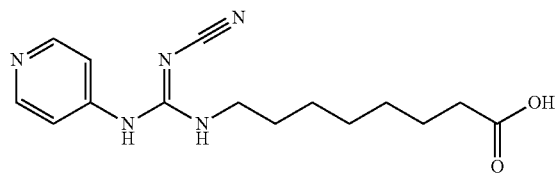

66

Example 66. (E)-8-(2-cyano-3-(pyridin-4-yl)guanidino)octanoic acid (66)

A solution of (Z)—N'-cyano-N-(pyridin-4-yl)methylsulfanylmethanimidamide (695 mg, 3.62 mmol), 8-aminooctanoic acid (576 mg, 3.62 mmol), DMAP (486 mg, 3.98 mmol), and DIEA (1.90 mL, 10.85 mmol) in 17 mL pyridine was heated at 70° C. under argon overnight, concentrated in vacuo, and purified by preparative HPLC to give the title compound (668 mg, 2.20 mmol, 61%). LCMS: $t_R$=0.63 min; m/z=304.2 [M+H]$^+$.

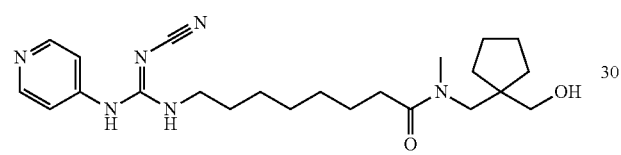

67

Example 67. (E)-8-(2-cyano-3-(pyridin-4-yl)guanidino)-N-((1-(hydroxymethyl)cyclopentyl)methyl)-N-methyloctanamide (67)

The title compound was prepared from compound 66 and (1-((methylamino)-methyl)cyclopentyl)methanol according to the method of compound 31. LCMS: $t_R$=0.92 min; m/z=429.3 [M+H]$^+$.

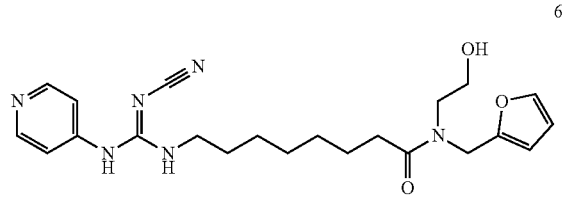

68

Example 68. (E)-8-(2-cyano-3-(pyridin-4-yl)guanidino)-N-(furan-2-ylmethyl)-N-(2-hydroxyethyl)octanamide (68)

The title compound was prepared from compound 66 and 2-((furan-2-ylmethyl)amino)ethan-1-ol according to the method of compound 31. LCMS: $t_R$=0.79 min; m/z=427.3 [M+H]$^+$.

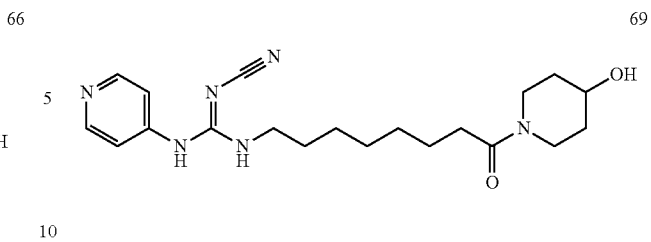

69

Example 69. (E)-2-cyano-1-(8-(4-hydroxypiperidin-1-yl)-8-oxooctyl)-3-(pyridin-4-yl)guanidine (69)

The title compound was prepared from compound 66 and piperidin-4-ol according to the method of compound 31. LCMS: $t_R$=0.95 min; m/z=387.3 [M+H]$^+$.

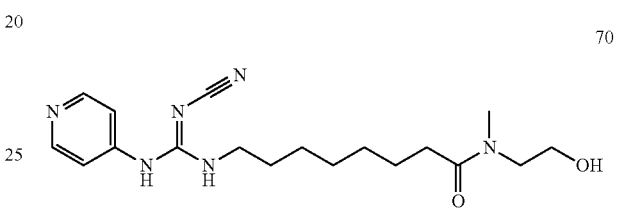

70

Example 70. (E)-8-(2-cyano-3-(pyridin-4-yl)guanidino)-N-(2-hydroxyethyl)-N-methyloctanamide (70)

The title compound was prepared from compound 63 and (Z)—N'-cyano-N-(pyridin-4-yl)methylsulfanylmethanimidamide by the method of compound 66. LCMS: $t_R$=0.66 min; m/z=361.4 [M+H]$^+$.

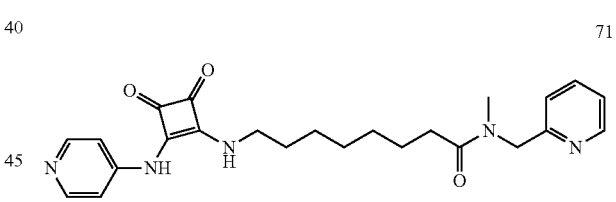

71

Example 71. 8-((3,4-dioxo-2-(pyridin-4-ylamino)cyclobut-1-en-1-yl)amino)-N-methyl-N-(pyridin-2-ylmethyl)octanamide (71)

The title compound was repaired according to the coupling method of compound 31 using compound 57 as the starting acid. LCMS: $t_R$=0.63 min; m/z=436.28 [M+H]$^+$.

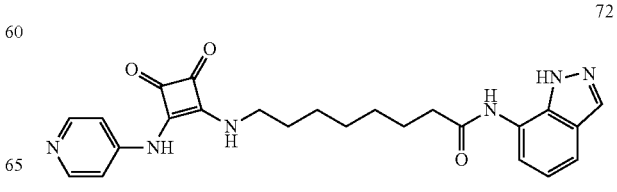

72

Example 72. 8-((3,4-dioxo-2-(pyridin-4-ylamino)cyclobut-1-en-1-yl)amino)-N-(1H-indazol-7-yl)octanamide (72)

The title compound was prepared according to the coupling method of compound 31 using compound 57 as the starting acid. LCMS: $t_R$=0.80 min; m/z=447.26 [M+H]$^+$.

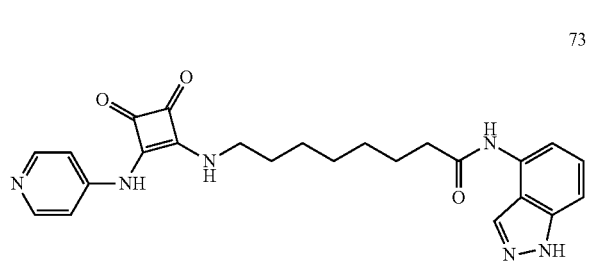 [SMILES: O=C(CCCCCCCNc1c(Nc2ccncc2)c(=O)c1=O)Nc1cccc2[nH]ncc12]

Example 73. 8-((3,4-dioxo-2-(pyridin-4-ylamino)cyclobut-1-en-1-yl)amino)-N-(1H-indazol-4-yl)octanamide (73)

The title compound was prepared according to the coupling method of compound 31 using compound 57 as the starting acid. LCMS: $t_R$=0.76 min; m/z=447.26 [M+H]$^+$.

Example 74. (E)-8-(2-cyano-3-(pyridin-4-yl)guanidino)-N-(1H-indazol-7-yl)octanamide (74)

The title compound was prepared according to the coupling method of compound 31 using compound 66 as the starting acid. LCMS: $t_R$=0.82 min; m/z=419.26 [M+H]$^+$.

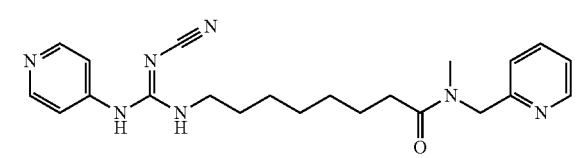

Example 75. (E)-8-(2-cyano-3-(pyridin-4-yl)guanidino)-N-methyl-N-(pyridin-2-ylmethyl)octanamide (75)

The title compound was prepared according to the coupling method of compound 31 using compound 66 as the starting acid. LCMS: $t_R$=0.65 min; m/z=408.29 [M+H]$^+$.

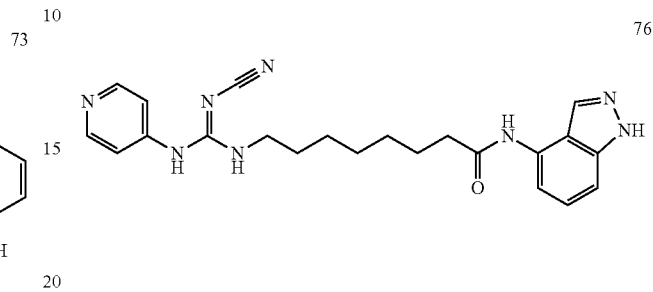

Example 76. (E)-8-(2-cyano-3-(pyridin-4-yl)guanidino)-N-(1H-indazol-4-yl)octanamide (76)

The title compound was prepared according to the method of coupling compound 31 using compound 66 as the starting acid. LCMS: $t_r$=0.77 min; m/z=419.26 [M+H]$^+$.

Example 77. (E)-8-(2-cyano-3-(pyridin-4-yl)guanidino)-N-(5-ethyl-4-hydroxypyrimidin-2-yl)octanamide (77)

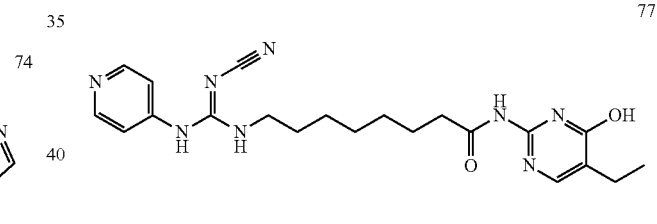

The title compound was prepared according to the method of coupling compound 31 using compound 66 as the starting acid. LCMS: $t_R$=0.75 min; m/z=425.27 [M+H]$^+$

Example 78. (9H-fluoren-9-yl)methyl (7-(cyclohexyl(2-(methylamino)-ethoxy)amino)-7-oxoheptyl)carbamate (78)

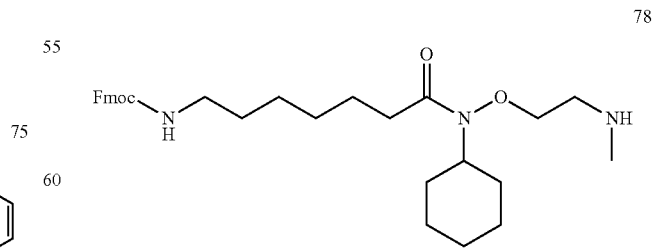

The title compound was prepared from compound 46 according to the deprotection method of compound 32. LCMS: $t_R$=1.18 min; m/z=522.30 [M+H]$^+$.

Example 79. (9H-fluoren-9-yl)methyl (7-((2-(3-((((9H-fluoren-9-yl)methoxy)carbonyl)amino)-N-methylbenzamido)ethoxy)(cyclohexyl)amino)-7-oxoheptyl)carbamate (79)

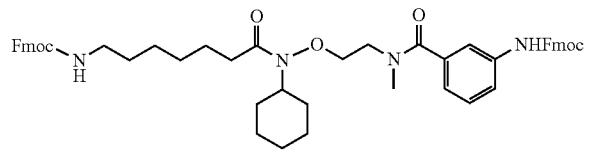

The title compound was prepared from compound 78 according to the method of compound 31. LCMS: $t_R$=1.82 min; m/z=864.41 [M+H]$^+$.

Example 80. 3-amino-N-(2-((7-amino-N-cyclohexylheptanamido)oxy)ethyl)-N-methylbenzamide (80)

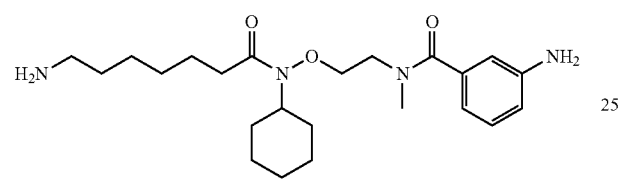

Compound 79 (42.0 mg, 0.049 mmol) was taken up in 1 mL 2% piperidine in DMF and stirred at room temperature 1 h. The product was purified by preparative HPLC to provide the title compound (27.9 mg, 0.043 mmol, 88%). LCMS: $t_R$=0.77 min; m/z=419.27 [M+H]$^+$.

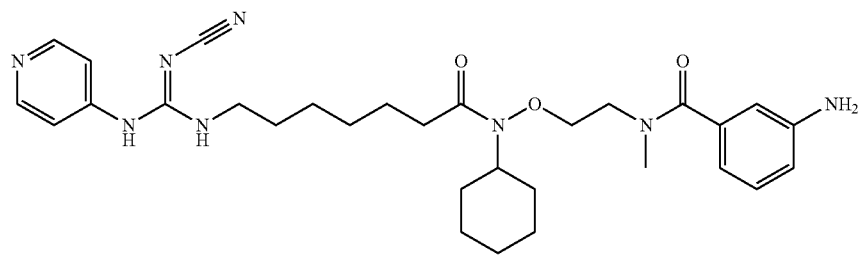

Example 81. (E)-3-amino-N-(1-cyano-11-cyclohexyl-10-oxo-2-(pyridin-4-ylamino)-12-oxa-1,3,11-triazatetradec-1-en-14-yl)-N-methylbenzamide (81)

The title compound was prepared from compound 80 according to the method of compound 66 LCMS: $t_r$=0.86 min; m/z=563.30 [M+H]$^+$.

Example 82. tert-butyl 4-(4-((3,4-dioxo-2-(pyridin-4-ylamino)cyclobut-1-en-1-yl)amino)butyl)piperidine-1-carboxylate (82)

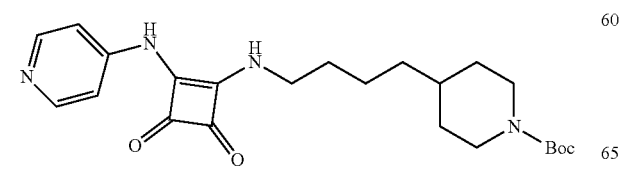

The title compound was prepared from tert-butyl 4-(4-aminobutyl)piperidine-1-carboxylate and 3-ethoxy-4-(pyridin-4-ylamino)cyclobut-3-ene-1,2-dione according to the method of compound 53. LCMS: $t_R$=1.00 min; m/z=429.17 [M+H]$^+$.

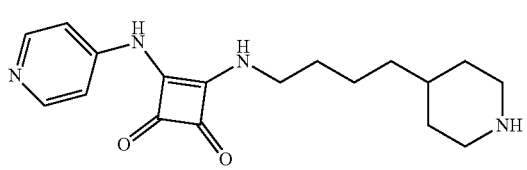

Example 82. 3-((4-(piperidin-4-yl)butyl)amino)-4-(pyridin-4-ylamino)-cyclobut-3-ene-1,2-dione (83)

The title compound was prepared according to the deprotection method of compound 32. LCMS: $t_R$=0.41 min; m/z=329.17 [M+H]$^+$.

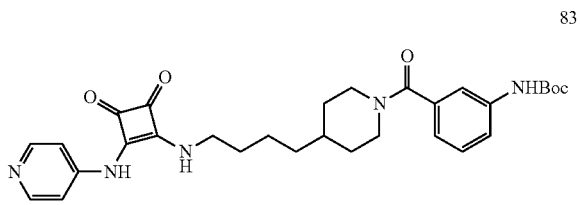 [SMILES: CC(C)(C)OC(=O)Nc1cccc(C(=O)N2CCC(CCCCNc3c(Nc4ccncc4)c(=O)c3=O)CC2)c1]

83

Example 83. tert-butyl (3-(4-(4-((3,4-dioxo-2-(pyridin-4-ylamino)cyclobut-1-en-1-yl)amino)butyl)piperidine-1-carbonyl)phenyl)carbamatedione (83)

The title compound was prepared from compound 82 and 3-((tert-butoxycarbonyl)amino)benzoic acid according to the condensation of method of compound 33. LCMS: $t_R$=1.00 min; m/z=548.24 [M+H]$^+$. $^1$HNMR (400 MHz, CD$_3$OD, δ): 1.05-1.26 (m, 2H), 1.30-1.39 (m, 3H), 1.39-1.48 (m, 2H), 1.50 (s, 9H), 1.54-1.61 (m, 1H), 1.61-1.73 (m, 3H), 1.84 (br d, J=12.0 Hz, 1H), 2.81 (t, J=12.0 Hz, 1H), 3.65-3.80 (m, 3H), 4.59 (d, J=12.0 Hz, 1H), 6.97 (dt, J=8.0 Hz, 2.0 Hz, 1H), 7.31 (t, J=8.0 Hz, 1H), 7.43 (ddd, J=12.0 Hz, 2.2 Hz, 1.1 Hz, 1H), 7.52 (s, 1H), 7.55 (d, J=8.0 Hz, 2H), 8.32-8.38 (m, 2H).

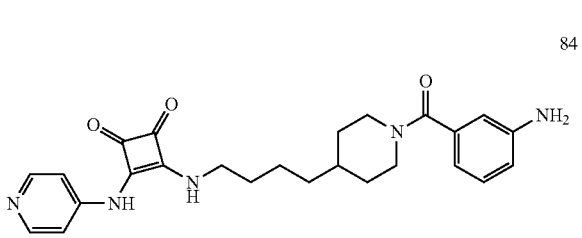 [SMILES: Nc1cccc(C(=O)N2CCC(CCCCNc3c(Nc4ccncc4)c(=O)c3=O)CC2)c1]

84

Example 84. 3-((4-(1-(3-aminobenzoyl)piperidin-4-yl)butyl)amino)-4-(pyridin-4-ylamino)cyclobut-3-ene-1,2-dione (84)

The title compound was prepared from compound according to the deprotection method of compound 32. LCMS: $t_R$=0.68 min; m/z=448.20 [M+H]$^+$.

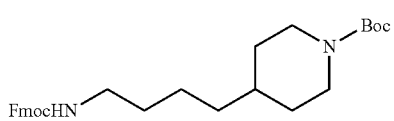

85

Example 85. tert-butyl 4-(4-((((9H-fluoren-9-yl)methoxy)carbonyl)amino)-butyl)piperidine-1-carboxylate (85)

Tert-butyl 4-(4-aminobutyl)piperidine-1-carboxylate (47.2 mg, 0.18 mmol) was taken up in 3 mL saturated sodium bicarbonate solution and 1.5 mL dioxane, and a solution of Fmoc-Cl (71.4 mg, 0.28 mmol) in 1.5 mL dioxane was slowly added at 0° C. The reaction mixture was allowed to warm to ambient temperature overnight under argon, then partitioned between EtOAc and 1M HCl, the organic layer washed once with brine, dried over MgSO$_4$, filtered, and concentrated in vacuo. The crude product was purified via silica gel chromatography using a gradient from 0-50% MeOH/CH$_2$Cl$_2$ to provide the title compound (74 mg, 0.16 mmol, 84%). LCMS: $t_R$=1.76 min; m/z=501.23 [M+Na]$^+$.

Example 86. (9H-fluoren-9-yl)methyl (4-(piperidin-4-yl)butyl)carbamate (86)

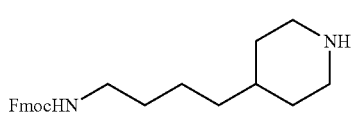

86

The title compound was prepared from compound 86 according to the deprotection method of compound 32. LCMS: $t_r$=1.69 min; m/z=379.18 [M+H]$^+$.

Example 87. (9H-fluoren-9-yl)methyl (3-(4-(4-((((9H-fluoren-9-yl)methoxy)carbonyl)amino)butyl)piperidine-1-carbonyl)phenyl)carbamate (87)

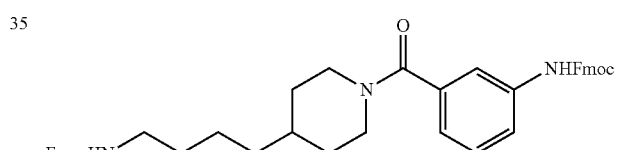

87

The title compound was prepared from compound 86 and 3-((((9H-fluoren-9-yl)methoxy)carbonyl)amino)benzoic acid according to the condensation method of compound 31. LCMS: $t_R$=1.91 min; m/z=720.49 [M+H]$^+$.

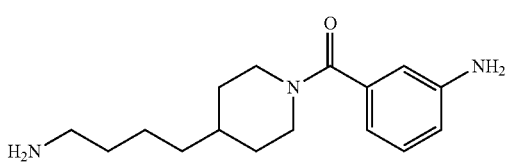

88

Example 88. (4-(4-aminobutyl)piperidin-1-yl)(3-aminophenyl)methanone (97)

The title compound was prepared according to the deprotection method of compound 80. LCMS: $t_R$=0.76 min; m/z=276.24 [M+H]$^+$. $^1$HNMR (400 MHz, CD$_3$OD, δ): 1.05-1.27 (m, 2H), 1.29-1.38 (m, 2H), 1.38-1.49 (m, 2H), 1.54-1.69 (m, 4H), 1.86 (d, J=12.0 Hz, 1H), 2.83 (t, J=14.0 Hz, 1H), 2.92 (t, J=6.0 Hz, 2H), 3.10 (t, J=14.0 Hz, 1H), 3.68 (d, J=12.0 Hz, 1H), 4.61 (d, J=12.0 Hz, 1H), 7.18-7.32 (m, 3H), 7.48 (t, J=8.0 Hz, 1H).

Example 89. (Z)-1-(4-(1-(3-aminobenzoyl)piperidin-4-yl)butyl)-2-cyano-3-(pyridin-4-yl)guanidine (98)

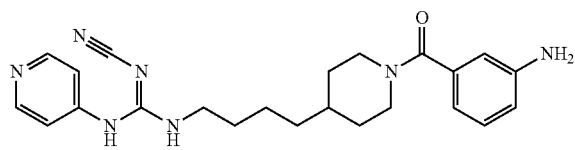

The title compound was prepared from compound 88 and (Z)—N'-cyano-N-(pyridin-4-yl)methylsulfanylmethanimidamide according to the method of compound 66. LCMS: $t_R$=1.02 min; m/z=420.42 [M+H]$^+$.

Example 89. Binding and Cytoxicity of NAMPTi Compounds

NAMPTi compounds corresponding to or incorporated as quaternized NAMPT Drug Units of Ligand Drug Conjugate were evaluated for binding to enzymatically competent NAMPT homodimer using a fluorescence polarization assay, and for cytotoxicity using the CellTiter-Glo™ assay, as described in the General Methods section. The results of those assays are presented in Table 1.

TABLE 1

IC$_{50}$ values (nM) for released NAMPTi compounds in the fluorescence polarization (FP) assay for binding to purified NAMPT, and in a cytotoxicity (CellTiter-Glo) assay

| linker ID | NAMPTi ID | FP assay (IC$_{50}$, nM) | CellTiter-Glo assay (IC$_{50}$, nM) | | | |
|---|---|---|---|---|---|---|
| | | | Karpas 299 | L540cy | Ramos | HepG2 |
| 3, 5, or 8 | 27 | 37 | 9.5 | 7.3 | 1.75 | 5.5 |
| 12 | 28 | 47 | | 8.5 | 1.0 | 8.0 |
| 26 | 29 | 36 | 0.78 | 0.71 | 1.08 | |

Karpas 299 (non-Hodgkin's lymphoma), L540cy (Hodgkin's lymphoma), Ramos (Burkitt's lymphoma), HepG2 (hepatocellular carcinoma), Hep3B (hepatocellular carcinoma). NAMPTi compounds of Table 1 have the following structures:

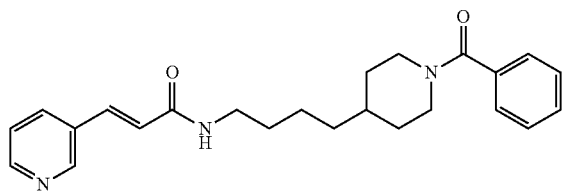

27

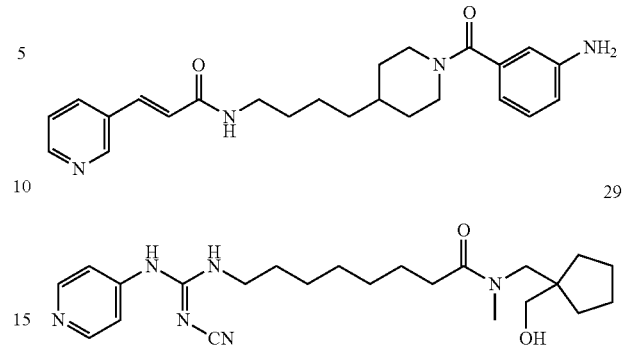

Example 90. Preparation of Quaternized NAMPT Conjugates

Antibody Drug Conjugate having a quaternized NAMPT Drug Unit were prepared by contacting antibody having fully reduced interchain disulfides bond cysteines/antibody susceptible to alkylation by the maleimide-containing drug-linkers. Representative conjugates using the pyridinium linker strategy were prepared on chimeric anti-Ag1, chimeric AC10 (anti-CD30), and humanized anti-Ag3). The ADCs are identified by the antigens that are recognized. Ag1 is an antigen ubiquitously displayed and readily internalizable by cancer cells, Ag2 is cAC10, which recognizes CD30$^+$ cancer cells, as described by U.S. Pat. No. 8,257,706, and Ag3 is an antigen preferentially displayed by hepatocarcinoma cells. All ADCs were loaded at 8-drugs/antibody and were monomeric by size-exclusion chromatography.

Example 91. In Vitro Biological Activities of Quaternized NAMPT Conjugates

Antibody Drug Conjugates (ADCs) of Table 2 (below) were tested for cytotoxicity against various cancer cell lines displaying antigens that are capable of selective binding by the Conjugates' antibody Ligand Units and for their ability to deplete NAD using the NAD-Glo assay.

TABLE 2

Cytotoxicity of antibody-drug conjugates having quaternized NAMPT Drug Units

| ADC ID | NAD depletion assay (IC$_{50}$, ng/mL) | | | | | |
|---|---|---|---|---|---|---|
| | Karpas 299 | L540cy | Ramos | HepG2 | Hep3B | JHH-7 |
| Ag1-3 | | 7.0 | 4.4 | 11 | | |
| Ag2-3 | 28 | 78 | | | | |
| Ag2-5 | 5 | 30 | | | | |
| Ag2-12 | 5 | 11 | | | | |
| Ag2-26 | 9 | 19 | | | | |
| Ag3-3 | | | | | 12 | 34 |
| Ag3-12 | | | | | 11 | 36 |

Conjugates targeting Ag1 showed strong activity against all cells lines tested, (Table 2). cAC10 conjugates were highly active against CD30$^+$ L540cy cells, while Ag3 conjugates were active against Ag3$^+$ Hep3B and JHH-7 cells. No activity for cAC10 ADCs was observed in CD30-negative cell lines which were otherwise sensitive to targeted ADCs, indicating the high degree of immunological specificity of the constructs.

Example 92. In Vivo Biological Activities of Quaternized NAMPT Conjugates

Anti-Ag2 chimeric antibody cAC10 were prepared from Drug Linker compounds 5 (MDPr-GlucQ-FK866), 12 (MDPr-GlucQ-6050) and 26 (MDPr-GlucQ-6553) to provide ADCs carrying 8 drugs per antibody. Animals were implanted with tumor cells on day 0. Tumors reached ~100 mm³ on day 8, and were then treated with a single 1 mg/kg dose (ip) of ADCs. Treatments resulted in varying levels of tumor growth delay depending on the drug-linker of the ADC as shown by the FIGURE. The treatments were well-tolerated, with no weight loss or outward signs of toxicity observed.

What is claimed is:

1. A Ligand Drug Conjugate compound represented by Formula 1:

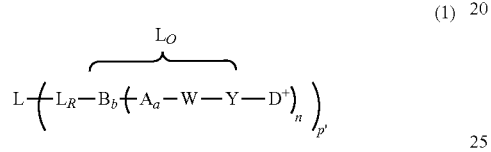

(1)

in salt form, wherein

L is a Ligand Unit which is an antibody or an antigen-binding fragment thereof,

W is a Peptide Cleavable Unit, or

W—Y is replaced by a Glucuronide Unit of formula —Y(W'), wherein W' represents a carbohydrate moiety with glycosidic bonding to Y through an optionally substituted heteroatom; and Y is a self-immolative Spacer Unit comprising a PAB or PAB-type moiety;

D⁺ is a quaternized NAMPT Drug Unit covalently attached to the remainder of the Formula 1 compound structure through a quaternized skeletal aromatic nitrogen atom of an optionally substituted $C_5$-$C_{24}$ heteroaryl of D⁺, or a quaternized skeletal non-aromatic nitrogen atom of a partially unsaturated or partially aromatic optionally substituted $C_9$-$C_{24}$ heterocyclyl of D⁺, wherein the quaternized NAMPT Drug Unit is represented by the general structure of:

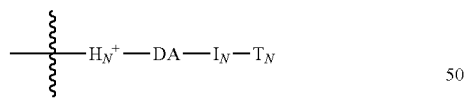

or a salt thereof, wherein $H_N^+$ is a quaternized NAMPT Head Unit as the quaternized component of D⁺ wherein the optionally substituted $C_5$-$C_{24}$ heteroaryl or partially unsaturated or partially aromatic optionally substituted $C_9$-$C_{24}$ heterocyclyl of $H_N^+$ comprises a 5- or 6-membered nitrogen-containing partially unsaturated or heteroaromatic ring system, the skeletal nitrogen atom of which is the site of quaternization to $L_O$, as indicated by the wavy line to $H_N^+$;

DA is a Donor-Acceptor Unit wherein the Donor-Acceptor Unit is or comprises a hydrogen bond donor or acceptor functional group and is bonded to a carbon skeletal atom at position 2 or 3 of the 5-membered nitrogen-containing partially unsaturated or heteroaromatic ring system or at position 3 or 4 of the 6-membered nitrogen-containing partially unsaturated or heteroaromatic ring system, with optional formal cyclization of DA back to an adjacent skeletal carbon atom of the 6-membered nitrogen-containing ring system through an introduced optionally substituted non-aromatic carbon atom or an optionally substituted nitrogen, oxygen or sulfur atom resulting in a partially unsaturated, partially aromatic or fully aromatic 6,5- or 6,6-fused ring system, wherein said bonding of DA is in relation to a skeletal nitrogen atom of the 5- or 6-membered nitrogen-containing partially unsaturated or heteroaromatic ring system and wherein said formal cyclization to the adjacent carbon atom of the 6-membered nitrogen-containing partially unsaturated or heteroaromatic ring system substantially retains the hydrogen bonding ability of the donor or acceptor functional group of DA in absence of said cyclization;

$I_N$ is an Interconnecting Unit, wherein the Interconnecting Unit is or comprises —$X^1$—[C(=O)]$_{0,1}$—, —$X^1$—S(=O)$_{1,2}$—, —$X^2$—$C_6$-$C_{24}$ arylene-[C(=O)]$_{0,1}$—, —$X^2$—$C_6$-$C_{24}$ arylene-[S(=O)$_{1,2}$]$_{0,1}$, —$X^2$—$C_6$-$C_{24}$ arylene-O—, —$X^2$—$C_5$-$C_{24}$ heteroarylene-[C(=O)$_{0,1}$]-, —$X^2$—$C_5$-$C_{24}$ heteroarylene-[S(=O)$_{1,2}$]$_{0,1}$, —$X^2$—$C_5$-$C_{24}$ heteroarylene-O— or —$X^2$—$C_3$-$C_{20}$ heterocyclo-[C(=O)$_{0,1}$]-, wherein the arylene, heteroarylene and heterocyclo are optionally substituted;

$X^1$ is optionally substituted $C_5$-$C_7$ alkylene;

$X^2$ is absent or is an optionally substituted $C_1$-$C_4$ alkylene;

$T_N$ is a NAMPT Tail Unit, wherein the NAMPT Tail Unit is or comprises an optionally substituted amino-alcohol residue or a carboxylic acid-alcohol residue, the amino nitrogen or carbonyl carbon of which is bonded to $I_N$, or $T_N$ is or comprises an optionally substituted benzamide moiety or a bioisostere thereof, wherein the amide nitrogen atom of the benzamide moiety is bonded to $I_N$ with optional cyclization of that atom back to $I_N$ or to the remainder of $T_N$, or $T_N$ is or comprises an optionally substituted $C_6$-$C_{24}$ aryl, $C_5$-$C_{24}$ heteroaryl or a biaryl comprising two independently selected $C_6$-$C_{24}$ aryl or $C_5$-$C_{24}$ heteroaryl rings, each of which is optionally substituted, an aromatic atom of which is bonded to $I_N$ or the remainder of $T_N$, wherein $T_N$ or the remainder thereof is bonded to $I_N$, wherein said remainder is an optionally substituted $C_2$-$C_7$ heteroalkylene or an optionally substituted $C_5$-$C_6$ heterocyclo, and wherein non-enzymatic or enzymatic action on W/W' of a drug linker moiety of a Ligand Drug Conjugate compound is capable of initiating release of the quaternized NAMPT Drug (D⁺) Unit as a NAMPTi compound of formula $H_N$-DA-$I_N$-$T_N$, wherein $H_N$ is a NAMPT Head Unit that is a fully aromatic optionally substituted $C_5$-$C_{24}$ heteroaryl comprising a 5- or 6-membered nitrogen-containing heteroaromatic ring system having the previously quaternized skeletal nitrogen atom, and the other variable groups are as previously defined, wherein $H_N$— or $H_N$-DA- of the NAMPTi compound is capable of interacting with enzymatically competent NAMPT homodimer at its nicotinamide binding site; and $L_R$ is a primary linker that interconnects the Ligand Unit and the quaternized NAMPT Drug Unit through $L_O$, wherein $L_O$ is a secondary linker;

subscripts a and b independently are 0 or 1, indicating the absence or presence, respectively, of A or B;
subscript n is 1, 2, 3 or 4;
A is a first optional Stretcher Unit;
B is a Branching Unit when subscript b is 1 and subscript n is 2, 3 or 4, and B is absent when subscript b is 0 and subscript n is 1,
wherein each of A and B is an independently selected single unit or optionally comprises or consists of two, three or four independently selected subunits; and
subscript p' is an integer ranging from 1 to 24.

2. The Ligand Drug Conjugate compound of claim 1, wherein the NAMPT Head ($H_N$) Unit has the structure of:

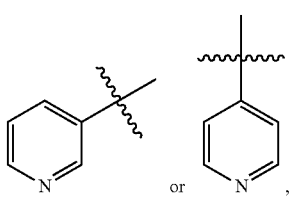 [SMILES: *c1cccnc1 ; *c1ccncc1]

or a salt thereof, and wherein the quaternized NAMPT ($H_N^+$) Unit has the structure of:

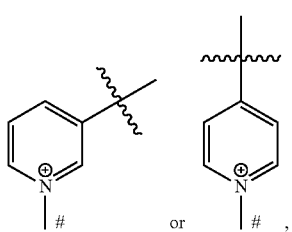

or a salt thereof, wherein said optional formal cyclization of DA is to an adjacent carbon atom of the pyridine or pyridinium aromatic ring system of $H_N$ or $H_N^+$, respectively, through an introduced aromatic oxygen, sulfur or an optionally substituted nitrogen atom so that $H_N/H_N^+$ contains a 6-5 fused aromatic ring system, wherein
the pound sign (#) indicates the point of covalent attachment to $L_O$; and
the wavy line indicates the site of covalent attachment to DA and an adjacent aromatic carbon atom thereto is the site of said optional formal cyclization by DA to $H_N/H_N^+$.

3. The Ligand Drug Conjugate compound of claim 1, wherein the Donor Acceptor (DA) Unit has the structure of:

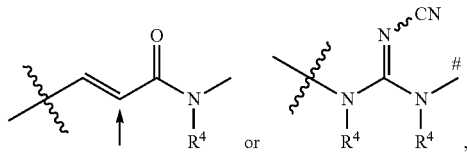

or a salt thereof, wherein each $R^4$ is independently selected from the group consisting of hydrogen and optionally substituted $C_1$-$C_4$ alkyl;
wherein said formal optional cyclization of DA to $H_N/H_N^+$ is from the sp² carbon atom of the DA Unit proximal to the carbonyl carbon atom (as indicated) through an introduced optionally substituted non-aromatic carbon atom or an optionally substituted aromatic heteroatom;
the wavy line indicates the site of covalent attachment to $H_N/H_N^+$; and
the pound sign (#) indicates the site of covalent attachment to $I_N$.

4. The Ligand Drug Conjugate compound of claim 1, wherein $H_N$-DA has the structure of:

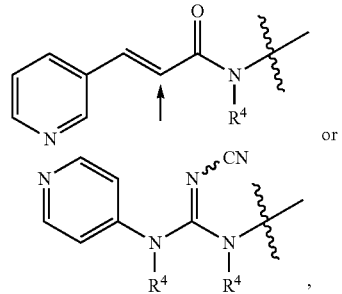

or a salt thereof, and $H_N^+$-DA has the structure of:

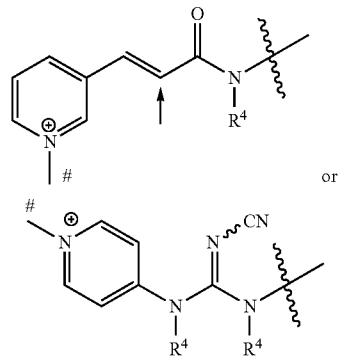

or a salt thereof, wherein
$R^4$ is independently selected from the group consisting of hydrogen and optionally substituted $C_1$-$C_4$ alkyl; and
the pound sign (#) indicates the point of covalent attachment to $L_O$;
the wavy line indicates the site of covalent attachment to $I_N$, and
wherein the sp² carbon atom proximal to the carbonyl carbon atom is the site (as indicated) of said formal optional cyclization to $H_N/H_N^+$ through an introduced optionally substituted non-aromatic carbon atom or an optionally substituted aromatic heteroatom.

5. The Ligand Drug Conjugate compound of claim 1, wherein the NAMPT Tail ($T_N$) Unit is an amino alcohol moiety having the structure of:

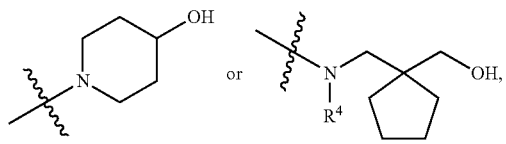

wherein

R⁴ is hydrogen or optionally substituted $C_1$-$C_4$ alkyl; and the wavy line indicates the site of covalent attachment to $I_N$, or wherein the Tail ($T_N$) Unit is a benzamide moiety covalently attached to $I_N$ through its amide nitrogen atom, wherein the benzamide moiety has the structure of:

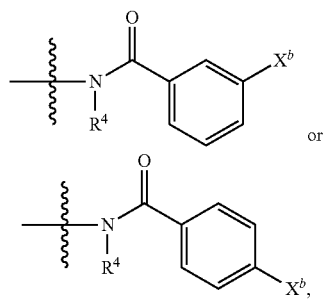

or wherein $X^b$ is —H, halogen, —OH, optionally substituted $C_1$-$C_4$ alkoxy, optionally substituted $C_1$-$C_4$ alkyl, or optionally substituted —NH₂;

R⁴ is hydrogen or optionally substituted $C_1$-$C_4$ alkyl; and the wavy line indicates the site of covalent attachment to $I_N$; and wherein the benzamide moiety is optionally cyclized to $I_N$ wherein the amide nitrogen atom of the benzamide moiety is the site of said cyclization so that R⁴ is replaced by a covalent bond, or wherein the benzamide moiety has the structure of:

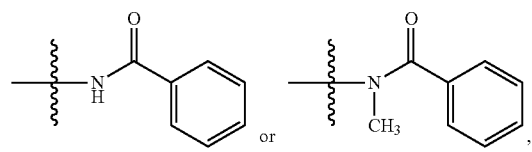 [SMILES: *NC(=O)c1ccccc1 ; *N(C)C(=O)c1ccccc1]

or wherein the NAMPT Tail ($T_N$) Unit is a (hetero)aryl or biaryl moiety having the structure of:

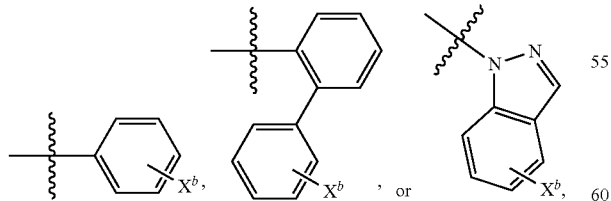

wherein $X^b$ is —H, halogen, —OH, optionally substituted $C_1$-$C_4$ alkoxy, optionally substituted $C_1$-$C_4$ alkyl, or optionally substituted —NH₂; and the wavy line indicates the site of covalent attachment to $I_N$.

6. The Ligand Drug Conjugate compound of claim 5, wherein $I_N$ has the structure of:

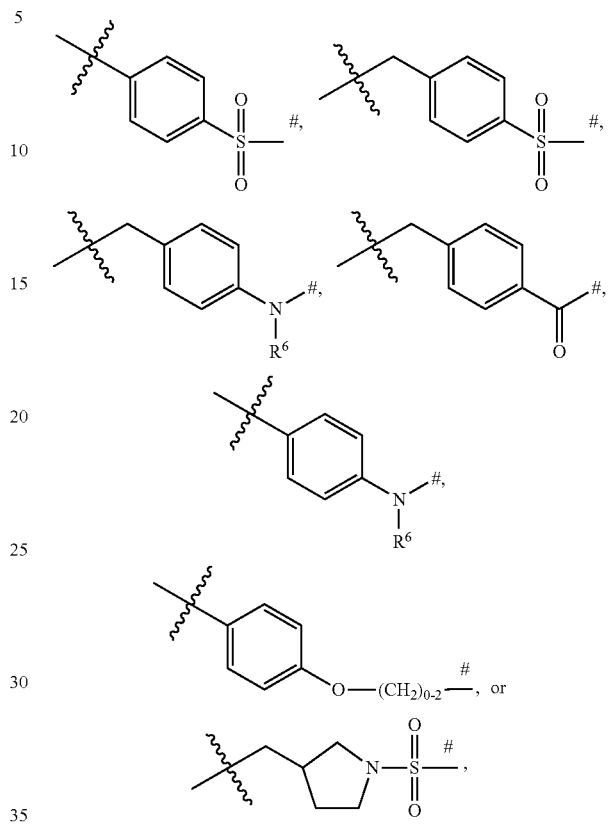

wherein the wavy line indicates the site of covalent attachment to DA and the pound sign (#) indicates the site of covalent attachment to $T_N$; and R⁶ is hydrogen, $C_1$-$C_4$ alkyl, —CH₂CH═C(CH₃)₂, or —CH₂—C≡CH.

7. The Ligand Drug Conjugate compound of claim 1, wherein —$I_N$-$T_N$ has the structure of:

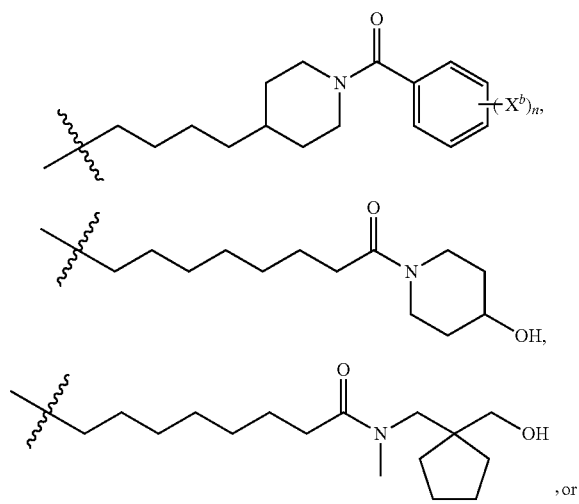

-continued

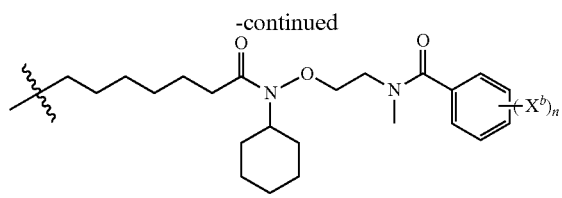

wherein

X[b] when present is independently selected from the group consisting of halogen, —OH, optionally substituted $C_1$-$C_4$ alkoxy, optionally substituted $C_1$-$C_4$ alkyl, and optionally substituted —NH$_2$, and subscript n is 0, 1, or 2; and the wavy line indicates the site of covalent attachment to DA, or wherein —I$_N$-T$_N$ has the structure of:

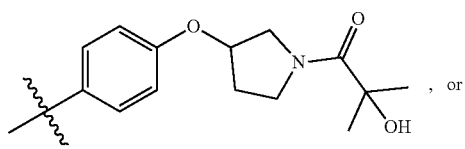

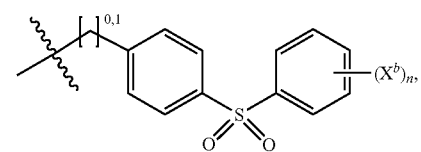

wherein

X[b] if present is selected from the group consisting of optionally substituted —OH, optionally substituted NH$_2$, and halogen, and subscript n is 0, 1, or 2, provided that when subscript n is 2 one of X[b] is optionally substituted —OH, optionally substituted —NH$_2$, or halogen and the other is halogen; and the wavy line indicates the site of covalent attachment to DA.

8. The Ligand Drug Conjugate compound of claim 1, wherein the quaternized NAMPT Drug (D$^+$) Unit has the structure of:

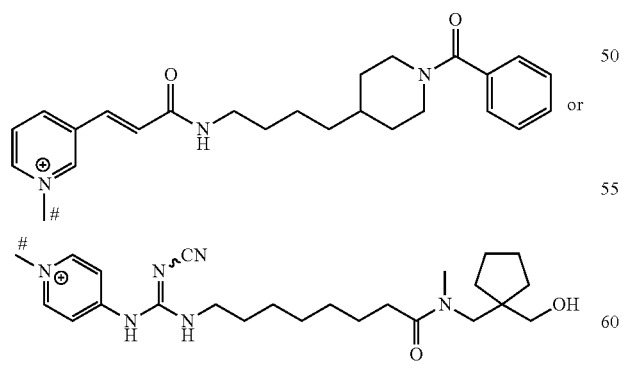

or a salt thereof, wherein the pound sign (#) indicates the point of attachment to the remainder of the compound.

9. The Ligand Drug Conjugate compound of claim 1, wherein L-(L$_R$- of Formula 1 has the structure of:

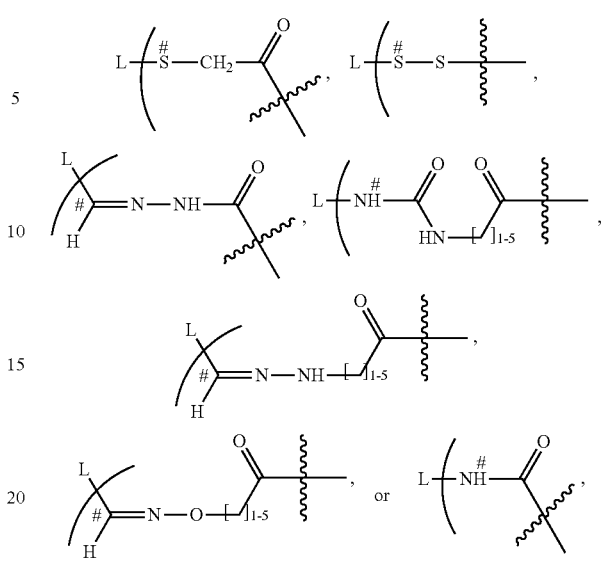

or a salt thereof, wherein the indicated (#) atom is from the Ligand Unit which is an antibody or an antigen-binding fragment thereof; and wherein the wavy line indicates the site of covalent attachment to the remainder of the Ligand Drug Conjugate compound structure, or wherein L-(L$_R$- of Formula 1 has the structure of:

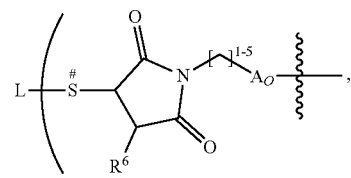

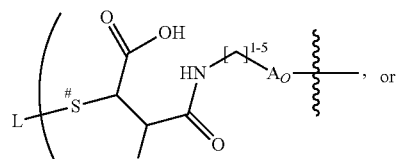

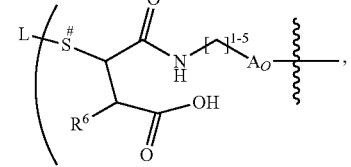

or a salt thereof, wherein the indicated (#) sulfur atom is from the Ligand Unit which is an antibody or an antigen-binding fragment thereof, R$^6$ is hydrogen or an optionally substituted $C_1$-$C_6$ alkyl;

A$_O$ is a second optional Stretcher Unit; and the wavy line indicates the site of covalent attachment to the remainder of the Conjugate structure, or wherein L-($L_R$- of Formula 1 has the structure of:

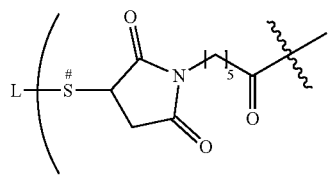

wherein the indicated (#) sulfur atom is from the Ligand Unit which is an antibody or an antigen-binding fragment thereof and the wavy line indicates the site of covalent attachment to the remainder of the Ligand Drug Conjugate compound structure, or wherein L-($L_R$- of Formula 1 has the structure of:

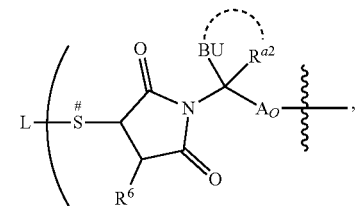

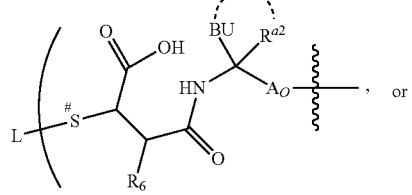

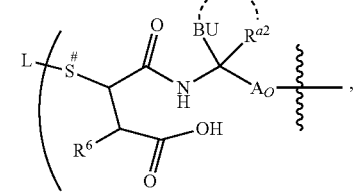

or a salt thereof, wherein
the indicated (#) sulfur atom is from the Ligand Unit which is an antibody or an antigen-binding fragment thereof, and
$R^6$ is hydrogen or an optionally substituted $C_1$-$C_6$ alkyl;
$A_O$ is a second optional Stretcher Unit;
BU is a Basic Unit;
$R^{a2}$ is —H or optionally substituted $C_1$-$C_{12}$ alkyl;
the dotted curved line indicates optional cyclization so that in the absence of said cyclization BU is an acyclic Basic Unit or in the presence of said cyclization BU is a cyclized Basic Unit in which $R^{a2}$ as $C_1$-$C_6$ alkyl and BU together with the carbon atom to which both are attached and a carbon atom of $R^{a2}$, define an optionally substituted $C_3$-$C_{20}$ heterocyclo containing a skeletal basic nitrogen atom of a secondary or tertiary amine functional group of BU,
wherein the basic nitrogen atom of the acyclic Basic Unit or cyclic Basic Unit is optionally suitably protected by a nitrogen protecting group, dependent on the degree of substitution of the basic nitrogen atom, or is optionally protonated; and the wavy line indicates the site of covalent attachment to the remainder of the Ligand Drug Conjugate compound structure, or
wherein L-($L_R$- of Formula 1 or a compound thereof has the structure of:

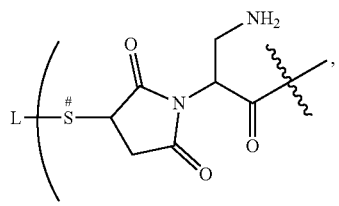

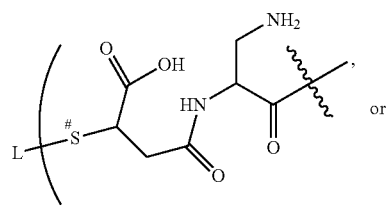

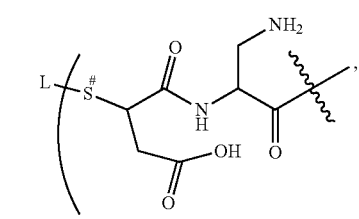

or a salt thereof, wherein the basic nitrogen atom is optionally suitably protected by a nitrogen protecting group, or is optionally protonated; and
the indicated (#) sulfur atom is from the Ligand Unit which is an antibody or an antigen-binding fragment thereof; and the wavy line indicates the site of covalent attachment to the remainder of the Ligand Drug Conjugate compound structure, or
wherein L-($L_R$- of Formula 1 or compound thereof has the structure of:

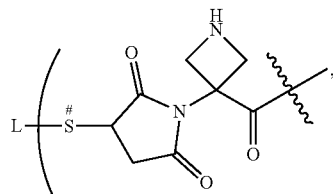

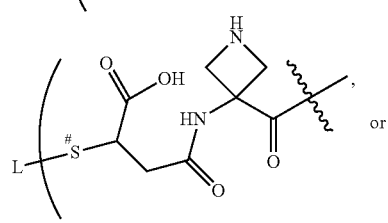

-continued

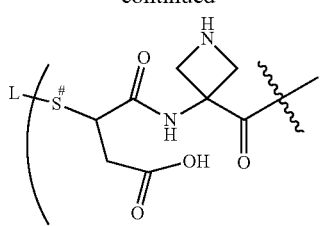

or a salt thereof, wherein
the basic nitrogen atom is optionally suitably protected by a nitrogen protecting group, or is optionally protonated; and
the indicated (#) sulfur atom is from the Ligand Unit which is an antibody or an antigen-binding fragment thereof; and the wavy line indicates the site of covalent attachment to the remainder of the Conjugate structure.

10. The Ligand Drug Conjugate compound of claim 9, wherein the compound is represented by the structure of Formula 1a or Formula 1b or is represented by the structure of Formula 1c or Formula 1d:

(Formula 1a)

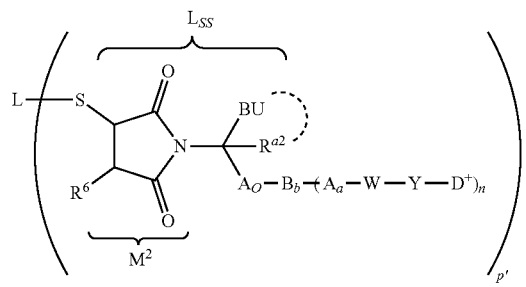

(Formula 1b)

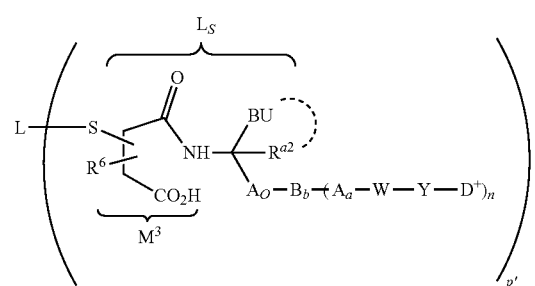

(Formula 1c)

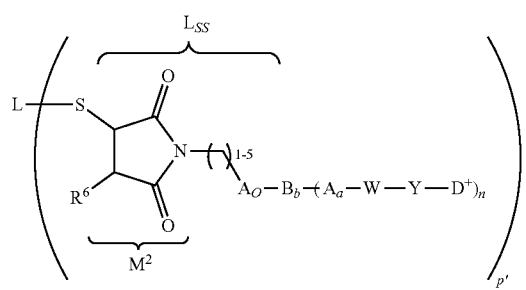

(Formula 1d)

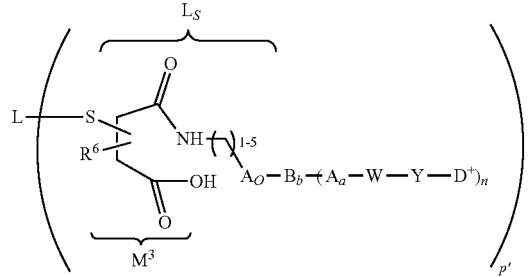

or a salt thereof, wherein
S is a sulfur atom of the Ligand Unit which is an antibody or an antigen-binding fragment thereof, which in Formula 1b or Formula 1d is bonded to the carbon atom α or β to the carboxylic acid functional group of the indicated succinic acid amide ($M^3$) moiety;
$R^6$ is hydrogen or an optionally substituted $C_1$-$C_6$ alkyl, which in Formula 1b or Formula 1d is bonded to the saturated carbon atom adjacent to the carbon atom substituted by L-S—;
or
wherein the compound is represented by the structure of Formula 1a' or Formula 1b':

(Formula 1a')

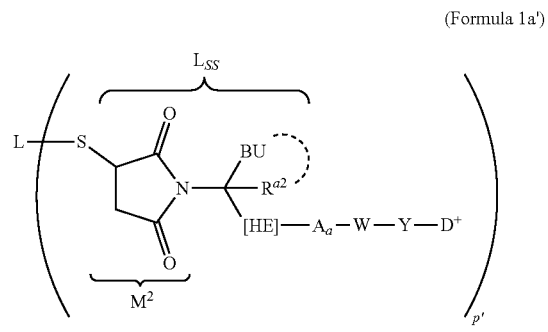

(Formula 1b')

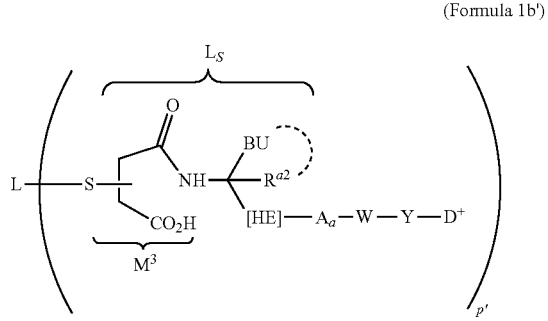

or a salt thereof, wherein
S is a sulfur atom of the Ligand Unit which is an antibody or an antigen-binding fragment thereof, which in Formula 1b' or Formula 1d' is bonded to the carbon atom α or β to the carboxylic acid functional group of the indicated succinic acid amide ($M^3$) moiety
[HE] is an optional Hydrolysis Enhancing Unit;
W is a Peptide Cleavable Unit, and Y is the self-immolative Spacer Unit and comprises a PAB or PAB-type moiety,
wherein the remaining variable groups are as previously described for Formula 1a' and Formula 1b', or W—Y is replaced by a Glucuronide Unit of formula —Y(W')— having the structure of:

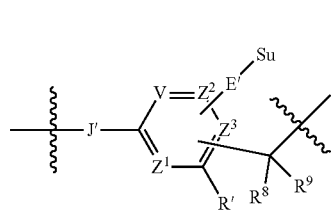

or a salt thereof, wherein Su is the carbohydrate moiety with glycosidic bonding to Y through an optionally substituted heteroatom represented by -E' so that Su-E' is W' and the remainder of the Glucuronide Unit structure is the self-immolative Spacer Unit (Y) bonded to W';

J' is an independently selected optionally substituted heteroatom;

V, $Z^1$, $Z^2$ and $Z^3$ are selected from the group consisting of =N— and =C($R^{24}$)—, wherein each $R^{24}$ is selected from the group consisting of hydrogen and optionally substituted $C_1$-$C_{12}$ alkyl, optionally substituted $C_2$-$C_{12}$ alkenyl, optionally substituted $C_2$-$C_{12}$ alkynyl, halogen, an electron withdrawing group, an electron donating group, -E'-Su, and —C($R^8$)($R^9$)—, provided that one and only one —C($R^8$)($R^9$)— moiety and one and only one -E'-Su moiety is present, and one of V, $Z^1$, $Z^2$ and $Z^3$ is =C($R^{24}$)— in which $R^{24}$ is —C($R^8$)($R^9$)— and another of V, $Z^1$, $Z^2$ and $Z^3$ is =C($R^{24}$)— in which $R^{24}$ is -E'-Su, and provided the —C($R^8$)($R^9$)— and -E'-Su moieties are ortho or para to each other;

one of $R^8$ and $R^9$ is hydrogen and the other is hydrogen, optionally substituted $C_1$-$C_{12}$ alkyl, optionally substituted $C_2$-$C_{12}$ alkenyl, optionally substituted $C_2$-$C_{12}$ alkynyl, optionally substituted $C_6$-$C_{20}$ aryl, or optionally substituted $C_5$-$C_{20}$ heteroaryl; and R' is hydrogen, —$NO_2$, or an electron withdrawing group; and wherein the wavy line adjacent to J' indicates the site of covalent attachment of the Glucuronide Unit to A when subscript a is 1 or to the indicated $L_{SS}$ or $L_S$ primary linker when subscript a is 0; and the wavy line adjacent to the —C($R^8$)($R^9$)— moiety indicates the site of covalent attachment of the Glucuronide Unit to $D^+$; and wherein glycosidase action on the Glucuronide Unit resulting in cleavage of its glycosidic bond initiates release of the quaternized NAMPT Drug ($D^+$) Unit as NAMPTi compound from a drug linker moiety of the Ligand Drug Conjugate compound; and the remaining variable groups are as previously described for Formula 1a' and Formula 1b';

or wherein the compound is represented by the structure of Formula 1c' or Formula 1d':

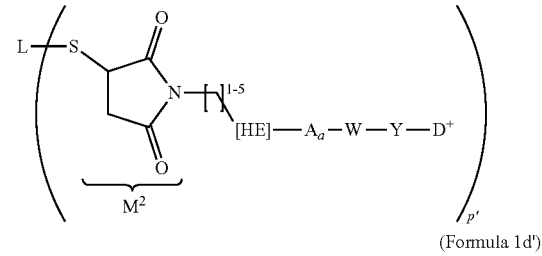

(Formula 1c')

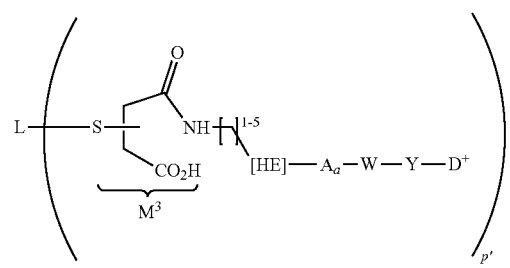

(Formula 1d')

or a salt thereof, wherein [HE] is an optional Hydrolysis Enhancing Unit; and

W is Peptide Cleavable Unit, and Y is the self-immolative Spacer Unit (Y) and comprises a PAB or PAB-type moiety, W—Y is replaced by a Glucuronide Unit of formula —Y(W')— having the structure of:

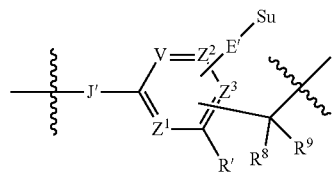

or a salt thereof, wherein

Su is the carbohydrate moiety with glycosidic bonding to Y through an optionally substituted heteroatom represented by -E' so that Su-E' is W' and the remainder of the Glucuronide Unit structure is the self-immolative Spacer Unit (Y) bonded to W';

J' is an independently selected optionally substituted heteroatom;

V, $Z^1$, $Z^2$ and $Z^3$ are selected from the group consisting of =N— and =C($R^{24}$)—, wherein each $R^{24}$ is selected from the group consisting of hydrogen, optionally substituted $C_1$-$C_{12}$ alkyl, optionally substituted $C_2$-$C_{12}$ alkenyl, optionally substituted $C_2$-$C_{12}$ alkynyl, halogen, an electron withdrawing group, an electron donating group, -E'-Su, and —C($R^8$)($R^9$)—, provided that one and only one —C($R^8$)($R^9$)— moiety and one and only one -E'-Su moiety is present, and one of V, $Z^1$, $Z^2$ and $Z^3$ is =C($R^{24}$)— in which $R^{24}$ is —C($R^8$)($R^9$)— and another of V, $Z^1$, $Z^2$ and $Z^3$ is =C($R^{24}$)— in which $R^{24}$ is -E'-Su, provided the —C($R^8$)($R^9$)— and -E'-Su moieties are ortho or para to each other;

one of $R^8$ and $R^9$ is hydrogen and the other is hydrogen, optionally substituted $C_1$-$C_{12}$ alkyl, optionally substituted $C_2$-$C_{12}$ alkenyl, optionally substituted $C_2$-$C_{12}$ alkynyl, optionally substituted $C_6$-$C_{20}$ aryl, or optionally substituted $C_5$-$C_{20}$ heteroaryl; and R' is hydrogen, —$NO_2$, or an electron withdrawing group; and wherein the wavy line adjacent to J' indicates the site of covalent attachment of the Glucuronide Unit to A when subscript a is 1 or to the indicated $L_{SS}$ or $L_S$ primary linker when subscript a is 0; and the wavy line adjacent to the —$C(R^8)(R^9)$— moiety indicates the site of covalent attachment of the Glucuronide Unit $D^+$; and wherein glycosidase action on the Glucuronide Unit resulting in cleavage of its glycosidic bond initiates release of the quaternized NAMPT Drug ($D^+$) Unit as a NAMPTi compound from a drug linker moiety of the Ligand Drug Conjugate compound.

11. The Ligand-Drug Conjugate compound of claim 10, wherein W—Y is replaced by the Glucuronide Unit of formula —Y(W')— for which —Y(W')-$D^+$ has the structure of:

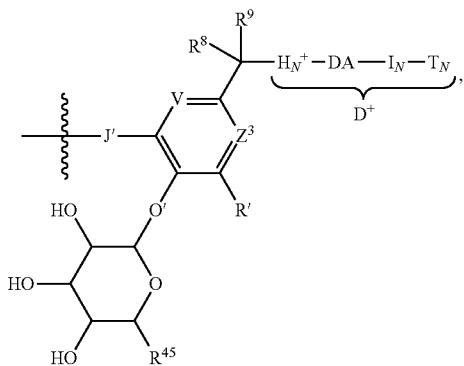

or a salt thereof, wherein the wavy line indicates the site of covalent attachment to the remainder of the Ligand Drug Conjugate compound structure;

one of $R^8$ and $R^9$ is hydrogen or $C_1$-$C_6$ alkyl and the other is hydrogen;

R' is hydrogen, —$NO_2$, or an electron withdrawing group;

$R^{45}$ is —$CH_2OH$ or —$CO_2H$; and

V and $Z^3$ are =$C(R^{24})$—, wherein one of $R^{24}$ is selected from the group consisting of hydrogen and an electron withdrawing group and the other is hydrogen; and J' is —NH—, wherein —O'— represents the oxygen atom of the O-glycosidic bond cleavable by the glycosidase, or wherein W is the Peptide Cleavable Unit for which —Y-$D^+$ has the structure of:

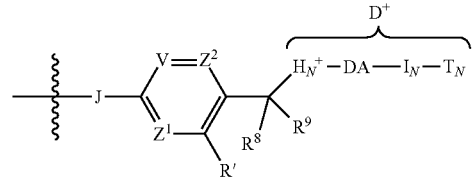

or a salt thereof, wherein the wavy line indicates the site of covalent attachment to the remainder of the Ligand Drug Conjugate compound structure, one of $R^8$ and $R^9$ is hydrogen or $C_1$-$C_6$ alkyl and the other is hydrogen;

R' is hydrogen, —$OC_1$-$C_6$ alkyl, or an electron donating group; and

V, $Z^1$ and $Z^2$ are =$C(R^{24})$—, wherein each of $R^{24}$ is hydrogen; and

J is —NH—.

12. The Ligand-Drug Conjugate compound of claim 11, wherein the Formula 1a' or Formula 1b' structure is represented by the structure of:

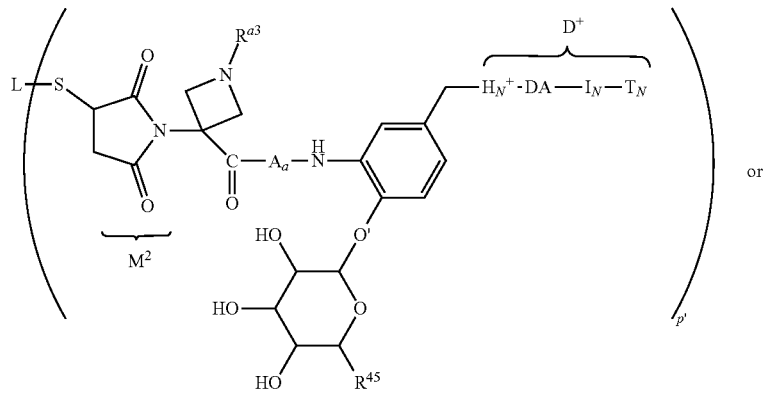

-continued

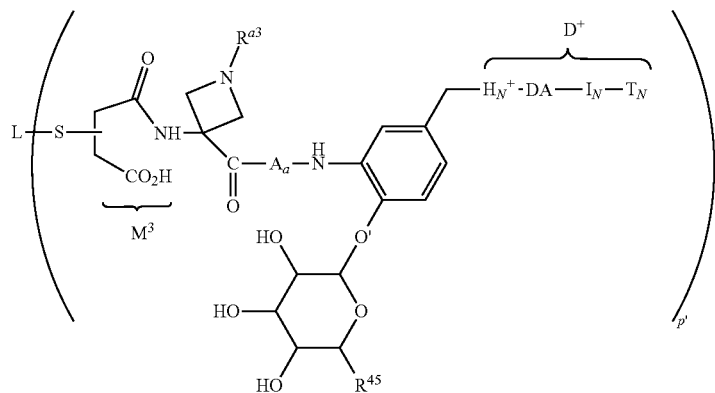

respectively, or a salt thereof, wherein
$R^{45}$ is —CH$_2$OH or —CO$_2$H;
$R^{a3}$ is —H, optionally substituted C$_1$-C$_6$ alkyl, optionally substituted —C$_1$-C$_4$ alkylene-(C$_6$-C$_{10}$ aryl), or —R$^{PEG1}$—O—(CH$_2$CH$_2$O)$_{1-36}$—R$^{PEG2}$, wherein R$^{PEG1}$ is C$_1$-C$_4$ alkylene and R$^{PEG2}$ is —H or C$_1$-C$_4$ alkyl; and
wherein the basic nitrogen atom bonded to $R^{a3}$ is optionally protonated;
—O'— represents the oxygen atom of the 0-glycosidic bond cleavable by the glycosidase,
or wherein the Formula 1a' or Formula 1b' structure is represented by the structure of:

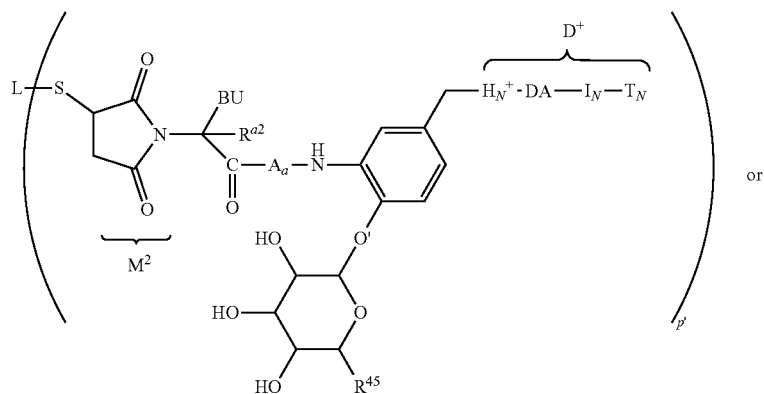

or

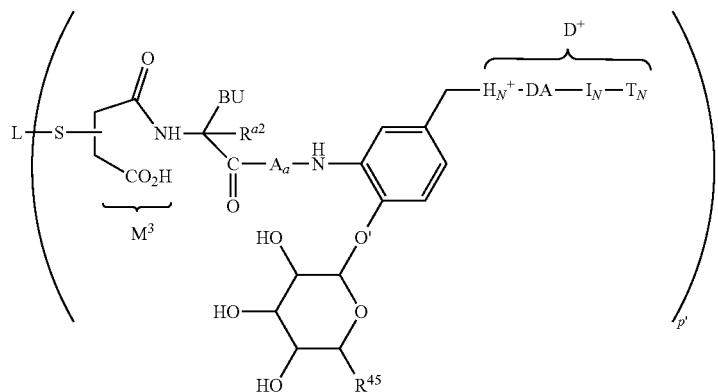
respectively, or a salt thereof, wherein
$R^{45}$ is —CH$_2$OH or —CO$_2$H;
BU is —CH$_2$—NH$_2$, optionally protonated;
$R^{a2}$ is hydrogen; and
—O'— represents the oxygen atom of the 0-glycosidic bond cleavable by the glycosidase,
or wherein the Formula 1c' or Formula 1d' structure is represented by the structure of:
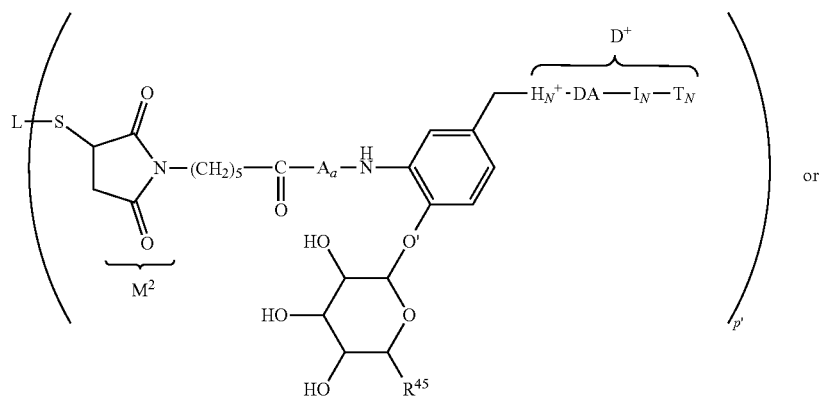
or

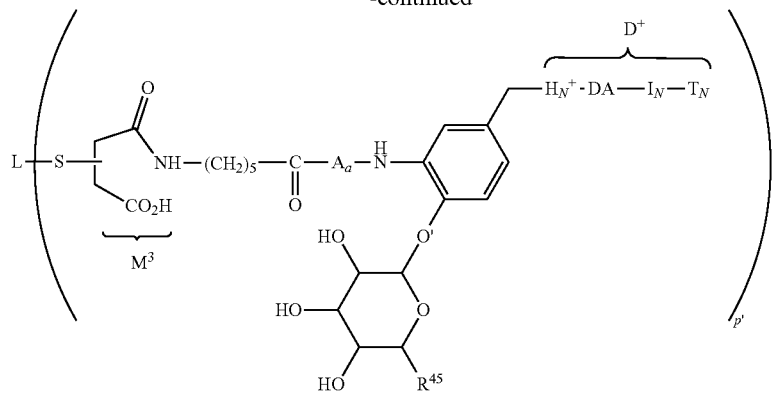

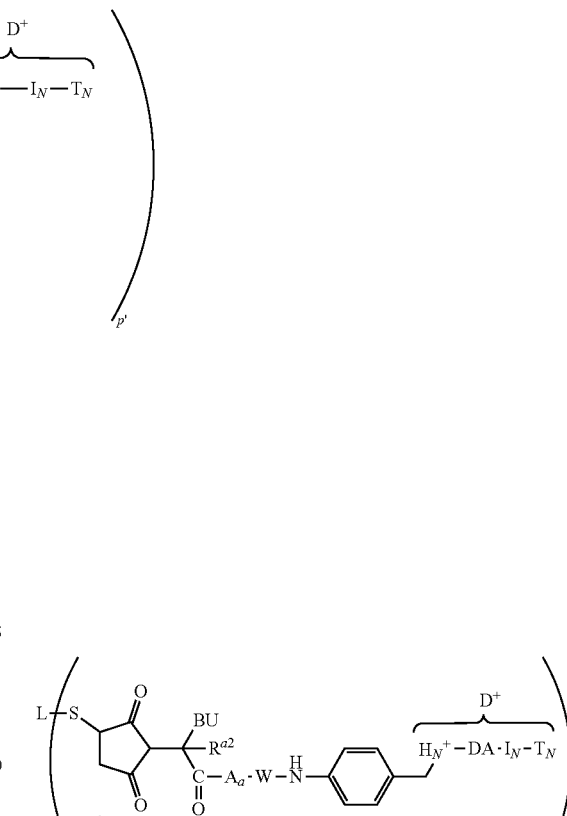

respectively, or a salt thereof, wherein
$R^{45}$ is —CH$_2$OH or —CO$_2$H; and
—O'— represents the oxygen atom of the 0-glycosidic bond cleavable by the glycosidase,
or wherein the Formula 1a' or Formula 1b' structure is represented by the structure of:

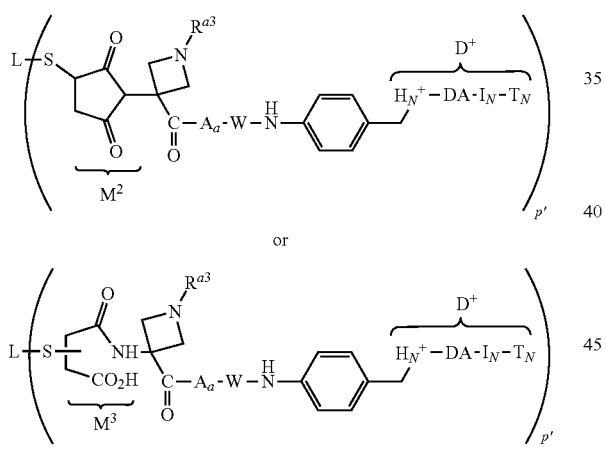

respectively, or a salt thereof, wherein
W is the Peptide Cleavable Unit;
$R^{a3}$ is —H, optionally substituted C$_1$-C$_6$ alkyl, optionally substituted —C$_1$-C$_4$ alkylene-(C$_6$-C$_{10}$ aryl), or —R$^{PEG1}$—O—(CH$_2$CH$_2$O)$_{1-36}$—R$^{PEG2}$, wherein R$^{PEG1}$ is C$_1$-C$_4$ alkylene and R$^{PEG2}$ is —H or C$_1$-C$_4$ alkyl; and
wherein the basic nitrogen atom bonded to $R^{a3}$ is optionally protonated; and
wherein protease action on the Peptide Cleavable Unit is capable of cleaving the W—NH bond, wherein said cleavage within a drug linker moiety of a Ligand Drug Conjugate compound initiates release of the quaternized NAMPT Drug (D$^+$) Unit as a NAMPTi compound from that Ligand Drug Conjugate compound,
or wherein the Formula 1a' or Formula 1b' structure is represented by the structure of:

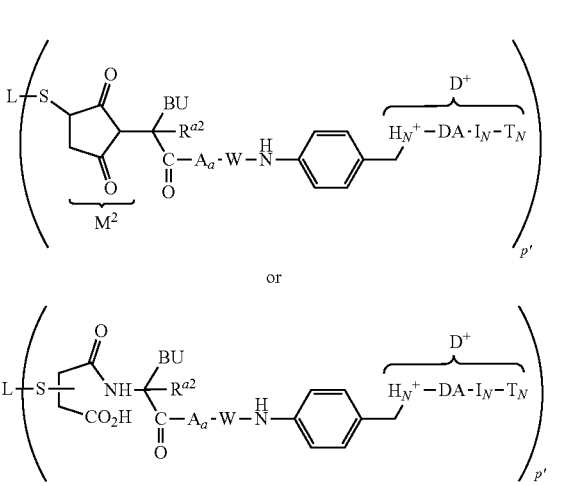

respectively, or a salt thereof, wherein
W is the Peptide Cleavable Unit;
BU is —CH$_2$—NH$_2$, optionally protonated;
$R^{a2}$ is hydrogen; and
wherein protease action on the Peptide Cleavable Unit is capable of cleaving the W—NH bond, wherein said cleavage within a drug linker moiety of a Ligand Drug Conjugate compound initiates release of the quaternized NAMPT Drug (D$^+$) Unit as a NAMPTi compound from that Ligand Drug Conjugate compound,
or wherein the Formula 1c' or Formula 1d' structure is represented by the structure of:

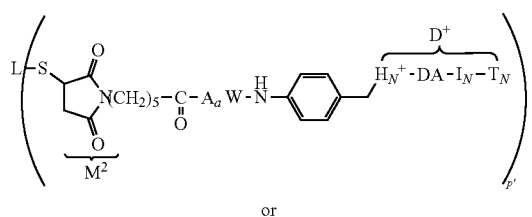

or

-continued

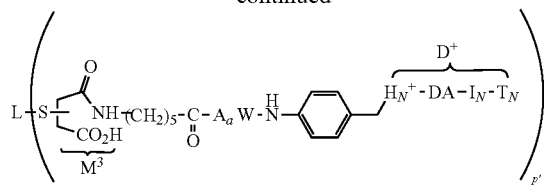

respectively, or a salt thereof, wherein

W is the Peptide Cleavable Unit, wherein protease action on the Peptide Cleavable Unit is capable of cleaving the W—NH bond, wherein said cleavage within a drug linker moiety of a Ligand Drug Conjugate compound initiates release of the quaternized NAMPT Drug Unit (D⁺) as a NAMPTi compound from that Ligand Drug Conjugate compound.

13. The Ligand-Drug Conjugate compound of claim 10 wherein the Peptide Cleavable Unit comprises a peptide sequence containing a dipeptide having the structure of:

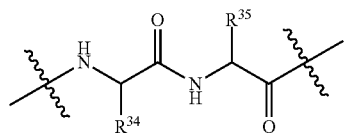

wherein $R^{34}$ is benzyl, methyl, isopropyl, isobutyl, sec-butyl, or —CH(OH)CH$_3$, or $R^{34}$ has the structure of

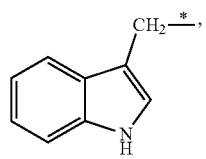

wherein the asterisk indicates the site of covalent attachment to the dipeptide backbone; and $R^{35}$ is methyl, —(CH$_2$)$_4$—NH$_2$, —(CH$_2$)$_3$NH(C=O)NH$_2$, —(CH$_2$)$_3$NH(C=NH)NH$_2$, or —(CH$_2$)$_2$CO$_2$H; and wherein the wavy line adjacent to the carbonyl carbon atom indicates the site of covalent attachment to Y and the wavy line adjacent to the nitrogen atom indicates the site of covalent attachment of the dipeptide to the remainder of the peptide sequence, wherein said covalent attachments are through amide bonds and wherein the dipeptide provides a recognition site for protease cleavage of the amide bond to Y to initiate release of D⁺ as a NAMPTi compound, or wherein the Peptide Cleavable Unit is a dipeptide selected from the group consisting of -Phe-Lys-, -Val-Ala-, -Val-Lys-, -Ala-Lys-, -Val-Cit-, -Phe-Cit-, -Leu-Cit-, -Ile-Cit-, -Phe-Arg-, and -Trp-Cit-, wherein Cit is citrulline.

14. The Ligand-Drug Conjugate compound of claim 10, wherein A or a subunit thereof is -L$^P$(PEG)-, wherein -L$^P$- or a subunit thereof has the structure of Formula L$^P$-1 or L$^P$-2:

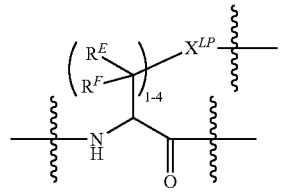

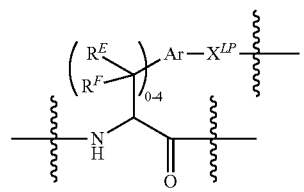

or a salt thereof, wherein $X^{LP}$ is selected from the group consisting of —O—, —NR$^{LP}$—, —S—, —S(=O)—, —S(=O)$_2$—, —C(=O)—, —C(=O)N(R$^{LP}$)—, —N(R$^{LP}$)C(=O)N (R$^{LP}$)—, —N(R$^{LP}$)C(=NR$^{LP}$)N(R$^{LP}$)—, and C$_3$-C$_8$ heterocyclo;

wherein each $R^{LP}$ is independently selected from the group consisting of hydrogen and optionally substituted C$_1$-C$_6$ alkyl, or two of $R^{LP}$ together along with the carbons atoms to which they are attached and their intervening atoms define a C$_5$-C$_6$ heterocyclo and any remaining $R^{LP}$ are as previously defined;

Ar is an optionally substituted C$_6$-C$_{10}$ arylene or an optionally substituted C$_5$-C$_{10}$ heteroarylene;

each $R^E$ and $R^F$ is independently selected from the group consisting of —H, optionally substituted C$_1$-C$_6$ alkyl, optionally substituted C$_2$-C$_6$ alkylene, optionally substituted C$_6$-C$_{10}$ arylene, and optionally substituted C$_5$-C$_{10}$ heteroarylene, or $R^E$ and $R^F$ together with the carbon atom to which both are attached defines an optionally substituted spiro C$_3$-C$_6$ carbocyclo, or $R^E$ and $R^F$ from adjacent carbon atoms together with these atoms and any intervening carbon atoms defines an optionally substituted C$_5$-C$_6$ carbocyclo with any remaining $R^E$ and $R^F$ as previously defined; and wherein one of the wavy lines indicates the site of covalent attachment of a PEG Unit and the other wavy line indicates covalent attachment of Formula L$^P$-1 or Formula L$^P$-2 within the structure representing the Ligand Drug Conjugate composition, or wherein -L$^P$(PEG)- has the structure of Formula L$^P$-3 or Formula L$^P$-4:

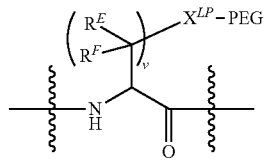

-continued (L$^P$-4)

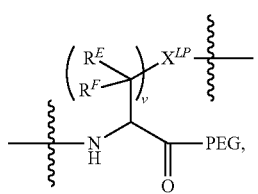

or a salt thereof, wherein
subscript v is an integer ranging from 1 to 4;
X$^{LP}$ is selected from the group consisting of —O—, —NR$^{LP}$—, —S—, —S(=O)—, —S(=O)$_2$—, —C(=O)—, —C(=O)N(R$^{LP}$)—, —N(R$^{LP}$)C(=O)N (R$^{LP}$)—, —N(R$^{LP}$)C(=NR$^{LP}$)N(R$^{LP}$)—, and C$_3$-C$_8$ heterocyclo, or X$^{LP}$ is selected from the group consisting of —O—, —NH, —S— and —C(=O)—;
wherein each R$^{LP}$ is independently selected from the group consisting of hydrogen and optionally substituted C$_1$-C$_6$ alkyl, or two of R$^{LP}$ together along with the carbons atoms to which they are attached and their intervening atoms define a C$_5$-C$_6$ heterocyclo and any remaining R$^{LP}$ are as previously defined;
Ar is an optionally substituted C$_6$-C$_{10}$ arylene or an optionally substituted C$_5$-C$_{10}$ heteroarylene;
each R$^E$ and R$^F$ is independently selected from the group consisting of —H, optionally substituted C$_1$-C$_6$ alkyl, optionally substituted C$_2$-C$_6$ alkylene, optionally substituted C$_6$-C$_{10}$ arylene, and optionally substituted C$_5$-C$_{10}$ heteroarylene, or R$^E$ and R$^F$ are independently selected from the group consisting of —H and —C$_1$-C$_4$ alkyl,
or R$^E$ and R$^F$ together with the carbon atom to which both are attached defines an optionally substituted spiro C$_3$-C$_6$ carbocyclo, or R$^E$ and R$^F$ from adjacent carbon atoms together with these atoms and any intervening carbon atoms defines an optionally substituted C$_5$-C$_6$ carbocyclo with any remaining R$^E$ and R$^F$ as previously defined, or wherein the side chain of —[C(R$^E$)(R$^F$)]$_v$—X$^{LP}$— is provided by a natural or un-natural amino acid side chain; and
wherein one of the wavy lines indicate the site of covalent attachment of a PEG Unit and the other line indicates covalent attachment of Formula L$^P$-1 or Formula L$^P$-2 within the structure representing the Ligand Drug Conjugate composition,
and wherein PEG in L$^P$-3 or L$^P$-4 has the structure selected from the group consisting of:

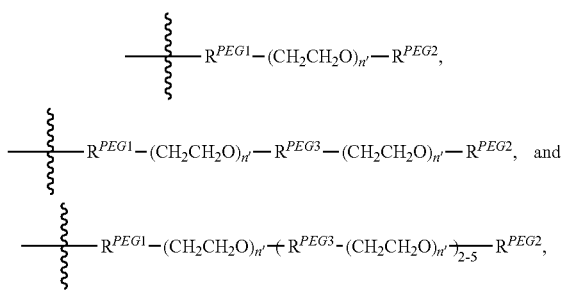

wherein the wavy line indicates site of covalent attachment to X$^{LP}$ of the Parallel Connector Unit (L$_P$);
subscript n' independently ranges from 1 to 72;
R$^{PEG1}$ is an optional PEG Attachment Unit;
R$^{PEG2}$ is a PEG Capping Unit; and
R$^{PEG3}$ is a PEG Coupling Unit,
or
wherein X$^{LP}$-PEG in L$^P$-3 has the structure of:

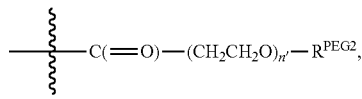

wherein subscript n' is 8, 12, or 24 and R$^{PEG2}$ is H or —CH$_3$,
or A or a subunit thereof has the structure of formula (3) or formula (4):

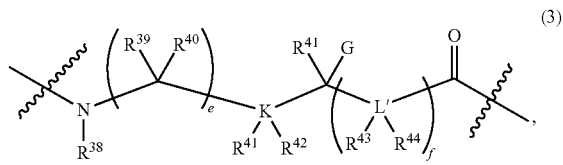

(3)

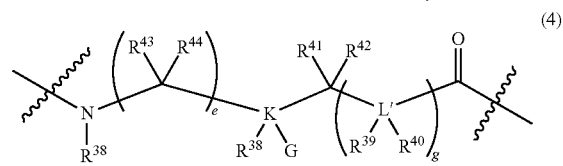

(4)

wherein the wavy lines indicated covalent attachment within the compound structure;
wherein K and L' independently are C, N, O, or S, provided that when K or L' is O or S, R$^{41}$ and R$^{42}$ to K or R$^{43}$ and R$^{44}$ to L' are absent, and when K or L' are N, one of R$^{41}$, R$^{42}$ to K or one of R$^{42}$, R$^{43}$ to L' are absent, and provided that no two adjacent L' are independently selected as N, O, or S;
wherein subscripts e and f are independently selected integers that range from 0 to 12, and subscript g is an integer ranging from 1 to 12;
wherein G is hydrogen, optionally substituted C$_1$-C$_6$ alkyl, —OH, —OR$^{PR}$, or —CO$_2$H, CO$_2$R$^{PR}$, wherein R$^{PR}$ is a suitable protecting, or
G is —N(R$^{PR}$)(R$^{PR}$), wherein R$^{PR}$ are independently a protecting group or R$^{PR}$ together form a suitable protecting group, or
G is —N(R$^{45}$)(R$^{46}$), wherein one of R$^{45}$, R$^{46}$ is hydrogen or R$^{PR}$, wherein R$^{PR}$ is a suitable protecting group, and the other is hydrogen or optionally substituted C$_1$-C$_6$ alkyl;
wherein R$^{38}$ is hydrogen or optionally substituted C$_1$-C$_6$ alkyl;
R$^{39}$-R$^{44}$ are independently selected from the group consisting of hydrogen, optionally substituted C$_1$-C$_6$ alkyl, optionally substituted aryl, and optionally substituted heteroaryl, or
R$^{39}$ and R$^{40}$ together with the carbon atom to which both are attached, or R$^{41}$, R$^{42}$ together with K to which both are attached when K is a carbon atom, define a C$_3$-C$_6$ carbocyclo, and R$^{41}$-R$^{44}$ are as defined herein,
or R$^{43}$, R$^{44}$ together with L' to which both are attached when L' is a carbon atom define a C$_3$-C$_6$ carbocyclo, and R$^{39}$-R$^{42}$ are as defined herein, or $R^{40}$ and $R^{41}$, or $R^{40}$ and $R^{43}$, or $R^{41}$ and $R^{43}$ together with the carbon atom or heteroatom to which both are attached and the atoms intervening between those carbon atoms and/or heteroatoms define a $C_5$-$C_6$ carbocyclo or a $C_5$-$C_6$ heterocyclo, and $R^{39}$, $R^{44}$ and the remainder of $R^{40}$-$R^{43}$ are as defined herein, provided that when K is O or S, $R^{41}$ and $R^{42}$ are absent, and when K is N, one of $R^{41}$ and $R^{42}$ is absent, and when L' is O or S, $R^{43}$ and $R^{44}$ are absent, and when L' is N, one of $R^{43}$, $R^{44}$ is absent, or A or a subunit thereof has the structure of formula (3a) or formula (4a):

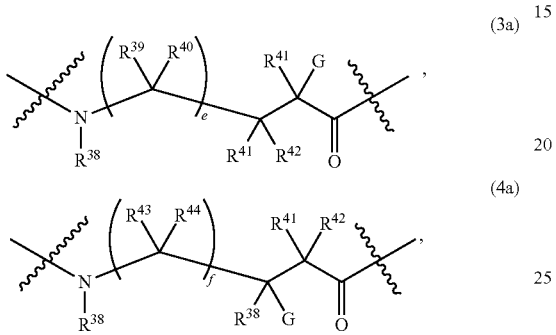

(3a)

(4a)

wherein subscript e and f are independently 0 or 1, or A, or a subunit thereof, is an alpha-amino, beta-amino, or another amine-containing acid residue.

15. The Ligand-Drug Conjugate compound of claim 10, wherein the Ligand Unit is an intact antibody or antigen binding fragment of an antibody, thereby defining an antibody Ligand Unit of an antibody drug conjugate (ADC), wherein the moiety targeted by the antibody Ligand Unit is an accessible cell-surface antigen of abnormal cells that is capable of cellular internalization when bound to ADC compound and is present in greater copy number on the abnormal cells in comparison to normal cells distant from the site of the abnormal cells, or wherein the Ligand Unit is a cognate ligand of an accessible cell-surface receptor on abnormal cell that is capable of cellular internalizatom when bound to a Ligand Drug Conjugate compound of the composition, and wherein the receptor is present in greater copy number on the abnormal cells in comparison to normal cells distant from the site of abnormal cells, or wherein the Ligand Unit is an antibody, thereby defining an antibody Ligand Unit of an antibody drug conjugate (ADC), wherein the moiety targeted by the antibody Ligand Unit is an accessible cell-surface antigen of a vascular epithelial cell in the vicinity of abnormal cells, wherein said antigen is capable of cellular internalization of bound ADC and is present in greater copy number on said cells in comparison to normal epithelial cells distant from the site of the abnormal cells.

16. The Ligand Drug Conjugate compound of claim 15, wherein the Ligand Unit is an intact antibody and subscript p' is 2, 4, or 8 and wherein each sulfur atom of the antibody Ligand Unit bonded to each succinic acid ($M^2$) moiety or succinic acid amide ($M^3$) moiety is that of a cysteine residue of the intact antibody or wherein each cysteine residue is an introduced cysteine residue in the heavy chain or light chain of the antibody or antigen binding-fragment thereof.

17. The Ligand Drug Conjugate compound of claim 1, wherein the compound is represented by the structure of:

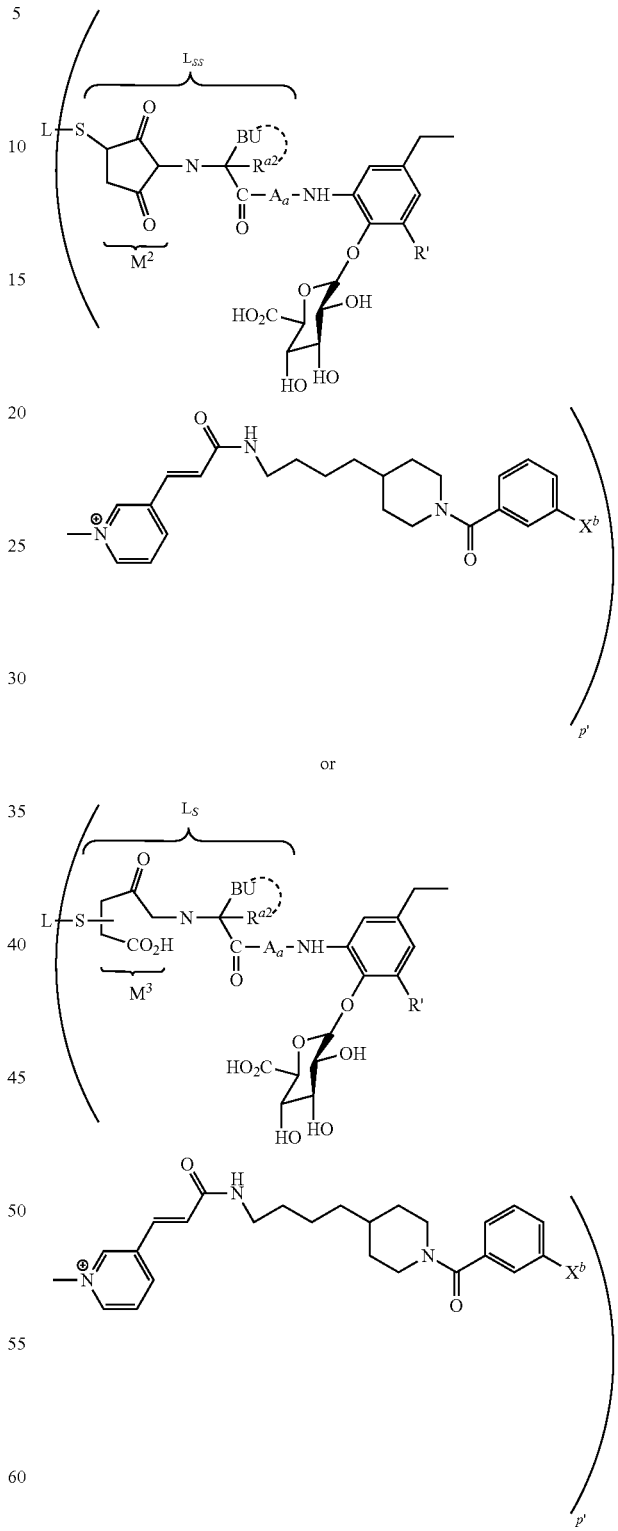

or a salt thereof, wherein

L is an intact antibody or antigen binding fragment of an antibody, thereby defining an antibody Ligand Unit of an antibody drug conjugate (ADC), and S is a sulfur atom from the antibody or the antigen-binding fragment of the antibody;

subscript a is 1 and A is an amino acid residue;

BU is an acyclic Basic Unit so that the dotted curve line is absent, and $R^{a2}$ is hydrogen, or BU together with $R^{a2}$ as $C_1$-$C_6$ alkyl and the carbon atom to which both are attached define a cyclic Basic Unit so that the dotted curved line is present; and R' is hydrogen or —$NO_2$; and $X^b$ is —H, —OH, or —$NH_2$, or wherein the compound is represented by the structure of:

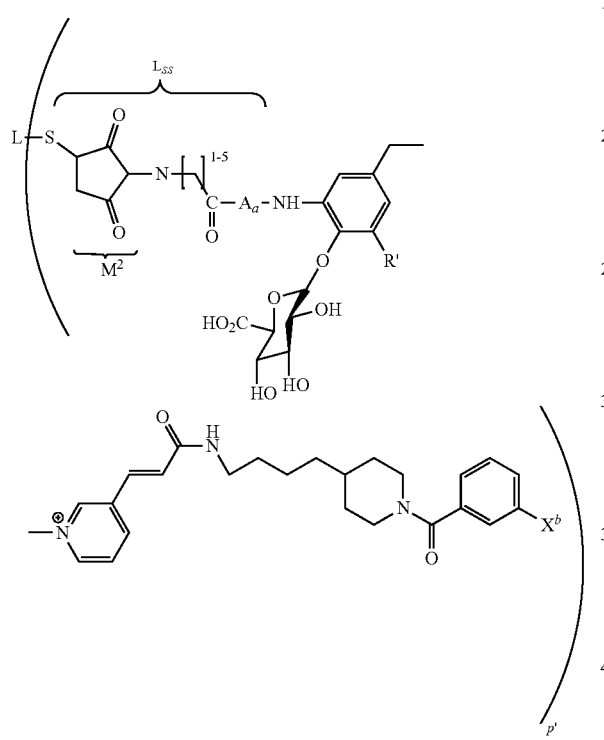

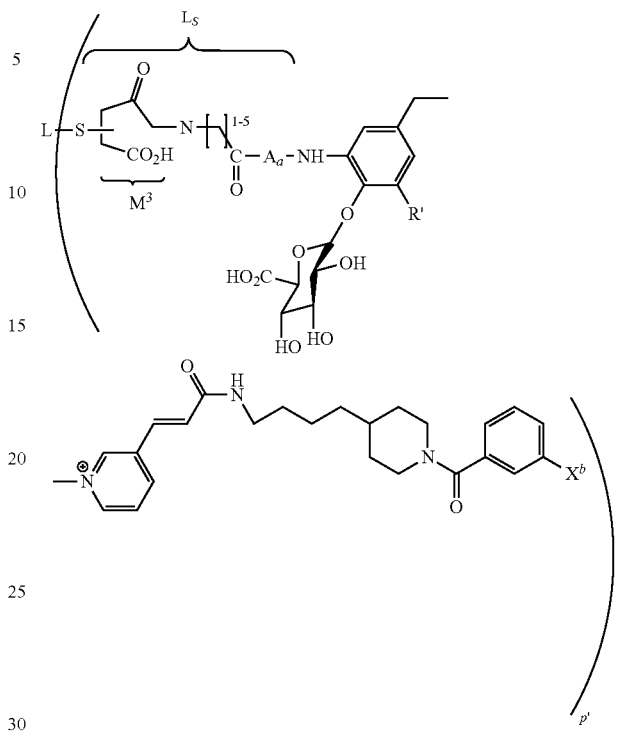

or a salt thereof, wherein

L is an intact antibody or antigen binding fragment of an antibody, thereby defining an antibody Ligand Unit of an antibody drug conjugate (ADC), and S is a sulfur atom from the antibody or the antigen-binding fragment of the antibody;

subscript a is 1 and A is an amino acid residue;

R' is hydrogen or —$NO_2$; and $X^b$ is —H, —OH, or —$NH_2$, or wherein the compound is represented by the structure of:

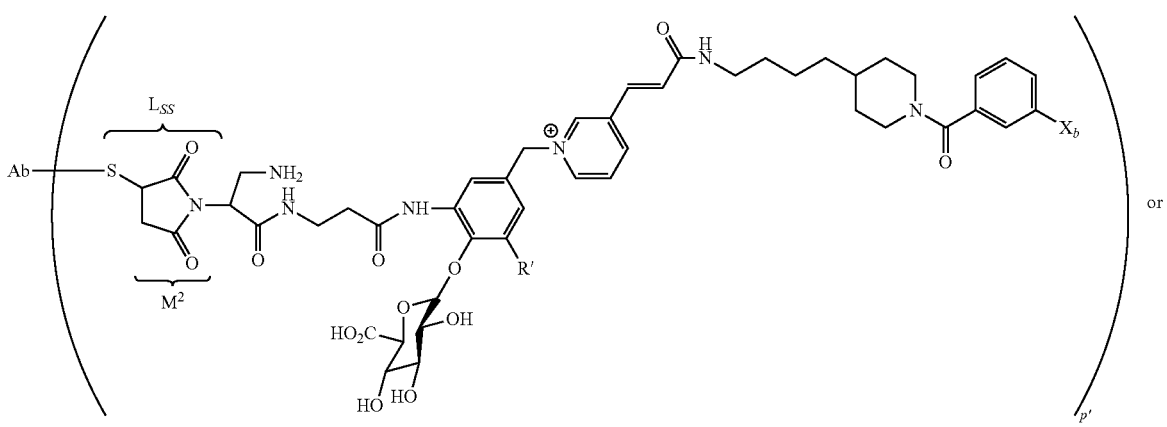

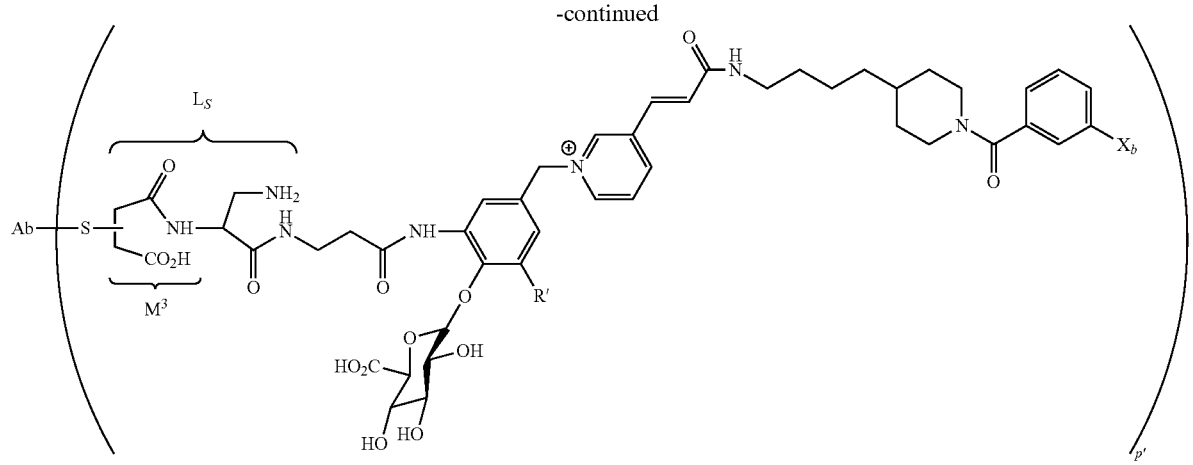

or a salt thereof, wherein Ab is an antibody Ligand Unit from an intact antibody or antigen-binding fragment of an antibody; S is a sulfur atom from the antibody or the antigen-binding fragment of the antibody; and subscript p' is 8, or wherein the compound is represented by the structure of:

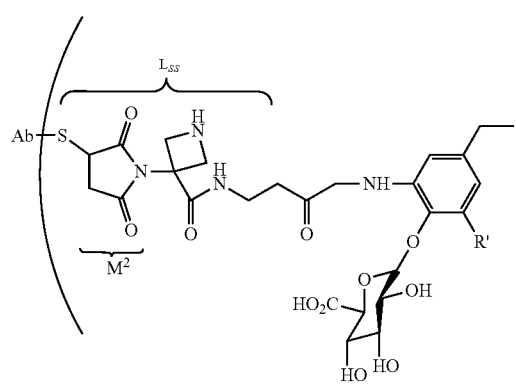

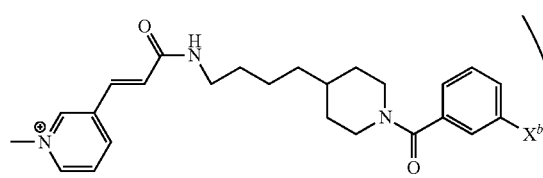

or

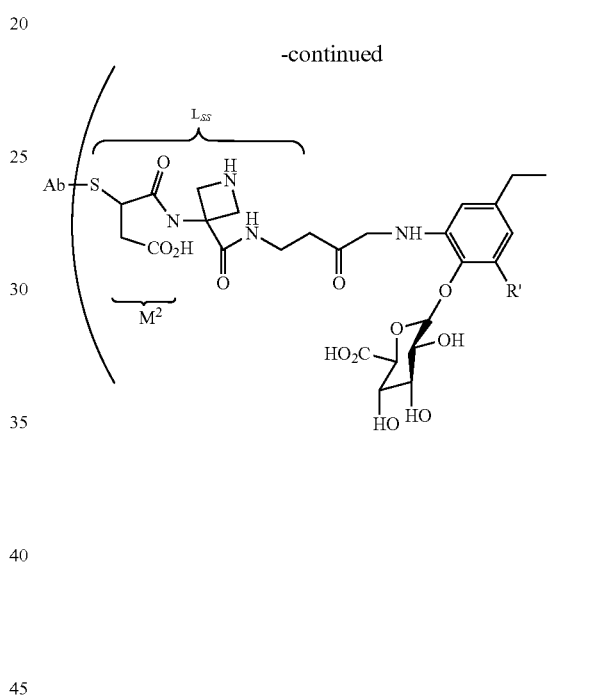

or a salt thereof, wherein Ab is an antibody Ligand Unit from an intact antibody or antigen-binding fragment of an antibody; S is a sulfur atom from the antibody or the antigen-binding fragment of the antibody; and subscript p' is 8.

18. The Ligand Drug Conjugate compound of claim 1, wherein the compound is represented by the structure of:

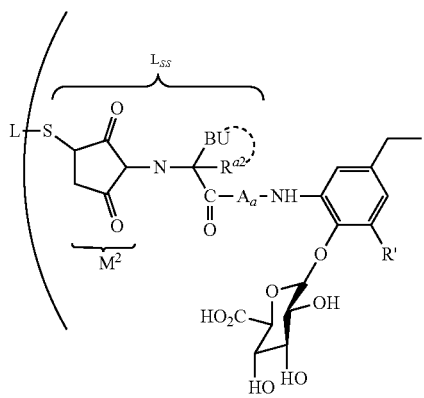

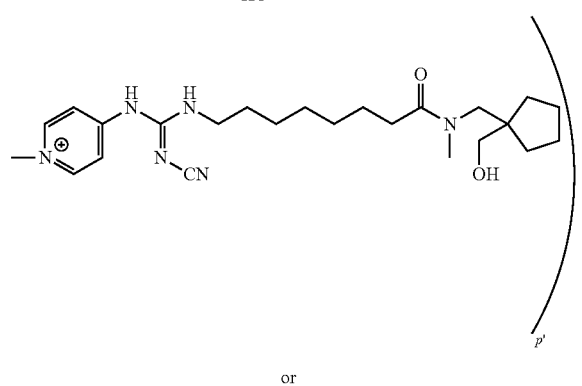

or

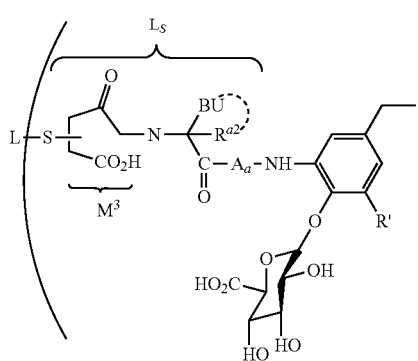

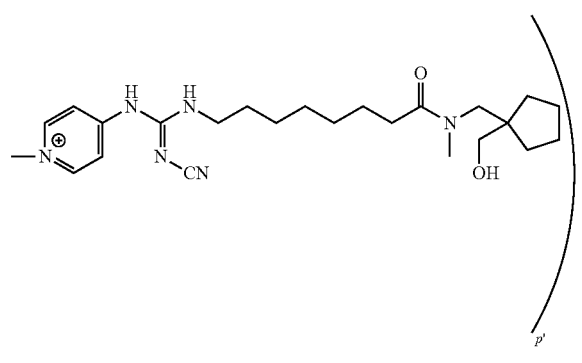

or a salt thereof, wherein

L is an intact antibody or an antigen-binding fragment of an antibody, thereby defining an antibody Ligand Unit of an antibody drug conjugate (ADC), and S is a sulfur atom from the antibody or the antigen-binding fragment of the antibody;

subscript a is 1 and A is an amino acid residue;

BU is an acyclic Basic Unit so that the dotted curve line is absent, and $R^{a2}$ is hydrogen, or BU together with $R^{a2}$ as $C_1$-$C_6$ alkyl and the carbon atom to which both are attached define a cyclic Basic Unit so that the dotted curved line is present; and R' is hydrogen or —$NO_2$; and $X^b$ is —H, —OH, or —$NH_2$, or wherein the compound is represented by the structure of:

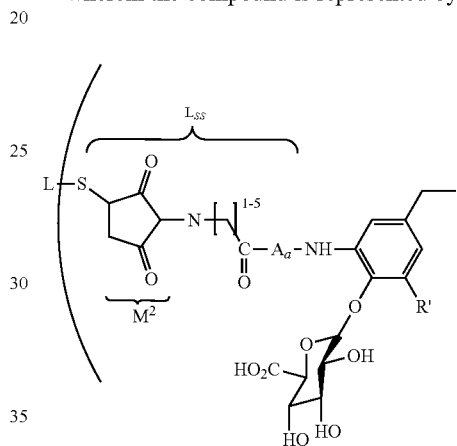

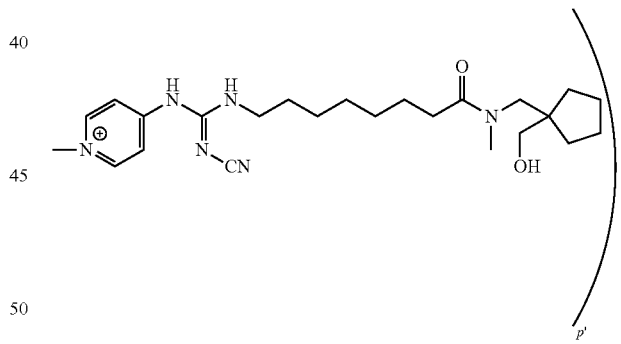

or

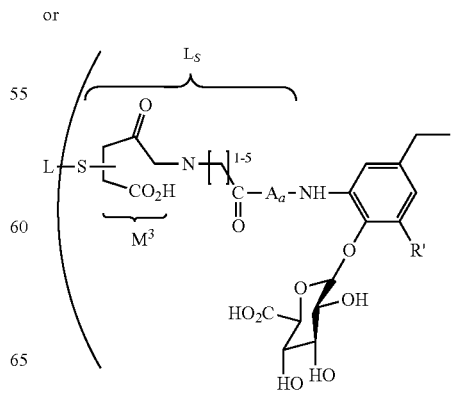

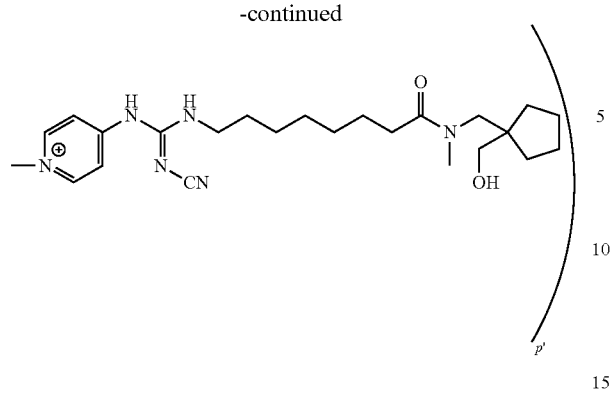

or a salt thereof, wherein
L is an intact antibody or an antigen-binding fragment of an antibody, thereby defining an antibody Ligand Unit of an antibody drug conjugate (ADC), and S is a sulfur atom from the antibody or the antigen-binding fragment of the antibody;
subscript a is 1 and A is an amino acid residue;
R' is hydrogen or —$NO_2$; and
$X^b$ is —H, —OH, or —$NH_2$, or
wherein the compound is represented by the structure of:

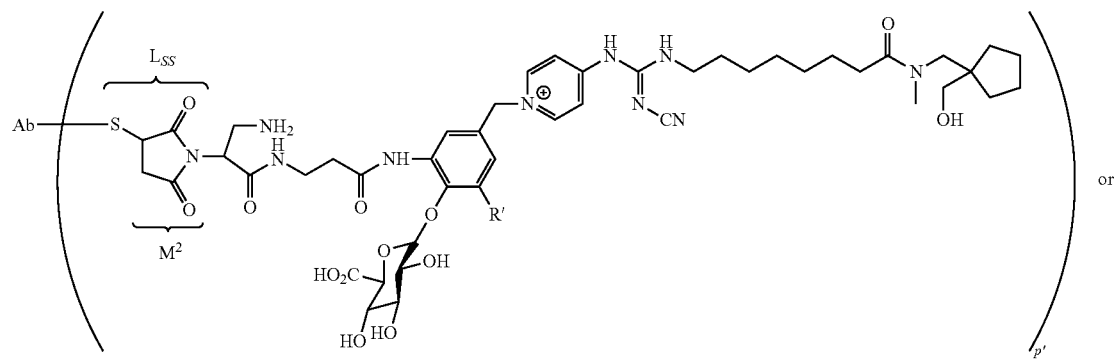

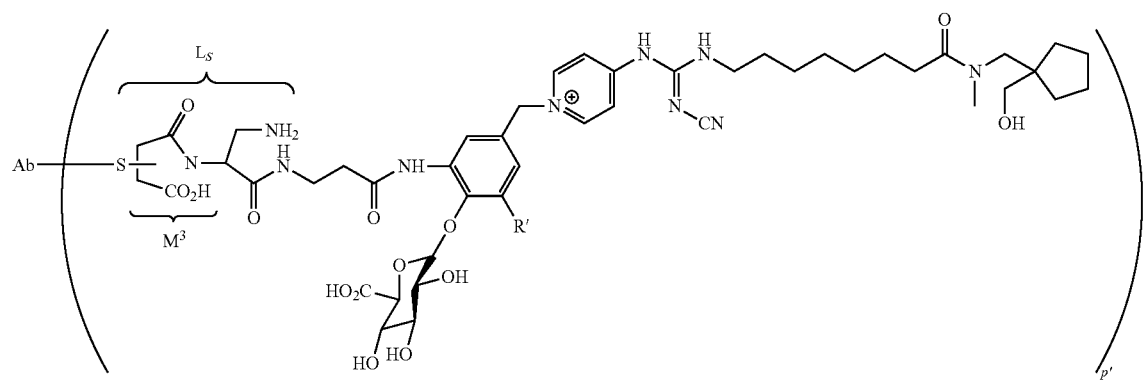

or a salt thereof, wherein Ab is an antibody Ligand Unit from an intact antibody or antigen-binding fragment of an antibody; S is a sulfur atom from the antibody or the antigen-binding fragment of the antibody; and subscript p' is 8, or wherein the compound is represented by the structure of:

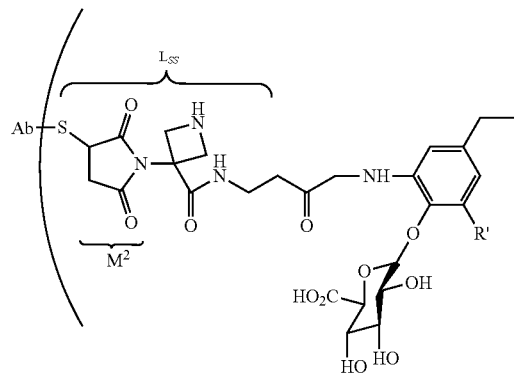

or

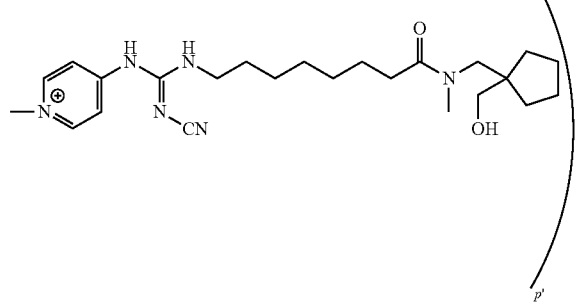

or

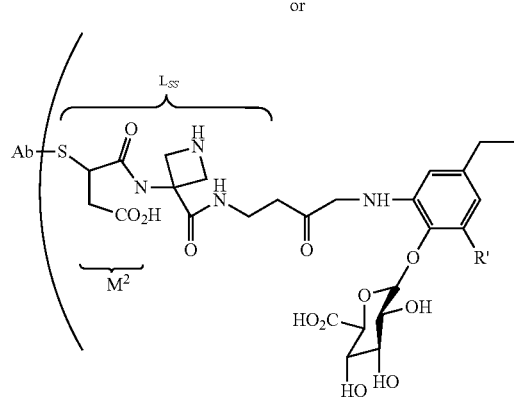

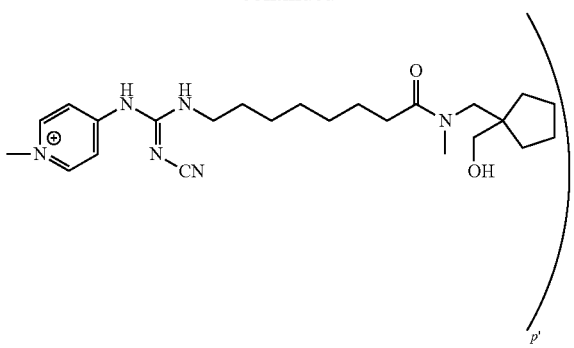

or a salt thereof, wherein Ab is an antibody Ligand Unit from an intact antibody or antigen-binding fragment of an antibody; S is a sulfur atom from the antibody or the antigen-binding fragment of the antibody; and subscript p' is 8.

19. The Ligand Drug Conjugate compound of claim 1, wherein the compound is represented by the structure of:

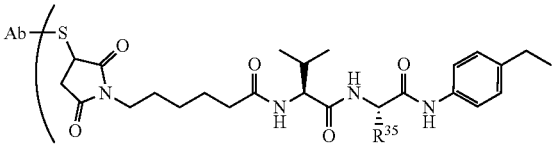

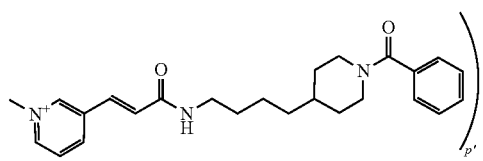

or

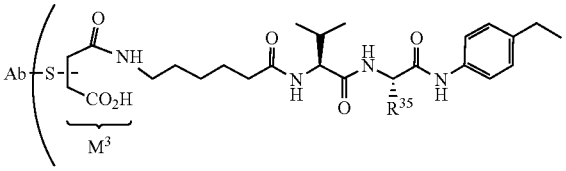

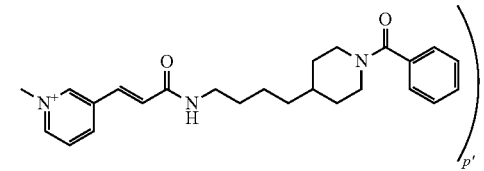

or a salt thereof, wherein Ab is an antibody Ligand Unit from an intact antibody or antigen-binding fragment of an antibody or the antigen-binding fragment of the antibody; S is a sulfur atom from the antibody; and subscript p' is 8, or wherein the compound is represented by the structure of:

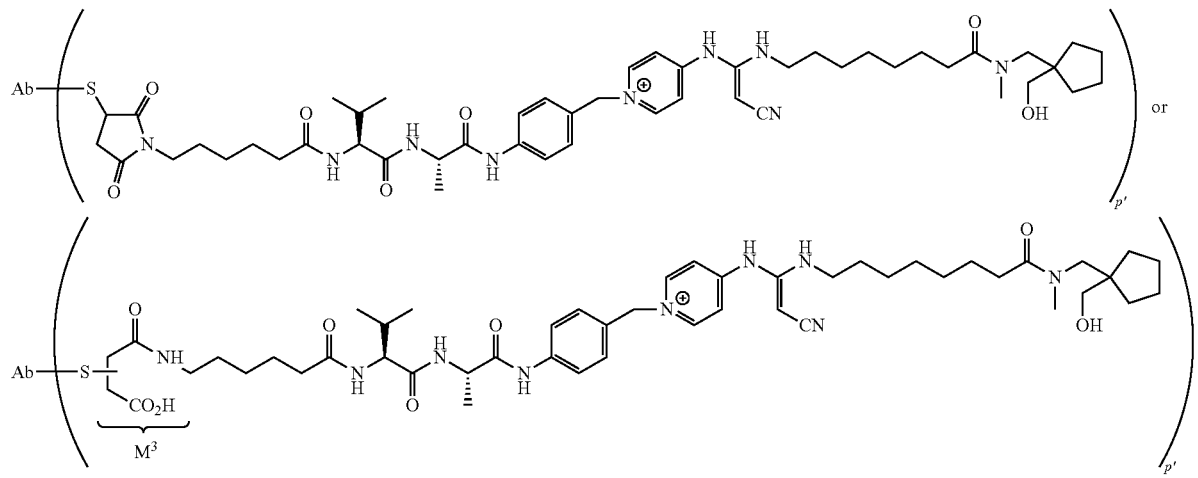

or a salt thereof, wherein Ab is an antibody Ligand Unit from an intact antibody or antigen-binding fragment of an antibody or the antigen-binding fragment of the antibody; S is a sulfur atom from the antibody; and subscript p' is 8.

20. A formulation comprising a Ligand Drug Conjugate compound of claim 1, and one, two, three, or more excipients.

21. The formulation of claim 20, wherein the formulation is a pharmaceutically acceptable formulation or a precursor thereof, or wherein the formulation is a pharmaceutically acceptable liquid formulation intended for intravenous injection to a subject or the formulation is a pharmaceutically acceptable formulation precursor, wherein the precursor is a solid suitable for reconstitution as a solution intended for intravenous injection to a subject.

* * * * *